(12) United States Patent
Heard et al.

(10) Patent No.: US 7,135,616 B2
(45) Date of Patent: Nov. 14, 2006

(54) BIOCHEMISTRY-RELATED POLYNUCLEOTIDES AND POLYPEPTIDES IN PLANTS

(75) Inventors: Jacqueline E. Heard, San Mateo, CA (US); Jose Luis Riechmann, Pasadena, CA (US); Robert A. Creelman, Castro Valley, CA (US); James Keddie, San Mateo, CA (US); Marsha L. Pilgrim, Phoenixville, PA (US); Arnold N. DuBell, San Lorenzo, CA (US); Cai-Zhong Jiang, Fremont, CA (US); Oliver Ratcliffe, Oakland, CA (US); Omaira Pineda, Vero Beach, FL (US); Guo-Liang Yu, Berkeley, CA (US); Pierre E. Broun, San Mateo, CA (US)

(73) Assignee: Mendel Biotechnology, Inc., Hayward, CA (US)

( * ) Notice: Subject to any disclaimer, the term of this patent is extended or adjusted under 35 U.S.C. 154(b) by 445 days.

(21) Appl. No.: 10/225,067

(22) Filed: Aug. 9, 2002

(65) Prior Publication Data

US 2004/0019925 A1    Jan. 29, 2004

Related U.S. Application Data

(63) Continuation-in-part of application No. 10/171,468, filed on Jun. 14, 2002, now abandoned, and a continuation-in-part of application No. 09/837,944, filed on Apr. 18, 2001, now abandoned, and a continuation-in-part of application No. 60/338,692, filed on Dec. 11, 2001.

(60) Provisional application No. 60/310,847, filed on Aug. 9, 2001, provisional application No. 60/336,049, filed on Nov. 19, 2001.

(51) Int. Cl.
C12N 15/82    (2006.01)
C12N 5/04    (2006.01)
A01H 5/00    (2006.01)
A01H 5/10    (2006.01)

(52) U.S. Cl. .................. 800/278; 800/287; 800/290; 800/289; 435/468

(58) Field of Classification Search ............... 800/290, 800/278, 298, 287, 289; 435/468, 320.1; 536/23.1, 23.6
See application file for complete search history.

(56) References Cited

U.S. PATENT DOCUMENTS

2002/0040490 A1    4/2002    Gorlach et al.
2003/0217383 A1    11/2003    Reuber et al.
2003/0226173 A1    12/2003    Ratcliffe et al.
2004/0019927 A1    1/2004    Sherman et al.

FOREIGN PATENT DOCUMENTS

EP    1033405 A2    9/2000

OTHER PUBLICATIONS

Bowie et al, Science 247:1306-1310, 1990.*
McConnell et al, Nature 411 (6838):709-713, 2001.*
Yang et al (2001, PNAS 98(20):11438-11443).*
Cheuk, R. et al (Jun. 5, 2004) *Arabidopsis thaliana* At1g71520 gene, complete cds., NCBI Accession No. BT014816.
Vysotskaia, V.S. et al. (Jan. 5, 2001) *Arabidopsis thaliana* chromosone 1 BAC T22J18 sequence, complete sequence., NCBI Accession No. AC003979, protein_id="AAC25505.1".
Vysotskaia, V.S. et al. (Jan. 5, 2001) Contains similarity to transcription factor (TINY) isolog T02004.22 gb 12062174 from *A. thaliana* BAC gb|AC001645. [*Arabidopsis thaliana*], NCBI Accession No. AAC25505.
Town, C.D. et al. (Feb. 23, 2005) *Arabidopsis thaliana* AP2 domain-containing transcription factor, putative (At1g22810) mRNA, complete cds., NCBI Accession No. NM_102128.
Vysotskaia, V.S., et al. (Feb. 12, 1999) Hypothetical protein T22J18. 2—*Arabidopsis thaliana*, PIR Entry T00763.
Lin, X., et al. (Jan. 19, 2001) *Arabidopsis thaliana* chromosome 1 BAC F3I17 genomic sequence, complete sequence. NCBI acc. No. AC016162, base coordinates 3814-4233.
Town, C.D. et al. (Aug. 20, 2002) *Arabidopsis thaliana* chromosome 1 CHR1v07142002 genomic sequence, NCBI Accession No. NM_102128.
Sakuma, Y. et al. (2002) DNA-Binding Specificity of the ERF/AP2 Domain of Arabidopsis DREBs, Transcription Factors Involved in Dehydration- and Cold-Inducible Gene Expression. Biochem. Biophys. Res. Comm. 290: 998-1009.
*Arabidopsis thaliana* DNA fragment SEQ ID No.: 53281 from Patent No. EP1033405A2 (Oct. 18, 2000) Derwent Accession No. AAC47292.
*Arabidopsis thaliana* DNA fragment SEQ ID No.: 54172 from Patent No. EP1033405A2 (Sep. 6, 2000) Derwent Accession No. AAG43349.
Lin, X., et al. (Jan. 19, 2001) *Arabidopsis thaliana* chromosome 1 BAC F26A9 gonomic sequence; complete sequence. NCBI acc. No. AC016163, gi:12323733, base coordinates 37030-37461 (Bethesda, MD, USA).
Mayer, K. et al. (May 15, 2001) putative AP2 domain transcription factor [*Oryaa sativa* ]. NCBI acc. No. CAC39072 (Bethesda, MD, USA).

(Continued)

*Primary Examiner*—David T. Fox
*Assistant Examiner*—Stuart F. Baum
(74) *Attorney, Agent, or Firm*—Jeffrey M. Libby

(57) ABSTRACT

The invention relates to plant transcription factor polypeptides, polynucleotides that encode them, homologs from a variety of plant species, and methods of using the polynucleotides and polypeptides to produce transgenic plants having advantageous properties compared to a reference plant. Sequence information related to these polynucleotides and polypeptides can also be used in bioinformatic search methods and is also disclosed.

29 Claims, 1 Drawing Sheet

OTHER PUBLICATIONS

Figure 1:
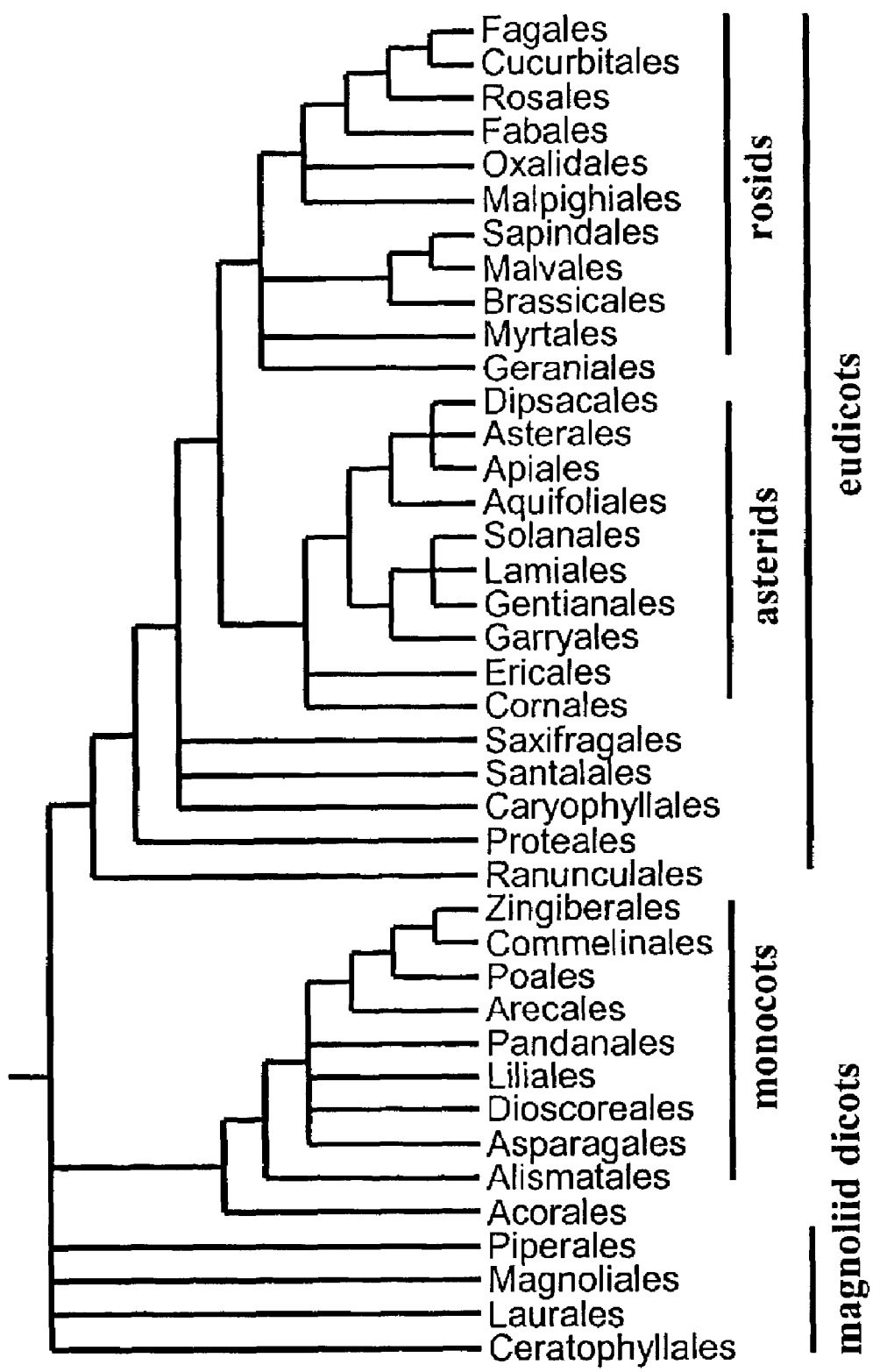

Watson et al. (Dec. 20, 2000) NF024B04RT1F1029 Developing root Medicago truncatula cDNA clone NF024B04RT 5', mRNA sequence. NCBI acc. No. BB320193 (Bethesda, MD, USA).

Watson et al. (Dec. 20, 2000) NF019G12RT1F1088 Developing root Medicago truncatula cDNA clone, NCBI acc. No. BE319522 (Bethesda, MD, USA).

Watson et al. (Jun. 15, 2000) NF03SD03NR1F1000 Nodulated root Medicago truncatula cDNA clone NF03SD03NR 5', mRNA sequence, NCBI acc. No. AW685808 (Bethesda, MD, USA).

Sasaki, T. et al. (Mar. 8, 2001) *Oryza sativa* chromosome 1 clone P0408G07, NCBI acc. No. AP003379 (Bethesda, MD, USA).

Torres-Jerex, I. (Dec. 20, 2000) NF060H11EC1F1096 Elicited cell culture Medicago truncatula cDNA clone NF060H11EC 5', mRNA sequence, NCBI acc. No. BF644218 (Bethesda, MD, USA).

Van Der Hoeven et al. (May 19, 2001) EST302937 tomato root during/after fruit set, Cornell University Lycopersicon esculentum cDNA clone cLEX10P20, mRNA sequence, NCBI acc. No. AW220454 (Bethesda, MD, USA).

Restrepo et al. (Apr.30, 2003) EST537314 P. infestans-challenged potato leaf, compatible reaction olanum tuberosum cDNA clone PPCBR81 5'sequence, mRNA sequence, NCBI acc No. BI434553 (Bethesda, MD, USA).

Okamura, J.K. et al. (1997) The AP2 domain of APETALA2 defines a large new family of DNA binding proteins in *Arabidopsis*. Proc. Natl. Acad. Sci. (USA) 94; 7076-7081 Washington, DC, USA).

Theologis, A., et al. (2000) Sequence and analysis of chromosome 1 of the plant *Arabidopsis thaliana*. Nature 108: 816-820 (London, England).

* cited by examiner

US 7,135,616 B2

BIOCHEMISTRY-RELATED POLYNUCLEOTIDES AND POLYPEPTIDES IN PLANTS

This application claims the benefit of U.S. Provisional Application No. 60/310,847, filed Aug. 9, 2001, U.S. Provisional Application No. 60/336,049, filed Nov. 19, 2001, and U.S. Provisional Application No. 60/338,692, filed Dec. 11, 2001; and this application is a continuation-in-part of application Ser. No. 09/837,944, filed Apr. 18, 2001 (abandoned), and this application is a continuation-in-part of application Ser. No. 10/171,468, filed Jun. 14, 2002 (abandoned), the entire contents of which are hereby incorporated by reference.

The claimed invention, in the field of functional genomics and the characterization of plant genes for the improvement of plants, was made by or on behalf of Mendel Biotechnology, Inc. and Monsanto Corporation as a result of activities undertaken within the scope of a joint research agreement, said agreement having been executed on Oct. 31, 1997, and in effect on or before the date the claimed invention was made.

FIELD OF THE INVENTION

This invention relates to the field of plant biology. More particularly, the present invention pertains to compositions and methods for phenotypically modifying a plant.

INTRODUCTION

A plant's traits, such as its biochemical, developmental, or phenotypic characteristics, may be controlled through a number of cellular processes. One important way to manipulate that control is through transcription factors—proteins that influence the expression of a particular gene or sets of genes. Transformed and transgenic plants that comprise cells having altered levels of at least one selected transcription factor, for example, possess advantageous or desirable traits. Strategies for manipulating traits by altering a plant cell's transcription factor content can therefore result in plants and crops with commercially valuable properties. Applicants have identified polynucleotides encoding transcription factors, developed numerous transgenic plants using these polynucleotides, and have analyzed the plants for a variety of important traits. In so doing, applicants have identified important polynucleotide and polypeptide sequences for producing commercially valuable plants and crops as well as the methods for making them and using them. Other aspects and embodiments of the invention are described below and can be derived from the teachings of this disclosure as a whole.

BACKGROUND OF THE INVENTION

Transcription factors can modulate gene expression, either increasing or decreasing (inducing or repressing) the rate of transcription. This modulation results in differential levels of gene expression at various developmental stages, in different tissues and cell types, and in response to different exogenous (e.g., environmental) and endogenous stimuli throughout the life cycle of the organism.

Because transcription factors are key controlling elements of biological pathways, altering the expression levels of one or more transcription factors can change entire biological pathways in an organism. For example, manipulation of the levels of selected transcription factors may result in increased expression of economically useful proteins or metabolic chemicals in plants or to improve other agriculturally relevant characteristics. Conversely, blocked or reduced expression of a transcription factor may reduce biosynthesis of unwanted compounds or remove an undesirable trait. Therefore, manipulating transcription factor levels in a plant offers tremendous potential in agricultural biotechnology for modifying a plant's traits.

The present invention provides novel transcription factors useful for modifying a plant's phenotype in desirable ways.

SUMMARY OF THE INVENTION

In a first aspect, the invention relates to a recombinant polynucleotide comprising a nucleotide sequence selected from the group consisting of: (a) a nucleotide sequence encoding a polypeptide comprising a polypeptide sequence selected from those of the Sequence Listing, SEQ ID NOs:2 to 2N, where N=2–74, or those listed in Table 4, or a complementary nucleotide sequence thereof; (b) a nucleotide sequence encoding a polypeptide comprising a variant of a polypeptide of (a) having one or more, or between 1 and about 5, or between 1 and about 10, or between 1 and about 30, conservative amino acid substitutions; (c) a nucleotide sequence comprising a sequence selected from those of SEQ ID NOs:1 to (2N−1), where N=2–74, or those included in Table 4, or a complementary nucleotide sequence thereof; (d) a nucleotide sequence comprising silent substitutions in a nucleotide sequence of (c); (e) a nucleotide sequence which hybridizes under stringent conditions over substantially the entire length of a nucleotide sequence of one or more of: (a), (b), (c), or (d); (f) a nucleotide sequence comprising at least 10 or 15, or at least about 20, or at least about 30 consecutive nucleotides of a sequence of any of (a)–(e), or at least 10 or 15, or at least about 20, or at least about 30 consecutive nucleotides outside of a region encoding a conserved domain of any of (a)–(e); (g) a nucleotide sequence comprising a subsequence or fragment of any of (a)–(f), which subsequence or fragment encodes a polypeptide having a biological activity that modifies a plant's characteristic, functions as a transcription factor, or alters the level of transcription of a gene or transgene in a cell; (h) a nucleotide sequence having at least 31% sequence identity to a nucleotide sequence of any of (a)–(g); (i) a nucleotide sequence having at least 60%, or at least 70%, or at least 80%, or at least 90%, or at least 95% sequence identity to a nucleotide sequence of any of (a)–(g) or a 10 or 15 nucleotide, or at least about 20, or at least about 30 nucleotide region of a sequence of (a)–(g) that is outside of a region encoding a conserved domain; (j) a nucleotide sequence that encodes a polypeptide having at least 31% sequence identity to a polypeptide listed in Table 4, or the Sequence Listing; (k) a nucleotide sequence which encodes a polypeptide having at least 60%, or at least 70%, or at least 80%, or at least 90%, or at least 95% sequence identity to a polypeptide listed in Table 4, or the Sequence Listing; and (l) a nucleotide sequence that encodes a conserved domain of a polypeptide having at least 85%, or at least 90%, or at least 95%, or at least 98% sequence identity to a conserved domain of a polypeptide listed in Table 4, or the Sequence Listing. The recombinant polynucleotide may further comprise a constitutive, inducible, or tissue-specific promoter operably linked to the nucleotide sequence. The invention also relates to compositions comprising at least two of the above-described polynucleotides.

In a second aspect, the invention comprises an isolated or recombinant polypeptide comprising a subsequence of at least about 10, or at least about 15, or at least about 20, or at least about 30 contiguous amino acids encoded by the recombinant or isolated polynucleotide described above, or comprising a subsequence of at least about 8, or at least about 12, or at least about 15, or at least about 20, or at least about 30 contiguous amino acids outside a conserved domain.

In a third aspect, the invention comprises an isolated or recombinant polynucleotide that encodes a polypeptide that is a paralog of the isolated polypeptide described in paragraph 6 above.

In one aspect, the invention is an paralog which, when expressed in *Arabidopsis*, modifies a trait of the *Arabidopsis* plant.

In a fourth aspect, the invention comprises an isolated or recombinant polynucleotide that encodes a polypeptide that is an ortholog of the isolated polypeptide described in paragraph 6 above. In one aspect, the invention is an ortholog which, when expressed in *Arabidopsis*, modifies a trait of the *Arabidopsis* plant.

In a fifth aspect, the invention comprises an isolated polypeptide that is a paralog of the isolated polypeptide described in paragraph 6 above. In one aspect, the invention is an paralog which, when expressed in *Arabidopsis*, modifies a trait of the *Arabidopsis* plant.

In a sixth aspect, the invention comprises an isolated polypeptide that is an ortholog of the isolated polypeptide described in paragraph 6 above. In one aspect, the invention is an ortholog which, when expressed in *Arabidopsis*, modifies a trait of the *Arabidopsis* plant.

The present invention also encompasses transcription factor variants. A preferred transcription factor variant is one having at least 40% amino acid sequence identity, a more preferred transcription factor variant is one having at least 50% amino acid sequence identity and a most preferred transcription factor variant is one having at least 65% amino acid sequence identity to the transcription factor amino acid sequence SEQ ID NOs:2 to 2N, where N=2–74, and which contains at least one functional or structural characteristic of the transcription factor amino acid sequence. Sequences having lesser degrees of identity but comparable biological activity are considered to be equivalents.

In another aspect, the invention is a transgenic plant comprising one or more of the above-described isolated or recombinant polynucleotides. In yet another aspect, the invention is a plant with altered expression levels of a polynucleotide described above or a plant with altered expression or activity levels of an above-described polypeptide. Further, the invention is a plant lacking a nucleotide sequence encoding a polypeptide described above or substantially lacking a polypeptide described above. The plant may be any plant, including, but not limited to, *Arabidopsis*, mustard, soybean, wheat, corn, potato, cotton, rice, oilseed rape, sunflower, alfalfa, sugarcane, turf, banana, blackberry, blueberry, strawberry, raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, watermelon, rosaceous fruits, vegetable brassicas, and mint or other labiates. In yet another aspect, the inventions is an isolated plant material of a plant, including, but not limited to, plant tissue, fruit, seed, plant cell, embryo, protoplast, pollen, and the like. In yet another aspect, the invention is a transgenic plant tissue culture of regenerable cells, including, but not limited to, embryos, meristematic cells microspores, protoplast, pollen, and the like.

In a further aspect the invention provides a method of using the polynucleotide composition to breed progeny from a parent plant including crossing plants, producing seeds from transgenic plants, and methods of breeding using transgenic plants.

In a further aspect, the invention provides a progeny plant derived from a parental plant wherein said progeny plant exhibits at least three fold greater messenger RNA levels than said parental plant, wherein the messenger RNA encodes a DNA-binding protein which is capable of binding to a DNA regulatory sequence and inducing expression of a plant trait gene, wherein the progeny plant is characterized by a change in the plant trait compared to said parental plant. In yet a further aspect, the progeny plant exhibits at least ten fold greater messenger RNA levels compared to said parental plant. In yet a further aspect, the progeny plant exhibits at least fifty fold greater messenger RNA levels compared to said parental plant.

In a further aspect, the invention relates to a cloning or expression vector comprising the isolated or recombinant polynucleotide described above or cells comprising the cloning or expression vector.

In yet a further aspect, the invention relates to a composition produced by incubating a polynucleotide of the invention with a nuclease, a restriction enzyme, a polymerase; a polymerase and a primer; a cloning vector, or with a cell.

Furthermore, the invention relates to a method for producing a plant having a modified trait. The method comprises altering the expression of an isolated or recombinant polynucleotide of the invention or altering the expression or activity of a polypeptide of the invention in a plant to produce a modified plant, and selecting the modified plant for a modified trait. In one aspect, the plant is a monocot plant. In another aspect, the plant is a dicot plant. In another aspect the recombinant polynucleotide is from a dicot plant and the plant is a monocot plant. In yet another aspect the recombinant polynucleotide is from a monocot plant and the plant is a dicot plant. In yet another aspect the recombinant polynucleotide is from a monocot plant and the plant is a monocot plant. In yet another aspect the recombinant polynucleotide is from a dicot plant and the plant is a dicot plant.

In another aspect, the invention is a transgenic plant comprising an isolated or recombinant polynucleotide encoding a polypeptide wherein the polypeptide is selected from the group consisting of SEQ ID NOs:2–2N where N=2–74. In yet another aspect, the invention is a plant with altered expression levels of a polypeptide described above or a plant with altered expression or activity levels of an above-described polypeptide. Further, the invention is a plant lacking a polynucleotide sequence encoding a polypeptide described above or substantially lacking a polypeptide described above. The plant may be any plant, including, but not limited to, *Arabidopsis*, mustard, soybean, wheat, corn, potato, cotton, rice, oilseed rape, sunflower, alfalfa, sugarcane, turf, banana, blackberry, blueberry, strawberry, raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, watermelon, rosaceous fruits, vegetable brassicas, and mint or other labiates. In yet another aspect, the inventions is an isolated plant material of a plant, including, but not limited to, plant tissue, fruit, seed, plant cell, embryo, protoplast, pollen, and the like. In yet another aspect, the invention is a transgenic plant tissue culture of regenerable cells, including, but not limited to, embryos, meristematic cells, microspores, protoplast, pollen, and the like.

In another aspect, the invention relates to a method of identifying a factor that is modulated by or interacts with a polypeptide encoded by a polynucleotide of the invention. The method comprises expressing a polypeptide encoded by the polynucleotide in a plant; and identifying at least one factor that is modulated by or interacts with the polypeptide. In one embodiment the method for identifying modulating or interacting factors is by detecting binding by the polypeptide to a promoter sequence, or by detecting interactions between an additional protein and the polypeptide in a yeast two hybrid system, or by detecting expression of a factor by hybridization to a microarray, subtractive hybridization, or differential display.

In yet another aspect, the invention is a method of identifying a molecule that modulates activity or expression of a polynucleotide or polypeptide of interest. The method comprises placing the molecule in contact with a plant comprising the polynucleotide or polypeptide encoded by the polynucleotide of the invention and monitoring one or more of the expression level of the polynucleotide in the plant, the expression level of the polypeptide in the plant, and modulation of an activity of the polypeptide in the plant.

In yet another aspect, the invention relates to an integrated system, computer or computer readable medium comprising one or more character strings corresponding to a polynucleotide of the invention, or to a polypeptide encoded by the polynucleotide. The integrated system, computer or computer readable medium may comprise a link between one or more sequence strings to a modified plant trait.

In yet another aspect, the invention is a method for identifying a sequence similar or homologous to one or more polynucleotides of the invention, or one or more polypeptides encoded by the polynucleotides. The method comprises providing a sequence database, and querying the sequence database with one or more target sequences corresponding to the one or more polynucleotides or to the one or more polypeptides to identify one or more sequence members of the database that display sequence similarity or homology to one or more of the one or more target sequences.

The method may further comprise of linking the one or more of the polynucleotides of the invention, or encoded polypeptides, to a modified plant phenotype.

BRIEF DESCRIPTION OF THE SEQUENCE LISTING, TABLES, AND FIGURE

The Sequence Listing provides exemplary polynucleotide and polypeptide sequences of the invention. The traits associated with the use of the sequences are included in the Examples.

CD-ROM1 (Copy 1) is a read-only memory computer-readable compact disc and contains a copy of the Sequence Listing in ASCII text format. The Sequence Listing is named "SeqList_0036-3 US.txt", file creation date Aug. 9, 2002, and is 525 kilobytes in size. The copy of the Sequence Listing on the CD-ROM disc is hereby incorporated by reference in their entirety.

CD-ROM2 (Copy 2) is an exact copy of CD-R1 (Copy 1).

CD-ROM3 contains a CRF copy of the Sequence Listing as a text (.txt) file. The CRF copy of the Sequence Listing is named "SeqList_0036-3US.txt", is 525 kilobytes in size and was created on Aug. 9, 2002.

Table 4 shows the polynucleotides and polypeptides identified by SEQ ID NO; Mendel Gene ID No.; conserved domain of the polypeptide; and if the polynucleotide was tested in a transgenic assay. The first column shows the polynucleotide SEQ ID NO; the second column shows the Mendel Gene ID No., GID; the third column shows the trait(s) resulting from the knock out or overexpression of the polynucleotide in the transgenic plant; the fourth column shows the category of the trait; the fifth column shows the transcription factor family to which the polynucleotide belongs; the sixth column ("Comment"), includes specific effects and utilities conferred by the polynucleotide of the first column; the seventh column shows the SEQ ID NO of the polypeptide encoded by the polynucleotide; and the eighth column shows the amino acid residue positions of the conserved domain in amino acid (AA) co-ordinates.

Table 5 lists a summary of orthologous and homologous sequences identified using BLAST (tblastx program). The first column shows the polynucleotide sequence identifier (SEQ ID NO), the second column shows the corresponding cDNA identifier (Gene ID), the third column shows the orthologous or homologous polynucleotide GenBank Accession Number (Test Sequence ID), the fourth column shows the calculated probability value that the sequence identity is due to chance (Smallest Sum Probability), the fifth column shows the plant species from which the test sequence was isolated (Test Sequence Species), and the sixth column shows the orthologous or homologous test sequence GenBank annotation (Test Sequence GenBank Annotation).

FIG. 1 shows a phylogenic tree of related plant families adapted from Daly et al. (2001 *Plant Physiology* 127: 1328–1333).

DETAILED DESCRIPTION OF EXEMPLARY EMBODIMENTS

In an important aspect, the present invention relates to polynucleotides and polypeptides, e.g. for modifying phenotypes of plants. Throughout this disclosure, various information sources are referred to and/or are specifically incorporated. The information sources include scientific journal articles, patent documents, textbooks, and World Wide Web browser-inactive page addresses, for example. While the reference to these information sources clearly indicates that they can be used by one of skill in the art, applicants specifically incorporate each and every one of the information sources cited herein, in their entirety, whether or not a specific mention of "incorporation by reference" is noted. The contents and teachings of each and every one of the information sources can be relied on and used to make and use embodiments of the invention.

It must be noted that as used herein and in the appended claims, the singular forms "a," "an," and "the" include plural reference unless the context clearly dictates otherwise. Thus, for example, a reference to "a plant" includes a plurality of such plants, and a reference to "a stress" is a reference to one or more stresses and equivalents thereof known to those skilled in the art, and so forth.

The polynucleotide sequences of the invention encode polypeptides that are members of well-known transcription factor families, including plant transcription factor families, as disclosed in Table 4. Generally, the transcription factors encoded by the present sequences are involved in cell differentiation and proliferation and the regulation of growth. Accordingly, one skilled in the art would recognize that by expressing the present sequences in a plant, one may change the expression of autologous genes or induce the expression of introduced genes. By affecting the expression of similar autologous sequences in a plant that have the biological activity of the present sequences, or by introducing the present sequences into a plant, one may alter a plant's phenotype to one with improved traits. The sequences of the invention may also be used to transform a plant and introduce desirable traits not found in the wild-type cultivar or strain. Plants may then be selected for those that produce the most desirable degree of over- or underexpression of target genes of interest and coincident trait improvement.

The sequences of the present invention may be from any species, particularly plant species, in a naturally occurring form or from any source whether natural, synthetic, semisynthetic or recombinant. The sequences of the invention may also include fragments of the present amino acid sequences. In this context, a "fragment" refers to a fragment of a polypeptide sequence which is at least 5 to about 15 amino acids in length, most preferably at least 14 amino acids, and which retain some biological activity of a transcription factor. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

As one of ordinary skill in the art recognizes, transcription factors can be identified by the presence of a region or domain of structural similarity or identity to a specific consensus sequence or the presence of a specific consensus DNA-binding site or DNA-binding site motif (see, for example, Riechmann et al., (2000) *Science* 290: 2105–2110). The plant transcription factors may belong to one of the following transcription factor families: the AP2 (APETALA2) domain transcription factor family (Riechmann and Meyerowitz (1998) *Biol. Chem.* 379:633–646); the MYB transcription factor family (Martin and Paz-Ares, (1997) *Trends Genet.* 13:67–73); the MADS domain transcription factor family (Riechmann and Meyerowitz (1997) *Biol. Chem.* 378:1079–1101); the WRKY protein family (Ishiguro and Nakamura (1994) *Mol. Gen. Genet.* 244: 563–571); the ankyrin-repeat protein family (Zhang et al. (1992) *Plant Cell* 4:1575–1588); the zinc finger protein (Z) family (Klug and Schwabe (1995) *FASEB J.* 9: 597–604); the homeobox (HB) protein family (Buerglin in *Guidebook to the Homeobox Genes,* Duboule (ed.) (1994) Oxford University Press); the CAAT-element binding proteins (Forsburg and Guarente (1989) *Genes Dev.* 3:1166–1178); the squamosa promoter binding proteins (SPB) (Klein et al. (1996) *Mol. Gen. Genet.* 1996 250:7–16); the NAM protein family (Souer et al. (1996) *Cell* 85:159–170); the IAA/AUX proteins (Rouse et al. (1998) *Science* 279:1371–1373); the HLH/MYC protein family (Littlewood et al. (1994) *Prot. Profile* 1:639–709); the DNA-binding protein (DBP) family (Tucker et al. (1994) *EMBO J.* 13:2994–3002); the bZIP family of transcription factors (Foster et al. (1994)*FASEB J.* 8:192–200); the Box P-binding protein (the BPF-1) family (da Costa e Silva et al. (1993) *Plant J.* 4:125–135); the high mobility group (HMG) family (Bustin and Reeves (1996) *Prog. Nucl. Acids Res. Mol. Biol.* 54:35–100); the scarecrow (SCR) family (Di Laurenzio et al. (1996) *Cell* 86:423–433); the GF14 family (Wu et al. (1997) *Plant Physiol.* 114: 1421–1431); the polycomb (PCOMB) family (Kennison (1995) *Annu. Rev. Genet.* 29:289–303); the teosinte branched (TEO) family (Luo et al. (1996) *Nature* 383: 794–799; the ABI3 family (Giraudat et al. (1992) *Plant Cell* 4:1251–1261); the triple helix (TH) family (Dehesh et al. (1990) *Science* 250:1397–1399); the EIL family (Chao et al. (1997) *Cell* 89:1133–44); the AT-HOOK family (Reeves and Nissen (1990) *J. Biol. Chem.* 265:8573–8582); the S1FA family (Zhou et al. (1995) *Nucleic Acids Res.* 23:1165–1169); the bZIPT2 family (Lu and Ferl (1995) *Plant Physiol.* 109:723); the YABBY family (Bowman et al. (1999) *Development* 126:2387–96); the PAZ family (Bohmert et al. (1998) *EMBO J.* 17:170–80); a family of miscellaneous (MISC) transcription factors including the DPBF family (Kim et al. (1997) *Plant J.* 11:1237–1251) and the SPF1 family (Ishiguro and Nakamura (1994) *Mol. Gen. Genet.* 244:563–571); the golden (GLD) family (Hall et al. (1998) *Plant Cell* 10:925–936), the TUBBY family (Boggin et al, (1999) *Science* 286:2119–2125), the heat shock family (Wu C (1995) *Annu Rev Cell Dev Biol* 11:441–469), the ENBP family (Christiansen et al (1996) *Plant Mol Biol* 32:809–821), the RING-zinc family (Jensen et al. (1998) *FEBS letters* 436:283–287), the PDBP family (Janik et al *Virology.* (1989) 168:320–329), the PCF family (Cubas P, et al. *Plant J.* (1999) 18:215–22), the SRS (SHI-related) family (Fridborg et al *Plant Cell* (1999) 11:1019–1032), the CPP (cysteine-rich polycomb-like) family (Cvitanich et al *Proc. Natl. Acad. Sci. U S A.* (2000) 97:8163–8168), the ARF (auxin response factor) family (Ulmasov, et al. (1999) *Proc. Natl. Acad. Sci.* USA 96: 5844–5849), the SWI/SNF family (Collingwood et al *J. Mol. End.* 23:255–275), the ACBF family (Seguin et al (1997) *Plant Mol. Biol.* 35:281–291), PCGL (CG-1 like) family (da Costa e Silva et al. (1994) *Plant Mol. Biol.* 25:921–924) the ARID family (Vazquez et al. (1999) *Development.* 126: 733–42), the Jumonji family, Balciunas et al (2000*, Trends Biochem Sci.* 25: 274–276), the bZIP-NIN family (Schauser et al (1999) *Nature* 402: 191–195), the E2F family Kaelin et al (1992) *Cell* 70: 351–364) and the GRF-like family (Knaap et al (2000) *Plant Physiol.* 122: 695–704). As indicated by any part of the list above and as known in the art, transcription factors have been sometimes categorized by class, family, and sub-family according to their structural content and consensus DNA-binding site motif, for example. Many of the classes and many of the families and sub-families are listed here. However, the inclusion of one sub-family and not another, or the inclusion of one family and not another, does not mean that the invention does not encompass polynucleotides or polypeptides of a certain family or sub-family. The list provided here is merely an example of the types of transcription factors and the knowledge available concerning the consensus sequences and consensus DNA-binding site motifs that help define them as known to those of skill in the art (each of the references noted above are specifically incorporated herein by reference). A transcription factor may include, but is not limited to, any polypeptide that can activate or repress transcription of a single gene or a number of genes. This polypeptide group includes, but is not limited to, DNA-binding proteins, DNA-binding protein binding proteins, protein kinases, protein phosphatases, GTP-binding proteins, and receptors, and the like.

In addition to methods for modifying a plant phenotype by employing one or more polynucleotides and polypeptides of the invention described herein, the polynucleotides and polypeptides of the invention have a variety of additional uses. These uses include their use in the recombinant production (i.e., expression) of proteins; as regulators of plant gene expression, as diagnostic probes for the presence of complementary or partially complementary nucleic acids (including for detection of natural coding nucleic acids); as substrates for further reactions, e.g., mutation reactions, PCR reactions, or the like; as substrates for cloning e.g., including digestion or ligation reactions; and for identifying exogenous or endogenous modulators of the transcription factors. A "polynucleotide" is a nucleic acid sequence comprising a plurality of polymerized nucleotides, e.g., at least about 15 consecutive polymerized nucleotides, optionally at least about 30 consecutive nucleotides, at least about 50 consecutive nucleotides. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single stranded or double stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can comprise a sequence in either sense or antisense orientations.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

An "isolated polynucleotide" is a polynucleotide whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

A "polypeptide" is an amino acid sequence comprising a plurality of consecutive polymerized amino acid residues e.g., at least about 15 consecutive polymerized amino acid residues, optionally at least about 30 consecutive polymerized amino acid residues, at least about 50 consecutive polymerized amino acid residues. In many instances, a polypeptide comprises a polymerized amino acid residue sequence that is a transcription factor or a domain or portion or fragment thereof. Additionally, the polypeptide may comprise a localization domain, 2) an activation domain, 3) a repression domain, 4) an oligomerization domain or 5) a DNA-binding domain, or the like. The polypeptide optionally comprises modified amino acid residues, naturally occurring amino acid residues not encoded by a codon, non-naturally occurring amino acid residues.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild type plant. Alternatively, or additionally, the isolated polypeptide is separated from other cellular components with which it is typically associated, e.g., by any of the various protein purification methods herein.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids, i.e., structurally related, at positions shared by the polypeptide sequences.

"Altered" nucleic acid sequences encoding polypeptide include those sequences with deletions, insertions, or substitutions of different nucleotides, resulting in a polynucleotide encoding a polypeptide with at least one functional characteristic of the polypeptide. Included within this definition are polymorphisms that may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide. The encoded polypeptide protein may also be "altered", and may contain deletions, insertions, or substitutions of amino acid residues that produce a silent change and result in a functionally equivalent polypeptide. Deliberate amino acid substitutions may be made on the basis of similarity in residue side chain chemistry, including, but not limited to, polarity, charge, solubility, hydrophobicity, hydrophilicity, and/or the amphipathic nature of the residues, as long as the biological activity of polypeptide is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine. Alignments between different polypeptide sequences may be used to calculate "percentage sequence similarity".

The term "plant" includes whole plants, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae. (See for example, FIG. 1, adapted from Daly et al. 2001 *Plant Physiology* 127:1328–1333; and see also Tudge, C., *The Variety of Life*, Oxford University Press, New York, 2000, pp. 547–606.)

A "transgenic plant" refers to a plant that contains genetic material not found in a wild type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression cassette typically comprises a polypeptide-encoding sequence operably linked (i.e., under regulatory control of) to appropriate inducible or constitutive regulatory sequences that allow for the expression of polypeptide. The expression cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

"Ectopic expression or altered expression" in reference to a polynucleotide indicates that the pattern of expression in, e.g., a transgenic plant or plant tissue, is different from the expression pattern in a wild type plant or a reference plant of the same species. The pattern of expression may also be compared with a reference expression pattern in a wild type plant of the same species. For example, the polynucleotide or polypeptide is expressed in a cell or tissue type other than a cell or tissue type in which the sequence is expressed in the wild type plant, or by expression at a time other than at the time the sequence is expressed in the wild type plant, or by a response to different inducible agents, such as hormones or environmental signals, or at different expression levels (either higher or lower) compared with those found in a wild type plant. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" further may relate to altered activity levels resulting from the interactions of the polypeptides with exogenous or endogenous modulators or from interactions with factors or as a result of the chemical modification of the polypeptides.

A "fragment" or "domain," with respect to a polypeptide, refers to a subsequence of the polypeptide. In some cases, the fragment or domain, is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions. Fragments can vary in size from as few as 6 amino acids to the full length of the intact polypeptide, but are preferably at least about 30 amino acids in length and more preferably at least about 60 amino acids in length. In reference to a polynucleotide sequence, "a fragment" refers to any subsequence of a polynucleotide, typically, of at least about 15 consecutive nucleotides, preferably at least about 30 nucleotides, more preferably at least about 50 nucleotides, of any of the sequences provided herein.

The invention also encompasses production of DNA sequences that encode transcription factors and transcription factor derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding transcription factors or any fragment thereof.

A "conserved domain", with respect to a polypeptide, refers to a domain within a transcription factor family which exhibits a higher degree of sequence homology, such as at least 65% sequence identity including conservative substitutions, and preferably at least 80% sequence identity, and more preferably at least 85%, or at least about 86%, or at least about 87%, or at least about 88%, or at least about 90%, or at least about 95%, or at least about 98% amino acid residue sequence identity of a polypeptide of consecutive amino acid residues. A fragment or domain can be referred to as outside a consensus sequence or outside a consensus DNA-binding site that is known to exist or that exists for a particular transcription factor class, family, or sub-family. In this case, the fragment or domain will not include the exact amino acids of a consensus sequence or consensus DNA-binding site of a transcription factor class, family or sub-family, or the exact amino acids of a particular transcription factor consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. The conserved domains for each of polypeptides of SEQ ID NOs:2–2N, where N=2–74, are listed in Table 4 as described in Example VII. Also, many of the polypeptides of Table 4 have conserved domains specifically indicated by start and stop sites. A comparison of the regions of the polypeptides in SEQ ID NOs:2–2N, where N=2–74, or of those in Table 4, allows one of skill in the art to identify conserved domain(s) for any of the polypeptides listed or referred to in this disclosure, including those in Table 4.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring uptake of carbon dioxide, or by the observation of the expression level of a gene or genes, e.g., by employing Northern analysis, RT-PCR, microarray gene expression assays, or reporter gene expression systems, or by agricultural observations such as stress tolerance, yield, or pathogen tolerance. Any technique can be used to measure the amount of, comparative level of, or difference in any selected chemical compound or macromolecule in the transgenic plants, however.

"Trait modification" refers to a detectable difference in a characteristic in a plant ectopically expressing a polynucleotide or polypeptide of the present invention relative to a plant not doing so, such as a wild type plant. In some cases, the trait modification can be evaluated quantitatively. For example, the trait modification can entail at least about a 2% increase or decrease in an observed trait (difference), at least a 5% difference, at least about a 10% difference, at least about a 20% difference, at least about a 30%, at least about a 50%, at least about a 70%, or at least about a 100%, or an even greater difference compared with a wild type plant. It is known that there can be a natural variation in the modified trait. Therefore, the trait modification observed entails a change of the normal distribution of the trait in the plants compared with the distribution observed in wild type plant.

I. Traits which May be Modified

Trait modifications of particular interest include those to seed (such as embryo or endosperm), fruit, root, flower, leaf, stem, shoot, seedling or the like, including: enhanced tolerance to environmental conditions including freezing, chilling, heat, drought, water saturation, radiation and ozone; improved tolerance to microbial, fungal or viral diseases; improved tolerance to pest infestations, including nematodes, mollicutes, parasitic higher plants or the like; decreased herbicide sensitivity; improved tolerance of heavy metals or enhanced ability to take up heavy metals; improved growth under poor photoconditions (e.g., low light and/or short day length), or changes in expression levels of genes of interest. Other phenotype that can be modified relate to the production of plant metabolites, such as variations in the production of taxol, tocopherol, tocotrienol, sterols, phytosterols, vitamins, wax monomers, anti-oxidants, amino acids, lignins, cellulose, tannins, prenyllipids (such as chlorophylls and carotenoids), glucosinolates, and terpenoids, enhanced or compositionally altered protein or oil production (especially in seeds), or modified sugar (insoluble or soluble) and/or starch composition. Physical plant characteristics that can be modified include cell development (such as the number of trichomes), fruit and seed size and number, yields of plant parts such as stems, leaves, inflorescences, and roots, the stability of the seeds during storage, characteristics of the seed pod (e.g., susceptibility to shattering), root hair length and quantity, internode distances, or the quality of seed coat. Plant growth characteristics that can be modified include growth rate, germination rate of seeds, vigor of plants and seedlings, leaf and flower senescence, male sterility, apomixis, flowering time, flower abscission, rate of nitrogen uptake, osmotic sensitivity to soluble sugar concentrations, biomass or transpiration characteristics, as well as plant architecture characteristics such as apical dominance, branching patterns, number of organs, organ identity, organ shape or size.

Transcription Factors Modify Expression of Endogenous Genes

Expression of genes which encode transcription factors that modify expression of endogenous genes, polynucleotides, and proteins are well known in the art. In addition, transgenic plants comprising isolated polynucleotides encoding transcription factors may also modify expression of endogenous genes, polynucleotides, and proteins. Examples include Peng et al. (1997, Genes and Development 11:3194–3205) and Peng et al. (1999, Nature, 400: 256–261). In addition, many others have demonstrated that an *Arabidopsis* transcription factor expressed in an exogenous plant species elicits the same or very similar phenotypic response. See, for example, Fu et al. (2001, Plant Cell 13:1791–1802); Nandi et al. (2000, Curr. Biol. 10:215–218); Coupland (1995, Nature 377:482–483); and Weigel and Nilsson (1995, Nature 377:482–500).

In another example, Mandel et al. (1992, Cell 71–133–143) and Suzuki et al. (2001, Plant J. 28:409–418) teach that a transcription factor expressed in another plant species elicits the same or very similar phenotypic response of the endogenous sequence, as often predicted in earlier studies of *Arabidopsis* transcription factors in *Arabidopsis* (see Mandel et al., 1992, supra; Suzuki et al., 2001, supra).

Other examples include Müller et al. (2001, Plant J. 28:169–179); Kim et al. (2001, Plant J. 25:247–259); Kyozuka and Shimamoto (2002, Plant Cell Physiol. 43:130–135); Boss and Thomas (2002, Nature, 416:847–850); He et al. (2000, Transgenic Res., 9:223–227); and Robson et al. (2001, Plant J. 28:619–631).

In yet another example, Gilmour et al. (1998, Plant J. 16:433–442) teach an *Arabidopsis* AP2 transcription factor, CBF1, which, when overexpressed in transgenic plants, increases plant freezing tolerance. Jaglo et al (2001, Plant Physiol. 127:910–017) further identified sequences in *Brassica napus* which encode CBF-like genes and that transcripts for these genes accumulated rapidly in response to low temperature. Transcripts encoding CBF-like proteins were also found to accumulate rapidly in response to low temperature in wheat, as well as in tomato. An alignment of the CBF proteins from *Arabidopsis, B. napus,* wheat, rye, and tomato revealed the presence of conserved amino acid sequences, PKK/RPAGRxKFxETRHP and DSAWR, that bracket the AP2/EREBP DNA binding domains of the proteins and distinguish them from other members of the AP2/EREBP protein family. (See Jaglo et al., supra.)

Polypeptides and Polynucleotides of the Invention

The present invention provides, among other things, transcription factors (TFs), and transcription factor homologue polypeptides, and isolated or recombinant polynucleotides encoding the polypeptides, or novel variant polypeptides or polynucleotides encoding novel variants of transcription factors derived from the specific sequences provided here. These polypeptides and polynucleotides may be employed to modify a plant's characteristic.

Exemplary polynucleotides encoding the polypeptides of the invention were identified in the *Arabidopsis thaliana* GenBank database using publicly available sequence analysis programs and parameters. Sequences initially identified were then further characterized to identify sequences comprising specified sequence strings corresponding to sequence motifs present in families of known transcription factors. In addition, further exemplary polynucleotides encoding the polypeptides of the invention were identified in the plant GenBank database using publicly available sequence analysis programs and parameters. Sequences initially identified were then further characterized to identify sequences comprising specified sequence strings corresponding to sequence motifs present in families of known transcription factors. Polynucleotide sequences meeting such criteria were confirmed as transcription factors.

Additional polynucleotides of the invention were identified by screening *Arabidopsis thaliana* and/or other plant cDNA libraries with probes corresponding to known transcription factors under low stringency hybridization conditions. Additional sequences, including full length coding sequences were subsequently recovered by the rapid amplification of cDNA ends (RACE) procedure, using a commercially available kit according to the manufacturer's instructions. Where necessary, multiple rounds of RACE are performed to isolate 5' and 3' ends. The full length cDNA was then recovered by a routine end-to-end polymerase chain reaction (PCR) using primers specific to the isolated 5' and 3' ends. Exemplary sequences are provided in the Sequence Listing.

The polynucleotides of the invention can be or were ectopically expressed in overexpressor or knockout plants and the changes in the characteristic(s) or trait(s) of the plants observed. Therefore, the polynucleotides and polypeptides can be employed to improve the characteristics of plants.

The polynucleotides of the invention can be or were ectopically expressed in overexpressor plant cells and the changes in the expression levels of a number of genes, polynucleotides, and/or proteins of the plant cells observed. Therefore, the polynucleotides and polypeptides can be employed to change expression levels of a genes, polynucleotides, and/or proteins of plants.

Producing Polypeptides

The polynucleotides of the invention include sequences that encode transcription factors and transcription factor homologue polypeptides and sequences complementary thereto, as well as unique fragments of coding sequence, or sequence complementary thereto. Such polynucleotides can be, e.g., DNA or RNA, e.g., mRNA, cRNA, synthetic RNA, genomic DNA, cDNA synthetic DNA, oligonucleotides, etc. The polynucleotides are either double-stranded or single-stranded, and include either, or both sense (i.e., coding) sequences and antisense (i.e., non-coding, complementary) sequences. The polynucleotides include the coding sequence of a transcription factor, or transcription factor homologue polypeptide, in isolation, in combination with additional coding sequences (e.g., a purification tag, a localization signal, as a fusion-protein, as a pre-protein, or the like), in combination with non-coding sequences (e.g., introns or inteins, regulatory elements such as promoters, enhancers, terminators, and the like), and/or in a vector or host environment in which the polynucleotide encoding a transcription factor or transcription factor homologue polypeptide is an endogenous or exogenous gene.

A variety of methods exist for producing the polynucleotides of the invention. Procedures for identifying and isolating DNA clones are well known to those of skill in the art, and are described in, e.g., Berger and Kimmel, *Guide to Molecular Cloning Techniques, Methods in Enzymology* volume 152 Academic Press, Inc., San Diego, Calif. ("Berger"); Sambrook et al., *Molecular Cloning—A Laboratory Manual* (2nd Ed.), Vol. 1–3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2000) ("Ausubel").

Alternatively, polynucleotides of the invention, can be produced by a variety of in vitro amplification methods adapted to the present invention by appropriate selection of specific or degenerate primers. Examples of protocols sufficient to direct persons of skill through in vitro amplification methods, including the polymerase chain reaction (PCR) the ligase chain reaction (LCR), Qbeta-replicase amplification and other RNA polymerase mediated techniques (e.g., NASBA), e.g., for the production of the homologous nucleic acids of the invention are found in Berger (supra), Sambrook (supra), and Ausubel (supra), as well as Mullis et al., (1987) *PCR Protocols A Guide to Methods and Applications* (Innis et al. eds) Academic Press Inc. San Diego, Calif. (1990) (Innis). Improved methods for cloning in vitro amplified nucleic acids are described in Wallace et al., U.S. Pat. No. 5,426,039. Improved methods for amplifying large nucleic acids by PCR are summarized in Cheng et al. (1994) *Nature* 369: 684–685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

Alternatively, polynucleotides and oligonucleotides of the invention can be assembled from fragments produced by solid-phase synthesis methods. Typically, fragments of up to approximately 100 bases are individually synthesized and then enzymatically or chemically ligated to produce a desired sequence, e.g., a polynucleotide encoding all or part of a transcription factor. For example, chemical synthesis using the phosphoramidite method is described, e.g., by Beaucage et al. (1981) *Tetrahedron Letters* 22:1859–1869; and Matthes et al. (1984) *EMBO J.* 3:801–805. According to such methods, oligonucleotides are synthesized, purified, annealed to their complementary strand, ligated and then optionally cloned into suitable vectors. And if so desired, the polynucleotides and polypeptides of the invention can be custom ordered from any of a number of commercial suppliers.

II. Homologous Sequences

Sequences homologous, i.e., that share significant sequence identity or similarity, to those provided in the Sequence Listing, derived from *Arabidopsis thaliana* or from other plants of choice are also an aspect of the invention. Homologous sequences can be derived from any plant including monocots and dicots and in particular agriculturally important plant species, including but not limited to, crops such as soybean, wheat, corn, potato, cotton, rice, rape, oilseed rape (including canola), sunflower, alfalfa, sugarcane and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, watermelon, rosaceous fruits (such as apple, peach, pear, cherry and plum) and vegetable brassicas (such as broccoli, cabbage, cauliflower, Brussels sprouts, and kohlrabi). Other crops, fruits and vegetables whose phenotype can be changed include barley, rye, millet, sorghum, currant, avocado, citrus fruits such as oranges, lemons, grapefruit and tangerines, artichoke, cherries, nuts such as the walnut and peanut, endive, leek, roots, such as arrowroot, beet, cassava, turnip, radish, yam, and sweet potato, and beans. The homologous sequences may also be derived from woody species, such pine, poplar and eucalyptus, or mint or other labiates.

Orthologs and Paralogs

Several different methods are known by those of skill in the art for identifying and defining these functionally homologous sequences. Three general methods for defining paralogs and orthologs are described; a paralog or ortholog or homolog may be identified by one or more of the methods described below.

Orthologs and paralogs are evolutionarily related genes that have similar sequence and similar functions. Orthologs are structurally related genes in different species that are derived from a speciation event. Paralogs are structurally related genes within a single species that are derived by a duplication event.

Within a single plant species, gene duplication may cause two copies of a particular gene, giving rise to two or more genes with similar sequence and similar function known as paralogs. A paralog is therefore a similar gene with a similar function within the same species. Paralogs typically cluster together or in the same clade (a group of similar genes) when a gene family phylogeny is analyzed using programs such as CLUSTAL (Thompson et al. (1994) Nucleic Acids Res. 22:4673–4680; Higgins et al. (1996) Methods Enzymol. 266 383–402). Groups of similar genes can also be identified with pair-wise BLAST analysis (Feng and Doolittle (1987) J. Mol. Evol. 25:351–360). For example, a lade of very similar MADS domain transcription factors from *Arabidop-*

*sis* all share a common function in flowering time (Ratcliffe et al. (2001) Plant Physiol. 126:122–132), and a group of very similar AP2 domain transcription factors from *Arabidopsis* are involved in tolerance of plants to freezing (Gilmour et al. (1998) Plant J. 16:433–442). Analysis of groups of similar genes with similar function that fall within one lade can yield sub-sequences that are particular to the lade. These sub-sequences, known as consensus sequences, can not only be used to define the sequences within each lade, but define the functions of these genes; genes within a clade may contain paralogous or orthologous sequences that share the same function. (See also, for example, Mount, D. W. (2001) *Bioinformatics: Sequence and Genome Analysis* Cold Spring Harbor Laboratory Press, Cold Spring Harbor, N.Y. page 543.)

Speciation, the production of new species from a parental species, can also give rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al. (1994) Nucleic Acids Res. 22:4673–4680; Higgins et al. (1996) Methods Enzymol. 266:383–402), potential orthologous sequences can placed into the phylogenetic tree and its relationship to genes from the species of interest can be determined. Once the ortholog pair has been identified, the function of the test ortholog can be determined by determining the function of the reference ortholog.

Transcription factors that are homologous to the listed sequences will typically share at least about 30% amino acid sequence identity, or at least about 30% amino acid sequence identity outside of a known consensus sequence or consensus DNA-binding site. More closely related transcription factors can share at least about 50%, about 60%, about 65%, about 70%, about 75% or about 80% or about 90% or about 95% or about 98% or more sequence identity with the listed sequences, or with the listed sequences but excluding or outside a known consensus sequence or consensus DNA-binding site, or with the listed sequences excluding one or all conserved domain. Factors that are most closely related to the listed sequences share, e.g., at least about 85%, about 90% or about 95% or more % sequence identity to the listed sequences, or to the listed sequences but excluding or outside a known consensus sequence or consensus DNA-binding site or outside one or all conserved domain. At the nucleotide level, the sequences will typically share at least about 40% nucleotide sequence identity, preferably at least about 50%, about 60%, about 70% or about 80% sequence identity, and more preferably about 85%, about 90%, about 95% or about 97% or more sequence identity to one or more of the listed sequences, or to a listed sequence but excluding or outside a known consensus sequence or consensus DNA-binding site, or outside one or all conserved domain. The degeneracy of the genetic code enables major variations in the nucleotide sequence of a polynucleotide while maintaining the amino acid sequence of the encoded protein. Conserved domains within a transcription factor family may exhibit a higher degree of sequence homology, such as at least 65% sequence identity including conservative substitutions, and preferably at least 80% sequence identity, and more preferably at least 85%, or at least about 86%, or at least about 87%, or at least about 88%, or at least about 90%, or at least about 95%, or at least about 98% sequence identity. Transcription factors that are homologous to the listed sequences should share at least 30%, or at least about 60%, or at least about 75%, or at least about 80%, or at least about 90%, or at least about 95% amino acid sequence identity over the entire length of the polypeptide or the homolog. In addition, transcription factors that are homologous to the listed sequences should share at least 30%, or at least about 60%, or at least about 75%, or at least about 80%, or at least about 90%, or at least about 95% amino acid sequence similarity over the entire length of the polypeptide or the homolog.

Percent identity can be determined electronically, e.g., by using the MEGALIGN program (DNASTAR, Inc. Madison, Wis.). The MEGALIGN program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. Other alignment algorithms or programs may be used, including FASTA, BLAST, or ENTREZ, FASTA and BLAST. These are available as a part of the GCG sequence analysis package (University of Wisconsin, Madison, Wis.), and can be used with or without default settings. ENTREZ is available through the National Center for Biotechnology Information. In one embodiment, the percent identity of two sequences can be determined by the GCG program with a gap weight of 1, e.g., each amino acid gap is weighted as if it were a single amino acid or nucleotide mismatch between the two sequences (see U.S. Pat. No. 6,262,333).

Other techniques for alignment are described in Methods in Enzymology, vol. 266: Computer Methods for Macromolecular Sequence Analysis (1996), ed. Doolittle, Academic Press, Inc., San Diego, Calif., USA. Preferably, an alignment program that permits gaps in the sequence is utilized to align the sequences. The Smith-Waterman is one type of algorithm that permits gaps in sequence alignments. See Methods Mol. Biol. 70: 173–187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The percentage similarity between two polypeptide sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between polynucleotide sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions (see US Patent Application No. 20010010913).

Thus, the invention provides methods for identifying a sequence similar or paralogous or orthologous or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an inter or intra net) and a query is made against the sequence database using the relevant sequences herein and associated plant phenotypes or gene functions.

In addition, one or more polynucleotide sequences or one or more polypeptides encoded by the polynucleotide sequences may be used to search against a BLOCKS (Bairoch et al. (1997) Nucleic Acids Res. 25:217–221), PFAM, and other databases which contain previously identified and annotated motifs, sequences and gene functions. Methods that search for primary sequence patterns with secondary structure gap penalties (Smith et al. (1992) Protein Engineering 5:35–51) as well as algorithms such as Basic Local Alignment Search Tool (BLAST; Altschul, S. F. (1993) J. Mol. Evol. 36:290–300; Altschul et al. (1990) supra), BLOCKS (Henikoff, S. and Henikoff, G. J. (1991) Nucleic Acids Research 19:6565–6572), Hidden Markov Models (HMM; Eddy, S. R. (1996) Cur. Opin. Str. Biol. 6:361–365; Sonnhammer et al. (1997) Proteins 28:405–420), and the like, can be used to manipulate and analyze polynucleotide and polypeptide sequences encoded by polynucleotides. These databases, algorithms and other methods are well known in the art and are described in Ausubel et al. (1997; Short Protocols in Molecular Biology, John Wiley & Sons, New York N.Y., unit 7.7) and in Meyers, R. A. (1995; Molecular Biology and Biotechnology, Wiley VCH, New York N.Y., p 856–853).

Furthermore, methods using manual alignment of sequences similar or homologous to one or more polynucleotide sequences or one or more polypeptides encoded by the polynucleotide sequences may be used to identify regions of similarity and conserved domains. Such manual methods are well-known of those of skill in the art and can include, for example, comparisons of tertiary structure between a polypeptide sequence encoded by a polynucleotide which comprises a known function with a polypeptide sequence encoded by a polynucleotide sequence which has a function not yet determined. Such examples of tertiary structure may comprise predicted alpha helices, beta-sheets, amphipathic helices, leucine zipper motifs, zinc finger motifs, proline-rich regions, cysteine repeat motifs, and the like.

VI. Identifying Polynucleotides or Nucleic Acids by Hybridization

Polynucleotides homologous to the sequences illustrated in the Sequence Listing and tables can be identified, e.g., by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in the references cited above. Encompassed by the invention are polynucleotide sequences that are capable of hybridizing to the claimed polynucleotide sequences, and, in particular, to those shown in SEQ ID NOs: 18; 144; 62; 64; 66; 90; 34; 52; 54; 68; 56; 38; and fragments thereof under various conditions of stringency. (See, e.g., Wahl, G. M. and S. L. Berger (1987) Methods Enzymol. 152:399–407; Kimmel, A. R. (1987) Methods Enzymol. 152:507–511.) Estimates of homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

In addition to the nucleotide sequences listed in Table 4, full length cDNA, orthologs, paralogs and homologs of the present nucleotide sequences may be identified and isolated using well known methods. The cDNA libraries orthologs, paralogs and homologs of the present nucleotide sequences may be screened using hybridization methods to determine their utility as hybridization target or amplification probes.

An example of stringent hybridization conditions for hybridization of complementary nucleic acids which have more than 100 complementary residues on a filter in a Southern or northern blot is about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Nucleic acid molecules that hybridize under stringent conditions will typically hybridize to a probe based on either the entire cDNA or selected portions, e.g., to a unique subsequence, of the cDNA under wash conditions of 0.2×SSC to 2.0×SSC, 0.1% SDS at 50–65° C. For example, high stringency is about 0.2×SSC, 0.1% SDS at 65° C. Ultra-high stringency will be the same conditions except the wash temperature is raised about 3 to about 5° C., and ultra-ultra-high stringency will be the same conditions except the wash temperature is raised about 6 to about 9° C. For identification of less closely related homologues washes can be performed at a lower temperature, e.g., 50° C. In general, stringency is increased by raising the wash temperature and/or decreasing the concentration of SSC, as known in the art.

In another example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C, and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C. Another preferred set of highly stringent conditions uses two final washes in 0.1×SSC, 0.1% SDS at 65° C. The most preferred high stringency washes are of at least about 68° C. For example, in a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, the wash steps will occur at 68° C. in 15 mM NaCl, 1.5 mM trisodium citrate, and 0.1% SDS. Additional variations on these conditions will be readily apparent to those skilled in the art (see U.S. Patent Application No. 20010010913).

As another example, stringent conditions can be selected such that an oligonucleotide that is perfectly complementary to the coding oligonucleotide hybridizes to the coding oligonucleotide with at least about a 5–10× higher signal to noise ratio than the ratio for hybridization of the perfectly complementary oligonucleotide to a nucleic acid encoding a transcription factor known as of the filing date of the application. Conditions can be selected such that a higher signal to noise ratio is observed in the particular assay which is used, e.g., about 15×, 25×, 35×, 50× or more. Accordingly, the subject nucleic acid hybridizes to the unique coding oligonucleotide with at least a 2× higher signal to noise ratio as compared to hybridization of the coding oligonucleotide to a nucleic acid encoding known polypeptide. Again, higher signal to noise ratios can be selected, e.g., about 5×, 10×, 25×, 35×, 50× or more. The particular signal will depend on the label used in the relevant assay, e.g., a fluorescent label, a colorimetric label, a radioactive label, or the like.

Alternatively, transcription factor homolog polypeptides can be obtained by screening an expression library using antibodies specific for one or more transcription factors. With the provision herein of the disclosed transcription factor, and transcription factor homologue nucleic acid sequences, the encoded polypeptide(s) can be expressed and purified in a heterologous expression system (e.g., *E. coli*) and used to raise antibodies (monoclonal or polyclonal) specific for the polypeptide(s) in question. Antibodies can also be raised against synthetic peptides derived from transcription factor, or transcription factor homologue, amino acid sequences. Methods of raising antibodies are well known in the art and are described in Harlow and Lane (1988) *Antibodies: A Laboratory Manual,* Cold Spring Harbor Laboratory, New York. Such antibodies can then be used to screen an expression library produced from the plant from which it is desired to clone additional transcription factor homologues, using the methods described above. The selected cDNAs can be confirmed by sequencing and enzymatic activity.

VII. Sequence Variations

It will readily be appreciated by those of skill in the art, that any of a variety of polynucleotide sequences are capable of encoding the transcription factors and transcription factor homologue polypeptides of the invention. Due to the degeneracy of the genetic code, many different polynucleotides can encode identical and/or substantially similar polypeptides in addition to those sequences illustrated in the Sequence Listing. Nucleic acids having a sequence that differs from the sequences shown in the Sequence Listing, or complementary sequences, that encode functionally equivalent peptides (i.e., peptides having some degree of equivalent or similar biological activity) but differ in sequence from the sequence shown in the sequence listing due to degeneracy in the genetic code, are also within the scope of the invention.

Altered polynucleotide sequences encoding polypeptides include those sequences with deletions, insertions, or substitutions of different nucleotides, resulting in a polynucleotide encoding a polypeptide with at least one functional characteristic of the instant polypeptides. Included within this definition are polymorphisms which may or may not be readily detectable using a particular oligonucleotide probe of the polynucleotide encoding the instant polypeptides, and improper or unexpected hybridization to allelic variants, with a locus other than the normal chromosomal locus for the polynucleotide sequence encoding the instant polypeptides.

Allelic variant refers to any of two or more alternative forms of a gene occupying the same chromosomal locus. Allelic variation arises naturally through mutation, and may result in phenotypic polymorphism within populations. Gene mutations can be silent (i.e., no change in the encoded polypeptide) or may encode polypeptides having altered amino acid sequence. The term allelic variant is also used herein to denote a protein encoded by an allelic variant of a gene. Splice variant refers to alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Those skilled in the art would recognize that G2340, SEQ ID NO: 18 represents a single transcription factor; allelic variation and alternative splicing may be expected to occur. Allelic variants of SEQ ID NO: 17 can be cloned by probing cDNA or genomic libraries from different individual organisms according to standard procedures. Allelic variants of the DNA sequence shown in SEQ ID NO: 17, including those containing silent mutations and those in which mutations result in amino acid sequence changes, are within the scope of the present invention, as are proteins which are allelic variants of SEQ ID NO: 18. cDNAs generated from alternatively spliced mRNAs, which retain the properties of the transcription factor are included within the scope of the present invention, as are polypeptides encoded by such cDNAs and mRNAs. Allelic variants and splice variants of these sequences can be cloned by probing cDNA or genomic libraries from different individual organisms or tissues according to standard procedures known in the art (see U.S. Pat. No. 6,388,064).

For example, Table 1 illustrates, e.g., that the codons AGC, AGT, TCA, TCC, TCG, and TCT all encode the same amino acid: serine. Accordingly, at each position in the sequence where there is a codon encoding serine, any of the above trinucleotide sequences can be used without altering the encoded polypeptide.

TABLE 1

| Amino acid | | | Possible Codons |
|---|---|---|---|
| Alanine | Ala | A | GCA GCC GCG GCU |
| Cysteine | Cys | C | TGC TGT |
| Aspartic acid | Asp | D | GAC GAT |
| Glutamic acid | Glu | E | GAA GAG |
| Phenylalanine | Phe | F | TTC TTT |
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGC AGT TCA TCC TCG TCT |
| Threonine | Thr | T | ACA ACC ACG ACT |
| Valine | Val | V | GTA GTC GTG GTT |
| Tryptophan | Trp | W | TGG |
| Tyrosine | Tyr | Y | TAC TAT |

Sequence alterations that do not change the amino acid sequence encoded by the polynucleotide are termed "silent" variations. With the exception of the codons ATG and TGG, encoding methionine and tryptophan, respectively, any of the possible codons for the same amino acid can be substituted by a variety of techniques, e.g., site-directed mutagenesis, available in the art. Accordingly, any and all such variations of a sequence selected from the above table are a feature of the invention.

In addition to silent variations, other conservative variations that alter one, or a few amino acids in the encoded polypeptide, can be made without altering the function of the polypeptide, these conservative variants are, likewise, a feature of the invention.

For example, substitutions, deletions and insertions introduced into the sequences provided in the Sequence Listing are also envisioned by the invention. Such sequence modifications can be engineered into a sequence by site-directed mutagenesis (Wu (ed.) *Meth. Enzymol.* (1993) vol. 217, Academic Press) or the other methods noted below. Amino acid substitutions are typically of single residues; insertions usually will be on the order of about from 1 to 10 amino acid residues; and deletions will range about from 1 to 30 residues. In preferred embodiments, deletions or insertions are made in adjacent pairs, e.g., a deletion of two residues or insertion of two residues. Substitutions, deletions, insertions or any combination thereof can be combined to arrive at a sequence. The mutations that are made in the polynucleotide encoding the transcription factor should not place the sequence out of reading frame and should not create complementary regions that could produce secondary mRNA structure. Preferably, the polypeptide encoded by the DNA performs the desired function.

Conservative substitutions are those in which at least one residue in the amino acid sequence has been removed and a different residue inserted in its place. Such substitutions generally are made in accordance with the Table 2 when it is desired to maintain the activity of the protein. Table 2 shows amino acids which can be substituted for an amino acid in a protein and which are typically regarded as conservative substitutions.

TABLE 2

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Similar substitutions are those in which at least one residue in the amino acid sequence has been removed and a different residue inserted in its place. Such substitutions generally are made in accordance with the Table 3 when it is desired to maintain the activity of the protein. Table 3 shows amino acids which can be substituted for an amino acid in a protein and which are typically regarded as structural and functional substitutions. For example, a residue in column 1 of Table 3 may be substituted with residue in column 2; in addition, a residue in column 2 of Table 3 may be substituted with the residue of column 1.

TABLE 3

| Residue | Similar Substitutions |
|---|---|
| Ala | Ser; Thr; Gly; Val; Leu; Ile |
| Arg | Lys; His; Gly |
| Asn | Gln; His; Gly; Ser; Thr |
| Asp | Glu, Ser; Thr |
| Gln | Asn; Ala |
| Cys | Ser; Gly |
| Glu | Asp |
| Gly | Pro; Arg |
| His | Asn; Gln; Tyr; Phe; Lys; Arg |

TABLE 3-continued

| Residue | Similar Substitutions |
|---|---|
| Ile | Ala; Leu; Val; Gly; Met |
| Leu | Ala; Ile; Val; Gly; Met |
| Lys | Arg; His; Gln; Gly; Pro |
| Met | Leu; Ile; Phe |
| Phe | Met; Leu; Tyr; Trp; His; Val; Ala |
| Ser | Thr; Gly; Asp; Ala; Val; Ile; His |
| Thr | Ser; Val; Ala; Gly |
| Trp | Tyr; Phe; His |
| Tyr | Trp; Phe; His |
| Val | Ala; Ile; Leu; Gly; Thr; Ser; Glu |

Substitutions that are less conservative than those in Table 2 can be selected by picking residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

IV. Further Modifying Sequences of the Invention—Mutation/Forced Evolution

In addition to generating silent or conservative substitutions as noted, above, the present invention optionally includes methods of modifying the sequences of the Sequence Listing. In the methods, nucleic acid or protein modification methods are used to alter the given sequences to produce new sequences and/or to chemically or enzymatically modify given sequences to change the properties of the nucleic acids or proteins.

Thus, in one embodiment, given nucleic acid sequences are modified, e.g., according to standard mutagenesis or artificial evolution methods to produce modified sequences. The modified sequences may be created using purified natural polynucleotides isolated from any organism or may be synthesized from purified compositions and chemicals using chemical means well know to those of skill in the art. For example, Ausubel, supra, provides additional details on mutagenesis methods. Artificial forced evolution methods are described, for example, by Stemmer (1994) *Nature* 370:389–391, Stemmer (1994) *Proc Natl. Acad. Sci. USA* 91:10747–10751, and U.S. Pat. Nos. 5,811,238, 5,837,500, and 6,242,568. Methods for engineering synthetic transcription factors and other polypeptides are described, for example, by Zhang et al. (2000) *J. Biol. Chem.* 275:33850–33860, Liu et al. (2001) *J. Biol. Chem.* 276: 11323–11334, and Isalan et al. (2001) *Nature Biotechnol.* 19:656–660. Many other mutation and evolution methods are also available and expected to be within the skill of the practitioner.

Similarly, chemical or enzymatic alteration of expressed nucleic acids and polypeptides can be performed by standard methods. For example, sequence can be modified by addition of lipids, sugars, peptides, organic or inorganic compounds, by the inclusion of modified nucleotides or amino acids, or the like. For example, protein modification techniques are illustrated in Ausubel, supra. Further details on chemical and enzymatic modifications can be found herein. These modification methods can be used to modify any given sequence, or to modify any sequence produced by the various mutation and artificial evolution modification methods noted herein.

Accordingly, the invention provides for modification of any given nucleic acid by mutation, evolution, chemical or enzymatic modification, or other available methods, as well as for the products produced by practicing such methods, e.g., using the sequences herein as a starting substrate for the various modification approaches.

For example, optimized coding sequence containing codons preferred by a particular prokaryotic or eukaryotic host can be used e.g., to increase the rate of translation or to produce recombinant RNA transcripts having desirable properties, such as a longer half-life, as compared with transcripts produced using a non-optimized sequence. Translation stop codons can also be modified to reflect host preference. For example, preferred stop codons for *Saccharomyces cerevisiae* and mammals are TAA and TGA, respectively. The preferred stop codon for monocotyledonous plants is TGA, whereas insects and *E. coli* prefer to use TAA as the stop codon.

The polynucleotide sequences of the present invention can also be engineered in order to alter a coding sequence for a variety of reasons, including but not limited to, alterations which modify the sequence to facilitate cloning, processing and/or expression of the gene product. For example, alterations are optionally introduced using techniques which are well known in the art, e.g., site-directed mutagenesis, to insert new restriction sites, to alter glycosylation patterns, to change codon preference, to introduce splice sites, etc.

Furthermore, a fragment or domain derived from any of the polypeptides of the invention can be combined with domains derived from other transcription factors or synthetic domains to modify the biological activity of a transcription factor. For instance, a DNA-binding domain derived from a transcription factor of the invention can be combined with the activation domain of another transcription factor or with a synthetic activation domain. A transcription activation domain assists in initiating transcription from a DNA-binding site. Examples include the transcription activation region of VP16 or GAL4 (Moore et al. (1998) *Proc. Natl. Acad. Sci. USA* 95: 376–381; and Aoyama et al. (1995) *Plant Cell* 7:1773–1785), peptides derived from bacterial sequences (Ma and Ptashne (1987) *Cell* 51; 113–119) and synthetic peptides (Giniger and Ptashne, (1987) *Nature* 330:670–672).

V. Expression and Modification of Polypeptides

Typically, polynucleotide sequences of the invention are incorporated into recombinant DNA (or RNA) molecules that direct expression of polypeptides of the invention in appropriate host cells, transgenic plants, in vitro translation systems, or the like. Due to the inherent degeneracy of the genetic code, nucleic acid sequences which encode substantially the same or a functionally equivalent amino acid sequence can be substituted for any listed sequence to provide for cloning and expressing the relevant homologue.

Vectors, Promoters, and Expression Systems

The present invention includes recombinant constructs comprising one or more of the nucleic acid sequences herein. The constructs typically comprise a vector, such as a plasmid, a cosmid, a phage, a virus (e.g., a plant virus), a bacterial artificial chromosome (BAC), a yeast artificial chromosome (YAC), or the like, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

General texts that describe molecular biological techniques useful herein, including the use and production of vectors, promoters and many other relevant topics, include Berger, Sambrook and Ausubel, supra. Any of the identified sequences can be incorporated into a cassette or vector, e.g., for expression in plants. A number of expression vectors suitable for stable transformation of plant cells or for the establishment of transgenic plants have been described including those described in Weissbach and Weissbach, (1989) *Methods for Plant Molecular Biology*, Academic Press, and Gelvin et al., (1990) *Plant Molecular Biology Manual*, Kluwer Academic Publishers. Specific examples include those derived from a Ti plasmid of *Agrobacterium tumefaciens*, as well as those disclosed by Herrera-Estrella et al. (1983) *Nature* 303: 209, Bevan (1984) *Nucl Acid Res.* 12: 8711–8721, Klee (1985) *Bio/Technology* 3: 637–642, for dicotyledonous plants.

Alternatively, non-Ti vectors can be used to transfer the DNA into monocotyledonous plants and cells by using free DNA delivery techniques. Such methods can involve, for example, the use of liposomes, electroporation, microprojectile bombardment, silicon carbide whiskers, and viruses. By using these methods transgenic plants such as wheat, rice (Christou (1991) *Bio/Technology* 9: 957–962) and corn (Gordon-Kamm (1990) *Plant Cell* 2: 603–618) can be produced. An immature embryo can also be a good target tissue for monocots for direct DNA delivery techniques by using the particle gun (Weeks et al. (1993) *Plant Physiol* 102: 1077–1084; Vasil (1993) *Bio/Technology* 10: 667–674; Wan and Lemeaux (1994) *Plant Physiol* 104: 37–48, and for *Agrobacterium*-mediated DNA transfer (Ishida et al. (1996) *Nature Biotech* 14: 745–750).

Typically, plant transformation vectors include one or more cloned plant coding sequence (genomic or cDNA) under the transcriptional control of 5' and 3' regulatory sequences and a dominant selectable marker. Such plant transformation vectors typically also contain a promoter (e.g., a regulatory region controlling inducible or constitutive, environmentally-or developmentally-regulated, or cell- or tissue-specific expression), a transcription initiation start site, an RNA processing signal (such as intron splice sites), a transcription termination site, and/or a polyadenylation signal.

Examples of constitutive plant promoters which can be useful for expressing the TF sequence include: the cauliflower mosaic virus (CaMV) 35S promoter, which confers constitutive, high-level expression in most plant tissues (see, e.g., Odell et al. (1985) *Nature* 313:810–812); the nopaline synthase promoter (An et al. (1988) *Plant Physiol* 88:547–552); and the octopine synthase promoter (Fromm et al. (1989) *Plant Cell* 1: 977–984).

A variety of plant gene promoters that regulate gene expression in response to environmental, hormonal, chemical, developmental signals, and in a tissue-active manner can be used for expression of a TF sequence in plants. Choice of a promoter is based largely on the phenotype of interest and is determined by such factors as tissue (e.g., seed, fruit, root, pollen, vascular tissue, flower, carpel, etc.), inducibility (e.g., in response to wounding, heat, cold, drought, light, pathogens, etc.), timing, developmental stage, and the like. Numerous known promoters have been characterized and can favorably be employed to promote expression of a polynucleotide of the invention in a transgenic plant or cell of interest. For example, tissue specific promoters include: seed-specific promoters (such as the napin, phaseolin or DC3 promoter described in U.S. Pat. No. 5,773,697), fruit-specific promoters that are active during fruit ripening (such as the dru 1 promoter (U.S. Pat. No. 5,783,393), or the 2A11 promoter (U.S. Pat. No. 4,943,674) and the tomato polygalacturonase promoter (Bird et al. (1988) *Plant Mol Biol* 11:651), root-specific promoters, such as those disclosed in U.S. Pat. Nos. 5,618,988, 5,837,848 and 5,905,186, pollen-active promoters such as PTA29, PTA26 and PTA13 (U.S. Pat. No. 5,792,929), promoters active in vascular tissue (Ringli and Keller (1998) *Plant Mol Biol* 37:977–988), flower-specific (Kaiser et al, (1995) *Plant Mol Biol* 28:231–243), pollen (Baerson et al. (1994) *Plant Mol Biol* 26:1947–1959), carpels (Ohl et al. (1990) *Plant Cell* 2:837–848), pollen and ovules (Baerson et al. (1993) *Plant Mol Biol* 22:255–267), auxin-inducible promoters (such as that described in van der Kop et al. (1999) *Plant Mol Biol* 39:979–990 or Baumann et al. (1999) *Plant Cell* 11:323–334), cytokinin-inducible promoter (Guevara-Garcia (1998) *Plant Mol Biol* 38:743–753), promoters responsive to gibberellin (Shi et al. (1998) *Plant Mol Biol* 38:1053–1060, Willmott et al. (1998) 38:817–825) and the like. Additional promoters are those that elicit expression in response to heat (Ainley et al. (1993) *Plant Mol Biol* 22: 13–23), light (e.g., the pea rbcS-3A promoter, Kuhlemeier et al. (1989) *Plant Cell* 1:471, and the maize rbcS promoter, Schaffner and Sheen (1991) *Plant Cell* 3: 997); wounding (e.g., wunI, Siebertz et al. (1989) *Plant Cell* 1: 961); pathogens (such as the PR-1 promoter described in Buchel et al. (1999) *Plant Mol. Biol.* 40:387–396, and the PDF1.2 promoter described in Manners et al. (1998) *Plant Mol. Biol.* 38:1071–80), and chemicals such as methyl jasmonate or salicylic acid (Gatz et al. (1997) *Plant Mol Biol* 48: 89–108). In addition, the timing of the expression can be controlled by using promoters such as those acting at senescence (An and Amazon (1995) *Science* 270: 1986–1988); or late seed development (Odell et al. (1994) *Plant Physiol* 106:447–458).

Plant expression vectors can also include RNA processing signals that can be positioned within, upstream or downstream of the coding sequence. In addition, the expression vectors can include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Additional Expression Elements

Specific initiation signals can aid in efficient translation of coding sequences. These signals can include, e.g., the ATG initiation codon and adjacent sequences. In cases where a coding sequence, its initiation codon and upstream sequences are inserted into the appropriate expression vector, no additional translational control signals may be needed. However, in cases where only coding sequence (e.g., a mature protein coding sequence), or a portion thereof, is inserted, exogenous transcriptional control signals including the ATG initiation codon can be separately provided. The initiation codon is provided in the correct reading frame to facilitate transcription. Exogenous transcriptional elements and initiation codons can be of various origins, both natural and synthetic. The efficiency of expression can be enhanced by the inclusion of enhancers appropriate to the cell system in use.

Expression Hosts

The present invention also relates to host cells which are transduced with vectors of the invention, and the production of polypeptides of the invention (including fragments thereof) by recombinant techniques. Host cells are genetically engineered (i.e., nucleic acids are introduced, e.g., transduced, transformed or transfected) with the vectors of this invention, which may be, for example, a cloning vector or an expression vector comprising the relevant nucleic acids herein. The vector is optionally a plasmid, a viral particle, a phage, a naked nucleic acid, etc. The engineered host cells can be cultured in conventional nutrient media modified as appropriate for activating promoters, selecting transformants, or amplifying the relevant gene. The culture conditions, such as temperature, pH and the like, are those previously used with the host cell selected for expression, and will be apparent to those skilled in the art and in the references cited herein, including, Sambrook and Ausubel.

The host cell can be a eukaryotic cell, such as a yeast cell, or a plant cell, or the host cell can be a prokaryotic cell, such as a bacterial cell. Plant protoplasts are also suitable for some applications. For example, the DNA fragments are introduced into plant tissues, cultured plant cells or plant protoplasts by standard methods including electroporation (Fromm et al., (1985) *Proc. Natl. Acad. Sci. USA* 82, 5824, infection by viral vectors such as cauliflower mosaic virus (CaMV) (Hohn et al., (1982) *Molecular Biology of Plant Tumors,* (Academic Press, New York) pp. 549–560; U.S. Pat. No. 4,407,956), high velocity ballistic penetration by small particles with the nucleic acid either within the matrix of small beads or particles, or on the surface (Klein et al., (1987) *Nature* 327, 70–73), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens,* and a portion is stably integrated into the plant genome (Horsch et al. (1984) *Science* 233:496–498; Fraley et al. (1983) *Proc. Natl. Acad. Sci. USA* 80, 4803).

The cell can include a nucleic acid of the invention which encodes a polypeptide, wherein the cells expresses a polypeptide of the invention. The cell can also include vector sequences, or the like. Furthermore, cells and transgenic plants that include any polypeptide or nucleic acid above or throughout this specification, e.g., produced by transduction of a vector of the invention, are an additional feature of the invention.

For long-term, high-yield production of recombinant proteins, stable expression can be used. Host cells transformed with a nucleotide sequence encoding a polypeptide of the invention are optionally cultured under conditions suitable for the expression and recovery of the encoded protein from cell culture. The protein or fragment thereof produced by a recombinant cell may be secreted, membrane-bound, or contained intracellularly, depending on the sequence and/or the vector used. As will be understood by those of skill in the art, expression vectors containing polynucleotides encoding mature proteins of the invention can be designed with signal sequences which direct secretion of the mature polypeptides through a prokaryotic or eukaryotic cell membrane.

Modified Amino Acid Residues

Polypeptides of the invention may contain one or more modified amino acid residues. The presence of modified amino acids may be advantageous in, for example, increasing polypeptide half-life, reducing polypeptide antigenicity or toxicity, increasing polypeptide storage stability, or the like. Amino acid residue(s) are modified, for example, co-translationally or post-translationally during recombinant production or modified by synthetic or chemical means.

Non-limiting examples of a modified amino acid residue include incorporation or other use of acetylated amino acids, glycosylated amino acids, sulfated amino acids, prenylated (e.g., farnesylated, geranylgeranylated) amino acids, PEG modified (e.g., "PEGylated") amino acids, biotinylated amino acids, carboxylated amino acids, phosphorylated amino acids, etc. References adequate to guide one of skill in the modification of amino acid residues are replete throughout the literature.

The modified amino acid residues may prevent or increase affinity of the polypeptide for another molecule, including, but not limited to, polynucleotide, proteins, carbohydrates, lipids and lipid derivatives, and other organic or synthetic compounds.

Identification of Additional Factors

A transcription factor provided by the present invention can also be used to identify additional endogenous or exogenous molecules that can affect a phentoype or trait of interest. On the one hand, such molecules include organic (small or large molecules) and/or inorganic compounds that affect expression of (i.e., regulate) a particular transcription factor. Alternatively, such molecules include endogenous molecules that are acted upon either at a transcriptional level by a transcription factor of the invention to modify a phenotype as desired. For example, the transcription factors can be employed to identify one or more downstream gene with which is subject to a regulatory effect of the transcription factor. In one approach, a transcription factor or transcription factor homologue of the invention is expressed in a host cell, e.g., a transgenic plant cell, tissue or explant, and expression products, either RNA or protein, of likely or random targets are monitored, e.g., by hybridization to a microarray of nucleic acid probes corresponding to genes expressed in a tissue or cell type of interest, by two-dimensional gel electrophoresis of protein products, or by any other method known in the art for assessing expression of gene products at the level of RNA or protein. Alternatively, a transcription factor of the invention can be used to identify promoter sequences (i.e., binding sites) involved in the regulation of a downstream target. After identifying a promoter sequence, interactions between the transcription factor and the promoter sequence can be modified by changing specific nucleotides in the promoter sequence or specific amino acids in the transcription factor that interact with the promoter sequence to alter a plant trait. Typically, transcription factor DNA-binding sites are identified by gel shift assays. After identifying the promoter regions, the promoter region sequences can be employed in double-stranded DNA arrays to identify molecules that affect the interactions of the transcription factors with their promoters (Bulyk et al. (1999) *Nature Biotechnology* 17:573–577).

The identified transcription factors are also useful to identify proteins that modify the activity of the transcription factor. Such modification can occur by covalent modification, such as by phosphorylation, or by protein-protein (homo or -heteropolymer) interactions. Any method suitable for detecting protein-protein interactions can be employed. Among the methods that can be employed are co-immunoprecipitation, cross-linking and co-purification through gradients or chromatographic columns, and the two-hybrid yeast system.

The two-hybrid system detects protein interactions in vivo and is described in Chien et al. ((1991), *Proc. Natl. Acad. Sci. USA* 88:9578–9582) and is commercially available from Clontech (Palo Alto, Calif.). In such a system, plasmids are constructed that encode two hybrid proteins: one consists of the DNA-binding domain of a transcription activator protein fused to the TF polypeptide and the other consists of the transcription activator protein's activation domain fused to an unknown protein that is encoded by a cDNA that has been recombined into the plasmid as part of a cDNA library. The DNA-binding domain fusion plasmid and the cDNA library are transformed into a strain of the yeast *Saccharomyces cerevisiae* that contains a reporter gene (e.g., lacZ) whose regulatory region contains the transcription activator's binding site. Either hybrid protein alone cannot activate transcription of the reporter gene. Interaction of the two hybrid proteins reconstitutes the functional activator protein and results in expression of the reporter gene, which is detected by an assay for the reporter gene product. Then, the library plasmids responsible for reporter gene expression are isolated and sequenced to identify the proteins encoded by the library plasmids. After identifying proteins that interact with the transcription factors, assays for compounds that interfere with the TF protein-protein interactions can be preformed.

VI. Identification of Modulators

In addition to the intracellular molecules described above, extracellular molecules that alter activity or expression of a transcription factor, either directly or indirectly, can be identified. For example, the methods can entail first placing a candidate molecule in contact with a plant or plant cell. The molecule can be introduced by topical administration, such as spraying or soaking of a plant, and then the molecule's effect on the expression or activity of the TF polypeptide or the expression of the polynucleotide monitored. Changes in the expression of the TF polypeptide can be monitored by use of polyclonal or monoclonal antibodies, gel electrophoresis or the like. Changes in the expression of the corresponding polynucleotide sequence can be detected by use of microarrays, Northerns, quantitative PCR, or any other technique for monitoring changes in mRNA expression. These techniques are exemplified in Ausubel et al. (eds) *Current Protocols in Molecular Biology*, John Wiley & Sons (1998, and supplements through 2001). Such changes in the expression levels can be correlated with modified plant traits and thus identified molecules can be useful for soaking or spraying on fruit, vegetable and grain crops to modify traits in plants.

Essentially any available composition can be tested for modulatory activity of expression or activity of any nucleic acid or polypeptide herein. Thus, available libraries of compounds such as chemicals, polypeptides, nucleic acids and the like can be tested for modulatory activity. Often, potential modulator compounds can be dissolved in aqueous or organic (e.g., DMSO-based) solutions for easy delivery to the cell or plant of interest in which the activity of the modulator is to be tested. Optionally, the assays are designed to screen large modulator composition libraries by automating the assay steps and providing compounds from any convenient source to assays, which are typically run in parallel (e.g., in microtiter formats on microtiter plates in robotic assays).

In one embodiment, high throughput screening methods involve providing a combinatorial library containing a large number of potential compounds (potential modulator compounds). Such "combinatorial chemical libraries" are then screened in one or more assays, as described herein, to identify those library members (particular chemical species or subclasses) that display a desired characteristic activity. The compounds thus identified can serve as target compounds.

A combinatorial chemical library can be, e.g., a collection of diverse chemical compounds generated by chemical synthesis or biological synthesis. For example, a combinatorial chemical library such as a polypeptide library is formed by combining a set of chemical building blocks (e.g., in one example, amino acids) in every possible way for a given compound length (i.e., the number of amino acids in a polypeptide compound of a set length). Exemplary libraries include peptide libraries, nucleic acid libraries, antibody libraries (see, e.g., Vaughn et al. (1996) *Nature Biotechnology*, 14(3):309–314 and PCT/US96/10287), carbohydrate libraries (see, e.g., Liang et al. *Science* (1996) 274:1520–1522 and U.S. Pat. No. 5,593,853), peptide nucleic acid libraries (see, e.g., U.S. Pat. No. 5,539,083), and small organic molecule libraries (see, e.g., benzodiazepines, Baum *C&EN* January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337) and the like.

Preparation and screening of combinatorial or other libraries is well known to those of skill in the art. Such combinatorial chemical libraries include, but are not limited to, peptide libraries (see, e.g., U.S. Pat. No. 5,010,175; Furka, (1991) *Int. J. Pept. Prot. Res.* 37:487–493; and Houghton et al. (1991) *Nature* 354:84–88). Other chemistries for generating chemical diversity libraries can also be used.

In addition, as noted, compound screening equipment for high-throughput screening is generally available, e.g., using any of a number of well known robotic systems that have also been developed for solution phase chemistries useful in assay systems. These systems include automated workstations including an automated synthesis apparatus and robotic systems utilizing robotic arms. Any of the above devices are suitable for use with the present invention, e.g., for high-throughput screening of potential modulators. The nature and implementation of modifications to these devices (if any) so that they can operate as discussed herein will be apparent to persons skilled in the relevant art.

Indeed, entire high throughput screening systems are commercially available. These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. Similarly, microfluidic implementations of screening are also commercially available.

The manufacturers of such systems provide detailed protocols the various high throughput. Thus, for example, Zymark Corp. provides technical bulletins describing screening systems for detecting the modulation of gene transcription, ligand binding, and the like. The integrated systems herein, in addition to providing for sequence alignment and, optionally, synthesis of relevant nucleic acids, can include such screening apparatus to identify modulators that have an effect on one or more polynucleotides or polypeptides according to the present invention.

In some assays it is desirable to have positive controls to ensure that the components of the assays are working properly. At least two types of positive controls are appropriate. That is, known transcriptional activators or inhibitors can be incubated with cells/plants/etc. in one sample of the assay, and the resulting increase/decrease in transcription can be detected by measuring the resulting increase in RNA/protein expression, etc., according to the methods herein. It will be appreciated that modulators can also be combined with transcriptional activators or inhibitors to find modulators that inhibit transcriptional activation or transcriptional repression. Either expression of the nucleic acids and proteins herein or any additional nucleic acids or proteins activated by the nucleic acids or proteins herein, or both, can be monitored.

In an embodiment, the invention provides a method for identifying compositions that modulate the activity or expression of a polynucleotide or polypeptide of the invention. For example, a test compound, whether a small or large molecule, is placed in contact with a cell, plant (or plant tissue or explant), or composition comprising the polynucleotide or polypeptide of interest and a resulting effect on the cell, plant, (or tissue or explant) or composition is evaluated by monitoring, either directly or indirectly, one or more of expression level of the polynucleotide or polypeptide, activity (or modulation of the activity) of the polynucleotide or polypeptide. In some cases, an alteration in a plant phenotype can be detected following contact of a plant (or plant cell, or tissue or explant) with the putative modulator, e.g., by modulation of expression or activity of a polynucleotide or polypeptide of the invention. Modulation of expression or activity of a polynucleotide or polypeptide of the invention may also be caused by molecular elements in a signal transduction second messenger pathway and such modulation can affect similar elements in the same or another signal transduction second messenger pathway.

Subsequences

Also contemplated are uses of polynucleotides, also referred to herein as oligonucleotides, typically having at least 12 bases, preferably at least 15, more preferably at least 20, 30, or 50 bases, which hybridize under at least highly stringent (or ultra-high stringent or ultra-ultra-high stringent conditions) conditions to a polynucleotide sequence described above. The polynucleotides may be used as probes, primers, sense and antisense agents, and the like, according to methods as noted supra.

Subsequences of the polynucleotides of the invention, including polynucleotide fragments and oligonucleotides are useful as nucleic acid probes and primers. An oligonucleotide suitable for use as a probe or primer is at least about 15 nucleotides in length, more often at least about 18 nucleotides, often at least about 21 nucleotides, frequently at least about 30 nucleotides, or about 40 nucleotides, or more in length. A nucleic acid probe is useful in hybridization protocols, e.g., to identify additional polypeptide homologues of the invention, including protocols for microarray experiments. Primers can be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods. See Sambrook and Ausubel, supra.

In addition, the invention includes an isolated or recombinant polypeptide including a subsequence of at least about 15 contiguous amino acids encoded by the recombinant or isolated polynucleotides of the invention. For example, such polypeptides, or domains or fragments thereof, can be used as immunogens, e.g., to produce antibodies specific for the polypeptide sequence, or as probes for detecting a sequence of interest. A subsequence can range in size from about 15 amino acids in length up to and including the full length of the polypeptide.

To be encompassed by the present invention, an expressed polypeptide which comprises such a polypeptide subsequence performs at least one biological function of the intact polypeptide in substantially the same manner, or to a similar extent, as does the intact polypeptide. For example, a polypeptide fragment can comprise a recognizable structural motif or functional domain such as a DNA binding domain that binds to a specific DNA promoter region, an activation domain or a domain for protein-protein interactions.

Production of Transgenic Plants

Modification of Traits

The polynucleotides of the invention are favorably employed to produce transgenic plants with various traits, or characteristics, that have been modified in a desirable manner, e.g., to improve the seed characteristics of a plant. For example, alteration of expression levels or patterns (e.g., spatial or temporal expression patterns) of one or more of the transcription factors (or transcription factor homologues) of the invention, as compared with the levels of the same protein found in a wild type plant, can be used to modify a plant's traits. An illustrative example of trait modification, improved characteristics, by altering expression levels of a particular transcription factor is described further in the Examples and the Sequence Listing.

*Arabidopsis* as a Model System

*Arabidopsis thaliana* is the object of rapidly growing attention as a model for genetics and metabolism in plants. *Arabidopsis* has a small genome, and well documented studies are available. It is easy to grow in large numbers and mutants defining important genetically controlled mechanisms are either available, or can readily be obtained. Various methods to introduce and express isolated homologous genes are available (see Koncz, et al., eds. *Methods in Arahidopsis Research*. et al. (1992), World Scientific, New Jersey, N.J., in "Preface"). Because of its small size, short life cycle, obligate autogamy and high fertility, *Arabidopsis* is also a choice organism for the isolation of mutants and studies in morphogenetic and development pathways, and control of these pathways by transcription factors (Koncz, supra, p. 72). A number of studies introducing transcription factors into *A. thaliana* have demonstrated the utility of this plant for understanding the mechanisms of gene regulation and trait alteration in plants. See, for example, Koncz, supra, and U.S. Pat. No. 6,417,428).

*Arabidopsis* Genes in Transgenic Plants.

Expression of genes which encode transcription factors modify expression of endogenous genes, polynucleotides, and proteins are well known in the art. In addition, transgenic plants comprising isolated polynucleotides encoding transcription factors may also modify expression of endogenous genes, polynucleotides, and proteins. Examples include Peng et al. (1997, Genes and Development 11:3194–3205) and Peng et al. (1999, Nature, 400:256–261). In addition, many others have demonstrated that an *Arabidopsis* transcription factor expressed in an exogenous plant species elicits the same or very similar phenotypic response. See, for example, Fu et al. (2001, Plant Cell 13:1791–1802); Nandi et al. (2000, Curr. Biol. 10:215–218); Coupland (1995, Nature 377:482–483); and Weigel and Nilsson (1995, Nature 377:482–500).

Homologous Genes Introduced into Transgenic Plants.

Homologous genes that may be derived from any plant, or from any source whether natural, synthetic, semi-synthetic or recombinant, and that share significant sequence identity or similarity to those provided by the present invention, may be introduced into plants, for example, crop plants, to confer desirable or improved traits. Consequently, transgenic plants may be produced that comprise a recombinant expression vector or cassette with a promoter operably linked to one or more sequences homologous to presently disclosed sequences. The promoter may be, for example, a plant or viral promoter.

The invention thus provides for methods for preparing transgenic plants, and for modifying plant traits. These methods include introducing into a plant a recombinant expression vector or cassette comprising a functional promoter operably linked to one or more sequences homologous to presently disclosed sequences. Plants and kits for producing these plants that result from the application of these methods are also encompassed by the present invention.

Traits of Interest

Examples of some of the traits that may be desirable in plants, and that may be provided by transforming the plants with the presently disclosed sequences, are listed in Table 6.

TABLE 6

Genes, traits and utilities that affect plant characteristics

| Trait Category | Traits | Transcription factor genes that impact traits | Utility Gene effect on: |
|---|---|---|---|
| Resistance and tolerance | Salt stress resistance | G22; G196; G226; G303; G312; G325; G353; G482; G545; G801; G867; G884; G922; G926; G1452; G1794; G1820; G1836; G1843; G1863; G2053; G2110; G2140; G2153; G2379; G2701; G2713; G2719; G2789 | Germination rate, survivability, yield; extended growth range |
| | Osmotic stress resistance | G47; G175; G188; G303; G325; G353; G489; G502; G526; G921; G922; G926; G1069; G1089; G1452; G1794; G1930; G2140; G2153; G2379; G2701; G2719; G2789; | Germination rate, survivability, yield |
| | Cold stress resistance; cold germination | G256; G394; G664; G864; G1322; G2130 | Germination, growth, earlier planting |
| | Tolerance to freezing | G303; G325; G353; G720; G912; G913; G1794; G2053; G2140; G2153; G2379; G2701; G2719; G2789 | Survivability, yield, appearance, extended range |
| | Heat stress resistance | G3; G464; G682; G864; G964; G1305; G1645; G2130 G2430 | Germination, growth, later planting |

TABLE 6-continued

Genes, traits and utilities that affect plant characteristics

| Trait Category | Traits | Transcription factor genes that impact traits | Utility Gene effect on: |
|---|---|---|---|
| | Drought, low humidity resistance | G303; G325; G353; G720; G912; G926; G1452; G1794; G1820; G1843; G2053; G2140; G2153; G2379; G2583; G2701; G2719; G2789 | Survivability, yield, extended range |
| | Radiation resistance | G1052 | Survivability, vigor, appearance |
| | Decreased herbicide sensitivity | G343; G2133; G2517 | Resistant to increased herbicide use |
| | Increased herbicide sensitivity | G374; G877; G1519 | Use as a herbicide target |
| | Oxidative stress | G477; G789; G1807; G2133; G2517 | Improved yield, appearance, reduced senescence |
| | Light response | G183; G354; G375; G1062; G1322; G1331; G1488; G1494; G1521; G1786; G1794; G2144; G2555; | Germination, growth, development, flowering time |
| Development, morphology | Overall plant architecture | G24; G27; G31; G33; G47; G147; G156; G160; G182; G187; G195; G196; G211; G221; G237; G280; G342; G352; G357; G358; G360; G362; G364; G365; G367; G373; G377; G396; G431; G447; G479; G546; G546; G551; G578; G580; G596; G615; G617; G620; G625; G638; G658; G716; G725; G727; G730; G740; G770; G858; G865; G869; G872; G904; G910; G912; G920; G939; G963; G977; G979; G987; G988; G993; G1007; G1010; G1014; G1035; G1046; G1049; G1062; G1069; G1070; G1076; G1089; G1093; G1127; G1131; G1145; G1229; G1246; G1304; G1318; G1320; G1330; G1331; G1352; G1354; G1360; G1364; G1379; G1384; G1399; G1415; G1417; G1442; G1453; G1454; G1459; G1460; G1471; G1475; G1477; G1487; G1487; G1492; G1499; G1499; G1531; G1540; G1543; G1543; G1544; G1548; G1584; G1587; G1588; G1589; G1636; G1642; G1747; G1749; G1749; G1751; G1752; G1763; G1766; G1767; G1778; G1789; G1790; G1791; G1793; G1794; G1795; G1800; G1806; G1811; G1835; G1836; G1838; G1839; G1843; G1853; G1855; G1865; G1881; G1882; G1883; | Vascular tissues, lignin content; cell wall content; appearance |

TABLE 6-continued

Genes, traits and utilities that affect plant characteristics

| Trait Category | Traits | Transcription factor genes that impact traits | Utility Gene effect on: |
|---|---|---|---|
| | | G1884; G1891; G1896; G1898; G1902; G1904; G1906; G1913; G1914; G1925; G1929; G1930; G1954; G1958; G1965; G1976; G2057; G2107; G2133; G2134; G2151; G2154; G2157; G2181; G2290; G2299; G2340; G2340; G2346; G2373; G2376; G2424; G2465; G2505; G2509; G2512; G2513; G2519; G2520; G2533; G2534; G2573; G2589; G2687; G2720; G2787; G2789; G2893 | |
| | Size: increased stature | G189; G1073; G1435; G2430 | |
| | Size: reduced stature or dwarfism | G3; G5; G21; G23; G39; G165; G184; G194; G258; G280; G340; G343; G353; G354; G362; G363; G370; G385; G396; G439; G440; G447; G450; G550; G557; G599; G636; G652; G670; G671; G674; G729; G760; G804; G831; G864; G884; G898; G900; G912; G913; G922; G932; G937; G939; G960; G962; G977; G991; G1000; G1008; G1020; G1023; G1053; G1067; G1075; G1137; G1181; G1198; G1228; G1266; G1267; G1275; G1277; G1309; G1311; G1314; G1317; G1322; G1323; G1326; G1332; G1334; G1367; G1381; G1382; G1386; G1421; G1488; G1494; G1537; G1545; G1560; G1586; G1641; G1652; G1655; G1671; G1750; G1756; G1757; G1782; G1786; G1794; G1839; G1845; G1879; G1886; G1888; G1933; G1939; G1943; G1944; G2011; G2094; G2115; G2130; G2132; G2144; G2145; G2147; G2156; G2294; G2313; G2344; G2431; G2510; G2517; G2521; G2893; G2893 | Ornamental; small stature provides wind resistance; creation of dwarf varieties |
| | Fruit size and number | G362 | Biomass, yield, cotton boll fiber density |
| | Flower structure, inflorescence | G47; G259; G353; G354; G671; G732; G988; G1000; G1063; G1140; G1326; G1449; G1543; G1560; G1587; G1645; G1947; G2108; G2143; G2893 | Ornamental horticulture; production of saffron or other edible flowers |
| | Number and development of trichomes | G225; G226; G247; G362; G585; G634; G676; G682; G1014; G1332; G1452; G1795; G2105 | Resistance to pests and desiccation; essential oil production |
| | Seed size, color, and number | G156; G450; G584; G652; G668; G858; G979; G1040; G1062; G1145; G1255; G1494; G1531; G1534; G1594; G2105; G2114; | Yield |
| | Root development, modifications | G9; G1482; G1534; G1794; G1852; G2053; G2136; G2140 | |
| | Modifications to root hairs | G225; G226 | Nutrient, water uptake, pathogen resistance |
| | Apical dominance | G559; G732; G1255; G1275; G1411; G1488; G1635; G2452; G2509 | Ornamental horticulture |
| | Branching patterns | G568; G988; G1548 | Ornamental horticulture, knot reduction, improved windscreen |
| | Leaf shape, color, modifications | G375; G377; G428; G438; G447; G464; G557; G577; G599; G635; G671; G674; G736; G804; G903; G977; G921; G922; G1038; G1063; G1067; G1073; G1075; G1146; G1152; G1198; G1267; G1269; G1452; G1484; G1586; G1594; G1767; G1786; G1792; G1886; G2059; G2094; G2105; G2113; G2117; G2143; G2144; G2431; G2452; G2465; G2587; G2583; G2724; | Appealing shape or shiny leaves for ornamental agriculture, increased biomass or photosynthesis |
| | Silique | G1134 | Ornamental |
| | Stem morphology | G47; G438; G671; G748; G988; G1000 | Ornamental; digestibility |
| | Shoot modifications | G390; G391 | Ornamental stem bifurcations |
| Disease, Pathogen Resistance | Bacterial | G211; G347; G367; G418; G525; G545; G578; G1049 | Yield, appearance, survivability, extended range |
| | Fungal | G19; G28; G28; G28; G147; G188; G207; G211; G237; G248; G278; G347; G367; G371; G378; G409; G477; G545; G545; G558; G569; G578; G591; G594; G616; G789; G805; G812; G865; G869; G872; G881; G896; G940; G1047; G1049; G1064; G1084; G1196; G1255; G1266; G1363; G1514; G1756; G1792; G1792; G1792; G1792; G1880; G1919; G1919; G1927; G1927; G1936; G1936; G1950; G2069; G2130; G2380; G2380; G2555 | Yield, appearance, survivability, extended range |
| Nutrients | Increased tolerance to nitrogen-limited soils | G225; G226; G1792 | |

TABLE 6-continued

Genes, traits and utilities that affect plant characteristics

| Trait Category | Traits | Transcription factor genes that impact traits | Utility Gene effect on: |
|---|---|---|---|
| | Increased tolerance to phosphate-limited soils | G419; G545; G561; G1946 | |
| | Increased tolerance to potassium-limited soils | G561; G911 | |
| Hormonal | Hormone sensitivity | G12; 6546; G926; G760; G913; G926; G1062; G1069; G1095; G1134; G1330; G1452; G1666; G1820; G2140; G2789 | Seed dormancy, drought tolerance; plant form, fruit ripening |
| Seed bio-chemistry | Production of seed prenyl lipids, including tocopherol | G214; G259; G490; G652; G748; G883; G1052; G1328; G1930; G2509; G2520 | Antioxidant activity, vitamin E |
| | Production of seed sterols | G20 | Precursors for human steroid hormones; cholesterol modulators |
| | Production of seed gluco-sinolates | G353; G484; G674; G1272; G1506; G1897; G1946; G2113; G2117; G2155; G2290; G2340 | Defense against insects; putative anticancer activity; undesirable in animal feeds |
| | Modified seed oil content | G162; G162; G180; G192; G241; G265; G286; G291; G427; G509; G519; G561; G567; G590; G818; G849; G892; G961; G974; G1063; G1143; G1190; G1198; G1226; G1229; G1323; G1451; G1471; G1478; G1496; G1526; G1543; G1640; G1644; G1646; G1672; G1677; G1750; G1765; G1777; G1793; G1838; G1902; G1946; G1948; G2059; G2123; G2138; G2139; G2343; G2792; G2830 | Vegetable oil production; increased caloric value for animal feeds; lutein content |
| | Modified seed oil composition | G217; G504; G622; G778; G791; G861; G869; G938; G965; G1417; G2192 | Heat stability, digestibility of seed oils |
| | Modified seed protein content | G162; G226; G241; G371; G427; G509; G567; G597; G732; G849; G865; G892; G963; G988; G1323; G1323; G1419; G1478; G1488; G1634; G1637; G1641; G1644; G1652; G1677; G1777; G1777; G1818; G1820; G1903; G1909; G1946; G1946; G1958; G2059; G2117; G2417; G2509 | Reduced caloric value for humans |
| Leaf biochemistry | Production of flavonoids | G1666* | Ornamental pigment production; pathogen resistance; health benefits |
| | Production of leaf glucosinolates | G264; G353; G484; G652; G674; G681; G1069; G1198; G1322; G1421; G1657; G1794; G1897; G1946; G2115; G2117; G2144; G2155; G2155; G2340; G2512; G2520; G2552 | Defense against insects; putative anticancer activity; undesirable in animal feeds |
| | Production of diterpenes | G229 | Induction of enzymes involved in alkaloid biosynthesis |
| | Production of anthocyanin | G546 | Ornamental pigment |
| | Production of leaf phyto-sterols, inc. stigmastanol, campesterol | G561; G2131; G2424 | Precursors for human steroid hormones; cholesterol modulators |
| | Leaf fatty acid composition | G214; G377; G861; G962; G975; G987; G1266; G1337; G1399; G1465; G1512; G2136; G2147; G2192 | Nutritional value; increase in waxes for disease resistance |
| | Production of leaf prenyl lipids, including tocopherol | G214; G259; G280; G652; G987; G1543; G2509; G2520 | Antioxidant activity, vitamin E |
| Bio-chemistry, general | Production of miscellaneous secondary metabolites | G229; G663 | |
| | Sugar, starch, hemicellulose composition, | G158; G211; G211; G237; G242; G274; G598; G1012; G1266; G1309; G1309; G1641; G1765; G1865; G2094; G2094; G2589; G2589 | Food digestibility, hemicellulose & pectin content; fiber content; plant tensile strength, wood quality, pathogen resistance, pulp production; tuber starch content |
| Sugar sensing | Plant response to sugars | G26; G38; G43; G207; G218; G241; G254; G263; G308; G536; G567; G567; G680; G867; G912; G956; G996; G1068; G1225; G1314; G1314; G1337; G1759; G1804; G2153; G2379 | Photosynthetic rate, carbohydrate accumulation, biomass production, source-sink relationships, senescence |
| Growth, Re-production | Plant growth rate and development | G447; G617; G674; G730; G917; G937; G1035; G1046; G1131; G1425; G1452; G1459; G1492; G1589; G1652; G1879; G1943; G2430; G2431; G2465; G2521 | Faster growth, increased biomass or yield, improved appearance; delay in bolting |
| | Embryo development | G167 | |
| | Seed germination rate | G979; G1792; G2130 | Yield |
| | Plant, seedling vigor | G561; G2346 | Survivability, yield |
| | Senescence; cell death | G571; G636; G878; G1050; G1463; G1749; G1944; G2130; G2155; G2340; G2383 | Yield, appearance; response to pathogens; |

TABLE 6-continued

Genes, traits and utilities that affect plant characteristics

| Trait Category | Traits | Transcription factor genes that impact traits | Utility Gene effect on: |
|---|---|---|---|
| | Modified fertility | G39; G340; G439; G470; G559; G615; G652; G671; G779; G962; G977; G988; G1000; G1063; G1067; G1075; G1266; G1311; G1321; G1326; G1367; G1386; G1421; G1453; G1471; G1453; G1560; G1594; G1635; G1750; G1947; G2011; G2094; G2113; G2115; G2130; G2143; G2147; G2294; G2510; G2893 | Prevents or minimizes escape of the pollen of GMOs |
| | Early flowering | G147; G157; G180; G183; G183; G184; G185; G208; G227; G294; G390; G390; G390; G391; G391; G427; G427; G490; G565; G590; G592; G720; G789; G865; G898; G898; G989; G989; G1037; G1037; G1142; G1225; G1225; G1226; G1242; G1305; G1305; G1380; G1380; G1480; G1480; G1488; G1494; G1545; G1545; G1649; G1706; G1760; G1767; G1767; G1820; G1841; G1841; G1842; G1843; G1843; G1946; G1946; G2010; G2030; G2030; G2144; G2144; G2295; G2295; G2347; G2348; G2348; G2373; G2373; G2509; G2509; G2555; G2555 | Faster generation time; synchrony of flowering; potential for introducing new traits to single variety |
| | Delayed flowering | G8; G47; G192; G214; G234; G361; G362; G562; G568; G571; G591; G680; G736; G748; G859; G878; G910; G912; G913; G971; G994; G1051; G1052; G1073; G1079; G1335; G1435; G1452; G1478; G1789; G1804; G1865; G1865; G1895; G1900; G2007; G2133; G2155; G2291; G2465 | Delayed time to pollen production of GMO plants; synchrony of flowering; increased yield |
| | Extended flowering phase | G1947 | |
| | Flower and leaf development | G259; G353; G377; G580; G638 G652; G858; G869; G917; G922; G932; G1063; G1075; G1140; G1425; G1452; G1499; G1548; G1645; G1865; G1897; G1933; G2094; G2124; G2140; G2143; G2535; G2557 | Ornamental applications; decreased fertility |
| | Flower abscission | G1897 | Ornamental: longer retention of flowers |

When co-expressed with G669 and G663

Significance of Modified Plant Traits

Currently, the existence of a series of maturity groups for different latitudes represents a major barrier to the introduction of new valuable traits. Any trait (e.g. disease resistance) has to be bred into each of the different maturity groups separately, a laborious and costly exercise. The availability of single strain, which could be grown at any latitude, would therefore greatly increase the potential for introducing new traits to crop species such as soybean and cotton.

For many of the traits, listed in Table 6 and below, that may be conferred to plants, a single transcription factor gene may be used to increase or decrease, advance or delay, or improve or prove deleterious to a given trait. For example, overexpression of a transcription factor gene that naturally occurs in a plant may cause early flowering relative to non-transformed or wild-type plants. By knocking out the gene, or suppressing the gene (with, for example, antisense suppression) the plant may experience delayed flowering. Similarly, overexpressing or suppressing one or more genes can impart significant differences in production of plant products, such as different fatty acid ratios. Thus, suppressing a gene that causes a plant to be more sensitive to cold may improve a plant's tolerance of cold.

Salt stress resistance. Soil salinity is one of the more important variables that determines where a plant may thrive. Salinity is especially important for the successful cultivation of crop plants, particular in many parts of the world that have naturally high soil salt concentrations, or where the soil has been over-utilized. Thus, presently disclosed transcription factor genes that provide increased salt tolerance during germination, the seedling stage, and throughout a plant's life cycle would find particular value for imparting survivability and yield in areas where a particular crop would not normally prosper.

Osmotic stress resistance. Presently disclosed transcription factor genes that confer resistance to osmotic stress may increase germination rate under adverse conditions, which could impact survivability and yield of seeds and plants.

Cold stress resistance. The potential utility of presently disclosed transcription factor genes that increase tolerance to cold is to confer better germination and growth in cold conditions. The germination of many crops is very sensitive to cold temperatures. Genes that would allow germination and seedling vigor in the cold would have highly significant utility in allowing seeds to be planted earlier in the season with a high rate of survivability. Transcription factor genes that confer better survivability in cooler climates allow a grower to move up planting time in the spring and extend the growing season further into autumn for higher crop yields.

Tolerance to freezing. The presently disclosed transcription factor genes that impart tolerance to freezing conditions are useful for enhancing the survivability and appearance of plants conditions or conditions that would otherwise cause extensive cellular damage. Thus, germination of seeds and survival may take place at temperatures significantly below that of the mean temperature required for germination of seeds and survival of non-transformed plants. As with salt tolerance, this has the added benefit of increasing the potential range of a crop plant into regions in which it would otherwise succumb. Cold tolerant transformed plants may also be planted earlier in the spring or later in autumn, with greater success than with non-transformed plants.

Heat stress tolerance. The germination of many crops is also sensitive to high temperatures. Presently disclosed transcription factor genes that provide increased heat tolerance are generally useful in producing plants that germilnate and grow in hot conditions, may find particular use for crops that are planted late in the season, or extend the range of a plant by allowing growth in relatively hot climates.

Drought, low humidity tolerance. Strategies that allow plants to survive in low water conditions may include, for example, reduced surface area or surface oil or wax production. A number of presently disclosed transcription factor genes increase a plant's tolerance to low water conditions and provide the benefits of improved survivability, increased yield and an extended geographic and temporal planting range.

Radiation resistance. Presently disclosed transcription factor genes have been shown to increase lutein production. Lutein, like other xanthophylls such as zeaxanthin and violaxanthin, are important in the protection of plants against the damaging effects of excessive light. Lutein contributes, directly or indirectly, to the rapid rise of non-photochemical quenching in plants exposed to high light. Increased tolerance of field plants to visible and ultraviolet light impacts survivability and vigor, particularly for recent transplants. Also affected are the yield and appearance of harvested plants or plant parts. Crop plants engineered with presently disclosed transcription factor genes that cause the plant to produce higher levels of lutein therefore would have improved photoprotection, leading to less oxidative damage and increase vigor, survivability and higher yields under high light and ultraviolet light conditions.

Decreased herbicide sensitivity. Presently disclosed transcription factor genes that confer resistance or tolerance to herbicides (e.g., glyphosate) may find use in providing means to increase herbicide applications without detriment to desirable plants. This would allow for the increased use of a particular herbicide in a local environment, with the effect of increased detriment to undesirable species and less harm to transgenic, desirable cultivars.

Increased herbicide sensitivity. Knockouts of a number of the presently disclosed transcription factor genes have been shown to be lethal to developing embryos. Thus, these genes are potentially useful as herbicide targets.

Oxidative stress. In plants, as in all living things, abiotic and biotic stresses induce the formation of oxygen radicals, including superoxide and peroxide radicals. This has the effect of accelerating senescence, particularly in leaves, with the resulting loss of yield and adverse effect on appearance. Generally, plants that have the highest level of defense mechanisms, such as, for example, polyunsaturated moieties of membrane lipids, are most likely to thrive under conditions that introduce oxidative stress (e.g., high light, ozone, water deficit, particularly in combination). Introduction of the presently disclosed transcription factor genes that increase the level of oxidative stress defense mechanisms would provide beneficial effects on the yield and appearance of plants. One specific oxidizing agent, ozone, has been shown to cause significant foliar injury, which impacts yield and appearance of crop and ornamental plants. In addition to reduced foliar injury that would be found in ozone resistant plant created by transforming plants with some of the presently disclosed transcription factor genes, the latter have also been shown to have increased chlorophyll fluorescence (Yu-Sen Chang et al. Bot. Bull. Acad. Sin. (2001) 42: 265–272).

Heavy metal tolerance. Heavy metals such as lead, mercury, arsenic, chromium and others may have a significant adverse impact on plant respiration. Plants that have been transformed with presently disclosed transcription factor genes that confer improved resistance to heavy metals, through, for example, sequestering or reduced uptake of the metals will show improved vigor and yield in soils with relatively high concentrations of these elements. Conversely, transgenic transcription factors may also be introduced into plants to confer an increase in heavy metal uptake, which may benefit efforts to clean up contaminated soils.

Light response. Presently disclosed transcription factor genes that modify a plant's response to light may be useful for modifying a plant's growth or development, for example, photomorphogenesis in poor light, or accelerating flowering time in response to various light intensities, quality or duration to which a non-transformed plant would not similarly respond. Examples of such responses that have been demonstrated include leaf number and arrangement, and early flower bud appearances.

Overall plant architecture. Several presently disclosed transcription factor genes have been introduced into plants to alter numerous aspects of the plant's morphology. For example, it has been demonstrated that a number of transcription factors may be used to manipulate branching, such as the means to modify lateral branching, a possible application in the forestry industry. Transgenic plants have also been produced that have altered cell wall content, lignin production, flower organ number, or overall shape of the plants. Presently disclosed transcription factor genes transformed into plants may be used to affect plant morphology by increasing or decreasing internode distance, both of which may be advantageous under different circumstances. For example, for fast growth of woody plants to provide more biomass, or fewer knots, increased internode distances are generally desirable. For improved wind screening of shrubs or trees, or harvesting characteristics of, for example, members of the Gramineae family, decreased internode distance may be advantageous. These modifications would also prove useful in the ornamental horticulture industry for the creation of unique phenotypic characteristics of ornamental plants.

Increased stature. For some ornamental plants, the ability to provide larger varieties may be highly desirable. For many plants, including t fruit-bearing trees or trees and shrubs that serve as view or wind screens, increased stature provides obvious benefits. Crop species may also produce higher yields on larger cultivars.

Reduced stature or dwarfism. Presently disclosed transcription factor genes that decrease plant stature can be used to produce plants that are more resistant to damage by wind and rain, or more resistant to heat or low humidity or water deficit. Dwarf plants are also of significant interest to the ornamental horticulture industry, and particularly for home garden applications for which space availability may be limited.

Fruit size and number. Introduction of presently disclosed transcription factor genes that affect fruit size will have desirable impacts on fruit size and number, which may comprise increases in yield for fruit crops, or reduced fruit yield, such as when vegetative growth is preferred (e.g., with bushy ornamentals, or where fruit is undesirable, as with ornamental olive trees).

Flower structure, inflorescence, and development. Presently disclosed transgenic transcription factors have been used to create plants with larger flowers or arrangements of flowers that are distinct from wild-type or non-transformed cultivars. This would likely have the most value for the ornamental horticulture industry, where larger flowers or interesting presentations generally are preferred and command the highest prices. Flower structure may have advantageous effects on fertility, and could be used, for example, to decrease fertility by the absence, reduction or screening of reproductive components. One interesting application for manipulation of flower structure, for example, by introduced transcription factors could be in the increased production of edible flowers or flower parts, including saffron, which is derived from the stigmas of *Crocus salivus*.

Number and development of trichomes. Several presently disclosed transcription factor genes have been used to modify trichome number and amount of trichome products in plants. Trichome glands on the surface of many higher plants produce and secrete exudates that give protection from the elements and pests such as insects, microbes and herbivores. These exudates may physically immobilize insects and spores, may be insecticidal or ant-microbial or they may act as allergens or irritants to protect against herbivores. Trichomes have also been suggested to decrease transpiration by decreasing leaf surface air flow, and by exuding chemicals that protect the leaf from the sun.

Seed size, color and number. The introduction of presently disclosed transcription factor genes into plants that alter the size or number of seeds may have a significant impact on yield, both when the product is the seed itself, or when biomass of the vegetative portion of the plant is increased by reducing seed production. In the case of fruit products, it is often advantageous to modify a plant to have reduced size or number of seeds relative to non-transformed plants to provide seedless or varieties with reduced numbers or smaller seeds. Presently disclosed transcription factor genes have also been shown to affect seed size, including the development of larger seeds. Seed size, in addition to seed coat integrity, thickness and permeability, seed water content and by a number of other components including antioxidants and oligosaccharides, may affect seed longevity in storage. This would be an important utility when the seed of a plant is the harvested crops, as with, for example, peas, beans, nuts, etc. Presently disclosed transcription factor genes have also been used to modify seed color, which could provide added appeal to a seed product.

Root development, modifications. By modifying the structure or development of roots by transforming into a plant one or more of the presently disclosed transcription factor genes, plants may be produced that have the capacity to thrive in otherwise unproductive soils. For example, grape roots that extend further into rocky soils, or that remain viable in waterlogged soils, would increase the effective planting range of the crop. It may be advantageous to manipulate a plant to produce short roots, as when a soil in which the plant will be growing is occasionally flooded, or when pathogenic fungi or disease-causing nematodes are prevalent.

Modifications to root hairs. Presently disclosed transcription factor genes that increase root hair length or number potentially could be used to increase root growth or vigor, which might in turn allow better plant growth under adverse conditions such as limited nutrient or water availability.

Apical dominance. The modified expression of presently disclosed transcription factors that control apical dominance could be used in ornamental horticulture, for example, to modify plant architecture.

Branching patterns. Several presently disclosed transcription factor genes have been used to manipulate branching, which could provide benefits in the forestry industry. For example, reduction in the formation of lateral branches could reduce knot formation. Conversely, increasing the number of lateral branches could provide utility when a plant is used as a windscreen, or may also provide ornamental advantages.

Leaf shape, color and modifications. It has been demonstrated in laboratory experiments that overexpression of some of the presently disclosed transcription factors produced marked effects on leaf development. At early stages of growth, these transgenic seedlings developed narrow, upward pointing leaves with long petioles, possibly indicating a disruption in circadian-clock controlled processes or nyctinastic movements. Other transcription factor genes can be used to increase plant biomass; large size would be useful in crops where the vegetative portion of the plant is the marketable portion.

Siliques. Genes that later silique conformation in brassicates may be used to modify fruit ripening processes in brassicates and other plants, which may positively affect seed or fruit quality.

Stem morphology and shoot modifications. Laboratory studies have demonstrated that introducing several of the presently disclosed transcription factor genes into plants can cause stem bifurcations in shoots, in which the shoot meristems split to form two or three separate shoots. This unique appearance would be desirable in ornamental applications.

Diseases, pathogens and pests. A number of the presently disclosed transcription factor genes have been shown to or are likely to confer resistance to various plant diseases, pathogens and pests. The offending organisms include fungal pathogens *Fusarium oxysporum, Botrytis cinerea, Sclerotinia sclerotiorum,* and *Erysiphe orontii*. Bacterial pathogens to which resistance may be conferred include *Pseudomonas syringae*. Other problem organisms may potentially include nematodes, mollicutes, parasites, or herbivorous arthropods. In each case, one or more transformed transcription factor genes may provide some benefit to the plant to help prevent or overcome infestation. The mechanisms by which the transcription factors work could include increasing surface waxes or oils, surface thickness, local senescence, or the activation of signal transduction pathways that regulate plant defense in response to attacks by herbivorous pests (including, for example, protease inhibitors).

Increased tolerance of plants to nutrient-limited soils. Presently disclosed transcription factor genes introduced into plants may provide the means to improve uptake of essential nutrients, including nitrogenous compounds, phosphates, potassium, and trace minerals. The effect of these modifications is to increase the seedling germination and range of ornamental and crop plants. The utilities of presently disclosed transcription factor genes conferring tolerance to conditions of low nutrients also include cost savings to the grower by reducing the amounts of fertilizer needed, environmental benefits of reduced fertilizer runoff; and improved yield and stress tolerance. In addition, this gene could be used to alter seed protein amounts and/or composition that could impact yield as well as the nutritional value and production of various food products.

Hormone sensitivity. One or more of the presently disclosed transcription factor genes have been shown to affect plant abscisic acid (ABA) sensitivity. This plant hormone is likely the most important hormone in mediating the adaptation of a plant to stress. For example, ABA mediates conversion of apical meristems into dormant buds. In response to increasingly cold conditions, the newly developing leaves growing above the meristem become converted into stiff bud scales that closely wrap the meristem and protect it from mechanical damage during winter. ABA in the bud also enforces dormancy; during premature warm spells, the buds are inhibited from sprouting. Bud dormancy is eliminated after either a prolonged cold period of cold or a significant number of lengthening days. Thus, by affecting ABA sensitivity, introduced transcription factor genes may affect cold sensitivity and survivability. ABA is also important in protecting plants from drought tolerance.

Several other of the present transcription factor genes have been used to manipulate ethylene signal transduction and response pathways. These genes can thus be used to manipulate the processes influenced by ethylene, such as seed germination or fruit ripening, and to improve seed or fruit quality.

Production of seed and leaf prenyl lipids, including tocopherol. Prenyl lipids play a role in anchoring proteins in membranes or membranous organelles. Thus, modifying the prenyl lipid content of seeds and leaves could affect membrane integrity and function. A number of presently disclosed transcription factor genes have been shown to modify the tocopherol composition of plants. Tocopherols have both anti-oxidant and vitamin E activity.

Production of seed and leaf phytosterols: Presently disclosed transcription factor genes that modify levels of phytosterols in plants may have at least two utilities. First, phytosterols are an important source of precursors for the manufacture of human steroid hormones. Thus, regulation of transcription factor expression or activity could lead to elevated levels of important human steroid precursors for steroid semi-synthesis. For example, transcription factors that cause elevated levels of campesterol in leaves, or sitosterols and stigmasterols in seed crops, would be useful for this purpose. Phytosterols and their hydrogenated derivatives phytostanols also have proven cholesterol-lowering properties, and transcription factor genes that modify the expression of these compounds in plants would thus provide health benefits.

Production of seed and leaf glucosinolates. Some glucosinolates have anti-cancer activity; thus, increasing the levels or composition of these compounds by introducing several of the presently disclosed transcription factors might be of interest from a nutraceutical standpoint. (3) Glucosinolates form part of a plants natural defense against insects. Modification of glucosinolate composition or quantity could therefore afford increased protection from predators. Furthermore, in edible crops, tissue specific promoters might be used to ensure that these compounds accumulate specifically in tissues, such as the epidermis, which are not taken for consumption.

Modified seed oil content. The composition of seeds, particularly with respect to seed oil amounts and/or composition, is very important for the nutritional value and production of various food and feed products. Several of the presently disclosed transcription factor genes in seed lipid saturation that alter seed oil content could be used to improve the heat stability of oils or to improve the nutritional quality of seed oil, by, for example, reducing the number of calories in seed, increasing the number of calories in animal feeds, or altering the ratio of saturated to unsaturated lipids comprising the oils.

Seed and leaf fatty acid composition. A number of the presently disclosed transcription factor genes have been shown to alter the fatty acid composition in plants, and seeds in particular. This modification may find particular value for improving the nutritional value of, for example, seeds or whole plants. Dietary fatty acids ratios have been shown to have an effect on, for example, bone integrity and remodeling (see, for example, Weiler, H. A., *Pediatr Res* (2000) 47:5 692–697). The ratio of dietary fatty acids may alter the precursor pools of long-chain polyunsaturated fatty acids that serve as precursors for prostaglandin synthesis. In mammalian connective tissue, prostaglandins serve as important signals regulating the balance between resorption and formation in bone and cartilage. Thus dietary fatty acid ratios altered in seeds may affect the etiology and outcome of bone loss.

Modified seed protein content. As with seed oils, the composition of seeds, particularly with respect to protein amounts and/or composition, is very important for the nutritional value and production of various food and feed products. A number of the presently disclosed transcription factor genes modify the protein concentrations in seeds would provide nutritional benefits, and may be used to prolong storage, increase seed pest or disease resistance, or modify germination rates.

Production of flavonoids in leaves and other plant parts. Expression of presently disclosed transcription factor genes that increase flavonoid production in plants, including anthocyanins and condensed tannins, may be used to alter in pigment production for horticultural purposes, and possibly increasing stress resistance. Flavonoids have antimicrobial activity and could be used to engineer pathogen resistance. Several flavonoid compounds have health promoting effects such as the inhibition of tumor growth and cancer, prevention of bone loss and the prevention of the oxidation of lipids. Increasing levels of condensed tannins, whose biosynthetic pathway is shared with anthocyanin biosynthesis, in forage legumes is an important agronomic trait because they prevent pasture bloat by collapsing protein foams within the rumen. For a review on the utilities of flavonoids and their derivatives, refer to Dixon et al. (1999) Trends Plant Sci. 4:394–400.

Production of diterpenes in leaves and other plant parts. Depending on the plant species, varying amounts of diverse secondary biochemicals (often lipophilic terpenes) are produced and exuded or volatilized by trichomes. These exotic secondary biochemicals, which are relatively easy to extract because they are on the surface of the leaf, have been widely used in such products as flavors and aromas, drugs, pesticides and cosmetics. Thus, the overexpression of genes that are used to produce diterpenes in plants may be accomplished by introducing transcription factor genes that induce said overexpression. One class of secondary metabolites, the diterpenes, can effect several biological systems such as tumor progression, prostaglandin synthesis and tissue inflammation. In addition, diterpenes can act as insect pheromones, termite allomones, and can exhibit neurotoxic, cytotoxic and antimitotic activities. As a result of this functional diversity, diterpenes have been the target of research several pharmaceutical ventures. In most cases where the metabolic pathways are impossible to engineer, increasing trichome density or size on leaves may be the only way to increase plant productivity.

Production of anthocyanin in leaves and other plant parts. Several presently disclosed transcription factor genes can be used to alter anthocyanin production in numerous plant species. The potential utilities of these genes include alterations in pigment production for horticultural purposes, and possibly increasing stress resistance in combination with another transcription factor.

Production of miscellaneous secondary metabolites. Microarray data suggests that flux through the aromatic amino acid biosynthetic pathways and primary and secondary metabolite biosynthetic pathways are up-regulated. Presently disclosed transcription factors have been shown to be involved in regulating alkaloid biosynthesis, in part by up-regulating the enzymes indole-3-glycerol phosphatase and strictosidine synthase. Phenylalanine ammonia lyase, chalcone synthase and trans-cinnamate mono-oxygenase are also induced, and are involved in phenylpropenoid biosynthesis.

Sugar, starch, hemicellulose composition. Overexpression of the presently disclosed transcription factors that affect sugar content resulted in plants with altered leaf insoluble sugar content. Transcription factors that alter plant cell wall composition have several potential applications including altering food digestibility, plant tensile strength, wood quality, pathogen resistance and in pulp production. The potential utilities of a gene involved in glucose-specific sugar sensing are to alter energy balance, photosynthetic rate, carbohydrate accumulation, biomass production, source-sink relationships, and senescence.

Hemicellulose is not desirable in paper pulps because of its lack of strength compared with cellulose. Thus modulating the amounts of cellulose vs. hemicellulose in the plant cell wall is desirable for the paper/lumber industry. Increasing the insoluble carbohydrate content in various fruits, vegetables, and other edible consumer products will result in enhanced fiber content. Increased fiber content would not only provide health benefits in food products, but might also increase digestibility of forage crops. In addition, the hemicellulose and pectin content of fruits and berries affects the quality of jam and catsup made from them. Changes in hemicellulose and pectin content could result in a superior consumer product.

Plant response to sugars and sugar composition. In addition to their important role as an energy source and structural component of the plant cell, sugars are central regulatory molecules that control several aspects of plant physiology, metabolism and development. It is thought that this control is achieved by regulating gene expression and, in higher plants, sugars have been shown to repress or activate plant genes involved in many essential processes such as photosynthesis, glyoxylate metabolism, respiration, starch and sucrose synthesis and degradation, pathogen response, wounding response, cell cycle regulation, pigmentation, flowering and senescence. The mechanisms by which sugars control gene expression are not understood.

Because sugars are important signaling molecules, the ability to control either the concentration of a signaling sugar or how the plant perceives or responds to a signaling sugar could be used to control plant development, physiology or metabolism. For example, the flux of sucrose (a disaccharide sugar used for systemically transporting carbon and energy in most plants) has been shown to affect gene expression and alter storage compound accumulation in seeds. Manipulation of the sucrose signaling pathway in seeds may therefore cause seeds to have more protein, oil or carbohydrate, depending on the type of manipulation. Similarly, in tubers, sucrose is converted to starch which is used as an energy store. It is thought that sugar signaling pathways may partially determine the levels of starch synthesized in the tubers. The manipulation of sugar signaling in tubers could lead to tubers with a higher starch content.

Thus, the presently disclosed transcription factor genes that manipulate the sugar signal transduction pathway may lead to altered gene expression to produce plants with desirable traits. In particular, manipulation of sugar signal transduction pathways could be used to alter source-sink relationships in seeds, tubers, roots and other storage organs leading to increase in yield.

Plant growth rate and development. A number of the presently disclosed transcription factor genes have been shown to have significant effects on plant growth rate and development. These observations have included, for example, more rapid or delayed growth and development of reproductive organs. This would provide utility for regions with short or long growing seasons, respectively. Accelerating plant growth would also improve early yield or increase biomass at an earlier stage, when such is desirable (for example, in producing forestry products).

Embryo development. Presently disclosed transcription factor genes that alter embryo development has been used to alter seed protein and oil amounts and/or composition which is very important for the nutritional value and production of various food products. Seed shape and seed coat may also be altered by these genes, which may provide for improved storage stability.

Seed germination rate. A number of the presently disclosed transcription factor genes have been shown to modify seed germination rate, including when the seeds are in conditions normally unfavorable for germination (e.g., cold, heat or salt stress, or in the presence of ABA), and may thus be used to modify and improve germination rates under adverse conditions.

Plant, seedling vigor. Seedlings transformed with presently disclosed transcription factors have been shown to possess larger cotyledons and appeared somewhat more advanced than control plants. This indicates that the seedlings developed more rapidly that the control plants. Rapid seedling development is likely to reduce loss due to diseases particularly prevalent at the seedling stage (e.g., damping off) and is thus important for survivability of plants germinating in the field or in controlled environments.

Senescence, cell death. Presently disclosed transcription factor genes may be used to alter senescence responses in plants. Although leaf senescence is thought to be an evolutionary adaptation to recycle nutrients, the ability to control senescence in an agricultural setting has significant value. For example, a delay in leaf senescence in some maize hybrids is associated with a significant increase in yields and a delay of a few days in the senescence of soybean plants can have a large impact on yield. Delayed flower senescence may also generate plants that retain their blossoms longer and this may be of potential interest to the ornamental horticulture industry.

Modified fertility. Plants that overexpress a number of the presently disclosed transcription factor genes have been shown to possess reduced fertility. This could be a desirable trait, as it could be exploited to prevent or minimize the escape of the pollen of genetically modified organisms (GMOs) into the environment.

Early and delayed flowering. Presently disclosed transcription factor genes that accelerate flowering could have valuable applications in such programs since they allow much faster generation times. In a number of species, for example, broccoli, cauliflower, where the reproductive parts of the plants constitute the crop and the vegetative tissues are discarded, it would be advantageous to accelerate time to flowering. Accelerating flowering could shorten crop and tree breeding programs. Additionally, in some instances, a faster generation time might allow additional harvests of a crop to be made within a given growing season. A number of *Arabidopsis* genes have already been shown to accelerate flowering when constitutively expressed. These include LEAFY, APETALA1 and CONSTANS (Mandel, M. et al., 1995, Nature 377, 522–524; Weigel, D. and Nilsson, O., 1995, Nature 377, 495–500; Simon et al., 1996, Nature 384, 59–62).

By regulating the expression of potential flowering using inducible promoters, flowering could be triggered by application of an inducer chemical. This would allow flowering to be synchronized across a crop and facilitate more efficient harvesting. Such inducible systems could also be used to tune the flowering of crop varieties to different latitudes. At present, species such as soybean and cotton are available as a series of maturity groups that are suitable for different latitudes on the basis of their flowering time (which is governed by day-length). A system in which flowering could be chemically controlled would allow a single high-yielding northern maturity group to be grown at any latitude. In southern regions such plants could be grown for longer, thereby increasing yields, before flowering was induced. In more northern areas, the induction would be used to ensure that the crop flowers prior to the first winter frosts.

In a sizeable number of species, for example, root crops, where the vegetative parts of the plants constitute the crop and the reproductive tissues are discarded, it would be advantageous to delay or prevent flowering. Extending vegetative development with presently disclosed transcription factor genes could thus bring about large increases in yields. Prevention of flowering might help maximize vegetative yields and prevent escape of genetically modified organism (GMO) pollen.

Extended flowering phase. Presently disclosed transcription factors that extend flowering time have utility in engineering plants with longer-lasting flowers for the horticulture industry, and for extending the time in which the plant is fertile.

Flower and leaf development. Presently disclosed transcription factor genes have been used to modify the development of flowers and leaves. This could be advantageous in the development of new ornamental cultivars that present unique configurations. In addition, some of these genes have been shown to reduce a plant's fertility, which is also useful for helping to prevent development of pollen of GMOs.

Flower abscission. Presently disclosed transcription factor genes introduced into plants have been used to retain flowers for longer periods. This would provide a significant benefit to the ornamental industry, for both cut flowers and woody plant varieties (of, for example, maize), as well as have the potential to lengthen the fertile period of a plant, which could positively impact yield and breeding programs.

A listing of specific effects and utilities that the presently disclosed transcription factor genes have on plants, as determined by direct observation and assay analysis, is provided in Table 4.

Antisense and Co-Suppression

In addition to expression of the nucleic acids of the invention as gene replacement or plant phenotype modification nucleic acids, the nucleic acids are also useful for sense and anti-sense suppression of expression, e.g., to down-regulate expression of a nucleic acid of the invention, e.g., as a further mechanism for modulating plant phenotype. That is, the nucleic acids of the invention, or subsequences or anti-sense sequences thereof, can be used to block expression of naturally occurring homologous nucleic acids. A variety of sense and anti-sense technologies are known in the art, e.g., as set forth in Lichtenstein and Nellen (1997) *Antisense Technology: A Practical Approach* IRL Press at Oxford University Press, Oxford, U.K. In general, sense or anti-sense sequences are introduced into a cell, where they are optionally amplified, e.g., by transcription. Such sequences include both simple oligonucleotide sequences and catalytic sequences such as ribozymes.

For example, a reduction or elimination of expression (i.e., a "knock-out") of a transcription factor or transcription factor homologue polypeptide in a transgenic plant, e.g., to modify a plant trait, can be obtained by introducing an antisense construct corresponding to the polypeptide of interest as a cDNA. For antisense suppression, the transcription factor or homologue cDNA is arranged in reverse orientation (with respect to the coding sequence) relative to the promoter sequence in the expression vector. The introduced sequence need not be the full length cDNA or gene, and need not be identical to the cDNA or gene found in the plant type to be transformed. Typically, the antisense sequence need only be capable of hybridizing to the target gene or RNA of interest. Thus, where the introduced sequence is of shorter length, a higher degree of homology to the endogenous transcription factor sequence will be needed for effective antisense suppression. While antisense sequences of various lengths can be utilized, preferably, the introduced antisense sequence in the vector will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous transcription factor gene in the plant cell.

Suppression of endogenous transcription factor gene expression can also be achieved using a ribozyme. Ribozymes are RNA molecules that possess highly specific endoribonuclease activity. The production and use of ribozymes are disclosed in U.S. Pat. No. 4,987,071 and U.S. Pat. No. 5,543,508. Synthetic ribozyme sequences including antisense RNAs can be used to confer RNA cleaving activity on the antisense RNA, such that endogenous mRNA molecules that hybridize to the antisense RNA are cleaved, which in turn leads to an enhanced antisense inhibition of endogenous gene expression.

Suppression of endogenous transcription factor gene expression can also be achieved using RNA interference, or RNAi. RNAi is a post-transcriptional, targeted gene-silencing technique that uses double-stranded RNA (dsRNA) to incite degradation of messenger RNA (mRNA) containing the same sequence as the dsRNA (Constans, (2002) *The Scientist* 16:36). Small interfering RNAs, or siRNAs are produced in at least two steps: an endogenous ribonuclease cleaves longer dsRNA into shorter, 21–23 nucleotide-long RNAs. The siRNA segments then mediate the degradation of the target mRNA (Zamore, (2001) *Nature Struct. Biol.*, 8:746–50). RNAi has been used for gene function determination in a manner similar to antisense oligonucleotides (Constans, (2002) *The Scientist* 16:36). Expression vectors that continually express siRNAs in transiently and stably transfected have been engineered to express small hairpin RNAs (shRNAs), which get processed in vivo into siRNAs-like molecules capable of carrying out gene-specific silencing (Brummelkamp et al., (2002) *Science* 296:550–553, and Paddison, et al. (2002) *Genes & Dev.* 16:948–958). Post-transcriptional gene silencing by double-stranded RNA is discussed in further detail by Hammond et al. (2001) *Nature Rev Gen* 2: 110–119, Fire et al. (1998) *Nature* 391: 806–811 and Timmons and Fire (1998) *Nature* 395: 854.

Vectors in which RNA encoded by a transcription factor or transcription factor homologue cDNA is over-expressed can also be used to obtain co-suppression of a corresponding endogenous gene, e.g., in the manner described in U.S. Pat. No. 5,231,020 to Jorgensen. Such co-suppression (also termed sense suppression) does not require that the entire transcription factor cDNA be introduced into the plant cells, nor does it require that the introduced sequence be exactly identical to the endogenous transcription factor gene of interest. However, as with antisense suppression, the suppressive efficiency will be enhanced as specificity of hybridization is increased, e.g., as the introduced sequence is lengthened, and/or as the sequence similarity between the introduced sequence and the endogenous transcription factor gene is increased.

Vectors expressing an untranslatable form of the transcription factor mRNA, e.g., sequences comprising one or more stop codon, or nonsense mutation) can also be used to suppress expression of an endogenous transcription factor, thereby reducing or eliminating it's activity and modifying one or more traits. Methods for producing such constructs are described in U.S. Pat. No. 5,583,021. Preferably, such constructs are made by introducing a premature stop codon into the transcription factor gene. Alternatively, a plant trait can be modified by gene silencing using double-strand RNA (Sharp (1999) *Genes and Development* 13: 139–141). Another method for abolishing the expression of a gene is by insertion mutagenesis using the T-DNA of *Agrobacterium tumefaciens*. After generating the insertion mutants, the mutants can be screened to identify those containing the insertion in a transcription factor or transcription factor homologue gene. Plants containing a single transgene insertion event at the desired gene can be crossed to generate homozygous plants for the mutation. Such methods are well known to those of skill in the art. (See for example Koncz et al. (1992) *Methods in Arabidopsis Research*, World Scientific.)

Alternatively, a plant phenotype can be altered by eliminating an endogenous gene, such as a transcription factor or transcription factor homologue, e.g., by homologous recombination (Kempin et al. (1997) *Nature* 389:802–803).

A plant trait can also be modified by using the Cre-lox system (for example, as described in U.S. Pat. No. 5,658,772). A plant genome can be modified to include first and second lox sites that are then contacted with a Cre recombinase. If the lox sites are in the same orientation, the intervening DNA sequence between the two sites is excised. If the lox sites are in the opposite orientation, the intervening sequence is inverted.

The polynucleotides and polypeptides of this invention can also be expressed in a plant in the absence of an expression cassette by manipulating the activity or expression level of the endogenous gene by other means. For example, by ectopically expressing a gene by T-DNA activation tagging (Ichikawa et al. (1997) *Nature* 390 698–701; Kakimoto et al. (1996) *Science* 274: 982–985). This method entails transforming a plant with a gene tag containing multiple transcriptional enhancers and once the tag has inserted into the genome, expression of a flanking gene coding sequence becomes deregulated. In another example, the transcriptional machinery in a plant can be modified so as to increase transcription levels of a polynucleotide of the invention (See, e.g., PCT Publications WO 96/06166 and WO 98/53057 which describe the modification of the DNA-binding specificity of zinc finger proteins by changing particular amino acids in the DNA-binding motif).

The transgenic plant can also include the machinery necessary for expressing or altering the activity of a polypeptide encoded by an endogenous gene, for example by altering the phosphorylation state of the polypeptide to maintain it in an activated state.

Transgenic plants (or plant cells, or plant explants, or plant tissues) incorporating the polynucleotides of the invention and/or expressing the polypeptides of the invention can be produced by a variety of well established techniques as described above. Following construction of a vector, most typically an expression cassette, including a polynucleotide, e.g., encoding a transcription factor or transcription factor homologue, of the invention, standard techniques can be used to introduce the polynucleotide into a plant, a plant cell, a plant explant or a plant tissue of interest. Optionally, the plant cell, explant or tissue can be regenerated to produce a transgenic plant.

The plant can be any higher plant, including gymnosperms, monocotyledonous and dicotyledenous plants. Suitable protocols are available for Leguminosae (alfalfa, soybean, clover, etc.), Umbelliferae (carrot, celery, parsnip), Cruciferae (cabbage, radish, rapeseed, broccoli, etc.), Curcurbitaceae (melons and cucumber), Gramineae (wheat, corn, rice, barley, millet, etc.), Solanaceae (potato, tomato, tobacco, peppers, etc.), and various other crops. See protocols described in Ammirato et al. (1984) *Handbook of Plant Cell Culture—Crop Species*, Macmillan Publ. Co. Shimamoto et al. (1989) *Nature* 338:274–276; Fromm et al. (1990) *Bio/Technology* 8:833–839; and Vasil et al. (1990) *Bio/Technology* 8:429–434.

Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens* mediated transformation. Transformation means introducing a nucleotide sequence into a plant in a manner to cause stable or transient expression of the sequence.

Successful examples of the modification of plant characteristics by transformation with cloned sequences which serve to illustrate the current knowledge in this field of technology, and which are herein incorporated by reference, include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Following transformation, plants are preferably selected using a dominant selectable marker incorporated into the transformation vector. Typically, such a marker will confer antibiotic or herbicide resistance on the transformed plants, and selection of transformants can be accomplished by exposing the plants to appropriate concentrations of the antibiotic or herbicide.

After transformed plants are selected and grown to maturity, those plants showing a modified trait are identified. The modified trait can be any of those traits described above. Additionally, to confirm that the modified trait is due to changes in expression levels or activity of the polypeptide or polynucleotide of the invention can be determined by analyzing mRNA expression using Northern blots, RT-PCR or microarrays, or protein expression using immunoblots or Western blots or gel shift assays.

Integrated Systems—Sequence Identity

Additionally, the present invention may be an integrated system, computer or computer readable medium that comprises an instruction set for determining the identity of one or more sequences in a database. In addition, the instruction set can be used to generate or identify sequences that meet any specified criteria. Furthermore, the instruction set may be used to associate or link certain functional benefits, such improved characteristics, with one or more identified sequence.

For example, the instruction set can include, e.g., a sequence comparison or other alignment program, e.g., an available program such as, for example, the Wisconsin Package Version 10.0, such as BLAST, FASTA, PILEUP, FINDPATTERNS or the like (GCG, Madison, Wis.). Public sequence databases such as GenBank, EMBL, Swiss-Prot and PIR or private sequence databases such as PHYTOSEQ sequence database (Incyte Genomics, Palo Alto, Calif.) can be searched.

Alignment of sequences for comparison can be conducted by the local homology algorithm of Smith and Waterman (1981) *Adv. Appl. Math.* 2:482, by the homology alignment algorithm of Needleman and Wunsch (1970) *J. Mol. Biol.* 48:443–453, by the search for similarity method of Pearson and Lipman (1988) *Proc. Natl. Acad. Sci. U.S.A.* 85:2444–2448, by computerized implementations of these algorithms. After alignment, sequence comparisons between two (or more) polynucleotides or polypeptides are typically performed by comparing sequences of the two sequences over a comparison window to identify and compare local regions of sequence similarity. The comparison window can be a segment of at least about 20 contiguous positions, usually about 50 to about 200, more usually about 100 to about 150 contiguous positions. A description of the method is provided in Ausubel et al., supra.

A variety of methods for determining sequence relationships can be used, including manual alignment and computer assisted sequence alignment and analysis. This later approach is a preferred approach in the present invention, due to the increased throughput afforded by computer assisted methods. As noted above, a variety of computer programs for performing sequence alignment are available, or can be produced by one of skill.

One example algorithm that is suitable for determining percent sequence identity and sequence similarity is the BLAST algorithm, which is described in Altschul et al. *J. Mol. Biol* 215:403–410 (1990). Software for performing BLAST analyses is publicly available, e.g., through the National Center for Biotechnology Information (see internet website at ncbi.nim.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915). Unless otherwise indicated, "sequence identity" here refers to the % sequence identity generated from a tblastx using the NCBI version of the algorithm at the default settings using gapped alignments with the filter "off" (see, for example, internet website at ncbi.nim.nih.gov).

In addition to calculating percent sequence identity, the BLAST algorithm also performs a statistical analysis of the similarity between two sequences (see, e.g., Karlin & Altschul (1993) *Proc. Natl. Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (and, therefore, in this context, homologous) if the smallest sum probability in a comparison of the test nucleic acid to the reference nucleic acid is less than about 0.1, or less than about 0.01, and or even less than about 0.001. An additional example of a useful sequence alignment algorithm is PILEUP. PILEUP creates a multiple sequence alignment from a group of related sequences using progressive, pairwise alignments. The program can align, e.g., up to 300 sequences of a maximum length of 5,000 letters.

The integrated system, or computer typically includes a user input interface allowing a user to selectively view one or more sequence records corresponding to the one or more character strings, as well as an instruction set which aligns the one or more character strings with each other or with an additional character string to identify one or more region of sequence similarity. The system may include a link of one or more character strings with a particular phenotype or gene function. Typically, the system includes a user readable output element that displays an alignment produced by the alignment instruction set.

The methods of this invention can be implemented in a localized or distributed computing environment. In a distributed environment, the methods may implemented on a single computer comprising multiple processors or on a multiplicity of computers. The computers can be linked, e.g. through a common bus, but more preferably the computer(s) are nodes on a network. The network can be a generalized or a dedicated local or wide-area network and, in certain preferred embodiments, the computers may be components of an intra-net or an internet.

Thus, the invention provides methods for identifying a sequence similar or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an inter or intra net) and a query is made against the sequence database using the relevant sequences herein and associated plant phenotypes or gene functions.

Any sequence herein can be entered into the database, before or after querying the database. This provides for both expansion of the database and, if done before the querying step, for insertion of control sequences into the database. The control sequences can be detected by the query to ensure the general integrity of both the database and the query. As noted, the query can be performed using a web browser based interface. For example, the database can be a centralized public database such as those noted herein, and the querying can be done from a remote terminal or computer across an internet or intranet.

EXAMPLES

The following examples are intended to illustrate but not limit the present invention. The complete descriptions of the traits associated with each polynucleotide of the invention is fully disclosed in Table 4 and Table 6.

Example I

Full Length Gene Identification and Cloning

Putative transcription factor sequences (genomic or ESTs) related to known transcription factors were identified in the *Arabidopsis thaliana* GenBank database using the tblastn sequence analysis program using default parameters and a P-value cutoff threshold of −4 or −5 or lower, depending on the length of the query sequence. Putative transcription factor sequence hits were then screened to identify those containing particular sequence strings. If the sequence hits contained such sequence strings, the sequences were confirmed as transcription factors.

Alternatively, *Arabidopsis thaliana* cDNA libraries derived from different tissues or treatments, or genomic libraries were screened to identify novel members of a transcription family using a low stringency hybridization approach. Probes were synthesized using gene specific primers in a standard PCR reaction (annealing temperature 60° C.) and labeled with $^{32}$P dCTP using the High Prime DNA Labeling Kit (Boehringer Mannheim). Purified radiolabelled probes were added to filters immersed in Church hybridization medium (0.5 M NaPO$_4$ pH 7.0, 7% SDS, 1% w/v bovine serum albumin) and hybridized overnight at 60° C. with shaking. Filters were washed two times for 45 to 60 minutes with 1×SCC, 1% SDS at 60° C.

To identify additional sequence 5' or 3' of a partial cDNA sequence in a cDNA library, 5' and 3' rapid amplification of cDNA ends (RACE) was performed using the Marathon™ cDNA amplification kit (Clontech, Palo Alto, Calif.). Generally, the method entailed first isolating poly(A) mRNA, performing first and second strand cDNA synthesis to generate double stranded cDNA, blunting cDNA ends, followed by ligation of the Marathon™ Adaptor to the cDNA to form a library of adaptor-ligated ds cDNA.

Gene-specific primers were designed to be used along with adaptor specific primers for both 5' and 3' RACE reactions. Nested primers, rather than single primers, were used to increase PCR specificity. Using 5' and 3' RACE reactions, 5' and 3' RACE fragments were obtained, sequenced and cloned. The process can be repeated until 5' and 3' ends of the full-length gene were identified. Then the full-length cDNA was generated by PCR using primers specific to 5' and 3' ends of the gene by end-to-end PCR.

Example II

Construction of Expression Vectors

The sequence was amplified from a genomic or cDNA library using primers specific to sequences upstream and downstream of the coding region. The expression vector was pMEN20 or pMEN65, which are both derived from pMON316 (Sanders et al, (1987) *Nucleic Acids Research* 15:1543–1558) and contain the CaMV 35S promoter to express transgenes. To clone the sequence into the vector, both pMEN20 and the amplified DNA fragment were digested separately with SalI and NotI restriction enzymes at 37° C. for 2 hours. The digestion products were subject to electrophoresis in a 0.8% agarose gel and visualized by ethidium bromide staining. The DNA fragments containing the sequence and the linearized plasmid were excised and purified by using a Qiaquick gel extraction kit (Qiagen, Valencia Calif.). The fragments of interest were ligated at a ratio of 3:1 (vector to insert). Ligation reactions using T4 DNA ligase (New England Biolabs, Beverly Mass.) were carried out at 16° C. for 16 hours. The ligated DNAs were transformed into competent cells of the *E. coli* strain DH5alpha by using the heat shock method. The transformations were plated on LB plates containing 50 mg/l kanamycin (Sigma, St. Louis, Mo.). Individual colonies were grown overnight in five milliliters of LB broth containing 50 mg/l kanamycin at 37° C. Plasmid DNA was purified by using Qiaquick Mini Prep kits (Qiagen).

Example III

Transformation of *Agrobacterium* with the Expression Vector

After the plasmid vector containing the gene was constructed, the vector was used to transform *Agrobacterium tumefaciens* cells expressing the gene products. The stock of *Agrobacterium tumefaciens* cells for transformation were made as described by Nagel et al. (1990) *FEMS Microbiol Letts.* 67: 325–328. *Agrobacterium* strain ABI was grown in 250 ml LB medium (Sigma) overnight at 28° C. with shaking until an absorbance ($A_{600}$) of 0.5–1.0 was reached. Cells were harvested by centrifugation at 4,000×g for 15 min at 4° C. Cells were then resuspended in 250 µl chilled buffer (1 mM HEPES, pH adjusted to 7.0 with KOH). Cells were centrifuged again as described above and resuspended in 125 µl chilled buffer. Cells were then centrifuged and resuspended two more times in the same HEPES buffer as described above at a volume of 100 µl and 750 µl, respectively. Resuspended cells were then distributed into 40 µl aliquots, quickly frozen in liquid nitrogen, and stored at −80° C.

*Agrobacterium* cells were transformed with plasmids prepared as described above following the protocol described by Nagel et al. For each DNA construct to be transformed, 50–100 ng DNA (generally resuspended in 10 mM Tris-HCl, 1 mM EDTA, pH 8.0) was mixed with 40 µl of *Agrobacterium* cells. The DNA/cell mixture was then transferred to a chilled cuvette with a 2 mm electrode gap and subject to a 2.5 kV charge dissipated at 25 µF and 200 µF using a Gene Pulser II apparatus (Bio-Rad, Hercules, Calif.). After electroporation, cells were immediately resuspended in 1.0 ml LB and allowed to recover without antibiotic selection for 2–4 hours at 28° C. in a shaking incubator. After recovery, cells were plated onto selective medium of LB broth containing 100 µg/ml spectinomycin (Sigma) and incubated for 24–48 hours at 28° C. Single colonies were then picked and inoculated in fresh medium. The presence of the plasmid construct was verified by PCR amplification and sequence analysis.

Example IV

Transformation of *Arabidopsis* Plants with *Agrobacterium tumefaciens* with Expression Vector After transformation of *Agrobacterium tumefaciens* with plasmid vectors containing the gene, single *Agrobacterium* colonies were identified, propagated, and used to transform *Arabidopsis* plants. Briefly, 500 ml cultures of LB medium containing 50 mg/l kanamycin were inoculated with the colonies and grown at 28° C. with shaking for 2 days until an optical absorbance at 600 nm wavelength over 1 cm ($A_{600}$) of >2.0 is reached. Cells were then harvested by centrifugation at 4,000×g for 10 min, and resuspended in infiltration medium (½× Murashige and Skoog salts (Sigma), 1× Gamborg's B-5 vitamins (Sigma), 5.0% (w/v) sucrose (Sigma), 0.044 µM benzylamino purine (Sigma), 200 µl/l Silwet L-77 (Lehle Seeds) until an $A_{600}$ of 0.8 was reached.

Prior to transformation, *Arabidopsis thaliana* seeds (ecotype Columbia) were sown at a density of ~10 plants per 4" pot onto Pro-Mix BX potting medium (Hummert International) covered with fiberglass mesh (18 mm×16 mm). Plants were grown under continuous illumination (50–75 µE/m$^2$/sec) at 22–23° C. with 65–70% relative humidity. After about 4 weeks, primary inflorescence stems (bolts) are cut off to encourage growth of multiple secondary bolts. After flowering of the mature secondary bolts, plants were prepared for transformation by removal of all siliques and opened flowers.

The pots were then immersed upside down in the mixture of *Agrobacterium* infiltration medium as described above for 30 sec, and placed on their sides to allow draining into a 1'×2' flat surface covered with plastic wrap. After 24 h, the plastic wrap was removed and pots are turned upright. The immersion procedure was repeated one week later, for a total of two immersions per pot. Seeds were then collected from each transformation pot and analyzed following the protocol described below.

Example V

Identification of *Arabidopsis* Primary Transformants

Seeds collected from the transformation pots were sterilized essentially as follows. Seeds were dispersed into in a solution containing 0.1% (v/v) Triton X-100 (Sigma) and sterile $H_2O$ and washed by shaking the suspension for 20 min. The wash solution was then drained and replaced with fresh wash solution to wash the seeds for 20 min with shaking. After removal of the second wash solution, a solution containing 0.1% (v/v) Triton X-100 and 70% ethanol (Equistar) was added to the seeds and the suspension was shaken for 5 min. After removal of the ethanol/detergent solution, a solution containing 0.1% (v/v) Triton X-100 and 30% (v/v) bleach (Clorox) was added to the seeds, and the suspension was shaken for 10 min. After removal of the bleach/detergent solution, seeds were then washed five times in sterile distilled $H_2O$. The seeds were stored in the last wash water at 4° C. for 2 days in the dark before being plated onto antibiotic selection medium (1× Murashige and Skoog salts (pH adjusted to 5.7 with 1 M KOH), 1× Gamborg's B-5 vitamins, 0.9% phytagar (Life Technologies), and 50 mg/l kanamycin). Seeds were germinated under continuous illumination (50–75 µE/m$^2$/sec) at 22–23° C. After 7–10 days of growth under these conditions, kanamycin resistant primary transformants ($T_1$ generation) were visible and obtained.

These seedlings were transferred first to fresh selection plates where the seedlings continued to grow for 3–5 more days, and then to soil (Pro-Mix BX potting medium).

Primary transformants were crossed and progeny seeds ($T_2$) collected; kanamycin resistant seedlings were selected and analyzed. The expression levels of the recombinant polynucleotides in the transformants varies from about a 5% expression level increase to a least a 100% expression level increase. Similar observations are made with respect to polypeptide level expression.

Example VI

Identification of *Arabidopsis* Plants with Transcription Factor Gene Knockouts The screening of insertion mutagenized *Arabidopsis* collections for null mutants in a known target gene was essentially as described in Krysan et al (1999) *Plant Cell* 11:2283–2290. Briefly, gene-specific primers, nested by 5–250 base pairs to each other, were designed from the 5' and 3' regions of a known target gene. Similarly, nested sets of primers were also created specific to each of the T-DNA or transposon ends (the "right" and "left" borders). All possible combinations of gene specific and T-DNA/transposon primers were used to detect by PCR an insertion event within or close to the target gene. The amplified DNA fragments were then sequenced which allows the precise determination of the T-DNA/transposon insertion point relative to the target gene. Insertion events within the coding or intervening sequence of the genes were deconvoluted from a pool comprising a plurality of insertion events to a single unique mutant plant for functional characterization. The method is described in more detail in Yu and Adam, U.S. application Ser. No. 09/177,733 filed Oct. 23, 1998.

Example VII

Identification of Modified Phenotypes in Overexpression or Gene Knockout Plants Experiments were performed to identify those transformants or knockouts that exhibited modified biochemical characteristics. Among the biochemicals that were assayed were insoluble sugars, such as arabinose, fucose, galactose, mannose, rhamnose or xylose or the like; prenyl lipids, such as lutein, beta-carotene, xanthophyll-1, xanthophyll-2, chlorophylls A or B, or alpha-, delta- or gamma-tocopherol or the like; fatty acids, such as 16:0 (palmitic acid), 16:1 (palmitoleic acid), 18:0 (stearic acid), 18:1 (oleic acid), 18:2 (linoleic acid), 20:0, 18:3 (linolenic acid), 20:1 (eicosenoic acid), 20:2, 22:1 (erucic acid) or the like; waxes, such as by altering the levels of C29, C31, or $C_{33}$ alkanes; sterols, such as brassicasterol, campesterol, stigmasterol, sitosterol or stigmastanol or the like, glucosinolates, protein or oil levels.

Fatty acids were measured using two methods depending on whether the tissue was from leaves or seeds. For leaves, lipids were extracted and esterified with hot methanolic $H_2SO_4$ and partitioned into hexane from methanolic brine. For seed fatty acids, seeds were pulverized and extracted in methanol:heptane:toluene:2,2-dimethoxypropane:$H_2SO_4$ (39:34:20:5:2) for 90 minutes at 80° C. After cooling to room temperature the upper phase, containing the seed fatty acid esters, was subjected to GC analysis. Fatty acid esters from both seed and leaf tissues were analyzed with a Supelco SP-2330 column.

Glucosinolates were purified from seeds or leaves by first heating the tissue at 95° C. for 10 minutes. Preheated ethanol:water (50:50) is and after heating at 95° C. for a further 10 minutes, the extraction solvent is applied to a DEAE Sephadex column which had been previously equilibrated with 0.5 M pyridine acetate. Desulfoglucosinolates were eluted with 300 ul water and analyzed by reverse phase HPLC monitoring at 226 nm.

For wax alkanes, samples were extracted using an identical method as fatty acids and extracts were analyzed on a HP 5890 GC coupled with a 5973 MSD. Samples were chromatographically isolated on a J&W DB35 mass spectrometer (J&W Scientific).

To measure prenyl lipids levels, seeds or leaves were pulverized with 1 to 2% pyrogallol as an antioxidant. For seeds, extracted samples were filtered and a portion removed for tocopherol and carotenoid/chlorophyll analysis by HPLC. The remaining material was saponified for sterol determination. For leaves, an aliquot was removed and diluted with methanol and chlorophyll A, chlorophyll B, and total carotenoids measured by spectrophotometry by determining optical absorbance at 665.2 nm, 652.5 nm, and 470 nm. An aliquot was removed for tocopherol and carotenoid/chlorophyll composition by HPLC using a Waters uBondapak C18 column (4.6 mm×150 mm). The remaining methanolic solution was saponified with 10% KOH at 80° C. for one hour. The samples were cooled and diluted with a mixture of methanol and water. A solution of 2% methylene chloride in hexane was mixed in and the samples were centrifuged. The aqueous methanol phase was again re-extracted 2% methylene chloride in hexane and, after centrifugation, the two upper phases were combined and evaporated. 2% methylene chloride in hexane was added to the tubes and the samples were then extracted with one ml of water. The upper phase was removed, dried, and resuspended in 400 ul of 2% methylene chloride in hexane and analyzed by gas chromatography using a 50 m DB-5 ms (0.25 mm ID, 0.25 um phase, J&W Scientific).

Insoluble sugar levels were measured by the method essentially described by Reiter et al., (1999) *Plant Journal* 12:335–345. This method analyzes the neutral sugar composition of cell wall polymers found in *Arabidopsis* leaves. Soluble sugars were separated from sugar polymers by extracting leaves with hot 70% ethanol. The remaining residue containing the insoluble polysaccharides was then acid hydrolyzed with allose added as an internal standard. Sugar monomers generated by the hydrolysis were then reduced to the corresponding alditols by treatment with NaBH4, then were acetylated to generate the volatile alditol acetates which were then analyzed by GC-FID. Identity of the peaks was determined by comparing the retention times of known sugars converted to the corresponding alditol acetates with the retention times of peaks from wild-type plant extracts. Alditol acetates were analyzed on a Supelco SP-2330 capillary column (30 m×250 um×0.2 um) using a temperature program beginning at 180° C. for 2 minutes followed by an increase to 220° C. in 4 minutes. After holding at 220° C. for 10 minutes, the oven temperature is increased to 240° C. in 2 minutes and held at this temperature for 10 minutes and brought back to room temperature.

To identify plants with alterations in total seed oil or protein content, 150 mg of seeds from T2 progeny plants were subjected to analysis by Near Infrared Reflectance Spectroscopy (NIRS) using a Foss NirSystems Model 6500 with a spinning cup transport system. NIRS is a non-destructive analytical method used to determine seed oil and protein composition. Infrared is the region of the electromagnetic spectrum located after the visible region in the direction of longer wavelengths. 'Near infrared' owns its name for being the infrared region near to the visible region of the electromagnetic spectrum. For practical purposes, near infrared comprises wavelengths between 800 and 2500 nm. NIRS is applied to organic compounds rich in O—H bonds (such as moisture, carbohydrates, and fats), C—H bonds (such as organic compounds and petroleum derivatives), and N—H bonds (such as proteins and amino acids). The NIRS analytical instruments operate by statistically correlating NIRS signals at several wavelengths with the characteristic or property intended to be measured. All biological substances contain thousands of C—H, O—H, and N—H bonds. Therefore, the exposure to near infrared radiation of a biological sample, such as a seed, results in a complex spectrum which contains qualitative and quantitative information about the physical and chemical composition of that sample.

The numerical value of a specific analyte in the sample, such as protein content or oil content, is mediated by a calibration approach known as chemometrics. Chemometrics applies statistical methods such as multiple linear regression (MLR), partial least squares (PLS), and principle component analysis (PCA) to the spectral data and correlates them with a physical property or other factor, that property or factor is directly determined rather than the analyte concentration itself. The method first provides "wet chemistry" data of the samples required to develop the calibration.

Calibration for *Arabidopsis* seed oil composition was performed using accelerated solvent extraction using 1 g seed sample size and was validated against certified canola seed. A similar wet chemistry approach was performed for seed protein composition calibration.

Data obtained from NIRS analysis was analyzed statistically using a nearest-neighbor (N—N) analysis. The N—N analysis allows removal of within-block spatial variability in a fairly flexible fashion which does not require prior knowledge of the pattern of variability in the chamber. Ideally, all hybrids are grown under identical experimental conditions within a block (rep). In reality, even in many block designs, significant within-block variability exists. Nearest-neighbor procedures are based on assumption that environmental effect of a plot is closely related to that of its neighbors. Nearest-neighbor methods use information from adjacent plots to adjust for within-block heterogeneity and so provide more precise estimates of treatment means and differences. If there is within-plot heterogeneity on a spatial scale that is larger than a single plot and smaller than the entire block, then yields from adjacent plots will be positively correlated. Information from neighboring plots can be used to reduce or remove the unwanted effect of the spatial heterogeneity, and hence improve the estimate of the treatment effect. Data from neighboring plots can also be used to reduce the influence of competition between adjacent plots. The Papadakis N—N analysis can be used with designs to remove within-block variability that would not be removed with the standard split plot analysis (Papadakis, 1973, Inst. d'Amelior. Plantes Thessaloniki (Greece) Bull. Scientif., No. 23; Papadakis, 1984, Proc. Acad. Athens, 59, 326–342).

Experiments were performed to identify those transformants or knockouts that exhibited an improved pathogen tolerance. For such studies, the transformants were exposed to biotropic fungal pathogens, such as *Erysiphe orontii*, and necrotropic fungal pathogens, such as *Fusarium oxysporum*. *Fusarium oxysporum* isolates cause vascular wilts and damping off of various annual vegetables, perennials and weeds (Mauch-Mani and Slusarenko (1994) *Molecular*

*Plant-Microbe Interactions* 7: 378–383). For *Fusarium oxysporum* experiments, plants grown on Petri dishes were sprayed with a fresh spore suspension of *F. oxysporum*. The spore suspension was prepared as follows: A plug of fungal hyphae from a plate culture was placed on a fresh potato dextrose agar plate and allowed to spread for one week. 5 ml sterile water was then added to the plate, swirled, and pipetted into 50 ml Armstrong *Fusarium* medium. Spores were grown overnight in *Fusarium* medium and then sprayed onto plants using a Preval paint sprayer. Plant tissue was harvested and frozen in liquid nitrogen 48 hours post infection.

*Erysiphe orontii* is a causal agent of powdery mildew. For *Erysiphe oronlii* experiments, plants were grown approximately 4 weeks in a greenhouse under 12 hour light (20° C., 30% relative humidity (rh)). Individual leaves were infected with *E. orontii* spores from infected plants using a camel's hair brush, and the plants were transferred to a Percival growth chamber (20° C., 80% rh.). Plant tissue was harvested and frozen in liquid nitrogen 7 days post infection.

*Botrytis cinerea* is a necrotrophic pathogen. *Botrytis cinerea* was grown on potato dextrose agar in the light. A spore culture was made by spreading 10 ml of sterile water on the fungus plate, swirling and transferring spores to 10 ml of sterile water. The spore inoculum (approx. 105 spores/ml) was used to spray 10 day-old seedlings grown under sterile conditions on MS (minus sucrose) media. Symptoms were evaluated every day up to approximately 1 week.

Infection with bacterial pathogens *Pseudomonas syringae* pv *maculicola* (Psm) strain 4326 and pv maculicola strain 4326 was performed by hand inoculation at two doses. Two inoculation doses allows the differentiation between plants with enhanced susceptibility and plants with enhanced resistance to the pathogen. Plants were grown for 3 weeks in the greenhouse, then transferred to the growth chamber for the remainder of their growth. Psm ES4326 was hand inoculated with 1 ml syringe on 3 fully-expanded leaves per plant (4½ wk old), using at least 9 plants per overexpressing line at two inoculation doses, OD=0.005 and OD=0.0005. Disease scoring occurred at day 3 post-inoculation with pictures of the plants and leaves taken in parallel.

In some instances, expression patterns of the pathogen-induced genes (such as defense genes) was monitored by microarray experiments. cDNAs were generated by PCR and resuspended at a final concentration of ~100 ng/ul in 3×SSC or 150 mM Na-phosphate (Eisen and Brown (1999) *Methods Enzymol.* 303:179–205). The cDNAs were spotted on microscope glass slides coated with polylysine. The prepared cDNAs were aliquoted into 384 well plates and spotted on the slides using an x-y-z gantry (OmniGrid) purchased from GeneMachines (Menlo Park, Calif.) outfitted with quill type pins purchased from Telechem International (Sunnyvale, Calif.). After spotting, the arrays were cured for a minimum of one week at room temperature, rehydrated and blocked following the protocol recommended by Eisen and Brown (1999; supra).

Sample total RNA (10 ug) samples were labeled using fluorescent Cy3 and Cy5 dyes. Labeled samples were resuspended in 4×SSC/0.03% SDS/4 ug salmon sperm DNA/2 ug tRNA/50 mM Na-pyrophosphate, heated for 95° C. for 2.5 minutes, spun down and placed on the array. The array was then covered with a glass coverslip and placed in a sealed chamber. The chamber was then kept in a water bath at 62° C. overnight. The arrays were washed as described in Eisen and Brown (1999) and scanned on a General Scanning 3000 laser scanner. The resulting files are subsequently quantified using Imagene, a software purchased from BioDiscovery (Los Angeles, Calif.).

Experiments were performed to identify those transformants or knockouts that exhibited an improved environmental stress tolerance. For such studies, the transformants were exposed to a variety of environmental stresses. Plants were exposed to chilling stress (6 hour exposure to 4–8° C.), heat stress (6 hour exposure to 32–37° C.), high salt stress (6 hour exposure to 200 mM NaCl), drought stress (168 hours after removing water from trays), osmotic stress (6 hour exposure to 3 M mannitol), or nutrient limitation (nitrogen, phosphate, and potassium) (Nitrogen: all components of MS medium remained constant except N was reduced to 20 mg/l of $NH_4NO_3$, or Phosphate: All components of MS medium except $KH_2PO_4$, which was replaced by $K_2SO_4$, Potassium: All components of MS medium except removal of $KNO_3$ and $KH_2PO_4$, which were replaced by $NaH_4PO_4$).

Experiments were performed to identify those transformants or knockouts that exhibited a modified structure and development characteristics. For such studies, the transformants were observed by eye to identify novel structural or developmental characteristics associated with the ectopic expression of the polynucleotides or polypeptides of the invention.

Experiments were performed to identify those transformants or knockouts that exhibited modified sugar-sensing. For such studies, seeds from transformants were germinated on media containing 5% glucose or 9.4% sucrose which normally partially restrict hypocotyl elongation.

Plants with altered sugar sensing may have either longer or shorter hypocotyls than normal plants when grown on this media. Additionally, other plant traits may be varied such as root mass.

Flowering time was measured by the number of rosette leaves present when a visible inflorescence of approximately 3 cm is apparent Rosette and total leaf number on the progeny stem are tightly correlated with the timing of flowering (Koornneef et al (1991) *Mol. Gen. Genet* 229: 57–66. The vernalization response was measured. For vernalization treatments, seeds were sown to MS agar plates, sealed with micropore tape, and placed in a 4° C. cold room with low light levels for 6–8 weeks. The plates were then transferred to the growth rooms alongside plates containing freshly sown non-vernalized controls. Rosette leaves were counted when a visible inflorescence of approximately 3 cm was apparent.

Modified phenotypes observed for particular overexpressor or knockout plants are provided in Table 4. For a particular overexpressor that shows a less beneficial characteristic, it may be more useful to select a plant with a decreased expression of the particular transcription factor. For a particular knockout that shows a less beneficial characteristic, it may be more useful to select a plant with an increased expression of the particular transcription factor.

The sequences of the Sequence Listing, those in Tables 4 or 5, or those disclosed here can be used to prepare transgenic plants and plants with altered traits. The specific transgenic plants listed below are produced from the sequences of the Sequence Listing, as noted Table 4 provides exemplary polynucleotide and polypeptide sequences of the invention. Table 4 includes, from left to right for each sequence: the first column shows the polynucleotide SEQ ID NO; the second column shows the Mendel Gene ID No., GID; the third column shows the trait(s) resulting from the knock out or overexpression of the polynucleotide in the transgenic plant; the fourth column shows the category of the trait; the fifth column shows the transcription factor family to which the polynucleotide belongs; the sixth column ("Comment"), includes specific effects and utilities conferred by the polynucleotide of the first column; the seventh column shows the SEQ ID NO of the polypeptide encoded by the polynucleotide; and the eighth column shows the amino acid residue positions of the conserved domain in amino acid (AA) co-ordinates.

G2340: G2340 (SEQ ID NO: 17) was analyzed using transgenic plants in which the gene was expressed under the control of the 35S promoter. Overexpression of G2340 produced a spectrum of deleterious effects on *Arabidopsis* growth and development. 35S::G2340 primary transformants were generally smaller than controls, and at early stages some displayed leaves that were held in a vertical orientation. The most severely affected lines died at early stages. Others survived, but displayed necrosis of the blades in later rosette leaves and cauline leaves. Inflorescence development was also highly abnormal; stems were typically shorter than wild type, often 'kinked' at nodes, and the tissue had a rather fleshy succulent appearance. Flower buds were frequently poorly formed, failed to open and withered away without siliques developing. Additionally, secondary shoot growth frequently failed the tips of such structures sometimes senesced. Due to these abnormalities, many of the primary transformants were completely infertile. Three T1 lines (#1, 5, 20) with a relatively weak phenotype, which did set some seed, were selected for further study. Plants from the T2-20 population displayed a strong phenotype, and died early in development. The other two T2 populations were slightly small, but the effects were much weaker than those seen in the parental plants, suggesting that activity of the transgene might have become reduced between the generations. It should be noted that G2340 and G671 (SEQ ID NO: 19) are part of the same clade and that they had very similar morphological phenotypes and a similar expression pattern. These two genes may have overlapping or redundant phenotypes in the plant. Small, pale seedlings with strap-like leaves that held a vertical orientation were found in the mixed line populations of 35S::G2340 transgenic seedlings when grown under sterile conditions, similar to those observed in soil grown plants in the T1 generation. The necrotic lesions observed on the T1 plants grown in soil were not observed on the plants grown in culture leaving uncertainty as to whether the necrotic lesion phenotype is a classic lesion mimic phenotype that would suggest that G2340 is involved in cell death responses or if the G2340 overexpressor plants are simply hypersensitive to stresses. One class of lesion mimic forms progressive lesions following an inductive stress. Lesion formation may be induced in G2340 overexpressing plants grown in culture. In addition to the morphological changes, overexpression of G2340 resulted in an extreme alteration in seed glucosinolate profile. This phenotype was observed in one line, line 1, in seed from two independent plantings. According to RT-PCR analysis, G2340 was expressed primarily in roots and was slightly induced in leaf tissue in response to auxin and heat treatments. G2340 can be used to engineer plants with an inducible cell death response. A gene that regulates cell death in plants can be used to induce a pathogen protective hyper-response (HR) in plants without the potentially detrimental consequences of a constitutive systemic acquired resistance (SAR). Other potential utilities include the creation of novel abscission zones or inducing death in reproductive organs to prevent the spread of pollen, transgenic or otherwise. In the case of necrotrophic pathogens that rely on dead plant tissue as a source of nutrients, prevention of cell death could confer tolerance to these diseases. Overexpression of G2340 in *Arabidopsis* also resulted in an extreme alteration in seed glucosinolate profile. Therefore, the gene can be used to alter glucosinolate composition in plants. Increases or decreases in specific glucosinolates or total glucosinolate content are desirable depending upon the particular application. For example: (1) Glucosinolates are undesirable components of the oilseeds used in animal feed, since they produce toxic effects. Low-glucosinolate varieties of canola have been developed to combat this problem. (2) Some glucosinolates have anti-cancer activity; thus, increasing the levels or composition of these compounds might be of interest from a nutraceutical standpoint. (3) Glucosinolates form part of a plants natural defense against insects. Modification of glucosinolate composition or quantity can therefore afford increased protection from predators. Furthermore, in edible crops, tissue specific promoters can be used to ensure that these compounds accumulate specifically in tissues, such as the epidermis, which are not taken for consumption.

Closely Related Genes from Other Species

G2340 shows some sequence similarity with known genes from other plant species within the conserved Myb domain.

G2583: G2583 (SEQ ID NO: 143) was studied using transgenic plants in which the gene was expressed under the control of the 35S promoter. Most notably, 35S::G2583 plants exhibited extremely glossy leaves. At early stages, 35S::G2583 seedlings appeared normal, but by about two weeks after sowing, the plants exhibited very striking shiny leaves, which were apparent until very late in development. In addition to this phenotype, it should be noted that many lines displayed a variety of other effects such as a reduction in overall size, narrow curled leaves, or various non-specific floral abnormalities, which reduced fertility. These effects on leaf appearance were observed in 18/20 primary transformants, and in all the plants from 4/6 of the T2 lines (#2, 4, 9 and 15) examined. The glossy nature of the leaves from 35S::G2583 plants can be a consequence of changes in epicuticular wax content or composition. G2583 belongs to a small clade within the large AP2/EREBP *Arabidopsis* family that also contains G975 (SEQ ID NO: 89), G1387 (SEQ ID NO: 145), and G977 (SEQ ID NO: 147). Overexpression of G975 (SEQ ID NO: 89) caused a substantial increase in leaf wax components, as well as morphological phenotypes resembling those observed in 35S::G2583 plants. G2583 was ubiquitously expressed (at higher levels in root, flower, embryo, and silique tissues). G2583 can be used to modify plant appearance (shiny leaves). In addition, it can be used to manipulate wax composition, amount, or distribution, which in turn can modify plant tolerance to drought and/or low humidity or resistance to insects.

Closely Related Genes from other Species

G2583 showed some sequence similarity with known genes from other plant species within the conserved AP2/EREBP domain.

G362: G362 (SEQ ID NO: 61) was analyzed using transgenic plants in which G362 was expressed under the control of the 35S promoter. 35S::G362 had a number of developmental effects with the most prominent result being an increase in trichome number as well as the ectopic formation of trichomes. Overexpression of G362 also increased anthocyanin levels in various tissues at different stages of growth. Seedlings sometimes showed high levels of pigment in the first true leaves. Late flowering lines also became darkly pigmented. Seeds from a number of lines were observed to develop patches of dark purple pigmentation. Inflorescences from 35S::G362 plants were thin, and flowers sometimes displayed poorly developed organs. The seed yield from many lines was somewhat poor. As determined by RT-PCR, G362 is expressed in roots, and is expressed at significantly lower levels in siliques, seedlings and shoots. No expression of G362 was detected in the other tissues tested. G362 expression was induced in rosette leaves by heat stress. G362 can be used to alter trichome number and distribution in plants. Trichome glands on the surface of many higher plants produce and secrete exudates which give protection from the elements and pests such as insects, microbes and herbivores. These exudates may physically immobilize insects and spores, may be insecticidal or ant-microbial or they may allergens or irritants to protect against herbivores. Trichomes have also been suggested to decrease transpiration by decreasing leaf surface air flow, and by exuding chemicals that protect the leaf from the sun. Another use for G362 is to increase the density of cotton fibers in cotton bolls. Cotton fibers are modified unicellular trichomes that are produced from the ovule epidermis. However, typically only 30% of the epidermal cells take on a trichome fate (Basra and Malik 1984 Int. Rev. Cytol. 89:65–113). Thus, cotton yields can be increased by inducing a greater proportion of the ovule epidermal cells to become fibers. Depending on the plant species, varying amounts of diverse secondary biochemicals (often lipophilic terpenes) are produced and exuded or volatilized by trichomes. These exotic secondary biochemicals, which are relatively easy to extract because they are on the surface of the leaf, have been widely used in such products as flavors and aromas, drugs, pesticides and cosmetics. One class of secondary metabolites, the diterpenes, can effect several biological systems such as tumor progression, prostaglandin synthesis and tissue inflammation. In addition, diterpenes can act as insect pheromones, termite allomones, and can exhibit neurotoxic, cytotoxic and antimitotic activities. As a result of this functional diversity, diterpenes have been the target of research several pharmaceutical ventures. In most cases where the metabolic pathways are impossible to engineer, increasing trichome density or size on leaves may be the only way to increase plant productivity. Thus, the use of G362 and its homologs to increase trichome density, size or type can have profound utilities in molecular farming practices (for example, the use of trichomes as a manufacturing system for complex secondary metabolites), and in producing insect resistant and herbivore resistant plants. In addition, G362 can be used to alter a plant's time to flowering.

Closely Related Genes from other Species

G362 had some similarity within of the conserved $C_2H2$ domain to non-*Arabidopsis* proteins.

G2105: The ORF boundary of G2105 (SEQ ID NO: 63) was determined and G2105 was analyzed using transgenic plants in which G2105 was expressed under the control of the 35S promoter. Two of four T2 lines examined appeared dark green and were smaller than wild type at all stages of development. Additionally, the adaxial leaf surfaces from these plants had a somewhat 'lumpy' appearance caused by trichomes being raised-up on small mounds of epidermal cells. Two lines of G2105 overexpressing plants had larger seed. G2105 expression was root specific and induced in leaves by auxin, abscisic acid, high temperature, salt and osmotic stress treatments. On the basis of the analyses, G2105 can be used to manipulate some aspect of plant growth or development, particularly in trichome development. In addition, G2105 can be used to modify seed size and/or morphology, which can have an impact on yield. The promoter of G2105 can have some utility as a root specific promoter.

Closely Related Genes from other Species

G2105 had some similarity within the conserved domain of non-*Arabidopsis* proteins.

G47: G47 (SEQ ID NO: 65) was studied using transgenic plants in which the gene was expressed under the control of the 35S promoter. Overexpression of G47 resulted in a variety of morphological and physiological phenotypic alterations. 35S::G47 plants showed enhanced tolerance to osmotic stress. In a root growth assay on PEG-containing media, G47 overexpressing transgenic seedlings were larger and had more root growth compared with wild-type controls. G47 expression levels may be altered by environmental conditions, in particular reduced by salt and osmotic stresses. In addition to the phenotype observed in the osmotic stress assay, germination efficiency for the seeds from G47 overexpressor plants was low. Overexpression of G47 also produced a substantial delay in flowering time and caused a marked change in shoot architecture. 35S::G47 transformants were small at early stages and switched to flowering more than a week later than wild-type controls (continuous light conditions). The inflorescences from these plants appeared thick and fleshy, had reduced apical dominance, and exhibited reduced internode elongation leading to a short compact stature. The branching pattern of the stems also appeared abnormal, with the primary shoot becoming 'kinked' at each coflorescence node. Additionally, the plants showed slightly reduced fertility and formed rather small siliques that were borne on short pedicels and held vertically, close against the stem. Additional alterations were detected in the inflorescence stems of 35S::G47 plants. Stem sections from T2-21 and T2-24 plants were of wider diameter, and had large irregular vascular bundles containing a much greater number of xylem vessels than wild type. Furthermore, some of the xylem vessels within the bundles appeared narrow and were possibly more lignified than were those of controls. G47 was expressed at higher levels in rosette leaves, and transcripts were detected in other tissues (flower, embryo, silique, and germinating seedling). G47 can be used to manipulate flowering time, to modify plant architecture and stem structure (including development of vascular tissues and lignin content) and to improve plant performance under osmotic stress. The use of G47 or of G47 orthologs from tree species can be used to modulate lignin content of a plant. This allows the quality of wood used for furniture or construction to be improved. Lignin is energy rich; increasing lignin composition could therefore be valuable in raising the energy content of wood used for fuel. Conversely, the pulp and paper industries seek wood with a reduced lignin content. Currently, lignin must be removed in a costly process that involves the use of many polluting chemicals. Consequently, lignin is a serious barrier to efficient pulp and paper production. In addition to forest biotechnology applications, changing lignin content might increase the palatability of various fruits and vegetables. A wide variety of applications exist for systems that either lengthen or shorten the time to flowering.

Closely Related Genes from other Species

G47 showed some sequence similarity with known genes from other plant species within the conserved AP2/EREBP domain.

G975: G975 (SEQ ID NO: 89) was identified as a new member of the AP2/EREBP family (EREBP subfamily) of transcription factors. G975 was expressed in flowers and, at lower levels, in shoots, leaves, and siliques. GC-FID and GC-MS analyses of leaves from G975 overexpressing plants showed that the levels of C29, C31, and C33 alkanes were substantially increased (up to 10-fold) compared with control plants. A number of additional compounds of similar molecular weight, presumably also wax components, also accumulated to significantly higher levels in G975 overexpressing plants. C29 alkanes constituted close to 50% of the wax content in wild-type plants (Millar et al. 1998 Plant Cell 11:1889–1902), suggesting that a major increase in total wax content occurred in the G975 transgenic plants. However, the transgenic plants had an almost normal phenotype (although small morphological differences are detected in leaf appearance), indicating that overexpression of G975 was not deleterious to the plant. Overexpression of G975 did not cause the dramatic alterations in plant morphology that had been reported for *Arabidopsis* plants in which the FATTY ACID ELONGATION1 gene was overexpressed (Millar et al. 1998, supra). G975 may regulate the expression of some of the genes involved in wax metabolism. One *Arabidopsis* AP2 sequence (G1387; SEQ ID NO: 145) that is significantly more closely related to G975 than the rest of the members of the AP2/EREBP family is predicted to have a function and a use related to that of G975. G975 can be used to manipulate wax composition, amount, or distribution, which in turn can modify plant tolerance to drought and/or low humidity or resistance to insects, as well as plant appearance (shiny leaves). G975 can also be used to specifically alter wax composition, amount, or distribution in those plants and crops from which wax is a valuable product.

Closely Related Genes from other Species

The non-*Arabidopsis* gene most highly related to G975 is represented by L46408 BNAF1258 Mustard flower buds *Brassica rapa* cDNA clone F1258. The similarity between G975 and the *Brassica rapa* gene represented by EST L46408 extends beyond the conserved AP2 domain that characterizes the AP2/EREBP family. This *Brassica rapa* gene appeared to be more closely related to 6975 than *Arabidopsis* G1387, indicating that EST L46408 may represent a true G975 ortholog. The similarity between G975 and *Arabidopsis* G1387 (SEQ ID NO: 145) also extends beyond the conserved AP2 domain.

G214: G214 (SEQ ID NO: 33) overexpressing lines were late bolting, showed larger biomass (increased leaf number and size), and were darker green in vegetative and reproductive tissues due to a higher chlorophyll content in the later stages of development. In these later stages, the overexpressor plants also had higher insoluble sugar, leaf fatty acid, and carotenoid content per unit area. Line 11 also showed a significant, repeatable increase in lutein levels in seeds. Micro-array data was consistent with the morphological and biochemical data in that the genes that were highly induced included chloroplast localized enzymes, and light regulated genes such as Rubisco, carbonic anhydrase, and the photosystem 1 reaction center subunit precursor. A chlorophyll biosynthetic enzyme was also highly induced, consistent with the dark green color of the adult leaves and perhaps a higher photosynthetic rate. A measurement of leaf fatty acid in the older overexpressors suggested that the overall levels were higher than wild-type levels (except for the percent composition of 16:3 in line 11). Percent composition of 16:1 and 16:3 (fatty acids found primarily in plastids) is similar to wild-type arguing against an increase in chloroplast number as an explanation for increase chlorophyll content in the leaves. G214 overexpressing lines 3, 11, and 15 were sensitive to germination on high glucose showing less cotyledon expansion and hypocotyl elongation suggesting the late bolting and dark green phenotype could be tied into carbon sensing which has been shown to regulate phytochrome A signaling. Sugars are key regulatory molecules that affect diverse processes in higher plants including germination, growth, flowering, senescence, sugar metabolism and photosynthesis. Glucose-specific hexose-sensing has also been described in plants and implicated in cell division and the repression of famine genes (photosynthetic or glyoxylate cycles). Potential utilities of G214 include increasing chlorophyll content allowing more growth and productivity in conditions of low light. With a potentially higher photosynthetic rate, fruits can have higher sugar content. Increased carotenoid content can be used as a nutraceutical to produce foods with greater antioxidant capability. Also G214 can be used to manipulate seed composition which is very important for the nutritional value and production of various food products.

Closely Related Genes from other Species

G214 is highly homologous to a tomato (*Cornell Lycopersicon esculentum*) EST (cLER12A11) generated from a *Pseudomonas* resistant line.

G974: The complete sequence of G974 (SEQ ID NO: 974) was obtained and G974 was studied using transgenic plants in which G974 was expressed under the control of the 35S promoter. Constitutive expression of G974 produced deleterious effects: the majority of 35S::G974 primary transformants showed a reduction in overall size and developed rather slowly compared to wild type controls. These phenotypic alterations were not observed in the T2 generation, perhaps indicating silencing of the transgene. The T2 plants were wild-type in the physiological and biochemical analyses performed. G974 was ubiquitously expressed. 35S::G974 had altered seed oil content Closely Related Genes from other Species Several AP2 proteins from a variety of species (*Atriplex hortensis, Lycopersicon esculentum, Glycine max, Populus balsamifera, Medicago truncatula*) exhibited some sequence similarity with G974 outside of the signature AP2 domain sequence, and bear nearly identical AP2 domains. These proteins may be related.

G2343: The complete sequence of G2343 (SEQ ID NO: 2343) was determined and G2343 was analyzed using transgenic plants in which G2343 was expressed under the control of the 35S promoter. The phenotype of these transgenic plants was wild-type in all assays performed. As determined by RT-PCR, G2343 is expressed in shoots, embryos and siliques. G2343 expression is induced in rosette leaves by auxin, heat stress, and infection by *Fusarium oxysporum*. 35S::G2343 had an altered seed oil content Closely Related Genes from other Species The most related gene to G2343 is tomato gene LETHM1 (CAA64615). Similarity between G2343 and LETHM1 extends beyond the signature motif of the family to a level that would suggest the genes are orthologs.

G2123: G2123 (SEQ ID NO: 67) was analyzed using transgenic plants in which G2123 was expressed under the control of the 35S promoter. The phenotype of these transgenic plants was wild-type in all assays performed. G2123 was expressed primarily in developing seeds and silique tissue in wild-type plants. G2123 corresponds to a predicted putative 14-3-3 protein in annotated BAC clone T11I11 (AC012680), from chromosome 1 of *Arabidopsis*.

Closely Related Genes from other Species

Because there is a high degree of similarity among all GF14 proteins, there are several GF14 protein from other plant species which are closely related to G2123.

G1777: G1777 (SEQ ID NO: 55) was analyzed using transgenic plants in which G1777 was expressed under the control of the 35S promoter. Overexpression of G1777 in *Arabidopsis* resulted in an increase in seed oil content and a decrease in seed protein content in T2 lines 1 and 13. The change in seed oil in line 1 was just below the significance cutoff, but the seed protein change was significant. G1777 was expressed in all examined tissue of *Arabidopsis*. G1777 was induced by auxin and ABA treatment, and by heat stress. G1777 has utility in manipulating seed oil and protein content.

Closely Related Genes from other Species

G1777 shows some homology to non-*Arabidopsis* proteins within the conserved RING finger domain.

G2520: G2520 (SEQ ID NO: 37) was analyzed using transgenic plants in which G2520 was expressed under the control of the 35S promoter. At early stages, 35S::G2520 transformants displayed abnormal curled cotyledons, long hypocotyls, and rather short roots. During the vegetative phase, these plants formed somewhat small flat leaves. Following the switch to reproductive growth, 35S::G2520 inflorescences were typically very spindly, slightly pale colored, and stems often split open at late stages. Flowers were frequently small with narrow organs and showed poor pollen production. As a result, the seed yield from 35S::G2520 plants was low compared to wild-type controls. These effects were observed in the majority of primary transformants, and to varying extents, in all three of the T2 populations. Overexpression of G2520 also resulted in an increase in the leaf glucosinolate M39478 in lines 11 and 14. In addition, these lines showed an increase in seed delta-tocopherol and a decrease in seed gamma-tocopherol. No altered phenotypes were detected in any of the physiological assays. G2520 was expressed throughout the plant and was induced by ABA, heat, salt, drought and osmotic stress. G2520 is useful for manipulating plant development and altering leaf glucosinolate composition. Increases or decreases in specific glucosinolates or total glucosinolate content are be desirable depending upon the particular application. For example: (1) Glucosinolates are undesirable components of the oilseeds used in animal feed, since they produce toxic effects. Low-glucosinolate varieties of canola have been developed to combat this problem. (2) Some glucosinolates have anti-cancer activity; thus, increasing the levels or composition of these compounds might be of interest from a nutraceutical standpoint. (3) Glucosinolates form part of a plant's natural defense against insects. Modification of glucosinolate composition or quantity can therefore afford increased protection from predators. Furthermore, in edible crops, tissue specific promoters can be used to ensure that these compounds accumulate specifically in tissues, such as the epidermis, which are not taken for consumption. G2520 can also be used to modify seed tocopherol composition. Tocopherols have anti-oxidant and vitamin E activity.

Closely Related Genes from other Species

G2520 shows some sequence similarity with known genes from other plant species within the conserved basic HLH domain.

Example VIII

Identification of Homologous Sequences

Homologous sequences from *Arabidopsis* and plant species other than *Arabidopsis* were identified using database sequence search tools, such as the Basic Local Alignment Search Tool (BLAST) (Altschul et al. (1990) *J. Mol. Biol.* 215:403–410; and Altschul et al. (1997) *Nucl. Acid Res.* 25: 3389–3402). The tblastx sequence analysis programs were employed using the BLOSUM-62 scoring matrix (Henikoff, S. and Henikoff, J. G. (1992) *Proc. Natl. Acad. Sci. USA* 89: 10915–10919).

Identified non-*Arabidopsis* sequences homologous to the *Arabidopsis* sequences are provided in Table 4. The percent sequence identity among these sequences can be as low as 47%, or even lower sequence identity. The entire NCBI GenBank database was filtered for sequences from all plants except *Arabidopsis thaliana* by selecting all entries in the NCBI GenBank database associated with NCBI taxonomic ID 33090 (Viridiplantae; all plants) and excluding entries associated with taxonomic ID 3701 (*Arabidopsis thaliana*). These sequences are compared to sequences representing genes of SEQ IDs NOs:2–2N, where N=2–74, using the Washington University TBLASTX algorithm (version 2.0a19 MP) at the default settings using gapped alignments with the filter "off". For each gene of SEQ IDs NOs:2–2N, where N=2–74, individual comparisons were ordered by probability score (P-value), where the score reflects the probability that a particular alignment occurred by chance. For example, a score of 3.6e–40 is $3.6 \times 10^{-40}$. In addition to P-values, comparisons were also scored by percentage identity. Percentage identity reflects the degree to which two segments of DNA or protein are identical over a particular length. Examples of sequences so identified are presented in Table 5. Homologous or orthologous sequences are readily identified and available in GenBank by Accession number (Table 5; Test sequence ID). The identified homologous polynucleotide and polypeptide sequences and homologues of the *Arabidopsis* polynucleotides and polypeptides may be orthologs of the *Arabidopsis* polynucleotides and polypeptides. (TBD: to be determined.)

Example IX

Introduction of Polynucleotides into Dicotyledonous Plants

SEQ ID NOs:1-(2N-1), wherein N=2–123, paralogous, orthologous, and homologous sequences recombined into pMEN20 or pMEN65 expression vectors are transformed into a plant for the purpose of modifying plant traits. The cloning vector may be introduced into a variety of cereal plants by means well-known in the art such as, for example, direct DNA transfer or *Agrobacterium tumefaciens*-mediated transformation. It is now routine to produce transgenic plants using most dicot plants (see Weissbach and Weissbach, (1989) supra; Gelvin et al., (1990) supra; Herrera-Estrella et al. (1983) supra; Bevan (1984) supra; and Klee (1985) supra). Methods for analysis of traits are routine in the art and examples are disclosed above.

Example X

Transformation of Cereal Plants with an Expression Vector

Cereal plants such as corn, wheat, rice, sorghum or barley, may also be transformed with the present polynucleotide sequences in pMEN20 or pMEN65 expression vectors for the purpose of modifying plant traits. For example, pMEN020 may be modified to replace the NptII coding region with the BAR gene of *Streptomyces hygroscopicus* that confers resistance to phosphinothricin. The KpnI and BglII sites of the Bar gene are removed by site-directed mutagenesis with silent codon changes.

The cloning vector may be introduced into a variety of cereal plants by means well-known in the art such as, for example, direct DNA transfer or *Agrobacterium tumefaciens*-mediated transformation. It is now routine to produce transgenic plants of most cereal crops (Vasil, I., Plant Molec. Biol. 25: 925–937 (1994)) such as corn, wheat, rice, sorghum (Cassas, A. et al., Proc. Natl. Acad Sci USA 90: 11212–11216 (1993) and barley (Wan, Y. and Lemeaux, P. Plant Physiol. 104:37–48 (1994). DNA transfer methods such as the microprojectile can be used for corn (Fromm. et al. Bio/Technology 8: 833–839 (1990); Gordon-Kamm et al. Plant Cell 2: 603–618 (1990); Ishida, Y., Nature Biotechnology 14:745–750 (1990)), wheat (Vasil, et al. Bio/Technology 10:667–674 (1992); Vasil et al., Bio/Technology 11: 1553–1558 (1993); Weeks et al., Plant Physiol. 102:1077–1084 (1993)), rice (Christou Bio/Technology 9:957–962 (1991); Hiei et al. Plant J. 6:271–282 (1994); Aldemita and Hodges, Planta 199:612–617; Hiei et al., Plant Mol. Biol. 35:205–18 (1997)). For most cereal plants, embryogenic cells derived from immature scutellum tissues are the preferred cellular targets for transformation (Hiei et al., Plant Mol. Biol. 35:205–18 (1997); Vasil, Plant Molec. Biol. 25: 925–937 (1994)).

Vectors according to the present invention may be transformed into corn embryogenic cells derived from immature scutellar tissue by using microprojectile bombardment, with the A188XB73 genotype as the preferred genotype (Fromm, et al., Bio/Technology 8: 833–839 (1990); Gordon-Kamm et al., Plant Cell 2: 603–618 (1990)). After microprojectile bombardment the tissues are selected on phosphinothricin to identify the transgenic embryogenic cells (Gordon-Kamm et al., Plant Cell 2: 603–618 (1990)). Transgenic plants are regenerated by standard corn regeneration techniques (Fromm, et al., Bio/Technology 8: 833–839 (1990); Gordon-Kamm et al., Plant Cell 2: 603–618 (1990)).

The plasmids prepared as described above can also be used to produce transgenic wheat and rice plants (Christou, Bio/Technology 9:957–962 (1991); Hiei et al., Plant J. 6:271–282 (1994); Aldemita and Hodges, Planta 199:612–617 (1996); Hiei et al., Plant Mol. Biol. 35:205–18 (1997)) that coordinately express genes of interest by following standard transformation protocols known to those skilled in the art for rice and wheat Vasil, et al. Bio/Technology 10:667–674 (1992); Vasil et al., Bio/Technology 11:1553–1558 (1993); Weeks et al., Plant Physiol. 102: 1077–1084 (1993)), where the bar gene is used as the selectable marker.

All references, publications, patent documents, web pages, and other documents cited or mentioned herein are hereby incorporated by reference in their entirety for all purposes. Although the invention has been described with reference to specific embodiments and examples, it should be understood that one of ordinary skill can make various modifications without departing from the spirit of the invention. The scope of the invention is not limited to the specific embodiments and examples provided.

TABLE 4

| Polynucleotide SEQ ID NO. | GID No | Trait | Category | Family | Comment | Polypeptide SEQ ID NO: | Conserved domains |
|---|---|---|---|---|---|---|---|
| 1 | G1272 | Seed glucosinolates | Seed biochemistry | PAZ | Altered composition | 2 | (TBD) |
| 3 | G1506 | Seed glucosinolates | Seed biochemistry | GATA/Zn | Altered composition | 4 | (7–33) |
| 5 | G1897 | Seed glicosinolates | Seed biochemistry | Z-Dof | Altered glucosinolate composition | 6 | (34–62) |
| 7 | G1946 | Seed glicosinolates | Seed biochemistry | HS | Increase in M3950 | 8 | (32–130) |
| 9 | G2113 | Seed glucosinolates | Seed biochemistry | AP2 | Altered composition | 10 | (TBD) |
| 11 | G2117 | Seed glucosinolates | Seed biochemistry | bZIP | Decrease in M39496 | 12 | (46–106) |
| 13 | G2155 | Seed glucosinolates | Seed biochemistry | AT-hook | Increase in M39497 | 14 | (18–38) |
| 15 | G2290 | Seed glucosinolates | Seed biochemistry | WRKY | Increase in M39496 | 16 | (147–205) |
| 17 | G2340 | Seed glucosinolates | Seed biochemistry | MYB-(R1)R2R3 | Altered glucosinolate profile | 18 | (14–120) |
| 19 | G671 | Seed glucosinolates | Seed biochemistry | MYB-(R1)R2R3 | Altered glucosinolate profile | 20 | (15–115) |
| 21 | G353 | Seed glucosinolates | Seed biochemistry | Z-C2H2 | Increase in M39494 | 22 | (41–61, 84–104) |
| 23 | G484 | Seed glucosinolates | Seed biochemistry | CAAT | Altered glucosinolate profile | 24 | (11–104) |
| 25 | G674 | Seed glucosinolates | Seed biochemistry | MYB-(R1)R2R3 | Increase in M39501 | 26 | (20–120) |
| 27 | G1052 | Seed prenyl lipids | Seed biochemistry | bZIP | Altered composition | 28 | (201–261) |
| 29 | G1328 | Seed prenyl lipids | Seed biochemistry | MYB-(R1)R2R3 | Decreased seed lutein | 30 | (14–119) |
| 31 | G1930 | Seed prenyl lipids | Seed biochemistry | AP2 | Increased chlorophyll content | 32 | (59–124) |
| 33 | G214 | Seed prenyl lipids; leaf fatty acids; prenyl lipids | Seed biochemistry; leaf biochemistry | MYB-related | Increased seed lutein; increased leaf fatty acids; increased chlorophyll, carotenoids | 34 | (22–71) |
| 35 | G2509 | Seed prenyl lipids | Seed biochemistry | AP2 | Increase in alpha-tocopherol | 36 | (89–156) |
| 37 | G2520 | Seed prenyl lipids; leaf glucosinolates | Seed biochemistry; leaf biochemistry | HLH/MYC | Altered tocopherol composition; increase in M39478 | 38 | (135–206) |
| 39 | G259 | Seed prenyl lipids | Seed biochemistry | HS | Increase in alpha-tocopherol | 40 | (27–131) |
| 41 | G490 | Seed prenyl lipids | Seed biochemistry | CAAT | Altered tocopherol composition | 42 | (48–143) |
| 43 | G652 | Seed prenyl lipids; leaf glucosinolates | Seed biochemistry; leaf biochemistry | Z-CLDSH | Increase in alpha-tocopherol; increase in M39480 | 44 | (28–49, 137–151, 182–196) |
| 45 | G748 | Seed prenyl lipids | Seed biochemistry | Z-Dof | Increased lutein content | 46 | (112–140) |
| 47 | G883 | Seed prenyl lipids | Seed biochemistry | WRKY | Decreased seed lutein | 48 | (245–302) |
| 49 | G20 | Seed sterols | Seed biochemistry | AP2 | Increase in campesterol | 50 | (68–144) |
| 51 | G974 | Seed oil content | Seed biochemistry | AP2 | Altered seed oil content | 52 | (81–140) |
| 53 | G2343 | Seed oil content | Seed biochemistry | MYB-(R1)R2R3 | Altered seed oil content | 54 | (14–116) |
| 55 | G1777 | Seed oil and protein content | Seed biochemistry | RING/C3HC4 | Altered seed oil and protein content | 56 | (124–247) |
| 57 | G229 | Biochemistry: other | Biochem: misc | MYB-(R1)R2R3 | Up-regulation of genes involved in secondary metabolism | 58 | (14–120) |

TABLE 4-continued

| Poly-nucleo-tide SEQ ID NO. | GID No | Trait | Category | Family | Comment | Poly-peptide SEQ ID NO: | Conserved domains |
|---|---|---|---|---|---|---|---|
| 59 | G663 | Biochemistry: other | Biochem: misc | MYB-(R1)R2R3 | Increased anthocyanins in leaf, root, seed | 60 | (9–111) |
| 61 | G362 | Biochemistry: other | Biochem: misc | Z-C2H2 | Increased trichome density and trichome products; increased anthocyanins in various tissues | 62 | (62–82) |
| 63 | G2105 | Biochemistry: other | Biochem: misc | TH | Increased trichome density and trichome products | 64 | (100–153) |
| 65 | G47 | Biochemistry: other | Biochem: misc | AP2 | Modification of lignin content | 66 | (11–80) |
| 67 | G2123 | Biochemistry: other | Biochem: misc | GF14 | Putative 14-3-3 protein | 68 | (99–109) |
| 69 | G1266 | Leaf fatty acids, insoluble sugars | Leaf biochemistry | AP2 | Changes in leaf fatty acids, insoluble sugars | 70 | (79–147) |
| 71 | G1337 | Leaf fatty acids | Leaf biochemistry | Z-CO-like | Altered leaf fatty acid composition | 72 | (9–75) |
| 73 | G1399 | Leaf fatty acids | Leaf biochemistry | AT-hook | Altered composition | 74 | (86–93) |
| 75 | G1465 | Leaf fatty acids | Leaf biochemistry | NAC | Altered composition | 76 | (242–306) |
| 77 | G1512 | Leaf fatty acids | Leaf biochemistry | RING/C3HC4 | Increase in 18:2 | 78 | (39–93) |
| 79 | G1537 | Leaf fatty acids | Leaf biochemistry | HB | Altered leaf fatty acid compositon | 80 | (14–74) |
| 81 | G2136 | Leaf fatty acids | Leaf biochemistry | MADS | Decreased in 18:3 | 82 | (43–100) |
| 83 | G2147 | Leaf fatty acids | Leaf biochemistry | HLH/MYC | Increase in 16:0, increase in 18:2 | 84 | (160–234) |
| 85 | G377 | Leaf fatty acids | Leaf biochemistry | RING/C3H2C3 | Altered composition | 86 | (85–128) |
| 87 | G962 | Leaf fatty acids | Leaf biochemistry | NAC | Altered composition | 88 | (53–175) |
| 89 | G975 | Leaf fatty acids | Leaf biochemistry | AP2 | Increased wax in leaves | 90 | (4–71) |
| 91 | G987 | Leaf fatty acids; leaf prenyl lipids | Leaf biochemistry | SCR | Reduction in 16:3 fatty acids; altered chlorophyll, tocopherol, carotenoid | 92 | (428–432, 704–708) |
| 93 | G1069 | Leaf glucosinolates | Leaf biochemistry | AT-hook | Altered composition | 94 | (67–74) |
| 95 | G1198 | Leaf glucosinolates | Leaf biochemistry | bZIP | Altered composition | 96 | (173–223) |
| 97 | G1322 | Leaf glucosinolates | Leaf biochemistry | MYB-(R1)R2R3 | Increase in M39480 | 98 | (26–130) |
| 99 | G1421 | Leaf glucosinolates | Leaf biochemistry | AP2 | Increased glucosinolate | 100 | (74–151) |
| 101 | G1794 | Leaf glucosinolates | Leaf biochemistry | AP2 | Increase in M39480 | 102 | (182–248) |
| 103 | G2144 | Leaf glucosinolates | Leaf biochemistry | HLH/MYC | Increase M39480 | 104 | (203–283) |
| 105 | G2512 | Leaf glucosinolates | Leaf biochemistry | AP2 | Increase in M39480 | 106 | (79–139) |
| 107 | G2552 | Leaf glucosinolates | Leaf biochemistry | HLH/MYC | Increase in M39480 | 108 | (121–187) |
| 109 | G264 | Leaf glucosinolates | Leaf biochemistry | HS | Increased M39481 | 110 | (24–114) |
| 111 | G681 | Leaf glucosinolates | Leaf biochemistry | MYB-(R1)R2R3 | Increase in M39480 | 112 | (14–120) |
| 113 | G1012 | Leaf insoluble sugars | Leaf biochemistry | WRKY | Decreased rhamnose | 114 | (30–86) |
| 115 | G1309 | Leaf insoluble sugars | Leaf biochemistry | MYB-(R1)R2R3 | Increased mannose | 116 | (9–114) |
| 117 | G158 | Leaf insoluble sugars | Leaf biochemistry | MADS | Increased rhamnose | 118 | (2–57) |
| 119 | G1641 | Leaf insoluble sugars | Leaf biochemistry | MYB-related | Increased rhamnose | 120 | (139–200) |
| 121 | G1865 | Leaf insoluble sugars | Leaf biochemistry | GRF-like | Increased galactose, decreased xylose | 122 | (124–149) |
| 123 | G2094 | Leaf insoluble sugars | Leaf biochemistry | GATA/Zn | Increase in arabinose | 124 | (43–68) |
| 125 | G211 | Leaf insoluble sugars | Leaf biochemistry | MYB-(R1)R2R3 | Increase in xylose | 126 | (24–137) |
| 127 | G242 | Leaf insoluble sugars | Leaf biochemistry | MYB-(R1)R2R3 | Increased arabinose | 128 | (6–105) |
| 129 | G2589 | Leaf insoluble sugars | Leaf biochemistry | MADS | Increase in arabinose | 130 | (2–57) |
| 131 | G274 | Leaf insoluble sugars | Leaf biochemistry | AKR | Increased leaf arabinose | 132 | (TBD) |
| 133 | G598 | Leaf insoluble sugars | Leaf biochemistry | DBP | Altered insoluble sugars | 134 | (205–263) |
| 135 | G1543 | Leaf prenyl lipids | Leaf biochemistry | HB | Increase in chlorophyll a and b | 136 | (135–195) |
| 137 | G280 | Leaf prenyl lipids | Leaf biochemistry | AT-hook | Increased delta and gamma tocopherol | 138 | (97–104, 130–137–155–162, 185–192) |
| 139 | G2131 | Leaf sterols | Leaf biochemistry | AP2 | Increase in campesterol | 140 | (50–186, 112–183) |
| 141 | G2424 | Leaf sterols | Leaf biochemistry | MYB-(R1)R2R3 | Increase in stigmastanol | 142 | (107–219) |
| 143 | G2583 | Leaf wax | Leaf biochemistry | AP2 | Altered epicuticular wax content or composition | 144 | (4–71) |
| 145 | G1387 | Leaf wax | Leaf biochemistry | AP2 | Altered epicuticular wax content or composition | 146 | (4–71) |
| 147 | G977 | Leaf wax | Leaf biochemistry | AP2 | Altered epicuticular wax content or composition | 148 | (5–72) |

TABLE 5

| SEQ ID NO | GID | Test Sequence ID | Smallest Sum Probability | Test Sequence Species | Test Sequence GenBank Annotation |
|---|---|---|---|---|---|
| 17 | G2340 | BG269414 | 1.60E − 45 | [Mesembryanthemum crystallinum] | LO-3478T3 Ice plant Lambda Un |
| 17 | G2340 | BG448527 | 5.30E − 41 | [Medicago truncatula] | NF036FO4RT1F1032 Developing root Medica |
| 17 | G2340 | AI730649 | 1.10E − 40 | [Gossypium hirsutum] | BNLGHi7595 Six-day Cotton fiber Gossypiu |
| 17 | G2340 | AW706006 | 1.20E − 39 | [Glycine max] | sk64f05.y1 Gm-c1016 Glycine max cDNA clone GENO |
| 17 | G2340 | PHMYBPH31 | 1.60E − 39 | [Petunia x hybrida] | P.hybrida myb.Ph3 gene encoding protein |
| 17 | G2340 | AI491024 | 4.10E − 39 | [Lycopersicon esculentum] | EST241733 tomato shoot, Cornell Lyc |
| 17 | G2340 | AMMIXTA | 1.40E − 38 | [Antirrhinum majus] | A. majus mixta mRNA. |
| 17 | G2340 | OSMYB1355 | 2.40E − 38 | [Oryza sativa] | O. sativa mRNA for myb factor, 1355 bp. |
| 17 | G2340 | BE495300 | 2.80E − 37 | [Secale cereale] | WHE1268_F02_K04ZS Secale cereale anther cDNA |
| 17 | G2340 | BG300704 | 4.70E − 36 | [Hordeum vulgare] | HVSMEb0018B03f Hordeum vulgare seedling sho |
| 17 | G2340 | gi2605617 | 1.50E − 44 | [Oryza sativa] | OSMYB1. |
| 17 | G2340 | gi20563 | 7.30E − 42 | [Petunia x hybrida] | protein 1. |
| 17 | G2340 | gi485867 | 4.00E − 41 | [Antirrhinum majus] | mixta. |
| 17 | G2340 | gi437327 | 2.00E − 39 | [Gossypium hirsutum] | MYB A; putative. |
| 17 | G2340 | gi19051 | 3.10E − 39 | [Hordeum vulgare] | MybHv1. |
| 17 | G2340 | gi227030 | 3.10E − 39 | [Hordeum vulgare var. distichum] | myb-related gene Hv1. |
| 17 | G2340 | gi1101770 | 6.40E − 38 | [Picea mariana] | MYB-like transcriptional factor MBF1. |
| 17 | G2340 | gi1430846 | 6.30E − 36 | [Lycopersicon esculentum] | myb-related transcription factor. |
| 17 | G2340 | gi5139814 | 2.50E − 35 | [Glycine max] | GmMYB29B2. |
| 17 | G2340 | gi6651292 | 1.70E − 34 | [Pimpinella brachycarpa] | myb-related transcription factor. |
| 143 | G2583 | AW928465 | 1.40E − 43 | [Lycopersicon esculentum] | EST337253 tomato flower buds 8 mm t |
| 143 | G2583 | BE023297 | 2.40E − 42 | [Glycine max] | sm80e10.y1 Gm-c1015 Glycine max cDNA clone GENO |
| 143 | G2583 | AP003615 | 1.60E − 30 | [Oryza sativa] | chromosome 6 clone P0486H12, *** SEQUENCING IN |
| 143 | G2583 | AU088998 | 2.90E − 21 | [Lotus japonicus] | AU088998 Lotus japonicus flower bud cDNA Lo |
| 143 | G2583 | AT001828 | 4.60E − 20 | [Brassica rapa subsp. pekinensis] | AT001828 Flower bud cDNA Br |
| 143 | G2583 | BG415973 | 2.40E − 18 | [Hordeum vulgare] | HVSMEk0009E06f Hordeum vulgare testa/perica |
| 143 | G2583 | BF647090 | 3.80E − 17 | [Medicago truncatula] | NF007A06EC1F1038 Elicited cell culture |
| 143 | G2583 | BG560598 | 2.90E − 16 | [Sorghum propinquum] | RHIZ2_59_D07.b1_A003 Rhizome2 (RHIZ2) So |
| 143 | G2583 | AW011200 | 6.60E − 16 | [Pinus taeda] | ST17H08 Pine TriplEx shoot tip library Pinus ta |
| 143 | G2583 | BF479478 | 1.60E − 15 | [Mesembryanthemum crystallinum] | L48-3155T3 Ice plant Lambda U |
| 143 | G2583 | gi19507 | 1.40E − 16 | [Lupinus polyphyllus] | put. pPLZ2 product (AA 1–164). |
| 143 | G2583 | gi10798644 | 1.00E − 12 | [Nicotiana tabacum] | AP2 domain-containing transcription fac |
| 143 | G2583 | gi8571476 | 4.70E − 12 | [Atriplex hortensis] | apetala2 domain-containing protein. |
| 143 | G2583 | gi2213783 | 8.40E − 12 | [Lycopersicon esculentum] | Pti5. |
| 143 | G2583 | gi8809573 | 5.30E − 11 | [Nicotiana sylvestris] | ethylene-responsive element binding |
| 143 | G2583 | gi4099914 | 8.40E − 11 | [Stylosanthes hamata] | ethylene-responsive element binding p |
| 143 | G2583 | gi6478845 | 8.90E − 11 | [Matricaria chamomilla] | ethylene-responsive element binding |
| 143 | G2583 | gi15290041 | 9.40E − 11 | [Oryza sativa] | hypothetical protein. |
| 143 | G2583 | gi12225884 | 1.70E − 10 | [Zea mays] | unnamed protein product. |
| 143 | G2583 | gi3264767 | 3.40E − 10 | [Prunus armeniaca] | AP2 domain containing protein. |
| 61 | G362 | BE581135 | 1.70E − 19 | [Medicago truncatula] | EST482865 GVN Medicago truncatula cDNA |
| 61 | G362 | BI206903 | 7.70E − 18 | [Lycopersicon esculentum] | EST524943 cTOS Lycopersicon esculen |
| 61 | G362 | BG047435 | 7.30E − 17 | [Glycine max] | saa71c12.y1 Gm-c1060 Glycine max cDNA clone GEN |
| 61 | G362 | AP003214 | 3.00E − 12 | [Oryza sativa] | chromosome 1 clone OSJNBa0063M16, SEQUENCI |
| 61 | G362 | BE366047 | 6.40E − 12 | [Sorghum bicolor] | PI1_30_G05.b2_A002 Pathogen induced (PI1) |
| 61 | G362 | BF616974 | 1.90E − 05 | [Hordeum vulgare] | HVSMEc0014C08f Hordeum vulgare seedling sho |
| 61 | G362 | BG444243 | 3.70E − 05 | [Gossypium arboreum] | GA_Ea0023L22f Gossypium arboreum 7–10 d |
| 61 | G362 | BE500265 | 0.00015 | [Triticum aestivum] | WHE0981_F11_L20ZS Wheat pre-anthesis spik |
| 61 | G362 | AB006604 | 0.00023 | [Petunia x hybrida] | mRNA for ZPT2-9, complete cds. |
| 61 | G362 | AI163084 | 0.0004 | [Populus tremula x Populus tremuloides] | A031p65u Hybrid aspen |
| 61 | G362 | gi15528588 | 4.20E − 15 | [Oryza sativa] | hypothetical protein. |
| 61 | G362 | gi2346984 | 3.80E − 08 | [Petunia x hybrida] | ZPT2-9. |
| 61 | G362 | gi7228329 | 0.012 | [Medicago sativa] | putative TFIIIA (or kruppel)-like zinc fi |
| 61 | G362 | gi1763063 | 0.016 | [Glycine max] | SCOF-1. |
| 61 | G362 | gi485614 | 0.026 | [Triticum aestivum] | WZF1. |
| 61 | G362 | gi4666360 | 0.03 | [Datisca glomerata] | zinc-finger protein 1. |
| 61 | G362 | gi2058504 | 0.079 | [Brassica rapa] | zinc-finger protein-1. |
| 61 | G362 | gi861091 | 0.08 | [Pisum sativum] | putative zinc finger protein. |
| 61 | G362 | gi2981169 | 0.42 | [Nicotiana tabacum] | osmotic stress-induced zinc-finger prot |
| 63 | G2105 | BM110736 | 3.70E − 45 | [Solanum tuberosum] | EST558272 potato roots Solanum tuberosum |
| 63 | G2105 | BF646615 | 6.60E − 36 | [Medicago truncatula] | NF066008EC1F1065 Elicited cell culture |
| 63 | G2105 | AB052729 | 9.50E − 30 | [Pisum sativum] | mRNA for DNA-binding protein DF1, complete cd |
| 63 | G2105 | OSJN00022 | 1.10E − 26 | [Oryza sativa] | chromosome 4 clone OSJNBa0011L07, *** SEQUENC |
| 63 | G2105 | AI777252 | 4.20E − 25 | [Lycopersicon esculentum] | EST258217 tomato resistant, Cornell |
| 63 | G2105 | BM500043 | 6.70E − 24 | [Zea mays] | 952036C09.y1 952 - BMS tissue from Walbot Lab (red ()chromosome 2 do |
| 63 | G2105 | AP004839 | 1.90E − 23 | [Oryza sativa (japonica cultivar-group)] | chromosome 2 do |
| 63 | G2105 | AW596787 | 2.30E − 20 | [Glycine max] | sj16f10.y1 Gm-c1032 Glycine max cDNA clone GENO |
| 63 | G2105 | AV410715 | 8.70E − 20 | [Lotus japonicus] | AV410715 Lotus japonicus young plants (two- |
| 63 | G2105 | BM357046 | 3.10E − 14 | [Triphysaria versicolor] | 16I-G5 Triphysaria versicolor root-t |
| 63 | G2105 | gi13646986 | 7.50E − 32 | [Pisum sativum] | DNA-binding protein DF1. |
| 63 | G2105 | gi20249 | 1.30E − 27 | [Oryza sativa] | gt-2. |
| 63 | G2105 | gi18182311 | 8.20E − 22 | [Glycine max] | GT-2 factor. |
| 63 | G2105 | gi8096269 | 0.24 | [Nicotiana tabacum] | KED. |
| 65 | G47 | BE320193 | 5.90E − 23 | [Medicago truncatula] | NF024B04RT1F1029 Developing root Medica |
| 65 | G47 | AP003379 | 8.90E − 20 | [Oryza sativa] | chromosome 1 clone P0408G07, *** SEQUENCING IN |

TABLE 5-continued

| SEQ ID NO | GID | Test Sequence ID | Smallest Sum Probability | Test Sequence Species | Test Sequence GenBank Annotation |
|---|---|---|---|---|---|
| 65 | G47 | AW220454 | 7.90E − 16 | [Lycopersicon esculentum] | EBT302937 tomato root during/after |
| 65 | G47 | BI434553 | 8.90E − 16 | [Solanum tuberosum] | EST537314 P. infestans-challenged leaf So |
| 65 | G47 | BF610198 | 1.30E − 15 | [Pinus taeda] | NXSI_055_H04_F NXSI (Nsf Xylem Side wood Inclin |
| 65 | G47 | BE659994 | 2.50E − 15 | [Glycine max] | 4-G2 GmaxSC Glycine max cDNA, mRNA sequence. |
| 65 | G47 | BG446456 | 5.00E − 15 | [Gossypium arboreum] | GA_Eb0034M18f Gossypium arboreum 7–10 d |
| 65 | G47 | BG321374 | 1.10E − 14 | [Descurainia sophia] | Ds01_06d08_R Ds01_AAFC_ECORC_cold_stress |
| 65 | G47 | AI728590 | 2.40E − 14 | [Gossypium hirsutum] | BNLGHi11133 Six-day Cotton fiber Gossypi |
| 65 | G47 | gi14140155 | 2.90E − 16 | [Oryza sativa] | putative AP2 domain transcription factor. |
| 65 | G47 | gi5616086 | 7.90E − 14 | [Brassica napus] | dehydration responsive element binding pro |
| 65 | G47 | gi12225916 | 8.70E − 14 | [Zea mays] | unnamed protein product. |
| 65 | G47 | gi8571476 | 1.30E − 13 | [Atriplex hortensis] | apetala2 domain-containing protein. |
| 65 | G47 | gi8980313 | 9.00E − 13 | [Catharanthus roseus] | AP2-domain DNA-binding protein. |
| 65 | G47 | gi6478845 | 5.00E − 12 | [Matricaria chamomilla] | ethylene-responsive element binding |
| 65 | G47 | gi1208498 | 6.40E − 12 | [Nicotiana tabacum] | EREBP-2. |
| 65 | G47 | gi8809573 | 2.20E − 11 | [Nicotiana sylvestris] | ethylene-responsive element binding |
| 65 | G47 | gi7528276 | 3.40E − 11 | [Mesembryanthemum crystallinum] | AP2-related transcription f |
| 65 | G47 | gi3342211 | 4.50E − 11 | [Lycopersicon esculentum] | Pti4. |
| 89 | G975 | AP003615 | 1.10E − 51 | [Oryza sativa] | chromosome 6 clone P0486H12, *** SEQUENCING IN |
| 89 | G975 | BG642554 | 1.10E − 50 | [Lycopersicon esculentum] | E5T356031 tomato flower buds, anthe |
| 89 | G975 | AW705973 | 3.20E − 45 | [Glycine max] | sk64c02.y1 Gm-c1016 Glycine max cDNA clone GENO |
| 89 | G975 | AT001828 | 4.80E − 34 | [Brassica rapa subsp. pekinensis] | AT001828 Flower bud cDNA Br |
| 89 | G975 | BG415973 | 3.70E − 29 | [Hordeum vulgare] | HVSMEk0009E06f Hordeum vulgare testa/perica |
| 89 | G975 | AU088998 | 2.10E − 27 | [Lotus japonicus] | AU088998 Lotus japonicus flower bud cDNA Lo |
| 89 | G975 | AL377839 | 8.40E − 21 | [Medicago truncatula] | MtBB34C04F1 MtBB Medicago truncatula cD |
| 89 | G975 | BF479478 | 2.20E − 18 | [Mesembryanthemum crystallinum] | L48-3155T3 Ice plant Lambda U |
| 89 | G975 | BG560598 | 3.40E − 18 | [Sorghum propinquum] | RHIZ2_59_D07.b1_A003 Rhizome2 (RH IZ2) So |
| 89 | G975 | L46408 | 5.90E − 18 | [Brassica rapa] | BNAF1258 Mustard flower buds Brassica rapa cD |
| 89 | G975 | gi19507 | 2.10E − 19 | [Lupinus polyphyllus] | put. pPLZ2 product (AA 1–164). |
| 89 | G975 | gi2213783 | 1.80E − 15 | [Lycopersicon esculentum] | Pti5. |
| 89 | G975 | gi8571476 | 2.80E − 14 | [Atriplex hortensis] | apetala2 domain-containing protein. |
| 89 | G975 | gi4099914 | 7.90E − 14 | [Stylosanthes hamata] | ethylene-responsive element binding p |
| 89 | G975 | qi6478845 | 3.40E − 13 | [Matricaria chamomilla] | ethylene-responsive element binding |
| 89 | G975 | gi12225884 | 5.70E − 13 | [Zea mays] | unnamed protein product. |
| 89 | G975 | qi8809573 | 7.00E − 13 | [Nicotiana sylvestris] | ethylene-responsive element binding |
| 89 | G975 | gi15290041 | 1.20E − 12 | [Oryza sativa] | hypothetical protein. |
| 89 | G975 | gi8980313 | 1.20E − 12 | [Catharanthus roseus] | AP2-domain DNA-binding protein. |
| 89 | G975 | gi7528276 | 1.30E − 12 | [Mesembryanthemum crystallinum] | AP2-related transcription f |
| 33 | G214 | AW979367 | 4.40E − 35 | [Lycopersicon esculentum] | EST310415 tomato root deficiency, C |
| 33 | G214 | BG156656 | 1.80E − 33 | [Glycine max] | sab31d11.y1 Gm-c1014 Glycine max cDNA clone GEN |
| 33 | G214 | BE597638 | 5.40E − 28 | [Sorghum bicolor] | PI1_72_C05.b1_A002 Pathogen induced 1 (PI1) |
| 33 | G214 | BI272895 | 5.70E − 26 | [Medicago truncatula] | NF091A11FL1F1084 Developing flower Medi |
| 33 | G214 | BE129981 | 3.90E − 23 | [Zea mays] | 945034C05.X1 945 - Mixed adult tissues from Walbot |
| 33 | G214 | BF889434 | 7.50E − 14 | [Oryza sativa] | EST003 Magnaporthe grisea infected 16-day-old |
| 33 | G214 | gi15528628 | 7.40E − 14 | [Oryza sativa] | hypothetical protein~similar to Oryza sativa |
| 33 | G214 | gi7677132 | 0.41 | [Secale cereale] | c-myb-like transcription factor. |
| 33 | G214 | gi13676413 | 0.43 | [Glycine max] | hypothetical protein. |
| 33 | G214 | gi12406993 | 0.57 | [Hordeum vulgare] | MCB1 protein. |
| 33 | G214 | gi940288 | 0.85 | [Pisum sativum] | protein localized in the nucleoli of pea nu |
| 33 | G214 | gi1279563 | 0.92 | [Medicago sativa] | nuM1. |
| 33 | G214 | gi12005328 | 0.98 | [Hevea brasiliensis] | unknown. |
| 33 | G214 | gi7688744 | 0.99 | [Lycopersicon esculentum] | ascl. |
| 33 | G214 | gi1070004 | 0.99 | [Brassica napus] | Biotin carboxyl carrier protein. |
| 33 | G214 | gi5326994 | 1 | [Daucus carota] | DNA topoisomerase I. |
| 51 | G974 | BI421315 | 7.10E − 54 | [Lycopersicon esculentum] | EST531981 tomato callus, TAMU Lycop |
| 51 | G974 | AI966402 | 9.40E − 47 | [Glycine max] | sc38e09.y1 Gm-c1014 Glycine max cDNA clone GENO |
| 51 | G974 | AF274033 | 1.70E − 43 | [Atriplex hortensis] | apetala2 domain-containing protein mRNA, |
| 51 | G974 | BG592917 | 8.40E − 43 | [Solanum tuberosum] | EST491595 cSTS Solanum tuberosum cDNA do |
| 51 | G974 | AI166481 | 6.20E − 42 | [Populus balsamifera subsp. trichocarpa] | xylem.est.309 Poplar |
| 51 | G974 | AW776927 | 2.10E − 41 | [Medicago truncatula] | EST335992 DSIL Medicago truncatula cDNA |
| 51 | G974 | AP004119 | 2.70E − 41 | [Oryza sativa] | chromosome 2 clone OJ1288G09 *** SEQUENCING |
| 51 | G974 | BE918036 | 6.60E − 38 | [Sorghum bicolori] | OV1_1_B03.b1_A002 Ovary 1 (OV1) Sorghum bic |
| 51 | G974 | gi8571476 | 7.00E − 45 | [Atriplex hortensis] | apetala2 domain-containing protein. |
| 51 | G974 | gi14140155 | 4.40E − 20 | [Oryza sativa] | putative AP2 domain transcription factor. |
| 51 | G974 | gi3342211 | 9.10E − 20 | [Lycopersicon esculentum] | Pti4. |
| 51 | G974 | gi1208498 | 1.50E − 19 | [Nicotiana tabacum] | EREBP-2. |
| 51 | G974 | gi12225884 | 1.50E − 19 | [Zea mays] | unnamed protein product. |
| 51 | G974 | gi7528276 | 3.90E − 19 | [Mesembryanthemum crystallinum] | AP2-related transcription f |
| 51 | G974 | gi6809571 | 3.90E − 19 | [Nicotiana sylvestris] | ethylene-responsive element binding |
| 51 | G974 | gi1688233 | 3.SOE − 18 | [Solanum tuberosum] | DNA binding protein homolog. |
| 51 | G974 | gi3264767 | 9.40E − 18 | [Prunus armeniaca] | AP2 domain containing protein. |
| 51 | G974 | gi6478845 | 2.00E − 17 | [Matricaria chamomilla] | ethylene-responsive element binding |

TABLE 5-continued

| SEQ ID NO | GID | Test Sequence ID | Smallest Sum Probability | Test Sequence Species | Test Sequence GenBank Annotation |
|---|---|---|---|---|---|
| 53 | G2343 | BI311137 | 4.00E − 45 | [Medicago truncatula] | EST5312887 GESD Medicago truncatula cDN |
| 53 | G2343 | BO130765 | 5.10E − 45 | [Lycopersicon esculentum] | EST463657 tomato crown gall Lycoper |
| 53 | G2343 | AW672062 | 2.30E − 44 | [Sorghum bicolor] | LG1_354_G05.b1_A002 Light Grown 1 (LG1) Sor |
| 53 | G2343 | AV421932 | 2.70E − 42 | [Lotus japonicus] | AV421932 Lotus japonicus young plants (two- |
| 53 | G2343 | BE611938 | 9.10E − 42 | [Glycine max] | sr01h04.y1 Gm-c1049 Glycine max cDNA clone GENO |
| 53 | G2343 | BF464214 | 1.90E − 37 | [Triticum aestiYum] | WHE2309_F07_K13ZS Wheat pre-anthesis spik |
| 53 | G2343 | BG301022 | 4.30E − 35 | [Hordeum vulgare] | HVSMEb0019E16f Hordeum vulgare seedling sho |
| 53 | G2343 | AP003018 | 3.20E − 34 | [Oryza sativa] | genomic DNA, chromosome 1, BAC clone:OSJNBa000 |
| 53 | G2343 | BE495300 | 3.30E − 34 | [Secale cereale] | WHE1268_F02_K04ZS Secale cereale anther cDNA |
| 53 | G2343 | AI657290 | 3.50E − 34 | [Zea mays] | 486093A08.y1 486 - leaf primordia cDNA library fro |
| 53 | G2343 | gi1167486 | 9.50E − 53 | [Lycopersicon esculentum] | transcription factor. |
| 53 | G2343 | gi13366181 | 1.30E − 48 | [Oryza sativa] | putative transcription factor. |
| 53 | G2343 | gi2130045 | 1.50E − 37 | [Hordeum vulgare] | MybHv33 protein - barley. |
| 53 | G2343 | gi82310 | 1.60E − 34 | [Antirrhinum majus] | myb protein 330 - garden snapdragon. |
| 53 | G2343 | gi1732247 | 4.20E − 34 | [Nicotiana tabacum] | transcription factor Myb1. |
| 53 | G2343 | gi1841475 | 7.30E − 33 | [Pisum sativum] | Myb26. |
| 53 | G2343 | gi5139814 | 2.80E − 31 | [Glycine max] | GmMYB29B2. |
| 53 | G2343 | gi13346178 | 4.90E − 31 | [Gossypium hirsutum] | BNLGHi233. |
| 53 | G2343 | gi6651292 | 2.70E − 30 | [Pimpinella brachycarpa] | myb-related transcription factor. |
| 53 | G2343 | gi8247759 | 1.10E − 29 | [Triticum aestivum] | GAMyb protein. |
| 67 | G2123 | AF272573 | 1.30E − 50 | [Populus alba x Populus tremula] | clone INRA717-1-B4 14-3-3 pr |
| 67 | G2123 | BG581482 | 3.70E − 49 | [Medicago truncatula] | EST483216 GVN Medicago truncatula cDNA |
| 67 | G2123 | BG351501 | 9.60E − 49 | [Solanum tuberosum] | 109A12 Mature tuber lambda ZAP Solanum tu |
| 67 | G2123 | LETFT7 | 1.20E − 48 | [Lycopersicon esculentum] | mRNA for 14-3-3 protein, TFT7. |
| 67 | G2123 | AF228501 | 4.50E − 44 | [Glycine max] | 14-3-3-like protein mRNA, complete cds. |
| 67 | G2123 | BE643058 | 5.30E − 44 | [Ceratopteris richardii] | Cri2_7_M14_SP6 Ceratopteris Spore Li |
| 67 | G2123 | AF222805 | 7.00E − 43 | [Euphorbia esula] | 14-3-3-like protein mRNA, complete cds. |
| 67 | G2123 | PSA238682 | 1.30E − 42 | [Pisum sativum] | mRNA for 14-3-3-like protein, sequence 2. |
| 67 | G2123 | BG443252 | 1.80E − 40 | [Gossypium arboreum] | GA_Ea0020A13f Gossypium arboreum 7–10 d |
| 67 | G2123 | AI727536 | 9.70E − 40 | [Gossypium hirsutum] | BNLGHi8338 Six-day Cotton fiber Gossypiu |
| 67 | G2123 | gi6515890 | 1.80E − 52 | [Populus alba x Populus tremula] | 14-3-3 protein. |
| 67 | G2123 | gi8099061 | 3.70E − 52 | [Populus x canescens] | 14-3-3 protein. |
| 67 | G2123 | gi7576887 | 1.00E − 50 | [Glycine max] | 14-3-3-like protein. |
| 67 | G2123 | gi3925703 | 8.90E − 50 | [Lycopersicon esculentum] | 14-3-3 protein. |
| 67 | G2123 | gi6752903 | 8.90E − 50 | [Euphorbia esula] | 14-3-3-like protein. |
| 67 | G2123 | gi913214 | 2.10E − 47 | [Nicotiana tabacum] | T14-3-3. |
| 67 | G2123 | gi11138322 | 3.40E − 47 | [Vicia faba] | vf14-3-3d protein. |
| 67 | G2123 | gi2879818 | 8.50E − 46 | [Solanum tuberosum] | 14-3-3 protein. |
| 67 | G2123 | gi1015462 | 8.90E − 46 | [Chiamydomonas reinhardtii] | 14-3-3 protein. |
| 67 | G2123 | gi2921512 | 1.10E − 45 | [Fritillaria agrestis] | GF14 protein. |
| 55 | G1777 | AC091246 | 3.50E − 96 | [Oryza sativa] | chromosome 3 clone OSJNBa0002103, *** SEQUENCI |
| 55 | G1777 | BG136684 | 1.10E − 67 | [Lycopersicon pennellii] | EST477126 wild tomato pollen Lycoper |
| 55 | G1777 | AW703793 | 2.50E − 65 | [Glycine max] | sk1 2f08.y1 Gm-c1023 Glycine max cDNA clone GENO |
| 55 | G1777 | BE051040 | 6.60E − 59 | [Zea mays] | za71g01.b50 Maize Glume cDNAs Library Zea mays cDN |
| 55 | G1777 | AW933922 | 2.90E − 53 | [Lycopersicon esculentum] | EST359765 tomato fruit mature green |
| 55 | G1777 | BG600834 | 3.40E − 53 | [Solanum tuberosum] | EST505729 cSTS Solanum tuberosum cDNA do |
| 55 | G1777 | BF440069 | 3.20E − 39 | [Thellungiella salsuginea] | Sc0136 Thellungiella salsuginea ZA |
| 55 | G1777 | BF587440 | 4.20E − 25 | [Sorghum propinquum] | FM1_36_D07.b1_A003 Floral-Induced Merist |
| 55 | G1777 | BI267961 | 2.10E − 23 | [Medicago truncatula] | NF118E09IN1F1071 Insect herbivory Medic |
| 55 | G1777 | BE415217 | 2.50E − 22 | [Triticum aestivum] | MWLO25.F02F000208 ITEC MWL Wheat Root Lib |
| 55 | G1777 | gi1666171 | 7.50E − 24 | [Nicotiana plumbaginifolia] | unknown. |
| 55 | G1777 | gi643082 | 1 | [Fragaria x ananassa] | unknown. |
| 37 | G2520 | AW928317 | 4.60E − 27 | [Lycopersicon esculentum] | EST307050 tomato flower buds 8 mm t |
| 37 | G2520 | BF271147 | 2.60E − 26 | [Gossypium arboreum] | GA_Eb0010K15f Gossypium arboreum 7–10 d |
| 37 | G2520 | BE329654 | 2.60E − 26 | [Glycine max] | so67c05.y1 Gm-c1040 Glycine max cDNA clone GENO |
| 37 | G2520 | BG103016 | 4.40E − 23 | [Sorghum propinquum] | RHIZ2_36A10.b1_A003 Rhizome2 (RHIZ2) So |
| 37 | G2520 | BE606980 | 1.00E − 22 | [Triticum aestivum] | WHE0914_F04_K08ZS Wheat 5–15 DAP spike CD |
| 37 | G2520 | BG048756 | 1.60E − 22 | [Sorghum bicolor] | OV1_22 F05.b1_A002 Ovary 1 (OV1) Sorghum bi |
| 37 | G2520 | AI162779 | 2.10E − 22 | [Populus tremula x Populus tremuloides] | A023P62U Hybrid aspen |
| 37 | G2520 | BI270049 | 2.90E − 22 | [Medicago truncatula] | NF004DO4FL1F1042 Developing flower Medi |
| 37 | G2520 | BE921054 | 3.90E − 22 | [Solanum tuberosum] | EST424823 potato leaves and petioles Sola |
| 37 | G2520 | BF200249 | 9.10E − 22 | [Triticum monococcum] | DWHE2254_F11_L22ZE Triticum monococcum s |
| 37 | G2520 | gi11862964 | 4.50E − 16 | [Oryza sativa] | hypothetical protein. |
| 37 | G2520 | gi5923912 | 6.30E − 16 | [Tulipagesneriana] | bHLH transcription factor GBOF-1. |
| 37 | G2520 | gi6166283 | 0.69 | [Pinus taeda] | helix-loop-helix protein 1A. |
| 37 | G2520 | gi1086538 | 1 | [Oryza rufipogon] | transcriptional activator Rb homolog. |

We claim:

1. A method for producing a transgenic plant having increased tolerance to osmotic stress or drought relative to a wild-type plant of the same species, the method steps comprising:
   (a) producing an expression vector comprising a nucleotide sequence encoding a polypeptide comprising a conserved domain with at least 80% sequence identity to amino acid coordinates 11–80 of SEQ ID NO: 66; and
   (b) introducing the expression vector into the plant to produce a transgenic plant; wherein the polypeptide is overexpressed in the transgenic plant and said overexpression results in the transgenic plant having increased tolerance to the osmotic stress or drought.

2. The method of claim 1, wherein the protein comprises a conserved domain with at least 85% sequence identity to amino acid coordinates 11–80 of SEQ ID NO: 66.

3. The method of claim 1, wherein the nucleotide sequence encodes SEQ ID NO: 66.

4. The method of claim 1, wherein the nucleotide sequence comprises SEQ ID NO: 65 or a sequence that is fully complementary to SEQ ID NO: 65.

5. The method of claim 1, wherein the transgenic plant is a seed comprising the polypeptide.

6. The method of claim 1, wherein under conditions of osmotic stress the transgenic plant has larger size and more root growth relative to the wild-type plant.

7. The method of claim 1, wherein the expression vector comprises a constitutive, inducible, or tissue-specific promoter operably linked to the nucleotide sequence.

8. The method of claim 1, wherein the polypeptide is expressed in the transgenic plant and regulates transcription of a gene.

9. The method of claim 1, wherein the expression vector is comprised within a host cell.

10. The method of claim 1, wherein the transgenic plant comprises a dominant selectable marker.

11. A method for producing a transgenic plant having delayed flowering relative to a wild-type plant of the same species, the method steps comprising:
    (a) producing an expression vector comprising a nucleotide sequence encoding a polypeptide comprising a conserved domain with at least 80% sequence identity to amino acid coordinates 11–80 of SEQ ID NO: 66; and
    (b) introducing the expression vector into the plant to produce a transgenic plant; wherein the polypeptide is overexpressed in the transgenic plant and said overexpression results in the transgenic plant having the delayed flowering.

12. The method of claim 11, wherein the protein comprises a conserved domain with at least 85% sequence identity to amino acid coordinates 11–80 of SEQ ID NO: 66.

13. The method of claim 11, wherein the nucleotide sequence encodes SEQ ID NO: 66.

14. The method of claim 11, wherein the nucleotide sequence comprises SEQ ID NO: 65 or a sequence that is fully complementary to SEQ ID NO: 65.

15. The method of claim 11, wherein the transgenic plant comprises a dominant selectable marker.

16. The method of claim 11, wherein the delayed flowering results in increases in yield.

17. The method of claim 11, wherein the expression vector comprises a constitutive, inducible, or tissue-specific promoter operably linked to the nucleotide sequence.

18. The method of claim 11, wherein the polypeptide is expressed in the transgenic plant and regulates transcription of a gene.

19. The method of claim 11, wherein the expression vector is comprised within a host cell.

20. The method of claim 11, wherein the transgenic plant is a seed comprising the polypeptide.

21. A method for producing a transgenic plant having increased lignin content relative to a wild-type plant of the same species, the method steps comprising:
    (a) producing an expression vector comprising a nucleotide sequence encoding a polypeptide comprising a conserved domain with at least 80% sequence identity to amino acid coordinates 11–80 of SEQ ID NO: 66; and
    (b) introducing the expression vector into the plant to produce a transgenic plant;
    wherein the polypeptide is overexpressed in the transgenic plant and said overexpression results in the transgenic plant having increased lignification relative to the wild-type plant.

22. The method of claim 21, wherein the protein comprises a conserved domain with at least 85% sequence identity to amino acid coordinates 11–80 of SEQ ID NO: 66.

23. The method of claim 21, wherein the nucleotide sequence encodes SEQ ID NO: 66.

24. The method of claim 21, wherein the nucleotide sequence comprises SEQ ID NO: 65 or a sequence that is fully complementary to SEQ ID NO: 65.

25. The method of claim 21, wherein the transgenic plant comprises a dominant selectable marker.

26. The method of claim 21, wherein the expression vector compnses a constitutive, inducible, or tissue-specific promoter operably linked to the nucleotide sequence.

27. The method of claim 21, wherein the polypepticle is expressed in the transgenic plant and regulates transcription of a gene.

28. The method of claim 21, wherein the expression vector is comprised within a host cell.

29. The method of claim 21, wherein the transgenic plant is a seed comprising the polypeptide.

* * * * *

SEQUENCE LISTING

<160> NUMBER OF SEQ ID NOS: 148

<210> SEQ ID NO 1
<211> LENGTH: 2793
<212> TYPE: DNA
<213> ORGANISM: Arabidopsis thaliana
<220> FEATURE:
<221> NAME/KEY: CDS
<222> LOCATION: (1)...(2793)

<400> SEQUENCE: 1

```
atg gat tca aca aat ggt aac gga gct gat ctt gaa tca gca aat ggg      48
Met Asp Ser Thr Asn Gly Asn Gly Ala Asp Leu Glu Ser Ala Asn Gly
 1               5                  10                  15 gca aac ggg agt ggg gtt act gag gca tta cca cct cct cca cca gtt      96
Ala Asn Gly Ser Gly Val Thr Glu Ala Leu Pro Pro Pro Pro Pro Val
             20                  25                  30 ata cct cca aat gtg gaa cca gtt cgt gtt aaa act gaa ctt gct gag     144
Ile Pro Pro Asn Val Glu Pro Val Arg Val Lys Thr Glu Leu Ala Glu
         35                  40                  45 aag aag ggg cca gtt cga gtt cct atg gct cga aaa gga ttt gga aca     192
Lys Lys Gly Pro Val Arg Val Pro Met Ala Arg Lys Gly Phe Gly Thr
     50                  55                  60 agg ggc caa aag atc ccc ttg tta aca aat cat ttc aaa gtc gat gtg     240
Arg Gly Gln Lys Ile Pro Leu Leu Thr Asn His Phe Lys Val Asp Val
 65                  70                  75                  80 gct aat ctt cag ggt cat ttc ttc cac tac agt gtg gct cta ttc tat     288
Ala Asn Leu Gln Gly His Phe Phe His Tyr Ser Val Ala Leu Phe Tyr
                 85                  90                  95 gat gat ggt cgt cct gtt gaa caa aag ggt gtt gga aga aaa atc ctt     336
Asp Asp Gly Arg Pro Val Glu Gln Lys Gly Val Gly Arg Lys Ile Leu
            100                 105                 110 gac aag gtg cat cag act tac cat tct gat ctg gat ggt aaa gag ttt     384
Asp Lys Val His Gln Thr Tyr His Ser Asp Leu Asp Gly Lys Glu Phe
        115                 120                 125 gct tat gac ggt gag aag acg ttg ttt aca tat gga gct ttg cct agt     432
Ala Tyr Asp Gly Glu Lys Thr Leu Phe Thr Tyr Gly Ala Leu Pro Ser
    130                 135                 140 aac aag atg gat ttt tct gtg gtg ctt gag gaa gta tct gct aca agt     480
Asn Lys Met Asp Phe Ser Val Val Leu Glu Glu Val Ser Ala Thr Ser
145                 150                 155                 160 aag gat ttt gtg agc agg gct aat gga aac gga agc ccc aat ggg aat     528
Lys Asp Phe Val Ser Arg Ala Asn Gly Asn Gly Ser Pro Asn Gly Asn
                165                 170                 175 gaa agt cca agt gat ggt gat agg aaa aga ctg cgt agg cct aac cgg     576
Glu Ser Pro Ser Asp Gly Asp Arg Lys Arg Leu Arg Arg Pro Asn Arg
            180                 185                 190 tcc aaa aac ttt aga gtg gag atc agc tat gcg gcc aaa att cct ctt     624
Ser Lys Asn Phe Arg Val Glu Ile Ser Tyr Ala Ala Lys Ile Pro Leu
        195                 200                 205 caa gct ctt gct aat gca atg cgg gga caa gaa tca gag aat tcc cag     672
Gln Ala Leu Ala Asn Ala Met Arg Gly Gln Glu Ser Glu Asn Ser Gln
    210                 215                 220 gag gca ata cgg gtt ctt gat atc ata ttg agg caa cat gct gct aga     720
Glu Ala Ile Arg Val Leu Asp Ile Ile Leu Arg Gln His Ala Ala Arg
225                 230                 235                 240 caa ggt tgc ttg ctt gtt cga cag tct ttt ttc cac aat gat cca acc     768
Gln Gly Cys Leu Leu Val Arg Gln Ser Phe Phe His Asn Asp Pro Thr
                245                 250                 255
```

-continued

| | | |
|---|---|---|
| aac tgt gaa cca gtt ggt ggt aac atc tta gga tgt agg gga ttt cac<br>Asn Cys Glu Pro Val Gly Gly Asn Ile Leu Gly Cys Arg Gly Phe His<br>260 265 270 | 816 |
| tcc agt ttc aga aca acg cag ggt ggc atg tca ctt aat atg gat gtt<br>Ser Ser Phe Arg Thr Thr Gln Gly Gly Met Ser Leu Asn Met Asp Val<br>275 280 285 | 864 |
| aca acc acc atg atc atc aag cct ggt cca gtg gtt gat ttc cta att<br>Thr Thr Thr Met Ile Ile Lys Pro Gly Pro Val Val Asp Phe Leu Ile<br>290 295 300 | 912 |
| gct aac caa aat gct agg gac cct tat tcg att gac tgg tct aag gct<br>Ala Asn Gln Asn Ala Arg Asp Pro Tyr Ser Ile Asp Trp Ser Lys Ala<br>305 310 315 320 | 960 |
| aaa cga acc ctt aag aac cta agg gta aag gtc agc ccc tca ggc caa<br>Lys Arg Thr Leu Lys Asn Leu Arg Val Lys Val Ser Pro Ser Gly Gln<br>325 330 335 | 1008 |
| gaa ttc aag ata acc gga ttg agt gac aag cct tgc agg gaa caa acg<br>Glu Phe Lys Ile Thr Gly Leu Ser Asp Lys Pro Cys Arg Glu Gln Thr<br>340 345 350 | 1056 |
| ttt gaa ttg aag aaa agg aac cca aat gaa aat gga gag ttc gaa act<br>Phe Glu Leu Lys Lys Arg Asn Pro Asn Glu Asn Gly Glu Phe Glu Thr<br>355 360 365 | 1104 |
| act gaa gtt aca gtt gct gac tac ttc cgc gat aca agg cat att gat<br>Thr Glu Val Thr Val Ala Asp Tyr Phe Arg Asp Thr Arg His Ile Asp<br>370 375 380 | 1152 |
| ttg caa tat tct gcg gat ttg cct tgc atc aat gtt ggg aag cca aag<br>Leu Gln Tyr Ser Ala Asp Leu Pro Cys Ile Asn Val Gly Lys Pro Lys<br>385 390 395 400 | 1200 |
| cga ccc act tac att cct ctc gag ctc tgc gcg ttg gtt cca ctt cag<br>Arg Pro Thr Tyr Ile Pro Leu Glu Leu Cys Ala Leu Val Pro Leu Gln<br>405 410 415 | 1248 |
| agg tac aca aaa gca ctt acc acg ttc caa aga tct gcc ctt gtt gag<br>Arg Tyr Thr Lys Ala Leu Thr Thr Phe Gln Arg Ser Ala Leu Val Glu<br>420 425 430 | 1296 |
| aaa tcc aga cag aaa ccc caa gag agg atg act gtt ctg tcc aaa gct<br>Lys Ser Arg Gln Lys Pro Gln Glu Arg Met Thr Val Leu Ser Lys Ala<br>435 440 445 | 1344 |
| ctg aaa gtt agc aac tat gat gcg gaa cca ctc ctg cga tcc tgt ggc<br>Leu Lys Val Ser Asn Tyr Asp Ala Glu Pro Leu Leu Arg Ser Cys Gly<br>450 455 460 | 1392 |
| att tcg atc agc tcc aac ttt act cag gtg gag ggt cgt gtt cta cca<br>Ile Ser Ile Ser Ser Asn Phe Thr Gln Val Glu Gly Arg Val Leu Pro<br>465 470 475 480 | 1440 |
| gct ccc aag ctg aaa atg gga tgt gga tct gaa acc ttt ccc aga aat<br>Ala Pro Lys Leu Lys Met Gly Cys Gly Ser Glu Thr Phe Pro Arg Asn<br>485 490 495 | 1488 |
| ggt cgc tgg aac ttc aac aac aag gaa ttt gtt gag ccc acc aaa att<br>Gly Arg Trp Asn Phe Asn Asn Lys Glu Phe Val Glu Pro Thr Lys Ile<br>500 505 510 | 1536 |
| caa cga tgg gtt gtt gtc aat ttc tct gct cgc tgt aat gta cgt caa<br>Gln Arg Trp Val Val Val Asn Phe Ser Ala Arg Cys Asn Val Arg Gln<br>515 520 525 | 1584 |
| gtt gtt gat gat ctg ata aaa att gga gga tca aaa gga att gaa att<br>Val Val Asp Asp Leu Ile Lys Ile Gly Gly Ser Lys Gly Ile Glu Ile<br>530 535 540 | 1632 |
| gct tct ccc ttt caa gtg ttt gag gag ggt aat caa ttc cgc cgt gct<br>Ala Ser Pro Phe Gln Val Phe Glu Glu Gly Asn Gln Phe Arg Arg Ala<br>545 550 555 560 | 1680 |
| cct cct atg att cgt gtt gag aac atg ttt aag gac atc caa tcg aaa<br>Pro Pro Met Ile Arg Val Glu Asn Met Phe Lys Asp Ile Gln Ser Lys<br>565 570 575 | 1728 |

| | | |
|---|---|---|
| ctc cct ggt gtc cca caa ttc ata cta tgt gtg ctc cct gac aaa aag<br>Leu Pro Gly Val Pro Gln Phe Ile Leu Cys Val Leu Pro Asp Lys Lys<br>580 585 590 | | 1776 |
| aac agt gat ctc tat ggt cca tgg aag aaa aaa aac tta act gaa ttt<br>Asn Ser Asp Leu Tyr Gly Pro Trp Lys Lys Lys Asn Leu Thr Glu Phe<br>595 600 605 | | 1824 |
| ggc att gtt act caa tgc atg gct cca acg cgg caa cct aat gat cag<br>Gly Ile Val Thr Gln Cys Met Ala Pro Thr Arg Gln Pro Asn Asp Gln<br>610 615 620 | | 1872 |
| tat ctt act aac tta ctt ctg aag att aat gca aag ctt gga ggc ctg<br>Tyr Leu Thr Asn Leu Leu Leu Lys Ile Asn Ala Lys Leu Gly Gly Leu<br>625 630 635 640 | | 1920 |
| aac tca atg tta agt gta gag cgt aca cct gcg ttc act gtg att tct<br>Asn Ser Met Leu Ser Val Glu Arg Thr Pro Ala Phe Thr Val Ile Ser<br>645 650 655 | | 1968 |
| aag gtt cca acc att atc ctt ggg atg gat gtt tca cat gga tct cct<br>Lys Val Pro Thr Ile Ile Leu Gly Met Asp Val Ser His Gly Ser Pro<br>660 665 670 | | 2016 |
| gga cag tct gat gtc ccg tcc atc gct gct gtg gtg agt tct agg gag<br>Gly Gln Ser Asp Val Pro Ser Ile Ala Ala Val Val Ser Ser Arg Glu<br>675 680 685 | | 2064 |
| tgg cca ctg ata tcc aaa tat aga gca tct gtt cgg aca cag cct tct<br>Trp Pro Leu Ile Ser Lys Tyr Arg Ala Ser Val Arg Thr Gln Pro Ser<br>690 695 700 | | 2112 |
| aag gct gag atg att gag tcc ctt gtc aag aaa aat gga act gaa gac<br>Lys Ala Glu Met Ile Glu Ser Leu Val Lys Lys Asn Gly Thr Glu Asp<br>705 710 715 720 | | 2160 |
| gat ggc att atc aag gag ttg ctg gta gat ttc tac acc agc tcg aat<br>Asp Gly Ile Ile Lys Glu Leu Leu Val Asp Phe Tyr Thr Ser Ser Asn<br>725 730 735 | | 2208 |
| aag aga aaa cca gag cat atc ata att ttc agg gat ggt gtg agt gaa<br>Lys Arg Lys Pro Glu His Ile Ile Ile Phe Arg Asp Gly Val Ser Glu<br>740 745 750 | | 2256 |
| tct caa ttc aat cag gtt ctg aat att gaa ctt gat cag atc atc gag<br>Ser Gln Phe Asn Gln Val Leu Asn Ile Glu Leu Asp Gln Ile Ile Glu<br>755 760 765 | | 2304 |
| gct tgc aag ctc tta gac gca aat tgg aac cca aag ttc ctt ttg ttg<br>Ala Cys Lys Leu Leu Asp Ala Asn Trp Asn Pro Lys Phe Leu Leu Leu<br>770 775 780 | | 2352 |
| gtg gct caa aag aat cat cat acc aag ttc ttc cag cca acg tct cct<br>Val Ala Gln Lys Asn His His Thr Lys Phe Phe Gln Pro Thr Ser Pro<br>785 790 795 800 | | 2400 |
| gaa aat gtt cct cca ggg aca atc att gac aac aaa ata tgt cac cca<br>Glu Asn Val Pro Pro Gly Thr Ile Ile Asp Asn Lys Ile Cys His Pro<br>805 810 815 | | 2448 |
| aag aac aat gat ttc tac ctc tgt gct cac gct gga atg att gga act<br>Lys Asn Asn Asp Phe Tyr Leu Cys Ala His Ala Gly Met Ile Gly Thr<br>820 825 830 | | 2496 |
| acc cgc cca act cac tac cac gtc ctg tat gat gag att ggt ttt tca<br>Thr Arg Pro Thr His Tyr His Val Leu Tyr Asp Glu Ile Gly Phe Ser<br>835 840 845 | | 2544 |
| gct gac gaa ctt cag gaa ctt gtc cac tcg ctc tcc tat gtg tac caa<br>Ala Asp Glu Leu Gln Glu Leu Val His Ser Leu Ser Tyr Val Tyr Gln<br>850 855 860 | | 2592 |
| aga agc acc agt gcc att tct gtt gtt gcg ccg atc tgc tat gct cac<br>Arg Ser Thr Ser Ala Ile Ser Val Val Ala Pro Ile Cys Tyr Ala His<br>865 870 875 880 | | 2640 |
| ttg gca gct gct cag ctt ggg acg ttc atg aag ttt gaa gat cag tct<br>Leu Ala Ala Ala Gln Leu Gly Thr Phe Met Lys Phe Glu Asp Gln Ser | | 2688 |

```
                        885               890               895
gag aca tca tca agc cat ggt ggt atc aca gct cca gga cca atc tct         2736
Glu Thr Ser Ser Ser His Gly Gly Ile Thr Ala Pro Gly Pro Ile Ser
            900               905               910 gtt gca cag ctc cca aga ctc aaa gac aac gtc gcc aac tcc atg ttc         2784
Val Ala Gln Leu Pro Arg Leu Lys Asp Asn Val Ala Asn Ser Met Phe
            915               920               925 ttc tgt taa                                                              2793
Phe Cys *
    930
```

<210> SEQ ID NO 2
<211> LENGTH: 930
<212> TYPE: PRT
<213> ORGANISM: Arabidopsis thaliana

<400> SEQUENCE: 2

```
Met Asp Ser Thr Asn Gly Asn Gly Ala Asp Leu Glu Ser Ala Asn Gly
 1               5                  10                  15

Ala Asn Gly Ser Gly Val Thr Glu Ala Leu Pro Pro Pro Pro Val
            20                  25                  30

Ile Pro Pro Asn Val Glu Pro Val Arg Val Lys Thr Glu Leu Ala Glu
            35                  40                  45

Lys Lys Gly Pro Val Arg Val Pro Met Ala Arg Lys Gly Phe Gly Thr
 50                  55                  60

Arg Gly Gln Lys Ile Pro Leu Leu Thr Asn His Phe Lys Val Asp Val
 65                  70                  75                  80

Ala Asn Leu Gln Gly His Phe His Tyr Ser Val Ala Leu Phe Tyr
                85                  90                  95

Asp Asp Gly Arg Pro Val Glu Gln Lys Gly Val Gly Arg Lys Ile Leu
                100                 105                 110

Asp Lys Val His Gln Thr Tyr His Ser Asp Leu Asp Gly Lys Glu Phe
            115                 120                 125

Ala Tyr Asp Gly Glu Lys Thr Leu Phe Thr Tyr Gly Ala Leu Pro Ser
130                 135                 140

Asn Lys Met Asp Phe Ser Val Val Leu Glu Glu Val Ser Ala Thr Ser
145                 150                 155                 160

Lys Asp Phe Val Ser Arg Ala Asn Gly Asn Gly Ser Pro Asn Gly Asn
                165                 170                 175

Glu Ser Pro Ser Asp Gly Asp Arg Lys Arg Leu Arg Arg Pro Asn Arg
            180                 185                 190

Ser Lys Asn Phe Arg Val Glu Ile Ser Tyr Ala Ala Lys Ile Pro Leu
        195                 200                 205

Gln Ala Leu Ala Asn Ala Met Arg Gly Gln Glu Ser Glu Asn Ser Gln
    210                 215                 220

Glu Ala Ile Arg Val Leu Asp Ile Ile Leu Arg Gln His Ala Ala Arg
225                 230                 235                 240

Gln Gly Cys Leu Leu Val Arg Gln Ser Phe Phe His Asn Asp Pro Thr
                245                 250                 255

Asn Cys Glu Pro Val Gly Gly Asn Ile Leu Gly Cys Arg Gly Phe His
            260                 265                 270

Ser Ser Phe Arg Thr Thr Gln Gly Gly Met Ser Leu Asn Met Asp Val
        275                 280                 285

Thr Thr Thr Met Ile Ile Lys Pro Gly Pro Val Val Asp Phe Leu Ile
    290                 295                 300
```

```
Ala Asn Gln Asn Ala Arg Asp Pro Tyr Ser Ile Asp Trp Ser Lys Ala
305                 310                 315                 320

Lys Arg Thr Leu Lys Asn Leu Arg Val Lys Val Ser Pro Ser Gly Gln
            325                 330             335

Glu Phe Lys Ile Thr Gly Leu Ser Asp Lys Pro Cys Arg Glu Gln Thr
                340                 345             350

Phe Glu Leu Lys Lys Arg Asn Pro Asn Glu Asn Gly Glu Phe Glu Thr
            355                 360             365

Thr Glu Val Thr Val Ala Asp Tyr Phe Arg Asp Thr Arg His Ile Asp
        370              375                380

Leu Gln Tyr Ser Ala Asp Leu Pro Cys Ile Asn Val Gly Lys Pro Lys
385                 390                 395                 400

Arg Pro Thr Tyr Ile Pro Leu Glu Leu Cys Ala Leu Val Pro Leu Gln
                405                 410                 415

Arg Tyr Thr Lys Ala Leu Thr Thr Phe Gln Arg Ser Ala Leu Val Glu
            420                 425             430

Lys Ser Arg Gln Lys Pro Gln Glu Arg Met Thr Val Leu Ser Lys Ala
            435             440                 445

Leu Lys Val Ser Asn Tyr Asp Ala Glu Pro Leu Leu Arg Ser Cys Gly
    450                 455                 460

Ile Ser Ile Ser Ser Asn Phe Thr Gln Val Glu Gly Arg Val Leu Pro
465             470                 475                 480

Ala Pro Lys Leu Lys Met Gly Cys Gly Ser Glu Thr Phe Pro Arg Asn
            485                 490                 495

Gly Arg Trp Asn Phe Asn Asn Lys Glu Phe Val Glu Pro Thr Lys Ile
            500                 505                 510

Gln Arg Trp Val Val Asn Phe Ser Ala Arg Cys Asn Val Arg Gln
            515                 520                 525

Val Val Asp Asp Leu Ile Lys Ile Gly Gly Ser Lys Gly Ile Glu Ile
        530                 535                 540

Ala Ser Pro Phe Gln Val Phe Glu Glu Gly Asn Gln Phe Arg Arg Ala
545                 550                 555                 560

Pro Pro Met Ile Arg Val Glu Asn Met Phe Lys Asp Ile Gln Ser Lys
                565                 570                 575

Leu Pro Gly Val Pro Gln Phe Ile Leu Cys Val Leu Pro Asp Lys Lys
            580                 585                 590

Asn Ser Asp Leu Tyr Gly Pro Trp Lys Lys Asn Leu Thr Glu Phe
            595                 600                 605

Gly Ile Val Thr Gln Cys Met Ala Pro Thr Arg Gln Pro Asn Asp Gln
    610                 615                 620

Tyr Leu Thr Asn Leu Leu Leu Lys Ile Asn Ala Lys Leu Gly Gly Leu
625                 630                 635                 640

Asn Ser Met Leu Ser Val Glu Arg Thr Pro Ala Phe Thr Val Ile Ser
                645                 650                 655

Lys Val Pro Thr Ile Ile Leu Gly Met Asp Val Ser His Gly Ser Pro
            660                 665                 670

Gly Gln Ser Asp Val Pro Ser Ile Ala Ala Val Val Ser Ser Arg Glu
            675                 680                 685

Trp Pro Leu Ile Ser Lys Tyr Arg Ala Ser Val Arg Thr Gln Pro Ser
            690                 695                 700

Lys Ala Glu Met Ile Glu Ser Leu Val Lys Lys Asn Gly Thr Glu Asp
705                 710                 715                 720

Asp Gly Ile Ile Lys Glu Leu Leu Val Asp Phe Tyr Thr Ser Ser Asn
```

-continued

```
                           725                 730                 735
Lys Arg Lys Pro Glu His Ile Ile Ile Phe Arg Asp Gly Val Ser Glu
                740                 745                 750
Ser Gln Phe Asn Gln Val Leu Asn Ile Glu Leu Asp Gln Ile Ile Glu
            755                 760                 765
Ala Cys Lys Leu Leu Asp Ala Asn Trp Asn Pro Lys Phe Leu Leu Leu
        770                 775                 780
Val Ala Gln Lys Asn His His Thr Lys Phe Phe Gln Pro Thr Ser Pro
785                 790                 795                 800
Glu Asn Val Pro Pro Gly Thr Ile Ile Asp Asn Lys Ile Cys His Pro
                805                 810                 815
Lys Asn Asn Asp Phe Tyr Leu Cys Ala His Ala Gly Met Ile Gly Thr
                820                 825                 830
Thr Arg Pro Thr His Tyr His Val Leu Tyr Asp Glu Ile Gly Phe Ser
            835                 840                 845
Ala Asp Glu Leu Gln Glu Leu Val His Ser Leu Ser Tyr Val Tyr Gln
        850                 855                 860
Arg Ser Thr Ser Ala Ile Ser Val Val Ala Pro Ile Cys Tyr Ala His
865                 870                 875                 880
Leu Ala Ala Ala Gln Leu Gly Thr Phe Met Lys Phe Glu Asp Gln Ser
                885                 890                 895
Glu Thr Ser Ser Ser His Gly Gly Ile Thr Ala Pro Gly Pro Ile Ser
                900                 905                 910
Val Ala Gln Leu Pro Arg Leu Lys Asp Asn Val Ala Asn Ser Met Phe
            915                 920                 925
Phe Cys
    930
```

<210> SEQ ID NO 3
<211> LENGTH: 1413
<212> TYPE: DNA
<213> ORGANISM: Arabidopsis thaliana
<220> FEATURE:
<221> NAME/KEY: CDS
<222> LOCATION: (1)...(1413)

<400> SEQUENCE: 3

```
atg ggg aag caa ggt cct tgc tat cac tgt gga gtt aca agt aca cct        48
Met Gly Lys Gln Gly Pro Cys Tyr His Cys Gly Val Thr Ser Thr Pro
  1               5                  10                  15 cta tgg aga aac ggg cca cca gag aag ccg gtg ttg tgc aat gcg tgt        96
Leu Trp Arg Asn Gly Pro Pro Glu Lys Pro Val Leu Cys Asn Ala Cys
             20                  25                  30 ggt tcg agg tgg aga act aaa gga tca tta gta aac tac aca cct ctt       144
Gly Ser Arg Trp Arg Thr Lys Gly Ser Leu Val Asn Tyr Thr Pro Leu
         35                  40                  45 cat gct cgt gct gaa ggt gat gag act gag att gag gat cat aga act       192
His Ala Arg Ala Glu Gly Asp Glu Thr Glu Ile Glu Asp His Arg Thr
     50                  55                  60 caa acg gtg atg att aag gga atg tct ttg aac aaa aag att ccc aag       240
Gln Thr Val Met Ile Lys Gly Met Ser Leu Asn Lys Lys Ile Pro Lys
 65                  70                  75                  80 agg aaa cca tat caa gaa aac ttc aca gtg aaa aga gct aac ttg gaa       288
Arg Lys Pro Tyr Gln Glu Asn Phe Thr Val Lys Arg Ala Asn Leu Glu
                 85                  90                  95 ttc cat acc ggt ttc aag agg aag gct ctg gat gaa gaa gct agc aat       336
Phe His Thr Gly Phe Lys Arg Lys Ala Leu Asp Glu Glu Ala Ser Asn
            100                 105                 110
```

| | |
|---|---|
| aga tcg agt tca gga tcg gtt gta tca aac tcc gag agc tgt gca caa<br>Arg Ser Ser Ser Gly Ser Val Val Ser Asn Ser Glu Ser Cys Ala Gln<br>115 120 125 | 384 |
| tct aat gcg tgg gac tcg act ttt cct tgt aag aga agg aca tgt gtg<br>Ser Asn Ala Trp Asp Ser Thr Phe Pro Cys Lys Arg Arg Thr Cys Val<br>130 135 140 | 432 |
| gga cgt cca aag gca gct tct tct gtt gaa aag ctc aca aag gat ctt<br>Gly Arg Pro Lys Ala Ala Ser Ser Val Glu Lys Leu Thr Lys Asp Leu<br>145 150 155 160 | 480 |
| tat act att cta caa gaa cag caa tct tct tgt ctc tct ggt act tca<br>Tyr Thr Ile Leu Gln Glu Gln Gln Ser Ser Cys Leu Ser Gly Thr Ser<br>165 170 175 | 528 |
| gag gaa gat ttg ctt ttt gag aat gaa aca cca atg ctg tta gga cat<br>Glu Glu Asp Leu Leu Phe Glu Asn Glu Thr Pro Met Leu Leu Gly His<br>180 185 190 | 576 |
| ggt agt gtt ctt atg aga gat cct cac tca ggt gct cga gaa gag gaa<br>Gly Ser Val Leu Met Arg Asp Pro His Ser Gly Ala Arg Glu Glu Glu<br>195 200 205 | 624 |
| tct gaa gct agc tca ctc tta gtt gag agc agc aag tct tca tca gtt<br>Ser Glu Ala Ser Ser Leu Leu Val Glu Ser Ser Lys Ser Ser Ser Val<br>210 215 220 | 672 |
| cat tct gtt aaa ttt ggt gga aaa gca atg aag cag gag caa gtg aag<br>His Ser Val Lys Phe Gly Gly Lys Ala Met Lys Gln Glu Gln Val Lys<br>225 230 235 240 | 720 |
| agg agc aaa tct caa gtc tta gga aga cat agt tca cta ctc tgt agc<br>Arg Ser Lys Ser Gln Val Leu Gly Arg His Ser Ser Leu Leu Cys Ser<br>245 250 255 | 768 |
| ata gat ttg aag gat gtt ttc aac ttt gat gag ttc ata gaa aat ttc<br>Ile Asp Leu Lys Asp Val Phe Asn Phe Asp Glu Phe Ile Glu Asn Phe<br>260 265 270 | 816 |
| aca gag gaa gaa cag caa aaa ctg atg aaa tta ctt cct caa gtt gac<br>Thr Glu Glu Glu Gln Gln Lys Leu Met Lys Leu Leu Pro Gln Val Asp<br>275 280 285 | 864 |
| tct gtt gat cgt cct gat agc ctc aga agc atg ttt gag agt tct caa<br>Ser Val Asp Arg Pro Asp Ser Leu Arg Ser Met Phe Glu Ser Ser Gln<br>290 295 300 | 912 |
| ttc aaa gag aac tta tcc ttg ttt cag caa ctt gtg gca gat ggt gtt<br>Phe Lys Glu Asn Leu Ser Leu Phe Gln Gln Leu Val Ala Asp Gly Val<br>305 310 315 320 | 960 |
| ttt gag aca aat tcg tct tat gca aaa ctt gaa gac att aag aca ctt<br>Phe Glu Thr Asn Ser Ser Tyr Ala Lys Leu Glu Asp Ile Lys Thr Leu<br>325 330 335 | 1008 |
| gca aag ctt gct tta tca gat cct aac aaa tcc cat ttg ttg gaa agc<br>Ala Lys Leu Ala Leu Ser Asp Pro Asn Lys Ser His Leu Leu Glu Ser<br>340 345 350 | 1056 |
| tat tac atg ctc aag aga aga gag att gaa gac tgt gtt act aca aca<br>Tyr Tyr Met Leu Lys Arg Arg Glu Ile Glu Asp Cys Val Thr Thr Thr<br>355 360 365 | 1104 |
| tca agg gtc tca agc ttg agt cca tcg aat aat aat agt ctt gta acc<br>Ser Arg Val Ser Ser Leu Ser Pro Ser Asn Asn Asn Ser Leu Val Thr<br>370 375 380 | 1152 |
| att gaa aga cct tgt gaa agc tta aac caa aac ttc tca gag aca aga<br>Ile Glu Arg Pro Cys Glu Ser Leu Asn Gln Asn Phe Ser Glu Thr Arg<br>385 390 395 400 | 1200 |
| ggt gtg atg aga agc ccg aaa gaa gtg atg aag att aga tca aag cac<br>Gly Val Met Arg Ser Pro Lys Glu Val Met Lys Ile Arg Ser Lys His<br>405 410 415 | 1248 |
| acc gaa gag aat tta gag aat agt gta tct tcc ttt aaa cct gtg agc<br>Thr Glu Glu Asn Leu Glu Asn Ser Val Ser Ser Phe Lys Pro Val Ser | 1296 |

-continued

```
                    420              425                430
tgt ggt gga cct ctg gtg ttt agc tat gaa gat aat gat att tct gat    1344
Cys Gly Gly Pro Leu Val Phe Ser Tyr Glu Asp Asn Asp Ile Ser Asp
        435                 440                445 cag gat ctt ctt ctt gat gtg ccg tcg aac ggc tca ttc cct caa gca    1392
Gln Asp Leu Leu Leu Asp Val Pro Ser Asn Gly Ser Phe Pro Gln Ala
450                 455                 460 gag ctt cta aac atg ata tga                                        1413
Glu Leu Leu Asn Met Ile *
465             470
```

<210> SEQ ID NO 4
<211> LENGTH: 470
<212> TYPE: PRT
<213> ORGANISM: Arabidopsis thaliana
<220> FEATURE:
<221> NAME/KEY: DOMAIN
<222> LOCATION: (7)...(33)
<223> OTHER INFORMATION: Conserved domain

<400> SEQUENCE: 4

Met Gly Lys Gln Gly Pro Cys Tyr His Cys Gly Val Thr Ser Thr Pro
1               5                   10                  15

Leu Trp Arg Asn Gly Pro Glu Lys Pro Val Leu Cys Asn Ala Cys
            20                  25                  30

Gly Ser Arg Trp Arg Thr Lys Gly Ser Leu Val Asn Tyr Thr Pro Leu
        35                  40                  45

His Ala Arg Ala Glu Gly Asp Glu Thr Glu Ile Glu Asp His Arg Thr
    50                  55                  60

Gln Thr Val Met Ile Lys Gly Met Ser Leu Asn Lys Lys Ile Pro Lys
65                  70                  75                  80

Arg Lys Pro Tyr Gln Glu Asn Phe Thr Val Lys Arg Ala Asn Leu Glu
                85                  90                  95

Phe His Thr Gly Phe Lys Arg Lys Ala Leu Asp Glu Glu Ala Ser Asn
            100                 105                 110

Arg Ser Ser Gly Ser Val Val Ser Asn Ser Glu Ser Cys Ala Gln
        115                 120                 125

Ser Asn Ala Trp Asp Ser Thr Phe Pro Cys Lys Arg Arg Thr Cys Val
130                 135                 140

Gly Arg Pro Lys Ala Ala Ser Ser Val Glu Lys Leu Thr Lys Asp Leu
145                 150                 155                 160

Tyr Thr Ile Leu Gln Glu Gln Gln Ser Ser Cys Leu Ser Gly Thr Ser
                165                 170                 175

Glu Glu Asp Leu Leu Phe Glu Asn Glu Thr Pro Met Leu Leu Gly His
            180                 185                 190

Gly Ser Val Leu Met Arg Asp Pro His Ser Gly Ala Arg Glu Glu Glu
        195                 200                 205

Ser Glu Ala Ser Ser Leu Leu Val Glu Ser Ser Lys Ser Ser Ser Val
    210                 215                 220

His Ser Val Lys Phe Gly Gly Lys Ala Met Lys Gln Glu Gln Val Lys
225                 230                 235                 240

Arg Ser Lys Ser Gln Val Leu Gly Arg His Ser Ser Leu Leu Cys Ser
                245                 250                 255

Ile Asp Leu Lys Asp Val Phe Asn Phe Asp Glu Phe Ile Glu Asn Phe
            260                 265                 270

Thr Glu Glu Glu Gln Gln Lys Leu Met Lys Leu Leu Pro Gln Val Asp
        275                 280                 285

```
Ser Val Asp Arg Pro Asp Ser Leu Arg Ser Met Phe Glu Ser Ser Gln
    290                 295                 300
Phe Lys Glu Asn Leu Ser Leu Phe Gln Gln Leu Val Ala Asp Gly Val
305                 310                 315                 320
Phe Glu Thr Asn Ser Ser Tyr Ala Lys Leu Glu Asp Ile Lys Thr Leu
                325                 330                 335
Ala Lys Leu Ala Leu Ser Asp Pro Asn Lys Ser His Leu Leu Glu Ser
            340                 345                 350
Tyr Tyr Met Leu Lys Arg Arg Glu Ile Glu Asp Cys Val Thr Thr Thr
        355                 360                 365
Ser Arg Val Ser Ser Leu Ser Pro Ser Asn Asn Asn Ser Leu Val Thr
    370                 375                 380
Ile Glu Arg Pro Cys Glu Ser Leu Asn Gln Asn Phe Ser Glu Thr Arg
385                 390                 395                 400
Gly Val Met Arg Ser Pro Lys Glu Val Met Lys Ile Arg Ser Lys His
                405                 410                 415
Thr Glu Glu Asn Leu Glu Asn Ser Val Ser Ser Phe Lys Pro Val Ser
            420                 425                 430
Cys Gly Gly Pro Leu Val Phe Ser Tyr Glu Asp Asn Asp Ile Ser Asp
        435                 440                 445
Gln Asp Leu Leu Leu Asp Val Pro Ser Asn Gly Ser Phe Pro Gln Ala
    450                 455                 460
Glu Leu Leu Asn Met Ile
465                 470

<210> SEQ ID NO 5
<211> LENGTH: 678
<212> TYPE: DNA
<213> ORGANISM: Arabidopsis thaliana
<220> FEATURE:
<221> NAME/KEY: CDS
<222> LOCATION: (1)...(678)

<400> SEQUENCE: 5 atg cct tct gaa ttc agt gaa tct cgt cgg gtt cct aag att ccc cac    48
Met Pro Ser Glu Phe Ser Glu Ser Arg Arg Val Pro Lys Ile Pro His
1               5                   10                  15 ggc caa gga gga tct gtt gcg att ccg acg gat caa caa gag cag ctt    96
Gly Gln Gly Gly Ser Val Ala Ile Pro Thr Asp Gln Gln Glu Gln Leu
            20                  25                  30 tct tgt cct cgc tgt gaa tca acc aac acc aag ttc tgt tac tac aac   144
Ser Cys Pro Arg Cys Glu Ser Thr Asn Thr Lys Phe Cys Tyr Tyr Asn
        35                  40                  45 aac tac aac ttc tca caa cct cgt cat ttc tgc aag tct tgt cgc cgt   192
Asn Tyr Asn Phe Ser Gln Pro Arg His Phe Cys Lys Ser Cys Arg Arg
    50                  55                  60 tac tgg act cat gga ggt act ctc cgt gac att ccc gtc ggt ggt gtt   240
Tyr Trp Thr His Gly Gly Thr Leu Arg Asp Ile Pro Val Gly Gly Val
65                  70                  75                  80 tcc cgt aaa agc tca aaa cgt tcc cgg act tat tcc tct gcc gct acc   288
Ser Arg Lys Ser Ser Lys Arg Ser Arg Thr Tyr Ser Ser Ala Ala Thr
                85                  90                  95 acc tcc gtt gtc gga agc cgg aac ttt ccc tta caa gct acg cct gtt   336
Thr Ser Val Val Gly Ser Arg Asn Phe Pro Leu Gln Ala Thr Pro Val
            100                 105                 110 ctt ttc cct cag tcg tct tcc aac ggc ggt atc acg acg gcg aag gga   384
Leu Phe Pro Gln Ser Ser Ser Asn Gly Gly Ile Thr Thr Ala Lys Gly
        115                 120                 125
```

| | | | | | | | | | | | | |
|---|---|---|---|---|---|---|---|---|---|---|---|---|
| agt | gct | tcg | tcg | ttc | tat | ggc | ggt | ttc | agc | tct | ttg | atc | aac | tac | aac | 432 |
| Ser | Ala | Ser | Ser | Phe | Tyr | Gly | Gly | Phe | Ser | Ser | Leu | Ile | Asn | Tyr | Asn | |
| | 130 | | | | | 135 | | | | | 140 | | | | | |
| gcc | gcc | gtg | agc | aga | aat | ggg | cct | ggt | ggc | ggg | ttt | aat | ggg | cca | gat | 480 |
| Ala | Ala | Val | Ser | Arg | Asn | Gly | Pro | Gly | Gly | Gly | Phe | Asn | Gly | Pro | Asp | |
| 145 | | | | | 150 | | | | | 155 | | | | | 160 | |
| gct | ttt | ggt | ctt | ggg | ctt | ggt | cac | ggg | tcg | tat | tat | gag | gac | gtc | aga | 528 |
| Ala | Phe | Gly | Leu | Gly | Leu | Gly | His | Gly | Ser | Tyr | Tyr | Glu | Asp | Val | Arg | |
| | | | | 165 | | | | | 170 | | | | | 175 | | |
| tat | ggg | caa | gga | ata | acg | gtc | tgg | ccg | ttt | tca | agt | ggc | gct | act | gat | 576 |
| Tyr | Gly | Gln | Gly | Ile | Thr | Val | Trp | Pro | Phe | Ser | Ser | Gly | Ala | Thr | Asp | |
| | | | 180 | | | | | 185 | | | | | 190 | | | |
| gct | gca | act | act | aca | agc | cac | att | gct | caa | ata | ccc | gcc | acg | tgg | cag | 624 |
| Ala | Ala | Thr | Thr | Thr | Ser | His | Ile | Ala | Gln | Ile | Pro | Ala | Thr | Trp | Gln | |
| | | 195 | | | | | 200 | | | | | 205 | | | | |
| ttt | gaa | ggt | caa | gag | agc | aaa | gtc | ggg | ttc | gtg | tct | gga | gac | tac | gta | 672 |
| Phe | Glu | Gly | Gln | Glu | Ser | Lys | Val | Gly | Phe | Val | Ser | Gly | Asp | Tyr | Val | |
| | 210 | | | | | 215 | | | | | 220 | | | | | |
| gcg | tga | | | | | | | | | | | | | | | 678 |
| Ala | * | | | | | | | | | | | | | | | |
| 225 | | | | | | | | | | | | | | | | |

<210> SEQ ID NO 6
<211> LENGTH: 225
<212> TYPE: PRT
<213> ORGANISM: Arabidopsis thaliana
<220> FEATURE:
<221> NAME/KEY: DOMAIN
<222> LOCATION: (34)...(62)
<223> OTHER INFORMATION: Conserved domain

<400> SEQUENCE: 6

```
Met Pro Ser Glu Phe Ser Glu Ser Arg Arg Val Pro Lys Ile Pro His
 1               5                  10                  15

Gly Gln Gly Gly Ser Val Ala Ile Pro Thr Asp Gln Gln Glu Gln Leu
            20                  25                  30

Ser Cys Pro Arg Cys Glu Ser Thr Asn Thr Lys Phe Cys Tyr Tyr Asn
        35                  40                  45

Asn Tyr Asn Phe Ser Gln Pro Arg His Phe Cys Lys Ser Cys Arg Arg
    50                  55                  60

Tyr Trp Thr His Gly Gly Thr Leu Arg Asp Ile Pro Val Gly Gly Val
65                  70                  75                  80

Ser Arg Lys Ser Ser Lys Arg Ser Arg Thr Tyr Ser Ser Ala Ala Thr
                85                  90                  95

Thr Ser Val Val Gly Ser Arg Asn Phe Pro Leu Gln Ala Thr Pro Val
            100                 105                 110

Leu Phe Pro Gln Ser Ser Ser Asn Gly Gly Ile Thr Thr Ala Lys Gly
        115                 120                 125

Ser Ala Ser Ser Phe Tyr Gly Gly Phe Ser Ser Leu Ile Asn Tyr Asn
    130                 135                 140

Ala Ala Val Ser Arg Asn Gly Pro Gly Gly Gly Phe Asn Gly Pro Asp
145                 150                 155                 160

Ala Phe Gly Leu Gly Leu Gly His Gly Ser Tyr Tyr Glu Asp Val Arg
                165                 170                 175

Tyr Gly Gln Gly Ile Thr Val Trp Pro Phe Ser Ser Gly Ala Thr Asp
            180                 185                 190

Ala Ala Thr Thr Thr Ser His Ile Ala Gln Ile Pro Ala Thr Trp Gln
        195                 200                 205
```

```
Phe Glu Gly Gln Glu Ser Lys Val Gly Phe Val Ser Gly Asp Tyr Val
    210                 215                 220

Ala
225

<210> SEQ ID NO 7
<211> LENGTH: 1605
<212> TYPE: DNA
<213> ORGANISM: Arabidopsis thaliana
<220> FEATURE:
<221> NAME/KEY: CDS
<222> LOCATION: (90)...(1547)

<400> SEQUENCE: 7
tctcacctat tgtaaaaatc accagtttcg tatataaaac cctaattttc tcaaaattcc    60
caaatattga cttggaatca aaatccga atg gat gtg agc aaa gta acc aca       113
                              Met Asp Val Ser Lys Val Thr Thr
                                1               5 agc gac ggc gga gga gat tca atg gag act aag cca tct cct caa cct     161
Ser Asp Gly Gly Gly Asp Ser Met Glu Thr Lys Pro Ser Pro Gln Pro
 10              15                  20 cag cct gcg gcg att cta agt tca aac gcg cct cct ccg ttt ctg agc     209
Gln Pro Ala Ala Ile Leu Ser Ser Asn Ala Pro Pro Pro Phe Leu Ser
 25                  30                  35                  40 aag acc tat gat atg gtt gat gat cac aat aca gat tcg att gtc tct     257
Lys Thr Tyr Asp Met Val Asp Asp His Asn Thr Asp Ser Ile Val Ser
                 45                  50                  55 tgg agt gct aat aac aac agt ttt atc gtt tgg aaa cca ccg gag ttc     305
Trp Ser Ala Asn Asn Asn Ser Phe Ile Val Trp Lys Pro Pro Glu Phe
             60                  65                  70 gct cgc gat ctt ctt cct aag aac ttt aag cat aat aat ttc tcc agc     353
Ala Arg Asp Leu Leu Pro Lys Asn Phe Lys His Asn Asn Phe Ser Ser
         75                  80                  85 ttc gtt aga cag ctt aat acc tat ggt ttc agg aag gtt gac cca gat     401
Phe Val Arg Gln Leu Asn Thr Tyr Gly Phe Arg Lys Val Asp Pro Asp
     90                  95                 100 aga tgg gaa ttt gcg aat gaa ggt ttt tta aga ggt cag aag cac ttg     449
Arg Trp Glu Phe Ala Asn Glu Gly Phe Leu Arg Gly Gln Lys His Leu
105                 110                 115                 120 cta caa tca ata act agg cga aaa cct gcc cat gga cag gga cag gga     497
Leu Gln Ser Ile Thr Arg Arg Lys Pro Ala His Gly Gln Gly Gln Gly
                125                 130                 135 cat cag cga tct cag cac tcg aat gga cag aac tca tct gtt agc gca    545
His Gln Arg Ser Gln His Ser Asn Gly Gln Asn Ser Ser Val Ser Ala
            140                 145                 150 tgt gtt gaa gtt ggc aaa ttt ggt ctc gaa gaa gaa gtt gaa agg ctt    593
Cys Val Glu Val Gly Lys Phe Gly Leu Glu Glu Glu Val Glu Arg Leu
        155                 160                 165 aaa aga gat aag aac gtc ctt atg caa gaa ctc gtc aga tta aga cag    641
Lys Arg Asp Lys Asn Val Leu Met Gln Glu Leu Val Arg Leu Arg Gln
    170                 175                 180 cag caa cag tcc act gat aac caa ctt caa acg atg gtt cag cgt ctc    689
Gln Gln Gln Ser Thr Asp Asn Gln Leu Gln Thr Met Val Gln Arg Leu
185                 190                 195                 200 cag ggc atg gag aat cgg caa caa caa tta atg tca ttc ctt gca aag    737
Gln Gly Met Glu Asn Arg Gln Gln Gln Leu Met Ser Phe Leu Ala Lys
                205                 210                 215 gca gta caa agc cct cat ttt cta tct caa ttc tta cag cag cag aat    785
Ala Val Gln Ser Pro His Phe Leu Ser Gln Phe Leu Gln Gln Gln Asn
            220                 225                 230
```

```
cag caa aac gag agt aat agg cgc atc agt gat acc agt aag aag cgg      833
Gln Gln Asn Glu Ser Asn Arg Arg Ile Ser Asp Thr Ser Lys Lys Arg
            235                 240                 245 aga ttc aag cga gac ggc att gtc cgt aat aat gat tct gct act cct      881
Arg Phe Lys Arg Asp Gly Ile Val Arg Asn Asn Asp Ser Ala Thr Pro
250                 255                 260 gat gga cag ata gtg aag tat caa cct cca atg cac gag caa gcc aaa      929
Asp Gly Gln Ile Val Lys Tyr Gln Pro Pro Met His Glu Gln Ala Lys
265                 270                 275                 280 gca atg ttt aaa cag ctt atg aag atg gaa cct tac aaa acc ggc gat      977
Ala Met Phe Lys Gln Leu Met Lys Met Glu Pro Tyr Lys Thr Gly Asp
            285                 290                 295 gat ggt ttc ctt cta ggt aat ggt acg tct act acc gag gga aca gag     1025
Asp Gly Phe Leu Leu Gly Asn Gly Thr Ser Thr Thr Glu Gly Thr Glu
300                 305                 310 atg gag act tca tca aac caa gta tcg ggt ata act ctt aag gaa atg     1073
Met Glu Thr Ser Ser Asn Gln Val Ser Gly Ile Thr Leu Lys Glu Met
            315                 320                 325 cct aca gct tct gag ata cag tca tca tca cca att gaa aca act cct     1121
Pro Thr Ala Ser Glu Ile Gln Ser Ser Ser Pro Ile Glu Thr Thr Pro
330                 335                 340 gaa aat gtt tcg gca gca tca gaa gca acc gag aac tgt att cct tca     1169
Glu Asn Val Ser Ala Ala Ser Glu Ala Thr Glu Asn Cys Ile Pro Ser
345                 350                 355                 360 cct gat gat cta act ctt ccc gac ttc act cat atg cta ccg gaa aat     1217
Pro Asp Asp Leu Thr Leu Pro Asp Phe Thr His Met Leu Pro Glu Asn
            365                 370                 375 aat tca gag aag cct cca gag agt ttc atg gaa cca aac ctg gga ggt     1265
Asn Ser Glu Lys Pro Pro Glu Ser Phe Met Glu Pro Asn Leu Gly Gly
380                 385                 390 tct agt cca tta cta gat cca gat ctg ttg atc gat gat tct ttg tcc     1313
Ser Ser Pro Leu Leu Asp Pro Asp Leu Leu Ile Asp Asp Ser Leu Ser
            395                 400                 405 ttc gac att gac gac ttt cca atg gat tct gat ata gac cct gtt gat     1361
Phe Asp Ile Asp Asp Phe Pro Met Asp Ser Asp Ile Asp Pro Val Asp
410                 415                 420 tac ggt tta ctc gaa cgc tta ctc atg tca agc ccg gtt cca gat aat     1409
Tyr Gly Leu Leu Glu Arg Leu Leu Met Ser Ser Pro Val Pro Asp Asn
425                 430                 435                 440 atg gat tca aca cca gtg gac aat gaa aca gag cag gaa caa aat gga     1457
Met Asp Ser Thr Pro Val Asp Asn Glu Thr Glu Gln Glu Gln Asn Gly
            445                 450                 455 tgg gac aaa act aag cat atg gat aat ctg act caa cag atg ggt ctc     1505
Trp Asp Lys Thr Lys His Met Asp Asn Leu Thr Gln Gln Met Gly Leu
460                 465                 470 ctc tct cct gaa acc tta gat ctc tca agg caa aat cct tga             1547
Leu Ser Pro Glu Thr Leu Asp Leu Ser Arg Gln Asn Pro  *
            475                 480                 485 ttttgggagt ttttaaagtc tttgaggta acacagtccc tgagagcagc atattcat      1605
```

<210> SEQ ID NO 8
<211> LENGTH: 485
<212> TYPE: PRT
<213> ORGANISM: Arabidopsis thaliana
<220> FEATURE:
<221> NAME/KEY: DOMAIN
<222> LOCATION: (32)...(130)
<223> OTHER INFORMATION: Conserved domain

<400> SEQUENCE: 8

-continued

```
Met Asp Val Ser Lys Val Thr Thr Ser Asp Gly Gly Asp Ser Met
 1               5                  10                 15

Glu Thr Lys Pro Ser Pro Gln Pro Gln Pro Ala Ala Ile Leu Ser Ser
                20              25                  30

Asn Ala Pro Pro Phe Leu Ser Lys Thr Tyr Asp Met Val Asp Asp
         35              40                  45

His Asn Thr Asp Ser Ile Val Ser Trp Ser Ala Asn Asn Ser Phe
 50                  55                  60

Ile Val Trp Lys Pro Pro Glu Phe Ala Arg Asp Leu Leu Pro Lys Asn
65                  70                  75                  80

Phe Lys His Asn Asn Phe Ser Ser Phe Val Arg Gln Leu Asn Thr Tyr
                 85                  90                  95

Gly Phe Arg Lys Val Asp Pro Asp Arg Trp Glu Phe Ala Asn Glu Gly
             100                 105                 110

Phe Leu Arg Gly Gln Lys His Leu Leu Gln Ser Ile Thr Arg Arg Lys
             115                 120                 125

Pro Ala His Gly Gln Gly Gln Gly His Gln Arg Ser Gln His Ser Asn
             130                 135                 140

Gly Gln Asn Ser Ser Val Ser Ala Cys Val Glu Val Gly Lys Phe Gly
145                 150                 155                 160

Leu Glu Glu Glu Val Glu Arg Leu Lys Arg Asp Lys Asn Val Leu Met
                165                 170                 175

Gln Glu Leu Val Arg Leu Arg Gln Gln Gln Ser Thr Asp Asn Gln
             180                 185                 190

Leu Gln Thr Met Val Gln Arg Leu Gln Gly Met Glu Asn Arg Gln Gln
             195                 200                 205

Gln Leu Met Ser Phe Leu Ala Lys Ala Val Gln Ser Pro His Phe Leu
210                 215                 220

Ser Gln Phe Leu Gln Gln Gln Asn Gln Gln Asn Glu Ser Asn Arg Arg
225                 230                 235                 240

Ile Ser Asp Thr Ser Lys Lys Arg Arg Phe Lys Arg Asp Gly Ile Val
             245                 250                 255

Arg Asn Asn Asp Ser Ala Thr Pro Asp Gly Gln Ile Val Lys Tyr Gln
             260                 265                 270

Pro Pro Met His Glu Gln Ala Lys Ala Met Phe Lys Gln Leu Met Lys
             275                 280                 285

Met Glu Pro Tyr Lys Thr Gly Asp Asp Gly Phe Leu Leu Gly Asn Gly
    290                 295                 300

Thr Ser Thr Thr Glu Gly Thr Glu Met Glu Thr Ser Ser Asn Gln Val
305                 310                 315                 320

Ser Gly Ile Thr Leu Lys Glu Met Pro Thr Ala Ser Glu Ile Gln Ser
             325                 330                 335

Ser Ser Pro Ile Glu Thr Thr Pro Glu Asn Val Ser Ala Ala Ser Glu
             340                 345                 350

Ala Thr Glu Asn Cys Ile Pro Ser Pro Asp Asp Leu Thr Leu Pro Asp
             355                 360                 365

Phe Thr His Met Leu Pro Glu Asn Asn Ser Glu Lys Pro Pro Glu Ser
             370                 375                 380

Phe Met Glu Pro Asn Leu Gly Ser Ser Pro Leu Leu Asp Pro Asp
385                 390                 395                 400

Leu Leu Ile Asp Asp Ser Leu Ser Phe Asp Ile Asp Asp Phe Pro Met
             405                 410                 415

Asp Ser Asp Ile Asp Pro Val Asp Tyr Gly Leu Leu Glu Arg Leu Leu
```

```
                420             425             430
Met Ser Ser Pro Val Pro Asp Asn Met Asp Ser Thr Pro Val Asp Asn
        435                 440                 445

Glu Thr Glu Gln Glu Gln Asn Gly Trp Asp Lys Thr Lys His Met Asp
    450                 455                 460

Asn Leu Thr Gln Gln Met Gly Leu Leu Ser Pro Glu Thr Leu Asp Leu
465                 470                 475                 480

Ser Arg Gln Asn Pro
                485

<210> SEQ ID NO 9
<211> LENGTH: 640
<212> TYPE: DNA
<213> ORGANISM: Arabidopsis thaliana
<220> FEATURE:
<221> NAME/KEY: CDS
<222> LOCATION: (90)...(590)

<400> SEQUENCE: 9
ataacaaact catcaaactt cctcagcgtt tcttttcttt acataaacaa ttttcttac     60 ataaacaaat cttgttgttt gttgttgtc atg gca ccg aca gtt aaa acg gcg    113
                                Met Ala Pro Thr Val Lys Thr Ala
                                  1               5 gcc gtc aaa acc aac gaa ggt aac gga gtc cgt tac aga gga gtg agg    161
Ala Val Lys Thr Asn Glu Gly Asn Gly Val Arg Tyr Arg Gly Val Arg
         10                  15                  20 aag aga cca tgg gga cgt tac gca gcc gag atc aga gat cct ttc aag    209
Lys Arg Pro Trp Gly Arg Tyr Ala Ala Glu Ile Arg Asp Pro Phe Lys
 25                  30                  35                  40 aag tca cgt gtc tgg ctc ggt act ttc gac act cct gaa gaa gcc gct    257
Lys Ser Arg Val Trp Leu Gly Thr Phe Asp Thr Pro Glu Glu Ala Ala
                 45                  50                  55 cgt gcc tac gac aaa cgt gct att gag ttt cgt gga gct aaa gcc aaa    305
Arg Ala Tyr Asp Lys Arg Ala Ile Glu Phe Arg Gly Ala Lys Ala Lys
             60                  65                  70 acc aac ttc cct tgt tac aac atc aac gcc cac tgc ttg agt ttg aca    353
Thr Asn Phe Pro Cys Tyr Asn Ile Asn Ala His Cys Leu Ser Leu Thr
         75                  80                  85 cag agc ctg agc cag agc agc acc gtg gaa tca tcg ttt cct aat ctc    401
Gln Ser Leu Ser Gln Ser Ser Thr Val Glu Ser Ser Phe Pro Asn Leu
     90                  95                 100 aac ctc gga tct gac tct gtt agt tcg aga ttc cct ttt cct aag att    449
Asn Leu Gly Ser Asp Ser Val Ser Ser Arg Phe Pro Phe Pro Lys Ile
105                 110                 115                 120 cag gtt aag gct ggg atg atg gtg ttc gat gaa agg agt gaa tcg gat    497
Gln Val Lys Ala Gly Met Met Val Phe Asp Glu Arg Ser Glu Ser Asp
                125                 130                 135 tct tcg tcg gtg gtg atg gat gtc gtt aga tat gaa gga cga cgt gtg    545
Ser Ser Ser Val Val Met Asp Val Val Arg Tyr Glu Gly Arg Arg Val
            140                 145                 150 gtt ttg gac ttg gat ctt aat ttc cct cct cca cct gag aac tga        590
Val Leu Asp Leu Asp Leu Asn Phe Pro Pro Pro Pro Glu Asn *
        155                 160                 165 ttaagattta attatgatta ttagatataa ttaaatgttt ctgaattgag              640

<210> SEQ ID NO 10
<211> LENGTH: 166
<212> TYPE: PRT
<213> ORGANISM: Arabidopsis thaliana
```

```
<400> SEQUENCE: 10

Met Ala Pro Thr Val Lys Thr Ala Ala Val Lys Thr Asn Glu Gly Asn
 1               5                  10                  15

Gly Val Arg Tyr Arg Gly Val Arg Lys Arg Pro Trp Gly Arg Tyr Ala
             20                  25                  30

Ala Glu Ile Arg Asp Pro Phe Lys Lys Ser Arg Val Trp Leu Gly Thr
         35                  40                  45

Phe Asp Thr Pro Glu Glu Ala Ala Arg Ala Tyr Asp Lys Arg Ala Ile
     50                  55                  60

Glu Phe Arg Gly Ala Lys Ala Lys Thr Asn Phe Pro Cys Tyr Asn Ile
 65                  70                  75                  80

Asn Ala His Cys Leu Ser Leu Thr Gln Ser Leu Ser Gln Ser Ser Thr
                 85                  90                  95

Val Glu Ser Ser Phe Pro Asn Leu Asn Leu Gly Ser Asp Ser Val Ser
             100                 105                 110

Ser Arg Phe Pro Phe Pro Lys Ile Gln Val Lys Ala Gly Met Met Val
             115                 120                 125

Phe Asp Glu Arg Ser Glu Ser Asp Ser Ser Ser Val Val Met Asp Val
     130                 135                 140

Val Arg Tyr Glu Gly Arg Arg Val Val Leu Asp Leu Asp Leu Asn Phe
145                 150                 155                 160

Pro Pro Pro Pro Glu Asn
                165

<210> SEQ ID NO 11
<211> LENGTH: 506
<212> TYPE: DNA
<213> ORGANISM: Arabidopsis thaliana
<220> FEATURE:
<221> NAME/KEY: CDS
<222> LOCATION: (49)...(465)

<400> SEQUENCE: 11
atacttgtca acaaaaattt tcttaaagaa cgcataactg ttttttttc atg gct ggt       57
                                                     Met Ala Gly
                                                       1 tct gtc tat aac ctt cca agt caa aac cct aat cca cag tct tta ttc       105
Ser Val Tyr Asn Leu Pro Ser Gln Asn Pro Asn Pro Gln Ser Leu Phe
      5                  10                  15 caa atc ttt gtt gat cga gta cca ctt tca aac ttg cct gcc acg tca       153
Gln Ile Phe Val Asp Arg Val Pro Leu Ser Asn Leu Pro Ala Thr Ser
 20                  25                  30                  35 gac gac tct agc cgg act gca gaa gat aat gag agg aag cgg aga agg       201
Asp Asp Ser Ser Arg Thr Ala Glu Asp Asn Glu Arg Lys Arg Arg Arg
                 40                  45                  50 aag gta tcg aac cgc gag tca gct cgg aga tcg cgt atg cgg aaa cag       249
Lys Val Ser Asn Arg Glu Ser Ala Arg Arg Ser Arg Met Arg Lys Gln
             55                  60                  65 cgt cac atg gaa gaa ctg tgg tcc atg ctt gtt caa ctc atc aat aag       297
Arg His Met Glu Glu Leu Trp Ser Met Leu Val Gln Leu Ile Asn Lys
         70                  75                  80 aac aaa tct cta gtc gat gag cta agc caa gcc agg gaa tgt tac gag       345
Asn Lys Ser Leu Val Asp Glu Leu Ser Gln Ala Arg Glu Cys Tyr Glu
 85                  90                  95 aag gtt ata gaa gag aac atg aaa ctt cga gag gaa aac tcc aag tcg       393
Lys Val Ile Glu Glu Asn Met Lys Leu Arg Glu Glu Asn Ser Lys Ser
100                 105                 110                 115 agg aag atg att ggt gag atc ggg ctt aat agg ttt ctt agc gta gag       441
```

```
Arg Lys Met Ile Gly Glu Ile Gly Leu Asn Arg Phe Leu Ser Val Glu
            120                 125                 130 gcc gat cag atc tgg acc ttc taa tcgtctcgta agcttgttgg tttttgttg      495
Ala Asp Gln Ile Trp Thr Phe *
            135 tttatttaaa g                                                         506

<210> SEQ ID NO 12
<211> LENGTH: 138
<212> TYPE: PRT
<213> ORGANISM: Arabidopsis thaliana
<220> FEATURE:
<221> NAME/KEY: DOMAIN
<222> LOCATION: (46)...(106)
<223> OTHER INFORMATION: Conserved domain

<400> SEQUENCE: 12

Met Ala Gly Ser Val Tyr Asn Leu Pro Ser Gln Asn Pro Asn Pro Gln
  1               5                  10                  15

Ser Leu Phe Gln Ile Phe Val Asp Arg Val Pro Leu Ser Asn Leu Pro
             20                  25                  30

Ala Thr Ser Asp Asp Ser Ser Arg Thr Ala Glu Asp Asn Glu Arg Lys
         35                  40                  45

Arg Arg Arg Lys Val Ser Asn Arg Glu Ser Ala Arg Ser Arg Met
 50                  55                  60

Arg Lys Gln Arg His Met Glu Glu Leu Trp Ser Met Leu Val Gln Leu
 65                  70                  75                  80

Ile Asn Lys Asn Lys Ser Leu Val Asp Glu Leu Ser Gln Ala Arg Glu
                 85                  90                  95

Cys Tyr Glu Lys Val Ile Glu Gly Asn Met Lys Leu Arg Glu Glu Asn
            100                 105                 110

Ser Lys Ser Arg Lys Met Ile Gly Glu Ile Gly Leu Asn Arg Phe Leu
        115                 120                 125

Ser Val Glu Ala Asp Gln Ile Trp Thr Phe
    130                 135

<210> SEQ ID NO 13
<211> LENGTH: 1050
<212> TYPE: DNA
<213> ORGANISM: Arabidopsis thaliana
<220> FEATURE:
<221> NAME/KEY: CDS
<222> LOCATION: (63)...(740)

<400> SEQUENCE: 13
ctcatatata ccaaccaaac ctctctctgc atctttatta acacaaaatt ccaaaagatt    60 aa atg ttg tcg aag ctc cct aca cag cga cac ttg cac ctc tct ccc     107
   Met Leu Ser Lys Leu Pro Thr Gln Arg His Leu His Leu Ser Pro
     1               5                  10                  15 tcc tct ccc tcc atg gaa acc gtc ggg cgt cca cgt ggc aga cct cga   155
Ser Ser Pro Ser Met Glu Thr Val Gly Arg Pro Arg Gly Arg Pro Arg
                 20                  25                  30 ggt tcc aaa aac aaa cct aaa gct cca atc ttt gtc acc att gac cct   203
Gly Ser Lys Asn Lys Pro Lys Ala Pro Ile Phe Val Thr Ile Asp Pro
         35                  40                  45 cct atg agt cct tac atc ctc gaa gtg cca tcc gga aac gat gtc gtt   251
Pro Met Ser Pro Tyr Ile Leu Glu Val Pro Ser Gly Asn Asp Val Val
     50                  55                  60 gaa gcc cta aac cgt ttc tgc cgc ggt aaa gcc atc ggc ttt tgc gtc   299
Glu Ala Leu Asn Arg Phe Cys Arg Gly Lys Ala Ile Gly Phe Cys Val
```

-continued

```
                65                  70                  75
ctc agt ggc tca ggc tcc gtt gct gat gtc act ttg cgt cag cct tct      347
Leu Ser Gly Ser Gly Ser Val Ala Asp Val Thr Leu Arg Gln Pro Ser
 80                  85                  90                  95 ccg gca gct cct ggc tca acc att act ttc cac gga aag ttc gat ctt      395
Pro Ala Ala Pro Gly Ser Thr Ile Thr Phe His Gly Lys Phe Asp Leu
                100                 105                 110 ctc tct gtc tcc gcc act ttc ctc cct cct cta cct cct acc tcc ttg      443
Leu Ser Val Ser Ala Thr Phe Leu Pro Pro Leu Pro Pro Thr Ser Leu
            115                 120                 125 tcc cct ccc gtc tcc aat ttc ttc acc gtc tct ctc gcc gga cct cag      491
Ser Pro Pro Val Ser Asn Phe Phe Thr Val Ser Leu Ala Gly Pro Gln
        130                 135                 140 ggg aaa gtc atc ggt gga ttc gtc gct ggt cct ctc gtt gcc gcc gga      539
Gly Lys Val Ile Gly Gly Phe Val Ala Gly Pro Leu Val Ala Ala Gly
    145                 150                 155 act gtt tac ttc gtc gcc act agt ttc aag aac cct tcc tat cac cgg      587
Thr Val Tyr Phe Val Ala Thr Ser Phe Lys Asn Pro Ser Tyr His Arg
160                 165                 170                 175 tta cct gct acg gag gaa gag caa aga aac tcg gcg gaa ggg gaa gag      635
Leu Pro Ala Thr Glu Glu Glu Gln Arg Asn Ser Ala Glu Gly Glu Glu
                180                 185                 190 gag gga caa tcg ccg ccg gtc tct gga ggt ggt gga gag tcg atg tac      683
Glu Gly Gln Ser Pro Pro Val Ser Gly Gly Gly Gly Glu Ser Met Tyr
            195                 200                 205 gtg ggt ggc tct gat gtc att tgg gat ccc aac gcc aaa gct cca tcg      731
Val Gly Gly Ser Asp Val Ile Trp Asp Pro Asn Ala Lys Ala Pro Ser
        210                 215                 220 ccg tac tga ccacaaatcc atctcgttca aactagggtt tcttcttctt              780
Pro Tyr *
    225 tagatcatca agaatcaaca aaaagattgc attttagat tctttgtaat atcataattg     840 actcactctt taatctctct atcacttctt ctttagcttt ttctgcagtg tcaaacttca    900 catatttgta gtttgatttg actatccccca agttttgtat tttatcatac aaattttttgc  960 ctgtctctaa tggttgtttt ttcgtttgta taatcttatg cattgtttat tggagctcca   1020 gagattgaat gtataatata atggtttaat                                   1050
```

<210> SEQ ID NO 14
<211> LENGTH: 225
<212> TYPE: PRT
<213> ORGANISM: Arabidopsis thaliana
<220> FEATURE:
<221> NAME/KEY: DOMAIN
<222> LOCATION: (18)...(38)
<223> OTHER INFORMATION: Conserved domain

<400> SEQUENCE: 14

```
Met Leu Ser Lys Leu Pro Thr Gln Arg His Leu His Leu Ser Pro Ser
 1               5                  10                  15

Ser Pro Ser Met Glu Thr Val Gly Arg Pro Arg Gly Arg Pro Arg Gly
            20                  25                  30

Ser Lys Asn Lys Pro Lys Ala Pro Ile Phe Val Thr Ile Asp Pro Pro
        35                  40                  45

Met Ser Pro Tyr Ile Leu Glu Val Pro Ser Gly Asn Asp Val Val Glu
    50                  55                  60

Ala Leu Asn Arg Phe Cys Arg Gly Lys Ala Ile Gly Phe Cys Val Leu
65                  70                  75                  80
```

```
Ser Gly Ser Gly Ser Val Ala Asp Val Thr Leu Arg Gln Pro Ser Pro
                85                  90                  95

Ala Ala Pro Gly Ser Thr Ile Thr Phe His Gly Lys Phe Asp Leu Leu
            100                 105                 110

Ser Val Ser Ala Thr Phe Leu Pro Pro Leu Pro Pro Thr Ser Leu Ser
        115                 120                 125

Pro Pro Val Ser Asn Phe Phe Thr Val Ser Leu Ala Gly Pro Gln Gly
    130                 135                 140

Lys Val Ile Gly Gly Phe Val Ala Gly Pro Leu Val Ala Ala Gly Thr
145                 150                 155                 160

Val Tyr Phe Val Ala Thr Ser Phe Lys Asn Pro Ser Tyr His Arg Leu
                165                 170                 175

Pro Ala Thr Glu Glu Glu Gln Arg Asn Ser Ala Glu Gly Glu Glu
            180                 185                 190

Gly Gln Ser Pro Pro Val Ser Gly Gly Gly Glu Ser Met Tyr Val
        195                 200                 205

Gly Gly Ser Asp Val Ile Trp Asp Pro Asn Ala Lys Ala Pro Ser Pro
    210                 215                 220

Tyr
225

<210> SEQ ID NO 15
<211> LENGTH: 1312
<212> TYPE: DNA
<213> ORGANISM: Arabidopsis thaliana
<220> FEATURE:
<221> NAME/KEY: CDS
<222> LOCATION: (119)...(982)

<400> SEQUENCE: 15
```

| | |
|---|---|
| ttctttcttt ctttctttct cttccaatca agaacaaacc ctagctcctc tcttttctc | 60 |
| tctctacctc tctttctcta tcttctctta tcactacttc tctcgccgat caatcatc | 118 |

```
atg aac gat cct gat aat ccc gat ctg agc aac gac gac tct gct tgg     166
Met Asn Asp Pro Asp Asn Pro Asp Leu Ser Asn Asp Asp Ser Ala Trp
  1               5                  10                  15 aga gaa ctc aca ctc aca gct caa gat tct gac ttc ttc gac cga gac     214
Arg Glu Leu Thr Leu Thr Ala Gln Asp Ser Asp Phe Phe Asp Arg Asp
             20                  25                  30 act tcc aat atc ctc tct gac ttc ggt tgg aac ctc cac cac tcc tcc     262
Thr Ser Asn Ile Leu Ser Asp Phe Gly Trp Asn Leu His His Ser Ser
         35                  40                  45 gat cat cct cac agt ctc aga ttc gac tcc gat tta aca caa acc acc     310
Asp His Pro His Ser Leu Arg Phe Asp Ser Asp Leu Thr Gln Thr Thr
     50                  55                  60 gga gtc aaa cct acc acc gtc act tct tct tgt tcc tca tcc gcc gcc     358
Gly Val Lys Pro Thr Thr Val Thr Ser Ser Cys Ser Ser Ser Ala Ala
 65                  70                  75                  80 gtt tcc gtt gcc gtt acc tct act aat aat aat ccc tca gct acc tca     406
Val Ser Val Ala Val Thr Ser Thr Asn Asn Asn Pro Ser Ala Thr Ser
                 85                  90                  95 agt tca agt gaa gat ccg gcc gag aac tca acc gcc tcc gcc gag aaa     454
Ser Ser Ser Glu Asp Pro Ala Glu Asn Ser Thr Ala Ser Ala Glu Lys
            100                 105                 110 gga cca ccg gag aca cca gtg aag gag aag aag aag gct caa aag         502
Pro Pro Glu Thr Pro Val Lys Glu Lys Lys Lys Ala Gln Lys
        115                 120                 125 gct cgg caa cca aga ttc gca ttc atg acc aag agt gat gtg gat         550
Phe Arg Gln Pro Arg Phe Ala Phe Met Thr Lys Ser Asp Val Asp
```

```
                 135                 140
t gaa gat gga tat cga tgg cgt aaa tat gga caa aaa gcc gtc           598
u Glu Asp Gly Tyr Arg Trp Arg Lys Tyr Gly Gln Lys Ala Val
              150                 155                 160 t agc cca ttc cca agg agc tac tat aga tgc aca aac agc aga           646
n Ser Pro Phe Pro Arg Ser Tyr Tyr Arg Cys Thr Asn Ser Arg
          165                 170                 175 g gtg aag aag aga gta gaa cgt tca tca gat gat cca tcg ata           694
r Val Lys Lys Arg Val Glu Arg Ser Ser Asp Asp Pro Ser Ile
      180                 185                 190 c aca aca tac gaa gga caa cat tgc cat caa acc att gga ttc           742
e Thr Thr Tyr Glu Gly Gln His Cys His Gln Thr Ile Gly Phe
  195                 200                 205 t ggt gga atc ctc act gca cac gac cca cat agc ttc act tct           790
g Gly Gly Ile Leu Thr Ala His Asp Pro His Ser Phe Thr Ser
0                 215                 220 t cat ctc cct cct cca tta cca aat cct tat tat tac caa gaa           838
s His Leu Pro Pro Pro Leu Pro Asn Pro Tyr Tyr Tyr Gln Glu
                  230                 235                 240 t cat caa ctt cac aga gac aat aat gct cct tca ccg cgg tta           886
u His Gln Leu His Arg Asp Asn Asn Ala Pro Ser Pro Arg Leu
              245                 250                 255 a cct act act gaa gat aca cct gcc gtg tct act cca tca gag           934
g Pro Thr Thr Glu Asp Thr Pro Ala Val Ser Thr Pro Ser Glu
          260                 265                 270 c tta ctt ggt gat att gta cct caa act atg cgc aac cct tga           982
y Leu Leu Gly Asp Ile Val Pro Gln Thr Met Arg Asn Pro  *
      275                 280                 285 ggtaagcttg gtacgtagca atagctaagg aggtgctaac tcattatata tagaagatat   1042
tgcagaccag aatatgcgca gggagggtat aacaatatgg cgttgtaaca atggatctat   1102
atattacctc attgttgatc aatagcacac caccggtacg tttgcaattt cttcatgtat   1162
atttcttgtt atatatgtag ttatatatcc aggtataatt ttgatgtaac acaacattaa   1222
tcttaatcgt ggatccatcc cacatttgat gcatgtatgt gcacttaaga aaagaacat    1282 ggaggaaata acgttatttt ttattattct                                    1312

<210> SEQ ID NO 16
<211> LENGTH: 287
<212> TYPE: PRT
<213> ORGANISM: Arabidopsis thaliana
<220> FEATURE:
<221> NAME/KEY: DOMAIN
<222> LOCATION: (147)...(205)
<223> OTHER INFORMATION: Conserved domain

<400> SEQUENCE: 16

Met Asn Asp Pro Asp Asn Pro Asp Leu Ser Asn Asp Asp Ser Ala Trp
 1               5                  10                  15

Arg Glu Leu Thr Leu Thr Ala Gln Asp Ser Asp Phe Phe Asp Arg Asp
             20                  25                  30

Thr Ser Asn Ile Leu Ser Asp Phe Gly Trp Asn Leu His His Ser Ser
         35                  40                  45

Asp His Pro His Ser Leu Arg Phe Asp Ser Asp Leu Thr Gln Thr Thr
     50                  55                  60

Gly Val Lys Pro Thr Thr Val Thr Ser Ser Cys Ser Ser Ser Ala Ala
65                  70                  75                  80

Val Ser Val Ala Val Thr Ser Thr Asn Asn Asn Pro Ser Ala Thr Ser
                 85                  90                  95
```

```
Ser Ser Ser Glu Asp Pro Ala Glu Asn Ser Thr Ala Ser Ala Glu Lys
            100                 105                 110

Thr Pro Pro Glu Thr Pro Val Lys Glu Lys Lys Ala Gln Lys
        115                 120                 125

Arg Ile Arg Gln Pro Arg Phe Ala Phe Met Thr Lys Ser Asp Val Asp
        130                 135                 140

Asn Leu Glu Asp Gly Tyr Arg Trp Arg Lys Tyr Gly Gln Lys Ala Val
145                 150                 155                 160

Lys Asn Ser Pro Phe Pro Arg Ser Tyr Tyr Arg Cys Thr Asn Ser Arg
                165                 170                 175

Cys Thr Val Lys Lys Arg Val Glu Arg Ser Ser Asp Asp Pro Ser Ile
            180                 185                 190

Val Ile Thr Thr Tyr Glu Gly Gln His Cys His Gln Thr Ile Gly Phe
        195                 200                 205

Pro Arg Gly Gly Ile Leu Thr Ala His Asp Pro His Ser Phe Thr Ser
        210                 215                 220

His His His Leu Pro Pro Leu Pro Asn Pro Tyr Tyr Tyr Gln Glu
225                 230                 235                 240

Leu Leu His Gln Leu His Arg Asp Asn Asn Ala Pro Ser Pro Arg Leu
                245                 250                 255

Pro Arg Pro Thr Thr Glu Asp Thr Pro Ala Val Ser Thr Pro Ser Glu
            260                 265                 270

Glu Gly Leu Leu Gly Asp Ile Val Pro Gln Thr Met Arg Asn Pro
        275                 280                 285

<210> SEQ ID NO 17
<211> LENGTH: 1406
<212> TYPE: DNA
<213> ORGANISM: Arabidopsis thaliana
<220> FEATURE:
<221> NAME/KEY: CDS
<222> LOCATION: (274)...(1275)

<400> SEQUENCE: 17
atacaaaact ccctcttctc tatcttcttc atcttaaaga aaaataaga gatattcgta      60 aagagagaac acaaaatttc agtttacgaa aagctagcaa agtcgagtat cgaggaataa    120
cagaataaga cgtatctatc cttgccttaa tgttcttacc aaaagatcta gtcctttctt    180
tgtatgatcg atccatcaca agcccacaac aacaacaact acatctcttt ctctatctct    240
agcttctatt tttaatacat tcaagaatca aga atg gta cgg acg ccg tgt tgt    294
                                   Met Val Arg Thr Pro Cys Cys
                                    1               5 aga gca gaa ggg ttg aag aaa gga gca tgg act caa gaa gaa gac caa    342
Arg Ala Glu Gly Leu Lys Lys Gly Ala Trp Thr Gln Glu Glu Asp Gln
        10                  15                  20 aag ctt atc gcc tat gtt caa cga cat ggt gaa ggc ggt tgg cga acc    390
Lys Leu Ile Ala Tyr Val Gln Arg His Gly Glu Gly Gly Trp Arg Thr
    25                  30                  35 ctt ccg gac aaa gct gga ctc aaa aga tgt ggc aaa agc tgc aga ttg    438
Leu Pro Asp Lys Ala Gly Leu Lys Arg Cys Gly Lys Ser Cys Arg Leu
40                  45                  50                  55 aga tgg gcg aat tac tta aga cct gac att aaa cgt gga gag ttt agc    486
Arg Trp Ala Asn Tyr Leu Arg Pro Asp Ile Lys Arg Gly Glu Phe Ser
                60                  65                  70 caa gac gag gaa gat tcc atc atc aac ctc cac gcc att cat ggc aac    534
Gln Asp Glu Glu Asp Ser Ile Ile Asn Leu His Ala Ile His Gly Asn
            75                  80                  85
```

```
aaa tgg tcg gcc ata gct cgt aaa ata cca aga aga aca gac aat gag    582
Lys Trp Ser Ala Ile Ala Arg Lys Ile Pro Arg Arg Thr Asp Asn Glu
         90                  95                 100 atc aag aac cat tgg aac act cac atc aag aaa tgt ctg gtc aag aaa    630
Ile Lys Asn His Trp Asn Thr His Ile Lys Lys Cys Leu Val Lys Lys
    105                 110                 115 ggt att gat ccg ttg acc cac aaa tcc ctt ctc gat gga gcc ggt aaa    678
Gly Ile Asp Pro Leu Thr His Lys Ser Leu Leu Asp Gly Ala Gly Lys
120                 125                 130                 135 tca tct gac cat tcc gcg cat ccc gag aaa agc agc gtt cat gac gac    726
Ser Ser Asp His Ser Ala His Pro Glu Lys Ser Ser Val His Asp Asp
                140                 145                 150 aaa gat gat cag aat tca aat aac aaa aag ttg tca gga tca tca tca    774
Lys Asp Asp Gln Asn Ser Asn Asn Lys Lys Leu Ser Gly Ser Ser Ser
        155                 160                 165 gct cgg ttt ttg aac aga gta gca aac aga ttc ggt cat aga atc aac    822
Ala Arg Phe Leu Asn Arg Val Ala Asn Arg Phe Gly His Arg Ile Asn
            170                 175                 180 cac aat gtt ctg tct gat att att gga agt aat ggc cta ctt act agt    870
His Asn Val Leu Ser Asp Ile Ile Gly Ser Asn Gly Leu Leu Thr Ser
        185                 190                 195 cac act act cca act aca agt gtt tca gaa ggt gag agg tca acg agt    918
His Thr Thr Pro Thr Thr Ser Val Ser Glu Gly Glu Arg Ser Thr Ser
200                 205                 210                 215 tct tcc tcc aca cat acc tct tcg aat ctc ccc atc aac cgt agc ata    966
Ser Ser Ser Thr His Thr Ser Ser Asn Leu Pro Ile Asn Arg Ser Ile
                220                 225                 230 acc gtt gat gca aca tct cta tcc tca tcc acg ttc tct gac tcc ccc   1014
Thr Val Asp Ala Thr Ser Leu Ser Ser Ser Thr Phe Ser Asp Ser Pro
            235                 240                 245 gac ccg tgt tta tac gag gaa ata gtc ggt gac att gaa gat atg acg   1062
Asp Pro Cys Leu Tyr Glu Glu Ile Val Gly Asp Ile Glu Asp Met Thr
        250                 255                 260 aga ttt tca tca aga tgt ttg agt cat gtt tta tct cat gaa gat tta   1110
Arg Phe Ser Ser Arg Cys Leu Ser His Val Leu Ser His Glu Asp Leu
265                 270                 275 ttg atg tcc gtt gag tct tgt ttg gag aat act tca ttc atg agg gaa   1158
Leu Met Ser Val Glu Ser Cys Leu Glu Asn Thr Ser Phe Met Arg Glu
280                 285                 290                 295 att aca atg atc ttt caa gag gat aaa atc gag acg acg tcg ttt aat   1206
Ile Thr Met Ile Phe Gln Glu Asp Lys Ile Glu Thr Thr Ser Phe Asn
                300                 305                 310 gat agc tac gtg acg ccg atc aat gaa gtt gat gac tcc tgt gaa ggg   1254
Asp Ser Tyr Val Thr Pro Ile Asn Glu Val Asp Asp Ser Cys Glu Gly
            315                 320                 325 att gac aat tat ttt gga tga gttatattga tgatgatgaa aatttgcatt      1305
Ile Asp Asn Tyr Phe Gly *
        330 tggcatgtaa atcaattaga gtttgatttg ctatggtgtt tttagtttgt gtgtgtagtg 1365 tgtttcgacc gtcaaaaaaa aaaaaaaaaa aaaaaaaaa a                      1406

<210> SEQ ID NO 18
<211> LENGTH: 333
<212> TYPE: PRT
<213> ORGANISM: Arabidopsis thaliana
<220> FEATURE:
<221> NAME/KEY: DOMAIN
<222> LOCATION: (14)...(120)
<223> OTHER INFORMATION: Conserved domain
```

-continued

<400> SEQUENCE: 18

```
Met Val Arg Thr Pro Cys Cys Arg Ala Glu Gly Leu Lys Lys Gly Ala
1               5                   10                  15

Trp Thr Gln Glu Glu Asp Gln Lys Leu Ile Ala Tyr Val Gln Arg His
            20                  25                  30

Gly Glu Gly Gly Trp Arg Thr Leu Pro Asp Lys Ala Gly Leu Lys Arg
        35                  40                  45

Cys Gly Lys Ser Cys Arg Leu Arg Trp Ala Asn Tyr Leu Arg Pro Asp
    50                  55                  60

Ile Lys Arg Gly Glu Phe Ser Gln Asp Glu Asp Ser Ile Ile Asn
65                  70                  75                  80

Leu His Ala Ile His Gly Asn Lys Trp Ser Ala Ile Ala Arg Lys Ile
                85                  90                  95

Pro Arg Arg Thr Asp Asn Glu Ile Lys Asn His Trp Asn Thr His Ile
            100                 105                 110

Lys Lys Cys Leu Val Lys Lys Gly Ile Asp Pro Leu Thr His Lys Ser
        115                 120                 125

Leu Leu Asp Gly Ala Gly Lys Ser Ser Asp His Ser Ala His Pro Glu
    130                 135                 140

Lys Ser Val His Asp Asp Lys Asp Gln Asn Ser Asn Asn Lys
145                 150                 155                 160

Lys Leu Ser Gly Ser Ser Ala Arg Phe Leu Asn Arg Val Ala Asn
                165                 170                 175

Arg Phe Gly His Arg Ile Asn His Asn Val Leu Ser Asp Ile Ile Gly
            180                 185                 190

Ser Asn Gly Leu Leu Thr Ser His Thr Thr Pro Thr Thr Ser Val Ser
        195                 200                 205

Glu Gly Glu Arg Ser Thr Ser Ser Ser Thr His Thr Ser Ser Asn
    210                 215                 220

Leu Pro Ile Asn Arg Ser Ile Thr Val Asp Ala Thr Ser Leu Ser Ser
225                 230                 235                 240

Ser Thr Phe Ser Asp Ser Pro Asp Pro Cys Leu Tyr Glu Glu Ile Val
                245                 250                 255

Gly Asp Ile Glu Asp Met Thr Arg Phe Ser Ser Arg Cys Leu Ser His
            260                 265                 270

Val Leu Ser His Glu Asp Leu Leu Met Ser Val Glu Ser Cys Leu Glu
        275                 280                 285

Asn Thr Ser Phe Met Arg Glu Ile Thr Met Ile Phe Gln Glu Asp Lys
    290                 295                 300

Ile Glu Thr Thr Ser Phe Asn Asp Ser Tyr Val Thr Pro Ile Asn Glu
305                 310                 315                 320

Val Asp Asp Ser Cys Glu Gly Ile Asp Asn Tyr Phe Gly
                325                 330
```

<210> SEQ ID NO 19
<211> LENGTH: 1384
<212> TYPE: DNA
<213> ORGANISM: Arabidopsis thaliana
<220> FEATURE:
<221> NAME/KEY: CDS
<222> LOCATION: (61)...(1119)

<400> SEQUENCE: 19
ttcacttgag aacaaccccc tttgaactcg atcaagaaag ctaagtttga agaatcaaga        60 atg gtg cgg aca ccg tgt tgc aaa gcc gaa cta ggg tta aag aaa gga       108

```
Met Val Arg Thr Pro Cys Cys Lys Ala Glu Leu Gly Leu Lys Lys Gly
1               5                   10                  15 gct tgg act ccc gag gaa gat cag aag ctt ctc tct tac ctt aac cgc    156
Ala Trp Thr Pro Glu Glu Asp Gln Lys Leu Leu Ser Tyr Leu Asn Arg
            20                  25                  30 cac ggt gaa ggt gga tgg cga act ctc ccc gaa aaa gct gga ctc aag    204
His Gly Glu Gly Gly Trp Arg Thr Leu Pro Glu Lys Ala Gly Leu Lys
        35                  40                  45 aga tgc ggc aaa agc tgc aga ctg aga tgg gcc aat tat ctt aga cct    252
Arg Cys Gly Lys Ser Cys Arg Leu Arg Trp Ala Asn Tyr Leu Arg Pro
    50                  55                  60 gac atc aaa aga gga gag ttc act gaa gac gaa gaa cgt tca atc atc    300
Asp Ile Lys Arg Gly Glu Phe Thr Glu Asp Glu Glu Arg Ser Ile Ile
65                  70                  75                  80 tct ctt cac gcc ctt cac ggc aac aaa tgg tct gct ata gct cgt gga    348
Ser Leu His Ala Leu His Gly Asn Lys Trp Ser Ala Ile Ala Arg Gly
                85                  90                  95 cta cca gga aga acc gat aac gag atc aag aac tac tgg aac act cat    396
Leu Pro Gly Arg Thr Asp Asn Glu Ile Lys Asn Tyr Trp Asn Thr His
            100                 105                 110 atc aaa aaa cgt ttg atc aag aaa ggt att gat cca gtt aca cac aag    444
Ile Lys Lys Arg Leu Ile Lys Lys Gly Ile Asp Pro Val Thr His Lys
        115                 120                 125 ggc ata acc tcc ggt acc gac aaa tca gaa aac ctc ccg gag aaa caa    492
Gly Ile Thr Ser Gly Thr Asp Lys Ser Glu Asn Leu Pro Glu Lys Gln
    130                 135                 140 aat gtt aat ctg aca act agt gac cat gat ctt gat aat gac aag gcg    540
Asn Val Asn Leu Thr Thr Ser Asp His Asp Leu Asp Asn Asp Lys Ala
145                 150                 155                 160 aag aag aac aac aag aat ttt gga tta tca tcg gct agt ttc ttg aac    588
Lys Lys Asn Asn Lys Asn Phe Gly Leu Ser Ser Ala Ser Phe Leu Asn
                165                 170                 175 aaa gta gct aat agg ttc gga aag aga atc aat cag agt gtt ctg tct    636
Lys Val Ala Asn Arg Phe Gly Lys Arg Ile Asn Gln Ser Val Leu Ser
            180                 185                 190 gag att atc gga agt gga ggc cca ctt gct tct act agt cac act act    684
Glu Ile Ile Gly Ser Gly Gly Pro Leu Ala Ser Thr Ser His Thr Thr
        195                 200                 205 aat act aca act aca agt gtt tcc gtt gac tct gaa tca gtt aag tca    732
Asn Thr Thr Thr Thr Ser Val Ser Val Asp Ser Glu Ser Val Lys Ser
    210                 215                 220 acg agt tct tcc ttc gca cca acc tcg aat ctt ctc tgc cat ggg acc    780
Thr Ser Ser Ser Phe Ala Pro Thr Ser Asn Leu Leu Cys His Gly Thr
225                 230                 235                 240 gtt gca aca aca cca gtt tca tcg aac ttt gac gtt gat ggt aac gtt    828
Val Ala Thr Thr Pro Val Ser Ser Asn Phe Asp Val Asp Gly Asn Val
                245                 250                 255 aat ctg acg tgt tct tcg tcc acg ttc tct gat tcc tcc gtt aac aat    876
Asn Leu Thr Cys Ser Ser Ser Thr Phe Ser Asp Ser Ser Val Asn Asn
            260                 265                 270 cct cta atg tac tgc gat aat ttc gtt ggt aat aac aac gtt gat gat    924
Pro Leu Met Tyr Cys Asp Asn Phe Val Gly Asn Asn Asn Val Asp Asp
        275                 280                 285 gag gat act atc ggg ttc tcc aca ttt ctg aat gat gaa gat ttc atg    972
Glu Asp Thr Ile Gly Phe Ser Thr Phe Leu Asn Asp Glu Asp Phe Met
    290                 295                 300 atg ttg gag gag tct tgt gtt gaa aac act gcg ttc atg aaa gaa ctt   1020
Met Leu Glu Glu Ser Cys Val Glu Asn Thr Ala Phe Met Lys Glu Leu
305                 310                 315                 320
```

-continued

```
acg agg ttt ctt cac gag gat gaa aac gac gtc gtt gat gtg acg ccg        1068
Thr Arg Phe Leu His Glu Asp Glu Asn Asp Val Val Asp Val Thr Pro
                325                 330                 335 gtc tat gaa cgt caa gac ttg ttt gac gaa att gat aac tat ttt gga        1116
Val Tyr Glu Arg Gln Asp Leu Phe Asp Glu Ile Asp Asn Tyr Phe Gly
            340                 345                 350 tga gtgaaactca taatcgatga atcccacgtg accatgtcaa tatgatgtct             1169
* atggatatgt taccttgatg atgttgatgg taataataat aaataataga tggtgatgat     1229
gaccatgcat gaatcatgaa tgtagttcgt gttgtcacat atgcttgtgt ttttgtgttt     1289 ttttttttg gtctgaagtg tgttgtttcg ttgtaaatgg attataaatg gtgatgtaat      1349
aattataatg ttaaaaaaaa aaaaaaaaaa aaaaa                                  1384
```

<210> SEQ ID NO 20
<211> LENGTH: 352
<212> TYPE: PRT
<213> ORGANISM: Arabidopsis thaliana
<220> FEATURE:
<221> NAME/KEY: DOMAIN
<222> LOCATION: (15)...(115)
<223> OTHER INFORMATION: Conserved domain

<400> SEQUENCE: 20

```
Met Val Arg Thr Pro Cys Cys Lys Ala Glu Leu Gly Leu Lys Lys Gly
1               5                   10                  15

Ala Trp Thr Pro Glu Glu Asp Gln Lys Leu Leu Ser Tyr Leu Asn Arg
            20                  25                  30

His Gly Glu Gly Gly Trp Arg Thr Leu Pro Glu Lys Ala Gly Leu Lys
        35                  40                  45

Arg Cys Gly Lys Ser Cys Arg Leu Arg Trp Ala Asn Tyr Leu Arg Pro
    50                  55                  60

Asp Ile Lys Arg Gly Glu Phe Thr Glu Asp Glu Glu Arg Ser Ile Ile
65                  70                  75                  80

Ser Leu His Ala Leu His Gly Asn Lys Trp Ser Ala Ile Ala Arg Gly
                85                  90                  95

Leu Pro Gly Arg Thr Asp Asn Glu Ile Lys Asn Tyr Trp Asn Thr His
            100                 105                 110

Ile Lys Lys Arg Leu Ile Lys Lys Gly Ile Asp Pro Val Thr His Lys
        115                 120                 125

Gly Ile Thr Ser Gly Thr Asp Lys Ser Glu Asn Leu Pro Glu Lys Gln
    130                 135                 140

Asn Val Asn Leu Thr Thr Ser Asp His Asp Leu Asp Asn Asp Lys Ala
145                 150                 155                 160

Lys Lys Asn Asn Lys Asn Phe Gly Leu Ser Ser Ala Ser Phe Leu Asn
                165                 170                 175

Lys Val Ala Asn Arg Phe Gly Lys Arg Ile Asn Gln Ser Val Leu Ser
            180                 185                 190

Glu Ile Ile Gly Ser Gly Gly Pro Leu Ala Ser Thr Ser His Thr Thr
        195                 200                 205

Asn Thr Thr Thr Thr Ser Val Ser Val Asp Ser Glu Ser Val Lys Ser
    210                 215                 220

Thr Ser Ser Ser Phe Ala Pro Ser Thr Ser Asn Leu Leu Cys His Gly Thr
225                 230                 235                 240

Val Ala Thr Thr Pro Val Ser Ser Asn Phe Asp Val Asp Gly Asn Val
                245                 250                 255
```

```
Asn Leu Thr Cys Ser Ser Thr Phe Ser Asp Ser Ser Val Asn Asn
            260                 265                 270

Pro Leu Met Tyr Cys Asp Asn Phe Val Gly Asn Asn Asn Val Asp Asp
        275                 280                 285

Glu Asp Thr Ile Gly Phe Ser Thr Phe Leu Asn Asp Glu Asp Phe Met
    290                 295                 300

Met Leu Glu Glu Ser Cys Val Glu Asn Thr Ala Phe Met Lys Glu Leu
305                 310                 315                 320

Thr Arg Phe Leu His Glu Asp Glu Asn Asp Val Val Asp Val Thr Pro
                325                 330                 335

Val Tyr Glu Arg Gln Asp Leu Phe Asp Glu Ile Asp Asn Tyr Phe Gly
            340                 345                 350

<210> SEQ ID NO 21
<211> LENGTH: 727
<212> TYPE: DNA
<213> ORGANISM: Arabidopsis thaliana
<220> FEATURE:
<221> NAME/KEY: CDS
<222> LOCATION: (82)...(570)

<400> SEQUENCE: 21
accaaactca aaaacacaa accacaagag gatcatttca ttttttattg tttcgtttta      60
atcatcatca tcagaagaaa a atg gtt gcg ata tcg gag atc aag tcg acg     111
              Met Val Ala Ile Ser Glu Ile Lys Ser Thr
                1               5                  10 gtg gat gtc acg gcg gcg aat tgt ttg atg ctt tta tct aga gtt gga     159
Val Asp Val Thr Ala Ala Asn Cys Leu Met Leu Leu Ser Arg Val Gly
             15                  20                  25 caa gaa aac gtt gac ggt ggc gat caa aaa cgc gtt ttc aca tgt aaa     207
Gln Glu Asn Val Asp Gly Gly Asp Gln Lys Arg Val Phe Thr Cys Lys
         30                  35                  40 acg tgt ttg aag cag ttt cat tcg ttc caa gcc tta gga ggt cac cgt     255
Thr Cys Leu Lys Gln Phe His Ser Phe Gln Ala Leu Gly Gly His Arg
     45                  50                  55 gcg agt cac aag aag cct aac aac gac gct ttg tcg tct gga ttg atg     303
Ala Ser His Lys Lys Pro Asn Asn Asp Ala Leu Ser Ser Gly Leu Met
 60                  65                  70 aag aag gtg aaa acg tcg tcg cat cct tgt ccc ata tgt gga gtg gag     351
Lys Lys Val Lys Thr Ser Ser His Pro Cys Pro Ile Cys Gly Val Glu
 75                  80                  85                  90 ttt ccg atg gga caa gct ttg gga gga cac atg agg aga cac agg aac     399
Phe Pro Met Gly Gln Ala Leu Gly Gly His Met Arg Arg His Arg Asn
                 95                 100                 105 gag agt ggg gct gct ggt ggc gcg ttg gtt aca cgc gct ttg ttg ccg     447
Glu Ser Gly Ala Ala Gly Gly Ala Leu Val Thr Arg Ala Leu Leu Pro
             110                 115                 120 gag ccc acg gtg act acg ttg aag aaa tct agc agt ggg aag aga gtg     495
Glu Pro Thr Val Thr Thr Leu Lys Lys Ser Ser Ser Gly Lys Arg Val
         125                 130                 135 gct tgt ttg gat ctg agt cta ggg atg gtg gac aat ttg aat ctc aag     543
Ala Cys Leu Asp Leu Ser Leu Gly Met Val Asp Asn Leu Asn Leu Lys
     140                 145                 150 ttg gag ctt gga aga aca gtt tat tga ttttatttat tttccttaaa           590
Leu Glu Leu Gly Arg Thr Val Tyr *
155                 160 ttttctgaat atatttgttt ctctcattct ttgaattttt cttaatattc tagattatac   650
atacatccgc agatttagga aactttcata gagtgtaatc ttttctttct gtaaaaatat   710
```

```
attttacttg tagcaaa                                            727
```

```
<210> SEQ ID NO 22
<211> LENGTH: 162
<212> TYPE: PRT
<213> ORGANISM: Arabidopsis thaliana
<220> FEATURE:
<221> NAME/KEY: DOMAIN
<222> LOCATION: (41)...(61)
<223> OTHER INFORMATION: Conserved domain
<220> FEATURE:
<221> NAME/KEY: DOMAIN
<222> LOCATION: (84)...(104)
<223> OTHER INFORMATION: Conserved domain

<400> SEQUENCE: 22

Met Val Ala Ile Ser Glu Ile Lys Ser Thr Val Asp Val Thr Ala Ala
 1               5                  10                  15

Asn Cys Leu Met Leu Leu Ser Arg Val Gly Gln Glu Asn Val Asp Gly
            20                  25                  30

Gly Asp Gln Lys Arg Val Phe Thr Cys Lys Thr Cys Leu Lys Gln Phe
        35                  40                  45

His Ser Phe Gln Ala Leu Gly Gly His Arg Ala Ser His Lys Lys Pro
    50                  55                  60

Asn Asn Asp Ala Leu Ser Ser Gly Leu Met Lys Lys Val Lys Thr Ser
65                  70                  75                  80

Ser His Pro Cys Pro Ile Cys Gly Val Glu Phe Pro Met Gly Gln Ala
                85                  90                  95

Leu Gly Gly His Met Arg Arg His Arg Asn Glu Ser Gly Ala Ala Gly
            100                 105                 110

Gly Ala Leu Val Thr Arg Ala Leu Leu Pro Glu Pro Thr Val Thr Thr
        115                 120                 125

Leu Lys Lys Ser Ser Ser Gly Lys Arg Val Ala Cys Leu Asp Leu Ser
    130                 135                 140

Leu Gly Met Val Asp Asn Leu Asn Leu Lys Leu Glu Leu Gly Arg Thr
145                 150                 155                 160

Val Tyr

<210> SEQ ID NO 23
<211> LENGTH: 922
<212> TYPE: DNA
<213> ORGANISM: Arabidopsis thaliana
<220> FEATURE:
<221> NAME/KEY: CDS
<222> LOCATION: (101)...(580)

<400> SEQUENCE: 23
attatattcc gtacaatccg atcgatttcc cggcgccaga tctcaccgcg actcgtctac    60
tttccgattt ggttcgtgtt gactcagtta cgattaaact atg gat cca atg gat   115
                                            Met Asp Pro Met Asp
                                             1               5 ata gtc ggc aaa tcc aag gaa gac gct tct ctt cca aaa gct acg atg   163
Ile Val Gly Lys Ser Lys Glu Asp Ala Ser Leu Pro Lys Ala Thr Met
             10                  15                  20 act aaa att ata aag gag atg tta cca cca gat gtt cgt gtt gca aga   211
Thr Lys Ile Ile Lys Glu Met Leu Pro Pro Asp Val Arg Val Ala Arg
         25                  30                  35 gat gct caa gat ctt ctc att gaa tgt tgt gta gag ttt ata aat ctt   259
Asp Ala Gln Asp Leu Leu Ile Glu Cys Cys Val Glu Phe Ile Asn Leu
     40                  45                  50
```

```
gta tct tca gaa tct aat gat gtt tgt aac aaa gag gat aaa cgg acg      307
Val Ser Ser Glu Ser Asn Asp Val Cys Asn Lys Glu Asp Lys Arg Thr
        55                  60                  65 att gct cct gag cat gtt ctc aag gca tta cag gtt ctt ggt ttt gga      355
Ile Ala Pro Glu His Val Leu Lys Ala Leu Gln Val Leu Gly Phe Gly
 70              75                  80                  85 gaa tac att gaa gaa gtc tat gct gcg tat gag caa cat aag tat gaa      403
Glu Tyr Ile Glu Glu Val Tyr Ala Ala Tyr Glu Gln His Lys Tyr Glu
                 90                  95                 100 aca atg cag gac aca cag agg agc gtg aaa tgg aac cct gga gct caa      451
Thr Met Gln Asp Thr Gln Arg Ser Val Lys Trp Asn Pro Gly Ala Gln
                105                 110                 115 atg act gag gag gaa gca gca gct gag caa caa cgt atg ttt gca gaa      499
Met Thr Glu Glu Glu Ala Ala Ala Glu Gln Gln Arg Met Phe Ala Glu
                120                 125                 130 gca cgt gca aga atg aat gga ggt gtt tcg gtt cct caa cct gaa cat      547
Ala Arg Ala Arg Met Asn Gly Gly Val Ser Val Pro Gln Pro Glu His
135                 140                 145 cca gaa act gac cag aga agt ccg caa agc taa ctgaaaccgt aagggtaagt    600
Pro Glu Thr Asp Gln Arg Ser Pro Gln Ser  *
150                 155 gttaggcaag aaaaaacaac atccttttaa cattcccttg taagttgcaa atgcgtatgt    660
tctctgttta tatgctctta gtatgatata tgttagttag tgtttcacga tctaaaaaca    720
cttgtgattc agatgtaatt agtaagcatt ccttgttttg tgtttacttt gtgtcttgac    780
taagcatggt gggtcaggtc tacacaaagc atctgattcg atgacttaca ggaatcttaa    840
tgtttgtaga ttggataaat ttggtgattg gtgtaattgt ttttccataa acacaatgca    900
atcattgttt agtgttgtta ac                                             922

<210> SEQ ID NO 24
<211> LENGTH: 159
<212> TYPE: PRT
<213> ORGANISM: Arabidopsis thaliana
<220> FEATURE:
<221> NAME/KEY: DOMAIN
<222> LOCATION: (11)...(104)
<223> OTHER INFORMATION: Conserved domain

<400> SEQUENCE: 24

Met Asp Pro Met Asp Ile Val Gly Lys Ser Lys Glu Asp Ala Ser Leu
 1               5                  10                  15

Pro Lys Ala Thr Met Thr Lys Ile Ile Lys Glu Met Leu Pro Pro Asp
             20                  25                  30

Val Arg Val Ala Arg Asp Ala Gln Asp Leu Leu Ile Glu Cys Cys Val
         35                  40                  45

Glu Phe Ile Asn Leu Val Ser Ser Glu Ser Asn Asp Val Cys Asn Lys
     50                  55                  60

Glu Asp Lys Arg Thr Ile Ala Pro Glu His Val Leu Lys Ala Leu Gln
 65                  70                  75                  80

Val Leu Gly Phe Gly Glu Tyr Ile Glu Glu Val Tyr Ala Ala Tyr Glu
                 85                  90                  95

Gln His Lys Tyr Glu Thr Met Gln Asp Thr Gln Arg Ser Val Lys Trp
            100                 105                 110

Asn Pro Gly Ala Gln Met Thr Glu Glu Glu Ala Ala Ala Glu Gln Gln
        115                 120                 125

Arg Met Phe Ala Glu Ala Arg Ala Arg Met Asn Gly Gly Val Ser Val
    130                 135                 140
```

Pro Gln Pro Glu His Pro Glu Thr Asp Gln Arg Ser Pro Gln Ser
145                 150                 155

<210> SEQ ID NO 25
<211> LENGTH: 786
<212> TYPE: DNA
<213> ORGANISM: Arabidopsis thaliana
<220> FEATURE:
<221> NAME/KEY: CDS
<222> LOCATION: (1)...(786)

<400> SEQUENCE: 25

| | | |
|---|---|---|
| atg gtg ttt aaa tca gaa aaa tca aac cgg gaa atg aaa tca aag gag<br>Met Val Phe Lys Ser Glu Lys Ser Asn Arg Glu Met Lys Ser Lys Glu<br>1               5                   10                  15 | 48 |
| aag caa agg aag gga tta tgg tca ccc gag gaa gat gag aag ctt agg<br>Lys Gln Arg Lys Gly Leu Trp Ser Pro Glu Glu Asp Glu Lys Leu Arg<br>                20                  25                  30 | 96 |
| agt cat gtc ctc aaa tat ggc cat gga tgc tgg agt act att cct ctt<br>Ser His Val Leu Lys Tyr Gly His Gly Cys Trp Ser Thr Ile Pro Leu<br>            35                  40                  45 | 144 |
| caa gct gga ttg cag agg aat ggg aag agt tgt aga tta agg tgg gtt<br>Gln Ala Gly Leu Gln Arg Asn Gly Lys Ser Cys Arg Leu Arg Trp Val<br>        50                  55                  60 | 192 |
| aat tat tta aga cct gga ctt aag aag tct tta ttc act aaa caa gag<br>Asn Tyr Leu Arg Pro Gly Leu Lys Lys Ser Leu Phe Thr Lys Gln Glu<br>65                  70                  75                  80 | 240 |
| gaa act ata ctt ctt tca ctt cat tcc atg ttg ggt aac aaa tgg tct<br>Glu Thr Ile Leu Leu Ser Leu His Ser Met Leu Gly Asn Lys Trp Ser<br>                    85                  90                  95 | 288 |
| cag ata tcg aaa ttc tta cca gga aga acc gac aac gag atc aaa aac<br>Gln Ile Ser Lys Phe Leu Pro Gly Arg Thr Asp Asn Glu Ile Lys Asn<br>                100                 105                 110 | 336 |
| tat tgg cat tct aat cta aag aag ggt gta act ttg aaa caa cat gaa<br>Tyr Trp His Ser Asn Leu Lys Lys Gly Val Thr Leu Lys Gln His Glu<br>            115                 120                 125 | 384 |
| acc aca aaa aaa cat caa aca cct tta atc aca aac tca ctt gag gcc<br>Thr Thr Lys Lys His Gln Thr Pro Leu Ile Thr Asn Ser Leu Glu Ala<br>        130                 135                 140 | 432 |
| ttg cag agt tca act gaa aga tct tct tca tct atc aat gtc gga gaa<br>Leu Gln Ser Ser Thr Glu Arg Ser Ser Ser Ser Ile Asn Val Gly Glu<br>145                 150                 155                 160 | 480 |
| acg tct aat gct caa acc tca agc ttt tcg cca aat ctc gtg ttc tcg<br>Thr Ser Asn Ala Gln Thr Ser Ser Phe Ser Pro Asn Leu Val Phe Ser<br>                165                 170                 175 | 528 |
| gaa tgg tta gat cat agt ttg ctt atg gat cag tca cct caa aag tct<br>Glu Trp Leu Asp His Ser Leu Leu Met Asp Gln Ser Pro Gln Lys Ser<br>                180                 185                 190 | 576 |
| agc tat gtt caa aat ctt gtt tta ccg gaa gag aga gga ttc att gga<br>Ser Tyr Val Gln Asn Leu Val Leu Pro Glu Glu Arg Gly Phe Ile Gly<br>            195                 200                 205 | 624 |
| cca tgt ggc cct cgt tat ttg gga aac gac tct ttg cct gat ttc gtg<br>Pro Cys Gly Pro Arg Tyr Leu Gly Asn Asp Ser Leu Pro Asp Phe Val<br>        210                 215                 220 | 672 |
| cca aat tca gaa ttt ttg ttg gat gat gag ata tca tct gag atc gag<br>Pro Asn Ser Glu Phe Leu Leu Asp Asp Glu Ile Ser Ser Glu Ile Glu<br>225                 230                 235                 240 | 720 |
| ttc tgt act tca ttt tca gac aac ttt ttg ttc gat ggt ctc atc aac<br>Phe Cys Thr Ser Phe Ser Asp Asn Phe Leu Phe Asp Gly Leu Ile Asn<br>                245                 250                 255 | 768 |
| gag cta cga cca atg taa | 786 |

```
Glu Leu Arg Pro Met *
            260
```

<210> SEQ ID NO 26
<211> LENGTH: 261
<212> TYPE: PRT
<213> ORGANISM: Arabidopsis thaliana
<220> FEATURE:
<221> NAME/KEY: DOMAIN
<222> LOCATION: (20)...(120)
<223> OTHER INFORMATION: Conserved domain

<400> SEQUENCE: 26

```
Met Val Phe Lys Ser Glu Lys Ser Asn Arg Glu Met Lys Ser Lys Glu
 1               5                  10                  15

Lys Gln Arg Lys Gly Leu Trp Ser Pro Glu Gly Asp Glu Lys Leu Arg
            20                  25                  30

Ser His Val Leu Lys Tyr Gly His Gly Cys Trp Ser Thr Ile Pro Leu
        35                  40                  45

Gln Ala Gly Leu Gln Arg Asn Gly Lys Ser Cys Arg Leu Arg Trp Val
    50                  55                  60

Asn Tyr Leu Arg Pro Gly Leu Lys Lys Ser Leu Phe Thr Lys Gln Glu
65                  70                  75                  80

Glu Thr Ile Leu Leu Ser Leu His Ser Met Leu Gly Asn Lys Trp Ser
                85                  90                  95

Gln Ile Ser Lys Phe Leu Pro Gly Arg Thr Asp Asn Glu Ile Lys Asn
            100                 105                 110

Tyr Trp His Ser Asn Leu Lys Lys Gly Val Thr Leu Lys Gln His Glu
        115                 120                 125

Thr Thr Lys Lys His Gln Thr Pro Leu Ile Thr Asn Ser Leu Glu Ala
    130                 135                 140

Leu Gln Ser Ser Thr Glu Arg Ser Ser Ser Ile Asn Val Gly Glu
145                 150                 155                 160

Thr Ser Asn Ala Gln Thr Ser Ser Phe Ser Pro Asn Leu Val Phe Ser
                165                 170                 175

Glu Trp Leu Asp His Ser Leu Leu Met Asp Gln Ser Pro Gln Lys Ser
            180                 185                 190

Ser Tyr Val Gln Asn Leu Val Leu Pro Glu Glu Arg Gly Phe Ile Gly
        195                 200                 205

Pro Cys Gly Pro Arg Tyr Leu Gly Asn Asp Ser Leu Pro Asp Phe Val
    210                 215                 220

Pro Asn Ser Glu Phe Leu Leu Asp Asp Glu Ile Ser Ser Glu Ile Glu
225                 230                 235                 240

Phe Cys Thr Ser Phe Ser Asp Asn Phe Leu Phe Asp Gly Leu Ile Asn
                245                 250                 255

Glu Leu Arg Pro Met
            260
```

<210> SEQ ID NO 27
<211> LENGTH: 1304
<212> TYPE: DNA
<213> ORGANISM: Arabidopsis thaliana
<220> FEATURE:
<221> NAME/KEY: CDS
<222> LOCATION: (138)...(1127)

<400> SEQUENCE: 27

```
tgatcatcta aaactttcaa tttctctctt gatcctcact tgaattttt gttgtttctc      60
```

-continued

```
tcaaatcttt gatcctttcc tttgttttc atttgacctc ttacaaaaaa atctggtgtg      120
ccattaaatc tttatta atg gca caa ctt cct ccg aaa atc cca acc atg       170
                   Met Ala Gln Leu Pro Pro Lys Ile Pro Thr Met
                    1               5                  10 acg acg cca aat tgg cct gac ttc tcc tcc cag aaa ctc cct tcc ata       218
Thr Thr Pro Asn Trp Pro Asp Phe Ser Ser Gln Lys Leu Pro Ser Ile
                15                  20                  25 gcc gca acg gcg gca gcc gca gca acc gct gga cct caa caa caa aac       266
Ala Ala Thr Ala Ala Ala Ala Ala Thr Ala Gly Pro Gln Gln Gln Asn
            30                  35                  40 cct tca tgg atg gat gag ttt ctc gac ttc tca gcg act cgc cgt ggg       314
Pro Ser Trp Met Asp Glu Phe Leu Asp Phe Ser Ala Thr Arg Arg Gly
        45                  50                  55 act cac cgt cgt tct ata agc gac tcc att gct ttc ctt gaa cca cct       362
Thr His Arg Arg Ser Ile Ser Asp Ser Ile Ala Phe Leu Glu Pro Pro
60                  65                  70                  75 tcc tcc ggc gtc gga aac cac cac ttc gat agg ttt gac gac gag caa       410
Ser Ser Gly Val Gly Asn His His Phe Asp Arg Phe Asp Asp Glu Gln
                80                  85                  90 ttc atg tcc atg ttc aac gac gac gta cac aac aat aac cac aat cat       458
Phe Met Ser Met Phe Asn Asp Asp Val His Asn Asn Asn His Asn His
            95                  100                 105 cat cat cat cac agc atc aac ggc aat gtg ggt ccc acg cgt tca tcc       506
His His His His Ser Ile Asn Gly Asn Val Gly Pro Thr Arg Ser Ser
        110                 115                 120 tcc aac acc tcc acg ccg tcc gat cat aat agc ctt agc gac gac gac       554
Ser Asn Thr Ser Thr Pro Ser Asp His Asn Ser Leu Ser Asp Asp Asp
125                 130                 135 aac aac aaa gaa gca cca ccg tcc gat cat gat cat cac atg gac aat       602
Asn Asn Lys Glu Ala Pro Pro Ser Asp His Asp His His Met Asp Asn
140                 145                 150                 155 aat gta gcc aat caa aac aac gcc gcc ggt aac aat tac aac gaa tca       650
Asn Val Ala Asn Gln Asn Asn Ala Ala Gly Asn Asn Tyr Asn Glu Ser
                160                 165                 170 gac gag gtc caa agc cag tgc aag acg gag cca caa gat ggt ccg tcg       698
Asp Glu Val Gln Ser Gln Cys Lys Thr Glu Pro Gln Asp Gly Pro Ser
            175                 180                 185 gcg aat caa aac tcc ggt gga agc tcc ggt aat cgt att cac gac cct       746
Ala Asn Gln Asn Ser Gly Gly Ser Ser Gly Asn Arg Ile His Asp Pro
        190                 195                 200 aaa agg gta aaa aga att tta gca aat agg caa tca gca cag aga tca       794
Lys Arg Val Lys Arg Ile Leu Ala Asn Arg Gln Ser Ala Gln Arg Ser
205                 210                 215 agg gtg agg aaa ttg caa tac ata tca gag ctt gaa agg agc gtt act       842
Arg Val Arg Lys Leu Gln Tyr Ile Ser Glu Leu Glu Arg Ser Val Thr
220                 225                 230                 235 tca ttg cag act gaa gtg tca gtg tta tcg cca aga gtt gcg ttt ttg       890
Ser Leu Gln Thr Glu Val Ser Val Leu Ser Pro Arg Val Ala Phe Leu
                240                 245                 250 gat cat cag cga ttg ctt ctc aac gtc gac aat agt gct atc aag caa       938
Asp His Gln Arg Leu Leu Leu Asn Val Asp Asn Ser Ala Ile Lys Gln
            255                 260                 265 cga atc gca gct tta gca caa gat aag att ttc aaa gac gct cat caa       986
Arg Ile Ala Ala Leu Ala Gln Asp Lys Ile Phe Lys Asp Ala His Gln
        270                 275                 280 gaa gca ttg aag aga gaa ata gag aga ctt cga caa gta tat cat caa      1034
Glu Ala Leu Lys Arg Glu Ile Glu Arg Leu Arg Gln Val Tyr His Gln
285                 290                 295 caa agc ctc aag aag atg gag aat aat gtc tcc gat caa tct ccg gcc      1082
```

```
Gln Ser Leu Lys Lys Met Glu Asn Asn Val Ser Asp Gln Ser Pro Ala
300                 305                 310                 315
gat atc aaa ccg tcc gtt gag aag gaa cag ctc ctc aat gtc taa          1127
Asp Ile Lys Pro Ser Val Glu Lys Glu Gln Leu Leu Asn Val  *
                320                 325 agctgttcgt tcactaagat ctttctttc atggcgaaaa gattcttgac tataaaacct     1187
ctttgtgtca agaaattaat ttatcaaaga agatggcctt ttttatttga tctaatcaca    1247 ttttttaag ttgtgatgaa tttgcttttg atgtatctgt tttttttttt ttttttt        1304

<210> SEQ ID NO 28
<211> LENGTH: 329
<212> TYPE: PRT
<213> ORGANISM: Arabidopsis thaliana
<220> FEATURE:
<221> NAME/KEY: DOMAIN
<222> LOCATION: (201)...(261)
<223> OTHER INFORMATION: Conserved domain

<400> SEQUENCE: 28

Met Ala Gln Leu Pro Pro Lys Ile Pro Thr Met Thr Thr Pro Asn Trp
1               5                   10                  15

Pro Asp Phe Ser Ser Gln Lys Leu Pro Ser Ile Ala Ala Thr Ala Ala
                20                  25                  30

Ala Ala Ala Thr Ala Gly Pro Gln Gln Gln Asn Pro Ser Trp Met Asp
            35                  40                  45

Glu Phe Leu Asp Phe Ser Ala Thr Arg Arg Gly Thr His Arg Arg Ser
    50                  55                  60

Ile Ser Asp Ser Ile Ala Phe Leu Glu Pro Pro Ser Ser Gly Val Gly
65                  70                  75                  80

Asn His His Phe Asp Arg Phe Asp Asp Glu Gln Phe Met Ser Met Phe
                85                  90                  95

Asn Asp Asp Val His Asn Asn His Asn His His His His Ser
                100                 105                 110

Ile Asn Gly Asn Val Gly Pro Thr Arg Ser Ser Ser Asn Thr Ser Thr
            115                 120                 125

Pro Ser Asp His Asn Ser Leu Ser Asp Asp Asn Asn Lys Glu Ala
    130                 135                 140

Pro Pro Ser Asp His Asp His His Met Asp Asn Asn Val Ala Asn Gln
145                 150                 155                 160

Asn Asn Ala Ala Gly Asn Asn Tyr Asn Glu Ser Asp Glu Val Gln Ser
                165                 170                 175

Gln Cys Lys Thr Glu Pro Gln Asp Gly Pro Ser Ala Asn Gln Asn Ser
            180                 185                 190

Gly Gly Ser Ser Gly Asn Arg Ile His Asp Pro Lys Arg Val Lys Arg
        195                 200                 205

Ile Leu Ala Asn Arg Gln Ser Ala Gln Arg Ser Arg Val Arg Lys Leu
    210                 215                 220

Gln Tyr Ile Ser Glu Leu Glu Arg Ser Val Thr Ser Leu Gln Thr Glu
225                 230                 235                 240

Val Ser Val Leu Ser Pro Arg Val Ala Phe Leu Asp His Gln Arg Leu
                245                 250                 255

Leu Leu Asn Val Asp Asn Ser Ala Ile Lys Gln Arg Ile Ala Ala Leu
            260                 265                 270

Ala Gln Asp Lys Ile Phe Lys Asp Ala His Gln Glu Ala Leu Lys Arg
    275                 280                 285
```

```
Glu Ile Glu Arg Leu Arg Gln Val Tyr His Gln Gln Ser Leu Lys Lys
    290                 295                 300

Met Glu Asn Asn Val Ser Asp Gln Ser Pro Ala Asp Ile Lys Pro Ser
305                 310                 315                 320

Val Glu Lys Glu Gln Leu Leu Asn Val
                325

<210> SEQ ID NO 29
<211> LENGTH: 1161
<212> TYPE: DNA
<213> ORGANISM: Arabidopsis thaliana
<220> FEATURE:
<221> NAME/KEY: CDS
<222> LOCATION: (67)...(1041)

<400> SEQUENCE: 29
aattcaatca ctatattttt ttaaaaacat ttgacttcat cgatcggtta acaattaatc      60 aaaaag atg gga cga tca cca tgt tgt gag aag aag aat ggt ctc aag        108
       Met Gly Arg Ser Pro Cys Cys Glu Lys Lys Asn Gly Leu Lys
           1               5                   10 aaa gga cca tgg act cct gag gag gat caa aag ctc att gat tat atc      156
Lys Gly Pro Trp Thr Pro Glu Glu Asp Gln Lys Leu Ile Asp Tyr Ile
 15              20                  25                  30 aat ata cat ggt tat gga aat tgg aga act ctt ccc aag aat gct ggg      204
Asn Ile His Gly Tyr Gly Asn Trp Arg Thr Leu Pro Lys Asn Ala Gly
                 35                  40                  45 tta caa aga tgt ggt aag agt tgt cgt ctc cgg tgg acc aac tat ctc      252
Leu Gln Arg Cys Gly Lys Ser Cys Arg Leu Arg Trp Thr Asn Tyr Leu
             50                  55                  60 cga cca gat att aag cgt gga aga ttc tct ttt gaa gaa gaa gaa acc      300
Arg Pro Asp Ile Lys Arg Gly Arg Phe Ser Phe Glu Glu Glu Glu Thr
         65                  70                  75 att att caa ctt cac agc atc atg gga aac aag tgg tct gcg att gcg      348
Ile Ile Gln Leu His Ser Ile Met Gly Asn Lys Trp Ser Ala Ile Ala
     80                  85                  90 gct cgt ttg cct gga aga aca gac aac gag atc aaa aac tat tgg aac      396
Ala Arg Leu Pro Gly Arg Thr Asp Asn Glu Ile Lys Asn Tyr Trp Asn
 95                 100                 105                 110 act cac atc aga aaa aga ctt cta aag atg gga atc gac ccg gtt aca      444
Thr His Ile Arg Lys Arg Leu Leu Lys Met Gly Ile Asp Pro Val Thr
                115                 120                 125 cac act cca cgt ctt gat ctt ctc gat atc tcc tcc att ctc agc tca      492
His Thr Pro Arg Leu Asp Leu Leu Asp Ile Ser Ser Ile Leu Ser Ser
            130                 135                 140 tct atc tac aac tct tcg cat cat cat cat cat cat caa caa cat          540
Ser Ile Tyr Asn Ser Ser His His His His His His Gln Gln His
        145                 150                 155 atg aac atg tcg agg ctc atg atg agt gat ggt aat cat caa cca ttg      588
Met Asn Met Ser Arg Leu Met Met Ser Asp Gly Asn His Gln Pro Leu
    160                 165                 170 gtt aac ccc gag ata ctc aaa ctc gca acc tct ctc ttt tca aac caa      636
Val Asn Pro Glu Ile Leu Lys Leu Ala Thr Ser Leu Phe Ser Asn Gln
175                 180                 185                 190 aac cac ccc aac aac aca cac gag aac aac acg gtt aac caa acc gaa      684
Asn His Pro Asn Asn Thr His Glu Asn Asn Thr Val Asn Gln Thr Glu
                195                 200                 205 gta aac caa tac caa acc ggt tac aac atg cct ggt aat gaa gaa tta      732
Val Asn Gln Tyr Gln Thr Gly Tyr Asn Met Pro Gly Asn Glu Glu Leu
            210                 215                 220 caa tct tgg ttc cct atc atg gat caa ttc acg aat ttc caa gac ctc      780
Gln Ser Trp Phe Pro Ile Met Asp Gln Phe Thr Asn Phe Gln Asp Leu
```

-continued

```
                Gln Ser Trp Phe Pro Ile Met Asp Gln Phe Thr Asn Phe Gln Asp Leu
                    225                 230                 235 atg cca atg aag acg acg gtc caa aat tca ttg tca tac gat gat gat                   828
Met Pro Met Lys Thr Thr Val Gln Asn Ser Leu Ser Tyr Asp Asp Asp
    240                 245                 250 tgt tcg aag tcc aat ttt gta tta gaa cct tat tac tcc gac ttt gct                   876
Cys Ser Lys Ser Asn Phe Val Leu Glu Pro Tyr Tyr Ser Asp Phe Ala
255                 260                 265                 270 tca gtc ttg acc aca cct tct tca agc ccg act ccg tta aac tca agt                   924
Ser Val Leu Thr Thr Pro Ser Ser Ser Pro Thr Pro Leu Asn Ser Ser
                275                 280                 285 tcc tca act tac atc aat agt agc act tgc agc acc gag gat gaa aaa                   972
Ser Ser Thr Tyr Ile Asn Ser Ser Thr Cys Ser Thr Glu Asp Glu Lys
            290                 295                 300 gag agt tat tac agt gat aat atc act aat tat tcg ttt gat gtt aat                  1020
Glu Ser Tyr Tyr Ser Asp Asn Ile Thr Asn Tyr Ser Phe Asp Val Asn
        305                 310                 315 ggt ttt ctc caa ttc caa taa acaaaacgcc attggaatag agttatgtaa                     1071
Gly Phe Leu Gln Phe Gln  *
    320 acatgcaatc attgtatttg ttatatagat tttgttacat atccaaaatc caaaatacta                1131 tagttttaaa ataaaaaaaa aaaaaaaaaa                                                 1161

<210> SEQ ID NO 30
<211> LENGTH: 324
<212> TYPE: PRT
<213> ORGANISM: Arabidopsis thaliana
<220> FEATURE:
<221> NAME/KEY: DOMAIN
<222> LOCATION: (14)...(119)
<223> OTHER INFORMATION: Conserved domain

<400> SEQUENCE: 30

Met Gly Arg Ser Pro Cys Cys Glu Lys Lys Asn Gly Leu Lys Lys Gly
  1               5                  10                  15

Pro Trp Thr Pro Glu Glu Asp Gln Lys Leu Ile Asp Tyr Ile Asn Ile
             20                  25                  30

His Gly Tyr Gly Asn Trp Arg Thr Leu Pro Lys Asn Ala Gly Leu Gln
         35                  40                  45

Arg Cys Gly Lys Ser Cys Arg Leu Arg Trp Thr Asn Tyr Leu Arg Pro
     50                  55                  60

Asp Ile Lys Arg Gly Arg Phe Ser Phe Glu Glu Glu Thr Ile Ile
 65                  70                  75                  80

Gln Leu His Ser Ile Met Gly Asn Lys Trp Ser Ala Ile Ala Ala Arg
                 85                  90                  95

Leu Pro Gly Arg Thr Asp Asn Glu Ile Lys Asn Tyr Trp Asn Thr His
            100                 105                 110

Ile Arg Lys Arg Leu Leu Lys Met Gly Ile Asp Pro Val Thr His Thr
        115                 120                 125

Pro Arg Leu Asp Leu Leu Asp Ile Ser Ser Ile Leu Ser Ser Ser Ile
    130                 135                 140

Tyr Asn Ser Ser His His His His His His Gln Gln His Met Asn
145                 150                 155                 160

Met Ser Arg Leu Met Met Ser Asp Gly Asn His Gln Pro Leu Val Asn
                165                 170                 175

Pro Glu Ile Leu Lys Leu Ala Thr Ser Leu Phe Ser Asn Gln Asn His
            180                 185                 190
```

-continued

```
Pro Asn Asn Thr His Glu Asn Asn Thr Val Asn Gln Thr Glu Val Asn
            195                 200                 205

Gln Tyr Gln Thr Gly Tyr Asn Met Pro Gly Asn Glu Glu Leu Gln Ser
    210                 215                 220

Trp Phe Pro Ile Met Asp Gln Phe Thr Asn Phe Gln Asp Leu Met Pro
225                 230                 235                 240

Met Lys Thr Thr Val Gln Asn Ser Leu Ser Tyr Asp Asp Asp Cys Ser
                245                 250                 255

Lys Ser Asn Phe Val Leu Glu Pro Tyr Tyr Ser Asp Phe Ala Ser Val
            260                 265                 270

Leu Thr Thr Pro Ser Ser Ser Pro Thr Pro Leu Asn Ser Ser Ser Ser
        275                 280                 285

Thr Tyr Ile Asn Ser Ser Thr Cys Ser Thr Glu Asp Glu Lys Glu Ser
    290                 295                 300

Tyr Tyr Ser Asp Asn Ile Thr Asn Tyr Ser Phe Asp Val Asn Gly Phe
305                 310                 315                 320

Leu Gln Phe Gln
```

<210> SEQ ID NO 31
<211> LENGTH: 1155
<212> TYPE: DNA
<213> ORGANISM: Arabidopsis thaliana
<220> FEATURE:
<221> NAME/KEY: CDS
<222> LOCATION: (76)...(1077)

<400> SEQUENCE: 31

```
attcacatta ctaatctctc aagatttcac aattttcttg tgattttctc tcagtttctt      60
atttcgtttc ataac atg gat gcc atg agt agc gta gac gag agc tct aca     111
                Met Asp Ala Met Ser Ser Val Asp Glu Ser Ser Thr
                  1               5                  10 act aca gat tcc att ccg gcg aga aag tca tcg tct ccg gcg agt tta     159
Thr Thr Asp Ser Ile Pro Ala Arg Lys Ser Ser Ser Pro Ala Ser Leu
            15                  20                  25 cta tat aga atg gga agc gga aca agc gtg gta ctt gat tca gag aac     207
Leu Tyr Arg Met Gly Ser Gly Thr Ser Val Val Leu Asp Ser Glu Asn
     30                  35                  40 ggt gtc gaa gtc gaa gtc gaa gcc gaa tca aga aag ctt cct tct tca     255
Gly Val Glu Val Glu Val Glu Ala Glu Ser Arg Lys Leu Pro Ser Ser
 45                  50                  55                  60 aga ttc aaa ggt gtt gtt cct caa cca aat gga aga tgg gga gct cag     303
Arg Phe Lys Gly Val Val Pro Gln Pro Asn Gly Arg Trp Gly Ala Gln
                 65                  70                  75 att tac gag aaa cat caa cgc gtg tgg ctt ggt act ttc aac gag gaa     351
Ile Tyr Glu Lys His Gln Arg Val Trp Leu Gly Thr Phe Asn Glu Glu
             80                  85                  90 gac gaa gca gct cgt gct tac gac gtc gcg gct cac cgt ttc cgt ggc     399
Asp Glu Ala Ala Arg Ala Tyr Asp Val Ala Ala His Arg Phe Arg Gly
         95                 100                 105 cgc gat gcc gtt act aat ttc aaa gac acg acg ttc gaa gaa gag gtt     447
Arg Asp Ala Val Thr Asn Phe Lys Asp Thr Thr Phe Glu Glu Glu Val
    110                 115                 120 gag ttc tta aac gcg cat tcg aaa tca gag atc gta gat atg ttg aga     495
Glu Phe Leu Asn Ala His Ser Lys Ser Glu Ile Val Asp Met Leu Arg
125                 130                 135                 140 aaa cac act tac aaa gaa gag tta gac caa agg aaa cgt aac cgt gac     543
Lys His Thr Tyr Lys Glu Glu Leu Asp Gln Arg Lys Arg Asn Arg Asp
                145                 150                 155
```

```
ggt aac gga aaa gag acg acg gcg ttt gct ttg gct tcg atg gtg gtt      591
Gly Asn Gly Lys Glu Thr Thr Ala Phe Ala Leu Ala Ser Met Val Val
        160                 165                 170 atg acg ggg ttt aaa acg gcg gag tta ctg ttt gag aaa acg gta acg      639
Met Thr Gly Phe Lys Thr Ala Glu Leu Leu Phe Glu Lys Thr Val Thr
175                 180                 185 cca agt gac gtc ggg aaa cta aac cgt tta gtt ata cca aaa cac caa      687
Pro Ser Asp Val Gly Lys Leu Asn Arg Leu Val Ile Pro Lys His Gln
        190                 195                 200 gcg gag aaa cat ttt ccg tta ccg tta ggt aat aat aac gtc tcc gtt      735
Ala Glu Lys His Phe Pro Leu Pro Leu Gly Asn Asn Asn Val Ser Val
205                 210                 215                 220 aaa ggt atg ctg ttg aat ttc gaa gac gtt aac ggg aaa gtg tgg agg      783
Lys Gly Met Leu Leu Asn Phe Glu Asp Val Asn Gly Lys Val Trp Arg
                225                 230                 235 ttc cgt tac tct tat tgg aat agt agt caa agt tat gtg ttg acc aaa      831
Phe Arg Tyr Ser Tyr Trp Asn Ser Ser Gln Ser Tyr Val Leu Thr Lys
                240                 245                 250 ggt tgg agt aga ttc gtt aaa gag aag aga ctt tgt gct ggt gat ttg      879
Gly Trp Ser Arg Phe Val Lys Glu Lys Arg Leu Cys Ala Gly Asp Leu
            255                 260                 265 atc agt ttt aaa aga tcc aac gat caa gat caa aaa ttc ttt atc ggg      927
Ile Ser Phe Lys Arg Ser Asn Asp Gln Asp Gln Lys Phe Phe Ile Gly
            270                 275                 280 tgg aaa tcg aaa tcc ggg ttg gat cta gag acg ggt cgg gtt atg aga      975
Trp Lys Ser Lys Ser Gly Leu Asp Leu Glu Thr Gly Arg Val Met Arg
285                 290                 295                 300 ttg ttt ggg gtt gat att tct tta aac gcc gtc gtt gta gtg aag gaa    1023
Leu Phe Gly Val Asp Ile Ser Leu Asn Ala Val Val Val Lys Glu
                305                 310                 315 aca acg gag gtg tta atg tcg tcg tta agg tgt aag aag caa cga gtt    1071
Thr Thr Glu Val Leu Met Ser Ser Leu Arg Cys Lys Lys Gln Arg Val
                320                 325                 330 ttg taa taacaattta acaacttggg aaagaaaaaa aagcttttg atttttaattt     1127
Leu * ctcttcaacg ttaatcttgc tgagatta                                      1155

<210> SEQ ID NO 32
<211> LENGTH: 333
<212> TYPE: PRT
<213> ORGANISM: Arabidopsis thaliana
<220> FEATURE:
<221> NAME/KEY: DOMAIN
<222> LOCATION: (59)...(124)
<223> OTHER INFORMATION: Conserved domain

<400> SEQUENCE: 32

Met Asp Ala Met Ser Ser Val Asp Glu Ser Thr Thr Thr Asp Ser
1               5                   10                  15

Ile Pro Ala Arg Lys Ser Ser Pro Ala Ser Leu Leu Tyr Arg Met
                20                  25                  30

Gly Ser Gly Thr Ser Val Val Leu Asp Ser Glu Asn Gly Val Glu Val
            35                  40                  45

Glu Val Glu Ala Glu Ser Arg Lys Leu Pro Ser Ser Arg Phe Lys Gly
50                  55                  60

Val Val Pro Gln Pro Asn Gly Arg Trp Gly Ala Gln Ile Tyr Glu Lys
65                  70                  75                  80

His Gln Arg Val Trp Leu Gly Thr Phe Asn Glu Glu Asp Glu Ala Ala
                85                  90                  95
```

```
Arg Ala Tyr Asp Val Ala Ala His Arg Phe Arg Gly Arg Asp Ala Val
            100                 105                 110

Thr Asn Phe Lys Asp Thr Thr Phe Glu Glu Val Glu Phe Leu Asn
        115                 120                 125

Ala His Ser Lys Ser Glu Ile Val Asp Met Leu Arg Lys His Thr Tyr
    130                 135                 140

Lys Glu Glu Leu Asp Gln Arg Lys Arg Asn Arg Asp Gly Asn Gly Lys
145                 150                 155                 160

Glu Thr Thr Ala Phe Ala Leu Ala Ser Met Val Val Met Thr Gly Phe
                165                 170                 175

Lys Thr Ala Glu Leu Leu Phe Glu Lys Thr Val Thr Pro Ser Asp Val
            180                 185                 190

Gly Lys Leu Asn Arg Leu Val Ile Pro Lys His Gln Ala Glu Lys His
        195                 200                 205

Phe Pro Leu Pro Leu Gly Asn Asn Asn Val Ser Val Lys Gly Met Leu
    210                 215                 220

Leu Asn Phe Glu Asp Val Asn Gly Lys Val Trp Arg Phe Arg Tyr Ser
225                 230                 235                 240

Tyr Trp Asn Ser Ser Gln Ser Tyr Val Leu Thr Lys Gly Trp Ser Arg
                245                 250                 255

Phe Val Lys Glu Lys Arg Leu Cys Ala Gly Asp Leu Ile Ser Phe Lys
            260                 265                 270

Arg Ser Asn Asp Gln Asp Gln Lys Phe Phe Ile Gly Trp Lys Ser Lys
        275                 280                 285

Ser Gly Leu Asp Leu Glu Thr Gly Arg Val Met Arg Leu Phe Gly Val
    290                 295                 300

Asp Ile Ser Leu Asn Ala Val Val Val Lys Glu Thr Thr Glu Val
305                 310                 315                 320

Leu Met Ser Ser Leu Arg Cys Lys Lys Gln Arg Val Leu
                325                 330

<210> SEQ ID NO 33
<211> LENGTH: 2240
<212> TYPE: DNA
<213> ORGANISM: Arabidopsis thaliana
<220> FEATURE:
<221> NAME/KEY: CDS
<222> LOCATION: (238)...(2064)

<400> SEQUENCE: 33
tgagatttct ccatttccgt agcttctggt ctcttttctt tgtttcattg atcaaaagca    60
aatcacttct tcttcttctt cttctcgatt tcttactgtt ttcttatcca acgaaatctg   120
gaattaaaaa tggaatcttt atcgaatcca agctgatttt gtttctttca ttgaatcatc   180
tctctaaagt ggaattttgt aaagagaaga tctgaagttg tgtagaggag cttagtg atg   240
                                                                Met
                                                                  1 gag aca aat tcg tct gga gaa gat ctg gtt att aag act cgg aag cca    288
Glu Thr Asn Ser Ser Gly Glu Asp Leu Val Ile Lys Thr Arg Lys Pro
          5                  10                  15 tat acg ata aca aag caa cgt gaa agg tgg act gag gaa gaa cat aat    336
Tyr Thr Ile Thr Lys Gln Arg Glu Arg Trp Thr Glu Glu Glu His Asn
         20                  25                  30 aga ttc att gaa gct ttg agg ctt tat ggt aga gca tgg cag aag att    384
Arg Phe Ile Glu Ala Leu Arg Leu Tyr Gly Arg Ala Trp Gln Lys Ile
     35                  40                  45 gaa gaa cat gta gca aca aaa act gct gtc cag ata aga agt cac gct    432
```

|     |     |     |     |     |     |     |     |     |     |     |     |     |     |     |     |
| --- | --- | --- | --- | --- | --- | --- | --- | --- | --- | --- | --- | --- | --- | --- | --- |
| Glu | Glu | His | Val | Ala | Thr | Lys | Thr | Ala | Val | Gln | Ile | Arg | Ser | His | Ala |
| 50  |     |     |     |     | 55  |     |     |     |     | 60  |     |     |     |     | 65  |

| cag | aaa | ttt | ttc | tcc | aag | gta | gag | aaa | gag | gct | gaa | gct | aaa | ggt | gta | 480 |
| --- | --- | --- | --- | --- | --- | --- | --- | --- | --- | --- | --- | --- | --- | --- | --- | --- |
| Gln | Lys | Phe | Phe | Ser | Lys | Val | Glu | Lys | Glu | Ala | Glu | Ala | Lys | Gly | Val |     |
|     |     |     |     | 70  |     |     |     |     | 75  |     |     |     |     | 80  |     |     |

| gct | atg | ggt | caa | gcg | cta | gac | ata | gct | att | cct | cct | cca | cgg | cct | aag | 528 |
| --- | --- | --- | --- | --- | --- | --- | --- | --- | --- | --- | --- | --- | --- | --- | --- | --- |
| Ala | Met | Gly | Gln | Ala | Leu | Asp | Ile | Ala | Ile | Pro | Pro | Pro | Arg | Pro | Lys |     |
|     |     |     |     | 85  |     |     |     |     | 90  |     |     |     |     | 95  |     |     |

| cgt | aaa | cca | aac | aat | cct | tat | cct | cga | aag | acg | gga | agt | gga | acg | atc | 576 |
| --- | --- | --- | --- | --- | --- | --- | --- | --- | --- | --- | --- | --- | --- | --- | --- | --- |
| Arg | Lys | Pro | Asn | Asn | Pro | Tyr | Pro | Arg | Lys | Thr | Gly | Ser | Gly | Thr | Ile |     |
|     |     | 100 |     |     |     |     | 105 |     |     |     |     | 110 |     |     |     |     |

| ctt | atg | tca | aaa | acg | ggt | gtg | aat | gat | gga | aaa | gag | tcc | ctt | gga | tca | 624 |
| --- | --- | --- | --- | --- | --- | --- | --- | --- | --- | --- | --- | --- | --- | --- | --- | --- |
| Leu | Met | Ser | Lys | Thr | Gly | Val | Asn | Asp | Gly | Lys | Glu | Ser | Leu | Gly | Ser |     |
|     |     | 115 |     |     |     |     | 120 |     |     |     |     | 125 |     |     |     |     |

| gaa | aaa | gtg | tcg | cat | cct | gag | atg | gcc | aat | gaa | gat | cga | caa | caa | tca | 672 |
| --- | --- | --- | --- | --- | --- | --- | --- | --- | --- | --- | --- | --- | --- | --- | --- | --- |
| Glu | Lys | Val | Ser | His | Pro | Glu | Met | Ala | Asn | Glu | Asp | Arg | Gln | Gln | Ser |     |
| 130 |     |     |     |     | 135 |     |     |     |     | 140 |     |     |     |     | 145 |     |

| aag | cct | gaa | gag | aaa | act | ctg | cag | gaa | gac | aac | tgt | tca | gat | tgt | ttc | 720 |
| --- | --- | --- | --- | --- | --- | --- | --- | --- | --- | --- | --- | --- | --- | --- | --- | --- |
| Lys | Pro | Glu | Glu | Lys | Thr | Leu | Gln | Glu | Asp | Asn | Cys | Ser | Asp | Cys | Phe |     |
|     |     |     |     | 150 |     |     |     |     | 155 |     |     |     |     | 160 |     |     |

| act | cat | cag | tat | ctc | tct | gct | gca | tcc | tcc | atg | aat | aaa | agt | tgt | ata | 768 |
| --- | --- | --- | --- | --- | --- | --- | --- | --- | --- | --- | --- | --- | --- | --- | --- | --- |
| Thr | His | Gln | Tyr | Leu | Ser | Ala | Ala | Ser | Ser | Met | Asn | Lys | Ser | Cys | Ile |     |
|     |     |     | 165 |     |     |     |     | 170 |     |     |     |     | 175 |     |     |     |

| gag | aca | tca | aac | gca | agc | act | ttc | cgc | gag | ttc | ttg | cct | tca | cgg | gaa | 816 |
| --- | --- | --- | --- | --- | --- | --- | --- | --- | --- | --- | --- | --- | --- | --- | --- | --- |
| Glu | Thr | Ser | Asn | Ala | Ser | Thr | Phe | Arg | Glu | Phe | Leu | Pro | Ser | Arg | Glu |     |
|     |     | 180 |     |     |     |     | 185 |     |     |     |     | 190 |     |     |     |     |

| gag | gga | agt | cag | aat | aac | agg | gta | aga | aag | gag | tca | aac | tca | gat | ttg | 864 |
| --- | --- | --- | --- | --- | --- | --- | --- | --- | --- | --- | --- | --- | --- | --- | --- | --- |
| Glu | Gly | Ser | Gln | Asn | Asn | Arg | Val | Arg | Lys | Glu | Ser | Asn | Ser | Asp | Leu |     |
| 195 |     |     |     |     | 200 |     |     |     |     | 205 |     |     |     |     |     |     |

| aat | gca | aaa | tct | ctg | gaa | aac | ggt | aat | gag | caa | gga | cct | cag | act | tat | 912 |
| --- | --- | --- | --- | --- | --- | --- | --- | --- | --- | --- | --- | --- | --- | --- | --- | --- |
| Asn | Ala | Lys | Ser | Leu | Glu | Asn | Gly | Asn | Glu | Gln | Gly | Pro | Gln | Thr | Tyr |     |
| 210 |     |     |     |     | 215 |     |     |     |     | 220 |     |     |     |     | 225 |     |

| ccg | atg | cat | atc | cct | gtg | cta | gtg | cca | ttg | ggg | agc | tca | ata | aca | agt | 960 |
| --- | --- | --- | --- | --- | --- | --- | --- | --- | --- | --- | --- | --- | --- | --- | --- | --- |
| Pro | Met | His | Ile | Pro | Val | Leu | Val | Pro | Leu | Gly | Ser | Ser | Ile | Thr | Ser |     |
|     |     |     |     | 230 |     |     |     |     | 235 |     |     |     |     | 240 |     |     |

| tct | cta | tca | cat | cct | cct | tca | gag | cca | gat | agt | cat | ccc | cac | aca | gtt | 1008 |
| --- | --- | --- | --- | --- | --- | --- | --- | --- | --- | --- | --- | --- | --- | --- | --- | --- |
| Ser | Leu | Ser | His | Pro | Pro | Ser | Glu | Pro | Asp | Ser | His | Pro | His | Thr | Val |     |
|     |     |     | 245 |     |     |     |     | 250 |     |     |     |     | 255 |     |     |     |

| gca | gga | gat | tat | cag | tcg | ttt | cct | aat | cat | ata | atg | tca | acc | ctt | tta | 1056 |
| --- | --- | --- | --- | --- | --- | --- | --- | --- | --- | --- | --- | --- | --- | --- | --- | --- |
| Ala | Gly | Asp | Tyr | Gln | Ser | Phe | Pro | Asn | His | Ile | Met | Ser | Thr | Leu | Leu |     |
|     |     |     | 260 |     |     |     |     | 265 |     |     |     |     | 270 |     |     |     |

| caa | aca | ccg | gct | ctt | tat | act | gcc | gca | act | ttc | gcc | tca | tca | ttt | tgg | 1104 |
| --- | --- | --- | --- | --- | --- | --- | --- | --- | --- | --- | --- | --- | --- | --- | --- | --- |
| Gln | Thr | Pro | Ala | Leu | Tyr | Thr | Ala | Ala | Thr | Phe | Ala | Ser | Ser | Phe | Trp |     |
|     |     | 275 |     |     |     |     | 280 |     |     |     |     | 285 |     |     |     |     |

| cct | ccc | gat | tct | agt | ggt | ggc | tca | cct | gtt | cca | ggg | aac | tca | cct | ccg | 1152 |
| --- | --- | --- | --- | --- | --- | --- | --- | --- | --- | --- | --- | --- | --- | --- | --- | --- |
| Pro | Pro | Asp | Ser | Ser | Gly | Gly | Ser | Pro | Val | Pro | Gly | Asn | Ser | Pro | Pro |     |
| 290 |     |     |     | 295 |     |     |     |     | 300 |     |     |     |     | 305 |     |     |

| aat | ctg | gct | gcc | atg | gcc | gca | gcc | act | gtt | gca | gct | gct | agt | gct | tgg | 1200 |
| --- | --- | --- | --- | --- | --- | --- | --- | --- | --- | --- | --- | --- | --- | --- | --- | --- |
| Asn | Leu | Ala | Ala | Met | Ala | Ala | Ala | Thr | Val | Ala | Ala | Ala | Ser | Ala | Trp |     |
|     |     |     | 310 |     |     |     |     | 315 |     |     |     |     | 320 |     |     |     |

| tgg | gct | gcc | aat | gga | tta | tta | cct | tta | tgt | gct | cct | ctt | agt | tca | ggt | 1248 |
| --- | --- | --- | --- | --- | --- | --- | --- | --- | --- | --- | --- | --- | --- | --- | --- | --- |
| Trp | Ala | Ala | Asn | Gly | Leu | Leu | Pro | Leu | Cys | Ala | Pro | Leu | Ser | Ser | Gly |     |
|     |     | 325 |     |     |     |     | 330 |     |     |     |     | 335 |     |     |     |     |

| ggt | ttc | act | agt | cat | cct | cca | tct | act | ttt | gga | cca | tca | tgt | gat | gta | 1296 |
| --- | --- | --- | --- | --- | --- | --- | --- | --- | --- | --- | --- | --- | --- | --- | --- | --- |
| Gly | Phe | Thr | Ser | His | Pro | Pro | Ser | Thr | Phe | Gly | Pro | Ser | Cys | Asp | Val |     |
|     |     | 340 |     |     |     |     | 345 |     |     |     |     | 350 |     |     |     |     |

| gag | tac | aca | aaa | gca | agc | act | tta | caa | cat | ggt | tct | gtg | cag | agc | cga | 1344 |
| --- | --- | --- | --- | --- | --- | --- | --- | --- | --- | --- | --- | --- | --- | --- | --- | --- |
| Glu | Tyr | Thr | Lys | Ala | Ser | Thr | Leu | Gln | His | Gly | Ser | Val | Gln | Ser | Arg |     |
|     |     | 355 |     |     |     |     | 360 |     |     |     |     | 365 |     |     |     |     |

```
gag caa gaa cac tcc gag gca tca aag gct cga tct tca ctg gac tca    1392
Glu Gln Glu His Ser Glu Ala Ser Lys Ala Arg Ser Ser Leu Asp Ser
370                 375                 380                 385 gag gat gtt gaa aat aag agt aaa cca gtt tgt cat gag cag cct tct    1440
Glu Asp Val Glu Asn Lys Ser Lys Pro Val Cys His Glu Gln Pro Ser
            390                 395                 400 gca aca cct gag agt gat gca aag ggt tca gat gga gca gga gac aga    1488
Ala Thr Pro Glu Ser Asp Ala Lys Gly Ser Asp Gly Ala Gly Asp Arg
        405                 410                 415 aaa caa gtt gac cgg tcc tcg tgt ggc tca aac act ccg tcg agt agt    1536
Lys Gln Val Asp Arg Ser Ser Cys Gly Ser Asn Thr Pro Ser Ser Ser
    420                 425                 430 gat gat gtt gag gcg gat gca tca gaa agg caa gag gat ggc acc aat    1584
Asp Asp Val Glu Ala Asp Ala Ser Glu Arg Gln Glu Asp Gly Thr Asn
435                 440                 445 ggt gag gtg aaa gaa acg aat gaa gac act aat aaa cct caa act tca    1632
Gly Glu Val Lys Glu Thr Asn Glu Asp Thr Asn Lys Pro Gln Thr Ser
450                 455                 460                 465 gag tcc aat gca cgc cgc agt aga atc agc tcc aat ata acc gat cca    1680
Glu Ser Asn Ala Arg Arg Ser Arg Ile Ser Ser Asn Ile Thr Asp Pro
            470                 475                 480 tgg aag tct gtg tct gac gag ggt cga att gcc ttc caa gct ctc ttc    1728
Trp Lys Ser Val Ser Asp Glu Gly Arg Ile Ala Phe Gln Ala Leu Phe
        485                 490                 495 tcc aga gag gta ttg ccg caa agt ttt aca tat cga gaa gaa cac aga    1776
Ser Arg Glu Val Leu Pro Gln Ser Phe Thr Tyr Arg Glu Glu His Arg
    500                 505                 510 gag gaa gaa caa caa caa caa gaa caa aga tat cca atg gca ctt gat    1824
Glu Glu Glu Gln Gln Gln Gln Glu Gln Arg Tyr Pro Met Ala Leu Asp
515                 520                 525 ctt aac ttc aca gct cag tta aca cca gtt gat gat caa gag gag aag    1872
Leu Asn Phe Thr Ala Gln Leu Thr Pro Val Asp Asp Gln Glu Glu Lys
530                 535                 540                 545 aga aac aca gga ttt ctt gga atc gga tta gat gct tca aag cta atg    1920
Arg Asn Thr Gly Phe Leu Gly Ile Gly Leu Asp Ala Ser Lys Leu Met
            550                 555                 560 agt aga gga aga aca ggt ttt aaa cca tac aaa aga tgt tcc atg gaa    1968
Ser Arg Gly Arg Thr Gly Phe Lys Pro Tyr Lys Arg Cys Ser Met Glu
        565                 570                 575 gcc aaa gaa agt aga atc ctc aac aac aat cct atc att cat gtg gaa    2016
Ala Lys Glu Ser Arg Ile Leu Asn Asn Asn Pro Ile Ile His Val Glu
    580                 585                 590 cag aaa gat ccc aaa cgg atg cgg ttg gaa act caa gct tcc aca tga    2064
Gln Lys Asp Pro Lys Arg Met Arg Leu Glu Thr Gln Ala Ser Thr *
595                 600                 605 gactctattt tcatctgatc tgttgtttgt actctgtttt taagttttca agaccactgc    2124
tacattttct ttttcttttg aggcctttgt atttgtttcc ttgtccatag tcttcctgta    2184
acatttgact ctgtattatt caacaaatca taaactgttt aatctttttt tttccca       2240

<210> SEQ ID NO 34
<211> LENGTH: 608
<212> TYPE: PRT
<213> ORGANISM: Arabidopsis thaliana
<220> FEATURE:
<221> NAME/KEY: DOMAIN
<222> LOCATION: (22)...(71)
<223> OTHER INFORMATION: Conserved domain

<400> SEQUENCE: 34

Met Glu Thr Asn Ser Ser Gly Glu Asp Leu Val Ile Lys Thr Arg Lys
```

```
            1               5                      10                     15
Pro Tyr Thr Ile Thr Lys Gln Arg Glu Arg Trp Thr Glu Glu His
                20                  25                  30

Asn Arg Phe Ile Glu Ala Leu Arg Leu Tyr Gly Arg Ala Trp Gln Lys
                35                  40                  45

Ile Glu Glu His Val Ala Thr Lys Thr Ala Val Gln Ile Arg Ser His
                50                  55                  60

Ala Gln Lys Phe Phe Ser Lys Val Glu Lys Glu Ala Glu Ala Lys Gly
 65                  70                  75                  80

Val Ala Met Gly Gln Ala Leu Asp Ile Ala Ile Pro Pro Arg Pro
                85                  90                  95

Lys Arg Lys Pro Asn Asn Pro Tyr Pro Arg Lys Thr Gly Ser Gly Thr
                100                 105                 110

Ile Leu Met Ser Lys Thr Gly Val Asn Asp Gly Lys Glu Ser Leu Gly
                115                 120                 125

Ser Glu Lys Val Ser His Pro Glu Met Ala Asn Glu Asp Arg Gln Gln
    130                 135                 140

Ser Lys Pro Glu Glu Lys Thr Leu Gln Glu Asp Asn Cys Ser Asp Cys
145                 150                 155                 160

Phe Thr His Gln Tyr Leu Ser Ala Ala Ser Met Asn Lys Ser Cys
                165                 170                 175

Ile Glu Thr Ser Asn Ala Ser Thr Phe Arg Glu Phe Leu Pro Ser Arg
                180                 185                 190

Glu Glu Gly Ser Gln Asn Asn Arg Val Arg Lys Glu Ser Asn Ser Asp
                195                 200                 205

Leu Asn Ala Lys Ser Leu Glu Asn Gly Asn Glu Gln Gly Pro Gln Thr
    210                 215                 220

Tyr Pro Met His Ile Pro Val Leu Val Pro Leu Gly Ser Ser Ile Thr
225                 230                 235                 240

Ser Ser Leu Ser His Pro Pro Ser Glu Pro Asp Ser His Pro His Thr
                245                 250                 255

Val Ala Gly Asp Tyr Gln Ser Phe Pro Asn His Ile Met Ser Thr Leu
                260                 265                 270

Leu Gln Thr Pro Ala Leu Tyr Thr Ala Ala Thr Phe Ala Ser Ser Phe
                275                 280                 285

Trp Pro Pro Asp Ser Ser Gly Gly Ser Pro Val Pro Gly Asn Ser Pro
                290                 295                 300

Pro Asn Leu Ala Ala Met Ala Ala Ala Thr Val Ala Ala Ala Ser Ala
305                 310                 315                 320

Trp Trp Ala Ala Asn Gly Leu Leu Pro Leu Cys Ala Pro Leu Ser Ser
                325                 330                 335

Gly Gly Phe Thr Ser His Pro Pro Ser Thr Phe Gly Pro Ser Cys Asp
                340                 345                 350

Val Glu Tyr Thr Lys Ala Ser Thr Leu Gln His Gly Ser Val Gln Ser
                355                 360                 365

Arg Glu Gln Glu His Ser Glu Ala Ser Lys Ala Arg Ser Ser Leu Asp
                370                 375                 380

Ser Glu Asp Val Glu Asn Lys Ser Lys Pro Val Cys His Glu Gln Pro
385                 390                 395                 400

Ser Ala Thr Pro Glu Ser Asp Ala Lys Gly Ser Asp Gly Ala Gly Asp
                405                 410                 415

Arg Lys Gln Val Asp Arg Ser Ser Cys Gly Ser Asn Thr Pro Ser Ser
                420                 425                 430
```

-continued

```
Ser Asp Asp Val Glu Ala Asp Ala Ser Glu Arg Gln Glu Asp Gly Thr
        435                 440                 445
Asn Gly Glu Val Lys Glu Thr Asn Glu Asp Thr Asn Lys Pro Gln Thr
        450                 455                 460
Ser Glu Ser Asn Ala Arg Arg Ser Arg Ile Ser Ser Asn Ile Thr Asp
465                 470                 475                 480
Pro Trp Lys Ser Val Ser Asp Glu Gly Arg Ile Ala Phe Gln Ala Leu
                485                 490                 495
Phe Ser Arg Glu Val Leu Pro Gln Ser Phe Thr Tyr Arg Glu Glu His
            500                 505                 510
Arg Glu Glu Gln Gln Gln Gln Glu Gln Arg Tyr Pro Met Ala Leu
            515                 520                 525
Asp Leu Asn Phe Thr Ala Gln Leu Thr Pro Val Asp Gln Glu Glu
        530                 535                 540
Lys Arg Asn Thr Gly Phe Leu Gly Ile Gly Leu Asp Ala Ser Lys Leu
545                 550                 555                 560
Met Ser Arg Gly Arg Thr Gly Phe Lys Pro Tyr Lys Arg Cys Ser Met
                565                 570                 575
Glu Ala Lys Glu Ser Arg Ile Leu Asn Asn Pro Ile Ile His Val
            580                 585                 590
Glu Gln Lys Asp Pro Lys Arg Met Arg Leu Glu Thr Gln Ala Ser Thr
            595                 600                 605
```

<210> SEQ ID NO 35
<211> LENGTH: 1000
<212> TYPE: DNA
<213> ORGANISM: Arabidopsis thaliana
<220> FEATURE:
<221> NAME/KEY: CDS
<222> LOCATION: (143)...(934)

<400> SEQUENCE: 35

```
atatattccc tctttcattc tccttcttcg tcttttcttt gtttctcata ttcaagacat    60
cctcaattcc aaatcttaaa ccctaaattt acagacacaa tcgagatcac ctgaaaaaag   120
aggtttaaag attttagcaa ag atg gcg aat tca gga aat tat gga aag agg   172
                         Met Ala Asn Ser Gly Asn Tyr Gly Lys Arg
                          1               5                  10 ccc ttt cga ggc gat gaa tcg gat gaa aag aaa gaa gcc gat gat gat   220
Pro Phe Arg Gly Asp Glu Ser Asp Glu Lys Lys Glu Ala Asp Asp Asp
            15                  20                  25 gag aac ata ttc cct ttc ttc tct gcc cga tcc caa tat gac atg cgt   268
Glu Asn Ile Phe Pro Phe Phe Ser Ala Arg Ser Gln Tyr Asp Met Arg
        30                  35                  40 gcc atg gtc tca gcc ttg act caa gtc att gga aac caa agc agc tct   316
Ala Met Val Ser Ala Leu Thr Gln Val Ile Gly Asn Gln Ser Ser Ser
    45                  50                  55 cat gat aat aac caa cat caa cct gtt gtg tat aat caa caa gat cct   364
His Asp Asn Asn Gln His Gln Pro Val Val Tyr Asn Gln Gln Asp Pro
60                  65                  70 aac cca ccg gct cct cca act caa gat caa ggg cta ttg agg aag agg   412
Asn Pro Pro Ala Pro Pro Thr Gln Asp Gln Gly Leu Leu Arg Lys Arg
75                  80                  85                  90 cac tat aga ggg gta aga caa cga cca tgg gga aag tgg gca gct gaa   460
His Tyr Arg Gly Val Arg Gln Arg Pro Trp Gly Lys Trp Ala Ala Glu
                95                 100                 105 att cgg gat ccg caa aag gca gca cgg gtg tgg ctc ggg aca ttt gag   508
Ile Arg Asp Pro Gln Lys Ala Ala Arg Val Trp Leu Gly Thr Phe Glu
```

```
                   110                 115                 120
act gct gaa gct gcg gct tta gct tat gat aac gca gct ctt aag ttc    556
Thr Ala Glu Ala Ala Ala Leu Ala Tyr Asp Asn Ala Ala Leu Lys Phe
        125                 130                 135 aaa gga agc aaa gcc aaa ctc aat ttc cct gag aga gct caa cta gca    604
Lys Gly Ser Lys Ala Lys Leu Asn Phe Pro Glu Arg Ala Gln Leu Ala
    140                 145                 150 agt aac act agt aca act acc ggt cca cca aac tat tat tct tct aat    652
Ser Asn Thr Ser Thr Thr Thr Gly Pro Pro Asn Tyr Tyr Ser Ser Asn
155                 160                 165                 170 aat caa att tac tac tca aat ccg cag act aat ccg caa acc ata cct    700
Asn Gln Ile Tyr Tyr Ser Asn Pro Gln Thr Asn Pro Gln Thr Ile Pro
            175                 180                 185 tat ttt aac caa tac tac tat aac caa tat ctt cat caa ggg ggg aat    748
Tyr Phe Asn Gln Tyr Tyr Tyr Asn Gln Tyr Leu His Gln Gly Gly Asn
                190                 195                 200 agt aac gat gca tta agt tat agc ttg gcc ggt gga gaa acc gga ggc    796
Ser Asn Asp Ala Leu Ser Tyr Ser Leu Ala Gly Gly Glu Thr Gly Gly
            205                 210                 215 tca atg tat aat cat cag acg tta tct act aca aat tct tca tct tct    844
Ser Met Tyr Asn His Gln Thr Leu Ser Thr Thr Asn Ser Ser Ser Ser
        220                 225                 230 ggt gga tct tca agg caa caa gat gat gaa caa gat tac gcc aga tat    892
Gly Gly Ser Ser Arg Gln Gln Asp Asp Glu Gln Asp Tyr Ala Arg Tyr
235                 240                 245                 250 ttg cgt ttt ggg gat tct tca cct cct aat tct ggt ttt tga            934
Leu Arg Phe Gly Asp Ser Ser Pro Pro Asn Ser Gly Phe *
            255                 260 gatcttcaat aaactgataa taaaggattt gggtcacttg ttatgagggg atcatatgtt    994
ttctaa                                                              1000

<210> SEQ ID NO 36
<211> LENGTH: 263
<212> TYPE: PRT
<213> ORGANISM: Arabidopsis thaliana
<220> FEATURE:
<221> NAME/KEY: DOMAIN
<222> LOCATION: (89)...(156)
<223> OTHER INFORMATION: Conserved domain

<400> SEQUENCE: 36

Met Ala Asn Ser Gly Asn Tyr Gly Lys Arg Pro Phe Arg Gly Asp Glu
 1               5                  10                  15

Ser Asp Glu Lys Lys Glu Ala Asp Asp Glu Asn Ile Phe Pro Phe
            20                  25                  30

Phe Ser Ala Arg Ser Gln Tyr Asp Met Arg Ala Met Val Ser Ala Leu
        35                  40                  45

Thr Gln Val Ile Gly Asn Gln Ser Ser His Asp Asn Asn Gln His
    50                  55                  60

Gln Pro Val Val Tyr Asn Gln Asp Pro Asn Pro Ala Pro Pro
65                  70                  75                  80

Thr Gln Asp Gln Gly Leu Leu Arg Lys Arg His Tyr Arg Gly Val Arg
                85                  90                  95

Gln Arg Pro Trp Gly Lys Trp Ala Ala Glu Ile Arg Asp Pro Gln Lys
            100                 105                 110

Ala Ala Arg Val Trp Leu Gly Thr Phe Glu Thr Ala Glu Ala Ala Ala
        115                 120                 125

Leu Ala Tyr Asp Asn Ala Ala Leu Lys Phe Lys Gly Ser Lys Ala Lys
```

|     | 130 |     |     |     | 135 |     |     |     | 140 |     |     |     |     |
| --- | --- | --- | --- | --- | --- | --- | --- | --- | --- | --- | --- | --- | --- |

| Leu | Asn | Phe | Pro | Glu | Arg | Ala | Gln | Leu | Ala | Ser | Asn | Thr | Ser | Thr | Thr |
| --- | --- | --- | --- | --- | --- | --- | --- | --- | --- | --- | --- | --- | --- | --- | --- |
| 145 |     |     |     |     | 150 |     |     |     |     | 155 |     |     |     |     | 160 |

| Thr | Gly | Pro | Pro | Asn | Tyr | Tyr | Ser | Ser | Asn | Asn | Gln | Ile | Tyr | Tyr | Ser |
| --- | --- | --- | --- | --- | --- | --- | --- | --- | --- | --- | --- | --- | --- | --- | --- |
|     |     |     |     | 165 |     |     |     |     | 170 |     |     |     |     | 175 |     |

| Asn | Pro | Gln | Thr | Asn | Pro | Gln | Thr | Ile | Pro | Tyr | Phe | Asn | Gln | Tyr | Tyr |
| --- | --- | --- | --- | --- | --- | --- | --- | --- | --- | --- | --- | --- | --- | --- | --- |
|     |     |     | 180 |     |     |     |     | 185 |     |     |     |     | 190 |     |     |

| Tyr | Asn | Gln | Tyr | Leu | His | Gln | Gly | Gly | Asn | Ser | Asn | Asp | Ala | Leu | Ser |
| --- | --- | --- | --- | --- | --- | --- | --- | --- | --- | --- | --- | --- | --- | --- | --- |
|     |     | 195 |     |     |     |     | 200 |     |     |     |     | 205 |     |     |     |

| Tyr | Ser | Leu | Ala | Gly | Gly | Glu | Thr | Gly | Gly | Ser | Met | Tyr | Asn | His | Gln |
| --- | --- | --- | --- | --- | --- | --- | --- | --- | --- | --- | --- | --- | --- | --- | --- |
|     | 210 |     |     |     |     | 215 |     |     |     |     | 220 |     |     |     |     |

| Thr | Leu | Ser | Thr | Thr | Asn | Ser | Ser | Ser | Ser | Gly | Gly | Ser | Ser | Arg | Gln |
| --- | --- | --- | --- | --- | --- | --- | --- | --- | --- | --- | --- | --- | --- | --- | --- |
| 225 |     |     |     |     | 230 |     |     |     |     | 235 |     |     |     |     | 240 |

| Gln | Asp | Asp | Glu | Gln | Asp | Tyr | Ala | Arg | Tyr | Leu | Arg | Phe | Gly | Asp | Ser |
| --- | --- | --- | --- | --- | --- | --- | --- | --- | --- | --- | --- | --- | --- | --- | --- |
|     |     |     |     | 245 |     |     |     |     | 250 |     |     |     |     | 255 |     |

| Ser | Pro | Pro | Asn | Ser | Gly | Phe |
| --- | --- | --- | --- | --- | --- | --- |
|     |     |     | 260 |     |     |     |

<210> SEQ ID NO 37
<211> LENGTH: 1197
<212> TYPE: DNA
<213> ORGANISM: Arabidopsis thaliana
<220> FEATURE:
<221> NAME/KEY: CDS
<222> LOCATION: (133)...(1197)

<400> SEQUENCE: 37

```
aaggagtttt gcatactcac caagccacaa tcatttctct cttctctatc tctctggttt      60
tgaatcggcg acgactgagt caactcggtg ttgttactgg tttcgtcgta tgtgttgtaa     120
ctgattaagt tg atg gat ccg agt ggg atg atg aac gaa gga gga ccg ttt     171
              Met Asp Pro Ser Gly Met Met Asn Glu Gly Gly Pro Phe
                1               5                   10 aat cta gcg gag atc tgg cag ttt ccg ttg aac gga gtt tca acc gcc     219
Asn Leu Ala Glu Ile Trp Gln Phe Pro Leu Asn Gly Val Ser Thr Ala
 15                  20                  25 gga gat tct tct aga aga agc ttc gtt gga ccg aat cag ttc ggt gat     267
Gly Asp Ser Ser Arg Arg Ser Phe Val Gly Pro Asn Gln Phe Gly Asp
 30                  35                  40                  45 gct gat cta acc aca gct gct aac ggt gat cca gcg cgt atg agt cac     315
Ala Asp Leu Thr Thr Ala Ala Asn Gly Asp Pro Ala Arg Met Ser His
                 50                  55                  60 gcg ttg tct cag gcg gtt att gaa ggt atc tcc ggc gct tgg aaa cgg     363
Ala Leu Ser Gln Ala Val Ile Glu Gly Ile Ser Gly Ala Trp Lys Arg
             65                  70                  75 agg gaa gat gag tct aag tcg gcg aag atc gtc tcc acc att ggc gct     411
Arg Glu Asp Glu Ser Lys Ser Ala Lys Ile Val Ser Thr Ile Gly Ala
         80                  85                  90 agt gaa ggt gag aac aaa aga cag aag ata gat gaa gtg tgt gat ggg     459
Ser Glu Gly Glu Asn Lys Arg Gln Lys Ile Asp Glu Val Cys Asp Gly
     95                 100                 105 aaa gca gaa gca gaa tcg cta gga aca gag acg gaa caa aag aag caa     507
Lys Ala Glu Ala Glu Ser Leu Gly Thr Glu Thr Glu Gln Lys Lys Gln
110                 115                 120                 125 cag atg gaa cca acg aaa gat tat att cat gtt cga gct aga aga ggt     555
Gln Met Glu Pro Thr Lys Asp Tyr Ile His Val Arg Ala Arg Arg Gly
                130                 135                 140 caa gct act gat agt cac agt tta gct gaa aga gcg aga aga gag aaa     603
Gln Ala Thr Asp Ser His Ser Leu Ala Glu Arg Ala Arg Arg Glu Lys
```

| | | | |
|---|---|---|---|
| ata agt gag cgg atg aaa atc ttg caa gat ctt gtt ccg gga tgt aac | | | 651 |
| Ile Ser Glu Arg Met Lys Ile Leu Gln Asp Leu Val Pro Gly Cys Asn | | | |
| 160 | 165 | 170 | |
| aag gtt att gga aaa gca ctt gtt cta gat gag ata att aac tat ata | | | 699 |
| Lys Val Ile Gly Lys Ala Leu Val Leu Asp Glu Ile Ile Asn Tyr Ile | | | |
| 175 | 180 | 185 | |
| caa tca ttg caa cgt caa gtt gag ttc tta tcg atg aag ctt gaa gca | | | 747 |
| Gln Ser Leu Gln Arg Gln Val Glu Phe Leu Ser Met Lys Leu Glu Ala | | | |
| 190 | 195 | 200 | 205 |
| gtc aac tca aga atg aac cct ggt atc gag gtt ttt cca ccc aaa gag | | | 795 |
| Val Asn Ser Arg Met Asn Pro Gly Ile Glu Val Phe Pro Pro Lys Glu | | | |
| | 210 | 215 | 220 |
| gtg atg att ctc atg atc atc aac tca atc ttc tcc att ttt ttc aca | | | 843 |
| Val Met Ile Leu Met Ile Ile Asn Ser Ile Phe Ser Ile Phe Phe Thr | | | |
| | 225 | 230 | 235 |
| aaa caa tac atg ttt cta tcg agg tat tct cgg ggt agg agt ctc gat | | | 891 |
| Lys Gln Tyr Met Phe Leu Ser Arg Tyr Ser Arg Gly Arg Ser Leu Asp | | | |
| | 240 | 245 | 250 |
| gtt tat gcg gtt cgg tca ttt aag cat tgc aat aaa cgg agt gac ctc | | | 939 |
| Val Tyr Ala Val Arg Ser Phe Lys His Cys Asn Lys Arg Ser Asp Leu | | | |
| 255 | 260 | 265 | |
| tgt ttt tgc tcc tgc tcc cca aaa aca gaa ctt aag aca act ata ttt | | | 987 |
| Cys Phe Cys Ser Cys Ser Pro Lys Thr Glu Leu Lys Thr Thr Ile Phe | | | |
| 270 | 275 | 280 | 285 |
| tca caa aac atg aca tgt ttc tgt cga tat tct cga gta gga gtc gct | | | 1035 |
| Ser Gln Asn Met Thr Cys Phe Cys Arg Tyr Ser Arg Val Gly Val Ala | | | |
| | 290 | 295 | 300 |
| att agt tca tct aag cat tgc aat gaa ccg ttt ggt cag caa gcg ttt | | | 1083 |
| Ile Ser Ser Ser Lys His Cys Asn Glu Pro Phe Gly Gln Gln Ala Phe | | | |
| | 305 | 310 | 315 |
| gag aat ccg gag ata cag ttc ggg tcg cag tct acg agg gaa tac agt | | | 1131 |
| Glu Asn Pro Glu Ile Gln Phe Gly Ser Gln Ser Thr Arg Glu Tyr Ser | | | |
| 320 | 325 | 330 | |
| aga gga gca tca cca gag tgg ttg cac atg cag ata gga tca ggt ggt | | | 1179 |
| Arg Gly Ala Ser Pro Glu Trp Leu His Met Gln Ile Gly Ser Gly Gly | | | |
| 335 | 340 | 345 | |
| ttc gaa aga acg tct tga | | | 1197 |
| Phe Glu Arg Thr Ser * | | | |
| 350 | | | |

<210> SEQ ID NO 38
<211> LENGTH: 354
<212> TYPE: PRT
<213> ORGANISM: Arabidopsis thaliana
<220> FEATURE:
<221> NAME/KEY: DOMAIN
<222> LOCATION: (135)...(206)
<223> OTHER INFORMATION: Conserved domain

<400> SEQUENCE: 38

Met Asp Pro Ser Gly Met Met Asn Glu Gly Gly Pro Phe Asn Leu Ala
1               5                   10                  15

Glu Ile Trp Gln Phe Pro Leu Asn Gly Val Ser Thr Ala Gly Asp Ser
                20                  25                  30

Ser Arg Arg Ser Phe Val Gly Pro Asn Gln Phe Gly Asp Ala Asp Leu
            35                  40                  45

Thr Thr Ala Ala Asn Gly Asp Pro Ala Arg Met Ser His Ala Leu Ser
        50                  55                  60

Gln Ala Val Ile Glu Gly Ile Ser Gly Ala Trp Lys Arg Arg Glu Asp

-continued

```
                65                  70                  75                  80
            Glu Ser Lys Ser Ala Lys Ile Val Ser Thr Ile Gly Ala Ser Glu Gly
                            85                  90                  95

Glu Asn Lys Arg Gln Lys Ile Asp Glu Val Cys Asp Gly Lys Ala Glu
                        100                 105                 110

Ala Glu Ser Leu Gly Thr Glu Thr Glu Gln Lys Lys Gln Gln Met Glu
                    115                 120                 125

Pro Thr Lys Asp Tyr Ile His Val Arg Ala Arg Gly Gln Ala Thr
                130                 135                 140

Asp Ser His Ser Leu Ala Glu Arg Ala Arg Glu Lys Ile Ser Glu
            145                 150                 155                 160

Arg Met Lys Ile Leu Gln Asp Leu Val Pro Gly Cys Asn Lys Val Ile
                            165                 170                 175

Gly Lys Ala Leu Val Leu Asp Glu Ile Ile Asn Tyr Ile Gln Ser Leu
                        180                 185                 190

Gln Arg Gln Val Glu Phe Leu Ser Met Lys Leu Glu Ala Val Asn Ser
                    195                 200                 205

Arg Met Asn Pro Gly Ile Glu Val Phe Pro Pro Lys Glu Val Met Ile
                210                 215                 220

Leu Met Ile Ile Asn Ser Ile Phe Ser Ile Phe Phe Thr Lys Gln Tyr
            225                 230                 235                 240

Met Phe Leu Ser Arg Tyr Ser Arg Gly Arg Ser Leu Asp Val Tyr Ala
                            245                 250                 255

Val Arg Ser Phe Lys His Cys Asn Lys Arg Ser Asp Leu Cys Phe Cys
                        260                 265                 270

Ser Cys Ser Pro Lys Thr Glu Leu Lys Thr Thr Ile Phe Ser Gln Asn
                    275                 280                 285

Met Thr Cys Phe Cys Arg Tyr Ser Arg Val Gly Val Ala Ile Ser Ser
                290                 295                 300

Ser Lys His Cys Asn Glu Pro Phe Gly Gln Gln Ala Phe Glu Asn Pro
            305                 310                 315                 320

Glu Ile Gln Phe Gly Ser Gln Ser Thr Arg Glu Tyr Ser Arg Gly Ala
                            325                 330                 335

Ser Pro Glu Trp Leu His Met Gln Ile Gly Ser Gly Gly Phe Glu Arg
                        340                 345                 350

Thr Ser
```

```
<210> SEQ ID NO 39
<211> LENGTH: 896
<212> TYPE: DNA
<213> ORGANISM: Arabidopsis thaliana
<220> FEATURE:
<221> NAME/KEY: CDS
<222> LOCATION: (52)...(786)

<400> SEQUENCE: 39
gagatcttct actacttgtt ttcttcaaga ataataattt tcgttttata t atg gaa        57
                                                         Met Glu
                                                           1 gat gct ggt gaa cat tta cgg tgt aac gat aac gtt aac gac gag gag       105
Asp Ala Gly Glu His Leu Arg Cys Asn Asp Asn Val Asn Asp Glu Glu
      5                  10                  15 cgt ttg cca ttg gag ttt atg atc gga aac tca aca tcc acg gcg gag       153
Arg Leu Pro Leu Glu Phe Met Ile Gly Asn Ser Thr Ser Thr Ala Glu
 20                  25                  30 cta cag ccg cct cca ccg ttc ttg gta aag aca tac aaa gtg gtg gag       201
```

-continued

```
Leu Gln Pro Pro Pro Phe Leu Val Lys Thr Tyr Lys Val Val Glu
 35              40                  45                  50 gat ccg acg acg gac ggg gtt ata tct tgg aac gaa tac gga act ggt    249
Asp Pro Thr Thr Asp Gly Val Ile Ser Trp Asn Glu Tyr Gly Thr Gly
                55                  60                  65 ttc gtc gtg tgg cag ccg gca gaa ttc gct aga gat ctg tta cca aca    297
Phe Val Val Trp Gln Pro Ala Glu Phe Ala Arg Asp Leu Leu Pro Thr
             70                  75                  80 ctt ttc aag cat tgc aac ttc tct agc ttc gtt cgc cag ctc aat act    345
Leu Phe Lys His Cys Asn Phe Ser Ser Phe Val Arg Gln Leu Asn Thr
         85                  90                  95 tac ggt ttt cga aaa gta acg acg ata aga tgg gaa ttt agt aat gag    393
Tyr Gly Phe Arg Lys Val Thr Thr Ile Arg Trp Glu Phe Ser Asn Glu
     100                 105                 110 atg ttt cga aag ggg caa aga gag ctt atg agc aat atc cga aga agg    441
Met Phe Arg Lys Gly Gln Arg Glu Leu Met Ser Asn Ile Arg Arg Arg
115                 120                 125                 130 aag agc caa cat tgg tca cac aac aag tct aat cac cag gtt gta cca    489
Lys Ser Gln His Trp Ser His Asn Lys Ser Asn His Gln Val Val Pro
                135                 140                 145 aca aca acg atg gtg aat caa gaa ggt cat caa cgg att ggg att gat    537
Thr Thr Thr Met Val Asn Gln Glu Gly His Gln Arg Ile Gly Ile Asp
            150                 155                 160 cat cac cat gag gat caa cag tct tcc gcc act tca tcc tct ttc gta    585
His His His Glu Asp Gln Gln Ser Ser Ala Thr Ser Ser Ser Phe Val
        165                 170                 175 tac act gca tta ctc gac gaa aac aaa tgc ttg aag aat gaa aac gag    633
Tyr Thr Ala Leu Leu Asp Glu Asn Lys Cys Leu Lys Asn Glu Asn Glu
    180                 185                 190 tta tta agc tgc gaa ctt ggg aaa acc aag aag aaa tgc aag cag ctt    681
Leu Leu Ser Cys Glu Leu Gly Lys Thr Lys Lys Lys Cys Lys Gln Leu
195                 200                 205                 210 atg gag ttg gtg gag aga tac aga gga gaa gac gaa gat gca act gat    729
Met Glu Leu Val Glu Arg Tyr Arg Gly Glu Asp Glu Asp Ala Thr Asp
                215                 220                 225 gaa agt gat gat gaa gaa gat gaa ggg ctt aag ttg ttc gga gta aaa    777
Glu Ser Asp Asp Glu Glu Asp Glu Gly Leu Lys Leu Phe Gly Val Lys
            230                 235                 240 ctt gaa tga aactagattg ctagattgat attcgtaata taccagtttc            826
Leu Glu * ttcatattct tagaagttttt gcataactat atatagtact cttttaagac atgcaagatc  886
agaacatatg                                                         896
```

<210> SEQ ID NO 40
<211> LENGTH: 244
<212> TYPE: PRT
<213> ORGANISM: Arabidopsis thaliana
<220> FEATURE:
<221> NAME/KEY: DOMAIN
<222> LOCATION: (27)...(131)
<223> OTHER INFORMATION: Conserved domain

<400> SEQUENCE: 40

```
Met Glu Asp Ala Gly Glu His Leu Arg Cys Asn Asp Asn Val Asn Asp
 1               5                  10                  15

Glu Glu Arg Leu Pro Leu Glu Phe Met Ile Gly Asn Ser Thr Ser Thr
                20                  25                  30

Ala Glu Leu Gln Pro Pro Pro Phe Leu Val Lys Thr Tyr Lys Val
         35                  40                  45
```

```
Val Glu Asp Pro Thr Thr Asp Gly Val Ile Ser Trp Asn Glu Tyr Gly
 50                  55                  60

Thr Gly Phe Val Val Trp Gln Pro Ala Glu Phe Ala Arg Asp Leu Leu
 65                  70                  75                  80

Pro Thr Leu Phe Lys His Cys Asn Phe Ser Ser Phe Val Arg Gln Leu
                 85                  90                  95

Asn Thr Tyr Gly Phe Arg Lys Val Thr Thr Ile Arg Trp Glu Phe Ser
            100                 105                 110

Asn Glu Met Phe Arg Lys Gly Gln Arg Glu Leu Met Ser Asn Ile Arg
        115                 120                 125

Arg Arg Lys Ser Gln His Trp Ser His Asn Lys Ser Asn His Gln Val
130                 135                 140

Val Pro Thr Thr Thr Met Val Asn Gln Glu Gly His Gln Arg Ile Gly
145                 150                 155                 160

Ile Asp His His His Glu Asp Gln Gln Ser Ser Ala Thr Ser Ser Ser
                165                 170                 175

Phe Val Tyr Thr Ala Leu Leu Asp Glu Asn Lys Cys Leu Lys Asn Glu
            180                 185                 190

Asn Glu Leu Leu Ser Cys Glu Leu Gly Lys Thr Lys Lys Lys Cys Lys
        195                 200                 205

Gln Leu Met Glu Leu Val Glu Arg Tyr Arg Gly Glu Asp Glu Asp Ala
210                 215                 220

Thr Asp Glu Ser Asp Asp Glu Glu Asp Glu Gly Leu Lys Leu Phe Gly
225                 230                 235                 240

Val Lys Leu Glu
```

<210> SEQ ID NO 41
<211> LENGTH: 588
<212> TYPE: DNA
<213> ORGANISM: Arabidopsis thaliana
<220> FEATURE:
<221> NAME/KEY: CDS
<222> LOCATION: (1)...(588)

<400> SEQUENCE: 41

```
atg agg agg cca aag tca tct cac gtc agg atg gaa cct gtt gcg cct      48
Met Arg Arg Pro Lys Ser Ser His Val Arg Met Glu Pro Val Ala Pro
 1               5                  10                  15 cgt tca cat aac acg atg cca atg ctt gat caa ttt cga tct aat cat      96
Arg Ser His Asn Thr Met Pro Met Leu Asp Gln Phe Arg Ser Asn His
             20                  25                  30 cct gaa aca agc aag atc gag ggg gtc tct tcg ttg gac aca gct ctg     144
Pro Glu Thr Ser Lys Ile Glu Gly Val Ser Ser Leu Asp Thr Ala Leu
         35                  40                  45 aag gtg ttt tgg aat aat caa agg gag cag cta gga aac ttt gca ggc     192
Lys Val Phe Trp Asn Asn Gln Arg Glu Gln Leu Gly Asn Phe Ala Gly
     50                  55                  60 caa act cat ttg ccg cta tct agg gtc aga aag att ttg aaa tct gat     240
Gln Thr His Leu Pro Leu Ser Arg Val Arg Lys Ile Leu Lys Ser Asp
 65                  70                  75                  80 cct gaa gtc aag aag ata agc tgt gat gtt cct gct ttg ttt tcg aaa     288
Pro Glu Val Lys Lys Ile Ser Cys Asp Val Pro Ala Leu Phe Ser Lys
                 85                  90                  95 gcc tgt gaa tac ttc att cta gag gta aca tta cga gct tgg atg cat     336
Ala Cys Glu Tyr Phe Ile Leu Glu Val Thr Leu Arg Ala Trp Met His
            100                 105                 110 act caa tca tgc act cgt gag acc atc cgg cgt tgt gat atc ttc cag     384
Thr Gln Ser Cys Thr Arg Glu Thr Ile Arg Arg Cys Asp Ile Phe Gln
```

```
              115                 120                 125
gcc gta aag aac tca gga act tat gat ttc ctg att gat cgt gtc cct         432
Ala Val Lys Asn Ser Gly Thr Tyr Asp Phe Leu Ile Asp Arg Val Pro
    130                 135                 140 ttt gga ccg cac tgt gtc acc cat cag ggt gtg caa cct cct gct gaa         480
Phe Gly Pro His Cys Val Thr His Gln Gly Val Gln Pro Pro Ala Glu
145                 150                 155                 160 atg att ttg ccg gat atg aat gtt cca atc gat atg gac cag att gag         528
Met Ile Leu Pro Asp Met Asn Val Pro Ile Asp Met Asp Gln Ile Glu
                165                 170                 175 gag gag aat atg atg gaa gag cgc tct gtc ggg ttt gac ctc aac tgt         576
Glu Glu Asn Met Met Glu Glu Arg Ser Val Gly Phe Asp Leu Asn Cys
            180                 185                 190 gat ctc cag tga                                                         588
Asp Leu Gln *
        195

<210> SEQ ID NO 42
<211> LENGTH: 195
<212> TYPE: PRT
<213> ORGANISM: Arabidopsis thaliana
<220> FEATURE:
<221> NAME/KEY: DOMAIN
<222> LOCATION: (48)...(143)
<223> OTHER INFORMATION: Conserved domain

<400> SEQUENCE: 42

Met Arg Arg Pro Lys Ser Ser His Val Arg Met Glu Pro Val Ala Pro
1               5                   10                  15

Arg Ser His Asn Thr Met Pro Met Leu Asp Gln Phe Arg Ser Asn His
            20                  25                  30

Pro Glu Thr Ser Lys Ile Glu Gly Val Ser Ser Leu Asp Thr Ala Leu
        35                  40                  45

Lys Val Phe Trp Asn Asn Gln Arg Glu Gln Leu Gly Asn Phe Ala Gly
    50                  55                  60

Gln Thr His Leu Pro Leu Ser Arg Val Arg Lys Ile Leu Lys Ser Asp
65                  70                  75                  80

Pro Glu Val Lys Lys Ile Ser Cys Asp Val Pro Ala Leu Phe Ser Lys
                85                  90                  95

Ala Cys Glu Tyr Phe Ile Leu Glu Val Thr Leu Arg Ala Trp Met His
            100                 105                 110

Thr Gln Ser Cys Thr Arg Glu Thr Ile Arg Arg Cys Asp Ile Phe Gln
        115                 120                 125

Ala Val Lys Asn Ser Gly Thr Tyr Asp Phe Leu Ile Asp Arg Val Pro
    130                 135                 140

Phe Gly Pro His Cys Val Thr His Gln Gly Val Gln Pro Pro Ala Glu
145                 150                 155                 160

Met Ile Leu Pro Asp Met Asn Val Pro Ile Asp Met Asp Gln Ile Glu
                165                 170                 175

Glu Glu Asn Met Met Glu Glu Arg Ser Val Gly Phe Asp Leu Asn Cys
            180                 185                 190

Asp Leu Gln
        195

<210> SEQ ID NO 43
<211> LENGTH: 606
<212> TYPE: DNA
<213> ORGANISM: Arabidopsis thaliana
<220> FEATURE:
```

```
<221> NAME/KEY: CDS
<222> LOCATION: (1)...(606)

<400> SEQUENCE: 43 atg agc gga gga gga gac gtg aac atg agt ggt gga gac aga cgc aag      48
Met Ser Gly Gly Gly Asp Val Asn Met Ser Gly Gly Asp Arg Arg Lys
1               5                   10                  15 gga acg gtg aag tgg ttt gat aca cag aag ggg ttt ggt ttc atc aca      96
Gly Thr Val Lys Trp Phe Asp Thr Gln Lys Gly Phe Gly Phe Ile Thr
            20                  25                  30 cct agc gac ggt ggt gac gat ctc ttc gtt cac cag tct tcc atc aga    144
Pro Ser Asp Gly Gly Asp Asp Leu Phe Val His Gln Ser Ser Ile Arg
        35                  40                  45 tct gaa gga ttt cgt agc ctc gca gct gag gaa tct gtt gag ttc gac    192
Ser Glu Gly Phe Arg Ser Leu Ala Ala Glu Glu Ser Val Glu Phe Asp
    50                  55                  60 gtt gag gtt gac aac tcc ggc cgt ccc aag gct att gaa gtg tct gga    240
Val Glu Val Asp Asn Ser Gly Arg Pro Lys Ala Ile Glu Val Ser Gly
65                  70                  75                  80 ccc gac ggt gct ccc gtt cag ggt aac agc ggt ggt ggt ggt tca tct    288
Pro Asp Gly Ala Pro Val Gln Gly Asn Ser Gly Gly Gly Gly Ser Ser
                85                  90                  95 ggt gga cgc ggt ggt ttt ggc ggc ggt ggt gga aga gga ggg gga cgt    336
Gly Gly Arg Gly Gly Phe Gly Gly Gly Gly Gly Arg Gly Gly Gly Arg
            100                 105                 110 ggt gga gga agc tac gga gga ggt tat ggt gga aga gga agc ggt ggc    384
Gly Gly Gly Ser Tyr Gly Gly Gly Tyr Gly Gly Arg Gly Ser Gly Gly
        115                 120                 125 cgt gga gga ggt ggt ggt gat aat tct tgc ttt aag tgc ggt gaa cca    432
Arg Gly Gly Gly Gly Gly Asp Asn Ser Cys Phe Lys Cys Gly Glu Pro
    130                 135                 140 ggt cac atg gcg aga gaa tgc tct caa ggt ggt gga gga tac agc gga    480
Gly His Met Ala Arg Glu Cys Ser Gln Gly Gly Gly Gly Tyr Ser Gly
145                 150                 155                 160 ggc ggg ggt ggt gga agg tac ggg tct ggc ggc ggc gga gga gga ggt    528
Gly Gly Gly Gly Gly Arg Tyr Gly Ser Gly Gly Gly Gly Gly Gly Gly
                165                 170                 175 ggt ggt ggc tta agc tgc tac agc tgt gga gag tct ggg cac ttt gca    576
Gly Gly Gly Leu Ser Cys Tyr Ser Cys Gly Glu Ser Gly His Phe Ala
            180                 185                 190 agg gat tgc act agc ggt ggt gct cgt tga                            606
Arg Asp Cys Thr Ser Gly Gly Ala Arg *
        195                 200

<210> SEQ ID NO 44
<211> LENGTH: 201
<212> TYPE: PRT
<213> ORGANISM: Arabidopsis thaliana
<220> FEATURE:
<221> NAME/KEY: DOMAIN
<222> LOCATION: (28)...(49)
<223> OTHER INFORMATION: Conserved domain
<220> FEATURE:
<221> NAME/KEY: DOMAIN
<222> LOCATION: (137)...(151)
<223> OTHER INFORMATION: Conserved domain
<220> FEATURE:
<221> NAME/KEY: DOMAIN
<222> LOCATION: (182)...(196)
<223> OTHER INFORMATION: Conserved domain

<400> SEQUENCE: 44

Met Ser Gly Gly Gly Asp Val Asn Met Ser Gly Gly Asp Arg Arg Lys
1               5                   10                  15
```

```
Gly Thr Val Lys Trp Phe Asp Thr Gln Lys Gly Phe Gly Phe Ile Thr
            20                  25                  30

Pro Ser Asp Gly Gly Asp Leu Phe Val His Gln Ser Ser Ile Arg
        35                  40                  45

Ser Glu Gly Phe Arg Ser Leu Ala Ala Glu Ser Val Glu Phe Asp
    50                  55                  60

Val Glu Val Asp Asn Ser Gly Arg Pro Lys Ala Ile Glu Val Ser Gly
65                  70                  75                  80

Pro Asp Gly Ala Pro Val Gln Gly Asn Ser Gly Gly Gly Ser Ser
                85                  90                  95

Gly Gly Arg Gly Gly Phe Gly Gly Gly Arg Gly Gly Arg
            100                 105                 110

Gly Gly Ser Tyr Gly Gly Tyr Gly Gly Arg Gly Ser Gly Gly
        115                 120                 125

Arg Gly Gly Gly Gly Asp Asn Ser Cys Phe Lys Cys Gly Glu Pro
    130                 135                 140

Gly His Met Ala Arg Glu Cys Ser Gln Gly Gly Gly Tyr Ser Gly
145                 150                 155                 160

Gly Gly Gly Gly Arg Tyr Gly Ser Gly Gly Gly Gly Gly
            165                 170                 175

Gly Gly Gly Leu Ser Cys Tyr Ser Cys Gly Glu Ser Gly His Phe Ala
        180                 185                 190

Arg Asp Cys Thr Ser Gly Gly Ala Arg
        195                 200
```

<210> SEQ ID NO 45
<211> LENGTH: 1707
<212> TYPE: DNA
<213> ORGANISM: Arabidopsis thaliana
<220> FEATURE:
<221> NAME/KEY: CDS
<222> LOCATION: (98)...(1444)

<400> SEQUENCE: 45

```
ccacgcgtcc gcactctccc aaatctctct tctttaacaa caaaaaaaaa atcacagaga        60
catagagaga agaagacgga acagaggctc caaaaaa atg atg atg gag act aga       115
                                        Met Met Met Glu Thr Arg
                                          1               5 gat cca gct att aag ctt ttc ggt atg aaa atc cct ttt ccg tcg gtt       163
Asp Pro Ala Ile Lys Leu Phe Gly Met Lys Ile Pro Phe Pro Ser Val
            10                  15                  20 ttt gaa tcg gca gtt acg gtg gag gat gac gaa gaa gat gac tgg agc       211
Phe Glu Ser Ala Val Thr Val Glu Asp Asp Glu Glu Asp Asp Trp Ser
        25                  30                  35 ggc gga gat gac aaa tca cca gag aag gta act cca gag tta tca gat       259
Gly Gly Asp Asp Lys Ser Pro Glu Lys Val Thr Pro Glu Leu Ser Asp
    40                  45                  50 aag aac aac aac aac tgt aac gac aac agt ttt aac aat tcg aaa ccc       307
Lys Asn Asn Asn Asn Cys Asn Asp Asn Ser Phe Asn Asn Ser Lys Pro
55                  60                  65                  70 gaa acc ttg gac aaa gag gaa gcg aca tca act gat cag ata gag agt       355
Glu Thr Leu Asp Lys Glu Glu Ala Thr Ser Thr Asp Gln Ile Glu Ser
            75                  80                  85 agt gac acg cct gag gat aat cag cag acg aca cct gat ggt aaa acc       403
Ser Asp Thr Pro Glu Asp Asn Gln Gln Thr Thr Pro Asp Gly Lys Thr
        90                  95                  100 cta aag aaa ccg act aag att cta ccg tgt ccg aga tgc aaa agc atg       451
```

```
                                                                                  -continued Leu Lys Lys Pro Thr Lys Ile Leu Pro Cys Pro Arg Cys Lys Ser Met
        105                 110                 115 gag acc aag ttc tgt tat tac aac aac tac aac ata aac cag cct cgt      499
Glu Thr Lys Phe Cys Tyr Tyr Asn Asn Tyr Asn Ile Asn Gln Pro Arg
    120                 125                 130 cat ttc tgc aag gct tgt cag aga tat tgg act gct gga ggg act atg      547
His Phe Cys Lys Ala Cys Gln Arg Tyr Trp Thr Ala Gly Gly Thr Met
135                 140                 145                 150 agg aat gtt cct gtg ggg gca gga cgt cgt aag aac aaa agc tca tct      595
Arg Asn Val Pro Val Gly Ala Gly Arg Arg Lys Asn Lys Ser Ser Ser
                155                 160                 165 tct cat tac cgt cac atc act att tcc gag gct ctt gag gct gcg agg      643
Ser His Tyr Arg His Ile Thr Ile Ser Glu Ala Leu Glu Ala Ala Arg
            170                 175                 180 ctt gac ccg ggc tta cag gca aac aca agg gtc ttg agt ttt ggt ctc      691
Leu Asp Pro Gly Leu Gln Ala Asn Thr Arg Val Leu Ser Phe Gly Leu
        185                 190                 195 gaa gct cag cag cag cac gtt gct gct ccc atg aca cct gtt atg aag      739
Glu Ala Gln Gln Gln His Val Ala Ala Pro Met Thr Pro Val Met Lys
    200                 205                 210 cta caa gaa gat caa aag gtc tca aac ggt gct agg aac agg ttt cac      787
Leu Gln Glu Asp Gln Lys Val Ser Asn Gly Ala Arg Asn Arg Phe His
215                 220                 225                 230 ggg tta gcg gat caa cgg ctt gta gct cgg gta gag aat gga gat gat      835
Gly Leu Ala Asp Gln Arg Leu Val Ala Arg Val Glu Asn Gly Asp Asp
                235                 240                 245 tgc tca agc gga tcc tct gtg acc acc tct aac aat cac tca gtg gat      883
Cys Ser Ser Gly Ser Ser Val Thr Thr Ser Asn Asn His Ser Val Asp
            250                 255                 260 gaa tca aga gca caa agc ggc agt gtt gtt gaa gca caa atg aac aac      931
Glu Ser Arg Ala Gln Ser Gly Ser Val Val Glu Ala Gln Met Asn Asn
        265                 270                 275 aac aac aac aat aac atg aat ggt tat gct tgc atc cca ggt gtt cca      979
Asn Asn Asn Asn Asn Met Asn Gly Tyr Ala Cys Ile Pro Gly Val Pro
    280                 285                 290 tgg cct tac acg tgg aat cca gcg atg cct cca cca ggt ttt tac ccg     1027
Trp Pro Tyr Thr Trp Asn Pro Ala Met Pro Pro Pro Gly Phe Tyr Pro
295                 300                 305                 310 cct cca ggg tat cca atg ccg ttt tac cct tac tgg acc atc cca atg     1075
Pro Pro Gly Tyr Pro Met Pro Phe Tyr Pro Tyr Trp Thr Ile Pro Met
                315                 320                 325 cta cca ccg cat caa tcc tca tcg cct ata agc caa aag tgt tca aat     1123
Leu Pro Pro His Gln Ser Ser Ser Pro Ile Ser Gln Lys Cys Ser Asn
            330                 335                 340 aca aac tct ccg act ctc gga aag cat ccg aga gat gaa gga tca tcg     1171
Thr Asn Ser Pro Thr Leu Gly Lys His Pro Arg Asp Glu Gly Ser Ser
        345                 350                 355 aaa aag gac aat gag aca gag cga aaa cag aag gcc ggg tgc gtt ctg     1219
Lys Lys Asp Asn Glu Thr Glu Arg Lys Gln Lys Ala Gly Cys Val Leu
    360                 365                 370 gtc ccg aaa acg ttg aga ata gat gat cct aac gaa gca gca aag agc     1267
Val Pro Lys Thr Leu Arg Ile Asp Asp Pro Asn Glu Ala Ala Lys Ser
375                 380                 385                 390 tcg ata tgg aca aca ttg gga atc aag aac gag gcg atg tgc aaa gcc     1315
Ser Ile Trp Thr Thr Leu Gly Ile Lys Asn Glu Ala Met Cys Lys Ala
                395                 400                 405 ggt ggt atg ttc aaa ggg ttt gat cat aag aca aag atg tat aac aac     1363
Gly Gly Met Phe Lys Gly Phe Asp His Lys Thr Lys Met Tyr Asn Asn
            410                 415                 420
```

-continued

```
gac aaa gct gag aac tcc cct gtt ctt tct gct aac cct gct gct cta    1411
Asp Lys Ala Glu Asn Ser Pro Val Leu Ser Ala Asn Pro Ala Ala Leu
        425                 430                 435 tca aga tca cac aat ttc cat gaa cag att tag agttacatat gtatatgtat  1464
Ser Arg Ser His Asn Phe His Glu Gln Ile *
    440                 445 atatgtatga ttgattgtat gtatagatga tactggagaa tgatgagttt ttgagaatca  1524
aactcttttc ttctttctag tgattgcctt tattccttta catgttttgg ttctctgtac  1584
actatttgat ttaccttttt tactttcttt cttcatttgt caggaaatgt tggaagataa  1644
cattaatggt aaaagttgg tgtggaccgt tgttgcgttg gcatttcaaa aaaaaaaaa   1704 aaa                                                                1707

<210> SEQ ID NO 46
<211> LENGTH: 448
<212> TYPE: PRT
<213> ORGANISM: Arabidopsis thaliana
<220> FEATURE:
<221> NAME/KEY: DOMAIN
<222> LOCATION: (112)...(140)
<223> OTHER INFORMATION: Conserved domain

<400> SEQUENCE: 46

Met Met Met Glu Thr Arg Asp Pro Ala Ile Lys Leu Phe Gly Met Lys
1               5                   10                  15

Ile Pro Phe Pro Ser Val Phe Glu Ser Ala Val Thr Val Glu Asp Asp
            20                  25                  30

Glu Glu Asp Asp Trp Ser Gly Gly Asp Asp Lys Ser Pro Glu Lys Val
        35                  40                  45

Thr Pro Glu Leu Ser Asp Lys Asn Asn Asn Cys Asn Asp Asn Ser
    50                  55                  60

Phe Asn Asn Ser Lys Pro Glu Thr Leu Asp Lys Glu Glu Ala Thr Ser
65                  70                  75                  80

Thr Asp Gln Ile Glu Ser Ser Asp Thr Pro Glu Asp Asn Gln Gln Thr
                85                  90                  95

Thr Pro Asp Gly Lys Thr Leu Lys Lys Pro Thr Lys Ile Leu Pro Cys
            100                 105                 110

Pro Arg Cys Lys Ser Met Glu Thr Lys Phe Cys Tyr Tyr Asn Asn Tyr
        115                 120                 125

Asn Ile Asn Gln Pro Arg His Phe Cys Lys Ala Cys Gln Arg Tyr Trp
    130                 135                 140

Thr Ala Gly Gly Thr Met Arg Asn Val Pro Val Gly Ala Gly Arg Arg
145                 150                 155                 160

Lys Asn Lys Ser Ser Ser His Tyr Arg His Ile Thr Ile Ser Glu
                165                 170                 175

Ala Leu Glu Ala Ala Arg Leu Asp Pro Gly Leu Gln Ala Asn Thr Arg
            180                 185                 190

Val Leu Ser Phe Gly Leu Glu Ala Gln Gln Gln His Val Ala Ala Pro
        195                 200                 205

Met Thr Pro Val Met Lys Leu Gln Glu Asp Gln Lys Val Ser Asn Gly
    210                 215                 220

Ala Arg Asn Arg Phe His Gly Leu Ala Asp Gln Arg Leu Val Ala Arg
225                 230                 235                 240

Val Glu Asn Gly Asp Asp Cys Ser Ser Gly Ser Ser Val Thr Thr Ser
                245                 250                 255

Asn Asn His Ser Val Asp Glu Ser Arg Ala Gln Ser Gly Ser Val Val
```

-continued

```
                   260                 265                 270
        Glu Ala Gln Met Asn Asn Asn Asn Asn Met Asn Gly Tyr Ala
                275                 280                 285

Cys Ile Pro Gly Val Pro Trp Pro Tyr Thr Trp Asn Pro Ala Met Pro
                290                 295                 300

Pro Pro Gly Phe Tyr Pro Pro Gly Tyr Pro Met Pro Phe Tyr Pro
        305                 310                 315                 320

Tyr Trp Thr Ile Pro Met Leu Pro Pro His Gln Ser Ser Pro Ile
                        325                 330                 335

Ser Gln Lys Cys Ser Asn Thr Asn Ser Pro Thr Leu Gly Lys His Pro
                        340                 345                 350

Arg Asp Glu Gly Ser Ser Lys Lys Asp Asn Glu Thr Glu Arg Lys Gln
                        355                 360                 365

Lys Ala Gly Cys Val Leu Val Pro Lys Thr Leu Arg Ile Asp Asp Pro
                        370                 375                 380

Asn Glu Ala Ala Lys Ser Ser Ile Trp Thr Thr Leu Gly Ile Lys Asn
        385                 390                 395                 400

Glu Ala Met Cys Lys Ala Gly Gly Met Phe Lys Gly Phe Asp His Lys
                        405                 410                 415

Thr Lys Met Tyr Asn Asn Asp Lys Ala Glu Asn Ser Pro Val Leu Ser
                        420                 425                 430

Ala Asn Pro Ala Ala Leu Ser Arg Ser His Asn Phe His Glu Gln Ile
                        435                 440                 445
```

```
<210> SEQ ID NO 47
<211> LENGTH: 1195
<212> TYPE: DNA
<213> ORGANISM: Arabidopsis thaliana
<220> FEATURE:
<221> NAME/KEY: CDS
<222> LOCATION: (67)...(1041)

<400> SEQUENCE: 47
ctctctcgtc ttcgtcttct tcttcttcaa cgttcctctc caaaatcctc agaccaagaa        60 atcatc atg gcc gtc gat cta atg cgt ttc cct aag ata gat gat caa        108
       Met Ala Val Asp Leu Met Arg Phe Pro Lys Ile Asp Asp Gln
        1               5                   10 acg gct att cag gaa gct gca tcg caa ggt tta caa agt atg gaa cat        156
Thr Ala Ile Gln Glu Ala Ala Ser Gln Gly Leu Gln Ser Met Glu His
 15                  20                  25                  30 ctg atc cgt gtc ctc tct aac cgt ccc gaa caa caa cac aac gtt gac        204
Leu Ile Arg Val Leu Ser Asn Arg Pro Glu Gln Gln His Asn Val Asp
                 35                  40                  45 tgc tcc gag atc act gac ttc acc gtt tct aaa ttc aaa acc gtc att        252
Cys Ser Glu Ile Thr Asp Phe Thr Val Ser Lys Phe Lys Thr Val Ile
             50                  55                  60 tct ctc ctt aac cgt act ggt cac gct cgg ttc aga cgc gga ccg gtt        300
Ser Leu Leu Asn Arg Thr Gly His Ala Arg Phe Arg Arg Gly Pro Val
         65                  70                  75 cac tcc act tcc tct gcc gca tct cag aaa cta cag agt cag atc gtt        348
His Ser Thr Ser Ser Ala Ala Ser Gln Lys Leu Gln Ser Gln Ile Val
     80                  85                  90 aaa aat act caa cct gag gct ccg ata gtg aga aca act acg aat cac        396
Lys Asn Thr Gln Pro Glu Ala Pro Ile Val Arg Thr Thr Thr Asn His
 95                 100                 105                 110 cct caa atc gtt cct cca ccg tct agt gta aca ctc gat ttc tct aaa        444
Pro Gln Ile Val Pro Pro Pro Ser Ser Val Thr Leu Asp Phe Ser Lys
                115                 120                 125
```

```
cca agc atc ttc ggc acc aaa gct aag agc gcc gag ctg gaa ttc tcc        492
Pro Ser Ile Phe Gly Thr Lys Ala Lys Ser Ala Glu Leu Glu Phe Ser
        130                 135                 140 aaa gaa aac ttc agt gtt tct tta aac tcc tca ttc atg tcg tcg gcg        540
Lys Glu Asn Phe Ser Val Ser Leu Asn Ser Ser Phe Met Ser Ser Ala
            145                 150                 155 ata acc gga gac ggc agc gtc tcc aat gga aaa atc ttc ctt gct tct        588
Ile Thr Gly Asp Gly Ser Val Ser Asn Gly Lys Ile Phe Leu Ala Ser
    160                 165                 170 gct ccg tcg cag cct gtt aac tct tcc gga aaa cca ccg ttg gct ggt        636
Ala Pro Ser Gln Pro Val Asn Ser Ser Gly Lys Pro Pro Leu Ala Gly
175                 180                 185                 190 cat cct tac aga aag aga tgt ctc gag cat gag cac tca gag agt ttc        684
His Pro Tyr Arg Lys Arg Cys Leu Glu His Glu His Ser Glu Ser Phe
                195                 200                 205 tcc gga aaa gtc tcc ggc tcc gcc tac gga aag tgc cat tgc aag aaa        732
Ser Gly Lys Val Ser Gly Ser Ala Tyr Gly Lys Cys His Cys Lys Lys
            210                 215                 220 agg aaa aat cgg atg aag aga acc gtg aga gta ccg gcg ata agt gca        780
Arg Lys Asn Arg Met Lys Arg Thr Val Arg Val Pro Ala Ile Ser Ala
        225                 230                 235 aag atc gcc gat att cca ccg gac gaa tat tcg tgg agg aag tac gga        828
Lys Ile Ala Asp Ile Pro Pro Asp Glu Tyr Ser Trp Arg Lys Tyr Gly
    240                 245                 250 caa aaa ccg atc aag ggc tca cca cac cca cgt ggt tac tac aag tgc        876
Gln Lys Pro Ile Lys Gly Ser Pro His Pro Arg Gly Tyr Tyr Lys Cys
255                 260                 265                 270 agt aca ttc aga gga tgt cca gcg agg aaa cac gtg gaa cga gca tta        924
Ser Thr Phe Arg Gly Cys Pro Ala Arg Lys His Val Glu Arg Ala Leu
                275                 280                 285 gat gat cca gcg atg ctt att gtg aca tac gaa gga gag cac cgt cat        972
Asp Asp Pro Ala Met Leu Ile Val Thr Tyr Glu Gly Glu His Arg His
            290                 295                 300 aac caa tcc gcg atg cag gag aat att tct tct tca ggc att aat gat       1020
Asn Gln Ser Ala Met Gln Glu Asn Ile Ser Ser Ser Gly Ile Asn Asp
        305                 310                 315 tta gtg ttt gcc tcg gct tga ctttttttg tactatttgt tttttgattt           1071
Leu Val Phe Ala Ser Ala  *
    320 tttgagtact ttagatggat tgaaatttgt aaattttttt attaagaaat caatttaaat    1131 agagaaaaat tagtggtggt gcaaaaaaaa aaaaaaaaa aaaaaaaaaa aaaaaaaaa      1191 aaaa                                                                  1195

<210> SEQ ID NO 48
<211> LENGTH: 324
<212> TYPE: PRT
<213> ORGANISM: Arabidopsis thaliana
<220> FEATURE:
<221> NAME/KEY: DOMAIN
<222> LOCATION: (245)...(302)
<223> OTHER INFORMATION: Conserved domain

<400> SEQUENCE: 48

Met Ala Val Asp Leu Met Arg Phe Pro Lys Ile Asp Asp Gln Thr Ala
 1               5                  10                  15

Ile Gln Glu Ala Ala Ser Gln Gly Leu Gln Ser Met Glu His Leu Ile
            20                  25                  30

Arg Val Leu Ser Asn Arg Pro Glu Gln Gln His Asn Val Asp Cys Ser
        35                  40                  45
```

```
Glu Ile Thr Asp Phe Thr Val Ser Lys Phe Lys Thr Val Ile Ser Leu
 50                  55                  60

Leu Asn Arg Thr Gly His Ala Arg Phe Arg Arg Gly Pro Val His Ser
 65                  70                  75                  80

Thr Ser Ser Ala Ala Ser Gln Lys Leu Gln Ser Gln Ile Val Lys Asn
                 85                  90                  95

Thr Gln Pro Glu Ala Pro Ile Val Arg Thr Thr Thr Asn His Pro Gln
            100                 105                 110

Ile Val Pro Pro Ser Ser Val Thr Leu Asp Phe Ser Lys Pro Ser
            115                 120                 125

Ile Phe Gly Thr Lys Ala Lys Ser Ala Glu Leu Glu Phe Ser Lys Glu
            130                 135                 140

Asn Phe Ser Val Ser Leu Asn Ser Ser Phe Met Ser Ser Ala Ile Thr
145                 150                 155                 160

Gly Asp Gly Ser Val Ser Asn Gly Lys Ile Phe Leu Ala Ser Ala Pro
                165                 170                 175

Ser Gln Pro Val Asn Ser Ser Gly Lys Pro Leu Ala Gly His Pro
            180                 185                 190

Tyr Arg Lys Arg Cys Leu Glu His Glu His Ser Glu Ser Phe Ser Gly
            195                 200                 205

Lys Val Ser Gly Ser Ala Tyr Gly Lys Cys His Cys Lys Lys Arg Lys
210                 215                 220

Asn Arg Met Lys Arg Thr Val Arg Val Pro Ala Ile Ser Ala Lys Ile
225                 230                 235                 240

Ala Asp Ile Pro Pro Asp Glu Tyr Ser Trp Arg Lys Tyr Gly Gln Lys
                245                 250                 255

Pro Ile Lys Gly Ser Pro His Pro Arg Gly Tyr Lys Cys Ser Thr
            260                 265                 270

Phe Arg Gly Cys Pro Ala Arg Lys His Val Glu Arg Ala Leu Asp Asp
            275                 280                 285

Pro Ala Met Leu Ile Val Thr Tyr Glu Gly Glu His Arg His Asn Gln
            290                 295                 300

Ser Ala Met Gln Glu Asn Ile Ser Ser Gly Ile Asn Asp Leu Val
305                 310                 315                 320

Phe Ala Ser Ala

<210> SEQ ID NO 49
<211> LENGTH: 1650
<212> TYPE: DNA
<213> ORGANISM: Arabidopsis thaliana
<220> FEATURE:
<221> NAME/KEY: CDS
<222> LOCATION: (107)...(1393)

<400> SEQUENCE: 49
ctctcactct cttttctct ctctttactt ctactgtatc aagaagctcc gttttgctta    60
gccatagtgc gtctagggtt tggttggtgg gaagaaggtt ccgatc atg gcg tcg    115
                                              Met Ala Ser
                                                1 gtg tcg tcg tcg gat caa gga cct aag aca gaa gca gga tgt agc ggc    163
Val Ser Ser Ser Asp Gln Gly Pro Lys Thr Glu Ala Gly Cys Ser Gly
  5                  10                  15 gga gga gga gga gag agc tcg gag aca gtg gcg gcg agt gat cag atg    211
Gly Gly Gly Gly Glu Ser Ser Glu Thr Val Ala Ala Ser Asp Gln Met
 20                  25                  30                  35
```

-continued

| | | |
|---|---|---|
| ttg ttg tat aga ggt ttt aag aag gcg aag aag gag aga ggt tgt aca<br>Leu Leu Tyr Arg Gly Phe Lys Lys Ala Lys Lys Glu Arg Gly Cys Thr<br>                  40                        45                    50 | 259 | |
| gct aag gag cgt att agt aaa atg cct ccg tgc act gct ggg aaa agg<br>Ala Lys Glu Arg Ile Ser Lys Met Pro Pro Cys Thr Ala Gly Lys Arg<br>              55                        60                       65 | 307 | |
| agt tcc ata tac cgg gga gtc acc aga cat aga tgg aca ggt cgt tat<br>Ser Ser Ile Tyr Arg Gly Val Thr Arg His Arg Trp Thr Gly Arg Tyr<br>        70                          75                        80 | 355 | |
| gaa gct cac ctt tgg gat aag agt acc tgg aac caa aac cag aac aag<br>Glu Ala His Leu Trp Asp Lys Ser Thr Trp Asn Gln Asn Gln Asn Lys<br>85                          90                        95 | 403 | |
| aag gga aaa caa gtt tat cta gga gca tat gat gat gaa gag gct gct<br>Lys Gly Lys Gln Val Tyr Leu Gly Ala Tyr Asp Asp Glu Glu Ala Ala<br>100                        105                       110                   115 | 451 | |
| gct aga gct tac gac ctt gct gcc tta aaa tat tgg ggt cct ggg aca<br>Ala Arg Ala Tyr Asp Leu Ala Ala Leu Lys Tyr Trp Gly Pro Gly Thr<br>                  120                       125                   130 | 499 | |
| ctt ata aat ttt ccg gtg act gat tat acc agg gat tta gaa gaa atg<br>Leu Ile Asn Phe Pro Val Thr Asp Tyr Thr Arg Asp Leu Glu Glu Met<br>                135                       140                   145 | 547 | |
| caa aat ctc tca agg gaa gaa tac ctt gca tct tta cgt aga tat ccc<br>Gln Asn Leu Ser Arg Glu Glu Tyr Leu Ala Ser Leu Arg Arg Tyr Pro<br>        150                       155                       160 | 595 | |
| ttt ggc aga aaa agc agc ggt ttc tct agg gga ata gcg aaa tat cgt<br>Phe Gly Arg Lys Ser Ser Gly Phe Ser Arg Gly Ile Ala Lys Tyr Arg<br>165                        170                       175 | 643 | |
| gga ctt caa agc cga tgg gac gca tca gcc agt cgt atg cct gga cct<br>Gly Leu Gln Ser Arg Trp Asp Ala Ser Ala Ser Arg Met Pro Gly Pro<br>180                        185                       190                   195 | 691 | |
| gaa tac ttc agt aac att cat tac ggg gca ggt gat gat cgt gga aca<br>Glu Tyr Phe Ser Asn Ile His Tyr Gly Ala Gly Asp Asp Arg Gly Thr<br>                200                       205                   210 | 739 | |
| gaa ggt gac ttt cta ggt agc ttt tgt ctg gaa aga aag att gat cta<br>Glu Gly Asp Phe Leu Gly Ser Phe Cys Leu Glu Arg Lys Ile Asp Leu<br>                215                       220                   225 | 787 | |
| aca gga tac ata aag tgg tgg gga gcc aac aag aac cgt caa cca gaa<br>Thr Gly Tyr Ile Lys Trp Trp Gly Ala Asn Lys Asn Arg Gln Pro Glu<br>        230                       235                       240 | 835 | |
| tct tca tca aaa gca tca gag gat gca aac gtc gaa gat gct ggt act<br>Ser Ser Ser Lys Ala Ser Glu Asp Ala Asn Val Glu Asp Ala Gly Thr<br>245                        250                       255 | 883 | |
| gag ctt aaa aca ctg gaa cac aca tcc cat gca aca gaa cca tac aag<br>Glu Leu Lys Thr Leu Glu His Thr Ser His Ala Thr Glu Pro Tyr Lys<br>260                        265                       270                   275 | 931 | |
| gcg cca aac ctt ggc gtc ctt tgt gga act cag aga aaa gaa aaa gaa<br>Ala Pro Asn Leu Gly Val Leu Cys Gly Thr Gln Arg Lys Glu Lys Glu<br>                280                       285                   290 | 979 | |
| ata tca tca cca tca agc tct tct gct tta agc atc ttg tct cag tcg<br>Ile Ser Ser Pro Ser Ser Ser Ser Ala Leu Ser Ile Leu Ser Gln Ser<br>                295                       300                   305 | 1027 | |
| cct gcc ttc aag agc cta gag gag aaa gtg ttg aag atc caa gaa agc<br>Pro Ala Phe Lys Ser Leu Glu Glu Lys Val Leu Lys Ile Gln Glu Ser<br>        310                       315                       320 | 1075 | |
| tgc aat aat gaa aac gat gag aat gca aac cgt aac atc atc aat atg<br>Cys Asn Asn Glu Asn Asp Glu Asn Ala Asn Arg Asn Ile Ile Asn Met<br>        325                       330                       335 | 1123 | |
| gag aag aat aac ggc aag gca ata gag aaa cca gtt gtg agt cat gga<br>Glu Lys Asn Asn Gly Lys Ala Ile Glu Lys Pro Val Val Ser His Gly<br>340                        345                       350                   355 | 1171 | |

```
gtt gct tta ggc ggt gct gct gct ttg tct ctt cag aaa agc atg tac      1219
Val Ala Leu Gly Gly Ala Ala Ala Leu Ser Leu Gln Lys Ser Met Tyr
            360                 365                 370 cca ctt acc tct ctc tta acg gct cca ttg ctc acc aac tac aat aca      1267
Pro Leu Thr Ser Leu Leu Thr Ala Pro Leu Leu Thr Asn Tyr Asn Thr
            375                 380                 385 ttg gat cct ctt gca gac cct att ctc tgg aca cca ttt ctt cct tca      1315
Leu Asp Pro Leu Ala Asp Pro Ile Leu Trp Thr Pro Phe Leu Pro Ser
            390                 395                 400 gga tcc tct ctt act tca gag gtg aca aag aca gag acc agc tgt tcc      1363
Gly Ser Ser Leu Thr Ser Glu Val Thr Lys Thr Glu Thr Ser Cys Ser
    405                 410                 415 acg tac agc tac ctc cca caa gag aaa tga gccgttccct ttagacttta        1413
Thr Tyr Ser Tyr Leu Pro Gln Glu Lys *
420                 425 tgtatgtcag attctccttt tttgagatga attcgtcgac ttgacatctc tttgtctctt    1473
ttatggagaa aaagttggga aaagtgtgac aatggtctga agcaggaatg tacaggtttt    1533
gttagtggtt gtgtttttt ttttccagtg tggaatatag aatcatgata ttttgtgtaa    1593
aacagaaaaa agttatcatt atagtataga agtttgctct taaaaaaaaa aaaaaaa      1650

<210> SEQ ID NO 50
<211> LENGTH: 428
<212> TYPE: PRT
<213> ORGANISM: Arabidopsis thaliana
<220> FEATURE:
<221> NAME/KEY: DOMAIN
<222> LOCATION: (68)...(144)
<223> OTHER INFORMATION: Conserved domain

<400> SEQUENCE: 50

Met Ala Ser Val Ser Ser Asp Gln Gly Pro Lys Thr Glu Ala Gly
 1               5                  10                  15

Cys Ser Gly Gly Gly Gly Glu Ser Ser Glu Thr Val Ala Ala Ser
            20                  25                  30

Asp Gln Met Leu Leu Tyr Arg Gly Phe Lys Lys Ala Lys Lys Glu Arg
        35                  40                  45

Gly Cys Thr Ala Lys Glu Arg Ile Ser Lys Met Pro Pro Cys Thr Ala
    50                  55                  60

Gly Lys Arg Ser Ser Ile Tyr Arg Gly Val Thr Arg His Arg Trp Thr
65                  70                  75                  80

Gly Arg Tyr Glu Ala His Leu Trp Asp Lys Ser Thr Trp Asn Gln Asn
                85                  90                  95

Gln Asn Lys Lys Gly Lys Gln Val Tyr Leu Gly Ala Tyr Asp Asp Glu
            100                 105                 110

Glu Ala Ala Ala Arg Ala Tyr Asp Leu Ala Ala Leu Lys Tyr Trp Gly
        115                 120                 125

Pro Gly Thr Leu Ile Asn Phe Pro Val Thr Asp Tyr Thr Arg Asp Leu
    130                 135                 140

Glu Glu Met Gln Asn Leu Ser Arg Glu Glu Tyr Leu Ala Ser Leu Arg
145                 150                 155                 160

Arg Tyr Pro Phe Gly Arg Lys Ser Ser Gly Phe Ser Arg Gly Ile Ala
                165                 170                 175

Lys Tyr Arg Gly Leu Gln Ser Arg Trp Asp Ala Ser Ala Ser Arg Met
            180                 185                 190

Pro Gly Pro Glu Tyr Phe Ser Asn Ile His Tyr Gly Ala Gly Asp Asp
        195                 200                 205
```

```
Arg Gly Thr Glu Gly Asp Phe Leu Gly Ser Phe Cys Leu Glu Arg Lys
    210                 215                 220
Ile Asp Leu Thr Gly Tyr Ile Lys Trp Trp Gly Ala Asn Lys Asn Arg
225                 230                 235                 240
Gln Pro Glu Ser Ser Ser Lys Ala Ser Glu Asp Ala Asn Val Glu Asp
                245                 250                 255
Ala Gly Thr Glu Leu Lys Thr Leu Glu His Thr Ser His Ala Thr Glu
            260                 265                 270
Pro Tyr Lys Ala Pro Asn Leu Gly Val Leu Cys Gly Thr Gln Arg Lys
        275                 280                 285
Glu Lys Glu Ile Ser Ser Pro Ser Ser Ser Ala Leu Ser Ile Leu
    290                 295                 300
Ser Gln Ser Pro Ala Phe Lys Ser Leu Glu Glu Lys Val Leu Lys Ile
305                 310                 315                 320
Gln Glu Ser Cys Asn Asn Glu Asn Asp Glu Asn Ala Asn Arg Asn Ile
                325                 330                 335
Ile Asn Met Glu Lys Asn Asn Gly Lys Ala Ile Glu Lys Pro Val Val
            340                 345                 350
Ser His Gly Val Ala Leu Gly Gly Ala Ala Leu Ser Leu Gln Lys
        355                 360                 365
Ser Met Tyr Pro Leu Thr Ser Leu Leu Thr Ala Pro Leu Leu Thr Asn
    370                 375                 380
Tyr Asn Thr Leu Asp Pro Leu Ala Asp Pro Ile Leu Trp Thr Pro Phe
385                 390                 395                 400
Leu Pro Ser Gly Ser Ser Leu Thr Ser Glu Val Thr Lys Thr Glu Thr
                405                 410                 415
Ser Cys Ser Thr Tyr Ser Tyr Leu Pro Gln Glu Lys
            420                 425

<210> SEQ ID NO 51
<211> LENGTH: 1430
<212> TYPE: DNA
<213> ORGANISM: Arabidopsis thaliana
<220> FEATURE:
<221> NAME/KEY: CDS
<222> LOCATION: (377)...(1162)

<400> SEQUENCE: 51
aaaaaaaaag ttgatatact ttctggtttt ctccttaact tttattcttt acaaatccat    60
cccccttaga tctgtttatt tcccgctact ttgattcatt tctgttagta atctgtcttt   120
cgtatagaag aaaactgatt tcttggtttg tattttctta aagagatcaa tcttttttta   180
tttttgatct tcttgtgttt tttttctttt gtagaattaa tcgtttgtga gggtattttt   240
ttaattccct cctctcagaa atctacacag aggttttta ttttataaac ctcttttcg     300 attttcttga aaacaaaaaa tcctgttctt tacttttttt acaagaacaa gggaaaaaaa   360
tttcttttta ttagaa atg aca act tct atg gat ttt tac agt aac aaa acg   412
              Met Thr Thr Ser Met Asp Phe Tyr Ser Asn Lys Thr
                1               5                   10 ttt caa caa tct gat cca ttc ggt ggt gaa tta atg gaa gcg ctt tta   460
Phe Gln Gln Ser Asp Pro Phe Gly Gly Glu Leu Met Glu Ala Leu Leu
         15                  20                  25 cct ttt atc aaa agc cct tcc aac gat tca tcc gcg ttt gcg ttc tct   508
Pro Phe Ile Lys Ser Pro Ser Asn Asp Ser Ser Ala Phe Ala Phe Ser
     30                  35                  40 cta ccc gct cca att tca tac ggg tcg gat ctc cac tca ttt tct cac   556
```

```
                                                                                          -continued Leu Pro Ala Pro Ile Ser Tyr Gly Ser Asp Leu His Ser Phe Ser His
 45                  50                  55                  60 cat ctt agt cct aaa ccg gtc tca atg aaa caa acc ggt act tcc gcg          604
His Leu Ser Pro Lys Pro Val Ser Met Lys Gln Thr Gly Thr Ser Ala
             65                  70                  75 gct aaa ccg acg aag cta tac aga gga gtg aga caa cgt cac tgg gga          652
Ala Lys Pro Thr Lys Leu Tyr Arg Gly Val Arg Gln Arg His Trp Gly
         80                  85                  90 aaa tgg gtg gct gag att cgt tta ccg agg aat cga act cga ctt tgg          700
Lys Trp Val Ala Glu Ile Arg Leu Pro Arg Asn Arg Thr Arg Leu Trp
     95                 100                 105 ctc gga aca ttc gac acg gcg gag gaa gct gct tta gct tat gac aag          748
Leu Gly Thr Phe Asp Thr Ala Glu Glu Ala Ala Leu Ala Tyr Asp Lys
110                 115                 120 gcg gcg tat aag ctc cga gga gat ttt gcg cgg ctt aat ttc cct gat          796
Ala Ala Tyr Lys Leu Arg Gly Asp Phe Ala Arg Leu Asn Phe Pro Asp
125                 130                 135                 140 ctc cgt cat aac gac gag tat caa cct ctt caa tca tca gtc gac gct          844
Leu Arg His Asn Asp Glu Tyr Gln Pro Leu Gln Ser Ser Val Asp Ala
                145                 150                 155 aag ctt gaa gct att tgt caa aac tta gct gag acg acg cag aaa cag          892
Lys Leu Glu Ala Ile Cys Gln Asn Leu Ala Glu Thr Thr Gln Lys Gln
            160                 165                 170 gtg aga tca acg aag aag tct tct tct cgg aaa cgt tca tca acc gtc          940
Val Arg Ser Thr Lys Lys Ser Ser Ser Arg Lys Arg Ser Ser Thr Val
        175                 180                 185 gca gtg aaa cta ccg gag gag gac tac tct agc gcc gga tct tcg ccg          988
Ala Val Lys Leu Pro Glu Glu Asp Tyr Ser Ser Ala Gly Ser Ser Pro
    190                 195                 200 ctg tta acg gag agt tat gga tct ggt gga tct tct tcg ccg ttg tcg         1036
Leu Leu Thr Glu Ser Tyr Gly Ser Gly Gly Ser Ser Ser Pro Leu Ser
205                 210                 215                 220 gag ctg acg ttt ggt gat acg gag gag gag att cag ccg ccg tgg aac         1084
Glu Leu Thr Phe Gly Asp Thr Glu Glu Glu Ile Gln Pro Pro Trp Asn
                225                 230                 235 gag aac gcg ttg gag aag tat ccg tcg tac gag atc gat tgg gat tcg         1132
Glu Asn Ala Leu Glu Lys Tyr Pro Ser Tyr Glu Ile Asp Trp Asp Ser
            240                 245                 250 att ctt cag tgt tcg agt ctt gta aat tag atgttgccat aggggtattt           1182
Ile Leu Gln Cys Ser Ser Leu Val Asn *
        255                 260 tagggacttt agagctctct gcgatggagt ttttggtcat tgcagagatt ttattattat       1242
taagggggtt tgttatgtta atatcaaata agtttatcta ctttgatgtt aattagtgtt       1302
aatctctgcg tcggtccaag ctgttttttt ttggcatgct tcgaccgtgt gagatttctt       1362
atgtaatttt tgtagttcct tgattttctt agttcaagtt aaattggcac aaaaaaaaaa       1422
aaaaaaaa                                                                1430

<210> SEQ ID NO 52
<211> LENGTH: 261
<212> TYPE: PRT
<213> ORGANISM: Arabidopsis thaliana
<220> FEATURE:
<221> NAME/KEY: DOMAIN
<222> LOCATION: (81)...(140)
<223> OTHER INFORMATION: Conserved domain

<400> SEQUENCE: 52

Met Thr Thr Ser Met Asp Phe Tyr Ser Asn Lys Thr Phe Gln Gln Ser
 1               5                  10                  15
```

```
Asp Pro Phe Gly Gly Glu Leu Met Glu Ala Leu Leu Pro Phe Ile Lys
         20                  25                  30

Ser Pro Ser Asn Asp Ser Ser Ala Phe Ala Phe Ser Leu Pro Ala Pro
             35                  40                  45

Ile Ser Tyr Gly Ser Asp Leu His Ser Phe Ser His His Leu Ser Pro
         50                  55                  60

Lys Pro Val Ser Met Lys Gln Thr Gly Thr Ser Ala Ala Lys Pro Thr
 65                  70                  75                  80

Lys Leu Tyr Arg Gly Val Arg Gln Arg His Trp Gly Lys Trp Val Ala
                 85                  90                  95

Glu Ile Arg Leu Pro Arg Asn Arg Thr Arg Leu Trp Leu Gly Thr Phe
            100                 105                 110

Asp Thr Ala Glu Glu Ala Ala Leu Ala Tyr Asp Lys Ala Ala Tyr Lys
            115                 120                 125

Leu Arg Gly Asp Phe Ala Arg Leu Asn Phe Pro Asp Leu Arg His Asn
        130                 135                 140

Asp Glu Tyr Gln Pro Leu Gln Ser Ser Val Asp Ala Lys Leu Glu Ala
145                 150                 155                 160

Ile Cys Gln Asn Leu Ala Glu Thr Thr Gln Lys Val Arg Ser Thr
                165                 170                 175

Lys Lys Ser Ser Arg Lys Arg Ser Ser Thr Val Ala Val Lys Leu
            180                 185                 190

Pro Glu Glu Asp Tyr Ser Ser Ala Gly Ser Ser Pro Leu Leu Thr Glu
            195                 200                 205

Ser Tyr Gly Ser Gly Gly Ser Ser Pro Leu Ser Glu Leu Thr Phe
    210                 215                 220

Gly Asp Thr Glu Glu Glu Ile Gln Pro Pro Trp Asn Glu Asn Ala Leu
225                 230                 235                 240

Glu Lys Tyr Pro Ser Tyr Glu Ile Asp Trp Asp Ser Ile Leu Gln Cys
                245                 250                 255

Ser Ser Leu Val Asn
            260

<210> SEQ ID NO 53
<211> LENGTH: 1113
<212> TYPE: DNA
<213> ORGANISM: Arabidopsis thaliana
<220> FEATURE:
<221> NAME/KEY: CDS
<222> LOCATION: (1)...(1113)

<400> SEQUENCE: 53 atg ggt cat cac tca tgc tgc aac cag caa aag gtg aag aga ggg ctt    48
Met Gly His His Ser Cys Cys Asn Gln Gln Lys Val Lys Arg Gly Leu
 1               5                  10                  15 tgg tca ccg gaa gaa gat gag aag ctt att aga tat atc aca act cat    96
Trp Ser Pro Glu Glu Asp Glu Lys Leu Ile Arg Tyr Ile Thr Thr His
             20                  25                  30 ggc tat gga tgt tgg agt gaa gtc cct gaa aaa gca ggg ctt caa aga   144
Gly Tyr Gly Cys Trp Ser Glu Val Pro Glu Lys Ala Gly Leu Gln Arg
         35                  40                  45 tgt gga aaa agt tgt aga ttg cga tgg ata aac tat ctt cga cct gat   192
Cys Gly Lys Ser Cys Arg Leu Arg Trp Ile Asn Tyr Leu Arg Pro Asp
     50                  55                  60 atc agg aga gga agg ttc tct cca gaa gaa gag aaa ttg atc ata agc   240
Ile Arg Arg Gly Arg Phe Ser Pro Glu Glu Glu Lys Leu Ile Ile Ser
 65                  70                  75                  80
```

```
ctt cat gga gtt gtg gga aac agg tgg gct cat ata gct agt cat tta    288
Leu His Gly Val Val Gly Asn Arg Trp Ala His Ile Ala Ser His Leu
                85                  90                  95 ccg gga aga aca gat aac gag att aaa aac tat tgg aat tca tgg att    336
Pro Gly Arg Thr Asp Asn Glu Ile Lys Asn Tyr Trp Asn Ser Trp Ile
            100                 105                 110 aag aaa aag ata cga aaa ccg cac cat cat tac agt cgt cat caa ccg    384
Lys Lys Lys Ile Arg Lys Pro His His His Tyr Ser Arg His Gln Pro
        115                 120                 125 tca gta act act gtg aca ttg aat gcg gac act aca tcg att gcc act    432
Ser Val Thr Thr Val Thr Leu Asn Ala Asp Thr Thr Ser Ile Ala Thr
    130                 135                 140 acc atc gag gcc tct acc acc aca aca tcg act atc gat aac tta cat    480
Thr Ile Glu Ala Ser Thr Thr Thr Thr Ser Thr Ile Asp Asn Leu His
145                 150                 155                 160 ttt gac ggt ttc act gat tct cct aac caa tta aat ttc acc aat gat    528
Phe Asp Gly Phe Thr Asp Ser Pro Asn Gln Leu Asn Phe Thr Asn Asp
                165                 170                 175 caa gaa act aat ata aag att caa gaa act ttt ttc tcc cat aaa cct    576
Gln Glu Thr Asn Ile Lys Ile Gln Glu Thr Phe Phe Ser His Lys Pro
            180                 185                 190 cct ctc ttc atg gta gac aca aca ctt cct atc cta gaa gga atg ttc    624
Pro Leu Phe Met Val Asp Thr Thr Leu Pro Ile Leu Glu Gly Met Phe
        195                 200                 205 tct gaa aac atc atc aca aac aat aac aag aac aat gat cat gat gac    672
Ser Glu Asn Ile Ile Thr Asn Asn Asn Lys Asn Asn Asp His Asp Asp
    210                 215                 220 acg caa aga gga gga aga gaa aat gtt tgt gaa caa gca ttt cta aca    720
Thr Gln Arg Gly Gly Arg Glu Asn Val Cys Glu Gln Ala Phe Leu Thr
225                 230                 235                 240 act aac acg gaa gaa tgg gat atg aat ctt cgt cag caa gag ccg ttt    768
Thr Asn Thr Glu Glu Trp Asp Met Asn Leu Arg Gln Gln Glu Pro Phe
                245                 250                 255 caa gtt cct aca ctg gcg tca cat gtg ttc aac aac tct tcc aat tca    816
Gln Val Pro Thr Leu Ala Ser His Val Phe Asn Asn Ser Ser Asn Ser
            260                 265                 270 aat att gac acg gtt ata agt tat aat cta ccg gcg cta ata gag gga    864
Asn Ile Asp Thr Val Ile Ser Tyr Asn Leu Pro Ala Leu Ile Glu Gly
        275                 280                 285 aat gtc gat aac atc gtc cat aat gaa aac agc aat gtc caa gat gga    912
Asn Val Asp Asn Ile Val His Asn Glu Asn Ser Asn Val Gln Asp Gly
    290                 295                 300 gaa atg gcg tcc aca ttc gaa tgt tta aag agg caa gaa cta agc tat    960
Glu Met Ala Ser Thr Phe Glu Cys Leu Lys Arg Gln Glu Leu Ser Tyr
305                 310                 315                 320 gat caa tgg gac gat tca caa caa tgc tct aac ttt ttc ttt tgg gac   1008
Asp Gln Trp Asp Asp Ser Gln Gln Cys Ser Asn Phe Phe Phe Trp Asp
                325                 330                 335 aac ctt aat ata aac gtg gaa ggt tca tct ctt gtt gga aac caa gac   1056
Asn Leu Asn Ile Asn Val Glu Gly Ser Ser Leu Val Gly Asn Gln Asp
            340                 345                 350 cca tca atg aat ttg gga tca tct gcc tta tct tct tct ttc cct tct   1104
Pro Ser Met Asn Leu Gly Ser Ser Ala Leu Ser Ser Ser Phe Pro Ser
        355                 360                 365 tcg ttt taa                                                        1113
Ser Phe *
    370
```

<210> SEQ ID NO 54

```
<211> LENGTH: 370
<212> TYPE: PRT
<213> ORGANISM: Arabidopsis thaliana
<220> FEATURE:
<221> NAME/KEY: DOMAIN
<222> LOCATION: (14)...(116)
<223> OTHER INFORMATION: Conserved domain

<400> SEQUENCE: 54

Met Gly His His Ser Cys Cys Asn Gln Gln Lys Val Lys Arg Gly Leu
 1               5                  10                  15

Trp Ser Pro Glu Glu Asp Glu Lys Leu Ile Arg Tyr Ile Thr Thr His
            20                  25                  30

Gly Tyr Gly Cys Trp Ser Glu Val Pro Glu Lys Ala Gly Leu Gln Arg
        35                  40                  45

Cys Gly Lys Ser Cys Arg Leu Arg Trp Ile Asn Tyr Leu Arg Pro Asp
    50                  55                  60

Ile Arg Arg Gly Arg Phe Ser Pro Glu Glu Lys Leu Ile Ile Ser
65                  70                  75                  80

Leu His Gly Val Val Gly Asn Arg Trp Ala His Ile Ala Ser His Leu
                85                  90                  95

Pro Gly Arg Thr Asp Asn Glu Ile Lys Asn Tyr Trp Asn Ser Trp Ile
            100                 105                 110

Lys Lys Lys Ile Arg Lys Pro His His Tyr Ser Arg His Gln Pro
        115                 120                 125

Ser Val Thr Thr Val Thr Leu Asn Ala Asp Thr Thr Ser Ile Ala Thr
    130                 135                 140

Thr Ile Glu Ala Ser Thr Thr Thr Ser Thr Ile Asp Asn Leu His
145                 150                 155                 160

Phe Asp Gly Phe Thr Asp Ser Pro Asn Gln Leu Asn Phe Thr Asn Asp
                165                 170                 175

Gln Glu Thr Asn Ile Lys Ile Gln Glu Thr Phe Phe Ser His Lys Pro
            180                 185                 190

Pro Leu Phe Met Val Asp Thr Thr Leu Pro Ile Leu Glu Gly Met Phe
        195                 200                 205

Ser Glu Asn Ile Ile Thr Asn Asn Lys Asn Asn Asp His Asp Asp
    210                 215                 220

Thr Gln Arg Gly Gly Arg Glu Asn Val Cys Gln Ala Phe Leu Thr
225                 230                 235                 240

Thr Asn Thr Glu Glu Trp Asp Met Asn Leu Arg Gln Gln Glu Pro Phe
                245                 250                 255

Gln Val Pro Thr Leu Ala Ser His Val Phe Asn Asn Ser Ser Asn Ser
            260                 265                 270

Asn Ile Asp Thr Val Ile Ser Tyr Asn Leu Pro Ala Leu Ile Glu Gly
        275                 280                 285

Asn Val Asp Asn Ile Val His Asn Glu Asn Ser Asn Val Gln Asp Gly
    290                 295                 300

Glu Met Ala Ser Thr Phe Glu Cys Leu Lys Arg Gln Glu Leu Ser Tyr
305                 310                 315                 320

Asp Gln Trp Asp Asp Ser Gln Gln Cys Ser Asn Phe Phe Trp Asp
                325                 330                 335

Asn Leu Asn Ile Asn Val Glu Gly Ser Leu Val Gly Asn Gln Asp
            340                 345                 350

Pro Ser Met Asn Leu Gly Ser Ser Ala Leu Ser Ser Ser Phe Pro Ser
        355                 360                 365
```

```
Ser Phe
    370

<210> SEQ ID NO 55
<211> LENGTH: 2006
<212> TYPE: DNA
<213> ORGANISM: Arabidopsis thaliana
<220> FEATURE:
<221> NAME/KEY: CDS
<222> LOCATION: (97)...(1878)

<400> SEQUENCE: 55
ctcgtacttt atcacctccg tcgttctata atactctctt ccgtcaatca tatcatttgt      60
cgacaatttc attctgatca gtttaaaaat tgatcc atg gat gat aat tta agc     114
                                        Met Asp Asp Asn Leu Ser
                                          1               5 ggc gag gaa gaa gat tac tat tac tcc tcc gat cag gaa tct ctc aac     162
Gly Glu Glu Glu Asp Tyr Tyr Tyr Ser Ser Asp Gln Glu Ser Leu Asn
             10                  15                  20 ggg att gat aat gat gaa tcc gtt tcg ata cct gtt tct tcc cga tca     210
Gly Ile Asp Asn Asp Glu Ser Val Ser Ile Pro Val Ser Ser Arg Ser
         25                  30                  35 aat act gtc aag gtt att acg aag gaa tca ctt ttg gct gca cag agg     258
Asn Thr Val Lys Val Ile Thr Lys Glu Ser Leu Leu Ala Ala Gln Arg
 40                  45                  50 gag gat ttg cgg aga gtg atg gaa ttg tta tcg gtt aag gag cac cat     306
Glu Asp Leu Arg Arg Val Met Glu Leu Leu Ser Val Lys Glu His His
 55                  60                  65                  70 gct cgg act ctt ctt ata cat tac cga tgg gat gtg gag aag ttg ttt     354
Ala Arg Thr Leu Leu Ile His Tyr Arg Trp Asp Val Glu Lys Leu Phe
                 75                  80                  85 gct gtt ctt gtt gag aaa ggg aaa gat agc ttg ttt tct ggt gct ggt     402
Ala Val Leu Val Glu Lys Gly Lys Asp Ser Leu Phe Ser Gly Ala Gly
             90                  95                 100 gtt aca ctt ctt gaa aac caa agt tgt gat tct tcc gtt tct ggt tct     450
Val Thr Leu Leu Glu Asn Gln Ser Cys Asp Ser Ser Val Ser Gly Ser
        105                 110                 115 tct tcg atg atg agt tgt gat atc tgc gta gag gat gta ccg ggt tat     498
Ser Ser Met Met Ser Cys Asp Ile Cys Val Glu Asp Val Pro Gly Tyr
    120                 125                 130 cag ctg aca agg atg gac tgt ggc cat agc ttt tgc aat aac tgt tgg     546
Gln Leu Thr Arg Met Asp Cys Gly His Ser Phe Cys Asn Asn Cys Trp
135                 140                 145                 150 act ggg cat ttt act gta aag ata aat gaa ggt cag agc aaa agg att     594
Thr Gly His Phe Thr Val Lys Ile Asn Glu Gly Gln Ser Lys Arg Ile
                155                 160                 165 ata tgc atg gct cat aag tgt aat gct att tgt gat gaa gat gtt gtc     642
Ile Cys Met Ala His Lys Cys Asn Ala Ile Cys Asp Glu Asp Val Val
            170                 175                 180 agg gct cta gtt agt aaa agc caa cca gat tta gct gag aag ttt gat     690
Arg Ala Leu Val Ser Lys Ser Gln Pro Asp Leu Ala Glu Lys Phe Asp
        185                 190                 195 cgt ttt ctt ctt gag tcg tat atc gaa gat aac aaa atg gtg aag tgg     738
Arg Phe Leu Leu Glu Ser Tyr Ile Glu Asp Asn Lys Met Val Lys Trp
    200                 205                 210 tgt ccg agt act cct cat tgt ggg aat gcc ata cgt gtt gag gat gac     786
Cys Pro Ser Thr Pro His Cys Gly Asn Ala Ile Arg Val Glu Asp Asp
215                 220                 225                 230 gag ctc tgt gag gtt gaa tgc tct tgt ggt ttg cag ttc tgt ttc agt     834
Glu Leu Cys Glu Val Glu Cys Ser Cys Gly Leu Gln Phe Cys Phe Ser
                235                 240                 245
```

-continued

| | | |
|---|---|---|
| tgt tca tct caa gct cac tcc cct tgc tct tgt gtg atg tgg gaa cta<br>Cys Ser Ser Gln Ala His Ser Pro Cys Ser Cys Val Met Trp Glu Leu<br>250 255 260 | 882 |
| tgg aga aag aag tgc ttt gat gag tcc gag act gtt aat tgg ata act<br>Trp Arg Lys Lys Cys Phe Asp Glu Ser Glu Thr Val Asn Trp Ile Thr<br>265 270 275 | 930 |
| gtt cac aca aag ccg tgt ccc aaa tgt cac aag cct gtt gaa aag aat<br>Val His Thr Lys Pro Cys Pro Lys Cys His Lys Pro Val Glu Lys Asn<br>280 285 290 | 978 |
| ggt gga tgc aat ctc gtg act tgt ctt tgt cga caa tct ttt tgt tgg<br>Gly Gly Cys Asn Leu Val Thr Cys Leu Cys Arg Gln Ser Phe Cys Trp<br>295 300 305 310 | 1026 |
| ttg tgt ggt gaa gct act gga agg gac cac act tgg gct aga atc tcg<br>Leu Cys Gly Glu Ala Thr Gly Arg Asp His Thr Trp Ala Arg Ile Ser<br>315 320 325 | 1074 |
| ggt cat agt tgt ggt cgg ttc caa gaa gat aaa gag aaa caa atg gag<br>Gly His Ser Cys Gly Arg Phe Gln Glu Asp Lys Glu Lys Gln Met Glu<br>330 335 340 | 1122 |
| aga gcg aaa agg gat ctc aag cgg tat atg cat tat cat aac cga tac<br>Arg Ala Lys Arg Asp Leu Lys Arg Tyr Met His Tyr His Asn Arg Tyr<br>345 350 355 | 1170 |
| aaa gca cat atc gac tcc tcc aag cta gag gct aag ctt agt aat aat<br>Lys Ala His Ile Asp Ser Ser Lys Leu Glu Ala Lys Leu Ser Asn Asn<br>360 365 370 | 1218 |
| att agt aaa aag gtg tct att tca gaa aag agg gag tta caa ctt aaa<br>Ile Ser Lys Lys Val Ser Ile Ser Glu Lys Arg Glu Leu Gln Leu Lys<br>375 380 385 390 | 1266 |
| gac ttc agc tgg gct acc aat gga ctc cat cgg tta ttt aga tca aga<br>Asp Phe Ser Trp Ala Thr Asn Gly Leu His Arg Leu Phe Arg Ser Arg<br>395 400 405 | 1314 |
| cga gtt ctt tca tat tca tac cct ttc gca ttt tac atg ttt gga gat<br>Arg Val Leu Ser Tyr Ser Tyr Pro Phe Ala Phe Tyr Met Phe Gly Asp<br>410 415 420 | 1362 |
| gag ctg ttt aaa gat gag atg agc tct gag gaa aga gaa ata aaa caa<br>Glu Leu Phe Lys Asp Glu Met Ser Ser Glu Glu Arg Glu Ile Lys Gln<br>425 430 435 | 1410 |
| aat ctg ttt gag gat cag cag cag cag ctt gag gct aat gtt gag aaa<br>Asn Leu Phe Glu Asp Gln Gln Gln Gln Leu Glu Ala Asn Val Glu Lys<br>440 445 450 | 1458 |
| ctt tct aag ttc ttg gag gaa cct ttt gat caa ttt gct gat gat aag<br>Leu Ser Lys Phe Leu Glu Glu Pro Phe Asp Gln Phe Ala Asp Asp Lys<br>455 460 465 470 | 1506 |
| gtc atg cag ata agg att caa gtc atc aat ttg tca gtt gcg gtc gat<br>Val Met Gln Ile Arg Ile Gln Val Ile Asn Leu Ser Val Ala Val Asp<br>475 480 485 | 1554 |
| aca ctc tgc gaa aat atg tat gaa tgc att gag aat gac ttg ttg ggt<br>Thr Leu Cys Glu Asn Met Tyr Glu Cys Ile Glu Asn Asp Leu Leu Gly<br>490 495 500 | 1602 |
| tct ctg caa ctt ggc atc cac aac att act cca tac aga tca aac ggc<br>Ser Leu Gln Leu Gly Ile His Asn Ile Thr Pro Tyr Arg Ser Asn Gly<br>505 510 515 | 1650 |
| ata gaa cga gca tct gat ttt tat agt tcc cag aat tcc aag gaa gct<br>Ile Glu Arg Ala Ser Asp Phe Tyr Ser Ser Gln Asn Ser Lys Glu Ala<br>520 525 530 | 1698 |
| gtt ggt cag tct tcg gat tgt gga tgg acg tcc agg ctc gat caa gct<br>Val Gly Gln Ser Ser Asp Cys Gly Trp Thr Ser Arg Leu Asp Gln Ala<br>535 540 545 550 | 1746 |
| ttg gag tca ggg aag tcg gaa gac aca agt tgc tct tcc ggg aag cgt<br>Leu Glu Ser Gly Lys Ser Glu Asp Thr Ser Cys Ser Ser Gly Lys Arg | 1794 |

```
                     555                560                565
gct aga ata gac gaa agt tac aga aac agc caa acc acc tta cta gat      1842
Ala Arg Ile Asp Glu Ser Tyr Arg Asn Ser Gln Thr Thr Leu Leu Asp
            570                575                580 tta aac ttg cca gcg gaa gcc att gag cgg aaa tga acacttatcc           1888
Leu Asn Leu Pro Ala Glu Ala Ile Glu Arg Lys *
        585                590 ttcttcacct cccaataaca ccctttttgt ccaaataaag tgtgttaccc ggatatttat    1948
agctctaaac ccaatcccct ctgcttaatt tgtcagtgac cttacctaac cctcttca     2006
```

<210> SEQ ID NO 56
<211> LENGTH: 593
<212> TYPE: PRT
<213> ORGANISM: Arabidopsis thaliana
<220> FEATURE:
<221> NAME/KEY: DOMAIN
<222> LOCATION: (124)...(247)
<223> OTHER INFORMATION: Conserved domain

<400> SEQUENCE: 56

```
Met Asp Asp Asn Leu Ser Gly Glu Glu Asp Tyr Tyr Ser Ser
 1               5                  10                  15

Asp Gln Glu Ser Leu Asn Gly Ile Asp Asn Asp Glu Ser Val Ser Ile
                20                  25                  30

Pro Val Ser Ser Arg Ser Asn Thr Val Lys Val Ile Thr Lys Glu Ser
            35                  40                  45

Leu Leu Ala Ala Gln Arg Glu Asp Leu Arg Arg Val Met Glu Leu Leu
     50                  55                      60

Ser Val Lys Glu His His Ala Arg Thr Leu Leu Ile His Tyr Arg Trp
 65                  70                      75                  80

Asp Val Glu Lys Leu Phe Ala Val Leu Val Glu Lys Gly Lys Asp Ser
                85                      90                  95

Leu Phe Ser Gly Ala Gly Val Thr Leu Leu Glu Asn Gln Ser Cys Asp
                100                 105                 110

Ser Ser Val Ser Gly Ser Ser Met Met Ser Cys Asp Ile Cys Val
            115                 120                 125

Glu Asp Val Pro Gly Tyr Gln Leu Thr Arg Met Asp Cys Gly His Ser
 130                 135                     140

Phe Cys Asn Asn Cys Trp Thr Gly His Phe Thr Val Lys Ile Asn Glu
145                 150                     155                 160

Gly Gln Ser Lys Arg Ile Ile Cys Met Ala His Lys Cys Asn Ala Ile
                165                     170                 175

Cys Asp Glu Asp Val Val Arg Ala Leu Val Ser Lys Ser Gln Pro Asp
            180                     185                 190

Leu Ala Glu Lys Phe Asp Arg Phe Leu Leu Glu Ser Tyr Ile Glu Asp
            195                     200                 205

Asn Lys Met Val Lys Trp Cys Pro Ser Thr Pro His Cys Gly Asn Ala
    210                     215                     220

Ile Arg Val Glu Asp Asp Glu Leu Cys Glu Val Glu Cys Ser Cys Gly
225                     230                     235                 240

Leu Gln Phe Cys Phe Ser Cys Ser Ser Gln Ala His Ser Pro Cys Ser
                245                     250                     255

Cys Val Met Trp Glu Leu Trp Arg Lys Lys Cys Phe Asp Glu Ser Glu
            260                     265                     270

Thr Val Asn Trp Ile Thr Val His Thr Lys Pro Cys Pro Lys Cys His
            275                     280                     285
```

```
Lys Pro Val Glu Lys Asn Gly Gly Cys Asn Leu Val Thr Cys Leu Cys
    290                 295                 300

Arg Gln Ser Phe Cys Trp Leu Cys Gly Glu Ala Thr Gly Arg Asp His
305                 310                 315                 320

Thr Trp Ala Arg Ile Ser Gly His Ser Cys Gly Arg Phe Gln Glu Asp
                325                 330                 335

Lys Glu Lys Gln Met Glu Arg Ala Lys Arg Asp Leu Lys Arg Tyr Met
            340                 345                 350

His Tyr His Asn Arg Tyr Lys Ala His Ile Asp Ser Ser Lys Leu Glu
        355                 360                 365

Ala Lys Leu Ser Asn Asn Ile Ser Lys Lys Val Ser Ile Ser Glu Lys
    370                 375                 380

Arg Glu Leu Gln Leu Lys Asp Phe Ser Trp Ala Thr Asn Gly Leu His
385                 390                 395                 400

Arg Leu Phe Arg Ser Arg Arg Val Leu Ser Tyr Ser Tyr Pro Phe Ala
                405                 410                 415

Phe Tyr Met Phe Gly Asp Glu Leu Phe Lys Asp Glu Met Ser Ser Glu
            420                 425                 430

Glu Arg Glu Ile Lys Gln Asn Leu Phe Glu Asp Gln Gln Gln Leu
        435                 440                 445

Glu Ala Asn Val Glu Lys Leu Ser Lys Phe Leu Glu Glu Pro Phe Asp
    450                 455                 460

Gln Phe Ala Asp Asp Lys Val Met Gln Ile Arg Ile Gln Val Ile Asn
465                 470                 475                 480

Leu Ser Val Ala Val Asp Thr Leu Cys Glu Asn Met Tyr Glu Cys Ile
                485                 490                 495

Glu Asn Asp Leu Leu Gly Ser Leu Gln Leu Gly Ile His Asn Ile Thr
            500                 505                 510

Pro Tyr Arg Ser Asn Gly Ile Glu Arg Ala Ser Asp Phe Tyr Ser Ser
        515                 520                 525

Gln Asn Ser Lys Glu Ala Val Gly Gln Ser Ser Asp Cys Gly Trp Thr
    530                 535                 540

Ser Arg Leu Asp Gln Ala Leu Glu Ser Gly Lys Ser Glu Asp Thr Ser
545                 550                 555                 560

Cys Ser Ser Gly Lys Arg Ala Arg Ile Asp Glu Ser Tyr Arg Asn Ser
                565                 570                 575

Gln Thr Thr Leu Leu Asp Leu Asn Leu Pro Ala Glu Ala Ile Glu Arg
            580                 585                 590

Lys

<210> SEQ ID NO 57
<211> LENGTH: 1209
<212> TYPE: DNA
<213> ORGANISM: Arabidopsis thaliana
<220> FEATURE:
<221> NAME/KEY: CDS
<222> LOCATION: (41)...(1156)

<400> SEQUENCE: 57
ttgtggtcag tggaataaac acatataacc gccggagaaa atg gga aga gcg cca      55
                                             Met Gly Arg Ala Pro
                                               1               5 tgt tgc gag aag gtc ggt atc aag aga ggg cgg tgg acg gcg gag gag    103
Cys Cys Glu Lys Val Gly Ile Lys Arg Gly Arg Trp Thr Ala Glu Glu
         10                  15                  20
```

```
gac cag att ctc tcc aac tac att caa tcc aat ggt gaa ggt tct tgg    151
Asp Gln Ile Leu Ser Asn Tyr Ile Gln Ser Asn Gly Glu Gly Ser Trp
            25                  30                  35 aga tct ctc ccc aaa aat gcc gga tta aaa agg tgt gga aag agc tgt    199
Arg Ser Leu Pro Lys Asn Ala Gly Leu Lys Arg Cys Gly Lys Ser Cys
        40                  45                  50 aga ttg aga tgg ata aac tat cta aga tca gac ctc aag cgt gga aac    247
Arg Leu Arg Trp Ile Asn Tyr Leu Arg Ser Asp Leu Lys Arg Gly Asn
    55                  60                  65 ata act cca gaa gaa gaa gaa ctc gtt gtt aaa ttg cat tcc act ttg    295
Ile Thr Pro Glu Glu Glu Glu Leu Val Val Lys Leu His Ser Thr Leu
70                  75                  80                  85 gga aac agg tgg tca cta atc gcg ggt cat cta cca ggg aga aca gac    343
Gly Asn Arg Trp Ser Leu Ile Ala Gly His Leu Pro Gly Arg Thr Asp
                90                  95                 100 aac gaa ata aaa aat tat tgg aac tct cat ctc agc cgt aaa ctc cac    391
Asn Glu Ile Lys Asn Tyr Trp Asn Ser His Leu Ser Arg Lys Leu His
            105                 110                 115 aac ttc att agg aag cca tcc atc tct caa gac gtc tcc gcc gta atc    439
Asn Phe Ile Arg Lys Pro Ser Ile Ser Gln Asp Val Ser Ala Val Ile
        120                 125                 130 atg gcg aac gct tct tca gcg cca ccg ccg ccg cag gca aaa cgc aga    487
Met Ala Asn Ala Ser Ser Ala Pro Pro Pro Pro Gln Ala Lys Arg Arg
    135                 140                 145 ctt ggg aga acg agt agg tcc gct atg aaa cca aaa atc cgc aga aca    535
Leu Gly Arg Thr Ser Arg Ser Ala Met Lys Pro Lys Ile Arg Arg Thr
150                 155                 160                 165 aaa act cgt aaa acg aag aaa acg tct gca cca ccg gag cct aac gcc    583
Lys Thr Arg Lys Thr Lys Lys Thr Ser Ala Pro Pro Glu Pro Asn Ala
                170                 175                 180 gat gta gct ggg gct gat aaa gaa gca tta atg gtg gag tca agt gga    631
Asp Val Ala Gly Ala Asp Lys Glu Ala Leu Met Val Glu Ser Ser Gly
            185                 190                 195 gcc gag gct gag cta gga cga cca tgt gac tac tat gga gat gat tgt    679
Ala Glu Ala Glu Leu Gly Arg Pro Cys Asp Tyr Tyr Gly Asp Asp Cys
        200                 205                 210 aac aaa aat ctc atg agc att aat ggc gat aat gga gtt tta acg ttt    727
Asn Lys Asn Leu Met Ser Ile Asn Gly Asp Asn Gly Val Leu Thr Phe
    215                 220                 225 gat gat gat atc atc gat ctt ttg ttg gac gag tca gat cct ggc cac    775
Asp Asp Asp Ile Ile Asp Leu Leu Leu Asp Glu Ser Asp Pro Gly His
230                 235                 240                 245 ttg tac aca aac aca acg tgc ggt ggt ggt ggg gag ttg cat aac ata    823
Leu Tyr Thr Asn Thr Thr Cys Gly Gly Gly Gly Glu Leu His Asn Ile
                250                 255                 260 aga gac tct gaa gga gcc aga ggg ttc tcg gat act tgg aac caa ggg    871
Arg Asp Ser Glu Gly Ala Arg Gly Phe Ser Asp Thr Trp Asn Gln Gly
            265                 270                 275 aat ctc gac tgt ctt ctt cag tct tgt cca tct gtg gag tcg ttt ctc    919
Asn Leu Asp Cys Leu Leu Gln Ser Cys Pro Ser Val Glu Ser Phe Leu
        280                 285                 290 aac tac gac cac caa gtt aac gac gcg tcg acg gat gag ttt atc gat    967
Asn Tyr Asp His Gln Val Asn Asp Ala Ser Thr Asp Glu Phe Ile Asp
    295                 300                 305 tgg gat tgt gtt tgg caa gaa ggt agt gat aat aat ctt tgg cat gag   1015
Trp Asp Cys Val Trp Gln Glu Gly Ser Asp Asn Asn Leu Trp His Glu
310                 315                 320                 325 aaa gag aat ccc gac tca atg gtc tcg tgg ctt tta gac ggt gat gat   1063
Lys Glu Asn Pro Asp Ser Met Val Ser Trp Leu Leu Asp Gly Asp Asp
                330                 335                 340
```

-continued

```
gag gcc acg atc ggg aat agt aat tgt gag aac ttt gga gaa ccg tta      1111
Glu Ala Thr Ile Gly Asn Ser Asn Cys Glu Asn Phe Gly Glu Pro Leu
        345                 350                 355 gat cat gac gac gaa agc gct ttg gtc gct tgg ctt ctg tca tga          1156
Asp His Asp Asp Glu Ser Ala Leu Val Ala Trp Leu Leu Ser *
        360                 365                 370 tgatattgat tgatccgtta tgtaatcttt tttgtgcatt cacagtttga atc           1209

<210> SEQ ID NO 58
<211> LENGTH: 371
<212> TYPE: PRT
<213> ORGANISM: Arabidopsis thaliana
<220> FEATURE:
<221> NAME/KEY: DOMAIN
<222> LOCATION: (14)...(120)
<223> OTHER INFORMATION: Conserved domain

<400> SEQUENCE: 58

Met Gly Arg Ala Pro Cys Cys Glu Lys Val Gly Ile Lys Arg Gly Arg
 1               5                  10                  15

Trp Thr Ala Glu Glu Asp Gln Ile Leu Ser Asn Tyr Ile Gln Ser Asn
            20                  25                  30

Gly Glu Gly Ser Trp Arg Ser Leu Pro Lys Asn Ala Gly Leu Lys Arg
        35                  40                  45

Cys Gly Lys Ser Cys Arg Leu Arg Trp Ile Asn Tyr Leu Arg Ser Asp
    50                  55                  60

Leu Lys Arg Gly Asn Ile Thr Pro Glu Glu Glu Leu Val Val Lys
65                  70                  75                  80

Leu His Ser Thr Leu Gly Asn Arg Trp Ser Leu Ile Ala Gly His Leu
                85                  90                  95

Pro Gly Arg Thr Asp Asn Glu Ile Lys Asn Tyr Trp Asn Ser His Leu
            100                 105                 110

Ser Arg Lys Leu His Asn Phe Ile Arg Lys Pro Ser Ile Ser Gln Asp
        115                 120                 125

Val Ser Ala Val Ile Met Ala Asn Ala Ser Ser Ala Pro Pro Pro
    130                 135                 140

Gln Ala Lys Arg Arg Leu Gly Arg Thr Ser Arg Ser Ala Met Lys Pro
145                 150                 155                 160

Lys Ile Arg Arg Thr Lys Thr Arg Lys Thr Lys Thr Ser Ala Pro
                165                 170                 175

Pro Glu Pro Asn Ala Asp Val Ala Gly Ala Asp Lys Glu Ala Leu Met
            180                 185                 190

Val Glu Ser Ser Gly Ala Glu Ala Glu Leu Gly Arg Pro Cys Asp Tyr
        195                 200                 205

Tyr Gly Asp Asp Cys Asn Lys Asn Leu Met Ser Ile Asn Gly Asp Asn
    210                 215                 220

Gly Val Leu Thr Phe Asp Asp Ile Ile Asp Leu Leu Asp Glu
225                 230                 235                 240

Ser Asp Pro Gly His Leu Tyr Thr Asn Thr Thr Cys Gly Gly Gly
                245                 250                 255

Glu Leu His Asn Ile Arg Asp Ser Glu Gly Ala Arg Gly Phe Ser Asp
            260                 265                 270

Thr Trp Asn Gln Gly Asn Leu Asp Cys Leu Leu Gln Ser Cys Pro Ser
        275                 280                 285

Val Glu Ser Phe Leu Asn Tyr Asp His Gln Val Asn Asp Ala Ser Thr
    290                 295                 300
```

| | | | | | | | | | | | | | | |
|---|---|---|---|---|---|---|---|---|---|---|---|---|---|---|
| Asp | Glu | Phe | Ile | Asp | Trp | Asp | Cys | Val | Trp | Gln | Glu | Gly | Ser | Asp | Asn |
| 305 | | | | 310 | | | | | 315 | | | | | 320 | |

Asn Leu Trp His Glu Lys Glu Asn Pro Asp Ser Met Val Ser Trp Leu
                  325                  330                  335

Leu Asp Gly Asp Asp Glu Ala Thr Ile Gly Asn Ser Asn Cys Glu Asn
            340                  345                  350

Phe Gly Glu Pro Leu Asp His Asp Asp Glu Ser Ala Leu Val Ala Trp
        355                  360                  365

Leu Leu Ser
    370

<210> SEQ ID NO 59
<211> LENGTH: 1033
<212> TYPE: DNA
<213> ORGANISM: Arabidopsis thaliana
<220> FEATURE:
<221> NAME/KEY: CDS
<222> LOCATION: (113)...(862)

<400> SEQUENCE: 59

| | |
|---|---|
| gtcgacccac gcgtccgtgg gaagccacaa taaccccta ttcctcggcc tttttaaaa | 60 |
| aagtttaga ataatccgat aaaatactt tatattaatt tttctttggt cc atg gag<br>                                                                            Met Glu<br>                                                                             1 | 118 |
| ggt tcg tcc aaa ggg ttg agg aaa ggt gca tgg act gct gaa gaa gat<br>Gly Ser Ser Lys Gly Leu Arg Lys Gly Ala Trp Thr Ala Glu Glu Asp<br>       5                     10                       15 | 166 |
| agt ctc ttg agg cta tgt att gat aag tat gga gaa ggc aaa tgg cat<br>Ser Leu Leu Arg Leu Cys Ile Asp Lys Tyr Gly Glu Gly Lys Trp His<br>    20                      25                      30 | 214 |
| caa gtt cct ttg aga gct ggg cta aat cga tgc aga aag agt tgt aga<br>Gln Val Pro Leu Arg Ala Gly Leu Asn Arg Cys Arg Lys Ser Cys Arg<br>35                    40                      45                   50 | 262 |
| cta aga tgg ttg aac tat ttg aag cca agt atc aag aga gga aga ctt<br>Leu Arg Trp Leu Asn Tyr Leu Lys Pro Ser Ile Lys Arg Gly Arg Leu<br>                55                      60                      65 | 310 |
| agc aat gat gaa gtt gat ctt ctt ctt cgc ctt cat aag ctt cta gga<br>Ser Asn Asp Glu Val Asp Leu Leu Leu Arg Leu His Lys Leu Leu Gly<br>                70                      75                      80 | 358 |
| aat agg tgg tcc ttg att gct ggt cga ttg cct ggt cgg acc gct aat<br>Asn Arg Trp Ser Leu Ile Ala Gly Arg Leu Pro Gly Arg Thr Ala Asn<br>                    85                      90                      95 | 406 |
| gat gtc aaa aat tac tgg aac acc cat ctg agt aaa aaa cat gag tct<br>Asp Val Lys Asn Tyr Trp Asn Thr His Leu Ser Lys Lys His Glu Ser<br>        100                    105                     110 | 454 |
| tcg tgt tgt aag tct aaa atg aaa aag aaa aac att att tcc cct cct<br>Ser Cys Cys Lys Ser Lys Met Lys Lys Lys Asn Ile Ile Ser Pro Pro<br>115                  120                    125                 130 | 502 |
| aca aca ccg gtc caa aaa atc ggt gtt ttt aag cct cga cct cga tcc<br>Thr Thr Pro Val Gln Lys Ile Gly Val Phe Lys Pro Arg Pro Arg Ser<br>                  135                    140                    145 | 550 |
| ttc tct gtt aac aat ggt tgc agc cat ctc aat ggt ctg cca gaa gtt<br>Phe Ser Val Asn Asn Gly Cys Ser His Leu Asn Gly Leu Pro Glu Val<br>                150                    155                    160 | 598 |
| gat tta att cct tca tgc ctt gga ctc aag aaa aat aat gtt tgt gaa<br>Asp Leu Ile Pro Ser Cys Leu Gly Leu Lys Lys Asn Asn Val Cys Glu<br>        165                    170                     175 | 646 |
| aat agt atc aca tgt aac aaa gat gat gag aaa gat gat ttt gtg aat<br>Asn Ser Ile Thr Cys Asn Lys Asp Asp Glu Lys Asp Asp Phe Val Asn | 694 |

```
                180                 185                 190
aat cta atg aat gga gat aat atg tgg ttg gag aat tta ctg ggg gaa    742
Asn Leu Met Asn Gly Asp Asn Met Trp Leu Glu Asn Leu Leu Gly Glu
195                 200                 205                 210 aac caa gaa gct gat gcg att gtt cct gaa gcg acg aca gct gaa cat    790
Asn Gln Glu Ala Asp Ala Ile Val Pro Glu Ala Thr Thr Ala Glu His
                215                 220                 225 ggg gcc act ttg gcg ttt gac gtt gag caa ctt tgg agt ctg ttt gat    838
Gly Ala Thr Leu Ala Phe Asp Val Glu Gln Leu Trp Ser Leu Phe Asp
            230                 235                 240 gga gag act gtt gaa ctt gat tag tgtttctcac cgtttgttta agattgtggg   892
Gly Glu Thr Val Glu Leu Asp *
        245 tggcttttct ttcgtatttt agtaatgtat ttttctgtat gaagtaaaga atttcagcat   952 tttaagaaaa atggttatgt ttctacgtaa taaaaaaaaa cgttatttat aaaaaaaaaa  1012 aaaaaaaaaa aaaaaaaaaa a                                            1033

<210> SEQ ID NO 60
<211> LENGTH: 249
<212> TYPE: PRT
<213> ORGANISM: Arabidopsis thaliana
<220> FEATURE:
<221> NAME/KEY: DOMAIN
<222> LOCATION: (9)...(111)
<223> OTHER INFORMATION: Conserved domain

<400> SEQUENCE: 60

Met Glu Gly Ser Ser Lys Gly Leu Arg Lys Gly Ala Trp Thr Ala Glu
1               5                   10                  15

Glu Asp Ser Leu Leu Arg Leu Cys Ile Asp Lys Tyr Gly Glu Gly Lys
            20                  25                  30

Trp His Gln Val Pro Leu Arg Ala Gly Leu Asn Arg Cys Arg Lys Ser
        35                  40                  45

Cys Arg Leu Arg Trp Leu Asn Tyr Leu Lys Pro Ser Ile Lys Arg Gly
    50                  55                  60

Arg Leu Ser Asn Asp Glu Val Asp Leu Leu Arg Leu His Lys Leu
65                  70                  75                  80

Leu Gly Asn Arg Trp Ser Leu Ile Ala Gly Arg Leu Pro Gly Arg Thr
                85                  90                  95

Ala Asn Asp Val Lys Asn Tyr Trp Asn Thr His Leu Ser Lys Lys His
            100                 105                 110

Glu Ser Ser Cys Cys Lys Ser Lys Met Lys Lys Asn Ile Ile Ser
        115                 120                 125

Pro Pro Thr Thr Pro Val Gln Lys Ile Gly Val Phe Lys Pro Arg Pro
    130                 135                 140

Arg Ser Phe Ser Val Asn Asn Gly Cys Ser His Leu Asn Gly Leu Pro
145                 150                 155                 160

Glu Val Asp Leu Ile Pro Ser Cys Leu Gly Leu Lys Lys Asn Asn Val
                165                 170                 175

Cys Glu Asn Ser Ile Thr Cys Asn Lys Asp Asp Glu Lys Asp Asp Phe
            180                 185                 190

Val Asn Asn Leu Met Asn Gly Asp Asn Met Trp Leu Glu Asn Leu Leu
        195                 200                 205

Gly Glu Asn Gln Glu Ala Asp Ala Ile Val Pro Glu Ala Thr Thr Ala
    210                 215                 220

Glu His Gly Ala Thr Leu Ala Phe Asp Val Glu Gln Leu Trp Ser Leu
```

```
                    225                 230                 235                 240
Phe Asp Gly Glu Thr Val Glu Leu Asp
                    245

<210> SEQ ID NO 61
<211> LENGTH: 977
<212> TYPE: DNA
<213> ORGANISM: Arabidopsis thaliana
<220> FEATURE:
<221> NAME/KEY: CDS
<222> LOCATION: (195)...(830)

<400> SEQUENCE: 61
ataaaaaacc cttcatacaa tataaaattt ctttagacat acaatatatt atactattac      60
agatgcaatg catcattagt tacaaactat taaactaaat atccccccgtc tctctcttgc    120 tatataaaga agatcattta cacatctcct taagcaaatt aaacccatcg ataaacacat    180
acgttcacac atat atg tct ata aat ccg aca atg tct cgt act ggc gaa      230
              Met Ser Ile Asn Pro Thr Met Ser Arg Thr Gly Glu
               1               5                  10 agt tct tca ggt tcg tcc tcc gac aag acg ata aag cta ttc ggc ttc      278
Ser Ser Ser Gly Ser Ser Ser Asp Lys Thr Ile Lys Leu Phe Gly Phe
             15                  20                  25 gaa ctc atc agc ggc agt cgt acg ccg gaa atc acg acg gcg gaa agc      326
Glu Leu Ile Ser Gly Ser Arg Thr Pro Glu Ile Thr Thr Ala Glu Ser
         30                  35                  40 gtg agc tcg tcc aca aac acg acg tcg tta aca gtg atg aaa aga cac      374
Val Ser Ser Thr Asn Thr Thr Ser Leu Thr Val Met Lys Arg His
 45                  50                  55                  60 gag tgc caa tac tgc ggt aaa gag ttt gca aat tct caa gcc tta gga      422
Glu Cys Gln Tyr Cys Gly Lys Glu Phe Ala Asn Ser Gln Ala Leu Gly
                     65                  70                  75 ggt cac caa aac gct cac aag aag gag agg ttg aag aag aag agg ctt      470
Gly His Gln Asn Ala His Lys Lys Glu Arg Leu Lys Lys Lys Arg Leu
             80                  85                  90 cag ctt caa gct cgg cga gcc agc atc ggc tat tat ctc acc aac cac      518
Gln Leu Gln Ala Arg Arg Ala Ser Ile Gly Tyr Tyr Leu Thr Asn His
         95                 100                 105 caa caa ccc ata acg acg tca ttt cag aga caa tac aaa acg ccg tcg      566
Gln Gln Pro Ile Thr Thr Ser Phe Gln Arg Gln Tyr Lys Thr Pro Ser
    110                 115                 120 tat tgt gca ttc tcc tcc atg cac gtg aat aat gat cag atg ggt gtg      614
Tyr Cys Ala Phe Ser Ser Met His Val Asn Asn Asp Gln Met Gly Val
125                 130                 135                 140 tac aac gaa gat tgg tcg tcg agg tcg tcg cag att aac ttc ggt aat      662
Tyr Asn Glu Asp Trp Ser Ser Arg Ser Ser Gln Ile Asn Phe Gly Asn
                145                 150                 155 aat gac acg tgc caa gat ctt aat gaa caa agc ggt gag atg ggt aag      710
Asn Asp Thr Cys Gln Asp Leu Asn Glu Gln Ser Gly Glu Met Gly Lys
            160                 165                 170 ctg tac ggt gtt cga ccg aac atg att cag ttc cag aga gat ctg agt      758
Leu Tyr Gly Val Arg Pro Asn Met Ile Gln Phe Gln Arg Asp Leu Ser
        175                 180                 185 tct cgt tct gat cag atg aga agt att aac tcg ctg gat ctt cat cta      806
Ser Arg Ser Asp Gln Met Arg Ser Ile Asn Ser Leu Asp Leu His Leu
    190                 195                 200 ggt ttt gcc gga gat gcg gca taa caaattaaag agagatatat gattaagatt    860
Gly Phe Ala Gly Asp Ala Ala  *
205                 210 atatgtacta tagtggcgta tttcattggg atcatgaagg ggaaaaaacg agacatatag    920
```

```
tattcttgat gcaatttgag ttttgtaatt tatttaggtt tatgtatgtt ttcgaag        977
```

```
<210> SEQ ID NO 62
<211> LENGTH: 211
<212> TYPE: PRT
<213> ORGANISM: Arabidopsis thaliana
<220> FEATURE:
<221> NAME/KEY: DOMAIN
<222> LOCATION: (62)...(82)
<223> OTHER INFORMATION: Conserved domain

<400> SEQUENCE: 62
```

```
Met Ser Ile Asn Pro Thr Met Ser Arg Thr Gly Glu Ser Ser Ser Gly
1               5                   10                  15

Ser Ser Ser Asp Lys Thr Ile Lys Leu Phe Gly Phe Glu Leu Ile Ser
            20                  25                  30

Gly Ser Arg Thr Pro Glu Ile Thr Thr Ala Glu Ser Val Ser Ser Ser
        35                  40                  45

Thr Asn Thr Thr Ser Leu Thr Val Met Lys Arg His Glu Cys Gln Tyr
    50                  55                  60

Cys Gly Lys Glu Phe Ala Asn Ser Gln Ala Leu Gly Gly His Gln Asn
65                  70                  75                  80

Ala His Lys Lys Glu Arg Leu Lys Lys Lys Arg Leu Gln Leu Gln Ala
                85                  90                  95

Arg Arg Ala Ser Ile Gly Tyr Tyr Leu Thr Asn His Gln Gln Pro Ile
            100                 105                 110

Thr Thr Ser Phe Gln Arg Gln Tyr Lys Thr Pro Ser Tyr Cys Ala Phe
        115                 120                 125

Ser Ser Met His Val Asn Asn Asp Gln Met Gly Val Tyr Asn Glu Asp
    130                 135                 140

Trp Ser Arg Ser Ser Gln Ile Asn Phe Gly Asn Asn Asp Thr Cys
145                 150                 155                 160

Gln Asp Leu Asn Glu Gln Ser Gly Glu Met Gly Lys Leu Tyr Gly Val
                165                 170                 175

Arg Pro Asn Met Ile Gln Phe Gln Arg Asp Leu Ser Ser Arg Ser Asp
            180                 185                 190

Gln Met Arg Ser Ile Asn Ser Leu Asp Leu His Leu Gly Phe Ala Gly
        195                 200                 205

Asp Ala Ala
    210
```

```
<210> SEQ ID NO 63
<211> LENGTH: 1536
<212> TYPE: DNA
<213> ORGANISM: Arabidopsis thaliana
<220> FEATURE:
<221> NAME/KEY: CDS
<222> LOCATION: (42)...(1487)

<400> SEQUENCE: 63
```

```
ctctctgact tgaactcttc tcttctaccg aatcaaacca a atg gag gat cat caa    56
                                            Met Glu Asp His Gln
                                            1               5 aac cat cca cag tac ggt ata gaa caa cca tct tct caa ttc tcc tct    104
Asn His Pro Gln Tyr Gly Ile Glu Gln Pro Ser Ser Gln Phe Ser Ser
            10                  15                  20 gat ctc ttc ggc ttc aac ctc gtt tca gcg ccg gac cag cac cat cgt    152
Asp Leu Phe Gly Phe Asn Leu Val Ser Ala Pro Asp Gln His His Arg
        25                  30                  35
```

```
ctt cat ttc acc gac cat gag ata agt tta ttg cca cgt gga ata caa    200
Leu His Phe Thr Asp His Glu Ile Ser Leu Leu Pro Arg Gly Ile Gln
         40                  45                  50 ggg ctt acg gtg gct gga aac aac agt aac act att aca acg atc cag    248
Gly Leu Thr Val Ala Gly Asn Asn Ser Asn Thr Ile Thr Thr Ile Gln
 55                  60                  65 agt ggt ggc tgt gtt ggt ggg ttt agt ggc ttt acg gac ggc gga gga    296
Ser Gly Gly Cys Val Gly Gly Phe Ser Gly Phe Thr Asp Gly Gly Gly
 70                  75                  80                  85 aca ggg agg tgg ccg agg caa gag acg ttg atg ttg gag gtc aga        344
Thr Gly Arg Trp Pro Arg Gln Glu Thr Leu Met Leu Glu Val Arg
                 90                  95                 100 tct cgt ctt gat cac aag ttc aaa gaa gct aat caa aag ggt cct ctc    392
Ser Arg Leu Asp His Lys Phe Lys Glu Ala Asn Gln Lys Gly Pro Leu
                105                 110                 115 tgg gat gaa gtt tct agg att atg tcg gag gaa cat gga tac act agg    440
Trp Asp Glu Val Ser Arg Ile Met Ser Glu Glu His Gly Tyr Thr Arg
        120                 125                 130 agt ggc aag aag tgt aga gag aag ttc gag aat ctc tac aag tac tat    488
Ser Gly Lys Lys Cys Arg Glu Lys Phe Glu Asn Leu Tyr Lys Tyr Tyr
135                 140                 145 aaa aaa aca aaa gaa ggc aaa tcc ggt cgg cga caa gat ggt aaa aac    536
Lys Lys Thr Lys Glu Gly Lys Ser Gly Arg Arg Gln Asp Gly Lys Asn
150                 155                 160                 165 tat aga ttt ttc cgg cag ctt gaa gcg ata tac ggc gaa tcc aaa gac    584
Tyr Arg Phe Phe Arg Gln Leu Glu Ala Ile Tyr Gly Glu Ser Lys Asp
                170                 175                 180 tcg gtt tct tgc tat aac aac acg cag ttc ata atg acc aat gct ctt    632
Ser Val Ser Cys Tyr Asn Asn Thr Gln Phe Ile Met Thr Asn Ala Leu
            185                 190                 195 cat agt aat ttc cgc gct tct aac att cat aac atc gtc cct cat cat    680
His Ser Asn Phe Arg Ala Ser Asn Ile His Asn Ile Val Pro His His
        200                 205                 210 cag aat ccc ttg atg acc aat acc aat act caa agt caa agc ctt agc    728
Gln Asn Pro Leu Met Thr Asn Thr Asn Thr Gln Ser Gln Ser Leu Ser
    215                 220                 225 att tct aac aat ttc aac tcc tcc tcc gat ttg gat cta act tct tcc    776
Ile Ser Asn Asn Phe Asn Ser Ser Ser Asp Leu Asp Leu Thr Ser Ser
230                 235                 240                 245 tct gaa gga aac gaa act act aaa aga gag ggg atg cat tgg aag gaa    824
Ser Glu Gly Asn Glu Thr Thr Lys Arg Glu Gly Met His Trp Lys Glu
                250                 255                 260 aag atc aag gaa ttc att ggt gtt cat atg gag agg ttg ata gag aag    872
Lys Ile Lys Glu Phe Ile Gly Val His Met Glu Arg Leu Ile Glu Lys
            265                 270                 275 caa gat ttt tgg ctt gag aag ttg atg aag att gtg gaa gac aaa gaa    920
Gln Asp Phe Trp Leu Glu Lys Leu Met Lys Ile Val Glu Asp Lys Glu
        280                 285                 290 cat caa agg atg ctg aga gaa gag gaa tgg aga agg att gaa gcg gaa    968
His Gln Arg Met Leu Arg Glu Glu Glu Trp Arg Arg Ile Glu Ala Glu
    295                 300                 305 agg atc gat aag gaa cgt tcg ttt tgg aca aaa gag agg gag agg att   1016
Arg Ile Asp Lys Glu Arg Ser Phe Trp Thr Lys Glu Arg Glu Arg Ile
310                 315                 320                 325 gaa gct cgg gat gtt gcg gtg att aat gcc ttg cag tac ttg acg gga   1064
Glu Ala Arg Asp Val Ala Val Ile Asn Ala Leu Gln Tyr Leu Thr Gly
                330                 335                 340 agg gca ttg ata agg ccg gat tct tcg tct cct aca gag agg att aat   1112
Arg Ala Leu Ile Arg Pro Asp Ser Ser Ser Pro Thr Glu Arg Ile Asn
```

```
                  345                 350                 355
ggg aat gga agc gat aaa atg atg gct gat aat gaa ttt gct gat gaa    1160
Gly Asn Gly Ser Asp Lys Met Met Ala Asp Asn Glu Phe Ala Asp Glu
            360                 365                 370 gga aat aag ggc aag atg gat aaa aaa caa atg aat aag aaa agg aag    1208
Gly Asn Lys Gly Lys Met Asp Lys Lys Gln Met Asn Lys Lys Arg Lys
        375                 380                 385 gag aaa tgg tca agc cac gga ggg aat cat cca aga acc aaa gag aat    1256
Glu Lys Trp Ser Ser His Gly Gly Asn His Pro Arg Thr Lys Glu Asn
390                 395                 400                 405 atg atg ata tac aac aat caa gaa act aag att aat gat ttt tgt cga    1304
Met Met Ile Tyr Asn Asn Gln Glu Thr Lys Ile Asn Asp Phe Cys Arg
                410                 415                 420 gat gat gac caa tgc cat cat gaa ggt tac tca cct tca aac tcc aag    1352
Asp Asp Asp Gln Cys His His Glu Gly Tyr Ser Pro Ser Asn Ser Lys
            425                 430                 435 aac gca gga act ccg agc tgc agc aat gcc atg gca gct agt aca aag    1400
Asn Ala Gly Thr Pro Ser Cys Ser Asn Ala Met Ala Ala Ser Thr Lys
        440                 445                 450 tgc ttt cca ttg ctt gaa gga gaa gga gat cag aac ttg tgg gag ggt    1448
Cys Phe Pro Leu Leu Glu Gly Glu Gly Asp Gln Asn Leu Trp Glu Gly
455                 460                 465 tat ggt ttg aag caa agg aaa gaa aat aat cat cag taa gctacatttt    1497
Tyr Gly Leu Lys Gln Arg Lys Glu Asn Asn His Gln   *
470                 475                 480 tcattctcaa aatgaagaat aagagaactt agaaacgat                        1536

<210> SEQ ID NO 64
<211> LENGTH: 481
<212> TYPE: PRT
<213> ORGANISM: Arabidopsis thaliana
<220> FEATURE:
<221> NAME/KEY: DOMAIN
<222> LOCATION: (100)...(153)
<223> OTHER INFORMATION: Conserved domain

<400> SEQUENCE: 64

Met Glu Asp His Gln Asn His Pro Gln Tyr Gly Ile Glu Gln Pro Ser
 1               5                  10                  15

Ser Gln Phe Ser Ser Asp Leu Phe Gly Phe Asn Leu Val Ser Ala Pro
            20                  25                  30

Asp Gln His His Arg Leu His Phe Thr Asp His Glu Ile Ser Leu Leu
        35                  40                  45

Pro Arg Gly Ile Gln Gly Leu Thr Val Ala Gly Asn Asn Ser Asn Thr
    50                  55                  60

Ile Thr Thr Ile Gln Ser Gly Cys Val Gly Phe Ser Gly Phe
65                  70                  75                  80

Thr Asp Gly Gly Gly Thr Gly Arg Trp Pro Arg Gln Glu Thr Leu Met
                85                  90                  95

Leu Leu Glu Val Arg Ser Arg Leu Asp His Lys Phe Lys Glu Ala Asn
            100                 105                 110

Gln Lys Gly Pro Leu Trp Asp Glu Val Ser Arg Ile Met Ser Glu Glu
        115                 120                 125

His Gly Tyr Thr Arg Ser Gly Lys Lys Cys Arg Glu Lys Phe Glu Asn
    130                 135                 140

Leu Tyr Lys Tyr Tyr Lys Lys Thr Lys Glu Gly Lys Ser Gly Arg Arg
145                 150                 155                 160

Gln Asp Gly Lys Asn Tyr Arg Phe Phe Arg Gln Leu Glu Ala Ile Tyr
```

```
                165                 170                 175
Gly Glu Ser Lys Asp Ser Val Ser Cys Tyr Asn Asn Thr Gln Phe Ile
            180                 185                 190
Met Thr Asn Ala Leu His Ser Asn Phe Arg Ala Ser Asn Ile His Asn
            195                 200                 205
Ile Val Pro His His Gln Asn Pro Leu Met Thr Asn Thr Asn Thr Gln
            210                 215                 220
Ser Gln Ser Leu Ser Ile Ser Asn Asn Phe Asn Ser Ser Ser Asp Leu
225                 230                 235                 240
Asp Leu Thr Ser Ser Glu Gly Asn Glu Thr Thr Lys Arg Glu Gly
            245                 250                 255
Met His Trp Lys Glu Lys Ile Lys Glu Phe Ile Gly Val His Met Glu
            260                 265                 270
Arg Leu Ile Glu Lys Gln Asp Phe Trp Leu Glu Lys Leu Met Lys Ile
            275                 280                 285
Val Glu Asp Lys Glu His Gln Arg Met Leu Arg Glu Glu Trp Arg
            290                 295                 300
Arg Ile Glu Ala Glu Arg Ile Asp Lys Glu Arg Ser Phe Trp Thr Lys
305                 310                 315                 320
Glu Arg Glu Arg Ile Glu Ala Arg Asp Val Ala Val Ile Asn Ala Leu
            325                 330                 335
Gln Tyr Leu Thr Gly Arg Ala Leu Ile Arg Pro Asp Ser Ser Pro
            340                 345                 350
Thr Glu Arg Ile Asn Gly Asn Gly Ser Asp Lys Met Met Ala Asp Asn
            355                 360                 365
Glu Phe Ala Asp Glu Gly Asn Lys Gly Lys Met Asp Lys Lys Gln Met
            370                 375                 380
Asn Lys Lys Arg Lys Glu Lys Trp Ser Ser His Gly Asn His Pro
385                 390                 395                 400
Arg Thr Lys Glu Asn Met Met Ile Tyr Asn Asn Gln Glu Thr Lys Ile
            405                 410                 415
Asn Asp Phe Cys Arg Asp Asp Gln Cys His His Glu Gly Tyr Ser
            420                 425                 430
Pro Ser Asn Ser Lys Asn Ala Gly Thr Pro Ser Cys Ser Asn Ala Met
            435                 440                 445
Ala Ala Ser Thr Lys Cys Phe Pro Leu Leu Glu Gly Glu Gly Asp Gln
            450                 455                 460
Asn Leu Trp Glu Gly Tyr Gly Leu Lys Gln Arg Lys Glu Asn Asn His
465                 470                 475                 480
Gln

<210> SEQ ID NO 65
<211> LENGTH: 785
<212> TYPE: DNA
<213> ORGANISM: Arabidopsis thaliana
<220> FEATURE:
<221> NAME/KEY: CDS
<222> LOCATION: (38)...(472)

<400> SEQUENCE: 65
cttcttcttc acatcgatca tcatacaaca acaaaaa atg gat tac aga gaa tcc    55
                                        Met Asp Tyr Arg Glu Ser
                                         1               5 acc ggt gaa agt cag tca aag tac aaa gga atc cgt cgt cgg aaa tgg   103
Thr Gly Glu Ser Gln Ser Lys Tyr Lys Gly Ile Arg Arg Arg Lys Trp
         10                  15                  20
```

```
ggc aaa tgg gta tca gag att aga gtt ccg gga act cgt gac cgt ctc      151
Gly Lys Trp Val Ser Glu Ile Arg Val Pro Gly Thr Arg Asp Arg Leu
        25                  30                  35 tgg tta ggt tca ttc tca aca gca gaa ggt gcc gcc gta gca cac gac      199
Trp Leu Gly Ser Phe Ser Thr Ala Glu Gly Ala Ala Val Ala His Asp
40                  45                  50 gtt gct ttc ttc tgt tta cac caa cct gat tct tta gaa tct ctc aat      247
Val Ala Phe Phe Cys Leu His Gln Pro Asp Ser Leu Glu Ser Leu Asn
    55                  60                  65                  70 ttc cct cat ttg ctt aat cct tca ctc gtt tcc aga act tct ccg aga      295
Phe Pro His Leu Leu Asn Pro Ser Leu Val Ser Arg Thr Ser Pro Arg
                75                  80                  85 tct atc cag caa gct gct tct aac gcc ggc atg gcc att gac gcc gga      343
Ser Ile Gln Gln Ala Ala Ser Asn Ala Gly Met Ala Ile Asp Ala Gly
                    90                  95                 100 atc gtc cac agt acc agc gtg aac tct gga tgc gga gat acg acg acg      391
Ile Val His Ser Thr Ser Val Asn Ser Gly Cys Gly Asp Thr Thr Thr
                        105                 110                 115 tat tac gag aat gga gct gat caa gtg gag ccg ttg aat att tca gtg      439
Tyr Tyr Glu Asn Gly Ala Asp Gln Val Glu Pro Leu Asn Ile Ser Val
            120                 125                 130 tat gat tat ctg ggc ggc cac gat cac gtt tga tttatctcga cggtcatgat   492
Tyr Asp Tyr Leu Gly Gly His Asp His Val *
135                 140 cacgtttgat cttcttttga gtaagatttt gtaccataat caaaacaggt gtggtgctaa    552
aatcttactc aaaacaagat taggtaccac agagaaacaa tcaaatggtt gtgaatatac    612
attataaggt tttgattaat gtttgtttca ctgatttagt gaagtttggt ccattgtata    672
caaatctatt caagaaacct agcgcgagat catgtttcgt gattgaagat tgagattttt    732
aagtattcgt aatattttg  taaaatacaa ataaaaaaaa aaaaaaaaa aaa            785
```

<210> SEQ ID NO 66
<211> LENGTH: 144
<212> TYPE: PRT
<213> ORGANISM: Arabidopsis thaliana

<400> SEQUENCE: 66

```
Met Asp Tyr Arg Glu Ser Thr Gly Glu Ser Gln Ser Lys Tyr Lys Gly
1               5                   10                  15

Ile Arg Arg Arg Lys Trp Gly Lys Trp Val Ser Glu Ile Arg Val Pro
            20                  25                  30

Gly Thr Arg Asp Arg Leu Trp Leu Gly Ser Phe Ser Thr Ala Glu Gly
        35                  40                  45

Ala Ala Val Ala His Asp Val Ala Phe Phe Cys Leu His Gln Pro Asp
    50                  55                  60

Ser Leu Glu Ser Leu Asn Phe Pro His Leu Leu Asn Pro Ser Leu Val
65                  70                  75                  80

Ser Arg Thr Ser Pro Arg Ser Ile Gln Gln Ala Ala Ser Asn Ala Gly
                85                  90                  95

Met Ala Ile Asp Ala Gly Ile Val His Ser Thr Ser Val Asn Ser Gly
            100                 105                 110

Cys Gly Asp Thr Thr Thr Tyr Tyr Glu Asn Gly Ala Asp Gln Val Glu
        115                 120                 125

Pro Leu Asn Ile Ser Val Tyr Asp Tyr Leu Gly Gly His Asp His Val
    130                 135                 140
```

<210> SEQ ID NO 67
<211> LENGTH: 657
<212> TYPE: DNA
<213> ORGANISM: Arabidopsis thaliana
<220> FEATURE:
<221> NAME/KEY: CDS
<222> LOCATION: (1)...(657)

<400> SEQUENCE: 67

| | | | | | | | | | | | | | | | | |
|---|---|---|---|---|---|---|---|---|---|---|---|---|---|---|---|---|
| atg | aga | aaa | gta | tgt | gag | ctt | gat | ata | gag | cta | agt | gaa | gag | gaa | aga | 48 |
| Met | Arg | Lys | Val | Cys | Glu | Leu | Asp | Ile | Glu | Leu | Ser | Glu | Glu | Glu | Arg | |
| 1 | | | | 5 | | | | | 10 | | | | | 15 | | |
| gac | cta | cta | aca | act | gga | tac | aag | aat | gtc | atg | gag | gct | aag | aga | gtt | 96 |
| Asp | Leu | Leu | Thr | Thr | Gly | Tyr | Lys | Asn | Val | Met | Glu | Ala | Lys | Arg | Val | |
| | | | 20 | | | | | 25 | | | | | 30 | | | |
| tca | ttg | aga | gta | ata | tca | tcc | att | gaa | aaa | atg | gaa | gac | tcg | aaa | gga | 144 |
| Ser | Leu | Arg | Val | Ile | Ser | Ser | Ile | Glu | Lys | Met | Glu | Asp | Ser | Lys | Gly | |
| | | 35 | | | | | 40 | | | | | 45 | | | | |
| aac | gac | caa | aat | gtg | aaa | ctg | ata | aaa | gga | caa | caa | gaa | atg | gtt | aaa | 192 |
| Asn | Asp | Gln | Asn | Val | Lys | Leu | Ile | Lys | Gly | Gln | Gln | Glu | Met | Val | Lys | |
| | 50 | | | | | 55 | | | | | 60 | | | | | |
| tat | gag | ttt | ttc | aat | gtt | tgt | aat | gac | att | ttg | tct | ctc | att | gat | tct | 240 |
| Tyr | Glu | Phe | Phe | Asn | Val | Cys | Asn | Asp | Ile | Leu | Ser | Leu | Ile | Asp | Ser | |
| 65 | | | | | 70 | | | | | 75 | | | | | 80 | |
| cat | ctc | ata | cca | tca | act | act | act | aat | gtc | gaa | tca | att | gtc | ctt | ttt | 288 |
| His | Leu | Ile | Pro | Ser | Thr | Thr | Thr | Asn | Val | Glu | Ser | Ile | Val | Leu | Phe | |
| | | | | 85 | | | | | 90 | | | | | 95 | | |
| aac | aga | gtg | aaa | gga | gat | tat | ttt | cga | tat | atg | gca | gag | ttt | ggt | tct | 336 |
| Asn | Arg | Val | Lys | Gly | Asp | Tyr | Phe | Arg | Tyr | Met | Ala | Glu | Phe | Gly | Ser | |
| | | | 100 | | | | | 105 | | | | | 110 | | | |
| gat | gct | gaa | cgt | aaa | gaa | aat | gca | gat | aat | tct | cta | gat | gca | tat | aag | 384 |
| Asp | Ala | Glu | Arg | Lys | Glu | Asn | Ala | Asp | Asn | Ser | Leu | Asp | Ala | Tyr | Lys | |
| | | | 115 | | | | | 120 | | | | | 125 | | | |
| gtt | gca | atg | gaa | atg | gca | gag | aat | agt | tta | gca | ccc | acc | aat | atg | gtt | 432 |
| Val | Ala | Met | Glu | Met | Ala | Glu | Asn | Ser | Leu | Ala | Pro | Thr | Asn | Met | Val | |
| | 130 | | | | | 135 | | | | | 140 | | | | | |
| aga | ctt | gga | ttg | gct | tta | aat | ttc | tcg | ata | ttc | aat | tat | gag | atc | cat | 480 |
| Arg | Leu | Gly | Leu | Ala | Leu | Asn | Phe | Ser | Ile | Phe | Asn | Tyr | Glu | Ile | His | |
| 145 | | | | | 150 | | | | | 155 | | | | | 160 | |
| aaa | tct | att | gaa | agc | gca | tgt | aaa | ttg | gtt | aag | aaa | gct | tac | gat | gaa | 528 |
| Lys | Ser | Ile | Glu | Ser | Ala | Cys | Lys | Leu | Val | Lys | Lys | Ala | Tyr | Asp | Glu | |
| | | | | 165 | | | | | 170 | | | | | 175 | | |
| gca | atc | act | gaa | ctc | gat | ggc | ctt | gac | aag | aat | ata | tgc | gaa | gag | agc | 576 |
| Ala | Ile | Thr | Glu | Leu | Asp | Gly | Leu | Asp | Lys | Asn | Ile | Cys | Glu | Glu | Ser | |
| | | | 180 | | | | | 185 | | | | | 190 | | | |
| atg | tat | atc | ata | gag | atg | ctt | aaa | tac | aat | ctt | tct | acg | tgg | act | tca | 624 |
| Met | Tyr | Ile | Ile | Glu | Met | Leu | Lys | Tyr | Asn | Leu | Ser | Thr | Trp | Thr | Ser | |
| | | | 195 | | | | | 200 | | | | | 205 | | | |
| ggc | gat | ggt | aat | ggt | aat | aag | aca | gac | ggt | tag | | | | | | 657 |
| Gly | Asp | Gly | Asn | Gly | Asn | Lys | Thr | Asp | Gly | * | | | | | | |
| | 210 | | | | | 215 | | | | | | | | | | |

<210> SEQ ID NO 68
<211> LENGTH: 218
<212> TYPE: PRT
<213> ORGANISM: Arabidopsis thaliana
<220> FEATURE:
<221> NAME/KEY: DOMAIN
<222> LOCATION: (99)...(109)
<223> OTHER INFORMATION: Conserved domain

<400> SEQUENCE: 68

Met Arg Lys Val Cys Glu Leu Asp Ile Glu Leu Ser Glu Glu Glu Arg

```
                 1               5                  10                 15
Asp Leu Leu Thr Thr Gly Tyr Lys Asn Val Met Glu Ala Lys Arg Val
                20                  25                  30

Ser Leu Arg Val Ile Ser Ser Ile Glu Lys Met Glu Asp Ser Lys Gly
                35                  40                  45

Asn Asp Gln Asn Val Lys Leu Ile Lys Gly Gln Gln Glu Met Val Lys
                50                  55                  60

Tyr Glu Phe Phe Asn Val Cys Asn Asp Ile Leu Ser Leu Ile Asp Ser
 65                  70                  75                  80

His Leu Ile Pro Ser Thr Thr Thr Asn Val Glu Ser Ile Val Leu Phe
                    85                  90                  95

Asn Arg Val Lys Gly Asp Tyr Phe Arg Tyr Met Ala Glu Phe Gly Ser
                    100                 105                 110

Asp Ala Glu Arg Lys Glu Asn Ala Asp Asn Ser Leu Asp Ala Tyr Lys
                    115                 120                 125

Val Ala Met Glu Met Ala Glu Asn Ser Leu Ala Pro Thr Asn Met Val
                    130                 135                 140

Arg Leu Gly Leu Ala Leu Asn Phe Ser Ile Phe Asn Tyr Glu Ile His
145                 150                 155                 160

Lys Ser Ile Glu Ser Ala Cys Lys Leu Val Lys Lys Ala Tyr Asp Glu
                    165                 170                 175

Ala Ile Thr Glu Leu Asp Gly Leu Asp Lys Asn Ile Cys Glu Ser
                    180                 185                 190

Met Tyr Ile Ile Glu Met Leu Lys Tyr Asn Leu Ser Thr Trp Thr Ser
                    195                 200                 205

Gly Asp Gly Asn Gly Asn Lys Thr Asp Gly
    210                 215
```

<210> SEQ ID NO 69
<211> LENGTH: 859
<212> TYPE: DNA
<213> ORGANISM: Arabidopsis thaliana
<220> FEATURE:
<221> NAME/KEY: CDS
<222> LOCATION: (62)...(718)

<400> SEQUENCE: 69

```
caatccacta acgatcccta accgaaaaca gagtagtcaa gaaacagagt attttttcta       60 c atg gat cca ttt tta att cag tcc cca ttc tcc ggc ttc tca ccg gaa     109
  Met Asp Pro Phe Leu Ile Gln Ser Pro Phe Ser Gly Phe Ser Pro Glu
   1               5                   10                  15 tat tct atc gga tct tct cca gat tct ttc tca tcc tct tct tct aac     157
Tyr Ser Ile Gly Ser Ser Pro Asp Ser Phe Ser Ser Ser Ser Ser Asn
                20                  25                  30 aat tac tct ctt ccc ttc aac gag aac gac tca gag gaa atg ttt ctc     205
Asn Tyr Ser Leu Pro Phe Asn Glu Asn Asp Ser Glu Glu Met Phe Leu
                35                  40                  45 tac ggt cta atc gag cag tcc acg caa caa acc tat att gac tcg gat     253
Tyr Gly Leu Ile Glu Gln Ser Thr Gln Gln Thr Tyr Ile Asp Ser Asp
        50                  55                  60 agt caa gac ctt ccg atc aaa tcc gta agc tca aga aag tca gag aag     301
Ser Gln Asp Leu Pro Ile Lys Ser Val Ser Ser Arg Lys Ser Glu Lys
 65                  70                  75                  80 tct tac aga ggc gta aga cga cgg cca tgg ggg aaa ttc gcg gcg gag     349
Ser Tyr Arg Gly Val Arg Arg Arg Pro Trp Gly Lys Phe Ala Ala Glu
                85                  90                  95 ata aga gat tcg act aga aac ggt att agg gtt tgg ctc ggg acg ttc     397
Ile Arg Asp Ser Thr Arg Asn Gly Ile Arg Val Trp Leu Gly Thr Phe
```

```
Ile Arg Asp Ser Thr Arg Asn Gly Ile Arg Val Trp Leu Gly Thr Phe
            100                 105                 110 gaa agc gcg gaa gag gcg gct tta gcc tac gat caa gct gct ttc tcg      445
Glu Ser Ala Glu Glu Ala Ala Leu Ala Tyr Asp Gln Ala Ala Phe Ser
        115                 120                 125 atg aga ggg tcc tcg gcg att ctc aat ttt tcg gcg gag aga gtt caa      493
Met Arg Gly Ser Ser Ala Ile Leu Asn Phe Ser Ala Glu Arg Val Gln
    130                 135                 140 gag tcg ctt tcg gag att aaa tat acc tac gag gat ggt tgt tct ccg      541
Glu Ser Leu Ser Glu Ile Lys Tyr Thr Tyr Glu Asp Gly Cys Ser Pro
145                 150                 155                 160 gtt gtg gcg ttg aag agg aaa cac tcg atg aga cgg aga atg acc aat      589
Val Val Ala Leu Lys Arg Lys His Ser Met Arg Arg Arg Met Thr Asn
                165                 170                 175 aag aag acg aaa gat agt gac ttt gat cac cgc tcc gtg aag tta gat      637
Lys Lys Thr Lys Asp Ser Asp Phe Asp His Arg Ser Val Lys Leu Asp
            180                 185                 190 aat gta gtt gtc ttt gag gat ttg gga gaa cag tac ctt gag gag ctt      685
Asn Val Val Val Phe Glu Asp Leu Gly Glu Gln Tyr Leu Glu Glu Leu
        195                 200                 205 ttg ggg tct tct gaa aat agt ggg act tgg tga aagattagga tttgtattag   738
Leu Gly Ser Ser Glu Asn Ser Gly Thr Trp *
    210                 215 ggaccttaag tttgaagtgg ttgattaatt ttaaccctaa tatgttttt gtttgcttaa     798 atatttgatt ctattgagaa acatcgaaaa cagtttgtat gtacttttgt gatacttggc    858
g                                                                     859
```

<210> SEQ ID NO 70
<211> LENGTH: 218
<212> TYPE: PRT
<213> ORGANISM: Arabidopsis thaliana
<220> FEATURE:
<221> NAME/KEY: DOMAIN
<222> LOCATION: (79)...(147)
<223> OTHER INFORMATION: Conserved domain

<400> SEQUENCE: 70

```
Met Asp Pro Phe Leu Ile Gln Ser Pro Phe Gly Phe Ser Pro Glu
  1               5                  10                  15

Tyr Ser Ile Gly Ser Ser Pro Asp Ser Phe Ser Ser Ser Ser Asn
                20                  25                  30

Asn Tyr Ser Leu Pro Phe Asn Glu Asn Asp Ser Glu Glu Met Phe Leu
            35                  40                  45

Tyr Gly Leu Ile Glu Gln Ser Thr Gln Gln Thr Tyr Ile Asp Ser Asp
    50                  55                  60

Ser Gln Asp Leu Pro Ile Lys Ser Val Ser Ser Arg Lys Ser Glu Lys
65                  70                  75                  80

Ser Tyr Arg Gly Val Arg Arg Arg Pro Trp Gly Lys Phe Ala Ala Glu
                85                  90                  95

Ile Arg Asp Ser Thr Arg Asn Gly Ile Arg Val Trp Leu Gly Thr Phe
            100                 105                 110

Glu Ser Ala Glu Glu Ala Ala Leu Ala Tyr Asp Gln Ala Ala Phe Ser
        115                 120                 125

Met Arg Gly Ser Ser Ala Ile Leu Asn Phe Ser Ala Glu Arg Val Gln
    130                 135                 140

Glu Ser Leu Ser Glu Ile Lys Tyr Thr Tyr Glu Asp Gly Cys Ser Pro
145                 150                 155                 160
```

```
Val Val Ala Leu Lys Arg Lys His Ser Met Arg Arg Met Thr Asn
            165                 170                 175

Lys Lys Thr Lys Asp Ser Asp Phe Asp His Arg Ser Val Lys Leu Asp
        180                 185                 190

Asn Val Val Val Phe Glu Asp Leu Gly Glu Gln Tyr Leu Glu Glu Leu
            195                 200                 205

Leu Gly Ser Ser Glu Asn Ser Gly Thr Trp
    210                 215

<210> SEQ ID NO 71
<211> LENGTH: 1630
<212> TYPE: DNA
<213> ORGANISM: Arabidopsis thaliana
<220> FEATURE:
<221> NAME/KEY: CDS
<222> LOCATION: (97)...(1398)

<400> SEQUENCE: 71
```

| | | |
|---|---|---|
| aatggatttg tcatcattct tctcaccgtc cttagtctct gaaaataaat tctgattttg | | 60 |
| atttcgaatt ttagggatttt tgagagagag tcagtt atg agt agt tcg gag aga<br>                                                                               Met Ser Ser Ser Glu Arg<br>                                                                               1                    5 | | 114 |
| gta ccg tgc gat ttc tgc ggc gag cgt acg gcg gtt ttg ttt tgt aga<br>Val Pro Cys Asp Phe Cys Gly Glu Arg Thr Ala Val Leu Phe Cys Arg<br>            10                    15                    20 | | 162 |
| gcc gat acg gcg aag ctg tgt ttg cct tgt gat cag caa gtt cac acg<br>Ala Asp Thr Ala Lys Leu Cys Leu Pro Cys Asp Gln Gln Val His Thr<br>       25                    30                    35 | | 210 |
| gcg aat ctg ttg tcg agg aag cac gtg cga tct cag atc tgc gat aat<br>Ala Asn Leu Leu Ser Arg Lys His Val Arg Ser Gln Ile Cys Asp Asn<br>40                        45                    50 | | 258 |
| tgc ggt aac gag cca gtc tct gtt cgg tgt ttc acc gat aat ctg att<br>Cys Gly Asn Glu Pro Val Ser Val Arg Cys Phe Thr Asp Asn Leu Ile<br>55                        60                    65                    70 | | 306 |
| ttg tgt cag gag tgt gat tgg gat gtt cac gga agt tgt tca gtt tcc<br>Leu Cys Gln Glu Cys Asp Trp Asp Val His Gly Ser Cys Ser Val Ser<br>               75                    80                    85 | | 354 |
| gat gct cat gtt cga tcc gcc gtg gaa ggt ttt tcc ggt tgt cca tcg<br>Asp Ala His Val Arg Ser Ala Val Glu Gly Phe Ser Gly Cys Pro Ser<br>          90                    95                    100 | | 402 |
| gcg ttg gag ctt gct gct tta tgg gga ctt gat ttg gag caa ggg agg<br>Ala Leu Glu Leu Ala Ala Leu Trp Gly Leu Asp Leu Glu Gln Gly Arg<br>       105                    110                    115 | | 450 |
| aaa gat gaa gag aat caa gtt ccg atg atg gcg atg atg gat aat<br>Lys Asp Glu Glu Asn Gln Val Pro Met Met Ala Met Met Met Asp Asn<br>120                        125                    130 | | 498 |
| ttc ggg atg cag ttg gat tct tgg gtt ttg gga tct aat gaa ttg att<br>Phe Gly Met Gln Leu Asp Ser Trp Val Leu Gly Ser Asn Glu Leu Ile<br>135                      140                    145                    150 | | 546 |
| gtt ccc agc gat acg acg ttt aag aag cgt gga tct tgt gga tct agt<br>Val Pro Ser Asp Thr Thr Phe Lys Lys Arg Gly Ser Cys Gly Ser Ser<br>               155                    160                    165 | | 594 |
| tgt ggg agg tat aag cag gta ttg tgt aag cag ctt gag gag ttg ctt<br>Cys Gly Arg Tyr Lys Gln Val Leu Cys Lys Gln Leu Glu Glu Leu Leu<br>          170                    175                    180 | | 642 |
| aag agt ggt gtt gtc ggt ggt gat ggc gat gat ggt gat cgt gac cgt<br>Lys Ser Gly Val Val Gly Gly Asp Gly Asp Asp Gly Asp Arg Asp Arg<br>              185                    190                    195 | | 690 |
| gat tgt gac cgt gag ggt gct tgt gat gga gat gga gat gga gaa gca<br>Asp Cys Asp Arg Glu Gly Ala Cys Asp Gly Asp Gly Asp Gly Glu Ala | | 738 |

-continued

| | | |
|---|---|---|
| gga gag ggg ctt atg gtt ccg gag atg tca gag aga ttg aaa tgg tca<br>Gly Glu Gly Leu Met Val Pro Glu Met Ser Glu Arg Leu Lys Trp Ser<br>215                  220                  225                230 | 786 |
| aga gat gtt gag gag atc aat ggt ggc gga gga gga gtt aac cag<br>Arg Asp Val Glu Glu Ile Asn Gly Gly Gly Gly Gly Val Asn Gln<br>                235                  240                  245 | 834 |
| cag tgg aat gct act act act aat cct agt ggt ggc cag agt tct cag<br>Gln Trp Asn Ala Thr Thr Thr Asn Pro Ser Gly Gly Gln Ser Ser Gln<br>              250                  255                  260 | 882 |
| ata tgg gat ttt aac ttg gga cag tca cgg gga cct gag gat acg agt<br>Ile Trp Asp Phe Asn Leu Gly Gln Ser Arg Gly Pro Glu Asp Thr Ser<br>265                  270                  275 | 930 |
| cga gtg gaa gct gca tat gta ggg aaa ggt gct gct tct tca ttc aca<br>Arg Val Glu Ala Ala Tyr Val Gly Lys Gly Ala Ala Ser Ser Phe Thr<br>        280                  285                  290 | 978 |
| atc aac aat ttt gtt gac cat atg aat gaa act tgt tcc act aat gtg<br>Ile Asn Asn Phe Val Asp His Met Asn Glu Thr Cys Ser Thr Asn Val<br>295                  300                  305                310 | 1026 |
| aaa ggt gtc aaa gag att aaa aag gat gac tac aag cga tca act tca<br>Lys Gly Val Lys Glu Ile Lys Lys Asp Asp Tyr Lys Arg Ser Thr Ser<br>                315                  320                  325 | 1074 |
| ggc cag gta caa cca aca aaa tct gag agc aac aat cgt cca att acc<br>Gly Gln Val Gln Pro Thr Lys Ser Glu Ser Asn Asn Arg Pro Ile Thr<br>        330                  335                  340 | 1122 |
| ttt ggc tct gag aaa ggt tcg aac tcc tcc agt gac ttg cat ttc aca<br>Phe Gly Ser Glu Lys Gly Ser Asn Ser Ser Ser Asp Leu His Phe Thr<br>345                  350                  355 | 1170 |
| gag cat att gct gga act agt tgt aag acc aca aga cta gtt gca act<br>Glu His Ile Ala Gly Thr Ser Cys Lys Thr Thr Arg Leu Val Ala Thr<br>        360                  365                  370 | 1218 |
| aag gct gat ctg gag cgg ctg gct cag aac aga gga gat gca atg cag<br>Lys Ala Asp Leu Glu Arg Leu Ala Gln Asn Arg Gly Asp Ala Met Gln<br>375                  380                  385                390 | 1266 |
| cgt tac aag gaa aag agg aag aca cgg aga tat gat aag acc ata agg<br>Arg Tyr Lys Glu Lys Arg Lys Thr Arg Arg Tyr Asp Lys Thr Ile Arg<br>                395                  400                  405 | 1314 |
| tat gaa tcg agg aag gca aga gct gac act agg ttg cgt gtc aga ggc<br>Tyr Glu Ser Arg Lys Ala Arg Ala Asp Thr Arg Leu Arg Val Arg Gly<br>        410                  415                  420 | 1362 |
| aga ttt gtg aaa gct agt gaa gct cct tac cct taa ccttaagttt<br>Arg Phe Val Lys Ala Ser Glu Ala Pro Tyr Pro *<br>425                  430 | 1408 |
| tttcacatag gcttcctttt agctacaaac ttagttactt ttttttactcc actgcctcat | 1468 |
| aaatgtacag accggtctcg tttcatctgg ccgcccttct tgtttttattg ccttatctgg | 1528 |
| ccctttatg taccttggaa tcttatctag tttaaaaaag attgtaacct tctagaaaac | 1588 |
| catattctgt tgacagtata tacatgtcta tccaagcaaa aa | 1630 |

<210> SEQ ID NO 72
<211> LENGTH: 433
<212> TYPE: PRT
<213> ORGANISM: Arabidopsis thaliana
<220> FEATURE:
<221> NAME/KEY: DOMAIN
<222> LOCATION: (9)...(75)
<223> OTHER INFORMATION: Conserved domain

<400> SEQUENCE: 72

Met Ser Ser Ser Glu Arg Val Pro Cys Asp Phe Cys Gly Glu Arg Thr

```
  1               5                   10                  15
Ala Val Leu Phe Cys Arg Ala Asp Thr Ala Lys Leu Cys Leu Pro Cys
                20                  25                  30

Asp Gln Gln Val His Thr Ala Asn Leu Leu Ser Arg Lys His Val Arg
                35                  40                  45

Ser Gln Ile Cys Asp Asn Cys Gly Asn Glu Pro Val Ser Val Arg Cys
                50                  55                  60

Phe Thr Asp Asn Leu Ile Leu Cys Gln Glu Cys Asp Trp Asp Val His
 65                 70                  75                  80

Gly Ser Cys Ser Val Ser Asp Ala His Val Arg Ser Ala Val Glu Gly
                85                  90                  95

Phe Ser Gly Cys Pro Ser Ala Leu Glu Leu Ala Ala Leu Trp Gly Leu
               100                 105                 110

Asp Leu Glu Gln Gly Arg Lys Asp Glu Glu Asn Gln Val Pro Met Met
               115                 120                 125

Ala Met Met Met Asp Asn Phe Gly Met Gln Leu Asp Ser Trp Val Leu
               130                 135                 140

Gly Ser Asn Glu Leu Ile Val Pro Ser Asp Thr Thr Phe Lys Lys Arg
145                 150                 155                 160

Gly Ser Cys Gly Ser Ser Cys Gly Arg Tyr Lys Gln Val Leu Cys Lys
               165                 170                 175

Gln Leu Glu Glu Leu Leu Lys Ser Gly Val Val Gly Gly Asp Gly Asp
               180                 185                 190

Asp Gly Asp Arg Asp Arg Asp Cys Asp Arg Glu Gly Ala Cys Asp Gly
               195                 200                 205

Asp Gly Asp Gly Glu Ala Gly Glu Gly Leu Met Val Pro Glu Met Ser
               210                 215                 220

Glu Arg Leu Lys Trp Ser Arg Asp Val Glu Glu Ile Asn Gly Gly Gly
225                 230                 235                 240

Gly Gly Gly Val Asn Gln Gln Trp Asn Ala Thr Thr Asn Pro Ser
               245                 250                 255

Gly Gly Gln Ser Ser Gln Ile Trp Asp Phe Asn Leu Gly Gln Ser Arg
               260                 265                 270

Gly Pro Glu Asp Thr Ser Arg Val Glu Ala Ala Tyr Val Gly Lys Gly
               275                 280                 285

Ala Ala Ser Ser Phe Thr Ile Asn Asn Phe Val Asp His Met Asn Glu
               290                 295                 300

Thr Cys Ser Thr Asn Val Lys Gly Val Lys Glu Ile Lys Lys Asp Asp
305                 310                 315                 320

Tyr Lys Arg Ser Thr Ser Gly Gln Val Gln Pro Thr Lys Ser Glu Ser
               325                 330                 335

Asn Asn Arg Pro Ile Thr Phe Gly Ser Glu Lys Gly Ser Asn Ser Ser
               340                 345                 350

Ser Asp Leu His Phe Thr Glu His Ile Ala Gly Thr Ser Cys Lys Thr
               355                 360                 365

Thr Arg Leu Val Ala Thr Lys Ala Asp Leu Glu Arg Leu Ala Gln Asn
               370                 375                 380

Arg Gly Asp Ala Met Gln Arg Tyr Lys Glu Lys Arg Lys Thr Arg Arg
385                 390                 395                 400

Tyr Asp Lys Thr Ile Arg Tyr Glu Ser Arg Lys Ala Arg Ala Asp Thr
               405                 410                 415

Arg Leu Arg Val Arg Gly Arg Phe Val Lys Ala Ser Glu Ala Pro Tyr
               420                 425                 430
```

Pro

<210> SEQ ID NO 73
<211> LENGTH: 1674
<212> TYPE: DNA
<213> ORGANISM: Arabidopsis thaliana
<220> FEATURE:
<221> NAME/KEY: CDS
<222> LOCATION: (261)...(1475)

<400> SEQUENCE: 73

```
aggtcgaatt ttctgaaatt aagattcatt cctccatgga agaagctctg tttttattct      60
ctttagctta gcttagcttc tactgatctg ttttttgctac aaaatcccat cttttttcttt    120 aaaactcttt atctctgaat cttgagtttc ttgtagaaga agaagcaatt ttgaatcttt     180
cgtaatcata aagattcgtg gaggatctct actgatttgt cggaatctct cactacagaa     240
tcacttgatc ttatgtccgg atg gag gag aga gaa gga acc aac atc aac aac    293
                      Met Glu Glu Arg Glu Gly Thr Asn Ile Asn Asn
                        1               5                  10 aac atc act agc agt ttc ggc ttg aag cag caa cat gaa gct gct gct      341
Asn Ile Thr Ser Ser Phe Gly Leu Lys Gln Gln His Glu Ala Ala Ala
            15                  20                  25 tct gat ggt ggt tac tca atg gac cca cca cca aga ccc gaa aac cct     389
Ser Asp Gly Gly Tyr Ser Met Asp Pro Pro Pro Arg Pro Glu Asn Pro
        30                  35                  40 aac ccg ttt tta gtc cca ccc act act gtc ccc gcg gcc gcc acc gta     437
Asn Pro Phe Leu Val Pro Pro Thr Thr Val Pro Ala Ala Ala Thr Val
    45                  50                  55 gca gca gct gtt act gag aat gcg gct act ccg ttt agc tta aca atg    485
Ala Ala Ala Val Thr Glu Asn Ala Ala Thr Pro Phe Ser Leu Thr Met
 60                  65                  70                  75 ccg acg gag aac act tca gct gag cag ctg aaa aag aag aga ggt agg    533
Pro Thr Glu Asn Thr Ser Ala Glu Gln Leu Lys Lys Lys Arg Gly Arg
                80                  85                  90 ccg aga aag tat aat ccc gat ggg act ctt gtc gtg act tta tcg ccg    581
Pro Arg Lys Tyr Asn Pro Asp Gly Thr Leu Val Val Thr Leu Ser Pro
            95                 100                 105 atg cca atc tcg tcc tct gtt ccg ttg acg tcg gag ttt cct cca agg    629
Met Pro Ile Ser Ser Ser Val Pro Leu Thr Ser Glu Phe Pro Pro Arg
        110                 115                 120 aaa cga gga aga gga cgt ggc aag tct aat cga tgg ctc aag aag tct    677
Lys Arg Gly Arg Gly Arg Gly Lys Ser Asn Arg Trp Leu Lys Lys Ser
    125                 130                 135 caa atg ttc caa ttc gat aga agt cct gtt gat acc aat ttg gca ggt    725
Gln Met Phe Gln Phe Asp Arg Ser Pro Val Asp Thr Asn Leu Ala Gly
140                 145                 150                 155 gta gga act gct gat ttt gtt ggt gcc aac ttt aca cct cat gta ctg    773
Val Gly Thr Ala Asp Phe Val Gly Ala Asn Phe Thr Pro His Val Leu
                160                 165                 170 atc gtc aac gcc gga gag gat gtg acg atg aag ata atg aca ttc tct    821
Ile Val Asn Ala Gly Glu Asp Val Thr Met Lys Ile Met Thr Phe Ser
            175                 180                 185 caa caa gga tct cgt gct atc tgc atc ctt tca gct aat ggt ccc atc    869
Gln Gln Gly Ser Arg Ala Ile Cys Ile Leu Ser Ala Asn Gly Pro Ile
        190                 195                 200 tcc aat gtt acg ctt cgt caa tct atg aca tcc ggt ggt act cta act    917
Ser Asn Val Thr Leu Arg Gln Ser Met Thr Ser Gly Gly Thr Leu Thr
    205                 210                 215 tat gag ggt cgt ttt gag att ctc tct ttg acg ggt tcg ttt atg caa    965
```

```
                Tyr Glu Gly Arg Phe Glu Ile Leu Ser Leu Thr Gly Ser Phe Met Gln
                220                 225                 230                 235 aat gac tct gga gga act cga agt aga gct ggt ggt atg agt gtt tgc           1013
Asn Asp Ser Gly Gly Thr Arg Ser Arg Ala Gly Gly Met Ser Val Cys
                240                 245                 250 ctt gca gga cca gat ggt cgt gtc ttt ggt gga ctc gct ggt ctc               1061
Leu Ala Gly Pro Asp Gly Arg Val Phe Gly Gly Leu Ala Gly Leu
                255                 260                 265 ttt ctt gct gct ggt cct gtc cag gta atg gta ggg act ttt ata gct           1109
Phe Leu Ala Ala Gly Pro Val Gln Val Met Val Gly Thr Phe Ile Ala
                270                 275                 280 ggt caa gag cag tca cag ctg gag cta gca aaa gaa cgg cta aga               1157
Gly Gln Glu Gln Ser Gln Leu Glu Leu Ala Lys Glu Arg Arg Leu Arg
285                 290                 295 ttt ggg gct caa cca tct tct atc tcc ttt aac ata tcc gca gaa gaa           1205
Phe Gly Ala Gln Pro Ser Ser Ile Ser Phe Asn Ile Ser Ala Glu Glu
300                 305                 310                 315 cgg aag gcg aga ttc gag agg ctt aac aag tct gtt gct att cct gca           1253
Arg Lys Ala Arg Phe Glu Arg Leu Asn Lys Ser Val Ala Ile Pro Ala
                320                 325                 330 cca acc act tca tac acg cat gta aac aca aca aat gcg gtt cac agt           1301
Pro Thr Thr Ser Tyr Thr His Val Asn Thr Thr Asn Ala Val His Ser
                335                 340                 345 tac tat aca aac tcg gtt aac cat gtc aag gat ccc ttc tcg tct atc           1349
Tyr Tyr Thr Asn Ser Val Asn His Val Lys Asp Pro Phe Ser Ser Ile
                350                 355                 360 cca gta gga gga gga gga ggt gga gag gta gga gaa gaa gag ggt gaa           1397
Pro Val Gly Gly Gly Gly Gly Glu Val Gly Glu Glu Glu Gly Glu
365                 370                 375 gaa gat gat gat gaa tta gaa ggt gaa gac gaa gaa ttc gga ggc gat           1445
Glu Asp Asp Asp Glu Leu Glu Gly Glu Asp Glu Glu Phe Gly Gly Asp
380                 385                 390                 395 agc caa tct gac aac gag att ccg agc tga tgatgatcat acgtttctt              1495
Ser Gln Ser Asp Asn Glu Ile Pro Ser *
                400 ttcgcggatt tgttaggttt gatggatttc agattttggt tgattgtttt tattaacaca         1555 gaatgtttag aagctgctat ctttaggttc ccatcctctt gtgattgttg agtatccttg         1615 ttagaaacaa acttactgtt gcaaaactct cttcaaaaaa gtttcacttt gctttccca          1674

<210> SEQ ID NO 74
<211> LENGTH: 404
<212> TYPE: PRT
<213> ORGANISM: Arabidopsis thaliana
<220> FEATURE:
<221> NAME/KEY: DOMAIN
<222> LOCATION: (86)...(93)
<223> OTHER INFORMATION: Conserved domain

<400> SEQUENCE: 74

Met Glu Glu Arg Glu Gly Thr Asn Ile Asn Asn Asn Ile Thr Ser Ser
1               5                   10                  15

Phe Gly Leu Lys Gln Gln His Glu Ala Ala Ala Ser Asp Gly Gly Tyr
                20                  25                  30

Ser Met Asp Pro Pro Arg Pro Glu Asn Pro Asn Pro Phe Leu Val
                35                  40                  45

Pro Pro Thr Thr Val Pro Ala Ala Ala Thr Val Ala Ala Val Thr
        50                  55                  60

Glu Asn Ala Ala Thr Pro Phe Ser Leu Thr Met Pro Thr Glu Asn Thr
65                  70                  75                  80
```

Ser Ala Glu Gln Leu Lys Lys Lys Arg Gly Arg Pro Arg Lys Tyr Asn
                85                  90                  95

Pro Asp Gly Thr Leu Val Val Thr Leu Ser Pro Met Pro Ile Ser Ser
            100                 105                 110

Ser Val Pro Leu Thr Ser Glu Phe Pro Pro Arg Lys Arg Gly Arg Gly
        115                 120                 125

Arg Gly Lys Ser Asn Arg Trp Leu Lys Lys Ser Gln Met Phe Gln Phe
    130                 135                 140

Asp Arg Ser Pro Val Asp Thr Asn Leu Ala Gly Val Gly Thr Ala Asp
145                 150                 155                 160

Phe Val Gly Ala Asn Phe Thr Pro His Val Leu Ile Val Asn Ala Gly
                165                 170                 175

Glu Asp Val Thr Met Lys Ile Met Thr Phe Ser Gln Gln Gly Ser Arg
            180                 185                 190

Ala Ile Cys Ile Leu Ser Ala Asn Gly Pro Ile Ser Asn Val Thr Leu
        195                 200                 205

Arg Gln Ser Met Thr Ser Gly Gly Thr Leu Thr Tyr Glu Gly Arg Phe
    210                 215                 220

Glu Ile Leu Ser Leu Thr Gly Ser Phe Met Gln Asn Asp Ser Gly Gly
225                 230                 235                 240

Thr Arg Ser Arg Ala Gly Gly Met Ser Val Cys Leu Ala Gly Pro Asp
                245                 250                 255

Gly Arg Val Phe Gly Gly Gly Leu Ala Gly Leu Phe Leu Ala Ala Gly
            260                 265                 270

Pro Val Gln Val Met Val Gly Thr Phe Ile Ala Gly Gln Glu Gln Ser
        275                 280                 285

Gln Leu Glu Leu Ala Lys Glu Arg Arg Leu Arg Phe Gly Ala Gln Pro
    290                 295                 300

Ser Ser Ile Ser Phe Asn Ile Ser Ala Glu Glu Arg Lys Ala Arg Phe
305                 310                 315                 320

Glu Arg Leu Asn Lys Ser Val Ala Ile Pro Ala Pro Thr Thr Ser Tyr
                325                 330                 335

Thr His Val Asn Thr Thr Asn Ala Val His Ser Tyr Tyr Thr Asn Ser
            340                 345                 350

Val Asn His Val Lys Asp Pro Phe Ser Ser Ile Pro Val Gly Gly Gly
        355                 360                 365

Gly Gly Gly Glu Val Gly Glu Glu Gly Glu Asp Asp Asp Glu
    370                 375                 380

Leu Glu Gly Glu Asp Glu Glu Phe Gly Gly Asp Ser Gln Ser Asp Asn
385                 390                 395                 400

Glu Ile Pro Ser

<210> SEQ ID NO 75
<211> LENGTH: 1236
<212> TYPE: DNA
<213> ORGANISM: Arabidopsis thaliana
<220> FEATURE:
<221> NAME/KEY: CDS
<222> LOCATION: (163)...(1125)

<400> SEQUENCE: 75
tatccttcgc aagacccttc ctctatataa ggaagttcat ttcatttgga gaggacacgc      60
tgacaagctg actctagctt atctggtacc gtcgacctca ttcttgcgtt tgatctttct     120
ttctctagat cccatatttt tcttgatcaa tttagtttca tt atg gag gaa gat       174

-continued

```
                                    Met Glu Glu Asp
                                     1
gca gct ttt gat cta ctc aaa gcc gaa ctc tta aac gca gaa gac gat      222
Ala Ala Phe Asp Leu Leu Lys Ala Glu Leu Leu Asn Ala Glu Asp Asp
 5              10                  15                  20 gca ata atc tca cgt tat ctg aag cgt atg gtc gtc aac gga gac tca      270
Ala Ile Ile Ser Arg Tyr Leu Lys Arg Met Val Val Asn Gly Asp Ser
             25                  30                  35 tgg cct gat cac ttc atc gaa gac gca gac gtg ttc aac aag aat cca      318
Trp Pro Asp His Phe Ile Glu Asp Ala Asp Val Phe Asn Lys Asn Pro
         40                  45                  50 aat gtg gag ttc gat gct gag agc cct agc ttc gta ata gtt aaa cct      366
Asn Val Glu Phe Asp Ala Glu Ser Pro Ser Phe Val Ile Val Lys Pro
     55                  60                  65 cga aca gag gct tgt ggt aaa acc gat gga tgt gaa act ggt tgc tgg      414
Arg Thr Glu Ala Cys Gly Lys Thr Asp Gly Cys Glu Thr Gly Cys Trp
 70                  75                  80 agg atc atg ggt cgt gat aaa ccg ata aaa tcg acg gag act gtg aag      462
Arg Ile Met Gly Arg Asp Lys Pro Ile Lys Ser Thr Glu Thr Val Lys
 85              90                  95                  100 att caa ggg ttc aag aag att ctc aag ttc tgc cta aag agg aaa cct      510
Ile Gln Gly Phe Lys Lys Ile Leu Lys Phe Cys Leu Lys Arg Lys Pro
             105                 110                 115 aga gga tac aag aga agt tgg gta atg gaa gag tat agg ctt acc aat      558
Arg Gly Tyr Lys Arg Ser Trp Val Met Glu Glu Tyr Arg Leu Thr Asn
         120                 125                 130 aac ttg aac tgg aag caa gat cat gtg att tgc aag att cgg ttt atg      606
Asn Leu Asn Trp Lys Gln Asp His Val Ile Cys Lys Ile Arg Phe Met
     135                 140                 145 ttt gaa gct gaa atc agt ttc ttg cta gcc aag cat ttc tac act aca      654
Phe Glu Ala Glu Ile Ser Phe Leu Leu Ala Lys His Phe Tyr Thr Thr
 150                 155                 160 tca gaa tca ctt cct cga aat gag ctg ttg cca gct tac gga ttc ctt      702
Ser Glu Ser Leu Pro Arg Asn Glu Leu Leu Pro Ala Tyr Gly Phe Leu
165                 170                 175                 180 tca tca gat aag caa ttg gag gat gta tct tat ccg gtg acg ata atg      750
Ser Ser Asp Lys Gln Leu Glu Asp Val Ser Tyr Pro Val Thr Ile Met
             185                 190                 195 act tct gaa gga aac gat tgg cct agc tac gtt acc aac aat gtg tat      798
Thr Ser Glu Gly Asn Asp Trp Pro Ser Tyr Val Thr Asn Asn Val Tyr
         200                 205                 210 tgt ctg cat cca ttg gag ctc gtt gat ctt caa gat cgg atg ttt aat      846
Cys Leu His Pro Leu Glu Leu Val Asp Leu Gln Asp Arg Met Phe Asn
     215                 220                 225 gat tac gga acc tgc atc ttc gct aac aag act tgt ggt aaa acc gat      894
Asp Tyr Gly Thr Cys Ile Phe Ala Asn Lys Thr Cys Gly Lys Thr Asp
 230                 235                 240 aga tgc att aat ggt ggt tac tgg aaa att ttg cac cgt gat agg ctg      942
Arg Cys Ile Asn Gly Gly Tyr Trp Lys Ile Leu His Arg Asp Arg Leu
245                 250                 255                 260 atc aag tca aag tcc ggg ata gtt att ggt ttc aag aag gtg ttt aag      990
Ile Lys Ser Lys Ser Gly Ile Val Ile Gly Phe Lys Lys Val Phe Lys
             265                 270                 275 ttt cat gaa acg gag aaa gaa aga tac ttc tgt ggt gga gaa gat gtg     1038
Phe His Glu Thr Glu Lys Glu Arg Tyr Phe Cys Gly Gly Glu Asp Val
         280                 285                 290 aag gta act tgg act cta gaa gag tat agg ctt agc gtg aag cag aat     1086
Lys Val Thr Trp Thr Leu Glu Glu Tyr Arg Leu Ser Val Lys Gln Asn
     295                 300                 305
```

```
aaa ttc ttg tgc gtt atc aag ttt act tat gat aac taa gaatcttttc    1135
Lys Phe Leu Cys Val Ile Lys Phe Thr Tyr Asp Asn *
    310                 315                 320 tttggatttt atgatcatct tagtatcgcg accgctctag acaggcctcg taccggatcc    1195
tctagctaga gctttcgttc gtatcatcgg tttcgacaac g                        1236
```

<210> SEQ ID NO 76
<211> LENGTH: 320
<212> TYPE: PRT
<213> ORGANISM: Arabidopsis thaliana
<220> FEATURE:
<221> NAME/KEY: DOMAIN
<222> LOCATION: (242)...(306)
<223> OTHER INFORMATION: Conserved domain

<400> SEQUENCE: 76

```
Met Glu Glu Asp Ala Ala Phe Asp Leu Leu Lys Ala Glu Leu Leu Asn
  1               5                  10                  15

Ala Glu Asp Asp Ala Ile Ile Ser Arg Tyr Leu Lys Arg Met Val Val
             20                  25                  30

Asn Gly Asp Ser Trp Pro Asp His Phe Ile Glu Asp Ala Asp Val Phe
         35                  40                  45

Asn Lys Asn Pro Asn Val Glu Phe Asp Ala Glu Ser Pro Ser Phe Val
     50                  55                  60

Ile Val Lys Pro Arg Thr Glu Ala Cys Gly Lys Thr Asp Gly Cys Glu
 65                  70                  75                  80

Thr Gly Cys Trp Arg Ile Met Gly Arg Asp Lys Pro Ile Lys Ser Thr
                 85                  90                  95

Glu Thr Val Lys Ile Gln Gly Phe Lys Lys Ile Leu Lys Phe Cys Leu
            100                 105                 110

Lys Arg Lys Pro Arg Gly Tyr Lys Arg Ser Trp Val Met Glu Glu Tyr
        115                 120                 125

Arg Leu Thr Asn Asn Leu Asn Trp Lys Gln Asp His Val Ile Cys Lys
    130                 135                 140

Ile Arg Phe Met Phe Glu Ala Glu Ile Ser Phe Leu Leu Ala Lys His
145                 150                 155                 160

Phe Tyr Thr Thr Ser Glu Ser Leu Pro Arg Asn Glu Leu Leu Pro Ala
                165                 170                 175

Tyr Gly Phe Leu Ser Ser Asp Lys Gln Leu Glu Asp Val Ser Tyr Pro
            180                 185                 190

Val Thr Ile Met Thr Ser Glu Gly Asn Asp Trp Pro Ser Tyr Val Thr
        195                 200                 205

Asn Asn Val Tyr Cys Leu His Pro Leu Glu Leu Val Asp Leu Gln Asp
    210                 215                 220

Arg Met Phe Asn Asp Tyr Gly Thr Cys Ile Phe Ala Asn Lys Thr Cys
225                 230                 235                 240

Gly Lys Thr Asp Arg Cys Ile Asn Gly Gly Tyr Trp Lys Ile Leu His
                245                 250                 255

Arg Asp Arg Leu Ile Lys Ser Lys Ser Gly Ile Val Ile Gly Phe Lys
            260                 265                 270

Lys Val Phe Lys Phe His Glu Thr Glu Lys Glu Arg Tyr Phe Cys Gly
        275                 280                 285

Gly Glu Asp Val Lys Val Thr Trp Thr Leu Glu Glu Tyr Arg Leu Ser
    290                 295                 300

Val Lys Gln Asn Lys Phe Leu Cys Val Ile Lys Phe Thr Tyr Asp Asn
305                 310                 315                 320
```

<210> SEQ ID NO 77
<211> LENGTH: 732
<212> TYPE: DNA
<213> ORGANISM: Arabidopsis thaliana
<220> FEATURE:
<221> NAME/KEY: CDS
<222> LOCATION: (1)...(732)

<400> SEQUENCE: 77

```
atg gaa ggg aac ttc ttc atc agg tct gat gct caa cga gca cat gac      48
Met Glu Gly Asn Phe Phe Ile Arg Ser Asp Ala Gln Arg Ala His Asp
 1               5                  10                  15 aat ggc ttc ata gcc aaa caa aaa cct aat ctc acc acg gct cca aca      96
Asn Gly Phe Ile Ala Lys Gln Lys Pro Asn Leu Thr Thr Ala Pro Thr
             20                  25                  30 gca ggt caa gct aat gaa agt ggc tgt ttt gac tgc aac atc tgt tta     144
Ala Gly Gln Ala Asn Glu Ser Gly Cys Phe Asp Cys Asn Ile Cys Leu
         35                  40                  45 gac aca gcc cat gat ccg gtg gtc act ctc tgc ggg cac ctt ttc tgc     192
Asp Thr Ala His Asp Pro Val Val Thr Leu Cys Gly His Leu Phe Cys
     50                  55                  60 tgg cct tgc att tac aag tgg tta cat gtt cag tta tct tct gtc tcc     240
Trp Pro Cys Ile Tyr Lys Trp Leu His Val Gln Leu Ser Ser Val Ser
 65                  70                  75                  80 gtt gat cag cac cag aac aat tgc cct gtt tgt aaa tcc aac att act     288
Val Asp Gln His Gln Asn Asn Cys Pro Val Cys Lys Ser Asn Ile Thr
                 85                  90                  95 atc acc tct ttg gtt cct ctc tat gga aga ggc atg tct tcg cct tct     336
Ile Thr Ser Leu Val Pro Leu Tyr Gly Arg Gly Met Ser Ser Pro Ser
            100                 105                 110 tcc acg ttt ggc tcc aag aaa caa gac gca ctg tcc act gac ata ccc     384
Ser Thr Phe Gly Ser Lys Lys Gln Asp Ala Leu Ser Thr Asp Ile Pro
        115                 120                 125 cgc aga cct gct cca tca gcc tta cgc aat ccg att acc tca gca tca     432
Arg Arg Pro Ala Pro Ser Ala Leu Arg Asn Pro Ile Thr Ser Ala Ser
    130                 135                 140 tct ctg aac cca agc ttg caa cat caa act ctg tct cct tca ttt cat     480
Ser Leu Asn Pro Ser Leu Gln His Gln Thr Leu Ser Pro Ser Phe His
145                 150                 155                 160 aat cat cag tat tcc cct cgt ggc ttc acc aca acc gaa tca acc gac     528
Asn His Gln Tyr Ser Pro Arg Gly Phe Thr Thr Thr Glu Ser Thr Asp
                165                 170                 175 ctt gcc aat gct gta atg atg agt ttc ctc tac cct gtg att gga atg     576
Leu Ala Asn Ala Val Met Met Ser Phe Leu Tyr Pro Val Ile Gly Met
            180                 185                 190 ttt gga gac ctg gtc tac acc agg ata ttc ggg acc ttc aca aac aca     624
Phe Gly Asp Leu Val Tyr Thr Arg Ile Phe Gly Thr Phe Thr Asn Thr
        195                 200                 205 ata gct cag cct tac caa agc cag agg atg atg cag cgt gag aag tct     672
Ile Ala Gln Pro Tyr Gln Ser Gln Arg Met Met Gln Arg Glu Lys Ser
    210                 215                 220 ctt aat cgg gta tcg ata ttc ttc ctt tgt tgc atc atc ctt tgc ctc     720
Leu Asn Arg Val Ser Ile Phe Phe Leu Cys Cys Ile Ile Leu Cys Leu
225                 230                 235                 240 ctt ctc ttc tag                                                     732
Leu Leu Phe *
```

<210> SEQ ID NO 78
<211> LENGTH: 243
<212> TYPE: PRT

<213> ORGANISM: Arabidopsis thaliana
<220> FEATURE:
<221> NAME/KEY: DOMAIN
<222> LOCATION: (39)...(93)
<223> OTHER INFORMATION: Conserved domain

<400> SEQUENCE: 78

```
Met Glu Gly Asn Phe Phe Ile Arg Ser Asp Ala Gln Arg Ala His Asp
 1               5                  10                  15

Asn Gly Phe Ile Ala Lys Gln Lys Pro Asn Leu Thr Thr Ala Pro Thr
             20                  25                  30

Ala Gly Gln Ala Asn Glu Ser Gly Cys Phe Asp Cys Asn Ile Cys Leu
         35                  40                  45

Asp Thr Ala His Asp Pro Val Val Thr Leu Cys Gly His Leu Phe Cys
     50                  55                  60

Trp Pro Cys Ile Tyr Lys Trp Leu His Val Gln Leu Ser Ser Val Ser
 65                  70                  75                  80

Val Asp Gln His Gln Asn Asn Cys Pro Val Cys Lys Ser Asn Ile Thr
                 85                  90                  95

Ile Thr Ser Leu Val Pro Leu Tyr Gly Arg Gly Met Ser Ser Pro Ser
            100                 105                 110

Ser Thr Phe Gly Ser Lys Lys Gln Asp Ala Leu Ser Thr Asp Ile Pro
        115                 120                 125

Arg Arg Pro Ala Pro Ser Ala Leu Arg Asn Pro Ile Thr Ser Ala Ser
    130                 135                 140

Ser Leu Asn Pro Ser Leu Gln His Gln Thr Leu Ser Pro Ser Phe His
145                 150                 155                 160

Asn His Gln Tyr Ser Pro Arg Gly Phe Thr Thr Thr Glu Ser Thr Asp
                165                 170                 175

Leu Ala Asn Ala Val Met Met Ser Phe Leu Tyr Pro Val Ile Gly Met
            180                 185                 190

Phe Gly Asp Leu Val Tyr Thr Arg Ile Phe Gly Thr Phe Thr Asn Thr
        195                 200                 205

Ile Ala Gln Pro Tyr Gln Ser Gln Arg Met Met Gln Arg Glu Lys Ser
    210                 215                 220

Leu Asn Arg Val Ser Ile Phe Phe Leu Cys Cys Ile Ile Leu Cys Leu
225                 230                 235                 240

Leu Leu Phe
```

<210> SEQ ID NO 79
<211> LENGTH: 783
<212> TYPE: DNA
<213> ORGANISM: Arabidopsis thaliana
<220> FEATURE:
<221> NAME/KEY: CDS
<222> LOCATION: (1)...(783)

<400> SEQUENCE: 79

```
atg gaa aac gaa gta aac gca gga aca gca agc agt tca aga tgg aac    48
Met Glu Asn Glu Val Asn Ala Gly Thr Ala Ser Ser Ser Arg Trp Asn
 1               5                  10                  15 cca acg aaa gat cag atc acg cta ctg gaa aat ctt tac aag gaa gga    96
Pro Thr Lys Asp Gln Ile Thr Leu Leu Glu Asn Leu Tyr Lys Glu Gly
             20                  25                  30 ata cga act ccg agc gcc gat cag att cag cag atc acc ggt agg ctt   144
Ile Arg Thr Pro Ser Ala Asp Gln Ile Gln Gln Ile Thr Gly Arg Leu
         35                  40                  45 cgt gcg tac ggc cat atc gaa ggt aaa aac gtc ttt tac tgg ttc cag   192
```

```
                                    Arg Ala Tyr Gly His Ile Glu Gly Lys Asn Val Phe Tyr Trp Phe Gln
                                         50                  55                  60 aac cat aag gct agg caa cgc caa aag cag aaa cag gag cgc atg gct        240
Asn His Lys Ala Arg Gln Arg Gln Lys Gln Lys Gln Glu Arg Met Ala
 65                  70                  75                  80 tac ttc aat cgc ctc ctc cac aaa acc tcc cgt ttc ttc tac ccc cct        288
Tyr Phe Asn Arg Leu Leu His Lys Thr Ser Arg Phe Phe Tyr Pro Pro
                 85                  90                  95 cct tgc tca aac gtg ggt tgt gtc agt ccg tac tat tta cag caa gca        336
Pro Cys Ser Asn Val Gly Cys Val Ser Pro Tyr Tyr Leu Gln Gln Ala
                100                 105                 110 agt gat cat cat atg aat caa cat gga agt gta tac aca aac gat ctt        384
Ser Asp His His Met Asn Gln His Gly Ser Val Tyr Thr Asn Asp Leu
            115                 120                 125 ctt cac aga aac aat gtg atg att cca agt ggt ggc tac gag aaa cgg        432
Leu His Arg Asn Asn Val Met Ile Pro Ser Gly Gly Tyr Glu Lys Arg
        130                 135                 140 aca gtc aca caa cat cag aaa caa ctt tca gac ata aga aca aca gca        480
Thr Val Thr Gln His Gln Lys Gln Leu Ser Asp Ile Arg Thr Thr Ala
145                 150                 155                 160 gcc aca aga atg cca att tct ccg agt tca ctc aga ttt gac aga ttt        528
Ala Thr Arg Met Pro Ile Ser Pro Ser Ser Leu Arg Phe Asp Arg Phe
                165                 170                 175 gcc ctc cgt gat aac tgt tat gcc ggt gag gac att aac gtc aat tcc        576
Ala Leu Arg Asp Asn Cys Tyr Ala Gly Glu Asp Ile Asn Val Asn Ser
                180                 185                 190 agt gga cgg aaa aca ctc cct ctt ttt cct ctt cag cct ttg aat gca        624
Ser Gly Arg Lys Thr Leu Pro Leu Phe Pro Leu Gln Pro Leu Asn Ala
            195                 200                 205 agt aat gct gat ggt atg gga agt tcc agt ttt gcc ctt ggt agt gat        672
Ser Asn Ala Asp Gly Met Gly Ser Ser Ser Phe Ala Leu Gly Ser Asp
        210                 215                 220 tct ccg gtg gat tgt tct agc gat gga gcc ggc cga gag cag ccg ttt        720
Ser Pro Val Asp Cys Ser Ser Asp Gly Ala Gly Arg Glu Gln Pro Phe
225                 230                 235                 240 att gat ttc ttt tct ggt ggt tct act tct act cgt ttc gat agt aat        768
Ile Asp Phe Phe Ser Gly Gly Ser Thr Ser Thr Arg Phe Asp Ser Asn
                245                 250                 255 ggt aat ggg ttg taa                                                    783
Gly Asn Gly Leu *
                260

<210> SEQ ID NO 80
<211> LENGTH: 260
<212> TYPE: PRT
<213> ORGANISM: Arabidopsis thaliana
<220> FEATURE:
<221> NAME/KEY: DOMAIN
<222> LOCATION: (14)...(74)
<223> OTHER INFORMATION: Conserved domain

<400> SEQUENCE: 80

Met Glu Asn Glu Val Asn Ala Gly Thr Ala Ser Ser Ser Arg Trp Asn
 1               5                  10                  15

Pro Thr Lys Asp Gln Ile Thr Leu Leu Glu Asn Leu Tyr Lys Glu Gly
                 20                  25                  30

Ile Arg Thr Pro Ser Ala Asp Gln Ile Gln Gln Ile Thr Gly Arg Leu
             35                  40                  45

Arg Ala Tyr Gly His Ile Glu Gly Lys Asn Val Phe Tyr Trp Phe Gln
         50                  55                  60
```

```
Asn His Lys Ala Arg Gln Arg Gln Lys Gln Lys Gln Glu Arg Met Ala
 65                  70                  75                  80

Tyr Phe Asn Arg Leu Leu His Lys Thr Ser Arg Phe Tyr Pro Pro
             85                  90                  95

Pro Cys Ser Asn Val Gly Cys Val Ser Pro Tyr Tyr Leu Gln Gln Ala
            100                 105                 110

Ser Asp His His Met Asn Gln His Gly Ser Val Tyr Thr Asn Asp Leu
            115                 120                 125

Leu His Arg Asn Asn Val Met Ile Pro Ser Gly Tyr Glu Lys Arg
130                 135                 140

Thr Val Thr Gln His Gln Lys Gln Leu Ser Asp Ile Arg Thr Thr Ala
145                 150                 155                 160

Ala Thr Arg Met Pro Ile Ser Pro Ser Ser Leu Arg Phe Asp Arg Phe
                165                 170                 175

Ala Leu Arg Asp Asn Cys Tyr Ala Gly Glu Asp Ile Asn Val Asn Ser
            180                 185                 190

Ser Gly Arg Lys Thr Leu Pro Leu Phe Pro Leu Gln Pro Leu Asn Ala
            195                 200                 205

Ser Asn Ala Asp Gly Met Gly Ser Ser Ser Phe Ala Leu Gly Ser Asp
210                 215                 220

Ser Pro Val Asp Cys Ser Ser Asp Gly Ala Gly Arg Glu Gln Pro Phe
225                 230                 235                 240

Ile Asp Phe Phe Ser Gly Gly Ser Thr Ser Thr Arg Phe Asp Ser Asn
                245                 250                 255

Gly Asn Gly Leu
            260

<210> SEQ ID NO 81
<211> LENGTH: 739
<212> TYPE: DNA
<213> ORGANISM: Arabidopsis thaliana
<220> FEATURE:
<221> NAME/KEY: CDS
<222> LOCATION: (32)...(706)

<400> SEQUENCE: 81
acaaaaatct cttgttcttc ttgtcttcaa t atg gag gat ggg gaa gct tca        52
                                   Met Glu Asp Gly Glu Ala Ser
                                     1               5 aca atc act ttc tta cca acc acg gaa cca aaa ccc cta caa aac cct      100
Thr Ile Thr Phe Leu Pro Thr Thr Glu Pro Lys Pro Leu Gln Asn Pro
         10                  15                  20 aac ttg ctg gcc aaa cca aaa aaa gag act aaa caa aaa aaa cct aaa      148
Asn Leu Leu Ala Lys Pro Lys Lys Glu Thr Lys Gln Lys Lys Pro Lys
 25                  30                  35 acc acc aaa ggt cga cag aag ata gag atc aag gag atc atg ctg gag      196
Thr Thr Lys Gly Arg Gln Lys Ile Glu Ile Lys Glu Ile Met Leu Glu
 40                  45                  50                  55 acc cga agg caa gtg acg ttt tcc aaa cga cga tcc ggg ctt ttc aaa      244
Thr Arg Arg Gln Val Thr Phe Ser Lys Arg Arg Ser Gly Leu Phe Lys
                 60                  65                  70 aaa gcg gca gaa tta agc gtt ctc tgc ggc gca cag att ggt atc ata      292
Lys Ala Ala Glu Leu Ser Val Leu Cys Gly Ala Gln Ile Gly Ile Ile
             75                  80                  85 acg ttt tca cgt tgc gat agg atc tac tcg ttt ggt aac gtg aac tca      340
Thr Phe Ser Arg Cys Asp Arg Ile Tyr Ser Phe Gly Asn Val Asn Ser
         90                  95                 100 ctc atc gat aaa tac ttg cgt aag gct ccg gtg atg ctg agg tca cat      388
```

-continued

```
Leu Ile Asp Lys Tyr Leu Arg Lys Ala Pro Val Met Leu Arg Ser His
    105                 110                 115 ccc ggt ggt aac gtg gca aac gga gag gaa gat aac gac ggt ttg atg    436
Pro Gly Gly Asn Val Ala Asn Gly Glu Glu Asp Asn Asp Gly Leu Met
120                 125                 130                 135 tgg tgg gag aga gcg gtg gag agt gtg ccg gag gag cat atg gaa gag    484
Trp Trp Glu Arg Ala Val Glu Ser Val Pro Glu Glu His Met Glu Glu
                140                 145                 150 tac aag aat gcc ttg agt gtg tta agg gag aat ttg ttg acg agg atc    532
Tyr Lys Asn Ala Leu Ser Val Leu Arg Glu Asn Leu Leu Thr Arg Ile
            155                 160                 165 tac cag atg agt ggt gat cgg acg gtt gag aat ctt ccg gca ttt cca    580
Tyr Gln Met Ser Gly Asp Arg Thr Val Glu Asn Leu Pro Ala Phe Pro
        170                 175                 180 aat gag atg gct atg gct gac tgg aaa tta acg aat gaa aat ctg atg    628
Asn Glu Met Ala Met Ala Asp Trp Lys Leu Thr Asn Glu Asn Leu Met
    185                 190                 195 gct agg aac gat cga ggt tat gga ggt aac aat ggt gat ttg gag ttt    676
Ala Arg Asn Asp Arg Gly Tyr Gly Gly Asn Asn Gly Asp Leu Glu Phe
200                 205                 210                 215 gcg ttt atg cct caa aac ggt aga cag tga ggtgttttttt ctttaattta    726
Ala Phe Met Pro Gln Asn Gly Arg Gln  *
                220 ttattacagt ttg    739
```

<210> SEQ ID NO 82
<211> LENGTH: 224
<212> TYPE: PRT
<213> ORGANISM: Arabidopsis thaliana
<220> FEATURE:
<221> NAME/KEY: DOMAIN
<222> LOCATION: (43)...(100)
<223> OTHER INFORMATION: Conserved domain

<400> SEQUENCE: 82

```
Met Glu Asp Gly Glu Ala Ser Thr Ile Thr Phe Leu Pro Thr Thr Glu
1               5                   10                  15

Pro Lys Pro Leu Gln Asn Pro Asn Leu Leu Ala Lys Pro Lys Lys Glu
            20                  25                  30

Thr Lys Gln Lys Lys Pro Lys Thr Thr Lys Gly Arg Gln Lys Ile Glu
        35                  40                  45

Ile Lys Glu Ile Met Leu Glu Thr Arg Arg Gln Val Thr Phe Ser Lys
    50                  55                  60

Arg Arg Ser Gly Leu Phe Lys Lys Ala Ala Glu Leu Ser Val Leu Cys
65                  70                  75                  80

Gly Ala Gln Ile Gly Ile Ile Thr Phe Ser Arg Cys Asp Arg Ile Tyr
                85                  90                  95

Ser Phe Gly Asn Val Asn Ser Leu Ile Asp Lys Tyr Leu Arg Lys Ala
            100                 105                 110

Pro Val Met Leu Arg Ser His Pro Gly Gly Asn Val Ala Asn Gly Glu
        115                 120                 125

Glu Asp Asn Asp Gly Leu Met Trp Trp Glu Arg Ala Val Glu Ser Val
    130                 135                 140

Pro Glu Glu His Met Glu Glu Tyr Lys Asn Ala Leu Ser Val Leu Arg
145                 150                 155                 160

Glu Asn Leu Leu Thr Arg Ile Tyr Gln Met Ser Gly Asp Arg Thr Val
                165                 170                 175

Glu Asn Leu Pro Ala Phe Pro Asn Glu Met Ala Met Ala Asp Trp Lys
```

```
                     180                 185                 190
Leu Thr Asn Glu Asn Leu Met Ala Arg Asn Asp Arg Gly Tyr Gly Gly
        195                 200                 205
Asn Asn Gly Asp Leu Glu Phe Ala Phe Met Pro Gln Asn Gly Arg Gln
    210                 215                 220

<210> SEQ ID NO 83
<211> LENGTH: 1366
<212> TYPE: DNA
<213> ORGANISM: Arabidopsis thaliana
<220> FEATURE:
<221> NAME/KEY: CDS
<222> LOCATION: (162)...(1262)

<400> SEQUENCE: 83
ctgtgattgt caagagtttg aacacacaaa gaagaaagaa gaactcaaca tttcaagcaa      60
gaagaaagag agaagagaga aggtccaata atagagagaa caaaaaaaaa gagagcttaa     120
ttgtcagttt attctctgca aacgtgcggc ctaagtaaca c atg tcg aat tat gga    176
                                             Met Ser Asn Tyr Gly
                                               1               5 gtt aaa gag ctc aca tgg gaa aat ggg caa cta acc gtt cat ggt cta      224
Val Lys Glu Leu Thr Trp Glu Asn Gly Gln Leu Thr Val His Gly Leu
                10                  15                  20 ggc gac gaa gta gaa cca acc acc tcg aat aac cct att tgg act caa      272
Gly Asp Glu Val Glu Pro Thr Thr Ser Asn Asn Pro Ile Trp Thr Gln
            25                  30                  35 agt ctc aac ggt tgt gag act ttg gag tct gtg gtt cat caa gcg gct      320
Ser Leu Asn Gly Cys Glu Thr Leu Glu Ser Val Val His Gln Ala Ala
        40                  45                  50 cta cag cag cca agc aag ttt cag ctg cag agt ccg aat ggt cca aac      368
Leu Gln Gln Pro Ser Lys Phe Gln Leu Gln Ser Pro Asn Gly Pro Asn
    55                  60                  65 cac aat tat gag agc aag gat gga tct tgt tca aga aaa cgc ggt tat      416
His Asn Tyr Glu Ser Lys Asp Gly Ser Cys Ser Arg Lys Arg Gly Tyr
70                  75                  80                  85 cct caa gaa atg gac cga tgg ttc gct gtt caa gag gag agc cat aga      464
Pro Gln Glu Met Asp Arg Trp Phe Ala Val Gln Glu Glu Ser His Arg
                90                  95                 100 gtt ggc cac agc gtc act gca agt gcg agt ggt acc aat atg tct tgg      512
Val Gly His Ser Val Thr Ala Ser Ala Ser Gly Thr Asn Met Ser Trp
            105                 110                 115 gcg tct ttt gaa tcc ggt cgg agc ttg aag aca gct aga acc gga gac      560
Ala Ser Phe Glu Ser Gly Arg Ser Leu Lys Thr Ala Arg Thr Gly Asp
        120                 125                 130 aga gac tat ttc cgc tct gga tcg gaa act caa gat act gaa gga gat      608
Arg Asp Tyr Phe Arg Ser Gly Ser Glu Thr Gln Asp Thr Glu Gly Asp
    135                 140                 145 gaa caa gag aca aga gga gaa gca ggt aga tct aat gga cga cgg gga      656
Glu Gln Glu Thr Arg Gly Glu Ala Gly Arg Ser Asn Gly Arg Arg Gly
150                 155                 160                 165 cga gca gca gcg att cac aac gag tcc gaa agg aga cgg cgt gat agg      704
Arg Ala Ala Ala Ile His Asn Glu Ser Glu Arg Arg Arg Arg Asp Arg
                170                 175                 180 ata aac cag agg atg aga aca ctt cag aag ctg ctt cct act gca agt      752
Ile Asn Gln Arg Met Arg Thr Leu Gln Lys Leu Leu Pro Thr Ala Ser
            185                 190                 195 aag gcg gat aaa gtc tca atc ttg gat gat gtt atc gaa cac ttg aaa      800
Lys Ala Asp Lys Val Ser Ile Leu Asp Asp Val Ile Glu His Leu Lys
        200                 205                 210
```

|  |  |  |  |  |  |  |  |  |  |  |  |  |  |  |  |
|---|---|---|---|---|---|---|---|---|---|---|---|---|---|---|---|
| cag | cta | caa | gca | caa | gta | cag | ttc | atg | agc | cta | aga | gcc | aac | ttg | cca | 848 |
| Gln | Leu | Gln | Ala | Gln | Val | Gln | Phe | Met | Ser | Leu | Arg | Ala | Asn | Leu | Pro |
|  | 215 |  |  |  | 220 |  |  |  |  | 225 |  |  |  |  |  |
| caa | caa | atg | atg | att | ccg | caa | cta | cct | cca | cca | cag | tca | gtt | ctc | agc | 896 |
| Gln | Gln | Met | Met | Ile | Pro | Gln | Leu | Pro | Pro | Pro | Gln | Ser | Val | Leu | Ser |
| 230 |  |  |  |  | 235 |  |  |  |  | 240 |  |  |  |  | 245 |
| atc | caa | cac | caa | caa | caa | caa | caa | cag | cag | cag | cag | caa | caa |  |  | 944 |
| Ile | Gln | His | Gln | Gln | Gln | Gln | Gln | Gln | Gln | Gln | Gln | Gln | Gln |
|  |  |  | 250 |  |  |  |  | 255 |  |  |  |  | 260 |
| cag | cag | caa | cag | ttt | cag | atg | tcg | ttg | ctt | gca | aca | atg | gca | aga | atg | 992 |
| Gln | Gln | Gln | Gln | Phe | Gln | Met | Ser | Leu | Leu | Ala | Thr | Met | Ala | Arg | Met |
|  |  |  | 265 |  |  |  |  | 270 |  |  |  |  | 275 |  |  |
| gga | atg | gga | ggt | ggt | gga | aat | ggt | tat | gga | ggt | tta | gtt | cct | cct | cct | 1040 |
| Gly | Met | Gly | Gly | Gly | Gly | Asn | Gly | Tyr | Gly | Gly | Leu | Val | Pro | Pro | Pro |
|  |  | 280 |  |  |  |  | 285 |  |  |  |  | 290 |  |  |  |
| cct | cct | cca | cca | atg | atg | gtc | cct | cct | atg | ggt | aac | aga | gac | tgc | acc | 1088 |
| Pro | Pro | Pro | Pro | Met | Met | Val | Pro | Pro | Met | Gly | Asn | Arg | Asp | Cys | Thr |
|  | 295 |  |  |  |  | 300 |  |  |  |  | 305 |  |  |  |  |
| aac | ggt | tct | tca | gcc | aca | tta | tct | gat | cca | tac | agc | gcc | ttt | ttc | gca | 1136 |
| Asn | Gly | Ser | Ser | Ala | Thr | Leu | Ser | Asp | Pro | Tyr | Ser | Ala | Phe | Phe | Ala |
| 310 |  |  |  |  | 315 |  |  |  |  | 320 |  |  |  |  | 325 |
| cag | aca | atg | aat | atg | gat | ctc | tac | aat | aaa | atg | gca | gca | gct | atc | tat | 1184 |
| Gln | Thr | Met | Asn | Met | Asp | Leu | Tyr | Asn | Lys | Met | Ala | Ala | Ala | Ile | Tyr |
|  |  |  | 330 |  |  |  |  | 335 |  |  |  |  | 340 |  |  |
| aga | caa | cag | tct | gat | caa | aca | aca | aag | gta | aat | atc | ggc | atg | cct | tca | 1232 |
| Arg | Gln | Gln | Ser | Asp | Gln | Thr | Thr | Lys | Val | Asn | Ile | Gly | Met | Pro | Ser |
|  |  | 345 |  |  |  |  | 350 |  |  |  |  | 355 |  |  |  |
| agt | tct | tcg | aat | cat | gag | aaa | aga | gat | tag | tctagcgacc | tagtattatt |  |  |  |  | 1282 |
| Ser | Ser | Ser | Asn | His | Glu | Lys | Arg | Asp | * |
|  |  |  | 360 |  |  |  |  | 365 | gatccatata tatagttctt gaaagattgt tgtatcatga ttgtaaaaac tgttttgagt 1342 atggaaaaag acttgcagat aaaa 1366

```
<210> SEQ ID NO 84
<211> LENGTH: 366
<212> TYPE: PRT
<213> ORGANISM: Arabidopsis thaliana
<220> FEATURE:
<221> NAME/KEY: DOMAIN
<222> LOCATION: (160)...(234)
<223> OTHER INFORMATION: Conserved domain
```

<400> SEQUENCE: 84

Met Ser Asn Tyr Gly Val Lys Glu Leu Thr Trp Glu Asn Gly Gln Leu
1               5                   10                  15

Thr Val His Gly Leu Gly Asp Glu Val Glu Pro Thr Thr Ser Asn Asn
            20                  25                  30

Pro Ile Trp Thr Gln Ser Leu Asn Gly Cys Glu Thr Leu Glu Ser Val
        35                  40                  45

Val His Gln Ala Ala Leu Gln Gln Pro Ser Lys Phe Gln Leu Gln Ser
    50                  55                  60

Pro Asn Gly Pro Asn His Asn Tyr Glu Ser Lys Asp Gly Ser Cys Ser
65                  70                  75                  80

Arg Lys Arg Gly Tyr Pro Gln Glu Met Asp Arg Trp Phe Ala Val Gln
                85                  90                  95

Glu Glu Ser His Arg Val Gly His Ser Val Thr Ala Ser Ala Ser Gly
            100                 105                 110

Thr Asn Met Ser Trp Ala Ser Phe Glu Ser Gly Arg Ser Leu Lys Thr
        115                 120                 125

```
Ala Arg Thr Gly Asp Arg Asp Tyr Phe Arg Ser Gly Ser Glu Thr Gln
        130                 135                 140

Asp Thr Glu Gly Asp Glu Gln Glu Thr Arg Gly Glu Ala Gly Arg Ser
145                 150                 155                 160

Asn Gly Arg Arg Gly Arg Ala Ala Ile His Asn Glu Ser Glu Arg
            165                 170                 175

Arg Arg Arg Asp Arg Ile Asn Gln Arg Met Arg Thr Leu Gln Lys Leu
            180                 185                 190

Leu Pro Thr Ala Ser Lys Ala Asp Lys Val Ser Ile Leu Asp Asp Val
            195                 200                 205

Ile Glu His Leu Lys Gln Leu Gln Ala Gln Val Gln Phe Met Ser Leu
    210                 215                 220

Arg Ala Asn Leu Pro Gln Gln Met Met Ile Pro Gln Leu Pro Pro Pro
225                 230                 235                 240

Gln Ser Val Leu Ser Ile Gln His Gln Gln Gln Gln Gln Gln Gln Gln
                245                 250                 255

Gln Gln Gln Gln Gln Gln Gln Gln Phe Gln Met Ser Leu Leu Ala
            260                 265                 270

Thr Met Ala Arg Met Gly Met Gly Gly Gly Asn Gly Tyr Gly Gly
        275                 280                 285

Leu Val Pro Pro Pro Pro Pro Pro Met Met Val Pro Pro Met Gly
    290                 295                 300

Asn Arg Asp Cys Thr Asn Gly Ser Ser Ala Thr Leu Ser Asp Pro Tyr
305                 310                 315                 320

Ser Ala Phe Phe Ala Gln Thr Met Asn Met Asp Leu Tyr Asn Lys Met
                325                 330                 335

Ala Ala Ala Ile Tyr Arg Gln Gln Ser Asp Gln Thr Thr Lys Val Asn
            340                 345                 350

Ile Gly Met Pro Ser Ser Ser Asn His Glu Lys Arg Asp
        355                 360                 365

<210> SEQ ID NO 85
<211> LENGTH: 396
<212> TYPE: DNA
<213> ORGANISM: Arabidopsis thaliana
<220> FEATURE:
<221> NAME/KEY: CDS
<222> LOCATION: (1)...(396)

<400> SEQUENCE: 85 atg ggt ctc tcg cat ttt cca aca gcg tca gaa gga gta cta cca ctt    48
Met Gly Leu Ser His Phe Pro Thr Ala Ser Glu Gly Val Leu Pro Leu
 1               5                  10                  15 ctg gtg atg aac acg gtt gtt tca atc act ctg ttg aag aac atg gtg    96
Leu Val Met Asn Thr Val Val Ser Ile Thr Leu Leu Lys Asn Met Val
            20                  25                  30 agg tct gtt ttt caa att gtt gca tcc gag act gaa tct tcc atg gag   144
Arg Ser Val Phe Gln Ile Val Ala Ser Glu Thr Glu Ser Ser Met Glu
        35                  40                  45 ata gac gac gag cct gaa gat gat ttt gtt act aga aga atc tcg ata   192
Ile Asp Asp Glu Pro Glu Asp Asp Phe Val Thr Arg Arg Ile Ser Ile
    50                  55                  60 aca cag ttc aag tct cta tgt gag aac ata gaa gag gaa gaa gaa gag   240
Thr Gln Phe Lys Ser Leu Cys Glu Asn Ile Glu Glu Glu Glu Glu Glu
65                  70                  75                  80 aaa ggt gtg gag tgt tgt gtg tgc ctt tgt ggg ttt aaa gag gaa gag   288
Lys Gly Val Glu Cys Cys Val Cys Leu Cys Gly Phe Lys Glu Glu Glu
```

```
                85                  90                  95
gaa gtg agt gag ttg gtt tct tgc aag cat ttc ttc cac aga gct tgt    336
Glu Val Ser Glu Leu Val Ser Cys Lys His Phe Phe His Arg Ala Cys
            100                 105                 110 cta gac aac tgg ttt ggt aat aac cac acc aca tgc cct ctt tgc agg    384
Leu Asp Asn Trp Phe Gly Asn Asn His Thr Thr Cys Pro Leu Cys Arg
        115                 120                 125 tcc att ctc tag                                                    396
Ser Ile Leu *
    130

<210> SEQ ID NO 86
<211> LENGTH: 131
<212> TYPE: PRT
<213> ORGANISM: Arabidopsis thaliana
<220> FEATURE:
<221> NAME/KEY: DOMAIN
<222> LOCATION: (85)...(128)
<223> OTHER INFORMATION: Conserved domain

<400> SEQUENCE: 86

Met Gly Leu Ser His Phe Pro Thr Ala Ser Glu Gly Val Leu Pro Leu
1               5                   10                  15

Leu Val Met Asn Thr Val Val Ser Ile Thr Leu Leu Lys Asn Met Val
            20                  25                  30

Arg Ser Val Phe Gln Ile Val Ala Ser Glu Thr Glu Ser Ser Met Glu
        35                  40                  45

Ile Asp Asp Glu Pro Glu Asp Asp Phe Val Thr Arg Arg Ile Ser Ile
    50                  55                  60

Thr Gln Phe Lys Ser Leu Cys Glu Asn Ile Glu Glu Glu Glu Glu Glu
65                  70                  75                  80

Lys Gly Val Glu Cys Cys Val Cys Leu Cys Gly Phe Lys Glu Glu Glu
                85                  90                  95

Glu Val Ser Glu Leu Val Ser Cys Lys His Phe Phe His Arg Ala Cys
            100                 105                 110

Leu Asp Asn Trp Phe Gly Asn Asn His Thr Thr Cys Pro Leu Cys Arg
        115                 120                 125

Ser Ile Leu
    130

<210> SEQ ID NO 87
<211> LENGTH: 1444
<212> TYPE: DNA
<213> ORGANISM: Arabidopsis thaliana
<220> FEATURE:
<221> NAME/KEY: CDS
<222> LOCATION: (148)...(1392)

<400> SEQUENCE: 87
cgtcgactct ctactcaaca ccactcaatt tcatctctct ttttcccttc cattgttagt    60
ataaaaacca agcaaaccct taatcacttt tcatcatcat atatcacctt aatccacatg   120
catacacata tctagtcttt ttgatat atg gca att gta tcc tcc aca aca agc   174
                              Met Ala Ile Val Ser Ser Thr Thr Ser
                                  1               5 atc att ccc atg agt aac caa gtc aac aat aac gaa aaa ggt ata gaa    222
Ile Ile Pro Met Ser Asn Gln Val Asn Asn Asn Glu Lys Gly Ile Glu
 10                  15                  20                  25 gac aat gat cat aga ggc ggc caa gag agt cat gtc caa aat gaa gat    270
Asp Asn Asp His Arg Gly Gly Gln Glu Ser His Val Gln Asn Glu Asp
                30                  35                  40
```

-continued

| | |
|---|---|
| gaa gct gat gat cat gat cat gac atg gtc atg ccc gga ttt aga ttc<br>Glu Ala Asp Asp His Asp His Asp Met Val Met Pro Gly Phe Arg Phe<br>                          45                                50                          55 | 318 |
| cat cct acc gaa gaa gaa ctc ata gag ttt tac ctt cgc cga aaa gtt<br>His Pro Thr Glu Glu Glu Leu Ile Glu Phe Tyr Leu Arg Arg Lys Val<br>                  60                            65                          70 | 366 |
| gaa ggc aaa cgc ttt aat gta gaa ctc atc act ttc ctc gat ctt tat<br>Glu Gly Lys Arg Phe Asn Val Glu Leu Ile Thr Phe Leu Asp Leu Tyr<br>75                        80                            85 | 414 |
| cgc tat gat cct tgg gaa ctt cct gct atg gcg gcg ata gga gag aaa<br>Arg Tyr Asp Pro Trp Glu Leu Pro Ala Met Ala Ala Ile Gly Glu Lys<br>90                        95                          100                        105 | 462 |
| gag tgg tac ttc tat gtg cca aga gat cgg aaa tat aga aat gga gat<br>Glu Trp Tyr Phe Tyr Val Pro Arg Asp Arg Lys Tyr Arg Asn Gly Asp<br>                        110                            115                          120 | 510 |
| aga ccg aac cga gta acg act tca gga tat tgg aaa gcc acc gga gct<br>Arg Pro Asn Arg Val Thr Thr Ser Gly Tyr Trp Lys Ala Thr Gly Ala<br>                    125                                130                          135 | 558 |
| gat agg atg atc aga tcg gag act tct cgg cct atc gga tta aag aaa<br>Asp Arg Met Ile Arg Ser Glu Thr Ser Arg Pro Ile Gly Leu Lys Lys<br>                140                              145                            150 | 606 |
| acc cta gtt ttc tac tct ggt aaa gcc cct aaa ggc act cgt act agt<br>Thr Leu Val Phe Tyr Ser Gly Lys Ala Pro Lys Gly Thr Arg Thr Ser<br>155                        160                              165 | 654 |
| tgg atc atg aac gag tat cgt ctt ccg cac cat gaa acc gag aag tac<br>Trp Ile Met Asn Glu Tyr Arg Leu Pro His His Glu Thr Glu Lys Tyr<br>170                        175                              180                        185 | 702 |
| caa aag gct gaa ata tca ttg tgc cga gtg tac aaa agg cca gga gta<br>Gln Lys Ala Glu Ile Ser Leu Cys Arg Val Tyr Lys Arg Pro Gly Val<br>                    190                                195                          200 | 750 |
| gaa gat cat cca tcg gta cca cgt tct ctc tcc aca aga cat cat aac<br>Glu Asp His Pro Ser Val Pro Arg Ser Leu Ser Thr Arg His His Asn<br>                205                              210                            215 | 798 |
| cat aac tca tcg aca tca tcc cgt tta gcc tta aga caa caa caa cac<br>His Asn Ser Ser Thr Ser Ser Arg Leu Ala Leu Arg Gln Gln Gln His<br>                220                              225                            230 | 846 |
| cat tca tcc tcc tct aat cat tcc gac aac aac ctt aac aac aac aac<br>His Ser Ser Ser Ser Asn His Ser Asp Asn Asn Leu Asn Asn Asn Asn<br>235                        240                              245 | 894 |
| aac atc aac aat ctc gag aag ctc tcc acc gaa tat tcc ggc gac ggc<br>Asn Ile Asn Asn Leu Glu Lys Leu Ser Thr Glu Tyr Ser Gly Asp Gly<br>250                        255                              260                        265 | 942 |
| agc aca aca aca acg acc aca aac agt aac tct gac gtt acc att gct<br>Ser Thr Thr Thr Thr Thr Thr Asn Ser Asn Ser Asp Val Thr Ile Ala<br>                    270                                275                          280 | 990 |
| cta gcc aat caa aac ata tat cgt cca atg cct tac gac aca agc aac<br>Leu Ala Asn Gln Asn Ile Tyr Arg Pro Met Pro Tyr Asp Thr Ser Asn<br>                285                              290                            295 | 1038 |
| aac aca ttg ata gtc tct acg aga aat cat caa gac gat gat gaa act<br>Asn Thr Leu Ile Val Ser Thr Arg Asn His Gln Asp Asp Asp Glu Thr<br>                    300                                305                          310 | 1086 |
| gcc att gtt gac gat ctt caa aga cta gtt aac tac caa ata tca gat<br>Ala Ile Val Asp Asp Leu Gln Arg Leu Val Asn Tyr Gln Ile Ser Asp<br>315                        320                              325 | 1134 |
| gga ggt aac atc aat cac caa tac ttt caa att gct caa cag ttt cat<br>Gly Gly Asn Ile Asn His Gln Tyr Phe Gln Ile Ala Gln Gln Phe His<br>330                        335                              340                        345 | 1182 |
| cat act caa caa caa aat gct aac gca aac gca tta caa ttg gtg gct<br>His Thr Gln Gln Gln Asn Ala Asn Ala Asn Ala Leu Gln Leu Val Ala | 1230 |

-continued

```
                    350                 355                 360
gcg gcg act aca gcg aca acg cta atg cct caa act caa gcg gcg tta     1278
Ala Ala Thr Thr Ala Thr Thr Leu Met Pro Gln Thr Gln Ala Ala Leu
            365                 370                 375 gct atg aac atg att cct gca gga acg att cca aac aat gct ttg tgg     1326
Ala Met Asn Met Ile Pro Ala Gly Thr Ile Pro Asn Asn Ala Leu Trp
        380                 385                 390 gat atg tgg aat cca ata gta cca gat gga aac aga gat cac tat act     1374
Asp Met Trp Asn Pro Ile Val Pro Asp Gly Asn Arg Asp His Tyr Thr
    395                 400                 405 aat att cct ttt aag taa tttaattaga tcatgattat tatccatgac            1422
Asn Ile Pro Phe Lys *
410 ataattaat gctgctttgc gc                                             1444
```

<210> SEQ ID NO 88
<211> LENGTH: 414
<212> TYPE: PRT
<213> ORGANISM: Arabidopsis thaliana
<220> FEATURE:
<221> NAME/KEY: DOMAIN
<222> LOCATION: (53)...(175)
<223> OTHER INFORMATION: Conserved domain

<400> SEQUENCE: 88

```
Met Ala Ile Val Ser Ser Thr Thr Ser Ile Ile Pro Met Ser Asn Gln
1               5                   10                  15

Val Asn Asn Glu Lys Gly Ile Glu Asp Asn Asp His Arg Gly Gly
            20                  25                  30

Gln Glu Ser His Val Gln Asn Glu Asp Glu Ala Asp Asp His Asp His
        35                  40                  45

Asp Met Val Met Pro Gly Phe Arg Phe His Pro Thr Glu Glu Glu Leu
    50                  55                  60

Ile Glu Phe Tyr Leu Arg Arg Lys Val Glu Gly Lys Arg Phe Asn Val
65                  70                  75                  80

Glu Leu Ile Thr Phe Leu Asp Leu Tyr Arg Tyr Asp Pro Trp Glu Leu
                85                  90                  95

Pro Ala Met Ala Ala Ile Gly Glu Lys Glu Trp Tyr Phe Tyr Val Pro
            100                 105                 110

Arg Asp Arg Lys Tyr Arg Asn Gly Asp Arg Pro Asn Arg Val Thr Thr
        115                 120                 125

Ser Gly Tyr Trp Lys Ala Thr Gly Ala Asp Arg Met Ile Arg Ser Glu
    130                 135                 140

Thr Ser Arg Pro Ile Gly Leu Lys Lys Thr Leu Val Phe Tyr Ser Gly
145                 150                 155                 160

Lys Ala Pro Lys Gly Thr Arg Thr Ser Trp Ile Met Asn Glu Tyr Arg
                165                 170                 175

Leu Pro His His Glu Thr Glu Lys Tyr Gln Lys Ala Glu Ile Ser Leu
            180                 185                 190

Cys Arg Val Tyr Lys Arg Pro Gly Val Glu Asp His Pro Ser Val Pro
        195                 200                 205

Arg Ser Leu Ser Thr Arg His His Asn His Asn Ser Ser Thr Ser Ser
    210                 215                 220

Arg Leu Ala Leu Arg Gln Gln Gln His His Ser Ser Ser Ser Asn His
225                 230                 235                 240

Ser Asp Asn Asn Leu Asn Asn Asn Asn Ile Asn Asn Leu Glu Lys
                245                 250                 255
```

```
Leu Ser Thr Glu Tyr Ser Gly Asp Gly Ser Thr Thr Thr Thr Thr
            260                 265                 270

Asn Ser Asn Ser Asp Val Thr Ile Ala Leu Ala Asn Gln Asn Ile Tyr
            275                 280                 285

Arg Pro Met Pro Tyr Asp Thr Ser Asn Asn Thr Leu Ile Val Ser Thr
            290                 295                 300

Arg Asn His Gln Asp Asp Asp Glu Thr Ala Ile Val Asp Asp Leu Gln
305                 310                 315                 320

Arg Leu Val Asn Tyr Gln Ile Ser Asp Gly Gly Asn Ile Asn His Gln
                325                 330                 335

Tyr Phe Gln Ile Ala Gln Gln Phe His His Thr Gln Gln Gln Asn Ala
            340                 345                 350

Asn Ala Asn Ala Leu Gln Leu Val Ala Ala Thr Thr Ala Thr Thr
            355                 360                 365

Leu Met Pro Gln Thr Gln Ala Ala Leu Ala Met Asn Met Ile Pro Ala
            370                 375                 380

Gly Thr Ile Pro Asn Asn Ala Leu Trp Asp Met Trp Asn Pro Ile Val
385                 390                 395                 400

Pro Asp Gly Asn Arg Asp His Tyr Thr Asn Ile Pro Phe Lys
                405                 410

<210> SEQ ID NO 89
<211> LENGTH: 768
<212> TYPE: DNA
<213> ORGANISM: Arabidopsis thaliana
<220> FEATURE:
<221> NAME/KEY: CDS
<222> LOCATION: (58)...(657)

<400> SEQUENCE: 89
attactcatc atcaagttcc tactttctct ctgacaaaca tcacagagta agtaaga atg      60
                                                              Met
                                                               1 gta cag acg aag aag ttc aga ggt gtc agg caa cgc cat tgg ggt tct       108
Val Gln Thr Lys Lys Phe Arg Gly Val Arg Gln Arg His Trp Gly Ser
        5                   10                  15 tgg gtc gct gag att cgt cat cct ctc ttg aaa cgg agg att tgg cta       156
Trp Val Ala Glu Ile Arg His Pro Leu Leu Lys Arg Arg Ile Trp Leu
    20                  25                  30 ggg acg ttc gag acc gca gag gag gca gca aga gca tac gac gag gcc       204
Gly Thr Phe Glu Thr Ala Glu Glu Ala Ala Arg Ala Tyr Asp Glu Ala
35                  40                  45 gcc gtt tta atg agc ggc cgc aac gcc aaa acc aac ttt ccc ctc aac       252
Ala Val Leu Met Ser Gly Arg Asn Ala Lys Thr Asn Phe Pro Leu Asn
 50                 55                  60                  65 aac aac aac acc gga gaa act tcc gag ggc aaa acc gat att tca gct       300
Asn Asn Asn Thr Gly Glu Thr Ser Glu Gly Lys Thr Asp Ile Ser Ala
                70                  75                  80 tcg tcc aca atg tca tcc tca aca tca tct tca tcg ctc tct tcc atc       348
Ser Ser Thr Met Ser Ser Ser Thr Ser Ser Ser Ser Leu Ser Ser Ile
            85                  90                  95 ctc agc gcc aaa ctg agg aaa tgc tgc aag tct cct tcc cca tcc ctc       396
Leu Ser Ala Lys Leu Arg Lys Cys Cys Lys Ser Pro Ser Pro Ser Leu
        100                 105                 110 acc tgc ctc cgt ctt gac aca gcc agc tcc cat atc ggc gtc tgg cag       444
Thr Cys Leu Arg Leu Asp Thr Ala Ser Ser His Ile Gly Val Trp Gln
    115                 120                 125 aaa cgg gcc ggt tca aag tct gac tcc agc tgg gtc atg acg gtg gag       492
Lys Arg Ala Gly Ser Lys Ser Asp Ser Ser Trp Val Met Thr Val Glu
```

```
Lys Arg Ala Gly Ser Lys Ser Asp Ser Ser Trp Val Met Thr Val Glu
130                 135                 140                 145 cta ggt ccc gca agc tcc tcc caa gag act act agt aaa gct tca caa      540
Leu Gly Pro Ala Ser Ser Ser Gln Glu Thr Thr Ser Lys Ala Ser Gln
            150                 155                 160 gac gct att ctt gct ccg acc act gaa gtt gaa att ggt ggc agc aga      588
Asp Ala Ile Leu Ala Pro Thr Thr Glu Val Glu Ile Gly Gly Ser Arg
        165                 170                 175 gaa gaa gta ttg gat gag gaa gaa aag gtt gct ttg caa atg ata gag      636
Glu Glu Val Leu Asp Glu Glu Glu Lys Val Ala Leu Gln Met Ile Glu
    180                 185                 190 gag ctt ctc aat aca aac taa atcttatttg cttatatata tgtacctatt         687
Glu Leu Leu Asn Thr Asn  *
195 ttcattgctg atttacagcc aaaataatca attataccgt gtattttata gatgttttat     747 attaaaaggt tgttagatat a                                               768

<210> SEQ ID NO 90
<211> LENGTH: 199
<212> TYPE: PRT
<213> ORGANISM: Arabidopsis thaliana
<220> FEATURE:
<221> NAME/KEY: DOMAIN
<222> LOCATION: (4)...(71)
<223> OTHER INFORMATION: Conserved domain

<400> SEQUENCE: 90

Met Val Gln Thr Lys Lys Phe Arg Gly Val Arg Gln Arg His Trp Gly
1               5                   10                  15

Ser Trp Val Ala Glu Ile Arg His Pro Leu Leu Lys Arg Arg Ile Trp
            20                  25                  30

Leu Gly Thr Phe Glu Thr Ala Glu Glu Ala Ala Arg Ala Tyr Asp Glu
        35                  40                  45

Ala Ala Val Leu Met Ser Gly Arg Asn Ala Lys Thr Asn Phe Pro Leu
    50                  55                  60

Asn Asn Asn Asn Thr Gly Glu Thr Ser Glu Gly Lys Thr Asp Ile Ser
65                  70                  75                  80

Ala Ser Ser Thr Met Ser Ser Ser Thr Ser Ser Ser Ser Leu Ser Ser
                85                  90                  95

Ile Leu Ser Ala Lys Leu Arg Lys Cys Cys Lys Ser Pro Ser Pro Ser
            100                 105                 110

Leu Thr Cys Leu Arg Leu Asp Thr Ala Ser Ser His Ile Gly Val Trp
        115                 120                 125

Gln Lys Arg Ala Gly Ser Lys Ser Asp Ser Ser Trp Val Met Thr Val
    130                 135                 140

Glu Leu Gly Pro Ala Ser Ser Ser Gln Glu Thr Thr Ser Lys Ala Ser
145                 150                 155                 160

Gln Asp Ala Ile Leu Ala Pro Thr Thr Glu Val Glu Ile Gly Gly Ser
                165                 170                 175

Arg Glu Glu Val Leu Asp Glu Glu Glu Lys Val Ala Leu Gln Met Ile
            180                 185                 190

Glu Glu Leu Leu Asn Thr Asn
        195

<210> SEQ ID NO 91
<211> LENGTH: 4011
<212> TYPE: DNA
<213> ORGANISM: Arabidopsis thaliana
```

```
<220> FEATURE:
<221> NAME/KEY: CDS
<222> LOCATION: (1)...(4011)

<400> SEQUENCE: 91 atg ggt tct tac tca gct ggc ttc cct gga tcc ttg gac tgg ttt gat        48
Met Gly Ser Tyr Ser Ala Gly Phe Pro Gly Ser Leu Asp Trp Phe Asp
1               5                   10                  15 ttt ccc ggt tta gga aac gga tcc tat cta aat gat caa cct ttg tta        96
Phe Pro Gly Leu Gly Asn Gly Ser Tyr Leu Asn Asp Gln Pro Leu Leu
            20                  25                  30 gat att gga tct gtt cct cct cct cta gac cca tat cct caa cag aat       144
Asp Ile Gly Ser Val Pro Pro Pro Leu Asp Pro Tyr Pro Gln Gln Asn
        35                  40                  45 ctt gct tct gcg gat gct gat ttc tct gat tct gtt ttg aag tac ata       192
Leu Ala Ser Ala Asp Ala Asp Phe Ser Asp Ser Val Leu Lys Tyr Ile
    50                  55                  60 agc caa gtt ctt atg gaa gag gac atg gaa gat aag cct tgt atg ttt       240
Ser Gln Val Leu Met Glu Glu Asp Met Glu Asp Lys Pro Cys Met Phe
65                  70                  75                  80 cat gat gct tta tct ctt caa gca gct gag aag tct ctc tat gaa gct       288
His Asp Ala Leu Ser Leu Gln Ala Ala Glu Lys Ser Leu Tyr Glu Ala
                85                  90                  95 ctc ggc gag aag tac ccg gtt gat gat tct gat cag cct ctg act act       336
Leu Gly Glu Lys Tyr Pro Val Asp Asp Ser Asp Gln Pro Leu Thr Thr
            100                 105                 110 act act agc ctt gct caa ttg gtt agt agt cct ggt ggt tct tct tat       384
Thr Thr Ser Leu Ala Gln Leu Val Ser Ser Pro Gly Gly Ser Ser Tyr
        115                 120                 125 gct tca agc acc aca acc act tcc tct gat tca caa tgg agt ttt gat       432
Ala Ser Ser Thr Thr Thr Thr Ser Ser Asp Ser Gln Trp Ser Phe Asp
130                 135                 140 tgt ttg gag aat aat agg cct tct tct tgg ttg cag aca ccg atc ccg       480
Cys Leu Glu Asn Asn Arg Pro Ser Ser Trp Leu Gln Thr Pro Ile Pro
145                 150                 155                 160 agt aac ttc att ttt cag tct aca tct act aga gcc agt agc ggt aac       528
Ser Asn Phe Ile Phe Gln Ser Thr Ser Thr Arg Ala Ser Ser Gly Asn
                165                 170                 175 gcg gtt ttc ggg tca agt ttt agc ggt gat ttg gtt tct aat atg ttt       576
Ala Val Phe Gly Ser Ser Phe Ser Gly Asp Leu Val Ser Asn Met Phe
            180                 185                 190 aat gat act gac ttg gcg tta caa ttc aag aaa ggg atg gag gaa gct       624
Asn Asp Thr Asp Leu Ala Leu Gln Phe Lys Lys Gly Met Glu Glu Ala
        195                 200                 205 agt aaa ttc ctt cct aag agc tct cag ttg gtt ata gat aac tct gtt       672
Ser Lys Phe Leu Pro Lys Ser Ser Gln Leu Val Ile Asp Asn Ser Val
    210                 215                 220 cct aac aga tta acc gga aag aag agc cat tgg cgc gaa gaa gaa cat       720
Pro Asn Arg Leu Thr Gly Lys Lys Ser His Trp Arg Glu Glu Glu His
225                 230                 235                 240 ttg act gaa gaa aga agt aag aaa caa tct gct att tat gtt gat gaa       768
Leu Thr Glu Glu Arg Ser Lys Lys Gln Ser Ala Ile Tyr Val Asp Glu
                245                 250                 255 act gat gag ctt act gat atg ttt gac aat att ctg ata ttt ggc gag       816
Thr Asp Glu Leu Thr Asp Met Phe Asp Asn Ile Leu Ile Phe Gly Glu
            260                 265                 270 gct aag gaa caa cct gta tgc att ctt aac gag agt ttc cct aag gaa       864
Ala Lys Glu Gln Pro Val Cys Ile Leu Asn Glu Ser Phe Pro Lys Glu
        275                 280                 285 cct gcg aaa gct tca acg ttt agt aag agt cct aaa ggc gaa aaa ccg       912
```

```
                Pro Ala Lys Ala Ser Thr Phe Ser Lys Ser Pro Lys Gly Glu Lys Pro
                    290                 295                 300 gaa gct agt ggt aac agt tat aca aaa gag aca cct gat ttg agg aca        960
Glu Ala Ser Gly Asn Ser Tyr Thr Lys Glu Thr Pro Asp Leu Arg Thr
305                 310                 315                 320 atg ctg gtt tct tgt gct caa gct gtt tcg att aac gat cgt aga act       1008
Met Leu Val Ser Cys Ala Gln Ala Val Ser Ile Asn Asp Arg Arg Thr
                325                 330                 335 gct gac gag ctg tta agt cgg ata agg caa cat tct tca tct tac ggc       1056
Ala Asp Glu Leu Leu Ser Arg Ile Arg Gln His Ser Ser Ser Tyr Gly
            340                 345                 350 gat gga aca gag aga ttg gct cat tat ttt gct aac agt ctt gaa gca       1104
Asp Gly Thr Glu Arg Leu Ala His Tyr Phe Ala Asn Ser Leu Glu Ala
        355                 360                 365 cgt ttg gct ggg ata ggt aca cag gtt tat act gcc ttg tct tcc aag       1152
Arg Leu Ala Gly Ile Gly Thr Gln Val Tyr Thr Ala Leu Ser Ser Lys
    370                 375                 380 aaa aca tct act tct gac atg ttg aaa gct tat cag aca tat ata tca       1200
Lys Thr Ser Thr Ser Asp Met Leu Lys Ala Tyr Gln Thr Tyr Ile Ser
385                 390                 395                 400 gtc tgt ccg ttc aag aaa atc gca atc ata ttc gcc aac cat agt att       1248
Val Cys Pro Phe Lys Lys Ile Ala Ile Ile Phe Ala Asn His Ser Ile
                405                 410                 415 atg cgg ttg gct tca agt gct aat gcc aaa acc atc cac atc ata gat       1296
Met Arg Leu Ala Ser Ser Ala Asn Ala Lys Thr Ile His Ile Ile Asp
                420                 425                 430 ttt gga ata tct gat ggt ttc cag tgg cct tct ctg att cat cga ctt       1344
Phe Gly Ile Ser Asp Gly Phe Gln Trp Pro Ser Leu Ile His Arg Leu
            435                 440                 445 gct tgg aga cgt ggt tca tct tgt aag ctt cgg ata acc ggt ata gag       1392
Ala Trp Arg Arg Gly Ser Ser Cys Lys Leu Arg Ile Thr Gly Ile Glu
        450                 455                 460 ttg cct caa cgt ggt ttt aga cca gcc gag gga gtt att gag act ggt       1440
Leu Pro Gln Arg Gly Phe Arg Pro Ala Glu Gly Val Ile Glu Thr Gly
465                 470                 475                 480 cgt cgc ttg gct aag tat tgt cag aag ttc aat att ccg ttt gag tac       1488
Arg Arg Leu Ala Lys Tyr Cys Gln Lys Phe Asn Ile Pro Phe Glu Tyr
                485                 490                 495 aat gcg att gcg cag aaa tgg gaa tca atc aag ttg gag gac ttg aag       1536
Asn Ala Ile Ala Gln Lys Trp Glu Ser Ile Lys Leu Glu Asp Leu Lys
                500                 505                 510 cta aaa gaa ggc gag ttt gtt gcg gta aac tct tta ttt cgg ttt agg       1584
Leu Lys Glu Gly Glu Phe Val Ala Val Asn Ser Leu Phe Arg Phe Arg
            515                 520                 525 aat ctt cta gat gag acg gtg gca gtg cat agc ccg aga gat acg gtt       1632
Asn Leu Leu Asp Glu Thr Val Ala Val His Ser Pro Arg Asp Thr Val
        530                 535                 540 ttg aag ctg ata agg aag ata aag cca gac gtg ttc atc ccc ggg atc       1680
Leu Lys Leu Ile Arg Lys Ile Lys Pro Asp Val Phe Ile Pro Gly Ile
545                 550                 555                 560 ctc agc gga tcc tac aac gcg cct ttc ttt gtc acg agg ttt aga gaa       1728
Leu Ser Gly Ser Tyr Asn Ala Pro Phe Phe Val Thr Arg Phe Arg Glu
                565                 570                 575 gtt ctg ttt cat tac tca tct ctg ttt gac atg tgt gac acg aat cta       1776
Val Leu Phe His Tyr Ser Ser Leu Phe Asp Met Cys Asp Thr Asn Leu
                580                 585                 590 aca cgg gaa gat cca atg agg gtt atg ttt gag aaa gag ttc tat ggg       1824
Thr Arg Glu Asp Pro Met Arg Val Met Phe Glu Lys Glu Phe Tyr Gly
            595                 600                 605
```

```
cgg gag atc atg aac gtg gtg gcg tgt gag ggg acg gag aga gtg gag    1872
Arg Glu Ile Met Asn Val Val Ala Cys Glu Gly Thr Glu Arg Val Glu
    610             615                 620 agg cca gag agt tat aag cag tgg cag gcg agg gcg atg aga gcc ggg    1920
Arg Pro Glu Ser Tyr Lys Gln Trp Gln Ala Arg Ala Met Arg Ala Gly
625             630                 635                 640 ttt aga cag att ccg ctg gag aag gaa cta gtt cag aaa ctg aag ttg    1968
Phe Arg Gln Ile Pro Leu Glu Lys Glu Leu Val Gln Lys Leu Lys Leu
                645                 650                 655 atg gtg gaa agt gga tac aaa ccc aaa gag ttt gat gtt gat caa gat    2016
Met Val Glu Ser Gly Tyr Lys Pro Lys Glu Phe Asp Val Asp Gln Asp
            660                 665                 670 tgt cac tgg ttg ctt cag ggc tgg aaa ggt aga att gta tac ggt tca    2064
Cys His Trp Leu Leu Gln Gly Trp Lys Gly Arg Ile Val Tyr Gly Ser
        675                 680                 685 tct att tgg gtt cct ttc ttt ttc tat gtg ggc aga gca act agg gtt    2112
Ser Ile Trp Val Pro Phe Phe Phe Tyr Val Gly Arg Ala Thr Arg Val
    690                 695                 700 ttg atc atg gat cca aac ttc tct gaa tct cta aac ggc ttt gag tat    2160
Leu Ile Met Asp Pro Asn Phe Ser Glu Ser Leu Asn Gly Phe Glu Tyr
705                 710                 715                 720 ttt gat ggt aac cct aat ttg ctt act gat cca atg gaa gat cag tat    2208
Phe Asp Gly Asn Pro Asn Leu Leu Thr Asp Pro Met Glu Asp Gln Tyr
                725                 730                 735 cca cca cca tct gat act ctg ttg aaa tac gtg agt gag att ctt atg    2256
Pro Pro Pro Ser Asp Thr Leu Leu Lys Tyr Val Ser Glu Ile Leu Met
            740                 745                 750 gaa gag agt aat gga gat tat aag caa tct atg ttc tat gat tca ttg    2304
Glu Glu Ser Asn Gly Asp Tyr Lys Gln Ser Met Phe Tyr Asp Ser Leu
        755                 760                 765 gct tta cga aaa act gaa gaa atg ttg cag caa gtc att act gat tct    2352
Ala Leu Arg Lys Thr Glu Glu Met Leu Gln Gln Val Ile Thr Asp Ser
    770                 775                 780 caa aat cag tcc ttt agt cct gct gat tca ttg att act aat tct tgg    2400
Gln Asn Gln Ser Phe Ser Pro Ala Asp Ser Leu Ile Thr Asn Ser Trp
785                 790                 795                 800 gat gca agc gga agc atc gat gaa tcg gct tat tcg gct gat ccg caa    2448
Asp Ala Ser Gly Ser Ile Asp Glu Ser Ala Tyr Ser Ala Asp Pro Gln
                805                 810                 815 cct gtg aat gaa att atg gtt aag agt atg ttt agt gat gca gaa tca    2496
Pro Val Asn Glu Ile Met Val Lys Ser Met Phe Ser Asp Ala Glu Ser
            820                 825                 830 gct tta cag ttt aag aaa ggg gtt gaa gaa gct agt aaa ttc ctt ccc    2544
Ala Leu Gln Phe Lys Lys Gly Val Glu Glu Ala Ser Lys Phe Leu Pro
        835                 840                 845 aat agt gat caa tgg gtt atc aat ctg gat atc gag aga tcc gaa agg    2592
Asn Ser Asp Gln Trp Val Ile Asn Leu Asp Ile Glu Arg Ser Glu Arg
    850                 855                 860 cgc gat tcg gtt aaa gaa gag atg gga ttg gat cag ttg aga gtt aag    2640
Arg Asp Ser Val Lys Glu Glu Met Gly Leu Asp Gln Leu Arg Val Lys
865                 870                 875                 880 aag aat cat gaa agg gat ttt gag gaa gtt agg agt agt aag caa ttt    2688
Lys Asn His Glu Arg Asp Phe Glu Glu Val Arg Ser Ser Lys Gln Phe
                885                 890                 895 gct agt aat gta gaa gat agt aag gtt aca gat atg ttt gat aag gtt    2736
Ala Ser Asn Val Glu Asp Ser Lys Val Thr Asp Met Phe Asp Lys Val
            900                 905                 910 ttg ctt ctt gac ggt gaa tgc gat ccg caa aca ttg tta gac agc gag    2784
Leu Leu Leu Asp Gly Glu Cys Asp Pro Gln Thr Leu Leu Asp Ser Glu
        915                 920                 925
```

| | |
|---|---|
| att caa gcg att cgg agt agt aag aac ata gga gag aaa ggg aag aag<br>Ile Gln Ala Ile Arg Ser Ser Lys Asn Ile Gly Glu Lys Gly Lys Lys<br>930                    935                    940 | 2832 |
| aag aag aag aag aag agt caa gtg gtt gat ttt cgt aca ctt ctc act<br>Lys Lys Lys Lys Lys Ser Gln Val Val Asp Phe Arg Thr Leu Leu Thr<br>945                    950                    955                    960 | 2880 |
| cat tgt gca caa gcc att tcc aca gga gat aaa acc acg gct ctt gag<br>His Cys Ala Gln Ala Ile Ser Thr Gly Asp Lys Thr Thr Ala Leu Glu<br>                965                    970                    975 | 2928 |
| ttt ctg tta cag ata agg caa cag tct tcg cct ctc ggt gac gcg ggg<br>Phe Leu Leu Gln Ile Arg Gln Gln Ser Ser Pro Leu Gly Asp Ala Gly<br>          980                    985                    990 | 2976 |
| caa aga cta gct cat tgt ttc gct aac gcg ctt gaa gct cgt cta cag<br>Gln Arg Leu Ala His Cys Phe Ala Asn Ala Leu Glu Ala Arg Leu Gln<br>995                    1000                  1005 | 3024 |
| gga agt acc ggt cct atg atc cag act tat tac aat gct tta acc tcg<br>Gly Ser Thr Gly Pro Met Ile Gln Thr Tyr Tyr Asn Ala Leu Thr Ser<br>1010                  1015                  1020 | 3072 |
| tcg ttg aag gat act gct gcg gat aca att aga gcg tat cga gtt tat<br>Ser Leu Lys Asp Thr Ala Ala Asp Thr Ile Arg Ala Tyr Arg Val Tyr<br>1025                  1030                  1035                  1040 | 3120 |
| ctt tct tcg tct ccg ttt gtt acc ttg atg tat ttc ttc tcc atc tgg<br>Leu Ser Ser Ser Pro Phe Val Thr Leu Met Tyr Phe Phe Ser Ile Trp<br>                  1045                  1050                  1055 | 3168 |
| atg att ctt gat gtg gct aaa gat gct cct gtt ctt cat ata gtt gat<br>Met Ile Leu Asp Val Ala Lys Asp Ala Pro Val Leu His Ile Val Asp<br>1060                  1065                  1070 | 3216 |
| ttt ggg att cta tac ggg ttt caa tgg ccg atg ttt att cag tct ata<br>Phe Gly Ile Leu Tyr Gly Phe Gln Trp Pro Met Phe Ile Gln Ser Ile<br>1075                  1080                  1085 | 3264 |
| tca gat cga aaa gat gta ccg cgg aag ctg cgg att act ggt atc gag<br>Ser Asp Arg Lys Asp Val Pro Arg Lys Leu Arg Ile Thr Gly Ile Glu<br>1090                  1095                  1100 | 3312 |
| ctt cct cag tgc ggg ttt cgg ccc gcg gag cga ata gag gag aca gga<br>Leu Pro Gln Cys Gly Phe Arg Pro Ala Glu Arg Ile Glu Glu Thr Gly<br>1105                  1110                  1115                  1120 | 3360 |
| cgg aga ttg gct gag tat tgt aaa cgg ttt aat gtt ccg ttt gag tac<br>Arg Arg Leu Ala Glu Tyr Cys Lys Arg Phe Asn Val Pro Phe Glu Tyr<br>                  1125                  1130                  1135 | 3408 |
| aaa gcc att gcg tct cag aac tgg gaa aca atc cgg ata gaa gat ctc<br>Lys Ala Ile Ala Ser Gln Asn Trp Glu Thr Ile Arg Ile Glu Asp Leu<br>1140                  1145                  1150 | 3456 |
| gat ata cga cca aac gaa gtc tta gcg gtt aat gct gga ctt aga ctc<br>Asp Ile Arg Pro Asn Glu Val Leu Ala Val Asn Ala Gly Leu Arg Leu<br>1155                  1160                  1165 | 3504 |
| aag aac ctt caa gat gaa aca gga agc gaa gag aat tgc ccg aga gat<br>Lys Asn Leu Gln Asp Glu Thr Gly Ser Glu Glu Asn Cys Pro Arg Asp<br>1170                  1175                  1180 | 3552 |
| gct gtc ttg aag cta ata aga aac atg aac ccg gac gtt ttc atc cac<br>Ala Val Leu Lys Leu Ile Arg Asn Met Asn Pro Asp Val Phe Ile His<br>1185                  1190                  1195                  1200 | 3600 |
| gcg att gtc aac ggt tca ttc aac gca ccc ttc ttt atc tcg cgg ttt<br>Ala Ile Val Asn Gly Ser Phe Asn Ala Pro Phe Phe Ile Ser Arg Phe<br>                  1205                  1210                  1215 | 3648 |
| aaa gaa gcg gtt tac cat tac tcc gct ctc ttc gac atg ttt gat tcg<br>Lys Glu Ala Val Tyr His Tyr Ser Ala Leu Phe Asp Met Phe Asp Ser<br>                  1220                  1225                  1230 | 3696 |
| acg ttg cct cgg gat aac aaa gag agg att agg ttc gag agg gag ttt<br>Thr Leu Pro Arg Asp Asn Lys Glu Arg Ile Arg Phe Glu Arg Glu Phe | 3744 |

```
                    1235                1240                1245
tac ggg aga gag gct atg aac gtg ata gcg tgc gag gaa gct gat cga      3792
Tyr Gly Arg Glu Ala Met Asn Val Ile Ala Cys Glu Glu Ala Asp Arg
    1250                1255                1260 gtg gag agg cct gag act tac agg caa tgg cag gtt aga atg gtt aga      3840
Val Glu Arg Pro Glu Thr Tyr Arg Gln Trp Gln Val Arg Met Val Arg
1265                1270                1275                1280 gcc ggg ttt aag cag aaa acg att aag cct gag ctg gta gag ttg ttt      3888
Ala Gly Phe Lys Gln Lys Thr Ile Lys Pro Glu Leu Val Glu Leu Phe
                1285                1290                1295 aga gga aag ctg aag aaa tgg cgt tac cat aaa gac ttt gtg gtt gat      3936
Arg Gly Lys Leu Lys Lys Trp Arg Tyr His Lys Asp Phe Val Val Asp
            1300                1305                1310 gaa aat agt aaa tgg ttg tta caa ggc tgg aaa ggt cga act ctc tat      3984
Glu Asn Ser Lys Trp Leu Leu Gln Gly Trp Lys Gly Arg Thr Leu Tyr
        1315                1320                1325 gct tct tct tgt tgg gtt cct gcc tag                                  4011
Ala Ser Ser Cys Trp Val Pro Ala *
    1330                1335

<210> SEQ ID NO 92
<211> LENGTH: 1336
<212> TYPE: PRT
<213> ORGANISM: Arabidopsis thaliana
<220> FEATURE:
<221> NAME/KEY: DOMAIN
<222> LOCATION: (428)...(432)
<223> OTHER INFORMATION: Conserved domain
<220> FEATURE:
<221> NAME/KEY: DOMAIN
<222> LOCATION: (704)...(708)
<223> OTHER INFORMATION: Conserved domain

<400> SEQUENCE: 92

Met Gly Ser Tyr Ser Ala Gly Phe Pro Gly Ser Leu Asp Trp Phe Asp
 1               5                  10                  15

Phe Pro Gly Leu Gly Asn Gly Ser Tyr Leu Asn Asp Gln Pro Leu Leu
                20                  25                  30

Asp Ile Gly Ser Val Pro Pro Leu Asp Pro Tyr Pro Gln Gln Asn
            35                  40                  45

Leu Ala Ser Ala Asp Ala Asp Phe Ser Asp Ser Val Leu Lys Tyr Ile
 50                  55                  60

Ser Gln Val Leu Met Glu Glu Asp Met Glu Asp Lys Pro Cys Met Phe
65                  70                  75                  80

His Asp Ala Leu Ser Leu Gln Ala Ala Glu Lys Ser Leu Tyr Glu Ala
                85                  90                  95

Leu Gly Glu Lys Tyr Pro Val Asp Asp Ser Asp Gln Pro Leu Thr Thr
               100                 105                 110

Thr Thr Ser Leu Ala Gln Leu Val Ser Ser Pro Gly Gly Ser Ser Tyr
           115                 120                 125

Ala Ser Ser Thr Thr Thr Thr Ser Ser Asp Ser Gln Trp Ser Phe Asp
       130                 135                 140

Cys Leu Glu Asn Asn Arg Pro Ser Ser Trp Leu Gln Thr Pro Ile Pro
145                 150                 155                 160

Ser Asn Phe Ile Phe Gln Ser Thr Ser Thr Arg Ala Ser Ser Gly Asn
                165                 170                 175

Ala Val Phe Gly Ser Ser Phe Ser Gly Asp Leu Val Ser Asn Met Phe
            180                 185                 190

Asn Asp Thr Asp Leu Ala Leu Gln Phe Lys Lys Gly Met Glu Glu Ala
```

```
            195                 200                 205
Ser Lys Phe Leu Pro Lys Ser Ser Gln Leu Val Ile Asp Asn Ser Val
    210                 215                 220

Pro Asn Arg Leu Thr Gly Lys Lys Ser His Trp Arg Glu Glu Glu His
225                 230                 235                 240

Leu Thr Glu Glu Arg Ser Lys Lys Gln Ser Ala Ile Tyr Val Asp Glu
                245                 250                 255

Thr Asp Glu Leu Thr Asp Met Phe Asp Asn Ile Leu Ile Phe Gly Glu
                260                 265                 270

Ala Lys Glu Gln Pro Val Cys Ile Leu Asn Glu Ser Phe Pro Lys Glu
            275                 280                 285

Pro Ala Lys Ala Ser Thr Phe Ser Lys Ser Pro Lys Gly Glu Lys Pro
290                 295                 300

Glu Ala Ser Gly Asn Ser Tyr Thr Lys Glu Thr Pro Asp Leu Arg Thr
305                 310                 315                 320

Met Leu Val Ser Cys Ala Gln Ala Val Ser Ile Asn Asp Arg Arg Thr
                325                 330                 335

Ala Asp Glu Leu Leu Ser Arg Ile Arg Gln His Ser Ser Ser Tyr Gly
                340                 345                 350

Asp Gly Thr Glu Arg Leu Ala His Tyr Phe Ala Asn Ser Leu Glu Ala
                355                 360                 365

Arg Leu Ala Gly Ile Gly Thr Gln Val Tyr Thr Ala Leu Ser Ser Lys
            370                 375                 380

Lys Thr Ser Thr Ser Asp Met Leu Lys Ala Tyr Gln Thr Tyr Ile Ser
385                 390                 395                 400

Val Cys Pro Phe Lys Lys Ile Ala Ile Ile Phe Ala Asn His Ser Ile
                405                 410                 415

Met Arg Leu Ala Ser Ala Asn Ala Lys Thr Ile His Ile Ile Asp
                420                 425                 430

Phe Gly Ile Ser Asp Gly Phe Gln Trp Pro Ser Leu Ile His Arg Leu
            435                 440                 445

Ala Trp Arg Arg Gly Ser Ser Cys Lys Leu Arg Ile Thr Gly Ile Glu
450                 455                 460

Leu Pro Gln Arg Gly Phe Arg Pro Ala Glu Gly Val Ile Glu Thr Gly
465                 470                 475                 480

Arg Arg Leu Ala Lys Tyr Cys Gln Lys Phe Asn Ile Pro Phe Glu Tyr
                485                 490                 495

Asn Ala Ile Ala Gln Lys Trp Glu Ser Ile Lys Leu Glu Asp Leu Lys
                500                 505                 510

Leu Lys Glu Gly Glu Phe Val Ala Val Asn Ser Leu Phe Arg Phe Arg
            515                 520                 525

Asn Leu Leu Asp Glu Thr Val Ala Val His Ser Pro Arg Asp Thr Val
530                 535                 540

Leu Lys Leu Ile Arg Lys Ile Lys Pro Asp Val Phe Ile Pro Gly Ile
545                 550                 555                 560

Leu Ser Gly Ser Tyr Asn Ala Pro Phe Phe Val Thr Arg Phe Arg Glu
                565                 570                 575

Val Leu Phe His Tyr Ser Ser Leu Phe Asp Met Cys Asp Thr Asn Leu
                580                 585                 590

Thr Arg Glu Asp Pro Met Arg Val Met Phe Glu Lys Glu Phe Tyr Gly
            595                 600                 605

Arg Glu Ile Met Asn Val Val Ala Cys Glu Gly Thr Glu Arg Val Glu
610                 615                 620
```

```
Arg Pro Glu Ser Tyr Lys Gln Trp Gln Ala Arg Ala Met Arg Ala Gly
625                 630                 635                 640

Phe Arg Gln Ile Pro Leu Glu Lys Glu Leu Val Gln Lys Leu Lys Leu
            645                 650                 655

Met Val Glu Ser Gly Tyr Lys Pro Lys Glu Phe Asp Val Asp Gln Asp
                660                 665                 670

Cys His Trp Leu Leu Gln Gly Trp Lys Gly Arg Ile Val Tyr Gly Ser
            675                 680                 685

Ser Ile Trp Val Pro Phe Phe Phe Tyr Val Gly Arg Ala Thr Arg Val
690                 695                 700

Leu Ile Met Asp Pro Asn Phe Ser Glu Ser Leu Asn Gly Phe Glu Tyr
705                 710                 715                 720

Phe Asp Gly Asn Pro Asn Leu Leu Thr Asp Pro Met Glu Asp Gln Tyr
                725                 730                 735

Pro Pro Pro Ser Asp Thr Leu Leu Lys Tyr Val Ser Glu Ile Leu Met
            740                 745                 750

Glu Glu Ser Asn Gly Asp Tyr Lys Gln Ser Met Phe Tyr Asp Ser Leu
            755                 760                 765

Ala Leu Arg Lys Thr Glu Glu Met Leu Gln Gln Val Ile Thr Asp Ser
770                 775                 780

Gln Asn Gln Ser Phe Ser Pro Ala Asp Ser Leu Ile Thr Asn Ser Trp
785                 790                 795                 800

Asp Ala Ser Gly Ser Ile Asp Glu Ser Ala Tyr Ser Ala Asp Pro Gln
                805                 810                 815

Pro Val Asn Glu Ile Met Val Lys Ser Met Phe Ser Asp Ala Glu Ser
            820                 825                 830

Ala Leu Gln Phe Lys Lys Gly Val Glu Glu Ala Ser Lys Phe Leu Pro
            835                 840                 845

Asn Ser Asp Gln Trp Val Ile Asn Leu Asp Ile Glu Arg Ser Glu Arg
850                 855                 860

Arg Asp Ser Val Lys Glu Glu Met Gly Leu Asp Gln Leu Arg Val Lys
865                 870                 875                 880

Lys Asn His Glu Arg Asp Phe Glu Glu Val Arg Ser Lys Gln Phe
                885                 890                 895

Ala Ser Asn Val Glu Asp Ser Lys Val Thr Asp Met Phe Asp Lys Val
            900                 905                 910

Leu Leu Leu Asp Gly Glu Cys Asp Pro Gln Thr Leu Leu Asp Ser Glu
            915                 920                 925

Ile Gln Ala Ile Arg Ser Ser Lys Asn Ile Gly Glu Lys Gly Lys Lys
930                 935                 940

Lys Lys Lys Lys Ser Gln Val Val Asp Phe Arg Thr Leu Leu Thr
945                 950                 955                 960

His Cys Ala Gln Ala Ile Ser Thr Gly Asp Lys Thr Thr Ala Leu Glu
                965                 970                 975

Phe Leu Leu Gln Ile Arg Gln Gln Ser Ser Pro Leu Gly Asp Ala Gly
            980                 985                 990

Gln Arg Leu Ala His Cys Phe Ala Asn Ala Leu Glu Ala Arg Leu Gln
            995                 1000                1005

Gly Ser Thr Gly Pro Met Ile Gln Thr Tyr Tyr Asn Ala Leu Thr Ser
    1010                1015                1020

Ser Leu Lys Asp Thr Ala Ala Asp Thr Ile Arg Ala Tyr Arg Val Tyr
1025                1030                1035                1040
```

-continued

```
Leu Ser Ser Ser Pro Phe Val Thr Leu Met Tyr Phe Ser Ile Trp
            1045                1050                1055

Met Ile Leu Asp Val Ala Lys Asp Ala Pro Val Leu His Ile Val Asp
        1060                1065                1070

Phe Gly Ile Leu Tyr Gly Phe Gln Trp Pro Met Phe Ile Gln Ser Ile
        1075                1080                1085

Ser Asp Arg Lys Asp Val Pro Arg Lys Leu Arg Ile Thr Gly Ile Glu
    1090                1095                1100

Leu Pro Gln Cys Gly Phe Arg Pro Ala Glu Arg Ile Glu Glu Thr Gly
1105                1110                1115                1120

Arg Arg Leu Ala Glu Tyr Cys Lys Arg Phe Asn Val Pro Phe Glu Tyr
            1125                1130                1135

Lys Ala Ile Ala Ser Gln Asn Trp Glu Thr Ile Arg Ile Glu Asp Leu
        1140                1145                1150

Asp Ile Arg Pro Asn Glu Val Leu Ala Val Asn Ala Gly Leu Arg Leu
        1155                1160                1165

Lys Asn Leu Gln Asp Glu Thr Gly Ser Glu Glu Asn Cys Pro Arg Asp
    1170                1175                1180

Ala Val Leu Lys Leu Ile Arg Asn Met Asn Pro Asp Val Phe Ile His
1185                1190                1195                1200

Ala Ile Val Asn Gly Ser Phe Asn Ala Pro Phe Phe Ile Ser Arg Phe
            1205                1210                1215

Lys Glu Ala Val Tyr His Tyr Ser Ala Leu Phe Asp Met Phe Asp Ser
        1220                1225                1230

Thr Leu Pro Arg Asp Asn Lys Glu Arg Ile Arg Phe Glu Arg Glu Phe
        1235                1240                1245

Tyr Gly Arg Glu Ala Met Asn Val Ile Ala Cys Glu Glu Ala Asp Arg
    1250                1255                1260

Val Glu Arg Pro Glu Thr Tyr Arg Gln Trp Gln Val Arg Met Val Arg
1265                1270                1275                1280

Ala Gly Phe Lys Gln Lys Thr Ile Lys Pro Glu Leu Val Glu Leu Phe
            1285                1290                1295

Arg Gly Lys Leu Lys Lys Trp Arg Tyr His Lys Asp Phe Val Val Asp
        1300                1305                1310

Glu Asn Ser Lys Trp Leu Leu Gln Gly Trp Lys Gly Arg Thr Leu Tyr
        1315                1320                1325

Ala Ser Ser Cys Trp Val Pro Ala
    1330                1335

<210> SEQ ID NO 93
<211> LENGTH: 1116
<212> TYPE: DNA
<213> ORGANISM: Arabidopsis thaliana
<220> FEATURE:
<221> NAME/KEY: CDS
<222> LOCATION: (89)...(934)

<400> SEQUENCE: 93
ttggaaccct agaggccttt caagcaaatc atcagggtaa caatttcttg atctttcttt      60
ttagcgaatt ccagtttttt ggtcaatc atg gca aac cct tgg tgg acg aac       112
                                Met Ala Asn Pro Trp Trp Thr Asn
                                  1               5 cag agt ggt tta gcg ggc atg gtg gac cat tcg gtc tcc tca ggc cat      160
Gln Ser Gly Leu Ala Gly Met Val Asp His Ser Val Ser Ser Gly His
     10                  15                  20 cac caa aac cat cac cac caa agt ctt ctt acc aaa gga gat ctt gga      208
```

| | | | | | | | | | | | | | | | |
|---|---|---|---|---|---|---|---|---|---|---|---|---|---|---|---|
|His|Gln|Asn|His|His|Gln|Ser|Leu|Leu|Thr|Lys|Gly|Asp|Leu|Gly| |
|25| | | |30| | | | |35| | | |40| | |

| | | | | | | | | | | | | | | | |
|---|---|---|---|---|---|---|---|---|---|---|---|---|---|---|---|
|ata|gcc|atg|aat|cag|agc|caa|gac|aac|gac|caa|gac|gaa|gaa|gat|gat|
|Ile|Ala|Met|Asn|Gln|Ser|Gln|Asp|Asn|Asp|Gln|Asp|Glu|Glu|Asp|Asp|
| | | | | |45| | | | |50| | | | |55|

256 cct aga gaa gga gcc gtt gag gtg gtc aac cgt aga cca aga ggt aga      304
Pro Arg Glu Gly Ala Val Glu Val Val Asn Arg Arg Pro Arg Gly Arg
            60                  65                  70 cca cca gga tcc aaa aac aaa ccc aaa gct cca atc ttt gtg aca aga      352
Pro Pro Gly Ser Lys Asn Lys Pro Lys Ala Pro Ile Phe Val Thr Arg
        75                  80                  85 gac agc ccc aac gca ctc cgt agc cat gtc ttg gag atc tcc gac ggc      400
Asp Ser Pro Asn Ala Leu Arg Ser His Val Leu Glu Ile Ser Asp Gly
    90                  95                 100 agt gac gtc gcc gac aca atc gct cac ttc tca aga cgc agg caa cgc      448
Ser Asp Val Ala Asp Thr Ile Ala His Phe Ser Arg Arg Arg Gln Arg
105                 110                 115                 120 ggc gtt tgc gtt ctc agc ggg aca ggc tca gtc gct aac gtc acc ctc      496
Gly Val Cys Val Leu Ser Gly Thr Gly Ser Val Ala Asn Val Thr Leu
                125                 130                 135 cgc caa gcc gcc gca cca gga ggt gtg gtc tct ctc caa ggc agg ttt      544
Arg Gln Ala Ala Ala Pro Gly Gly Val Val Ser Leu Gln Gly Arg Phe
            140                 145                 150 gaa atc tta tct tta acc ggt gct ttc ctc cct gga cct tcc cca ccc      592
Glu Ile Leu Ser Leu Thr Gly Ala Phe Leu Pro Gly Pro Ser Pro Pro
        155                 160                 165 ggg tca acc ggt tta acg gtt tac tta gcc ggg gtc cag ggt cag gtc      640
Gly Ser Thr Gly Leu Thr Val Tyr Leu Ala Gly Val Gln Gly Gln Val
170                 175                 180 gtt gga ggt agc gtt gta ggc cca ctc tta gcc ata ggg tcg gtc atg      688
Val Gly Gly Ser Val Val Gly Pro Leu Leu Ala Ile Gly Ser Val Met
185                 190                 195                 200 gtg att gct gct act ttc tct aac gct act tat gag aga ttg ccc atg      736
Val Ile Ala Ala Thr Phe Ser Asn Ala Thr Tyr Glu Arg Leu Pro Met
                205                 210                 215 gaa gaa gag gaa gac ggt ggc ggc tca aga cag att cac gga ggc ggt      784
Glu Glu Glu Glu Asp Gly Gly Gly Ser Arg Gln Ile His Gly Gly Gly
            220                 225                 230 gac tca ccg ccc aga atc ggt agt aac ctg cct gat cta tca ggg atg      832
Asp Ser Pro Pro Arg Ile Gly Ser Asn Leu Pro Asp Leu Ser Gly Met
        235                 240                 245 gcc ggg cca ggc tac aat atg ccg ccg cat ctg att cca aat ggg gct      880
Ala Gly Pro Gly Tyr Asn Met Pro Pro His Leu Ile Pro Asn Gly Ala
250                 255                 260 ggt cag cta ggg cac gaa cca tat aca tgg gtc cac gca aga cca cct      928
Gly Gln Leu Gly His Glu Pro Tyr Thr Trp Val His Ala Arg Pro Pro
265                 270                 275                 280 tac tga ctcagtgagc catttctata tataatggtc tatataaata aatatataga       984
Tyr * tgaatataag caagcaattt gaggtagtct attacaaagc ttttgctctg gttggaaaaa   1044
taaataagta tcaaagcttt gtttgttctt aatggaaata tagagcttgg gaaggtagaa   1104
agagacgaca tt                                                       1116

<210> SEQ ID NO 94
<211> LENGTH: 281
<212> TYPE: PRT
<213> ORGANISM: Arabidopsis thaliana
<220> FEATURE:
<221> NAME/KEY: DOMAIN
<222> LOCATION: (67)...(74)
<223> OTHER INFORMATION: Conserved domain

<400> SEQUENCE: 94

```
Met Ala Asn Pro Trp Trp Thr Asn Gln Ser Gly Leu Ala Gly Met Val
 1               5                  10                  15
Asp His Ser Val Ser Ser Gly His His Gln Asn His His His Gln Ser
            20                  25                  30
Leu Leu Thr Lys Gly Asp Leu Gly Ile Ala Met Asn Gln Ser Gln Asp
        35                  40                  45
Asn Asp Gln Asp Glu Glu Asp Pro Arg Gly Ala Val Glu Val
50                  55                  60
Val Asn Arg Arg Pro Arg Gly Arg Pro Gly Ser Lys Asn Lys Pro
65                  70                  75                  80
Lys Ala Pro Ile Phe Val Thr Arg Asp Ser Pro Asn Ala Leu Arg Ser
                85                  90                  95
His Val Leu Glu Ile Ser Asp Gly Ser Asp Val Ala Asp Thr Ile Ala
            100                 105                 110
His Phe Ser Arg Arg Arg Gln Arg Gly Val Cys Val Leu Ser Gly Thr
        115                 120                 125
Gly Ser Val Ala Asn Val Thr Leu Arg Gln Ala Ala Pro Gly Gly
    130                 135                 140
Val Val Ser Leu Gln Gly Arg Phe Glu Ile Leu Ser Leu Thr Gly Ala
145                 150                 155                 160
Phe Leu Pro Gly Pro Ser Pro Pro Gly Ser Thr Gly Leu Thr Val Tyr
                165                 170                 175
Leu Ala Gly Val Gln Gly Gln Val Val Gly Ser Val Val Gly Pro
            180                 185                 190
Leu Leu Ala Ile Gly Ser Val Met Val Ile Ala Ala Thr Phe Ser Asn
        195                 200                 205
Ala Thr Tyr Glu Arg Leu Pro Met Glu Glu Glu Asp Gly Gly
    210                 215                 220
Ser Arg Gln Ile His Gly Gly Gly Asp Ser Pro Pro Arg Ile Gly Ser
225                 230                 235                 240
Asn Leu Pro Asp Leu Ser Gly Met Ala Gly Pro Gly Tyr Asn Met Pro
                245                 250                 255
Pro His Leu Ile Pro Asn Gly Ala Gly Gln Leu Gly His Glu Pro Tyr
            260                 265                 270
Thr Trp Val His Ala Arg Pro Pro Tyr
        275                 280
```

<210> SEQ ID NO 95
<211> LENGTH: 1780
<212> TYPE: DNA
<213> ORGANISM: Arabidopsis thaliana
<220> FEATURE:
<221> NAME/KEY: CDS
<222> LOCATION: (230)...(1675)

<400> SEQUENCE: 95

| | | |
|---|---|---|
| tcttttcaaa ttccaatcat tgatcaact aatcaagaat taattataag actttgcaat | 60 |
| ctctctccct ctccctctcc ctagctagtt ctctcttgtg tttcttaact cgagcttctc | 120 |
| tcaatagtga ttatcatctc tttcatcatt tcaagattta atgtgttttg cagaaaagag | 180 |
| actaatcaag aagagatatc atcaattgaa gctgttttct tgagtagag atg gcg aac | 238 |
| | Met Ala Asn |
| | 1 |

-continued

| | |
|---|---|
| cat aga atg agc gaa gct aca aac cat aac cac aat cat cat ctt cct<br>His Arg Met Ser Glu Ala Thr Asn His Asn His Asn His His Leu Pro<br>5                    10                   15 | 286 |
| tat tca ctt att cat ggt ctc aac aac aat cat cca tct tct ggt ttc<br>Tyr Ser Leu Ile His Gly Leu Asn Asn Asn His Pro Ser Ser Gly Phe<br>20                   25                 30                  35 | 334 |
| att aac caa gat gga tcg tcc agt ttc gat ttt gga gag cta gaa gaa<br>Ile Asn Gln Asp Gly Ser Ser Ser Phe Asp Phe Gly Glu Leu Glu Glu<br>              40                   45                   50 | 382 |
| gca att gtt ctg caa ggt gtc aag tat agg aac gag gaa gcc aag cca<br>Ala Ile Val Leu Gln Gly Val Lys Tyr Arg Asn Glu Glu Ala Lys Pro<br>      55                   60                   65 | 430 |
| cct tta tta gga gga gga gga gga gct acg act ctg gag atg ttc cct<br>Pro Leu Leu Gly Gly Gly Gly Gly Ala Thr Thr Leu Glu Met Phe Pro<br>        70                   75                   80 | 478 |
| tcg tgg cca atc aga act cac caa act ctt cct act gag agt tcc aag<br>Ser Trp Pro Ile Arg Thr His Gln Thr Leu Pro Thr Glu Ser Ser Lys<br>85                    90                   95 | 526 |
| tca gga gga gag agc agc gat tca gga tcg gct aat ttc tcc ggc aaa<br>Ser Gly Gly Glu Ser Ser Asp Ser Gly Ser Ala Asn Phe Ser Gly Lys<br>100                  105                 110               115 | 574 |
| gct gaa agt caa caa ccg gag tct cct atg agt agc aaa cat cat ctc<br>Ala Glu Ser Gln Gln Pro Glu Ser Pro Met Ser Ser Lys His His Leu<br>              120                     125               130 | 622 |
| atg ctt caa cct cat cat aat aac atg gca aac tca agt tca aca tct<br>Met Leu Gln Pro His His Asn Asn Met Ala Asn Ser Ser Ser Thr Ser<br>                135                    140                  145 | 670 |
| gga ctt cct tcc act tct cga act tta gct cct cct aaa cct tcg gaa<br>Gly Leu Pro Ser Thr Ser Arg Thr Leu Ala Pro Pro Lys Pro Ser Glu<br>150                  155                 160 | 718 |
| gat aag agg aag gct aca act tca ggc aaa cag ctt gat gct aag acg<br>Asp Lys Arg Lys Ala Thr Thr Ser Gly Lys Gln Leu Asp Ala Lys Thr<br>      165                   170                   175 | 766 |
| ttg aga cgt ttg gcc caa aat aga gaa gct gct cgc aaa agc cgt ctt<br>Leu Arg Arg Leu Ala Gln Asn Arg Glu Ala Ala Arg Lys Ser Arg Leu<br>180                  185                 190               195 | 814 |
| agg aaa aag gcg tat gtg caa cag cta gaa tca agt agg ata aag ctt<br>Arg Lys Lys Ala Tyr Val Gln Gln Leu Glu Ser Ser Arg Ile Lys Leu<br>              200                     205               210 | 862 |
| tcc caa ttg gag caa gaa ctt cag cga gct cgt tct cag ggg ctg ttc<br>Ser Gln Leu Glu Gln Glu Leu Gln Arg Ala Arg Ser Gln Gly Leu Phe<br>                215                    220                  225 | 910 |
| atg ggt ggt tgt gga cca cca gga cct aac atc act tcc gga gct gca<br>Met Gly Gly Cys Gly Pro Pro Gly Pro Asn Ile Thr Ser Gly Ala Ala<br>              230                     235               240 | 958 |
| ata ttt gac atg gaa tat ggg aga tgg cta gag gat gat aac cgg cat<br>Ile Phe Asp Met Glu Tyr Gly Arg Trp Leu Glu Asp Asp Asn Arg His<br>245                  250                 255 | 1006 |
| atg tcg gag att cga acc ggt ctt cag gct cat tta tct gac aat gat<br>Met Ser Glu Ile Arg Thr Gly Leu Gln Ala His Leu Ser Asp Asn Asp<br>260                265                 270               275 | 1054 |
| tta agg ttg atc gtt gac ggt tac att gct cat ttt gat gag ata ttc<br>Leu Arg Leu Ile Val Asp Gly Tyr Ile Ala His Phe Asp Glu Ile Phe<br>              280                     285               290 | 1102 |
| cga tta aaa gcc gtg gca gcg aaa gcc gat gtt ttt cac ctc atc att<br>Arg Leu Lys Ala Val Ala Ala Lys Ala Asp Val Phe His Leu Ile Ile<br>      295                   300                   305 | 1150 |
| ggg aca tgg atg tcc cca gcc gaa cgt tgt ttt att tgg atg gct ggt<br>Gly Thr Trp Met Ser Pro Ala Glu Arg Cys Phe Ile Trp Met Ala Gly | 1198 |

-continued

```
                    310                 315                 320
ttc cgt cca tcc gac cta atc aag ata ttg gtg tcg caa atg gat cta    1246
Phe Arg Pro Ser Asp Leu Ile Lys Ile Leu Val Ser Gln Met Asp Leu
    325                 330                 335 ttg acg gag caa caa ctg atg gga ata tat agc cta caa cac tcg tcg    1294
Leu Thr Glu Gln Gln Leu Met Gly Ile Tyr Ser Leu Gln His Ser Ser
340                 345                 350                 355 caa caa gca gag gag gct ctc tcg caa ggc ctc gaa caa ctt cag caa    1342
Gln Gln Ala Glu Glu Ala Leu Ser Gln Gly Leu Glu Gln Leu Gln Gln
                360                 365                 370 tct ctc atc gat act ctc gcc gca tct cca gtc att gac gga atg caa    1390
Ser Leu Ile Asp Thr Leu Ala Ala Ser Pro Val Ile Asp Gly Met Gln
            375                 380                 385 caa atg gct gtc gct ctc gga aag atc tct aat ctc gaa ggc ttt atc    1438
Gln Met Ala Val Ala Leu Gly Lys Ile Ser Asn Leu Glu Gly Phe Ile
        390                 395                 400 cgc cag gct gat aac ttg agg cag cag acc gtt cac cag ctg agg cgg    1486
Arg Gln Ala Asp Asn Leu Arg Gln Gln Thr Val His Gln Leu Arg Arg
    405                 410                 415 atc ttg acc gtc cga caa gct gca cgg tgt ttc cta gtc atc gga gag    1534
Ile Leu Thr Val Arg Gln Ala Ala Arg Cys Phe Leu Val Ile Gly Glu
420                 425                 430                 435 tac tat gga cgg ctc aga gct ctt agc tcc ctt tgg ttg tca cgc cca    1582
Tyr Tyr Gly Arg Leu Arg Ala Leu Ser Ser Leu Trp Leu Ser Arg Pro
                440                 445                 450 cga gag aca ctg atg agt gat gaa acc tct tgt caa acg acg acg gat    1630
Arg Glu Thr Leu Met Ser Asp Glu Thr Ser Cys Gln Thr Thr Thr Asp
            455                 460                 465 ttg cag att gtt cag tca tct cgg aac cac ttc tcc aat ttc tga        1675
Leu Gln Ile Val Gln Ser Ser Arg Asn His Phe Ser Asn Phe *
        470                 475                 480 atggaatgaa actttgtata actaaaaggc caagtttcat tgtctgtcgt aatttcacct  1735
atttccttta aagttgtact agagaaaaga taggatcttc cttcg                  1780
```

<210> SEQ ID NO 96
<211> LENGTH: 481
<212> TYPE: PRT
<213> ORGANISM: Arabidopsis thaliana
<220> FEATURE:
<221> NAME/KEY: DOMAIN
<222> LOCATION: (173)...(223)
<223> OTHER INFORMATION: Conserved domain

<400> SEQUENCE: 96

```
Met Ala Asn His Arg Met Ser Glu Ala Thr Asn His Asn His Asn His
 1               5                  10                  15

His Leu Pro Tyr Ser Leu Ile His Gly Leu Asn Asn Asn His Pro Ser
                20                  25                  30

Ser Gly Phe Ile Asn Gln Asp Gly Ser Ser Ser Phe Asp Phe Gly Glu
            35                  40                  45

Leu Glu Glu Ala Ile Val Leu Gln Gly Val Lys Tyr Arg Asn Glu Glu
    50                  55                  60

Ala Lys Pro Pro Leu Leu Gly Gly Gly Gly Ala Thr Thr Leu Glu
65                  70                  75                  80

Met Phe Pro Ser Trp Pro Ile Arg Thr His Gln Thr Leu Pro Thr Glu
                85                  90                  95

Ser Ser Lys Ser Gly Gly Glu Ser Ser Asp Ser Gly Ser Ala Asn Phe
            100                 105                 110
```

```
Ser Gly Lys Ala Glu Ser Gln Gln Pro Glu Ser Pro Met Ser Ser Lys
        115                 120                 125

His His Leu Met Leu Gln Pro His His Asn Asn Met Ala Asn Ser Ser
        130                 135                 140

Ser Thr Ser Gly Leu Pro Ser Thr Ser Arg Thr Leu Ala Pro Pro Lys
145                 150                 155                 160

Pro Ser Glu Asp Lys Arg Lys Ala Thr Thr Ser Gly Lys Gln Leu Asp
                165                 170                 175

Ala Lys Thr Leu Arg Arg Leu Ala Gln Asn Arg Glu Ala Ala Arg Lys
            180                 185                 190

Ser Arg Leu Arg Lys Lys Ala Tyr Val Gln Gln Leu Glu Ser Ser Arg
        195                 200                 205

Ile Lys Leu Ser Gln Leu Glu Gln Glu Leu Gln Arg Ala Arg Ser Gln
        210                 215                 220

Gly Leu Phe Met Gly Gly Cys Gly Pro Pro Gly Pro Asn Ile Thr Ser
225                 230                 235                 240

Gly Ala Ala Ile Phe Asp Met Glu Tyr Gly Arg Trp Leu Glu Asp Asp
                245                 250                 255

Asn Arg His Met Ser Glu Ile Arg Thr Gly Leu Gln Ala His Leu Ser
            260                 265                 270

Asp Asn Asp Leu Arg Leu Ile Val Asp Gly Tyr Ile Ala His Phe Asp
        275                 280                 285

Glu Ile Phe Arg Leu Lys Ala Val Ala Ala Lys Ala Asp Val Phe His
        290                 295                 300

Leu Ile Ile Gly Thr Trp Met Ser Pro Ala Glu Arg Cys Phe Ile Trp
305                 310                 315                 320

Met Ala Gly Phe Arg Pro Ser Asp Leu Ile Lys Ile Leu Val Ser Gln
                325                 330                 335

Met Asp Leu Leu Thr Glu Gln Gln Leu Met Gly Ile Tyr Ser Leu Gln
            340                 345                 350

His Ser Ser Gln Gln Ala Glu Glu Ala Leu Ser Gln Gly Leu Glu Gln
        355                 360                 365

Leu Gln Gln Ser Leu Ile Asp Thr Leu Ala Ala Ser Pro Val Ile Asp
        370                 375                 380

Gly Met Gln Gln Met Ala Val Ala Leu Gly Lys Ile Ser Asn Leu Glu
385                 390                 395                 400

Gly Phe Ile Arg Gln Ala Asp Asn Leu Arg Gln Gln Thr Val His Gln
                405                 410                 415

Leu Arg Arg Ile Leu Thr Val Arg Gln Ala Ala Arg Cys Phe Leu Val
            420                 425                 430

Ile Gly Glu Tyr Tyr Gly Arg Leu Arg Ala Leu Ser Ser Leu Trp Leu
        435                 440                 445

Ser Arg Pro Arg Glu Thr Leu Met Ser Asp Glu Thr Ser Cys Gln Thr
        450                 455                 460

Thr Thr Asp Leu Gln Ile Val Gln Ser Ser Arg Asn His Phe Ser Asn
465                 470                 475                 480

Phe

<210> SEQ ID NO 97
<211> LENGTH: 1011
<212> TYPE: DNA
<213> ORGANISM: Arabidopsis thaliana
<220> FEATURE:
<221> NAME/KEY: CDS
<222> LOCATION: (213)...(833)
```

<400> SEQUENCE: 97

```
aaagttattg atagtttctg ttacttatta attttttaagg ttatgtgtat tattaccaat       60
tggaggacta tatagtcgca agtctcaacc ctataaaaga aaacattcgt cgatcatctt      120
cccgcctcga gtatctctct ctctctctct cttctctgtt ttctttattg attgcataga      180
caaaaataca cacatacaca acagaaagaa ag atg gag acg acg atg aag aag        233
                                   Met Glu Thr Thr Met Lys Lys
                                     1               5 aaa ggg aga gtg aaa gcg aca ata acg tca cag aaa gaa gaa gaa gga        281
Lys Gly Arg Val Lys Ala Thr Ile Thr Ser Gln Lys Glu Glu Glu Gly
         10                  15                  20 aca gtg aga aaa gga cct tgg act atg gaa gaa gat ttc atc ctc ttt        329
Thr Val Arg Lys Gly Pro Trp Thr Met Glu Glu Asp Phe Ile Leu Phe
 25                  30                  35 aat tac atc ctt aat cat ggt gaa ggt ctt tgg aac tct gtc gcc aaa        377
Asn Tyr Ile Leu Asn His Gly Glu Gly Leu Trp Asn Ser Val Ala Lys
 40                  45                  50                  55 gcc tct ggt cta aaa cgt act gga aaa agt tgt cgg ctc cgg tgg ctg        425
Ala Ser Gly Leu Lys Arg Thr Gly Lys Ser Cys Arg Leu Arg Trp Leu
                 60                  65                  70 aac tat ctc cga cca gat gtg cgg cga ggg aac ata acc gaa gaa gaa        473
Asn Tyr Leu Arg Pro Asp Val Arg Arg Gly Asn Ile Thr Glu Glu Glu
             75                  80                  85 cag ctt ttg atc att cag ctt cat gct aag ctt gga aac agg tgg tcg        521
Gln Leu Leu Ile Ile Gln Leu His Ala Lys Leu Gly Asn Arg Trp Ser
         90                  95                 100 aag att gcg aag cat ctt ccg gga aga acg gac aac gag ata aag aac        569
Lys Ile Ala Lys His Leu Pro Gly Arg Thr Asp Asn Glu Ile Lys Asn
     105                 110                 115 ttc tgg agg aca aag att cag aga cac atg aaa gtg tca tcg gaa aat        617
Phe Trp Arg Thr Lys Ile Gln Arg His Met Lys Val Ser Ser Glu Asn
120                 125                 130                 135 atg atg aat cat caa cat cat tgt tcg gga aac tca cag agc tcg ggg        665
Met Met Asn His Gln His His Cys Ser Gly Asn Ser Gln Ser Ser Gly
                140                 145                 150 atg acg acg caa ggc agc tcc ggc aaa gcc ata gac acg gct gag agc        713
Met Thr Thr Gln Gly Ser Ser Gly Lys Ala Ile Asp Thr Ala Glu Ser
            155                 160                 165 ttc tct cag gcg aag acg acg acg ttt aat gtg gtg gaa caa cag tca        761
Phe Ser Gln Ala Lys Thr Thr Thr Phe Asn Val Val Glu Gln Gln Ser
        170                 175                 180 aac gag aat tac tgg aac gtt gaa gat ctg tgg ccc gtc cac ttg ctt        809
Asn Glu Asn Tyr Trp Asn Val Glu Asp Leu Trp Pro Val His Leu Leu
    185                 190                 195 aat ggt gac cac cat gtg att taa gatatatata tagacctcct atacatttat      863
Asn Gly Asp His His Val Ile *
200                 205 atgccccagc tgggtttttt tgtatggtac gttatttggt ttttctattg ctgaaatgtc      923
gttgcattta atttacatac gaaaagtgca ttaaatcatt aaatcttcaa tacatatgga      983
ggtggtgttt gagtaaaaaa aaaaaaaa                                        1011
```

<210> SEQ ID NO 98
<211> LENGTH: 206
<212> TYPE: PRT
<213> ORGANISM: Arabidopsis thaliana
<220> FEATURE:
<221> NAME/KEY: DOMAIN
<222> LOCATION: (26)...(130)

<223> OTHER INFORMATION: Conserved domain

<400> SEQUENCE: 98

| | | | | | | | | | | | | | | |
|---|---|---|---|---|---|---|---|---|---|---|---|---|---|---|
| Met | Glu | Thr | Thr | Met | Lys | Lys | Gly | Arg | Val | Lys | Ala | Thr | Ile | Thr |
| 1 | | | | 5 | | | | | 10 | | | | | 15 |
| Ser | Gln | Lys | Glu | Glu | Gly | Thr | Val | Arg | Lys | Gly | Pro | Trp | Thr | Met |
| | | | 20 | | | | | 25 | | | | | 30 | |
| Glu | Glu | Asp | Phe | Ile | Leu | Phe | Asn | Tyr | Ile | Leu | Asn | His | Gly | Glu | Gly |
| | | | 35 | | | | | 40 | | | | | 45 | | |
| Leu | Trp | Asn | Ser | Val | Ala | Lys | Ala | Ser | Gly | Leu | Lys | Arg | Thr | Gly | Lys |
| | 50 | | | | | 55 | | | | | 60 | | | | |
| Ser | Cys | Arg | Leu | Arg | Trp | Leu | Asn | Tyr | Leu | Arg | Pro | Asp | Val | Arg | Arg |
| 65 | | | | | 70 | | | | | 75 | | | | | 80 |
| Gly | Asn | Ile | Thr | Glu | Glu | Gln | Leu | Leu | Ile | Ile | Gln | Leu | His | Ala |
| | | | | 85 | | | | | 90 | | | | | 95 |
| Lys | Leu | Gly | Asn | Arg | Trp | Ser | Lys | Ile | Ala | Lys | His | Leu | Pro | Gly | Arg |
| | | | | 100 | | | | | 105 | | | | | 110 | |
| Thr | Asp | Asn | Glu | Ile | Lys | Asn | Phe | Trp | Arg | Thr | Lys | Ile | Gln | Arg | His |
| | | | 115 | | | | | 120 | | | | | 125 | | |
| Met | Lys | Val | Ser | Ser | Glu | Asn | Met | Met | Asn | His | Gln | His | His | Cys | Ser |
| | 130 | | | | | 135 | | | | | 140 | | | | |
| Gly | Asn | Ser | Gln | Ser | Ser | Gly | Met | Thr | Thr | Gln | Gly | Ser | Ser | Gly | Lys |
| 145 | | | | | 150 | | | | | 155 | | | | | 160 |
| Ala | Ile | Asp | Thr | Ala | Glu | Ser | Phe | Ser | Gln | Ala | Lys | Thr | Thr | Thr | Phe |
| | | | | 165 | | | | | 170 | | | | | 175 | |
| Asn | Val | Val | Glu | Gln | Gln | Ser | Asn | Glu | Asn | Tyr | Trp | Asn | Val | Glu | Asp |
| | | | 180 | | | | | 185 | | | | | 190 | | |
| Leu | Trp | Pro | Val | His | Leu | Leu | Asn | Gly | Asp | His | His | Val | Ile | | |
| | | | | 195 | | | | | 200 | | | | | 205 | | |

<210> SEQ ID NO 99
<211> LENGTH: 1260
<212> TYPE: DNA
<213> ORGANISM: Arabidopsis thaliana
<220> FEATURE:
<221> NAME/KEY: CDS
<222> LOCATION: (292)...(1155)

<400> SEQUENCE: 99

| | |
|---|---|
| gaaatttcat ccctaaataa gaaaaaagca tctccttctt tagtgtcctc cttcaccaaa | 60 |
| ctcttgattc cataagcata tattaaaaaa gctctctgct ttcttcaact ttcccgggaa | 120 |
| aatcttcttg ttacaaagca tcaatctctt gttttaccaa ttttctctct ttattccttt | 180 |
| tttgcccttt acttttccta actttggtct ttatatataa acacacgaca caagaagaa | 240 |
| cacacataag ttaaaactat tacaacagtt ttaaagagag agatttaaaa a atg gag  Met Glu  1 | 297 |
| aca gag aag aaa gtt tct ctc cca aga atc tta cga atc tct gtt act<br>Thr Glu Lys Lys Val Ser Leu Pro Arg Ile Leu Arg Ile Ser Val Thr<br>5 10 15 | 345 |
| gat cct tac gca aca gat tcg tca agc gac gaa gaa gaa gtt gat<br>Asp Pro Tyr Ala Thr Asp Ser Ser Ser Asp Glu Glu Glu Val Asp<br>20 25 30 | 393 |
| ttt gat gca tta tct aca aaa cga cgt cgt gtt aag aag tac gtg aag<br>Phe Asp Ala Leu Ser Thr Lys Arg Arg Arg Val Lys Lys Tyr Val Lys<br>35 40 45 50 | 441 |
| gaa gtg gtg ctt gat tcg gtg gtt tct gat aaa gag aag ccg atg aag | 489 |

| | | |
|---|---|---|
| Glu Val Val Leu Asp Ser Val Val Ser Asp Lys Glu Lys Pro Met Lys | | |
| 55 60 65 | | |
| aag aag aga aag aag cgc gtt gtt act gtt cca gtg gtt gtt acg acg | 537 | |
| Lys Lys Arg Lys Lys Arg Val Val Thr Val Pro Val Val Val Thr Thr | | |
| 70 75 80 | | |
| gcg acg agg aag ttt cgt gga gtg agg caa aga ccg tgg gga aaa tgg | 585 | |
| Ala Thr Arg Lys Phe Arg Gly Val Arg Gln Arg Pro Trp Gly Lys Trp | | |
| 85 90 95 | | |
| gcg gcg gag att aga gat ccg agt aga cgt gtt agg gtt tgg tta ggt | 633 | |
| Ala Ala Glu Ile Arg Asp Pro Ser Arg Arg Val Arg Val Trp Leu Gly | | |
| 100 105 110 | | |
| act ttt gac acg gcg gag gaa gct gcc att gtt tac gat aac gca gct | 681 | |
| Thr Phe Asp Thr Ala Glu Glu Ala Ala Ile Val Tyr Asp Asn Ala Ala | | |
| 115 120 125 130 | | |
| att cag cta cgt ggt cct aac gca gag ctt aac ttc cct cct cct ccg | 729 | |
| Ile Gln Leu Arg Gly Pro Asn Ala Glu Leu Asn Phe Pro Pro Pro Pro | | |
| 135 140 145 | | |
| gtg acg gag aat gtt gaa gaa gct tcg acg gag gtg aaa gga gtt tcg | 777 | |
| Val Thr Glu Asn Val Glu Glu Ala Ser Thr Glu Val Lys Gly Val Ser | | |
| 150 155 160 | | |
| gat ttt atc att ggc ggt gga gaa tgt ctt cgt tcg ccg gtt tct gtt | 825 | |
| Asp Phe Ile Ile Gly Gly Gly Glu Cys Leu Arg Ser Pro Val Ser Val | | |
| 165 170 175 | | |
| ctc gaa tct ccg ttc tcc ggc gag tct act gcg gtt aaa gag gag ttt | 873 | |
| Leu Glu Ser Pro Phe Ser Gly Glu Ser Thr Ala Val Lys Glu Glu Phe | | |
| 180 185 190 | | |
| gtc ggt gta tcg acg gcg gag att gtg gtt aaa aag gag ccg tct ttt | 921 | |
| Val Gly Val Ser Thr Ala Glu Ile Val Val Lys Lys Glu Pro Ser Phe | | |
| 195 200 205 210 | | |
| aac ggt tca gat ttc tcg gcg ccg ttg ttc tcg gac gac gac gtt ttt | 969 | |
| Asn Gly Ser Asp Phe Ser Ala Pro Leu Phe Ser Asp Asp Asp Val Phe | | |
| 215 220 225 | | |
| ggt ttc tcg acg tcg atg agt gaa agt ttc ggc ggc gat tta ttt gga | 1017 | |
| Gly Phe Ser Thr Ser Met Ser Glu Ser Phe Gly Gly Asp Leu Phe Gly | | |
| 230 235 240 | | |
| gat aat ctt ttt gcg gat atg agt ttt gga tcc ggg ttt gga ttc ggg | 1065 | |
| Asp Asn Leu Phe Ala Asp Met Ser Phe Gly Ser Gly Phe Gly Phe Gly | | |
| 245 250 255 | | |
| tct ggg tct gga ttc tcc agc tgg cac gtt gag gac cat ttt caa gat | 1113 | |
| Ser Gly Ser Gly Phe Ser Ser Trp His Val Glu Asp His Phe Gln Asp | | |
| 260 265 270 | | |
| att ggg gat tta ttc ggg tcg gat cct gtc tta act gtt taa | 1155 | |
| Ile Gly Asp Leu Phe Gly Ser Asp Pro Val Leu Thr Val * | | |
| 275 280 285 | | |
| gaaataactg gccgtttaac ggcgtttagt gaagttttgt taccggcgac ggcgaggatt | 1215 | |
| aaaaaaaaac ggcgatttat ttttgaatg aagatttgtt aaata | 1260 | |

<210> SEQ ID NO 100
<211> LENGTH: 287
<212> TYPE: PRT
<213> ORGANISM: Arabidopsis thaliana
<220> FEATURE:
<221> NAME/KEY: DOMAIN
<222> LOCATION: (74)...(151)
<223> OTHER INFORMATION: Conserved domain

<400> SEQUENCE: 100

Met Glu Thr Glu Lys Lys Val Ser Leu Pro Arg Ile Leu Arg Ile Ser
1               5                   10                  15

Val Thr Asp Pro Tyr Ala Thr Asp Ser Ser Ser Asp Glu Glu Glu Glu

-continued

```
                 20                  25                  30
Val Asp Phe Asp Ala Leu Ser Thr Lys Arg Arg Val Lys Lys Tyr
         35                  40                  45
Val Lys Glu Val Val Leu Asp Ser Val Ser Asp Lys Glu Lys Pro
 50                  55                  60
Met Lys Lys Arg Lys Lys Arg Val Val Thr Val Pro Val Val Val
 65                  70                  75                  80
Thr Thr Ala Thr Arg Lys Phe Arg Gly Val Arg Gln Arg Pro Trp Gly
                 85                  90                  95
Lys Trp Ala Ala Glu Ile Arg Asp Pro Ser Arg Val Arg Val Trp
         100                 105                 110
Leu Gly Thr Phe Asp Thr Ala Glu Glu Ala Ala Ile Val Tyr Asp Asn
                 115                 120                 125
Ala Ala Ile Gln Leu Arg Gly Pro Asn Ala Glu Leu Asn Phe Pro Pro
 130                 135                 140
Pro Pro Val Thr Glu Asn Val Glu Glu Ala Ser Thr Glu Val Lys Gly
 145                 150                 155                 160
Val Ser Asp Phe Ile Ile Gly Gly Glu Cys Leu Arg Ser Pro Val
                 165                 170                 175
Ser Val Leu Glu Ser Pro Phe Ser Gly Glu Ser Thr Ala Val Lys Glu
         180                 185                 190
Glu Phe Val Gly Val Ser Thr Ala Glu Ile Val Val Lys Lys Glu Pro
                 195                 200                 205
Ser Phe Asn Gly Ser Asp Phe Ser Ala Pro Leu Phe Ser Asp Asp
         210                 215                 220
Val Phe Gly Phe Ser Thr Ser Met Ser Glu Ser Phe Gly Gly Asp Leu
 225                 230                 235                 240
Phe Gly Asp Asn Leu Phe Ala Asp Met Ser Phe Gly Ser Gly Phe Gly
                 245                 250                 255
Phe Gly Ser Gly Ser Gly Phe Ser Ser Trp His Val Glu Asp His Phe
         260                 265                 270
Gln Asp Ile Gly Asp Leu Phe Gly Ser Asp Pro Val Leu Thr Val
         275                 280                 285
```

<210> SEQ ID NO 101
<211> LENGTH: 1562
<212> TYPE: DNA
<213> ORGANISM: Arabidopsis thaliana
<220> FEATURE:
<221> NAME/KEY: CDS
<222> LOCATION: (160)...(1335)

<400> SEQUENCE: 101

```
tctttctttc ttcctctttg tctctgtttc ttgtttctct ctctctctct ctacagagtt      60
ttctttccct cgaagaaaaa gaatatttt aaatttaatt ttctctgcgt ttataagctt      120
taagtttcag aggaggagga tttagaagga gggttttgt atg tgt gtc tta aaa        174
                                              Met Cys Val Leu Lys
                                               1               5 gtg gca aat cag gaa gat aac gtt ggc aaa aaa gcc gag tct att aga      222
Val Ala Asn Gln Glu Asp Asn Val Gly Lys Lys Ala Glu Ser Ile Arg
             10                  15                  20 gac gat gat cat cgg acg tta tct gaa atc gat caa tgg ctt tac tta      270
Asp Asp Asp His Arg Thr Leu Ser Glu Ile Asp Gln Trp Leu Tyr Leu
         25                  30                  35 ttc gca gcc gaa gac gac cac cac cgt cat agc ttc cct acg cag cag      318
Phe Ala Ala Glu Asp Asp His His Arg His Ser Phe Pro Thr Gln Gln
```

-continued

```
                40                   45                      50
ccg cct cca tcg tcg tcg tcc tca tct ctt atc tca ggt ttc agt aga        366
Pro Pro Pro Ser Ser Ser Ser Ser Ser Leu Ile Ser Gly Phe Ser Arg
         55                      60                  65 gag atg gag atg tct gct att gtc tct gct ttg act cac gtt gtt gct        414
Glu Met Glu Met Ser Ala Ile Val Ser Ala Leu Thr His Val Val Ala
 70                      75                  80                  85 gga aat gtt cct cag cat caa caa gga ggc ggt gaa ggt agc gga gaa        462
Gly Asn Val Pro Gln His Gln Gln Gly Gly Gly Glu Gly Ser Gly Glu
                 90                      95                  100 ggg act tcg aat tcg tct tct tcc tcg ggg cag aaa agg agg aga gag        510
Gly Thr Ser Asn Ser Ser Ser Ser Ser Gly Gln Lys Arg Arg Arg Glu
                     105                     110                 115 gtg gag gaa ggt ggc gcc aaa gcg gtt aag gca gct aat act ttg acg        558
Val Glu Glu Gly Gly Ala Lys Ala Val Lys Ala Ala Asn Thr Leu Thr
                 120                     125                 130 gtt gat caa tat ttc tcc ggt ggt agc tct act tct aaa gtg aga gaa        606
Val Asp Gln Tyr Phe Ser Gly Gly Ser Ser Thr Ser Lys Val Arg Glu
135                     140                     145 gct tcg agt aac atg tca ggt ccg ggc cca aca tac gag tat aca act        654
Ala Ser Ser Asn Met Ser Gly Pro Gly Pro Thr Tyr Glu Tyr Thr Thr
150                     155                     160                 165 acg gca act gct agt agc gaa acg tcg tcg ttt agt ggg gac caa cct        702
Thr Ala Thr Ala Ser Ser Glu Thr Ser Ser Phe Ser Gly Asp Gln Pro
                 170                     175                 180 cgg cga aga tac aga gga gtt aga caa aga cca tgg gga aag tgg gcg        750
Arg Arg Arg Tyr Arg Gly Val Arg Gln Arg Pro Trp Gly Lys Trp Ala
                 185                     190                 195 gct gag att cga gat cca ttt aaa gca gct aga gtt tgg ctc ggt acg        798
Ala Glu Ile Arg Asp Pro Phe Lys Ala Ala Arg Val Trp Leu Gly Thr
                 200                     205                 210 ttc gac aat gct gaa tca gca gca aga gct tac gac gaa gct gca ctt        846
Phe Asp Asn Ala Glu Ser Ala Ala Arg Ala Tyr Asp Glu Ala Ala Leu
                 215                     220                     225 cgg ttt aga ggc aac aaa gcc aaa ctc aac ttc cct gaa aac gtc aaa        894
Arg Phe Arg Gly Asn Lys Ala Lys Leu Asn Phe Pro Glu Asn Val Lys
230                     235                     240                 245 ctc gtt aga cct gct tca acc gaa gca caa cct gtg cac caa acc gct        942
Leu Val Arg Pro Ala Ser Thr Glu Ala Gln Pro Val His Gln Thr Ala
                 250                     255                 260 gct caa aga ccg acc cag tca agg aac tcg ggt tca acg act acc ctt        990
Ala Gln Arg Pro Thr Gln Ser Arg Asn Ser Gly Ser Thr Thr Thr Leu
                 265                     270                 275 ttg ccc ata aga cct gct tcg aat caa agc gtt cat tcg cag ccg ttg       1038
Leu Pro Ile Arg Pro Ala Ser Asn Gln Ser Val His Ser Gln Pro Leu
                 280                     285                 290 atg caa tca tac aac ttg agt tac tct gaa atg gct cgt caa caa caa       1086
Met Gln Ser Tyr Asn Leu Ser Tyr Ser Glu Met Ala Arg Gln Gln Gln
             295                     300                 305 cag ttt cag caa cat cat caa caa tct ttg gat tta tac gat caa atg       1134
Gln Phe Gln Gln His His Gln Gln Ser Leu Asp Leu Tyr Asp Gln Met
310                     315                     320                 325 tcg ttt ccg ttg cgt ttc ggt cac act gga ggt tca atg atg caa tct       1182
Ser Phe Pro Leu Arg Phe Gly His Thr Gly Gly Ser Met Met Gln Ser
                 330                     335                 340 acg tcg tca tca tca tct cat tct cgt cct ctg ttt tcc ccg gct gct       1230
Thr Ser Ser Ser Ser Ser His Ser Arg Pro Leu Phe Ser Pro Ala Ala
             345                     350                 355 gtt cag ccg cca cca gaa tca gct agc gaa acc ggt tat ctc cag gat       1278
```

-continued

```
Val Gln Pro Pro Glu Ser Ala Ser Glu Thr Gly Tyr Leu Gln Asp
        360                 365                 370 ata caa tgg cca tca gac aag act agt aat aac tac aat aat agt cca    1326
Ile Gln Trp Pro Ser Asp Lys Thr Ser Asn Asn Tyr Asn Asn Ser Pro
        375                 380                 385 tcc tcc tga tgacttgctt catttatt gtttcactat agagtaatag              1375
Ser Ser *
390 aaaacaggaa aatgattata tgttatagag ttattttcc aaatattata gggtttaggt   1435 tgtttgtatt gttctgcttt catcctctca tgcttttttt cttaatttat tatattttg   1495 cattataatt tcgtttcatt gtaacaaaca ttaaaaagac cacatggaga aggaaaaaa   1555 aagagag                                                            1562
```

<210> SEQ ID NO 102
<211> LENGTH: 391
<212> TYPE: PRT
<213> ORGANISM: Arabidopsis thaliana

<400> SEQUENCE: 102

```
Met Cys Val Leu Lys Val Ala Asn Gln Glu Asp Asn Val Gly Lys Lys
 1               5                  10                  15

Ala Glu Ser Ile Arg Asp Asp His Arg Thr Leu Ser Glu Ile Asp
            20                  25                  30

Gln Trp Leu Tyr Leu Phe Ala Ala Glu Asp Asp His His Arg His Ser
        35                  40                  45

Phe Pro Thr Gln Gln Pro Pro Pro Ser Ser Ser Ser Ser Leu Ile
    50                  55                  60

Ser Gly Phe Ser Arg Glu Met Glu Met Ser Ala Ile Val Ser Ala Leu
65                  70                  75                  80

Thr His Val Val Ala Gly Asn Val Pro Gln His Gln Gln Gly Gly Gly
                85                  90                  95

Glu Gly Ser Gly Glu Gly Thr Ser Asn Ser Ser Ser Ser Gly Gln
            100                 105                 110

Lys Arg Arg Arg Glu Val Glu Glu Gly Gly Ala Lys Ala Val Lys Ala
        115                 120                 125

Ala Asn Thr Leu Thr Val Asp Gln Tyr Phe Ser Gly Gly Ser Ser Thr
    130                 135                 140

Ser Lys Val Arg Glu Ala Ser Ser Asn Met Ser Gly Pro Gly Pro Thr
145                 150                 155                 160

Tyr Glu Tyr Thr Thr Thr Ala Thr Ala Ser Ser Glu Thr Ser Ser Phe
                165                 170                 175

Ser Gly Asp Gln Pro Arg Arg Arg Tyr Arg Gly Val Arg Gln Arg Pro
            180                 185                 190

Trp Gly Lys Trp Ala Ala Glu Ile Arg Asp Pro Phe Lys Ala Ala Arg
        195                 200                 205

Val Trp Leu Gly Thr Phe Asp Asn Ala Glu Ser Ala Ala Arg Ala Tyr
    210                 215                 220

Asp Glu Ala Ala Leu Arg Phe Arg Gly Asn Lys Ala Lys Leu Asn Phe
225                 230                 235                 240

Pro Glu Asn Val Lys Leu Val Arg Pro Ala Ser Thr Glu Ala Gln Pro
                245                 250                 255

Val His Gln Thr Ala Ala Gln Arg Pro Thr Gln Ser Arg Asn Ser Gly
            260                 265                 270

Ser Thr Thr Thr Leu Leu Pro Ile Arg Pro Ala Ser Asn Gln Ser Val
```

-continued

```
                275                 280                 285
His Ser Gln Pro Leu Met Gln Ser Tyr Asn Leu Ser Tyr Ser Glu Met
    290                 295                 300

Ala Arg Gln Gln Gln Phe Gln Gln His His Gln Gln Ser Leu Asp
305                 310                 315                 320

Leu Tyr Asp Gln Met Ser Phe Pro Leu Arg Phe Gly His Thr Gly Gly
                325                 330                 335

Ser Met Met Gln Ser Thr Ser Ser Ser Ser His Ser Arg Pro Leu
                340                 345                 350

Phe Ser Pro Ala Ala Val Gln Pro Pro Glu Ser Ala Ser Glu Thr
    355                 360                 365

Gly Tyr Leu Gln Asp Ile Gln Trp Pro Ser Asp Lys Thr Ser Asn Asn
    370                 375                 380

Tyr Asn Asn Ser Pro Ser Ser
385                 390

<210> SEQ ID NO 103
<211> LENGTH: 1456
<212> TYPE: DNA
<213> ORGANISM: Arabidopsis thaliana
<220> FEATURE:
<221> NAME/KEY: CDS
<222> LOCATION: (102)...(1241)

<400> SEQUENCE: 103
attagggttt tgttgtcgtg agatttgatt acacaaattg ctgaatttgg tttcgattat      60
tggtgttatt gttttcgaag atttccagtg agtttccgtt t atg gat ctg act gga    116
                                              Met Asp Leu Thr Gly
                                                1               5 gga ttt gga gct aga tcc ggc ggt gtt gga ccg tgc cgg gaa cca ata       164
Gly Phe Gly Ala Arg Ser Gly Gly Val Gly Pro Cys Arg Glu Pro Ile
            10                  15                  20 ggc ctt gaa tcg cta cat ctc ggt gac gaa ttt cgg caa cta gtg acg       212
Gly Leu Glu Ser Leu His Leu Gly Asp Glu Phe Arg Gln Leu Val Thr
        25                  30                  35 act tta cct ccc gag aac ccc ggc ggt tcg ttc acg gct ttg ctt gag       260
Thr Leu Pro Pro Glu Asn Pro Gly Gly Ser Phe Thr Ala Leu Leu Glu
    40                  45                  50 ctt cca cct aca caa gca gtg gag ctt ctc cat ttc act gat tct tcg       308
Leu Pro Pro Thr Gln Ala Val Glu Leu Leu His Phe Thr Asp Ser Ser
55                  60                  65 tct tct caa caa gcg gca gtg aca ggg atc ggt gga gag att cct ccg       356
Ser Ser Gln Gln Ala Ala Val Thr Gly Ile Gly Gly Glu Ile Pro Pro
70                  75                  80                  85 ccg ctt cac tct ttc ggt ggg aca ttg gct ttt cct tct aac tca gtt       404
Pro Leu His Ser Phe Gly Gly Thr Leu Ala Phe Pro Ser Asn Ser Val
            90                  95                  100 ctc atg gag cga gca gct cgt ttc tcg gtg att gcc act gag caa caa       452
Leu Met Glu Arg Ala Ala Arg Phe Ser Val Ile Ala Thr Glu Gln Gln
        105                 110                 115 aac gga aat atc tcc ggg gag act ccg acg agc tct gta cct tcc aat       500
Asn Gly Asn Ile Ser Gly Glu Thr Pro Thr Ser Ser Val Pro Ser Asn
    120                 125                 130 tca agt gct aat ctc gac aga gtc aag acg gag cct gct gag acc gat       548
Ser Ser Ala Asn Leu Asp Arg Val Lys Thr Glu Pro Ala Glu Thr Asp
135                 140                 145 tca tct cag cgg ttg att tct gat tca gcg att gag aat caa atc cct       596
Ser Ser Gln Arg Leu Ile Ser Asp Ser Ala Ile Glu Asn Gln Ile Pro
150                 155                 160                 165
```

```
tgc cct aac cag aac aat cga aat ggg aag agg aaa gat ttc gaa aag        644
Cys Pro Asn Gln Asn Asn Arg Asn Gly Lys Arg Lys Asp Phe Glu Lys
            170                 175                 180 aag ggt aaa agc tcg acg aag aag aac aaa agc tct gaa gag aac gag        692
Lys Gly Lys Ser Ser Thr Lys Lys Asn Lys Ser Ser Glu Glu Asn Glu
185                 190                 195 aag ctg cca tat gtt cac gtt aga gct cgt cgt ggt caa gca acc gat        740
Lys Leu Pro Tyr Val His Val Arg Ala Arg Arg Gly Gln Ala Thr Asp
        200                 205                 210 agc cat agc tta gca gaa cga gca aga aga gag aag ata aat gca cga        788
Ser His Ser Leu Ala Glu Arg Ala Arg Arg Glu Lys Ile Asn Ala Arg
    215                 220                 225 atg aag ctg tta cag gaa ctg gtc cca ggc tgt gat aag att caa ggt        836
Met Lys Leu Leu Gln Glu Leu Val Pro Gly Cys Asp Lys Ile Gln Gly
230                 235                 240                 245 acc gcg ctg gtg ctg gat gaa atc att aac cat gtc cag tca tta caa        884
Thr Ala Leu Val Leu Asp Glu Ile Ile Asn His Val Gln Ser Leu Gln
            250                 255                 260 cgt caa gtg gag atg cta tca atg aga ctt gct gcg gta aac ccc aga        932
Arg Gln Val Glu Met Leu Ser Met Arg Leu Ala Ala Val Asn Pro Arg
        265                 270                 275 atc gac ttc aat ctc gac acc ata ttg gct tca gaa aac ggt tct tta        980
Ile Asp Phe Asn Leu Asp Thr Ile Leu Ala Ser Glu Asn Gly Ser Leu
    280                 285                 290 atg gat ggg agc ttc aat gcc gca cca atg cag ctt gct tgg cct cag       1028
Met Asp Gly Ser Phe Asn Ala Ala Pro Met Gln Leu Ala Trp Pro Gln
295                 300                 305 caa gcc att gag acc gaa cag tcc ttt cat cac cgg caa ctg caa caa       1076
Gln Ala Ile Glu Thr Glu Gln Ser Phe His His Arg Gln Leu Gln Gln
310                 315                 320                 325 cca cca aca caa caa tgg cct ttt gac ggc ttg aac cag ccg gta tgg       1124
Pro Pro Thr Gln Gln Trp Pro Phe Asp Gly Leu Asn Gln Pro Val Trp
            330                 335                 340 gga aga gaa gag gat caa gct cat ggc aat gat aac agc aat ttg atg       1172
Gly Arg Glu Glu Asp Gln Ala His Gly Asn Asp Asn Ser Asn Leu Met
        345                 350                 355 gca gtt tct gaa aat gta atg gtg gct tct gct aat ttg cac cca aat       1220
Ala Val Ser Glu Asn Val Met Val Ala Ser Ala Asn Leu His Pro Asn
    360                 365                 370 cag gtc aaa atg gag ctg taa gttgggaaaa cggtagagat catgaatgtg          1271
Gln Val Lys Met Glu Leu  *
        375 tatatacatc gtataagctc gtttctctct atataaatat aatcataaat atagatatct     1331 gttaagaagg tatcagtcat ttgattcaga gagacaacac tggtatgatt gtttcttatt     1391 cttgtaccag atttcgacaa tgtagaattt agtaggatat gatcattttg atctcgttat     1451 atata                                                                 1456

<210> SEQ ID NO 104
<211> LENGTH: 379
<212> TYPE: PRT
<213> ORGANISM: Arabidopsis thaliana
<220> FEATURE:
<221> NAME/KEY: DOMAIN
<222> LOCATION: (203)...(283)
<223> OTHER INFORMATION: Conserved domain

<400> SEQUENCE: 104

Met Asp Leu Thr Gly Gly Phe Gly Ala Arg Ser Gly Gly Val Gly Pro
1               5                   10                  15
```

Cys Arg Glu Pro Ile Gly Leu Glu Ser Leu His Leu Gly Asp Glu Phe
            20                  25                  30

Arg Gln Leu Val Thr Thr Leu Pro Pro Glu Asn Pro Gly Gly Ser Phe
                35                  40                  45

Thr Ala Leu Leu Glu Leu Pro Pro Thr Gln Ala Val Glu Leu Leu His
 50                  55                  60

Phe Thr Asp Ser Ser Ser Gln Gln Ala Ala Val Thr Gly Ile Gly
 65                  70                  75                  80

Gly Glu Ile Pro Pro Pro Leu His Ser Phe Gly Gly Thr Leu Ala Phe
                85                  90                  95

Pro Ser Asn Ser Val Leu Met Glu Arg Ala Ala Arg Phe Ser Val Ile
            100                 105                 110

Ala Thr Glu Gln Gln Asn Gly Asn Ile Ser Gly Glu Thr Pro Thr Ser
            115                 120                 125

Ser Val Pro Ser Asn Ser Ser Ala Asn Leu Asp Arg Val Lys Thr Glu
130                 135                 140

Pro Ala Glu Thr Asp Ser Ser Gln Arg Leu Ile Ser Asp Ser Ala Ile
145                 150                 155                 160

Glu Asn Gln Ile Pro Cys Pro Asn Gln Asn Asn Arg Asn Gly Lys Arg
                165                 170                 175

Lys Asp Phe Glu Lys Lys Gly Lys Ser Ser Thr Lys Lys Asn Lys Ser
            180                 185                 190

Ser Glu Glu Asn Glu Lys Leu Pro Tyr Val His Val Arg Ala Arg Arg
            195                 200                 205

Gly Gln Ala Thr Asp Ser His Ser Leu Ala Glu Arg Ala Arg Arg Glu
            210                 215                 220

Lys Ile Asn Ala Arg Met Lys Leu Leu Gln Glu Leu Val Pro Gly Cys
225                 230                 235                 240

Asp Lys Ile Gln Gly Thr Ala Leu Val Leu Asp Glu Ile Ile Asn His
                245                 250                 255

Val Gln Ser Leu Gln Arg Gln Val Glu Met Leu Ser Met Arg Leu Ala
            260                 265                 270

Ala Val Asn Pro Arg Ile Asp Phe Asn Leu Asp Thr Ile Leu Ala Ser
            275                 280                 285

Glu Asn Gly Ser Leu Met Asp Gly Ser Phe Asn Ala Ala Pro Met Gln
            290                 295                 300

Leu Ala Trp Pro Gln Gln Ala Ile Glu Thr Glu Gln Ser Phe His His
305                 310                 315                 320

Arg Gln Leu Gln Gln Pro Thr Gln Gln Trp Pro Phe Asp Gly Leu
                325                 330                 335

Asn Gln Pro Val Trp Gly Arg Glu Glu Asp Gln Ala His Gly Asn Asp
            340                 345                 350

Asn Ser Asn Leu Met Ala Val Ser Glu Asn Val Met Val Ala Ser Ala
            355                 360                 365

Asn Leu His Pro Asn Gln Val Lys Met Glu Leu
        370                 375

<210> SEQ ID NO 105
<211> LENGTH: 832
<212> TYPE: DNA
<213> ORGANISM: Arabidopsis thaliana
<220> FEATURE:
<221> NAME/KEY: CDS
<222> LOCATION: (64)...(798)

```
<400> SEQUENCE: 105
aacttagtgc cacttagaca caataagaaa accgttaaca agaagaaaaa aaaaagatcg     60 aaa atg gaa tat caa act aac ttc tta agt gga gag ttt tcc ccg gag     108
    Met Glu Tyr Gln Thr Asn Phe Leu Ser Gly Glu Phe Ser Pro Glu
    1               5                   10                  15 aac tct tct tca agc tca tgg agc tca caa gaa tca ttc ttg tgg gaa     156
Asn Ser Ser Ser Ser Ser Trp Ser Ser Gln Glu Ser Phe Leu Trp Glu
                20                  25                  30 gag agt ttc tta cat caa tca ttt gac caa tcc ttc ctt tta tct agc     204
Glu Ser Phe Leu His Gln Ser Phe Asp Gln Ser Phe Leu Leu Ser Ser
            35                  40                  45 cct act gat aac tac tgt gat gac ttc ttt gca ttt gaa tca tca atc     252
Pro Thr Asp Asn Tyr Cys Asp Asp Phe Phe Ala Phe Glu Ser Ser Ile
        50                  55                  60 ata aaa gaa gaa gga aaa gaa gcc acc gtg gcg gcc gag gag gag gag     300
Ile Lys Glu Glu Gly Lys Glu Ala Thr Val Ala Ala Glu Glu Glu Glu
65                  70                  75 aag tca tac aga gga gtg agg aaa cgg ccg tgg ggg aaa ttc gcg gcc     348
Lys Ser Tyr Arg Gly Val Arg Lys Arg Pro Trp Gly Lys Phe Ala Ala
80                  85                  90                  95 gag ata aga gac tca acg agg aaa ggg ata aga gtg tgg ctt ggg aca     396
Glu Ile Arg Asp Ser Thr Arg Lys Gly Ile Arg Val Trp Leu Gly Thr
                100                 105                 110 ttc gac acc gcg gag gcg gcg gct ctc gct tat gat cag gcg gct ttc     444
Phe Asp Thr Ala Glu Ala Ala Ala Leu Ala Tyr Asp Gln Ala Ala Phe
            115                 120                 125 gct ttg aaa ggc agc ctc gca gta ctc aat ttc ccc gcg gat gtc gtt     492
Ala Leu Lys Gly Ser Leu Ala Val Leu Asn Phe Pro Ala Asp Val Val
        130                 135                 140 gaa gaa tct ctc cgg aag atg gag aat gtg aat ctc aat gat gga gag     540
Glu Glu Ser Leu Arg Lys Met Glu Asn Val Asn Leu Asn Asp Gly Glu
145                 150                 155 tct ccg gtg ata gcc ttg aag aga aaa cac tcc atg aga aac cgt cct     588
Ser Pro Val Ile Ala Leu Lys Arg Lys His Ser Met Arg Asn Arg Pro
160                 165                 170                 175 aga gga aag aag aaa tct tct tct tct tcg acg ttg aca tct tct cct     636
Arg Gly Lys Lys Lys Ser Ser Ser Ser Ser Thr Leu Thr Ser Ser Pro
                180                 185                 190 tct tcc tcc tcc tcc tat tca tct tct tcg tct tct tct tct ttg tcg     684
Ser Ser Ser Ser Ser Tyr Ser Ser Ser Ser Ser Ser Ser Ser Leu Ser
            195                 200                 205 tca aga agt aga aaa cag agt gtt gtt atg acg caa gaa agt aat aca     732
Ser Arg Ser Arg Lys Gln Ser Val Val Met Thr Gln Glu Ser Asn Thr
        210                 215                 220 aca ctt gtg gtt ctt gag gat tta ggt gct gaa tac tta gaa gag ctt     780
Thr Leu Val Val Leu Glu Asp Leu Gly Ala Glu Tyr Leu Glu Glu Leu
225                 230                 235 atg aga tca tgt tct tga taatctctgc ttctacaatt tttatgtaat            828
Met Arg Ser Cys Ser *
240 ttga                                                                832

<210> SEQ ID NO 106
<211> LENGTH: 244
<212> TYPE: PRT
<213> ORGANISM: Arabidopsis thaliana
<220> FEATURE:
<221> NAME/KEY: DOMAIN
<222> LOCATION: (79)...(139)
<223> OTHER INFORMATION: Conserved domain
```

-continued

```
<400> SEQUENCE: 106

Met Glu Tyr Gln Thr Asn Phe Leu Ser Gly Glu Phe Ser Pro Glu Asn
1               5                   10                  15

Ser Ser Ser Ser Trp Ser Ser Gln Glu Ser Phe Leu Trp Glu Glu
            20                  25                  30

Ser Phe Leu His Gln Ser Phe Asp Gln Ser Phe Leu Ser Ser Pro
        35                  40                  45

Thr Asp Asn Tyr Cys Asp Asp Phe Phe Ala Phe Glu Ser Ser Ile Ile
    50                  55                  60

Lys Glu Glu Gly Lys Glu Ala Thr Val Ala Ala Glu Glu Glu Lys
65                  70                  75                  80

Ser Tyr Arg Gly Val Arg Lys Arg Pro Trp Gly Lys Phe Ala Ala Glu
                85                  90                  95

Ile Arg Asp Ser Thr Arg Lys Gly Ile Arg Val Trp Leu Gly Thr Phe
            100                 105                 110

Asp Thr Ala Glu Ala Ala Ala Leu Ala Tyr Asp Gln Ala Ala Phe Ala
        115                 120                 125

Leu Lys Gly Ser Leu Ala Val Leu Asn Phe Pro Ala Asp Val Val Glu
    130                 135                 140

Glu Ser Leu Arg Lys Met Glu Asn Val Asn Leu Asn Asp Gly Glu Ser
145                 150                 155                 160

Pro Val Ile Ala Leu Lys Arg Lys His Ser Met Arg Asn Arg Pro Arg
                165                 170                 175

Gly Lys Lys Lys Ser Ser Ser Ser Thr Leu Thr Ser Ser Pro Ser
            180                 185                 190

Ser Ser Ser Ser Tyr Ser Ser Ser Ser Ser Ser Leu Ser Ser
        195                 200                 205

Arg Ser Arg Lys Gln Ser Val Val Met Thr Gln Glu Ser Asn Thr Thr
    210                 215                 220

Leu Val Val Leu Glu Asp Leu Gly Ala Glu Tyr Leu Glu Glu Leu Met
225                 230                 235                 240

Arg Ser Cys Ser

<210> SEQ ID NO 107
<211> LENGTH: 1182
<212> TYPE: DNA
<213> ORGANISM: Arabidopsis thaliana
<220> FEATURE:
<221> NAME/KEY: CDS
<222> LOCATION: (6)...(962)

<400> SEQUENCE: 107 cacaa atg gaa gga aga gtc aac gct ctg tca aac ata aac gat ctc gaa      50
      Met Glu Gly Arg Val Asn Ala Leu Ser Asn Ile Asn Asp Leu Glu
      1               5                   10                  15 ctt cac aat ttc ttg gtc gat cca aac ttc gat cag ttc ata aac ctc       98
Leu His Asn Phe Leu Val Asp Pro Asn Phe Asp Gln Phe Ile Asn Leu
                20                  25                  30 ata aga gga gat cat caa acc att gac gaa aac cca gtt ctt gat ttc      146
Ile Arg Gly Asp His Gln Thr Ile Asp Glu Asn Pro Val Leu Asp Phe
            35                  40                  45 gat ctt ggt cca tta caa aac agc ccc tgt ttc ata gac gag aac cag      194
Asp Leu Gly Pro Leu Gln Asn Ser Pro Cys Phe Ile Asp Glu Asn Gln
        50                  55                  60 ttc atc cca aca cct gtc gat gac ctc ttc gac gaa ttg cct gac tta      242
Phe Ile Pro Thr Pro Val Asp Asp Leu Phe Asp Glu Leu Pro Asp Leu
```

-continued

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
|     |     | 65  |     |     |     |     | 70  |     |     |     |     | 75  |     |     |     |     |
| gac | tcc | aac | gtt | gct | gaa | tca | ttc | cgt | agc | ttc | gac | ggt | gat | agt | gtt | 290 |
| Asp | Ser | Asn | Val | Ala | Glu | Ser | Phe | Arg | Ser | Phe | Asp | Gly | Asp | Ser | Val |     |
| 80  |     |     |     |     | 85  |     |     |     |     | 90  |     |     |     |     | 95  |     |
| aga | gcc | ggt | ggt | gaa | gaa | gat | gaa | gaa | gat | tac | aac | gac | ggt | gat | gat | 338 |
| Arg | Ala | Gly | Gly | Glu | Glu | Asp | Glu | Glu | Asp | Tyr | Asn | Asp | Gly | Asp | Asp |     |
|     |     |     |     | 100 |     |     |     |     | 105 |     |     |     |     | 110 |     |     |
| tct | tca | gcc | act | act | acg | aat | aat | gat | ggg | acc | cgt | aag | acg | aag | act | 386 |
| Ser | Ser | Ala | Thr | Thr | Thr | Asn | Asn | Asp | Gly | Thr | Arg | Lys | Thr | Lys | Thr |     |
|     |     |     |     | 115 |     |     |     |     | 120 |     |     |     |     | 125 |     |     |
| gat | cgg | tct | agg | act | ttg | atc | tct | gag | aga | aga | agg | aga | ggg | cgt | atg | 434 |
| Asp | Arg | Ser | Arg | Thr | Leu | Ile | Ser | Glu | Arg | Arg | Arg | Arg | Gly | Arg | Met |     |
|     |     |     | 130 |     |     |     |     | 135 |     |     |     |     | 140 |     |     |     |
| aag | gat | aag | ctt | tat | gca | ttg | aga | tct | ctt | gtt | ccc | aat | att | act | aag | 482 |
| Lys | Asp | Lys | Leu | Tyr | Ala | Leu | Arg | Ser | Leu | Val | Pro | Asn | Ile | Thr | Lys |     |
|     | 145 |     |     |     |     | 150 |     |     |     |     | 155 |     |     |     |     |     |
| atg | gat | aaa | gca | tcc | att | gtt | gga | gat | gca | gtg | ttg | tat | gtt | caa | gaa | 530 |
| Met | Asp | Lys | Ala | Ser | Ile | Val | Gly | Asp | Ala | Val | Leu | Tyr | Val | Gln | Glu |     |
| 160 |     |     |     |     | 165 |     |     |     |     | 170 |     |     |     |     | 175 |     |
| ctt | cag | tca | caa | gcg | aag | aaa | ctc | aaa | tcc | gat | atc | gcg | ggt | ctt | gaa | 578 |
| Leu | Gln | Ser | Gln | Ala | Lys | Lys | Leu | Lys | Ser | Asp | Ile | Ala | Gly | Leu | Glu |     |
|     |     |     |     | 180 |     |     |     |     | 185 |     |     |     |     | 190 |     |     |
| gct | tct | tta | aac | tct | act | gga | ggg | tac | caa | gaa | cat | gct | cct | gat | gct | 626 |
| Ala | Ser | Leu | Asn | Ser | Thr | Gly | Gly | Tyr | Gln | Glu | His | Ala | Pro | Asp | Ala |     |
|     |     |     | 195 |     |     |     |     | 200 |     |     |     |     | 205 |     |     |     |
| caa | aag | act | caa | cct | ttt | cgc | ggt | atc | aat | cct | cct | gct | tcc | aaa | aaa | 674 |
| Gln | Lys | Thr | Gln | Pro | Phe | Arg | Gly | Ile | Asn | Pro | Pro | Ala | Ser | Lys | Lys |     |
|     | 210 |     |     |     |     | 215 |     |     |     |     | 220 |     |     |     |     |     |
| atc | att | cag | atg | gat | gtt | ata | caa | gtg | gag | gag | aaa | ggg | ttt | tat | gtg | 722 |
| Ile | Ile | Gln | Met | Asp | Val | Ile | Gln | Val | Glu | Glu | Lys | Gly | Phe | Tyr | Val |     |
| 225 |     |     |     |     | 230 |     |     |     |     | 235 |     |     |     |     |     |     |
| aga | ttg | gtg | tgt | aac | aaa | gga | gaa | ggt | gtt | gct | cca | tct | ctt | tac | aag | 770 |
| Arg | Leu | Val | Cys | Asn | Lys | Gly | Glu | Gly | Val | Ala | Pro | Ser | Leu | Tyr | Lys |     |
| 240 |     |     |     |     | 245 |     |     |     |     | 250 |     |     |     |     | 255 |     |
| tct | ttg | gag | tct | ctt | aca | agt | ttc | caa | gtg | cag | aac | tct | aac | cta | agc | 818 |
| Ser | Leu | Glu | Ser | Leu | Thr | Ser | Phe | Gln | Val | Gln | Asn | Ser | Asn | Leu | Ser |     |
|     |     |     |     | 260 |     |     |     |     | 265 |     |     |     |     | 270 |     |     |
| tct | cct | tct | ccg | gac | aca | tac | ctc | tta | aca | tat | acc | tta | gat | ggg | aca | 866 |
| Ser | Pro | Ser | Pro | Asp | Thr | Tyr | Leu | Leu | Thr | Tyr | Thr | Leu | Asp | Gly | Thr |     |
|     |     |     | 275 |     |     |     |     | 280 |     |     |     |     | 285 |     |     |     |
| tgc | ttc | gaa | cag | agc | tta | aac | ttg | cct | aac | ctg | aag | ctg | tgg | atc | act | 914 |
| Cys | Phe | Glu | Gln | Ser | Leu | Asn | Leu | Pro | Asn | Leu | Lys | Leu | Trp | Ile | Thr |     |
|     | 290 |     |     |     |     | 295 |     |     |     |     | 300 |     |     |     |     |     |
| gga | tca | ctt | tta | aat | caa | ggt | ttt | gaa | ttc | atc | aag | tca | ttt | act | tga | 962 |
| Gly | Ser | Leu | Leu | Asn | Gln | Gly | Phe | Glu | Phe | Ile | Lys | Ser | Phe | Thr | *   |     |
| 305 |     |     |     |     | 310 |     |     |     |     | 315 |     |     |     |     |     |     | ttctataacg cttgctctaa cgtgagtcaa atccggttct gcactatatt gattgtgtac      1022 ctttcttaca tgtttcataa cttccagggc tctaatttct attctagtga tgatgtaacc      1082 gagattgttg attctctatt gaataaacac catgttatat agtaatttag cgacaaattg      1142 tatggttaaa tgaagtaata tttatgtttt gtttataaaa                           1182

<210> SEQ ID NO 108
<211> LENGTH: 318
<212> TYPE: PRT
<213> ORGANISM: Arabidopsis thaliana
<220> FEATURE:
<221> NAME/KEY: DOMAIN
<222> LOCATION: (121)...(187)
<223> OTHER INFORMATION: Conserved domain -continued

<400> SEQUENCE: 108

```
Met Glu Gly Arg Val Asn Ala Leu Ser Asn Ile Asn Asp Leu Glu Leu
  1               5                  10                  15

His Asn Phe Leu Val Asp Pro Asn Phe Asp Gln Phe Ile Asn Leu Ile
             20                  25                  30

Arg Gly Asp His Gln Thr Ile Asp Glu Asn Pro Val Leu Asp Phe Asp
         35                  40                  45

Leu Gly Pro Leu Gln Asn Ser Pro Cys Phe Ile Asp Glu Asn Gln Phe
     50                  55                  60

Ile Pro Thr Pro Val Asp Asp Leu Phe Asp Glu Leu Pro Asp Leu Asp
 65                  70                  75                  80

Ser Asn Val Ala Glu Ser Phe Arg Ser Phe Asp Gly Asp Ser Val Arg
                 85                  90                  95

Ala Gly Gly Glu Glu Asp Glu Glu Asp Tyr Asn Asp Gly Asp Asp Ser
            100                 105                 110

Ser Ala Thr Thr Thr Asn Asn Asp Gly Thr Arg Lys Thr Lys Thr Asp
        115                 120                 125

Arg Ser Arg Thr Leu Ile Ser Glu Arg Arg Arg Gly Arg Met Lys
    130                 135                 140

Asp Lys Leu Tyr Ala Leu Arg Ser Leu Val Pro Asn Ile Thr Lys Met
145                 150                 155                 160

Asp Lys Ala Ser Ile Val Gly Asp Ala Val Leu Tyr Val Gln Glu Leu
                165                 170                 175

Gln Ser Gln Ala Lys Lys Leu Lys Ser Asp Ile Ala Gly Leu Glu Ala
            180                 185                 190

Ser Leu Asn Ser Thr Gly Gly Tyr Gln Glu His Ala Pro Asp Ala Gln
        195                 200                 205

Lys Thr Gln Pro Phe Arg Gly Ile Asn Pro Pro Ala Ser Lys Lys Ile
    210                 215                 220

Ile Gln Met Asp Val Ile Gln Val Glu Glu Lys Gly Phe Tyr Val Arg
225                 230                 235                 240

Leu Val Cys Asn Lys Gly Glu Gly Val Ala Pro Ser Leu Tyr Lys Ser
                245                 250                 255

Leu Glu Ser Leu Thr Ser Phe Gln Val Gln Asn Ser Asn Leu Ser Ser
            260                 265                 270

Pro Ser Pro Asp Thr Tyr Leu Leu Thr Tyr Thr Leu Asp Gly Thr Cys
        275                 280                 285

Phe Glu Gln Ser Leu Asn Leu Pro Asn Leu Lys Leu Trp Ile Thr Gly
    290                 295                 300

Ser Leu Leu Asn Gln Gly Phe Glu Phe Ile Lys Ser Phe Thr
305                 310                 315
```

<210> SEQ ID NO 109
<211> LENGTH: 1613
<212> TYPE: DNA
<213> ORGANISM: Arabidopsis thaliana
<220> FEATURE:
<221> NAME/KEY: CDS
<222> LOCATION: (30)...(1430)

<400> SEQUENCE: 109

```
cttgtaccag tttctgatta gattcaaca atg aac ggc gca tta ggt aac tcc        53
                                 Met Asn Gly Ala Leu Gly Asn Ser
                                   1               5 tcc gcc tcc gtt agc ggc gga gaa gga gcc gga gga cca gcg cct ttc       101
```

```
Ser Ala Ser Val Ser Gly Gly Glu Gly Ala Gly Gly Pro Ala Pro Phe
    10                  15                  20 ttg gtg aaa acc tac gag atg gtc gac gat tca tca acg gac cag atc         149
Leu Val Lys Thr Tyr Glu Met Val Asp Asp Ser Ser Thr Asp Gln Ile
25                  30                  35                  40 gta tcg tgg agc gct aac aac aac agc ttc atc gtt tgg aat cat gcc         197
Val Ser Trp Ser Ala Asn Asn Asn Ser Phe Ile Val Trp Asn His Ala
                45                  50                  55 gaa ttt tca cgc ctc ctt ctt cca acc tac ttc aaa cac aat aac ttc         245
Glu Phe Ser Arg Leu Leu Leu Pro Thr Tyr Phe Lys His Asn Asn Phe
                60                  65                  70 tct tcc ttc att cgt cag ctc aat acc tat ggg ttt agg aag att gat         293
Ser Ser Phe Ile Arg Gln Leu Asn Thr Tyr Gly Phe Arg Lys Ile Asp
            75                  80                  85 cca gag agg tgg gag ttt ttg aat gat gat ttt att aag gat cag aag         341
Pro Glu Arg Trp Glu Phe Leu Asn Asp Asp Phe Ile Lys Asp Gln Lys
        90                  95                  100 cat ctt ctc aag aat ata cat aga agg aaa cct ata cac agc cac agt         389
His Leu Leu Lys Asn Ile His Arg Arg Lys Pro Ile His Ser His Ser
105                 110                 115                 120 cat cca cct gct tcg tcg act gat caa gaa aga gca gtg ttg caa gag         437
His Pro Pro Ala Ser Ser Thr Asp Gln Glu Arg Ala Val Leu Gln Glu
                125                 130                 135 caa atg gac aag ctt tca cgt gag aaa gct gca att gaa gct aag ctt         485
Gln Met Asp Lys Leu Ser Arg Glu Lys Ala Ala Ile Glu Ala Lys Leu
            140                 145                 150 tta aag ttc aaa caa cag aag gtt gta gca aag cat cag ttt gaa gaa         533
Leu Lys Phe Lys Gln Gln Lys Val Val Ala Lys His Gln Phe Glu Glu
        155                 160                 165 atg act gag cat gtt gat gat atg gag aat agg cag aag aag ctg ctg         581
Met Thr Glu His Val Asp Asp Met Glu Asn Arg Gln Lys Lys Leu Leu
170                 175                 180 aat ttt ttg gaa act gcg att cgg aat cct act ttt gtt aag aat ttt         629
Asn Phe Leu Glu Thr Ala Ile Arg Asn Pro Thr Phe Val Lys Asn Phe
185                 190                 195                 200 ggt aag aaa gtc gag cag ttg gat att tca gct tac aac aaa aag cga         677
Gly Lys Lys Val Glu Gln Leu Asp Ile Ser Ala Tyr Asn Lys Lys Arg
                205                 210                 215 agg ctc cct gaa gtt gag caa tca aag cca cct tca gaa gat tct cat         725
Arg Leu Pro Glu Val Glu Gln Ser Lys Pro Pro Ser Glu Asp Ser His
            220                 225                 230 ctg gat aat agt agt ggt agc tcg aga cgc gag tct gga aac att ttt         773
Leu Asp Asn Ser Ser Gly Ser Ser Arg Arg Glu Ser Gly Asn Ile Phe
        235                 240                 245 cat caa aat ttc tct aat aaa ttg cga cta gag ctt tct cca gct gat         821
His Gln Asn Phe Ser Asn Lys Leu Arg Leu Glu Leu Ser Pro Ala Asp
250                 255                 260 tca gat atg aac atg gtt tca cac agt ata caa agt tcc aat gaa gaa         869
Ser Asp Met Asn Met Val Ser His Ser Ile Gln Ser Ser Asn Glu Glu
265                 270                 275                 280 ggt gcg agt ccc aaa ggg ata ctg tca gga ggt gat cca aat act aca         917
Gly Ala Ser Pro Lys Gly Ile Leu Ser Gly Gly Asp Pro Asn Thr Thr
                285                 290                 295 cta aca aaa aga gaa ggc cta cca ttt gca cct gaa gct cta gag ctt         965
Leu Thr Lys Arg Glu Gly Leu Pro Phe Ala Pro Glu Ala Leu Glu Leu
            300                 305                 310 gcg gat acc ggg aca tgc ccg agg aga tta ctg tta aat gat aat aca        1013
Ala Asp Thr Gly Thr Cys Pro Arg Arg Leu Leu Leu Asn Asp Asn Thr
        315                 320                 325
```

-continued

```
agg gtg gag acc ttg cag cag agg cta act tct tca gag gag act gat    1061
Arg Val Glu Thr Leu Gln Gln Arg Leu Thr Ser Ser Glu Glu Thr Asp
    330                 335                 340 ggt agc ttt tca tgt cat tta aat cta acc ctg gct tct gct ccg tta    1109
Gly Ser Phe Ser Cys His Leu Asn Leu Thr Leu Ala Ser Ala Pro Leu
345                 350                 355                 360 ccg gac aaa aca gct tca cag ata gct aag acg act ctt aaa agt cag    1157
Pro Asp Lys Thr Ala Ser Gln Ile Ala Lys Thr Thr Leu Lys Ser Gln
                365                 370                 375 gag tta aac ttt aac tca ata gaa aca agt gca agt gag aaa aat cgg    1205
Glu Leu Asn Phe Asn Ser Ile Glu Thr Ser Ala Ser Glu Lys Asn Arg
            380                 385                 390 ggt aga caa gag att gca gtt gga ggt agc caa gca aat gca gct cct    1253
Gly Arg Gln Glu Ile Ala Val Gly Gly Ser Gln Ala Asn Ala Ala Pro
        395                 400                 405 cca gca aga gtg aat gat gta ttc tgg gaa cag ttc cta aca gaa agg    1301
Pro Ala Arg Val Asn Asp Val Phe Trp Glu Gln Phe Leu Thr Glu Arg
    410                 415                 420 cca ggg tct tca gat aat gag gag gca agt tcg act tat aga ggt aac    1349
Pro Gly Ser Ser Asp Asn Glu Glu Ala Ser Ser Thr Tyr Arg Gly Asn
425                 430                 435                 440 cca tac gaa gag caa gag gag aaa aga aac ggg agt atg atg tta cgt    1397
Pro Tyr Glu Glu Gln Glu Glu Lys Arg Asn Gly Ser Met Met Leu Arg
                445                 450                 455 aat aca aag aat atc gag cag ctg acc tta taa actatttgga cggttacatc  1450
Asn Thr Lys Asn Ile Glu Gln Leu Thr Leu *
            460                 465 aacgagagta cgaactgagg ttttggtaag aagtatgggt gagtaagtaa tgaaacattg   1510
gactgaaaaa gcgtaagtag ctttgttgta aacacttgcg tctctgtcta cacaagtaat   1570
ttgactgtaa atgtaagtgt acaggattta aattgaataa gca                    1613
```

<210> SEQ ID NO 110
<211> LENGTH: 466
<212> TYPE: PRT
<213> ORGANISM: Arabidopsis thaliana
<220> FEATURE:
<221> NAME/KEY: DOMAIN
<222> LOCATION: (24)...(114)
<223> OTHER INFORMATION: Conserved domain

<400> SEQUENCE: 110

```
Met Asn Gly Ala Leu Gly Asn Ser Ser Ala Ser Val Ser Gly Gly Glu
  1               5                  10                  15

Gly Ala Gly Gly Pro Ala Pro Phe Leu Val Lys Thr Tyr Glu Met Val
             20                  25                  30

Asp Asp Ser Ser Thr Asp Gln Ile Val Ser Trp Ser Ala Asn Asn Asn
         35                  40                  45

Ser Phe Ile Val Trp Asn His Ala Glu Phe Ser Arg Leu Leu Leu Pro
     50                  55                  60

Thr Tyr Phe Lys His Asn Asn Phe Ser Ser Phe Ile Arg Gln Leu Asn
 65                  70                  75                  80

Thr Tyr Gly Phe Arg Lys Ile Asp Pro Glu Arg Trp Glu Phe Leu Asn
                 85                  90                  95

Asp Asp Phe Ile Lys Asp Gln Lys His Leu Leu Lys Asn Ile His Arg
            100                 105                 110

Arg Lys Pro Ile His Ser His Ser His Pro Pro Ala Ser Ser Thr Asp
        115                 120                 125

Gln Glu Arg Ala Val Leu Gln Glu Gln Met Asp Lys Leu Ser Arg Glu
```

```
            130                 135                 140
Lys Ala Ala Ile Glu Ala Lys Leu Leu Lys Phe Lys Gln Gln Lys Val
145                 150                 155                 160

Val Ala Lys His Gln Phe Glu Glu Met Thr Glu His Val Asp Asp Met
                165                 170                 175

Glu Asn Arg Gln Lys Lys Leu Leu Asn Phe Leu Glu Thr Ala Ile Arg
            180                 185                 190

Asn Pro Thr Phe Val Lys Asn Phe Gly Lys Lys Val Glu Gln Leu Asp
        195                 200                 205

Ile Ser Ala Tyr Asn Lys Lys Arg Arg Leu Pro Glu Val Glu Gln Ser
    210                 215                 220

Lys Pro Pro Ser Glu Asp Ser His Leu Asp Asn Ser Ser Gly Ser Ser
225                 230                 235                 240

Arg Arg Glu Ser Gly Asn Ile Phe His Gln Asn Phe Ser Asn Lys Leu
                245                 250                 255

Arg Leu Glu Leu Ser Pro Ala Asp Ser Asp Met Asn Met Val Ser His
            260                 265                 270

Ser Ile Gln Ser Ser Asn Glu Glu Gly Ala Ser Pro Lys Gly Ile Leu
        275                 280                 285

Ser Gly Gly Asp Pro Asn Thr Thr Leu Thr Lys Arg Glu Gly Leu Pro
    290                 295                 300

Phe Ala Pro Glu Ala Leu Glu Leu Ala Asp Thr Gly Thr Cys Pro Arg
305                 310                 315                 320

Arg Leu Leu Leu Asn Asp Asn Thr Arg Val Glu Thr Leu Gln Gln Arg
                325                 330                 335

Leu Thr Ser Ser Glu Glu Thr Asp Gly Ser Phe Ser Cys His Leu Asn
            340                 345                 350

Leu Thr Leu Ala Ser Ala Pro Leu Pro Asp Lys Thr Ala Ser Gln Ile
        355                 360                 365

Ala Lys Thr Thr Leu Lys Ser Gln Glu Leu Asn Phe Asn Ser Ile Glu
    370                 375                 380

Thr Ser Ala Ser Glu Lys Asn Arg Gly Arg Gln Glu Ile Ala Val Gly
385                 390                 395                 400

Gly Ser Gln Ala Asn Ala Ala Pro Pro Ala Arg Val Asn Asp Val Phe
                405                 410                 415

Trp Glu Gln Phe Leu Thr Glu Arg Pro Gly Ser Ser Asp Asn Glu Glu
            420                 425                 430

Ala Ser Ser Thr Tyr Arg Gly Asn Pro Tyr Glu Glu Gln Glu Glu Lys
        435                 440                 445

Arg Asn Gly Ser Met Met Leu Arg Asn Thr Lys Asn Ile Glu Gln Leu
    450                 455                 460

Thr Leu
465

<210> SEQ ID NO 111
<211> LENGTH: 840
<212> TYPE: DNA
<213> ORGANISM: Arabidopsis thaliana
<220> FEATURE:
<221> NAME/KEY: CDS
<222> LOCATION: (1)...(804)

<400> SEQUENCE: 111 atg ggg agg acg aca tgg ttc gac gtc gac ggg atg aag aaa gga gag    48
Met Gly Arg Thr Thr Trp Phe Asp Val Asp Gly Met Lys Lys Gly Glu
 1               5                  10                  15
```

```
tgg acg gca gag gaa gac cag aag ctc ggc gct tac atc aac gag cat    96
Trp Thr Ala Glu Glu Asp Gln Lys Leu Gly Ala Tyr Ile Asn Glu His
            20                  25                  30 ggc gtt tgt gat tgg cgt tcc ctc ccc aaa aga gct ggt ttg cag aga   144
Gly Val Cys Asp Trp Arg Ser Leu Pro Lys Arg Ala Gly Leu Gln Arg
        35                  40                  45 tgt gga aag agc tgc aga tta agg tgg ctt aac tat cta aag cct ggg   192
Cys Gly Lys Ser Cys Arg Leu Arg Trp Leu Asn Tyr Leu Lys Pro Gly
 50                  55                  60 att aga aga ggc aaa ttc act cct caa gaa gaa gaa atc atc caa       240
Ile Arg Arg Gly Lys Phe Thr Pro Gln Glu Glu Glu Ile Ile Gln
 65                  70                  75                  80 ctt cat gct gtt ctc gga aac agg tgg gca gcc atg gcg aag aag atg   288
Leu His Ala Val Leu Gly Asn Arg Trp Ala Ala Met Ala Lys Lys Met
                85                  90                  95 cag aat cga aca gac aat gat atc aag aac cat tgg aac tct tgt ctc   336
Gln Asn Arg Thr Asp Asn Asp Ile Lys Asn His Trp Asn Ser Cys Leu
            100                 105                 110 aag aaa aga ctt tcg aga aag gga atc gac cct atg acc cac gag ccc   384
Lys Lys Arg Leu Ser Arg Lys Gly Ile Asp Pro Met Thr His Glu Pro
        115                 120                 125 atc atc aaa cac ctc acc gtc aat acc act aac gca gat tgt ggt aac   432
Ile Ile Lys His Leu Thr Val Asn Thr Thr Asn Ala Asp Cys Gly Asn
130                 135                 140 tct tcc acc acg acg tcc ccg tcg acg acg gaa agc tct cct tcc tcc   480
Ser Ser Thr Thr Thr Ser Pro Ser Thr Thr Glu Ser Ser Pro Ser Ser
145                 150                 155                 160 ggc tcg tct cgt ctt ctt aac aaa ctc gcc gca ggt atc tca tct aga   528
Gly Ser Ser Arg Leu Leu Asn Lys Leu Ala Ala Gly Ile Ser Ser Arg
                165                 170                 175 caa cat agt ctc gat agg atc aag tac atc ttg tcg aat tca ata atc   576
Gln His Ser Leu Asp Arg Ile Lys Tyr Ile Leu Ser Asn Ser Ile Ile
            180                 185                 190 gaa agc agt gat caa gca aaa gag gaa gaa gaa aaa gaa gaa gaa gaa   624
Glu Ser Ser Asp Gln Ala Lys Glu Glu Glu Glu Lys Glu Glu Glu Glu
        195                 200                 205 gaa gaa aga gat tca atg atg ggt cag aag att gac ggt agt gaa gga   672
Glu Glu Arg Asp Ser Met Met Gly Gln Lys Ile Asp Gly Ser Glu Gly
210                 215                 220 gaa gat att cag att tgg ggc gag gag gaa gtt agg cgt tta atg gag   720
Glu Asp Ile Gln Ile Trp Gly Glu Glu Glu Val Arg Arg Leu Met Glu
225                 230                 235                 240 att gat gca atg gat atg tac gag atg act tcg tac gac gct gtc atg   768
Ile Asp Ala Met Asp Met Tyr Glu Met Thr Ser Tyr Asp Ala Val Met
                245                 250                 255 tac gag agt agt cac ata ctt gat cat ctc ttt tga cttaatatag        814
Tyr Glu Ser Ser His Ile Leu Asp His Leu Phe *
            260                 265 tgtgactgtg tgagtgcatg catgtt                                      840

<210> SEQ ID NO 112
<211> LENGTH: 267
<212> TYPE: PRT
<213> ORGANISM: Arabidopsis thaliana
<220> FEATURE:
<221> NAME/KEY: DOMAIN
<222> LOCATION: (14)...(120)
<223> OTHER INFORMATION: Conserved domain

<400> SEQUENCE: 112
```

```
Met Gly Arg Thr Thr Trp Phe Asp Val Asp Gly Met Lys Lys Gly Glu
 1               5                  10                  15

Trp Thr Ala Glu Glu Asp Gln Lys Leu Gly Ala Tyr Ile Asn Glu His
             20                  25                  30

Gly Val Cys Asp Trp Arg Ser Leu Pro Lys Arg Ala Gly Leu Gln Arg
         35                  40                  45

Cys Gly Lys Ser Cys Arg Leu Arg Trp Leu Asn Tyr Leu Lys Pro Gly
     50                  55                  60

Ile Arg Arg Gly Lys Phe Thr Pro Gln Glu Glu Glu Ile Ile Gln
 65              70                  75                  80

Leu His Ala Val Leu Gly Asn Arg Trp Ala Met Ala Lys Lys Met
                 85                  90                  95

Gln Asn Arg Thr Asp Asn Asp Ile Lys Asn His Trp Asn Ser Cys Leu
             100                 105                 110

Lys Lys Arg Leu Ser Arg Lys Gly Ile Asp Pro Met Thr His Glu Pro
             115                 120                 125

Ile Ile Lys His Leu Thr Val Asn Thr Thr Asn Ala Asp Cys Gly Asn
 130                 135                 140

Ser Ser Thr Thr Thr Ser Pro Ser Thr Thr Glu Ser Ser Pro Ser Ser
 145                 150                 155                 160

Gly Ser Ser Arg Leu Leu Asn Lys Leu Ala Ala Gly Ile Ser Ser Arg
             165                 170                 175

Gln His Ser Leu Asp Arg Ile Lys Tyr Ile Leu Ser Asn Ser Ile Ile
             180                 185                 190

Glu Ser Ser Asp Gln Ala Lys Glu Glu Glu Lys Glu Glu Glu Glu
             195                 200                 205

Glu Glu Arg Asp Ser Met Met Gly Gln Lys Ile Asp Gly Ser Glu Gly
 210                 215                 220

Glu Asp Ile Gln Ile Trp Gly Glu Glu Val Arg Arg Leu Met Glu
 225                 230                 235                 240

Ile Asp Ala Met Asp Met Tyr Glu Met Thr Ser Tyr Asp Ala Val Met
             245                 250                 255

Tyr Glu Ser Ser His Ile Leu Asp His Leu Phe
             260                 265

<210> SEQ ID NO 113
<211> LENGTH: 476
<212> TYPE: DNA
<213> ORGANISM: Arabidopsis thaliana
<220> FEATURE:
<221> NAME/KEY: CDS
<222> LOCATION: (41)...(370)

<400> SEQUENCE: 113
aacacacaat tcgttgattc atcatatctc ctcttcatta atg aat ggc ctc gtc        55
                                              Met Asn Gly Leu Val
                                               1               5 gac tct tct cga gat aag aag atg aaa aat ccg cga ttt tcg ttt cgc      103
Asp Ser Ser Arg Asp Lys Lys Met Lys Asn Pro Arg Phe Ser Phe Arg
             10                  15                  20 aca aag agt gat gca gat att ctc gat gat ggt tat cga tgg aga aag      151
Thr Lys Ser Asp Ala Asp Ile Leu Asp Asp Gly Tyr Arg Trp Arg Lys
         25                  30                  35 tac ggt cag aaa tcc gtc aag aac agc ttg tat ccc agg agc tat tat      199
Tyr Gly Gln Lys Ser Val Lys Asn Ser Leu Tyr Pro Arg Ser Tyr Tyr
     40                  45                  50 aga tgc aca caa cac atg tgt aac gtg aag aag caa gtt cag agg ctg      247
```

```
Arg Cys Thr Gln His Met Cys Asn Val Lys Lys Gln Val Gln Arg Leu
     55                  60                  65 tcg aag gag acg agc att gtg gag aca act tat gaa gga atc cat aac      295
Ser Lys Glu Thr Ser Ile Val Glu Thr Thr Tyr Glu Gly Ile His Asn
     70                  75                  80                  85 cat cct tgt gag gag ctc atg caa acc cta act cct ctt ctt cat caa      343
His Pro Cys Glu Glu Leu Met Gln Thr Leu Thr Pro Leu Leu His Gln
             90                  95                 100 ttg cag ttc ctc tct aag ttc acc taa ttatgtttgt atatatatta            390
Leu Gln Phe Leu Ser Lys Phe Thr *
            105 acgttctaag agcatctcca atggaagtat ctcaatgaga tacctaacaa agaaaaaaa      450 atttaaaaaa aaaaaaaaaa aaaaaa                                          476

<210> SEQ ID NO 114
<211> LENGTH: 109
<212> TYPE: PRT
<213> ORGANISM: Arabidopsis thaliana
<220> FEATURE:
<221> NAME/KEY: DOMAIN
<222> LOCATION: (30)...(86)
<223> OTHER INFORMATION: Conserved domain

<400> SEQUENCE: 114

Met Asn Gly Leu Val Asp Ser Ser Arg Asp Lys Lys Met Lys Asn Pro
 1               5                  10                  15

Arg Phe Ser Phe Arg Thr Lys Ser Asp Ala Asp Ile Leu Asp Asp Gly
             20                  25                  30

Tyr Arg Trp Arg Lys Tyr Gly Gln Lys Ser Val Lys Asn Ser Leu Tyr
         35                  40                  45

Pro Arg Ser Tyr Tyr Arg Cys Thr Gln His Met Cys Asn Val Lys Lys
     50                  55                  60

Gln Val Gln Arg Leu Ser Lys Glu Thr Ser Ile Val Glu Thr Thr Tyr
 65                  70                  75                  80

Glu Gly Ile His Asn His Pro Cys Glu Glu Leu Met Gln Thr Leu Thr
                 85                  90                  95

Pro Leu Leu His Gln Leu Gln Phe Leu Ser Lys Phe Thr
            100                 105

<210> SEQ ID NO 115
<211> LENGTH: 912
<212> TYPE: DNA
<213> ORGANISM: Arabidopsis thaliana
<220> FEATURE:
<221> NAME/KEY: CDS
<222> LOCATION: (53)...(859)

<400> SEQUENCE: 115
cgtcgacctc ttaattaaga cgacttgaga gagaaagaaa gatacgtgga ag atg acc     58
                                                          Met Thr
                                                            1 aaa tct gga gag aga cca aaa cag aga cag agg aaa ggg tta tgg tca     106
Lys Ser Gly Glu Arg Pro Lys Gln Arg Gln Arg Lys Gly Leu Trp Ser
         5                  10                  15 cct gaa gaa gac cag aag ctc aag agt ttc atc ctc tct cgt ggc cat     154
Pro Glu Glu Asp Gln Lys Leu Lys Ser Phe Ile Leu Ser Arg Gly His
         20                  25                  30 gct tgc tgg acc act gtt ccc atc cta gct gga ttg caa agg aat ggg     202
Ala Cys Trp Thr Thr Val Pro Ile Leu Ala Gly Leu Gln Arg Asn Gly
 35                  40                  45                  50
```

```
aaa agc tgc aga tta agg tgg att aat tac cta aga cca gga cta aag      250
Lys Ser Cys Arg Leu Arg Trp Ile Asn Tyr Leu Arg Pro Gly Leu Lys
         55                  60                  65 agg ggg tcg ttt agt gaa gaa gaa gag acc atc ttg act tta cat          298
Arg Gly Ser Phe Ser Glu Glu Glu Glu Thr Ile Leu Thr Leu His
         70                  75                  80 tct tcc ttg ggt aac aag tgg tct cgg att gca aaa tat tta ccg gga      346
Ser Ser Leu Gly Asn Lys Trp Ser Arg Ile Ala Lys Tyr Leu Pro Gly
         85                  90                  95 aga aca gac aac gag att aag aac tat tgg cat tcc tat ctg aag aag      394
Arg Thr Asp Asn Glu Ile Lys Asn Tyr Trp His Ser Tyr Leu Lys Lys
        100                 105                 110 aga tgg ctc aaa tct caa cca caa ctc aaa agc caa ata tca gac ctc      442
Arg Trp Leu Lys Ser Gln Pro Gln Leu Lys Ser Gln Ile Ser Asp Leu
115                 120                 125                 130 aca gaa tct cct tct tca cta ctt tct tgc ggg aaa aga aat ctg gaa      490
Thr Glu Ser Pro Ser Ser Leu Leu Ser Cys Gly Lys Arg Asn Leu Glu
                135                 140                 145 acc gaa acc cta gat cac gtg atc tcc ttc cag aaa ttt tca gag aat      538
Thr Glu Thr Leu Asp His Val Ile Ser Phe Gln Lys Phe Ser Glu Asn
        150                 155                 160 cca act tca tca cca tcc aaa gaa agc aac aac aac atg atc atg aac      586
Pro Thr Ser Ser Pro Ser Lys Glu Ser Asn Asn Asn Met Ile Met Asn
        165                 170                 175 aac agt aat aac ttg cct aaa ctg ttc ttc tct gag tgg atc agt tct      634
Asn Ser Asn Asn Leu Pro Lys Leu Phe Phe Ser Glu Trp Ile Ser Ser
        180                 185                 190 tca aat cca cac atc gat tac tcc tct gct ttt aca gat tcc aag cac      682
Ser Asn Pro His Ile Asp Tyr Ser Ser Ala Phe Thr Asp Ser Lys His
195                 200                 205                 210 att aat gaa act caa gat caa atc aat gaa gag gaa gtg atg atg atc      730
Ile Asn Glu Thr Gln Asp Gln Ile Asn Glu Glu Glu Val Met Met Ile
                215                 220                 225 aat aac aac aac tac tct tca ctt gag gat gtc atg ctc cgt aca gat      778
Asn Asn Asn Asn Tyr Ser Ser Leu Glu Asp Val Met Leu Arg Thr Asp
        230                 235                 240 ttt ttg cag cct gat cat gaa tat gca aat tat tat tct tct gga gat      826
Phe Leu Gln Pro Asp His Glu Tyr Ala Asn Tyr Tyr Ser Ser Gly Asp
        245                 250                 255 ttc ttc atc aac agt gac caa aat tat gtc taa gaagagtgaa tatgatcgta    879
Phe Phe Ile Asn Ser Asp Gln Asn Tyr Val *
        260                 265 agaggaacat aagctagtta cttgtgttac agc                                 912

<210> SEQ ID NO 116
<211> LENGTH: 268
<212> TYPE: PRT
<213> ORGANISM: Arabidopsis thaliana
<220> FEATURE:
<221> NAME/KEY: DOMAIN
<222> LOCATION: (9)...(114)
<223> OTHER INFORMATION: Conserved domain

<400> SEQUENCE: 116

Met Thr Lys Ser Gly Glu Arg Pro Lys Gln Arg Gln Arg Lys Gly Leu
1               5                   10                  15

Trp Ser Pro Glu Glu Asp Gln Lys Leu Lys Ser Phe Ile Leu Ser Arg
            20                  25                  30

Gly His Ala Cys Trp Thr Thr Val Pro Ile Leu Ala Gly Leu Gln Arg
        35                  40                  45
```

```
            Asn Gly Lys Ser Cys Arg Leu Arg Trp Ile Asn Tyr Leu Arg Pro Gly
                 50                  55                  60

Leu Lys Arg Gly Ser Phe Ser Glu Glu Glu Thr Ile Leu Thr
            65                  70                  75                  80

Leu His Ser Ser Leu Gly Asn Lys Trp Ser Arg Ile Ala Lys Tyr Leu
                             85                  90                  95

Pro Gly Arg Thr Asp Asn Glu Ile Lys Asn Tyr Trp His Ser Tyr Leu
                        100                 105                 110

Lys Lys Arg Trp Leu Lys Ser Gln Pro Gln Leu Lys Ser Gln Ile Ser
                        115                 120                 125

Asp Leu Thr Glu Ser Pro Ser Ser Leu Leu Ser Cys Gly Lys Arg Asn
                    130                 135                 140

Leu Glu Thr Glu Thr Leu Asp His Val Ile Ser Phe Gln Lys Phe Ser
            145                 150                 155                 160

Glu Asn Pro Thr Ser Ser Pro Ser Lys Glu Ser Asn Asn Asn Met Ile
                                165                 170                 175

Met Asn Asn Ser Asn Asn Leu Pro Lys Leu Phe Phe Ser Glu Trp Ile
                            180                 185                 190

Ser Ser Ser Asn Pro His Ile Asp Tyr Ser Ser Ala Phe Thr Asp Ser
                        195                 200                 205

Lys His Ile Asn Glu Thr Gln Asp Gln Ile Asn Glu Glu Val Met
                    210                 215                 220

Met Ile Asn Asn Asn Asn Tyr Ser Ser Leu Glu Asp Val Met Leu Arg
            225                 230                 235                 240

Thr Asp Phe Leu Gln Pro Asp His Glu Tyr Ala Asn Tyr Tyr Ser Ser
                                245                 250                 255

Gly Asp Phe Phe Ile Asn Ser Asp Gln Asn Tyr Val
                        260                 265

<210> SEQ ID NO 117
            <211> LENGTH: 1414
            <212> TYPE: DNA
            <213> ORGANISM: Arabidopsis thaliana
            <220> FEATURE:
            <221> NAME/KEY: CDS
            <222> LOCATION: (171)...(1169)

<400> SEQUENCE: 117
gatctgggta ttatagattg cagattctgg aaacgtatta tgttaatgat tcatttcaag     60
ttttgatttt ttgtgttgga ttgaagagaa gaatagttta ttgatgtttt gtgaagaaga    120
agaagaagag attttgattt tggtttaata tatagttggg gattaacagg atg gga       176
                                                                      Met Gly
                                                                        1 agg gta aaa ttg aag ata aag aag tta gag aac aca aat gga cgc caa       224
            Arg Val Lys Leu Lys Ile Lys Lys Leu Glu Asn Thr Asn Gly Arg Gln
                      5                  10                  15 tct aca ttt gct aaa agg aaa aat ggg atc ttg aaa aag gct aat gag       272
            Ser Thr Phe Ala Lys Arg Lys Asn Gly Ile Leu Lys Lys Ala Asn Glu
                    20                  25                  30 cta tct att ctt tgt gac att gat att gtt ctt ctt atg ttc tct cct       320
            Leu Ser Ile Leu Cys Asp Ile Asp Ile Val Leu Leu Met Phe Ser Pro
            35                  40                  45                  50 act ggc aag gct gca ata tgt tgc ggt aca cga aga tgt ttc tct ttc       368
            Thr Gly Lys Ala Ala Ile Cys Cys Gly Thr Arg Arg Cys Phe Ser Phe
                        55                  60                  65 gaa agc tca gaa ctt gaa gaa aac ttt cca aaa gtt gga tca cga tgt       416
            Glu Ser Ser Glu Leu Glu Glu Asn Phe Pro Lys Val Gly Ser Arg Cys
```

```
                     70                   75                   80
aaa  tat  acg  cga  att  tat  agc  ctc  aag  gac  ttg  agt  act  caa  gca  agg       464
Lys  Tyr  Thr  Arg  Ile  Tyr  Ser  Leu  Lys  Asp  Leu  Ser  Thr  Gln  Ala  Arg
               85                   90                   95 att  ctg  cag  gct  cgg  att  tct  gag  ata  cat  gga  aga  tta  agt  tat  tgg       512
Ile  Leu  Gln  Ala  Arg  Ile  Ser  Glu  Ile  His  Gly  Arg  Leu  Ser  Tyr  Trp
          100                  105                  110 acg  gaa  cca  gat  aag  att  aac  aat  gtt  gaa  cac  ttg  gga  cag  ctc  gaa       560
Thr  Glu  Pro  Asp  Lys  Ile  Asn  Asn  Val  Glu  His  Leu  Gly  Gln  Leu  Glu
115                  120                  125                  130 att  tcg  att  agg  caa  tcc  ctt  gat  caa  ttg  cgt  gca  cac  aag  atg  caa       608
Ile  Ser  Ile  Arg  Gln  Ser  Leu  Asp  Gln  Leu  Arg  Ala  His  Lys  Met  Gln
                    135                  140                  145 gat  ggg  att  cag  att  cct  tta  gaa  caa  cag  ctt  caa  tct  atg  tca  tgg       656
Asp  Gly  Ile  Gln  Ile  Pro  Leu  Glu  Gln  Gln  Leu  Gln  Ser  Met  Ser  Trp
               150                  155                  160 att  ctt  aat  agc  aac  acc  acc  aac  att  gtc  acc  gag  gaa  cac  aat  tca       704
Ile  Leu  Asn  Ser  Asn  Thr  Thr  Asn  Ile  Val  Thr  Glu  Glu  His  Asn  Ser
          165                  170                  175 atc  ccg  cag  agg  gaa  gtc  gag  tgc  tca  gcg  agt  tct  tca  ttc  ggg  agc       752
Ile  Pro  Gln  Arg  Glu  Val  Glu  Cys  Ser  Ala  Ser  Ser  Ser  Phe  Gly  Ser
180                  185                  190 tat  cca  ggc  tac  ttt  gga  aca  ggg  aaa  tct  cct  gaa  atg  aca  att  ccg       800
Tyr  Pro  Gly  Tyr  Phe  Gly  Thr  Gly  Lys  Ser  Pro  Glu  Met  Thr  Ile  Pro
195                  200                  205                  210 ggt  caa  gaa  aca  agc  ttt  ctt  gat  gaa  cta  aac  acc  gga  cag  ctg  aaa       848
Gly  Gln  Glu  Thr  Ser  Phe  Leu  Asp  Glu  Leu  Asn  Thr  Gly  Gln  Leu  Lys
                    215                  220                  225 cag  gac  aca  agc  tcg  cag  cag  cag  ttc  act  aat  aat  aat  aat  atc  aca       896
Gln  Asp  Thr  Ser  Ser  Gln  Gln  Gln  Phe  Thr  Asn  Asn  Asn  Asn  Ile  Thr
               230                  235                  240 gca  tac  aat  ccc  aat  ctt  cac  aat  gat  atg  aat  cat  cac  caa  acg  ttg       944
Ala  Tyr  Asn  Pro  Asn  Leu  His  Asn  Asp  Met  Asn  His  His  Gln  Thr  Leu
          245                  250                  255 cct  cct  cct  cct  ctt  cct  ctt  act  ctt  ccg  cat  gct  cag  gtg  tat  att       992
Pro  Pro  Pro  Pro  Leu  Pro  Leu  Thr  Leu  Pro  His  Ala  Gln  Val  Tyr  Ile
260                  265                  270 cca  atg  aat  cag  aga  gag  tat  cat  atg  aat  gga  ttc  ttt  gaa  gca  cca      1040
Pro  Met  Asn  Gln  Arg  Glu  Tyr  His  Met  Asn  Gly  Phe  Phe  Glu  Ala  Pro
275                  280                  285                  290 cca  cct  gat  tct  tct  gct  tac  aac  gac  aac  acc  aac  caa  acc  agg  ttt      1088
Pro  Pro  Asp  Ser  Ser  Ala  Tyr  Asn  Asp  Asn  Thr  Asn  Gln  Thr  Arg  Phe
                    295                  300                  305 ggt  tct  agc  agc  agc  tcc  ttg  cct  tgc  tca  atc  tca  atg  ttc  gac  gaa      1136
Gly  Ser  Ser  Ser  Ser  Ser  Leu  Pro  Cys  Ser  Ile  Ser  Met  Phe  Asp  Glu
               310                  315                  320 tac  ttg  ttt  tcc  cag  atg  cag  cag  ccg  aac  tga  gagagatttg  atgaatgatg         1189
Tyr  Leu  Phe  Ser  Gln  Met  Gln  Gln  Pro  Asn  *
          325                  330 ataaacatc  tcactgaaga  aactcaaacc  aatattttttt  ttcagaaaca  gcaagaaagc              1249
taaaactctg  ccgatttctg  aattggttcc  aagaagaaaa  aaaccagtgg  taatccctgg             1309
tagattgtgc  aaccaaacca  cacacaatac  gtgttcattt  atttttttcta  tatcttcaat             1369 agatgtcact  taattctttt  ctatacataa  tttctcagtc  agaat                              1414

<210> SEQ ID NO 118
<211> LENGTH: 332
<212> TYPE: PRT
<213> ORGANISM: Arabidopsis thaliana
```

```
<220> FEATURE:
<221> NAME/KEY: DOMAIN
<222> LOCATION: (2)...(57)
<223> OTHER INFORMATION: Conserved domain

<400> SEQUENCE: 118

Met Gly Arg Val Lys Leu Lys Ile Lys Lys Leu Glu Asn Thr Asn Gly
1               5                   10                  15

Arg Gln Ser Thr Phe Ala Lys Arg Lys Asn Gly Ile Leu Lys Lys Ala
            20                  25                  30

Asn Glu Leu Ser Ile Leu Cys Asp Ile Asp Ile Val Leu Leu Met Phe
        35                  40                  45

Ser Pro Thr Gly Lys Ala Ala Ile Cys Cys Gly Thr Arg Arg Cys Phe
    50                  55                  60

Ser Phe Glu Ser Ser Glu Leu Glu Glu Asn Phe Pro Lys Val Gly Ser
65                  70                  75                  80

Arg Cys Lys Tyr Thr Arg Ile Tyr Ser Leu Lys Asp Leu Ser Thr Gln
                85                  90                  95

Ala Arg Ile Leu Gln Ala Arg Ile Ser Glu Ile His Gly Arg Leu Ser
            100                 105                 110

Tyr Trp Thr Glu Pro Asp Lys Ile Asn Asn Val Glu His Leu Gly Gln
        115                 120                 125

Leu Glu Ile Ser Ile Arg Gln Ser Leu Asp Gln Leu Arg Ala His Lys
    130                 135                 140

Met Gln Asp Gly Ile Gln Ile Pro Leu Glu Gln Gln Leu Gln Ser Met
145                 150                 155                 160

Ser Trp Ile Leu Asn Ser Asn Thr Thr Asn Ile Val Thr Glu Glu His
                165                 170                 175

Asn Ser Ile Pro Gln Arg Glu Val Glu Cys Ser Ala Ser Ser Ser Phe
            180                 185                 190

Gly Ser Tyr Pro Gly Tyr Phe Gly Thr Gly Lys Ser Pro Glu Met Thr
        195                 200                 205

Ile Pro Gly Gln Glu Thr Ser Phe Leu Asp Glu Leu Asn Thr Gly Gln
    210                 215                 220

Leu Lys Gln Asp Thr Ser Ser Gln Gln Gln Phe Thr Asn Asn Asn Asn
225                 230                 235                 240

Ile Thr Ala Tyr Asn Pro Asn Leu His Asn Asp Met Asn His His Gln
                245                 250                 255

Thr Leu Pro Pro Pro Pro Leu Pro Leu Thr Leu Pro His Ala Gln Val
            260                 265                 270

Tyr Ile Pro Met Asn Gln Arg Glu Tyr His Met Asn Gly Phe Phe Glu
        275                 280                 285

Ala Pro Pro Asp Ser Ser Ala Tyr Asn Asp Asn Thr Asn Gln Thr
    290                 295                 300

Arg Phe Gly Ser Ser Ser Ser Ser Leu Pro Cys Ser Ile Ser Met Phe
305                 310                 315                 320

Asp Glu Tyr Leu Phe Ser Gln Met Gln Gln Pro Asn
                325                 330

<210> SEQ ID NO 119
<211> LENGTH: 867
<212> TYPE: DNA
<213> ORGANISM: Arabidopsis thaliana
<220> FEATURE:
<221> NAME/KEY: CDS
<222> LOCATION: (1)...(867)
```

<400> SEQUENCE: 119

| | | | | |
|---|---|---|---|---|
| atg gag gtt atg aga ccg tcg acg tca cac gtg tca ggt ggg aac tgg<br>Met Glu Val Met Arg Pro Ser Thr Ser His Val Ser Gly Gly Asn Trp<br>1                      5                        10                      15 | 48 |
| ctc atg gag gaa act aag agc ggc gtc gca gct tct ggt gaa ggt gcc<br>Leu Met Glu Glu Thr Lys Ser Gly Val Ala Ala Ser Gly Glu Gly Ala<br>                20                        25                        30 | 96 |
| acg tgg acg gcg gca gag aac aag gca ttc gag aat gct ttg gcg gtt<br>Thr Trp Thr Ala Ala Glu Asn Lys Ala Phe Glu Asn Ala Leu Ala Val<br>                      35                        40                        45 | 144 |
| tac gac gac aac act cct gat cgg tgg cag aag gtg gct gcg gtg att<br>Tyr Asp Asp Asn Thr Pro Asp Arg Trp Gln Lys Val Ala Ala Val Ile<br>50                        55                        60 | 192 |
| ccg ggg aag aca gtg agt gac gta att aga cag tat aac gat ttg gaa<br>Pro Gly Lys Thr Val Ser Asp Val Ile Arg Gln Tyr Asn Asp Leu Glu<br>65                        70                        75                        80 | 240 |
| gct gat gtc agc agc atc gag gcc ggt tta atc ccg gtc ccc ggt tac<br>Ala Asp Val Ser Ser Ile Glu Ala Gly Leu Ile Pro Val Pro Gly Tyr<br>                          85                        90                        95 | 288 |
| atc acc tcg ccg cct ttc act cta gat tgg gcc ggc ggc ggt ggc gga<br>Ile Thr Ser Pro Pro Phe Thr Leu Asp Trp Ala Gly Gly Gly Gly Gly<br>                    100                       105                   110 | 336 |
| tgt aac ggg ttt aaa ccg ggt cat cag gtt tgt aat aaa cgg tcg cag<br>Cys Asn Gly Phe Lys Pro Gly His Gln Val Cys Asn Lys Arg Ser Gln<br>                 115                       120                   125 | 384 |
| gcc ggt aga tcg ccg gag ctg gag cgg aag aaa ggc gtt cct tgg acg<br>Ala Gly Arg Ser Pro Glu Leu Glu Arg Lys Lys Gly Val Pro Trp Thr<br>130                       135                       140 | 432 |
| gag gaa gaa cac aag cta ttt cta atg ggt ttg aag aaa tat ggg aaa<br>Glu Glu Glu His Lys Leu Phe Leu Met Gly Leu Lys Lys Tyr Gly Lys<br>145                     150                       155                   160 | 480 |
| gga gat tgg aga aac ata tct cgg aac ttt gtg ata acg cga acg cca<br>Gly Asp Trp Arg Asn Ile Ser Arg Asn Phe Val Ile Thr Arg Thr Pro<br>                 165                       170                   175 | 528 |
| aca caa gta gct agc cac gcc caa aag tac ttc atc cgg caa ctt tcc<br>Thr Gln Val Ala Ser His Ala Gln Lys Tyr Phe Ile Arg Gln Leu Ser<br>                   180                       185                   190 | 576 |
| ggc ggc aag gac aag aga cga gca agc att cac gac ata acc acc gta<br>Gly Gly Lys Asp Lys Arg Arg Ala Ser Ile His Asp Ile Thr Thr Val<br>195                     200                       205 | 624 |
| aat ctc gaa gag gag gct tct ttg gag acc aat aag agc tcc att gtt<br>Asn Leu Glu Glu Glu Ala Ser Leu Glu Thr Asn Lys Ser Ser Ile Val<br>210                     215                       220 | 672 |
| gtt gga gat cag cgt tca agg cta acc gcg ttt cct tgg aac caa acg<br>Val Gly Asp Gln Arg Ser Arg Leu Thr Ala Phe Pro Trp Asn Gln Thr<br>225                     230                       235                   240 | 720 |
| gac aac aat gga aca cag gca gac gct ttc aat ata acg att gga aac<br>Asp Asn Asn Gly Thr Gln Ala Asp Ala Phe Asn Ile Thr Ile Gly Asn<br>                   245                       250                   255 | 768 |
| gct att agt ggc gtt cat tca tac ggc cag gtt atg att gga ggg tat<br>Ala Ile Ser Gly Val His Ser Tyr Gly Gln Val Met Ile Gly Gly Tyr<br>                 260                       265                   270 | 816 |
| aac aat gca gat tct tgc tat gac gcc caa aac aca atg ttt caa cta<br>Asn Asn Ala Asp Ser Cys Tyr Asp Ala Gln Asn Thr Met Phe Gln Leu<br>                 275                       280                   285 | 864 |
| tag<br>* | 867 |

<210> SEQ ID NO 120

<211> LENGTH: 288
<212> TYPE: PRT
<213> ORGANISM: Arabidopsis thaliana
<220> FEATURE:
<221> NAME/KEY: DOMAIN
<222> LOCATION: (139)...(200)
<223> OTHER INFORMATION: Conserved domain

<400> SEQUENCE: 120

```
Met Glu Val Met Arg Pro Ser Thr Ser His Val Ser Gly Gly Asn Trp
 1               5                  10                  15

Leu Met Glu Glu Thr Lys Ser Gly Val Ala Ala Ser Gly Glu Gly Ala
                20                  25                  30

Thr Trp Thr Ala Ala Glu Asn Lys Ala Phe Glu Asn Ala Leu Ala Val
            35                  40                  45

Tyr Asp Asp Asn Thr Pro Asp Arg Trp Gln Lys Val Ala Ala Val Ile
 50                  55                  60

Pro Gly Lys Thr Val Ser Asp Val Ile Arg Gln Tyr Asn Asp Leu Glu
 65                  70                  75                  80

Ala Asp Val Ser Ser Ile Glu Ala Gly Leu Ile Pro Val Pro Gly Tyr
                85                  90                  95

Ile Thr Ser Pro Pro Phe Thr Leu Asp Trp Ala Gly Gly Gly Gly Gly
                100                 105                 110

Cys Asn Gly Phe Lys Pro Gly His Gln Val Cys Asn Lys Arg Ser Gln
            115                 120                 125

Ala Gly Arg Ser Pro Glu Leu Glu Arg Lys Gly Val Pro Trp Thr
        130                 135                 140

Glu Glu Glu His Lys Leu Phe Leu Met Gly Leu Lys Lys Tyr Gly Lys
145                 150                 155                 160

Gly Asp Trp Arg Asn Ile Ser Arg Asn Phe Val Ile Thr Arg Thr Pro
                165                 170                 175

Thr Gln Val Ala Ser His Ala Gln Lys Tyr Phe Ile Arg Gln Leu Ser
                180                 185                 190

Gly Gly Lys Asp Lys Arg Arg Ala Ser Ile His Asp Ile Thr Thr Val
            195                 200                 205

Asn Leu Glu Glu Glu Ala Ser Leu Glu Thr Asn Lys Ser Ser Ile Val
210                 215                 220

Val Gly Asp Gln Arg Ser Arg Leu Thr Ala Phe Pro Trp Asn Gln Thr
225                 230                 235                 240

Asp Asn Asn Gly Thr Gln Ala Asp Ala Phe Asn Ile Thr Ile Gly Asn
                245                 250                 255

Ala Ile Ser Gly Val His Ser Tyr Gly Gln Val Met Ile Gly Gly Tyr
            260                 265                 270

Asn Asn Ala Asp Ser Cys Tyr Asp Ala Gln Asn Thr Met Phe Gln Leu
        275                 280                 285
```

<210> SEQ ID NO 121
<211> LENGTH: 952
<212> TYPE: DNA
<213> ORGANISM: Arabidopsis thaliana
<220> FEATURE:
<221> NAME/KEY: CDS
<222> LOCATION: (48)...(899)

<400> SEQUENCE: 121

```
aagaagagga catgaagcac agagattctg cagactgcag gtgacca atg gac act        56
                                                 Met Asp Thr
                                                  1
```

| | | | | | | | | | | | | | | | |
|---|---|---|---|---|---|---|---|---|---|---|---|---|---|---|---|
| tta | tca | ata | aaa | aca | tac | cta | cta | ctc | tct | tac | act | ttc | aat | ttt | cca |
| Leu | Ser | Ile | Lys | Thr | Tyr | Leu | Leu | Leu | Ser | Tyr | Thr | Phe | Asn | Phe | Pro |
| | 5 | | | | 10 | | | | | 15 | | | | | |

104

| ata | caa | atc | cca | atc | ttt | aat | ctc | tct | ttc | ttc | ttc | atc | tct | ctt | tct |
|---|---|---|---|---|---|---|---|---|---|---|---|---|---|---|---|
| Ile | Gln | Ile | Pro | Ile | Phe | Asn | Leu | Ser | Phe | Phe | Phe | Ile | Ser | Leu | Ser |
| 20 | | | | | 25 | | | | | 30 | | | | | 35 |

152

| ctt | tct | ctc | ttc | atg | gct | aca | agg | att | cca | ttc | aca | gaa | tca | caa | tgg |
|---|---|---|---|---|---|---|---|---|---|---|---|---|---|---|---|
| Leu | Ser | Leu | Phe | Met | Ala | Thr | Arg | Ile | Pro | Phe | Thr | Glu | Ser | Gln | Trp |
| | | | | 40 | | | | | 45 | | | | | 50 | |

200

| gaa | gaa | ctt | gaa | aac | caa | gct | ctt | gtg | ttc | aag | tac | tta | gct | gca | aat |
|---|---|---|---|---|---|---|---|---|---|---|---|---|---|---|---|
| Glu | Glu | Leu | Glu | Asn | Gln | Ala | Leu | Val | Phe | Lys | Tyr | Leu | Ala | Ala | Asn |
| | | | 55 | | | | | 60 | | | | | 65 | | |

248

| atg | cct | gtt | cca | cct | cat | ctt | ctc | ttc | ctc | atc | aaa | aga | ccc | ttt | ctc |
|---|---|---|---|---|---|---|---|---|---|---|---|---|---|---|---|
| Met | Pro | Val | Pro | Pro | His | Leu | Leu | Phe | Leu | Ile | Lys | Arg | Pro | Phe | Leu |
| | 70 | | | | | 75 | | | | | 80 | | | | |

296

| ttc | tct | tct | tct | tct | tct | tca | tct | tct | tct | tca | agc | ttc | ttc | tct | ccc |
|---|---|---|---|---|---|---|---|---|---|---|---|---|---|---|---|
| Phe | Ser | Ser | Ser | Ser | Ser | Ser | Ser | Ser | Ser | Ser | Ser | Phe | Phe | Ser | Pro |
| 85 | | | | | 90 | | | | | 95 | | | | | |

344

| act | ctt | tct | cca | cac | ttt | ggg | tgg | aat | gtg | tat | gag | atg | gga | atg | gga |
|---|---|---|---|---|---|---|---|---|---|---|---|---|---|---|---|
| Thr | Leu | Ser | Pro | His | Phe | Gly | Trp | Asn | Val | Tyr | Glu | Met | Gly | Met | Gly |
| 100 | | | | | 105 | | | | | 110 | | | | | 115 |

392

| aga | aag | ata | gat | gca | gag | cca | gga | aga | tgt | aga | aga | act | gat | ggc | aag |
|---|---|---|---|---|---|---|---|---|---|---|---|---|---|---|---|
| Arg | Lys | Ile | Asp | Ala | Glu | Pro | Gly | Arg | Cys | Arg | Arg | Thr | Asp | Gly | Lys |
| | | | | 120 | | | | | 125 | | | | | 130 | |

440

| aaa | tgg | aga | tgc | tct | aaa | gaa | gct | tac | cct | gac | tct | aag | tac | tgt | gag |
|---|---|---|---|---|---|---|---|---|---|---|---|---|---|---|---|
| Lys | Trp | Arg | Cys | Ser | Lys | Glu | Ala | Tyr | Pro | Asp | Ser | Lys | Tyr | Cys | Glu |
| | | | 135 | | | | | 140 | | | | | 145 | | |

488

| aga | cat | atg | cat | aga | ggc | aag | aac | cgt | tct | tcc | tca | aga | aag | cct | cct |
|---|---|---|---|---|---|---|---|---|---|---|---|---|---|---|---|
| Arg | His | Met | His | Arg | Gly | Lys | Asn | Arg | Ser | Ser | Ser | Arg | Lys | Pro | Pro |
| | | 150 | | | | | 155 | | | | | 160 | | | |

536

| cct | act | caa | ttc | act | cca | aat | ctc | ttt | ctc | gac | tct | tct | tcc | aga | aga |
|---|---|---|---|---|---|---|---|---|---|---|---|---|---|---|---|
| Pro | Thr | Gln | Phe | Thr | Pro | Asn | Leu | Phe | Leu | Asp | Ser | Ser | Ser | Arg | Arg |
| | 165 | | | | | 170 | | | | | 175 | | | | |

584

| aga | aga | agt | gga | tac | atg | gat | gat | ttc | ttc | tcc | ata | gaa | cct | tcc | ggg |
|---|---|---|---|---|---|---|---|---|---|---|---|---|---|---|---|
| Arg | Arg | Ser | Gly | Tyr | Met | Asp | Asp | Phe | Phe | Ser | Ile | Glu | Pro | Ser | Gly |
| 180 | | | | | 185 | | | | | 190 | | | | | 195 |

632

| tca | atc | aaa | agc | tgc | tct | ggc | tca | gca | atg | gaa | gat | aat | gat | gat | ggc |
|---|---|---|---|---|---|---|---|---|---|---|---|---|---|---|---|
| Ser | Ile | Lys | Ser | Cys | Ser | Gly | Ser | Ala | Met | Glu | Asp | Asn | Asp | Asp | Gly |
| | | | | 200 | | | | | 205 | | | | | 210 | |

680

| tca | tgt | aga | ggc | atc | aac | aac | gag | gag | aag | cag | ccg | gat | cga | cat | tgc |
|---|---|---|---|---|---|---|---|---|---|---|---|---|---|---|---|
| Ser | Cys | Arg | Gly | Ile | Asn | Asn | Glu | Glu | Lys | Gln | Pro | Asp | Arg | His | Cys |
| | | | 215 | | | | | 220 | | | | | 225 | | |

728

| ttc | atc | ctt | ggt | act | gac | ttg | agg | aca | cgt | gag | agg | cca | ttg | atg | tta |
|---|---|---|---|---|---|---|---|---|---|---|---|---|---|---|---|
| Phe | Ile | Leu | Gly | Thr | Asp | Leu | Arg | Thr | Arg | Glu | Arg | Pro | Leu | Met | Leu |
| | | 230 | | | | | 235 | | | | | 240 | | | |

776

| gag | gag | aag | ctg | aaa | caa | aga | gat | cat | gat | aat | gaa | gaa | gag | caa | gga |
|---|---|---|---|---|---|---|---|---|---|---|---|---|---|---|---|
| Glu | Glu | Lys | Leu | Lys | Gln | Arg | Asp | His | Asp | Asn | Glu | Glu | Glu | Gln | Gly |
| | 245 | | | | | 250 | | | | | 255 | | | | |

824

| agc | aag | agg | ttt | tat | agg | ttt | ctt | gat | gaa | tgg | cct | tct | tct | aaa | tct |
|---|---|---|---|---|---|---|---|---|---|---|---|---|---|---|---|
| Ser | Lys | Arg | Phe | Tyr | Arg | Phe | Leu | Asp | Glu | Trp | Pro | Ser | Ser | Lys | Ser |
| 260 | | | | | 265 | | | | | 270 | | | | | 275 |

872

| tct | gtt | tct | act | tca | ctc | ttc | att | tga | tcatcttttg | ttcttataac | | | | | |
|---|---|---|---|---|---|---|---|---|---|---|---|---|---|---|---|
| Ser | Val | Ser | Thr | Ser | Leu | Phe | Ile | * | | | | | | | |
| | | | | 280 | | | | | | | | | | | |

919 cttgtatttc ttgttaagat ggtaatgcaa att                            952

<210> SEQ ID NO 122
<211> LENGTH: 283
<212> TYPE: PRT
<213> ORGANISM: Arabidopsis thaliana

```
<220> FEATURE:
<221> NAME/KEY: DOMAIN
<222> LOCATION: (124)...(149)
<223> OTHER INFORMATION: Conserved domain

<400> SEQUENCE: 122

Met Asp Thr Leu Ser Ile Lys Thr Tyr Leu Leu Ser Tyr Thr Phe
1               5                   10                  15

Asn Phe Pro Ile Gln Ile Pro Ile Phe Asn Leu Ser Phe Phe Ile
            20                  25                  30

Ser Leu Ser Leu Ser Leu Phe Met Ala Thr Arg Ile Pro Phe Thr Glu
        35                  40                  45

Ser Gln Trp Glu Glu Leu Glu Asn Gln Ala Leu Val Phe Lys Tyr Leu
    50                  55                  60

Ala Ala Asn Met Pro Val Pro Pro His Leu Leu Phe Leu Ile Lys Arg
65                  70                  75                  80

Pro Phe Leu Phe Ser Ser Ser Ser Ser Ser Ser Ser Ser Ser Phe
                85                  90                  95

Phe Ser Pro Thr Leu Ser Pro His Phe Gly Trp Asn Val Tyr Glu Met
            100                 105                 110

Gly Met Gly Arg Lys Ile Asp Ala Glu Pro Gly Arg Cys Arg Arg Thr
        115                 120                 125

Asp Gly Lys Lys Trp Arg Cys Ser Lys Glu Ala Tyr Pro Asp Ser Lys
    130                 135                 140

Tyr Cys Glu Arg His Met His Arg Gly Lys Asn Arg Ser Ser Ser Arg
145                 150                 155                 160

Lys Pro Pro Pro Thr Gln Phe Thr Pro Asn Leu Phe Leu Asp Ser Ser
            165                 170                 175

Ser Arg Arg Arg Arg Ser Gly Tyr Met Asp Asp Phe Phe Ser Ile Glu
        180                 185                 190

Pro Ser Gly Ser Ile Lys Ser Cys Ser Gly Ser Ala Met Glu Asp Asn
    195                 200                 205

Asp Asp Gly Ser Cys Arg Gly Ile Asn Asn Glu Glu Lys Gln Pro Asp
210                 215                 220

Arg His Cys Phe Ile Leu Gly Thr Asp Leu Arg Thr Arg Glu Arg Pro
225                 230                 235                 240

Leu Met Leu Glu Glu Lys Leu Lys Gln Arg Asp His Asp Asn Glu Glu
            245                 250                 255

Glu Gln Gly Ser Lys Arg Phe Tyr Arg Phe Leu Asp Glu Trp Pro Ser
        260                 265                 270

Ser Lys Ser Ser Val Ser Thr Ser Leu Phe Ile
    275                 280

<210> SEQ ID NO 123
<211> LENGTH: 450
<212> TYPE: DNA
<213> ORGANISM: Arabidopsis thaliana
<220> FEATURE:
<221> NAME/KEY: CDS
<222> LOCATION: (1)...(450)

<400> SEQUENCE: 123 atg cta gat ccc acc gag aaa gta atc gat tca gaa tca atg gaa agc    48
Met Leu Asp Pro Thr Glu Lys Val Ile Asp Ser Glu Ser Met Glu Ser
1               5                   10                  15 aaa ctc aca tca gta gat gcg atc gaa gaa cac agc agc agt agc agt    96
Lys Leu Thr Ser Val Asp Ala Ile Glu Glu His Ser Ser Ser Ser Ser
            20                  25                  30
```

```
aat gaa gct atc agc aac gag aag aag agt tgt gcc att tgt ggt acc    144
Asn Glu Ala Ile Ser Asn Glu Lys Lys Ser Cys Ala Ile Cys Gly Thr
        35                  40                  45 agc aaa acc cct ctt tgg cga ggc ggt cct gcc ggt ccc aag tcg ctt    192
Ser Lys Thr Pro Leu Trp Arg Gly Gly Pro Ala Gly Pro Lys Ser Leu
    50                  55                  60 tgt aac gca tgc ggg atc aga aac aga aag aaa aga aga aca ctg atc    240
Cys Asn Ala Cys Gly Ile Arg Asn Arg Lys Lys Arg Arg Thr Leu Ile
65                  70                  75                  80 tca aat aga tca gaa gat aag aag aag agt cat aac aga aac ccg        288
Ser Asn Arg Ser Glu Asp Lys Lys Lys Ser His Asn Arg Asn Pro
                85                  90                  95 aag ttt ggt gac tcg ttg aag cag cga tta atg gaa ttg ggg aga gaa    336
Lys Phe Gly Asp Ser Leu Lys Gln Arg Leu Met Glu Leu Gly Arg Glu
            100                 105                 110 gtg atg atg cag cga tca acg gct gag aat caa cgg cgg aat aag ctt    384
Val Met Met Gln Arg Ser Thr Ala Glu Asn Gln Arg Arg Asn Lys Leu
        115                 120                 125 ggc gaa gaa gag caa gcc gcc gtg tta ctc atg gct ctc tct tat gct    432
Gly Glu Glu Glu Gln Ala Ala Val Leu Leu Met Ala Leu Ser Tyr Ala
    130                 135                 140 tct tcc gtt tat gct taa                                            450
Ser Ser Val Tyr Ala *
145

<210> SEQ ID NO 124
<211> LENGTH: 149
<212> TYPE: PRT
<213> ORGANISM: Arabidopsis thaliana
<220> FEATURE:
<221> NAME/KEY: DOMAIN
<222> LOCATION: (43)...(68)
<223> OTHER INFORMATION: Conserved domain

<400> SEQUENCE: 124

Met Leu Asp Pro Thr Glu Lys Val Ile Asp Ser Glu Ser Met Glu Ser
1               5                   10                  15

Lys Leu Thr Ser Val Asp Ala Ile Glu Glu His Ser Ser Ser Ser Ser
            20                  25                  30

Asn Glu Ala Ile Ser Asn Glu Lys Lys Ser Cys Ala Ile Cys Gly Thr
        35                  40                  45

Ser Lys Thr Pro Leu Trp Arg Gly Gly Pro Ala Gly Pro Lys Ser Leu
    50                  55                  60

Cys Asn Ala Cys Gly Ile Arg Asn Arg Lys Lys Arg Arg Thr Leu Ile
65                  70                  75                  80

Ser Asn Arg Ser Glu Asp Lys Lys Lys Ser His Asn Arg Asn Pro
                85                  90                  95

Lys Phe Gly Asp Ser Leu Lys Gln Arg Leu Met Glu Leu Gly Arg Glu
            100                 105                 110

Val Met Met Gln Arg Ser Thr Ala Glu Asn Gln Arg Arg Asn Lys Leu
        115                 120                 125

Gly Glu Glu Glu Gln Ala Ala Val Leu Leu Met Ala Leu Ser Tyr Ala
    130                 135                 140

Ser Ser Val Tyr Ala
145

<210> SEQ ID NO 125
<211> LENGTH: 750
<212> TYPE: DNA
```

<213> ORGANISM: Arabidopsis thaliana
<220> FEATURE:
<221> NAME/KEY: CDS
<222> LOCATION: (1)...(750)

<400> SEQUENCE: 125

| | | | | | | | | | | | | | | | | |
|---|---|---|---|---|---|---|---|---|---|---|---|---|---|---|---|---|
| atg | atg | tca | tgt | ggt | ggg | aag | aag | cca | gtg | tct | aag | aaa | aca | acg | ccg | 48 |
| Met | Met | Ser | Cys | Gly | Gly | Lys | Lys | Pro | Val | Ser | Lys | Lys | Thr | Thr | Pro | |
| 1 | | | | 5 | | | | | 10 | | | | | 15 | | |
| tgt | tgc | acg | aag | atg | ggg | atg | aag | aga | gga | cca | tgg | acg | gtg | gag | gaa | 96 |
| Cys | Cys | Thr | Lys | Met | Gly | Met | Lys | Arg | Gly | Pro | Trp | Thr | Val | Glu | Glu | |
| | | | 20 | | | | | 25 | | | | | 30 | | | |
| gac | gag | att | ctt | gtg | agc | ttc | att | aag | aaa | gaa | ggt | gaa | gga | cgg | tgg | 144 |
| Asp | Glu | Ile | Leu | Val | Ser | Phe | Ile | Lys | Lys | Glu | Gly | Glu | Gly | Arg | Trp | |
| | | | | 35 | | | | | 40 | | | | | 45 | | |
| cga | tcg | ctt | cct | aag | aga | gct | ggt | tta | ctc | aga | tgt | gga | aag | agc | tgt | 192 |
| Arg | Ser | Leu | Pro | Lys | Arg | Ala | Gly | Leu | Leu | Arg | Cys | Gly | Lys | Ser | Cys | |
| | 50 | | | | | 55 | | | | | 60 | | | | | |
| cgt | cta | cgg | tgg | atg | aac | tat | ctc | cga | ccc | tcg | gtt | aaa | cgt | gga | gga | 240 |
| Arg | Leu | Arg | Trp | Met | Asn | Tyr | Leu | Arg | Pro | Ser | Val | Lys | Arg | Gly | Gly | |
| 65 | | | | | 70 | | | | | 75 | | | | | 80 | |
| att | acg | tcg | gac | gag | gaa | gat | ctc | atc | ctc | cgt | ctt | cac | cgc | ctc | ctc | 288 |
| Ile | Thr | Ser | Asp | Glu | Glu | Asp | Leu | Ile | Leu | Arg | Leu | His | Arg | Leu | Leu | |
| | | | | 85 | | | | | 90 | | | | | 95 | | |
| ggc | aac | agg | tgg | tca | ttg | atc | gcg | gga | agg | ata | ccg | gga | agg | act | gat | 336 |
| Gly | Asn | Arg | Trp | Ser | Leu | Ile | Ala | Gly | Arg | Ile | Pro | Gly | Arg | Thr | Asp | |
| | | | 100 | | | | | 105 | | | | | 110 | | | |
| aat | gaa | att | aag | aac | tat | tgg | aac | act | cat | ctt | cgt | aag | aaa | ctt | tta | 384 |
| Asn | Glu | Ile | Lys | Asn | Tyr | Trp | Asn | Thr | His | Leu | Arg | Lys | Lys | Leu | Leu | |
| | | | | 115 | | | | | 120 | | | | | 125 | | |
| agg | caa | gga | att | gat | cct | caa | acc | cac | aag | cct | ctt | gat | gca | aac | aac | 432 |
| Arg | Gln | Gly | Ile | Asp | Pro | Gln | Thr | His | Lys | Pro | Leu | Asp | Ala | Asn | Asn | |
| | | | 130 | | | | | 135 | | | | | 140 | | | |
| atc | cat | aaa | cca | gaa | gaa | gaa | gtt | tcc | ggt | gga | caa | aag | tac | cct | cta | 480 |
| Ile | His | Lys | Pro | Glu | Glu | Glu | Val | Ser | Gly | Gly | Gln | Lys | Tyr | Pro | Leu | |
| 145 | | | | | 150 | | | | | 155 | | | | | 160 | |
| gag | cct | att | tct | agt | tct | cat | act | gat | gat | acc | act | gtt | aat | ggc | ggg | 528 |
| Glu | Pro | Ile | Ser | Ser | Ser | His | Thr | Asp | Asp | Thr | Thr | Val | Asn | Gly | Gly | |
| | | | | 165 | | | | | 170 | | | | | 175 | | |
| gat | gga | gat | agc | aag | aac | agt | atc | aat | gtc | ttt | ggt | ggt | gaa | cac | ggc | 576 |
| Asp | Gly | Asp | Ser | Lys | Asn | Ser | Ile | Asn | Val | Phe | Gly | Gly | Glu | His | Gly | |
| | | | 180 | | | | | 185 | | | | | 190 | | | |
| tac | gaa | gac | ttt | ggt | ttc | tgc | tac | gac | gac | aag | ttc | tca | tcg | ttt | ctt | 624 |
| Tyr | Glu | Asp | Phe | Gly | Phe | Cys | Tyr | Asp | Asp | Lys | Phe | Ser | Ser | Phe | Leu | |
| | | | | 195 | | | | | 200 | | | | | 205 | | |
| aat | tcg | ctc | atc | aac | gat | gtt | ggt | gat | cct | ttt | ggt | aat | att | atc | cca | 672 |
| Asn | Ser | Leu | Ile | Asn | Asp | Val | Gly | Asp | Pro | Phe | Gly | Asn | Ile | Ile | Pro | |
| | | | 210 | | | | | 215 | | | | | 220 | | | |
| ata | tct | caa | cct | ttg | cag | atg | gat | gat | tgt | aag | gat | ggg | att | gtt | gga | 720 |
| Ile | Ser | Gln | Pro | Leu | Gln | Met | Asp | Asp | Cys | Lys | Asp | Gly | Ile | Val | Gly | |
| 225 | | | | | 230 | | | | | 235 | | | | | 240 | |
| gcg | tcg | tct | tct | agc | tta | gga | cat | gac | tag | | | | | | | 750 |
| Ala | Ser | Ser | Ser | Ser | Leu | Gly | His | Asp | * | | | | | | | |
| | | | | 245 | | | | | | | | | | | | |

<210> SEQ ID NO 126
<211> LENGTH: 249
<212> TYPE: PRT
<213> ORGANISM: Arabidopsis thaliana
<220> FEATURE:
<221> NAME/KEY: DOMAIN
<222> LOCATION: (24)...(137)

<223> OTHER INFORMATION: Conserved domain

<400> SEQUENCE: 126

```
Met Met Ser Cys Gly Gly Lys Lys Pro Val Ser Lys Lys Thr Thr Pro
 1               5                  10                  15
Cys Cys Thr Lys Met Gly Met Lys Arg Gly Pro Trp Thr Val Glu Glu
             20                  25                  30
Asp Glu Ile Leu Val Ser Phe Ile Lys Lys Glu Gly Glu Gly Arg Trp
         35                  40                  45
Arg Ser Leu Pro Lys Arg Ala Gly Leu Leu Arg Cys Gly Lys Ser Cys
     50                  55                  60
Arg Leu Arg Trp Met Asn Tyr Leu Arg Pro Ser Val Lys Arg Gly Gly
 65                  70                  75                  80
Ile Thr Ser Asp Glu Asp Leu Ile Leu Arg Leu His Arg Leu Leu
                 85                  90                  95
Gly Asn Arg Trp Ser Leu Ile Ala Gly Arg Ile Pro Gly Arg Thr Asp
            100                 105                 110
Asn Glu Ile Lys Asn Tyr Trp Asn Thr His Leu Arg Lys Lys Leu Leu
        115                 120                 125
Arg Gln Gly Ile Asp Pro Gln Thr His Lys Pro Leu Asp Ala Asn Asn
    130                 135                 140
Ile His Lys Pro Glu Glu Val Ser Gly Gly Gln Lys Tyr Pro Leu
145                 150                 155                 160
Glu Pro Ile Ser Ser His Thr Asp Thr Thr Val Asn Gly Gly
                165                 170                 175
Asp Gly Asp Ser Lys Asn Ser Ile Asn Val Phe Gly Gly Glu His Gly
            180                 185                 190
Tyr Glu Asp Phe Gly Phe Cys Tyr Asp Asp Lys Phe Ser Ser Phe Leu
        195                 200                 205
Asn Ser Leu Ile Asn Asp Val Gly Asp Pro Phe Gly Asn Ile Ile Pro
    210                 215                 220
Ile Ser Gln Pro Leu Gln Met Asp Asp Cys Lys Asp Gly Ile Val Gly
225                 230                 235                 240
Ala Ser Ser Ser Ser Leu Gly His Asp
                245
```

<210> SEQ ID NO 127
<211> LENGTH: 1195
<212> TYPE: DNA
<213> ORGANISM: Arabidopsis thaliana
<220> FEATURE:
<221> NAME/KEY: CDS
<222> LOCATION: (66)...(983)

<400> SEQUENCE: 127

```
ctctcaaaac caaatcact aaagaggaga agattgctaa agtttgataa aacattccaa       60 aatca atg gct gat agg atc aaa ggt cca tgg agt cct gaa gaa gac gag    110
      Met Ala Asp Arg Ile Lys Gly Pro Trp Ser Pro Glu Glu Asp Glu
        1               5                  10                  15 cag ctt cgt agg ctt gtt gtt aaa tac ggt cca aga aac tgg aca gtg     158
Gln Leu Arg Arg Leu Val Val Lys Tyr Gly Pro Arg Asn Trp Thr Val
             20                  25                  30 att agc aaa tct att ccc ggt aga tcg ggg aaa tcg tgt cgt tta cgg     206
Ile Ser Lys Ser Ile Pro Gly Arg Ser Gly Lys Ser Cys Arg Leu Arg
         35                  40                  45 tgg tgc aac cag ctt tcg ccg caa gtt gag cat cgg ccg ttt tcg gct     254
Trp Cys Asn Gln Leu Ser Pro Gln Val Glu His Arg Pro Phe Ser Ala
```

|   |   |   |   |   |   |   |   |   |   |   |   |   |   |   |   |
|---|---|---|---|---|---|---|---|---|---|---|---|---|---|---|---|
|   |   |   | 50 |   |   |   |   | 55 |   |   |   |   | 60 |   |   |
| gag | gaa | gac | gag | acg | atc | gca | cgt | gct | cac | gct | cag | ttc | ggg | aat | aaa | 302 |
| Glu | Glu | Asp | Glu | Thr | Ile | Ala | Arg | Ala | His | Ala | Gln | Phe | Gly | Asn | Lys |
|   | 65 |   |   |   | 70 |   |   |   |   | 75 |   |   |   |   |   |
| tgg | gcg | acg | att | gct | cgt | ctt | ctc | aac | ggt | cgt | acg | gac | aac | gcc | gtg | 350 |
| Trp | Ala | Thr | Ile | Ala | Arg | Leu | Leu | Asn | Gly | Arg | Thr | Asp | Asn | Ala | Val |
| 80 |   |   |   |   | 85 |   |   |   |   | 90 |   |   |   |   | 95 |
| aag | aat | cac | tgg | aac | tcg | acg | ctc | aag | agg | aaa | tgc | ggc | ggt | tac | gac | 398 |
| Lys | Asn | His | Trp | Asn | Ser | Thr | Leu | Lys | Arg | Lys | Cys | Gly | Gly | Tyr | Asp |
|   |   |   |   | 100 |   |   |   |   | 105 |   |   |   |   | 110 |   |
| cat | cgg | ggt | tac | gat | ggt | tcg | gag | gat | cat | cgg | ccg | gtt | aag | aga | tcg | 446 |
| His | Arg | Gly | Tyr | Asp | Gly | Ser | Glu | Asp | His | Arg | Pro | Val | Lys | Arg | Ser |
|   |   | 115 |   |   |   |   | 120 |   |   |   |   | 125 |   |   |   |
| gtg | agt | gcg | gga | tct | cca | cct | gtt | gtt | act | ggg | ctt | tac | atg | agc | cca | 494 |
| Val | Ser | Ala | Gly | Ser | Pro | Pro | Val | Val | Thr | Gly | Leu | Tyr | Met | Ser | Pro |
| 130 |   |   |   |   | 135 |   |   |   |   | 140 |   |   |   |   |   |
| gga | agc | cca | act | gga | tct | gat | gtc | agt | gat | tca | agt | act | atc | ccg | ata | 542 |
| Gly | Ser | Pro | Thr | Gly | Ser | Asp | Val | Ser | Asp | Ser | Ser | Thr | Ile | Pro | Ile |
| 145 |   |   |   |   | 150 |   |   |   |   | 155 |   |   |   |   |   |
| tta | cct | tcc | gtt | gag | ctt | ttc | aag | cct | gtg | cct | aga | cct | ggt | gct | gtt | 590 |
| Leu | Pro | Ser | Val | Glu | Leu | Phe | Lys | Pro | Val | Pro | Arg | Pro | Gly | Ala | Val |
| 160 |   |   |   |   | 165 |   |   |   |   | 170 |   |   |   |   | 175 |
| gtg | cta | ccg | ctt | cct | atc | gaa | acg | tcg | tct | ttt | tcc | gat | gat | cca | ccg | 638 |
| Val | Leu | Pro | Leu | Pro | Ile | Glu | Thr | Ser | Ser | Phe | Ser | Asp | Asp | Pro | Pro |
|   |   |   | 180 |   |   |   |   | 185 |   |   |   |   | 190 |   |   |
| act | tcg | tta | agc | ttg | tca | ctt | cct | ggt | gcc | gac | gta | agc | gag | gag | tca | 686 |
| Thr | Ser | Leu | Ser | Leu | Ser | Leu | Pro | Gly | Ala | Asp | Val | Ser | Glu | Glu | Ser |
|   |   | 195 |   |   |   |   | 200 |   |   |   |   | 205 |   |   |   |
| aac | cgt | agc | cac | gag | tca | acg | aat | atc | aac | aac | acc | act | tcg | agc | cgc | 734 |
| Asn | Arg | Ser | His | Glu | Ser | Thr | Asn | Ile | Asn | Asn | Thr | Thr | Ser | Ser | Arg |
|   |   | 210 |   |   |   |   | 215 |   |   |   |   | 220 |   |   |   |
| cac | aac | cac | aac | aat | acg | gtg | tcg | ttt | atg | ccg | ttt | agt | ggt | ggg | ttt | 782 |
| His | Asn | His | Asn | Asn | Thr | Val | Ser | Phe | Met | Pro | Phe | Ser | Gly | Gly | Phe |
|   | 225 |   |   |   |   | 230 |   |   |   |   | 235 |   |   |   |   |
| aga | ggt | gcg | att | gag | gaa | atg | ggg | aag | tct | ttt | ccc | ggt | aac | gga | ggc | 830 |
| Arg | Gly | Ala | Ile | Glu | Glu | Met | Gly | Lys | Ser | Phe | Pro | Gly | Asn | Gly | Gly |
| 240 |   |   |   |   | 245 |   |   |   |   | 250 |   |   |   |   | 255 |
| gag | ttt | atg | gcg | gtg | gtg | caa | gag | atg | att | aag | gcg | gaa | gtg | agg | agt | 878 |
| Glu | Phe | Met | Ala | Val | Val | Gln | Glu | Met | Ile | Lys | Ala | Glu | Val | Arg | Ser |
|   |   |   |   | 260 |   |   |   |   | 265 |   |   |   |   | 270 |   |
| tac | atg | acg | gag | atg | caa | cgg | aac | aat | ggt | ggc | gga | ttc | gtc | gga | gga | 926 |
| Tyr | Met | Thr | Glu | Met | Gln | Arg | Asn | Asn | Gly | Gly | Gly | Phe | Val | Gly | Gly |
|   |   | 275 |   |   |   |   | 280 |   |   |   |   | 285 |   |   |   |
| ttc | att | gat | aat | ggc | atg | att | ccg | atg | agt | caa | att | gga | gtt | ggg | aga | 974 |
| Phe | Ile | Asp | Asn | Gly | Met | Ile | Pro | Met | Ser | Gln | Ile | Gly | Val | Gly | Arg |
|   |   | 290 |   |   |   |   | 295 |   |   |   |   | 300 |   |   |   |
| atc | gag | tag | acaaagtgag | attattagga | aactgtttaa | attggagaag |   |   |   |   |   |   |   |   | 1023 |
| Ile | Glu | * |
|   | 305 |   |

```
aagaaaaatg ctctgttttt ttctcctttg gattaggctt aagaattttg ggttttaagg    1083
aaatgtatag aggaaatcga gtgaacaaag ctcgagagct ggggacgtag tgacgaagac    1143
gaagatcaaa tttctcttaa gctattcagg aaaataaaat aaattttat tt              1195

<210> SEQ ID NO 128
<211> LENGTH: 305
<212> TYPE: PRT
<213> ORGANISM: Arabidopsis thaliana
<220> FEATURE:
<221> NAME/KEY: DOMAIN
```

<222> LOCATION: (6)...(105)
<223> OTHER INFORMATION: Conserved domain

<400> SEQUENCE: 128

| Met | Ala | Asp | Arg | Ile | Lys | Gly | Pro | Trp | Ser | Pro | Glu | Glu | Asp | Glu | Gln |
|---|---|---|---|---|---|---|---|---|---|---|---|---|---|---|---|
| 1 | | | | 5 | | | | | 10 | | | | | 15 | |

| Leu | Arg | Arg | Leu | Val | Val | Lys | Tyr | Gly | Pro | Arg | Asn | Trp | Thr | Val | Ile |
|---|---|---|---|---|---|---|---|---|---|---|---|---|---|---|---|
| | | | | 20 | | | | 25 | | | | | 30 | | |

| Ser | Lys | Ser | Ile | Pro | Gly | Arg | Ser | Gly | Lys | Ser | Cys | Arg | Leu | Arg | Trp |
|---|---|---|---|---|---|---|---|---|---|---|---|---|---|---|---|
| | 35 | | | | | 40 | | | | | 45 | | | | |

| Cys | Asn | Gln | Leu | Ser | Pro | Gln | Val | Glu | His | Arg | Pro | Phe | Ser | Ala | Glu |
|---|---|---|---|---|---|---|---|---|---|---|---|---|---|---|---|
| 50 | | | | | 55 | | | | | 60 | | | | | |

| Glu | Asp | Glu | Thr | Ile | Ala | Arg | Ala | His | Ala | Gln | Phe | Gly | Asn | Lys | Trp |
|---|---|---|---|---|---|---|---|---|---|---|---|---|---|---|---|
| 65 | | | | | 70 | | | | | 75 | | | | | 80 |

| Ala | Thr | Ile | Ala | Arg | Leu | Leu | Asn | Gly | Arg | Thr | Asp | Asn | Ala | Val | Lys |
|---|---|---|---|---|---|---|---|---|---|---|---|---|---|---|---|
| | | | | 85 | | | | | 90 | | | | | 95 | |

| Asn | His | Trp | Asn | Ser | Thr | Leu | Lys | Arg | Lys | Cys | Gly | Gly | Tyr | Asp | His |
|---|---|---|---|---|---|---|---|---|---|---|---|---|---|---|---|
| | | | 100 | | | | | 105 | | | | | 110 | | |

| Arg | Gly | Tyr | Asp | Gly | Ser | Glu | Asp | His | Arg | Pro | Val | Lys | Arg | Ser | Val |
|---|---|---|---|---|---|---|---|---|---|---|---|---|---|---|---|
| | | 115 | | | | | 120 | | | | | 125 | | | |

| Ser | Ala | Gly | Ser | Pro | Pro | Val | Val | Thr | Gly | Leu | Tyr | Met | Ser | Pro | Gly |
|---|---|---|---|---|---|---|---|---|---|---|---|---|---|---|---|
| | 130 | | | | | 135 | | | | | 140 | | | | |

| Ser | Pro | Thr | Gly | Ser | Asp | Val | Ser | Asp | Ser | Ser | Thr | Ile | Pro | Ile | Leu |
|---|---|---|---|---|---|---|---|---|---|---|---|---|---|---|---|
| 145 | | | | | 150 | | | | | 155 | | | | | 160 |

| Pro | Ser | Val | Glu | Leu | Phe | Lys | Pro | Val | Pro | Arg | Pro | Gly | Ala | Val | Val |
|---|---|---|---|---|---|---|---|---|---|---|---|---|---|---|---|
| | | | | 165 | | | | | 170 | | | | | 175 | |

| Leu | Pro | Leu | Pro | Ile | Glu | Thr | Ser | Ser | Phe | Ser | Asp | Asp | Pro | Pro | Thr |
|---|---|---|---|---|---|---|---|---|---|---|---|---|---|---|---|
| | | | 180 | | | | | 185 | | | | | 190 | | |

| Ser | Leu | Ser | Leu | Ser | Leu | Pro | Gly | Ala | Asp | Val | Ser | Glu | Glu | Ser | Asn |
|---|---|---|---|---|---|---|---|---|---|---|---|---|---|---|---|
| | | 195 | | | | | 200 | | | | | 205 | | | |

| Arg | Ser | His | Glu | Ser | Thr | Asn | Ile | Asn | Asn | Thr | Thr | Ser | Ser | Arg | His |
|---|---|---|---|---|---|---|---|---|---|---|---|---|---|---|---|
| | 210 | | | | | 215 | | | | | 220 | | | | |

| Asn | His | Asn | Asn | Thr | Val | Ser | Phe | Met | Pro | Phe | Ser | Gly | Gly | Phe | Arg |
|---|---|---|---|---|---|---|---|---|---|---|---|---|---|---|---|
| 225 | | | | | 230 | | | | | 235 | | | | | 240 |

| Gly | Ala | Ile | Glu | Glu | Met | Gly | Lys | Ser | Phe | Pro | Gly | Asn | Gly | Gly | Glu |
|---|---|---|---|---|---|---|---|---|---|---|---|---|---|---|---|
| | | | | 245 | | | | | 250 | | | | | 255 | |

| Phe | Met | Ala | Val | Val | Gln | Glu | Met | Ile | Lys | Ala | Glu | Val | Arg | Ser | Tyr |
|---|---|---|---|---|---|---|---|---|---|---|---|---|---|---|---|
| | | | 260 | | | | | 265 | | | | | 270 | | |

| Met | Thr | Glu | Met | Gln | Arg | Asn | Asn | Gly | Gly | Phe | Val | Gly | Gly | Phe |
|---|---|---|---|---|---|---|---|---|---|---|---|---|---|---|
| | 275 | | | | | 280 | | | | | 285 | | | |

| Ile | Asp | Asn | Gly | Met | Ile | Pro | Met | Ser | Gln | Ile | Gly | Val | Gly | Arg | Ile |
|---|---|---|---|---|---|---|---|---|---|---|---|---|---|---|---|
| | 290 | | | | | 295 | | | | | 300 | | | | |

Glu
305

<210> SEQ ID NO 129
<211> LENGTH: 1379
<212> TYPE: DNA
<213> ORGANISM: Arabidopsis thaliana
<220> FEATURE:
<221> NAME/KEY: CDS
<222> LOCATION: (23)...(1354)

<400> SEQUENCE: 129

```
aaagaaaaga aaaataaaga ta atg agg acg aag act aag tta gta ctc ata        52
                         Met Arg Thr Lys Thr Lys Leu Val Leu Ile
                          1               5                  10
```

| | |
|---|---|
| cct gat aga cac ttt cgg aga gcc aca ttc agg aag agg aat gca ggg<br>Pro Asp Arg His Phe Arg Arg Ala Thr Phe Arg Lys Arg Asn Ala Gly<br>              15                    20                25 | 100 |
| ata agg aag aaa ctc cac gag ctg aca act ctc tgt gac atc aaa gca<br>Ile Arg Lys Lys Leu His Glu Leu Thr Thr Leu Cys Asp Ile Lys Ala<br>          30                    35                    40 | 148 |
| tgt gcg gta atc tac agt ccg ttc gag aat cca acg gtg tgg ccg tca<br>Cys Ala Val Ile Tyr Ser Pro Phe Glu Asn Pro Thr Val Trp Pro Ser<br>              45                    50                    55 | 196 |
| acc gaa ggt gtt caa gag gtg att tcg gag ttc atg gag aag ccg gcg<br>Thr Glu Gly Val Gln Glu Val Ile Ser Glu Phe Met Glu Lys Pro Ala<br>60                    65                    70 | 244 |
| aca gaa cgg tcc aag acg atg atg agt cat gag act ttc ttg cgg gac<br>Thr Glu Arg Ser Lys Thr Met Met Ser His Glu Thr Phe Leu Arg Asp<br>75                    80                    85                    90 | 292 |
| caa atc acc aaa gaa caa aac aaa cta gag agt cta cgt cgt gaa aac<br>Gln Ile Thr Lys Glu Gln Asn Lys Leu Glu Ser Leu Arg Arg Glu Asn<br>              95                    100                 105 | 340 |
| cga gaa act cag ctt aag cat ttt atg ttt gat tgc gtt gga ggc aag<br>Arg Glu Thr Gln Leu Lys His Phe Met Phe Asp Cys Val Gly Gly Lys<br>             110                    115                 120 | 388 |
| atg agt gag caa cag tat ggt gca agg gac ctt caa gat tta agt ctt<br>Met Ser Glu Gln Gln Tyr Gly Ala Arg Asp Leu Gln Asp Leu Ser Leu<br>             125                    130                 135 | 436 |
| ttt act gat caa tat ctt aat cag ctt aat gcc agg aag aag ttc ctt<br>Phe Thr Asp Gln Tyr Leu Asn Gln Leu Asn Ala Arg Lys Lys Phe Leu<br>140                    145                    150 | 484 |
| aca gaa tat ggt gag tct tct tct tct gtt cct cct ctg ttt gat gtt<br>Thr Glu Tyr Gly Glu Ser Ser Ser Ser Val Pro Pro Leu Phe Asp Val<br>155                    160                    165                 170 | 532 |
| gcg ggt gcc aat cct cct gtt gtt gca gat caa gct gcg gta act gtt<br>Ala Gly Ala Asn Pro Pro Val Val Ala Asp Gln Ala Ala Val Thr Val<br>             175                    180                 185 | 580 |
| cct cct ttg ttt gct gtt gcg ggt gcc aat ctt cct gtt gtt gct gat<br>Pro Pro Leu Phe Ala Val Ala Gly Ala Asn Leu Pro Val Val Ala Asp<br>             190                    195                 200 | 628 |
| caa gct gcg gta act gtt cct cct ctg ttt gct gtt gcg ggt gcc aat<br>Gln Ala Ala Val Thr Val Pro Pro Leu Phe Ala Val Ala Gly Ala Asn<br>             205                    210                 215 | 676 |
| ctt cct gtt gtt gca gat caa gct gcg gtt aat gtt cct act gga ttt<br>Leu Pro Val Val Ala Asp Gln Ala Ala Val Asn Val Pro Thr Gly Phe<br>220                    225                    230 | 724 |
| cat aac atg aat gtg aac cag aat cag tat gag ccg gtt cag ccc tat<br>His Asn Met Asn Val Asn Gln Asn Gln Tyr Glu Pro Val Gln Pro Tyr<br>235                    240                    245                 250 | 772 |
| gtc cct act ggt ttt agt gat cat att caa tat cag aat atg aac ttc<br>Val Pro Thr Gly Phe Ser Asp His Ile Gln Tyr Gln Asn Met Asn Phe<br>             255                    260                 265 | 820 |
| aat caa aac caa caa gag ccg gtt cat tac cag gct ctt gct gtt gcg<br>Asn Gln Asn Gln Gln Glu Pro Val His Tyr Gln Ala Leu Ala Val Ala<br>             270                    275                 280 | 868 |
| ggt gcc ggt ctt cct atg act cag aat cag tat gag ccc gtt cac tac<br>Gly Ala Gly Leu Pro Met Thr Gln Asn Gln Tyr Glu Pro Val His Tyr<br>             285                    290                 295 | 916 |
| cag agt ctt gct gtc gcg ggt ggc ggt ctt cct atg agt cag ttg cag<br>Gln Ser Leu Ala Val Ala Gly Gly Gly Leu Pro Met Ser Gln Leu Gln<br>300                    305                    310 | 964 |
| tat gag ccg gtt cag cct tat atc cct act gtt ttt agt gat aat gtt<br>Tyr Glu Pro Val Gln Pro Tyr Ile Pro Thr Val Phe Ser Asp Asn Val | 1012 |

-continued

```
                  315                 320                 325                 330
caa tat cag cat atg aat ttg tat caa aat caa caa gag ccg gtt cac       1060
Gln Tyr Gln His Met Asn Leu Tyr Gln Asn Gln Gln Glu Pro Val His
                    335                 340                 345 tac caa gct ctt ggt gtt gca ggt gcc ggt ctt cct atg aat cag aat       1108
Tyr Gln Ala Leu Gly Val Ala Gly Ala Gly Leu Pro Met Asn Gln Asn
            350                 355                 360 cag tat gag ccg gtt cag ccc tat gtc cct act ggt ttt agt gat cat       1156
Gln Tyr Glu Pro Val Gln Pro Tyr Val Pro Thr Gly Phe Ser Asp His
        365                 370                 375 ttt cag ttt gag aat atg aat ttg aat caa aat caa cag gag ccg gtt       1204
Phe Gln Phe Glu Asn Met Asn Leu Asn Gln Asn Gln Gln Glu Pro Val
    380                 385                 390 caa tac caa gct cct gtt gat ttt aat cat cag att caa caa gga aac       1252
Gln Tyr Gln Ala Pro Val Asp Phe Asn His Gln Ile Gln Gln Gly Asn
395                 400                 405                 410 tat gat atg aat ttg aac cag aat atg agt ttg gat cca aat cag tat       1300
Tyr Asp Met Asn Leu Asn Gln Asn Met Ser Leu Asp Pro Asn Gln Tyr
                415                 420                 425 ccg ttt caa aat gat cca ttc atg aat atg ttg aca gaa tat cct tat       1348
Pro Phe Gln Asn Asp Pro Phe Met Asn Met Leu Thr Glu Tyr Pro Tyr
            430                 435                 440 gaa taa gcgggttatg ttggagagca tgcac                                   1379
Glu *
```

<210> SEQ ID NO 130
<211> LENGTH: 443
<212> TYPE: PRT
<213> ORGANISM: Arabidopsis thaliana

<400> SEQUENCE: 130

```
Met Arg Thr Lys Thr Lys Leu Val Leu Ile Pro Asp Arg His Phe Arg
  1               5                  10                  15

Arg Ala Thr Phe Arg Lys Arg Asn Ala Gly Ile Arg Lys Lys Leu His
                 20                  25                  30

Glu Leu Thr Thr Leu Cys Asp Ile Lys Ala Cys Ala Val Ile Tyr Ser
             35                  40                  45

Pro Phe Glu Asn Pro Thr Val Trp Pro Ser Thr Glu Gly Val Gln Glu
     50                  55                  60

Val Ile Ser Glu Phe Met Glu Lys Pro Ala Thr Glu Arg Ser Lys Thr
 65                  70                  75                  80

Met Met Ser His Glu Thr Phe Leu Arg Asp Gln Ile Thr Lys Glu Gln
                 85                  90                  95

Asn Lys Leu Glu Ser Leu Arg Arg Glu Asn Arg Glu Thr Gln Leu Lys
            100                 105                 110

His Phe Met Phe Asp Cys Val Gly Gly Lys Met Ser Glu Gln Gln Tyr
        115                 120                 125

Gly Ala Arg Asp Leu Gln Asp Leu Ser Leu Phe Thr Asp Gln Tyr Leu
    130                 135                 140

Asn Gln Leu Asn Ala Arg Lys Lys Phe Leu Thr Glu Tyr Gly Glu Ser
145                 150                 155                 160

Ser Ser Ser Val Pro Pro Leu Phe Asp Val Ala Gly Ala Asn Pro Pro
                165                 170                 175

Val Val Ala Asp Gln Ala Ala Val Thr Val Pro Pro Leu Phe Ala Val
            180                 185                 190

Ala Gly Ala Asn Leu Pro Val Val Ala Asp Gln Ala Ala Val Thr Val
        195                 200                 205
```

```
Pro Pro Leu Phe Ala Val Ala Gly Ala Asn Leu Pro Val Ala Asp
    210                 215                 220
Gln Ala Ala Val Asn Val Pro Thr Gly Phe His Asn Met Asn Val Asn
225                 230                 235                 240
Gln Asn Gln Tyr Glu Pro Val Gln Pro Tyr Val Pro Thr Gly Phe Ser
                245                 250                 255
Asp His Ile Gln Tyr Gln Asn Met Asn Phe Asn Gln Asn Gln Gln Glu
            260                 265                 270
Pro Val His Tyr Gln Ala Leu Ala Val Ala Gly Ala Gly Leu Pro Met
        275                 280                 285
Thr Gln Asn Gln Tyr Glu Pro Val His Tyr Gln Ser Leu Ala Val Ala
    290                 295                 300
Gly Gly Gly Leu Pro Met Ser Gln Leu Gln Tyr Glu Pro Val Gln Pro
305                 310                 315                 320
Tyr Ile Pro Thr Val Phe Ser Asp Asn Val Gln Tyr Gln His Met Asn
                325                 330                 335
Leu Tyr Gln Asn Gln Gln Glu Pro Val His Tyr Gln Ala Leu Gly Val
            340                 345                 350
Ala Gly Ala Gly Leu Pro Met Asn Gln Asn Gln Tyr Glu Pro Val Gln
        355                 360                 365
Pro Tyr Val Pro Thr Gly Phe Ser Asp His Phe Gln Phe Glu Asn Met
    370                 375                 380
Asn Leu Asn Gln Asn Gln Gln Glu Pro Val Gln Tyr Gln Ala Pro Val
385                 390                 395                 400
Asp Phe Asn His Gln Ile Gln Gln Gly Asn Tyr Asp Met Asn Leu Asn
                405                 410                 415
Gln Asn Met Ser Leu Asp Pro Asn Gln Tyr Pro Phe Gln Asn Asp Pro
            420                 425                 430
Phe Met Asn Met Leu Thr Glu Tyr Pro Tyr Glu
        435                 440

<210> SEQ ID NO 131
<211> LENGTH: 2330
<212> TYPE: DNA
<213> ORGANISM: Arabidopsis thaliana
<220> FEATURE:
<221> NAME/KEY: CDS
<222> LOCATION: (131)...(1996)

<400> SEQUENCE: 131
agctttatac tttctggcta ctgcaagctc atcagtgaaa agagcttaaa ccagagagat      60
ctgataagag aaattttaga gtctctctgc ttcaacaaga tctacatcga ccaggagatt     120
agaaagaatc atg ggt tct aag cat aac cca cca ggg aat aac aga tcg        169
            Met Gly Ser Lys His Asn Pro Pro Gly Asn Asn Arg Ser
              1               5                  10 aga agt aca cta tct cta ctc gtt gtg gtt ggt tta tgt tgt ttc ttc        217
Arg Ser Thr Leu Ser Leu Leu Val Val Val Gly Leu Cys Cys Phe Phe
         15                  20                  25 tat ctt ctt gga gca tgg caa aag agt ggg ttt ggt aaa gga gat agc        265
Tyr Leu Leu Gly Ala Trp Gln Lys Ser Gly Phe Gly Lys Gly Asp Ser
 30                  35                  40                  45 ata gct atg gag att aca aag caa gcg cag tgt act gac att gtc act        313
Ile Ala Met Glu Ile Thr Lys Gln Ala Gln Cys Thr Asp Ile Val Thr
                 50                  55                  60 gat ctt gat ttt gaa cct cat cac aac aca gtg aag atc cca cat aaa        361
Asp Leu Asp Phe Glu Pro His His Asn Thr Val Lys Ile Pro His Lys
```

-continued

|  |  |  |  |  |  |  |  | 65 |  |  |  |  |  | 70 |  |  |  |  |  | 75 |  |  |  |  |  |  |
|---|---|---|---|---|---|---|---|---|---|---|---|---|---|---|---|---|---|---|---|---|---|---|---|---|---|---|

```
gct gat ccc aaa cct gtt tct ttc aaa ccg tgt gat gtg aag ctc aag      409
Ala Asp Pro Lys Pro Val Ser Phe Lys Pro Cys Asp Val Lys Leu Lys
         80                  85                  90 gat tac acg cct tgt caa gag caa gac cga gct atg aag ttc ccg aga      457
Asp Tyr Thr Pro Cys Gln Glu Gln Asp Arg Ala Met Lys Phe Pro Arg
 95                 100                 105 gag aac atg att tac aga gag aga cat tgt cct cct gat aat gag aag      505
Glu Asn Met Ile Tyr Arg Glu Arg His Cys Pro Pro Asp Asn Glu Lys
110                 115                 120                 125 ctg cgt tgt ctt gtt cca gct cct aaa ggg tat atg act cct ttc cct      553
Leu Arg Cys Leu Val Pro Ala Pro Lys Gly Tyr Met Thr Pro Phe Pro
                130                 135                 140 tgg cct aaa agc aga gat tat gtt cac tat gct aat gct cct ttc aag      601
Trp Pro Lys Ser Arg Asp Tyr Val His Tyr Ala Asn Ala Pro Phe Lys
            145                 150                 155 agc ttg act gtc gaa aaa gct gga cag aat tgg gtt cag ttt caa ggg      649
Ser Leu Thr Val Glu Lys Ala Gly Gln Asn Trp Val Gln Phe Gln Gly
        160                 165                 170 aat gtg ttt aaa ttc cct ggt gga gga act atg ttt cct caa ggt gct      697
Asn Val Phe Lys Phe Pro Gly Gly Gly Thr Met Phe Pro Gln Gly Ala
175                 180                 185 gat gcg tat att gaa gag cta gct tct gtt atc cct atc aaa gat ggc      745
Asp Ala Tyr Ile Glu Glu Leu Ala Ser Val Ile Pro Ile Lys Asp Gly
190                 195                 200                 205 tct gtt aga acc gca ttg gac act gga tgt ggg gtt gct agt tgg ggt      793
Ser Val Arg Thr Ala Leu Asp Thr Gly Cys Gly Val Ala Ser Trp Gly
                210                 215                 220 gct tat atg ctt aag agg aat gtt ttg act atg tcg ttt gcg cca agg      841
Ala Tyr Met Leu Lys Arg Asn Val Leu Thr Met Ser Phe Ala Pro Arg
            225                 230                 235 gat aac cac gaa gca caa gtc cag ttt gcg ctt gag aga ggt gtt cca      889
Asp Asn His Glu Ala Gln Val Gln Phe Ala Leu Glu Arg Gly Val Pro
        240                 245                 250 gcg att atc gct gtt ctt gga tca atc ctt ctt cct tac cct gca aga      937
Ala Ile Ile Ala Val Leu Gly Ser Ile Leu Leu Pro Tyr Pro Ala Arg
255                 260                 265 gcc ttt gac atg gct caa tgc tct cga tgc ttg ata cca tgg acc gca      985
Ala Phe Asp Met Ala Gln Cys Ser Arg Cys Leu Ile Pro Trp Thr Ala
270                 275                 280                 285 aac gag gga aca tac tta atg gaa gta gat aga gtc ttg aga cct gga     1033
Asn Glu Gly Thr Tyr Leu Met Glu Val Asp Arg Val Leu Arg Pro Gly
                290                 295                 300 ggt tac tgg gtc tta tcg ggt cct cca atc aac tgg aag aca tgg cac     1081
Gly Tyr Trp Val Leu Ser Gly Pro Pro Ile Asn Trp Lys Thr Trp His
            305                 310                 315 aag acg tgg aac cga act aaa gca gag cta aat gcc gag caa aag aga     1129
Lys Thr Trp Asn Arg Thr Lys Ala Glu Leu Asn Ala Glu Gln Lys Arg
        320                 325                 330 ata gag gga atc gca gag tcc tta tgc tgg gag aag aag tat gag aag     1177
Ile Glu Gly Ile Ala Glu Ser Leu Cys Trp Glu Lys Lys Tyr Glu Lys
335                 340                 345 gga gac att gca att ttc aga aag aaa ata aac gat aga tca tgc gat     1225
Gly Asp Ile Ala Ile Phe Arg Lys Lys Ile Asn Asp Arg Ser Cys Asp
350                 355                 360                 365 aga tca aca ccg gtt gac acc tgc aaa aga aag gac act gac gat gtc     1273
Arg Ser Thr Pro Val Asp Thr Cys Lys Arg Lys Asp Thr Asp Asp Val
                370                 375                 380 tgg tac aag gag ata gaa acg tgt gta aca cca ttc cct aaa gta tca     1321
```

```
Trp Tyr Lys Glu Ile Glu Thr Cys Val Thr Pro Phe Pro Lys Val Ser
            385                 390                 395 aac gaa gaa gaa gtt gct gga gga aag cta aag aag ttc ccc gag agg      1369
Asn Glu Glu Glu Val Ala Gly Gly Lys Leu Lys Lys Phe Pro Glu Arg
        400                 405                 410 cta ttc gca gtg cct cca agt atc tct aaa ggt ttg att aat ggc gtc      1417
Leu Phe Ala Val Pro Pro Ser Ile Ser Lys Gly Leu Ile Asn Gly Val
415                 420                 425 gac gag gaa tca tac caa gaa gac atc aat cta tgg aag aag cga gtg      1465
Asp Glu Glu Ser Tyr Gln Glu Asp Ile Asn Leu Trp Lys Lys Arg Val
430                 435                 440                 445 acc gga tac aag aga att aac aga ctg ata ggt tcc acc aga tac cgt      1513
Thr Gly Tyr Lys Arg Ile Asn Arg Leu Ile Gly Ser Thr Arg Tyr Arg
                450                 455                 460 aat gtg atg gat atg aac gcc ggt ctt ggt gga ttc gct gct gcg ctt      1561
Asn Val Met Asp Met Asn Ala Gly Leu Gly Gly Phe Ala Ala Ala Leu
            465                 470                 475 gaa tcg cct aaa tcg tgg gtt atg aat gtg att cca acc att aac aag      1609
Glu Ser Pro Lys Ser Trp Val Met Asn Val Ile Pro Thr Ile Asn Lys
        480                 485                 490 aac aca ttg agt gtt gtt tat gag aga ggt ctc att ggt atc tat cat      1657
Asn Thr Leu Ser Val Val Tyr Glu Arg Gly Leu Ile Gly Ile Tyr His
495                 500                 505 gac tgg tgt gaa ggc ttt tca act tat cca aga aca tac gat ttc att      1705
Asp Trp Cys Glu Gly Phe Ser Thr Tyr Pro Arg Thr Tyr Asp Phe Ile
510                 515                 520                 525 cac gct agt ggt gtc ttc agc ttg tat cag cac agc tgc aaa ctt gag      1753
His Ala Ser Gly Val Phe Ser Leu Tyr Gln His Ser Cys Lys Leu Glu
                530                 535                 540 gat att ctt ctt gaa act gat cgg att tta cga ccg gaa ggg att gtg      1801
Asp Ile Leu Leu Glu Thr Asp Arg Ile Leu Arg Pro Glu Gly Ile Val
            545                 550                 555 att ttc cgg gat gag gtt gat gtt ttg aat gat gtg agg aag atc gtt      1849
Ile Phe Arg Asp Glu Val Asp Val Leu Asn Asp Val Arg Lys Ile Val
        560                 565                 570 gat gga atg aga tgg gat act aag tta atg gat cat gaa gac ggt cct      1897
Asp Gly Met Arg Trp Asp Thr Lys Leu Met Asp His Glu Asp Gly Pro
575                 580                 585 ctc gtg ccg gag aag att ctt gtc gcc acg aag cag tat tgg gta gcc      1945
Leu Val Pro Glu Lys Ile Leu Val Ala Thr Lys Gln Tyr Trp Val Ala
590                 595                 600                 605 ggc gac gat gga aac aat tct ccg tcg tct tct aat agt gaa gaa gaa      1993
Gly Asp Asp Gly Asn Asn Ser Pro Ser Ser Ser Asn Ser Glu Glu Glu
                610                 615                 620 taa aacaaaaaca aaaaactcct caggttacta agcttgaagt gtagatctat           2046
*
tttacaacat ctggaaaatt cttatcaaaa aaggaaggaa tcagaatttc cattaaagaa    2106
aggtgtcaaa aaaagttgt aaaactatat agtagtgatc aagacgaata tgtgcattta     2166
tgttttattt ttgttcccta gtttttaatt ttatttttt gaaggaagaa aaaattagtt     2226
ccatgtgttt ttgcaagata gttgaaacct tggacgcttg ttatgtatga tgcgatcttg    2286 acattttta ataacagtta ttttaaataa atttatgata taaa                      2330

<210> SEQ ID NO 132
<211> LENGTH: 621
<212> TYPE: PRT
<213> ORGANISM: Arabidopsis thaliana

<400> SEQUENCE: 132
```

-continued

```
Met Gly Ser Lys His Asn Pro Pro Gly Asn Asn Arg Ser Arg Ser Thr
 1               5                  10                  15

Leu Ser Leu Leu Val Val Gly Leu Cys Cys Phe Phe Tyr Leu Leu
             20                  25                  30

Gly Ala Trp Gln Lys Ser Gly Phe Gly Lys Gly Asp Ser Ile Ala Met
             35                  40                  45

Glu Ile Thr Lys Gln Ala Gln Cys Thr Asp Ile Val Thr Asp Leu Asp
 50                  55                  60

Phe Glu Pro His His Asn Thr Val Lys Ile Pro His Lys Ala Asp Pro
 65                  70                  75                  80

Lys Pro Val Ser Phe Lys Pro Cys Asp Val Lys Leu Lys Asp Tyr Thr
             85                  90                  95

Pro Cys Gln Glu Gln Asp Arg Ala Met Lys Phe Pro Arg Glu Asn Met
            100                 105                 110

Ile Tyr Arg Glu Arg His Cys Pro Pro Asp Asn Glu Lys Leu Arg Cys
            115                 120                 125

Leu Val Pro Ala Pro Lys Gly Tyr Met Thr Pro Phe Pro Trp Pro Lys
    130                 135                 140

Ser Arg Asp Tyr Val His Tyr Ala Asn Ala Pro Phe Lys Ser Leu Thr
145                 150                 155                 160

Val Glu Lys Ala Gly Gln Asn Trp Val Gln Phe Gln Gly Asn Val Phe
            165                 170                 175

Lys Phe Pro Gly Gly Gly Thr Met Phe Pro Gln Gly Ala Asp Ala Tyr
            180                 185                 190

Ile Glu Glu Leu Ala Ser Val Ile Pro Ile Lys Asp Gly Ser Val Arg
            195                 200                 205

Thr Ala Leu Asp Thr Gly Cys Gly Val Ala Ser Trp Gly Ala Tyr Met
    210                 215                 220

Leu Lys Arg Asn Val Leu Thr Met Ser Phe Ala Pro Arg Asp Asn His
225                 230                 235                 240

Glu Ala Gln Val Gln Phe Ala Leu Glu Arg Gly Val Pro Ala Ile Ile
            245                 250                 255

Ala Val Leu Gly Ser Ile Leu Leu Pro Tyr Pro Ala Arg Ala Phe Asp
            260                 265                 270

Met Ala Gln Cys Ser Arg Cys Leu Ile Pro Trp Thr Ala Asn Glu Gly
            275                 280                 285

Thr Tyr Leu Met Glu Val Asp Arg Val Leu Arg Pro Gly Gly Tyr Trp
    290                 295                 300

Val Leu Ser Gly Pro Pro Ile Asn Trp Lys Thr Trp His Lys Thr Trp
305                 310                 315                 320

Asn Arg Thr Lys Ala Glu Leu Asn Ala Glu Gln Lys Arg Ile Glu Gly
            325                 330                 335

Ile Ala Glu Ser Leu Cys Trp Glu Lys Lys Tyr Glu Lys Gly Asp Ile
            340                 345                 350

Ala Ile Phe Arg Lys Lys Ile Asn Asp Arg Ser Cys Asp Arg Ser Thr
            355                 360                 365

Pro Val Asp Thr Cys Lys Arg Lys Asp Thr Asp Val Trp Tyr Lys
    370                 375                 380

Glu Ile Glu Thr Cys Val Thr Pro Phe Pro Lys Val Ser Asn Glu Glu
385                 390                 395                 400

Glu Val Ala Gly Gly Lys Leu Lys Lys Phe Pro Glu Arg Leu Phe Ala
            405                 410                 415

Val Pro Pro Ser Ile Ser Lys Gly Leu Ile Asn Gly Val Asp Glu Glu
```

```
                       420                 425                 430
Ser Tyr Gln Glu Asp Ile Asn Leu Trp Lys Lys Arg Val Thr Gly Tyr
                435                 440                 445

Lys Arg Ile Asn Arg Leu Ile Gly Ser Thr Arg Tyr Arg Asn Val Met
        450                 455                 460

Asp Met Asn Ala Gly Leu Gly Gly Phe Ala Ala Leu Glu Ser Pro
465                 470                 475                 480

Lys Ser Trp Val Met Asn Val Ile Pro Thr Ile Asn Lys Asn Thr Leu
                    485                 490                 495

Ser Val Val Tyr Glu Arg Gly Leu Ile Gly Ile Tyr His Asp Trp Cys
                500                 505                 510

Glu Gly Phe Ser Thr Tyr Pro Arg Thr Tyr Asp Phe Ile His Ala Ser
            515                 520                 525

Gly Val Phe Ser Leu Tyr Gln His Ser Cys Lys Leu Glu Asp Ile Leu
            530                 535                 540

Leu Glu Thr Asp Arg Ile Leu Arg Pro Glu Gly Ile Val Ile Phe Arg
545                 550                 555                 560

Asp Glu Val Asp Val Leu Asn Asp Val Arg Lys Ile Val Asp Gly Met
                565                 570                 575

Arg Trp Asp Thr Lys Leu Met Asp His Glu Asp Gly Pro Leu Val Pro
                580                 585                 590

Glu Lys Ile Leu Val Ala Thr Lys Gln Tyr Trp Val Ala Gly Asp Asp
            595                 600                 605

Gly Asn Asn Ser Pro Ser Ser Ser Asn Ser Glu Glu Glu
        610                 615                 620

<210> SEQ ID NO 133
<211> LENGTH: 1226
<212> TYPE: DNA
<213> ORGANISM: Arabidopsis thaliana
<220> FEATURE:
<221> NAME/KEY: CDS
<222> LOCATION: (248)...(1039)

<400> SEQUENCE: 133
gtccgttgtc atattttaaa tttatcacct tcttgagaat tccacatttt tatccttttt     60
gtcatgtagt gtatattttt tcctctaacc taattaaaat caaaacaaaa tcctttgacc    120
caattagctt cgcgatatat cagaagagat caaactactt tgatcagacc atgatcttct    180
tcttcttctt cttcttcttc ttcttctttt tagacgatca caattcctaa accctatttc    240 tcagatt atg ctg act ctt tac cat caa gaa agg tca ccg gac gcc aca       289
        Met Leu Thr Leu Tyr His Gln Glu Arg Ser Pro Asp Ala Thr
        1               5                   10 agt aat gat cgc gat gag acg cca gag act gtg gtt aga gaa gtc cac       337
Ser Asn Asp Arg Asp Glu Thr Pro Glu Thr Val Val Arg Glu Val His
15                  20                  25                  30 gcg cta act cca gcg ccg gag gat aat tcc cgg acg atg acg gcg acg       385
Ala Leu Thr Pro Ala Pro Glu Asp Asn Ser Arg Thr Met Thr Ala Thr
                35                  40                  45 cta cct cca ccg cct gct ttc cga ggc tat ttt tct cct cca agg tca       433
Leu Pro Pro Pro Pro Ala Phe Arg Gly Tyr Phe Ser Pro Pro Arg Ser
            50                  55                  60 gcg acg acg atg agc gaa gga gag aac ttc aca act ata agc aga gag       481
Ala Thr Thr Met Ser Glu Gly Glu Asn Phe Thr Thr Ile Ser Arg Glu
        65                  70                  75 ttc aac gct cta gtc atc gcc gga tcc tcc atg gag aac aac gaa cta       529
Phe Asn Ala Leu Val Ile Ala Gly Ser Ser Met Glu Asn Asn Glu Leu
```

```
       80                  85                  90
atg act cgt gac gtc acg cag cgt gaa gat gag aga caa gac gag ttg      577
Met Thr Arg Asp Val Thr Gln Arg Glu Asp Glu Arg Gln Asp Glu Leu
 95                 100                 105                 110 atg aga atc cac gag gac acg gat cat gaa gag gaa acg aat cct tta      625
Met Arg Ile His Glu Asp Thr Asp His Glu Glu Glu Thr Asn Pro Leu
                115                 120                 125 gca atc gtg ccg gat cag tat cct ggt tcg ggt ttg gat cct gga agt      673
Ala Ile Val Pro Asp Gln Tyr Pro Gly Ser Gly Leu Asp Pro Gly Ser
            130                 135                 140 gat aat ggg ccg ggt cag agt cgg gtt ggg tcg acg gtg caa aga gtt      721
Asp Asn Gly Pro Gly Gln Ser Arg Val Gly Ser Thr Val Gln Arg Val
        145                 150                 155 aag agg gaa gag gtg gaa gcg aag ata acg gcg tgg cag acg gca aaa      769
Lys Arg Glu Glu Val Glu Ala Lys Ile Thr Ala Trp Gln Thr Ala Lys
    160                 165                 170 ctg gct aag att aat aac agg ttt aag agg gaa gac gcc gtt att aac      817
Leu Ala Lys Ile Asn Asn Arg Phe Lys Arg Glu Asp Ala Val Ile Asn
175                 180                 185                 190 ggt tgg ttt aat gaa caa gtt aac aag gcc aac tct tgg atg aag aaa      865
Gly Trp Phe Asn Glu Gln Val Asn Lys Ala Asn Ser Trp Met Lys Lys
                195                 200                 205 att gag tat aat gta ggt tca ttc aac aat cgt cta aat gag gaa gct      913
Ile Glu Tyr Asn Val Gly Ser Phe Asn Asn Arg Leu Asn Glu Glu Ala
            210                 215                 220 aga gga gag aaa agc aaa agc gat gga gaa aac gca aaa caa tgt ggc      961
Arg Gly Glu Lys Ser Lys Ser Asp Gly Glu Asn Ala Lys Gln Cys Gly
        225                 230                 235 gaa agc gca gag gaa agc gga gga gag aag agc gac ggc aga ggc aaa     1009
Glu Ser Ala Glu Glu Ser Gly Gly Glu Lys Ser Asp Gly Arg Gly Lys
    240                 245                 250 gag agg gac aga ggt tgc aaa agt agt tga agttgctaat ctcatgagag       1059
Glu Arg Asp Arg Gly Cys Lys Ser Ser  *
255                 260 cccttggacg tcctcctgcc aaacgctcct tcttctcttt ctcctaattt ttagttatat   1119
caaaccatta aattaaacag tactcgttat atatctagtt agtaaacaaa ggggcagttt   1179
tatagctcat gtacacataa ttgagagtgt agtactgttg tgtcaaa                 1226

<210> SEQ ID NO 134
<211> LENGTH: 263
<212> TYPE: PRT
<213> ORGANISM: Arabidopsis thaliana
<220> FEATURE:
<221> NAME/KEY: DOMAIN
<222> LOCATION: (205)...(263)
<223> OTHER INFORMATION: Conserved domain

<400> SEQUENCE: 134

Met Leu Thr Leu Tyr His Gln Glu Arg Ser Pro Asp Ala Thr Ser Asn
 1               5                  10                  15

Asp Arg Asp Glu Thr Pro Glu Thr Val Val Arg Glu Val His Ala Leu
            20                  25                  30

Thr Pro Ala Pro Glu Asp Asn Ser Arg Thr Met Thr Ala Thr Leu Pro
        35                  40                  45

Pro Pro Pro Ala Phe Arg Gly Tyr Phe Ser Pro Arg Ser Ala Thr
    50                  55                  60

Thr Met Ser Glu Gly Glu Asn Phe Thr Thr Ile Ser Arg Glu Phe Asn
65                  70                  75                  80
```

```
Ala Leu Val Ile Ala Gly Ser Ser Met Glu Asn Asn Glu Leu Met Thr
                85                  90                  95

Arg Asp Val Thr Gln Arg Glu Asp Glu Arg Gln Asp Glu Leu Met Arg
            100                 105                 110

Ile His Glu Asp Thr Asp His Glu Glu Thr Asn Pro Leu Ala Ile
        115                 120                 125

Val Pro Asp Gln Tyr Pro Gly Ser Gly Leu Asp Pro Gly Ser Asp Asn
    130                 135                 140

Gly Pro Gly Gln Ser Arg Val Gly Ser Thr Val Gln Arg Val Lys Arg
145                 150                 155                 160

Glu Glu Val Glu Ala Lys Ile Thr Ala Trp Gln Thr Ala Lys Leu Ala
                165                 170                 175

Lys Ile Asn Asn Arg Phe Lys Arg Glu Asp Ala Val Ile Asn Gly Trp
            180                 185                 190

Phe Asn Glu Gln Val Asn Lys Ala Asn Ser Trp Met Lys Lys Ile Glu
        195                 200                 205

Tyr Asn Val Gly Ser Phe Asn Asn Arg Leu Asn Glu Glu Ala Arg Gly
    210                 215                 220

Glu Lys Ser Lys Ser Asp Gly Glu Asn Ala Lys Gln Cys Gly Glu Ser
225                 230                 235                 240

Ala Glu Glu Ser Gly Gly Glu Lys Ser Asp Gly Arg Gly Lys Glu Arg
                245                 250                 255

Asp Arg Gly Cys Lys Ser Ser
            260

<210> SEQ ID NO 135
<211> LENGTH: 828
<212> TYPE: DNA
<213> ORGANISM: Arabidopsis thaliana
<220> FEATURE:
<221> NAME/KEY: CDS
<222> LOCATION: (1)...(828)

<400> SEQUENCE: 135 atg ata aaa cta cta ttt acg tac ata tgc aca tac aca tat aaa cta        48
Met Ile Lys Leu Leu Phe Thr Tyr Ile Cys Thr Tyr Thr Tyr Lys Leu
  1               5                  10                  15 tat gct cta tat cat atg gat tac gca tgc gtg tgt atg tat aaa tat       96
Tyr Ala Leu Tyr His Met Asp Tyr Ala Cys Val Cys Met Tyr Lys Tyr
             20                  25                  30 aaa ggc atc gtc acg ctt caa gtt tgt ctc ttt tat att aaa ctg aga      144
Lys Gly Ile Val Thr Leu Gln Val Cys Leu Phe Tyr Ile Lys Leu Arg
         35                  40                  45 gtt ttc ctc tca aac ttt acc ttt tct tct tcg atc cta gct ctt aag      192
Val Phe Leu Ser Asn Phe Thr Phe Ser Ser Ser Ile Leu Ala Leu Lys
     50                  55                  60 aac cct aat aat tca ttg atc aaa ata atg gcg att ttg ccg gaa aac      240
Asn Pro Asn Asn Ser Leu Ile Lys Ile Met Ala Ile Leu Pro Glu Asn
 65                  70                  75                  80 tct tca aac ttg gat ctt act atc tcc gtt cca ggc ttc tct tca tcc      288
Ser Ser Asn Leu Asp Leu Thr Ile Ser Val Pro Gly Phe Ser Ser Ser
                 85                  90                  95 cct ctc tcc gat gaa gga agt ggc gga gga aga gac cag cta agg cta      336
Pro Leu Ser Asp Glu Gly Ser Gly Gly Gly Arg Asp Gln Leu Arg Leu
            100                 105                 110 gac atg aat cgg tta ccg tcg tct gaa gac gga gac gat gaa gaa ttc      384
Asp Met Asn Arg Leu Pro Ser Ser Glu Asp Gly Asp Asp Glu Glu Phe
        115                 120                 125
```

```
agt cac gat gat ggc tct gct cct ccg cga aag aaa ctc cgt cta acc      432
Ser His Asp Asp Gly Ser Ala Pro Pro Arg Lys Lys Leu Arg Leu Thr
    130                 135                 140 aga gaa cag tca cgt ctt ctt gaa gat agt ttc aga cag aat cat acc      480
Arg Glu Gln Ser Arg Leu Leu Glu Asp Ser Phe Arg Gln Asn His Thr
145                 150                 155                 160 ctt aat ccc aaa caa aag gaa gta ctt gcc aag cat ttg atg cta cgg      528
Leu Asn Pro Lys Gln Lys Glu Val Leu Ala Lys His Leu Met Leu Arg
                165                 170                 175 cca aga caa att gaa gtt tgg ttt caa aac cgt aga gca agg agc aaa      576
Pro Arg Gln Ile Glu Val Trp Phe Gln Asn Arg Arg Ala Arg Ser Lys
            180                 185                 190 ttg aag caa acc gag atg gaa tgc gag tat ctc aaa agg tgg ttt ggt      624
Leu Lys Gln Thr Glu Met Glu Cys Glu Tyr Leu Lys Arg Trp Phe Gly
        195                 200                 205 tca tta acg gaa gaa aac cac agg ctc cat aga gaa gta gaa gag ctt      672
Ser Leu Thr Glu Glu Asn His Arg Leu His Arg Glu Val Glu Glu Leu
    210                 215                 220 aga gcc ata aag gtt ggc cca aca acg gtg aac tct gcc tcg agc ctt      720
Arg Ala Ile Lys Val Gly Pro Thr Thr Val Asn Ser Ala Ser Ser Leu
225                 230                 235                 240 act atg tgt cct cgc tgc gag cga gtt acc cct gcc gcg agc cct tcg      768
Thr Met Cys Pro Arg Cys Glu Arg Val Thr Pro Ala Ala Ser Pro Ser
                245                 250                 255 agg gcg gtg gtg ccg gtt ccg gct aag aaa acg ttt ccg ccg caa gag      816
Arg Ala Val Val Pro Val Pro Ala Lys Lys Thr Phe Pro Pro Gln Glu
            260                 265                 270 cgt gat cgt tga                                                       828
Arg Asp Arg  *
        275
```

<210> SEQ ID NO 136
<211> LENGTH: 275
<212> TYPE: PRT
<213> ORGANISM: Arabidopsis thaliana
<220> FEATURE:
<221> NAME/KEY: DOMAIN
<222> LOCATION: (135)...(195)
<223> OTHER INFORMATION: Conserved domain

<400> SEQUENCE: 136

```
Met Ile Lys Leu Leu Phe Thr Tyr Ile Cys Thr Tyr Thr Tyr Lys Leu
 1               5                  10                  15

Tyr Ala Leu Tyr His Met Asp Tyr Ala Cys Val Cys Met Tyr Lys Tyr
            20                  25                  30

Lys Gly Ile Val Thr Leu Gln Val Cys Leu Phe Tyr Ile Lys Leu Arg
        35                  40                  45

Val Phe Leu Ser Asn Phe Thr Phe Ser Ser Ile Leu Ala Leu Lys
    50                  55                  60

Asn Pro Asn Ser Leu Ile Lys Ile Met Ala Ile Leu Pro Glu Asn
65                  70                  75                  80

Ser Ser Asn Leu Asp Leu Thr Ile Ser Val Pro Gly Phe Ser Ser
                85                  90                  95

Pro Leu Ser Asp Glu Gly Ser Gly Gly Arg Asp Gln Leu Arg Leu
            100                 105                 110

Asp Met Asn Arg Leu Pro Ser Ser Glu Asp Gly Asp Glu Glu Phe
        115                 120                 125

Ser His Asp Asp Gly Ser Ala Pro Pro Arg Lys Lys Leu Arg Leu Thr
    130                 135                 140
```

-continued

```
Arg Glu Gln Ser Arg Leu Leu Glu Asp Ser Phe Arg Gln Asn His Thr
145                 150                 155                 160

Leu Asn Pro Lys Gln Lys Glu Val Leu Ala Lys His Leu Met Leu Arg
            165                 170                 175

Pro Arg Gln Ile Glu Val Trp Phe Gln Asn Arg Arg Ala Arg Ser Lys
        180                 185                 190

Leu Lys Gln Thr Glu Met Glu Cys Glu Tyr Leu Lys Arg Trp Phe Gly
    195                 200                 205

Ser Leu Thr Glu Glu Asn His Arg Leu His Arg Glu Val Glu Glu Leu
210                 215                 220

Arg Ala Ile Lys Val Gly Pro Thr Thr Val Asn Ser Ala Ser Ser Leu
225                 230                 235                 240

Thr Met Cys Pro Arg Cys Glu Arg Val Thr Pro Ala Ala Ser Pro Ser
                245                 250                 255

Arg Ala Val Val Pro Val Pro Ala Lys Lys Thr Phe Pro Pro Gln Glu
            260                 265                 270

Arg Asp Arg
        275
```

```
<210> SEQ ID NO 137
<211> LENGTH: 983
<212> TYPE: DNA
<213> ORGANISM: Arabidopsis thaliana
<220> FEATURE:
<221> NAME/KEY: CDS
<222> LOCATION: (108)...(722)

<400> SEQUENCE: 137
```

```
aagttaatat gagaataatg agaaaaccac tttcccaaat tgcttttaa aatccctcct      60 cacacagatt ccttccttca tcacctcaca cactctctac gcttgac atg gcc ttc     116
                                                   Met Ala Phe
                                                     1 gat ctc cac cat ggc tca gct tca gat acg cat tca tca gaa ctt ccg    164
Asp Leu His His Gly Ser Ala Ser Asp Thr His Ser Ser Glu Leu Pro
        5                  10                  15 tcg ttt tct ctc cca cct tat cct cag atg ata atg gaa gcg att gag    212
Ser Phe Ser Leu Pro Pro Tyr Pro Gln Met Ile Met Glu Ala Ile Glu
 20                  25                  30                  35 tcc ttg aac gat aag aac ggc tgc aac aaa acg acg att gct aag cac    260
Ser Leu Asn Asp Lys Asn Gly Cys Asn Lys Thr Thr Ile Ala Lys His
                 40                  45                  50 atc gag tcg act caa caa act cta ccg ccg tca cac atg acg ctg ctc    308
Ile Glu Ser Thr Gln Gln Thr Leu Pro Pro Ser His Met Thr Leu Leu
             55                  60                  65 agc tac cat ctc aac cag atg aag aaa acc ggt cag cta atc atg gtg    356
Ser Tyr His Leu Asn Gln Met Lys Lys Thr Gly Gln Leu Ile Met Val
         70                  75                  80 aag aac aat tat atg aaa cca gat cca gat gct cct cct aag cgt ggt    404
Lys Asn Asn Tyr Met Lys Pro Asp Pro Asp Ala Pro Pro Lys Arg Gly
     85                  90                  95 cgt ggc cgt cct ccg aag cag aag act cag gcc gaa tct gac gcc gct    452
Arg Gly Arg Pro Pro Lys Gln Lys Thr Gln Ala Glu Ser Asp Ala Ala
100                 105                 110                 115 gct gct gct gtt gtt gct gcc acc gtc gtc tct aca gat ccg cct aga    500
Ala Ala Ala Val Val Ala Ala Thr Val Val Ser Thr Asp Pro Pro Arg
                120                 125                 130 tct cgt ggc cgt cca ccg aag ccg aaa gat cca tcg gag cct ccc cag    548
Ser Arg Gly Arg Pro Pro Lys Pro Lys Asp Pro Ser Glu Pro Pro Gln
            135                 140                 145
```

```
gag aag gtc att acc gga tct gga agg cca cga gga cga cca ccg aag      596
Glu Lys Val Ile Thr Gly Ser Gly Arg Pro Arg Gly Arg Pro Pro Lys
        150                 155                 160 aga ccg aga aca gat tcg gag acg gtt gct gcg ccg gaa ccg gca gct      644
Arg Pro Arg Thr Asp Ser Glu Thr Val Ala Ala Pro Glu Pro Ala Ala
165                 170                 175 cag gcg aca ggt gag cgt agg gga cgt ggg aga cct ccg aag gtg aag      692
Gln Ala Thr Gly Glu Arg Arg Gly Arg Gly Arg Pro Pro Lys Val Lys
180                 185                 190                 195 ccg acg gtg gtt gct ccg gtt ggg tgc tga attaatcggt acttatgcaa        742
Pro Thr Val Val Ala Pro Val Gly Cys *
                200 tttcggaatc tttagttact gaaaaatgga atctcttaga gagtaagaga gtgctttaat    802 ttagcttaat tagatttatt tggatttctt tcagtatttg gattgtaaac tttagaattt    862 gtgtgtgtgt tgttgcttag tcctgagata agatataaca ttagcgactg tgtattatta    922 ttattactgc attgtgttat gtgaaacttt gttctcttgt tgaaaaaaaa aaaaaaaaaa    982 a                                                                    983

<210> SEQ ID NO 138
<211> LENGTH: 204
<212> TYPE: PRT
<213> ORGANISM: Arabidopsis thaliana
<220> FEATURE:
<221> NAME/KEY: DOMAIN
<222> LOCATION: (97)...(104)
<223> OTHER INFORMATION: Conserved domain
<220> FEATURE:
<221> NAME/KEY: DOMAIN
<222> LOCATION: (130)...(137)
<223> OTHER INFORMATION: Conserved domain
<220> FEATURE:
<221> NAME/KEY: DOMAIN
<222> LOCATION: (155)...(162)
<223> OTHER INFORMATION: Conserved domain
<220> FEATURE:
<221> NAME/KEY: DOMAIN
<222> LOCATION: (185)...(192)
<223> OTHER INFORMATION: Conserved domain

<400> SEQUENCE: 138

Met Ala Phe Asp Leu His His Gly Ser Ala Ser Asp Thr His Ser Ser
 1               5                  10                  15

Glu Leu Pro Ser Phe Ser Leu Pro Pro Tyr Pro Gln Met Ile Met Glu
            20                  25                  30

Ala Ile Glu Ser Leu Asn Asp Lys Asn Gly Cys Asn Lys Thr Thr Ile
        35                  40                  45

Ala Lys His Ile Glu Ser Thr Gln Gln Thr Leu Pro Pro Ser His Met
    50                  55                  60

Thr Leu Leu Ser Tyr His Leu Asn Gln Met Lys Lys Thr Gly Gln Leu
65                  70                  75                  80

Ile Met Val Lys Asn Asn Tyr Met Lys Pro Asp Pro Asp Ala Pro Pro
                85                  90                  95

Lys Arg Gly Arg Gly Arg Pro Pro Lys Gln Lys Thr Gln Ala Glu Ser
            100                 105                 110

Asp Ala Ala Ala Ala Val Val Ala Ala Thr Val Val Ser Thr Asp
        115                 120                 125

Pro Pro Arg Ser Arg Gly Arg Pro Lys Pro Lys Asp Pro Ser Glu
    130                 135                 140

Pro Pro Gln Glu Lys Val Ile Thr Gly Ser Gly Arg Pro Arg Gly Arg
```

```
                145                 150                 155                 160
Pro Pro Lys Arg Pro Arg Thr Asp Ser Glu Thr Val Ala Ala Pro Glu
                    165                 170                 175

Pro Ala Ala Gln Ala Thr Gly Glu Arg Arg Gly Arg Gly Arg Pro Pro
                180                 185                 190

Lys Val Lys Pro Thr Val Val Ala Pro Val Gly Cys
            195                 200

<210> SEQ ID NO 139
<211> LENGTH: 1065
<212> TYPE: DNA
<213> ORGANISM: Arabidopsis thaliana
<220> FEATURE:
<221> NAME/KEY: CDS
<222> LOCATION: (69)...(1010)

<400> SEQUENCE: 139
gtctctcatt ttcataattc cattttcagg attgtctctc aatctttat tcttctcatt      60 caccggta atg gca aaa gtc tct ggg agg agc aag aaa aca atc gtt gac     110
         Met Ala Lys Val Ser Gly Arg Ser Lys Lys Thr Ile Val Asp
           1               5                  10 gat gaa atc agc gat aaa aca gcg tct gcg tct gag tct gcg tcc att     158
Asp Glu Ile Ser Asp Lys Thr Ala Ser Ala Ser Glu Ser Ala Ser Ile
 15                  20                  25                  30 gcc tta aca tcc aaa cgc aaa cgt aag tcg ccg cct cga aac gct cct     206
Ala Leu Thr Ser Lys Arg Lys Arg Lys Ser Pro Pro Arg Asn Ala Pro
                 35                  40                  45 ctt caa cgc agc tcc cct tac aga ggc gtc aca agg cat aga tgg act     254
Leu Gln Arg Ser Ser Pro Tyr Arg Gly Val Thr Arg His Arg Trp Thr
             50                  55                  60 ggg aga tac gaa gcg cat ttg tgg gat aag aac agc tgg aac gat aca     302
Gly Arg Tyr Glu Ala His Leu Trp Asp Lys Asn Ser Trp Asn Asp Thr
         65                  70                  75 cag acc aag aaa gga cgt caa gtt tat cta ggg gct tac gac gaa gaa     350
Gln Thr Lys Lys Gly Arg Gln Val Tyr Leu Gly Ala Tyr Asp Glu Glu
     80                  85                  90 gaa gca gca gca cgt gcc tac gac tta gca gca ttg aag tac tgg gga     398
Glu Ala Ala Ala Arg Ala Tyr Asp Leu Ala Ala Leu Lys Tyr Trp Gly
 95                 100                 105                 110 cga gac aca ctc ttg aac ttc cct ttg ccg agt tat gac gaa gac gtc     446
Arg Asp Thr Leu Leu Asn Phe Pro Leu Pro Ser Tyr Asp Glu Asp Val
                 115                 120                 125 aaa gaa atg gaa ggc caa tcc aag gaa gag tat att gga tca ttg aga     494
Lys Glu Met Glu Gly Gln Ser Lys Glu Glu Tyr Ile Gly Ser Leu Arg
             130                 135                 140 aga aaa agt agt gga ttt tct cgc ggt gta tca aaa tac aga ggc gtt     542
Arg Lys Ser Ser Gly Phe Ser Arg Gly Val Ser Lys Tyr Arg Gly Val
         145                 150                 155 gca agg cat cac cat aat ggg aga tgg gaa gct aga att gga agg gtg     590
Ala Arg His His His Asn Gly Arg Trp Glu Ala Arg Ile Gly Arg Val
     160                 165                 170 ttt ggt aat aaa tat cta tat ctt gga aca tac gcc acg caa gaa gaa     638
Phe Gly Asn Lys Tyr Leu Tyr Leu Gly Thr Tyr Ala Thr Gln Glu Glu
175                 180                 185                 190 gca gca atc gcc tac gac atc gcg gca ata gag tac cgt gga ctt aac     686
Ala Ala Ile Ala Tyr Asp Ile Ala Ala Ile Glu Tyr Arg Gly Leu Asn
                 195                 200                 205 gcc gtt acc aat ttc gac gtc agc cgt tat cta aac cct aac gcc gcc     734
Ala Val Thr Asn Phe Asp Val Ser Arg Tyr Leu Asn Pro Asn Ala Ala
             210                 215                 220
```

-continued

```
gcg gat aaa gcc gat tcc gat tct aag ccc att cga agc cct agt cgc    782
Ala Asp Lys Ala Asp Ser Asp Ser Lys Pro Ile Arg Ser Pro Ser Arg
        225                 230                 235 gag ccc gaa tcg tcg gat gat aac aaa tct ccg aaa tca gag gaa gta    830
Glu Pro Glu Ser Ser Asp Asp Asn Lys Ser Pro Lys Ser Glu Glu Val
240                 245                 250 atc gaa cca tct aca tcg ccg gaa gtg att cca act cgc cgg agc ttc    878
Ile Glu Pro Ser Thr Ser Pro Glu Val Ile Pro Thr Arg Arg Ser Phe
255                 260                 265                 270 ccc gac gat atc cag acg tat ttt ggg tgt caa gat tcc ggc aag tta    926
Pro Asp Asp Ile Gln Thr Tyr Phe Gly Cys Gln Asp Ser Gly Lys Leu
            275                 280                 285 gcg act gag gaa gac gta ata ttc gat tgt ttc aat tct tat ata aat    974
Ala Thr Glu Glu Asp Val Ile Phe Asp Cys Phe Asn Ser Tyr Ile Asn
        290                 295                 300 cct ggc ttc tat aac gag ttt gat tat gga cct taa tcgtattttc         1020
Pro Gly Phe Tyr Asn Glu Phe Asp Tyr Gly Pro  *
                305                 310 tacaagtttt gttttgatta tctacacaat acatcaatat attct                  1065

<210> SEQ ID NO 140
<211> LENGTH: 313
<212> TYPE: PRT
<213> ORGANISM: Arabidopsis thaliana
<220> FEATURE:
<221> NAME/KEY: DOMAIN
<222> LOCATION: (50)...(86)
<223> OTHER INFORMATION: Conserved domain
<220> FEATURE:
<221> NAME/KEY: DOMAIN
<222> LOCATION: (112)...(183)
<223> OTHER INFORMATION: Conserved domain

<400> SEQUENCE: 140

Met Ala Lys Val Ser Gly Arg Ser Lys Lys Thr Ile Val Asp Asp Glu
1               5                   10                  15

Ile Ser Asp Lys Thr Ala Ser Ala Ser Glu Ser Ala Ser Ile Ala Leu
            20                  25                  30

Thr Ser Lys Arg Lys Arg Lys Ser Pro Pro Arg Asn Ala Pro Leu Gln
        35                  40                  45

Arg Ser Ser Pro Tyr Arg Gly Val Thr Arg His Arg Trp Thr Gly Arg
    50                  55                  60

Tyr Glu Ala His Leu Trp Asp Lys Asn Ser Trp Asn Asp Thr Gln Thr
65                  70                  75                  80

Lys Lys Gly Arg Gln Val Tyr Leu Gly Ala Tyr Asp Glu Glu Glu Ala
                85                  90                  95

Ala Ala Arg Ala Tyr Asp Leu Ala Ala Leu Lys Tyr Trp Gly Arg Asp
            100                 105                 110

Thr Leu Leu Asn Phe Pro Leu Pro Ser Tyr Asp Glu Asp Val Lys Glu
        115                 120                 125

Met Glu Gly Gln Ser Lys Glu Glu Tyr Ile Gly Ser Leu Arg Arg Lys
    130                 135                 140

Ser Ser Gly Phe Ser Arg Gly Val Ser Lys Tyr Arg Gly Val Ala Arg
145                 150                 155                 160

His His His Asn Gly Arg Trp Glu Ala Arg Ile Gly Arg Val Phe Gly
                165                 170                 175

Asn Lys Tyr Leu Tyr Leu Gly Thr Tyr Ala Thr Gln Glu Glu Ala Ala
            180                 185                 190
```

```
Ile Ala Tyr Asp Ile Ala Ala Ile Glu Tyr Arg Gly Leu Asn Ala Val
            195                 200                 205

Thr Asn Phe Asp Val Ser Arg Tyr Leu Asn Pro Asn Ala Ala Ala Asp
    210                 215                 220

Lys Ala Asp Ser Asp Ser Lys Pro Ile Arg Ser Pro Ser Arg Glu Pro
225                 230                 235                 240

Glu Ser Ser Asp Asp Asn Lys Ser Pro Lys Ser Glu Glu Val Ile Glu
                245                 250                 255

Pro Ser Thr Ser Pro Glu Val Ile Pro Thr Arg Arg Ser Phe Pro Asp
            260                 265                 270

Asp Ile Gln Thr Tyr Phe Gly Cys Gln Asp Ser Gly Lys Leu Ala Thr
        275                 280                 285

Glu Glu Asp Val Ile Phe Asp Cys Phe Asn Ser Tyr Ile Asn Pro Gly
290                 295                 300

Phe Tyr Asn Glu Phe Asp Tyr Gly Pro
305                 310
```

<210> SEQ ID NO 141
<211> LENGTH: 999
<212> TYPE: DNA
<213> ORGANISM: Arabidopsis thaliana
<220> FEATURE:
<221> NAME/KEY: CDS
<222> LOCATION: (1)...(999)

<400> SEQUENCE: 141

```
atg agg atg gag atg gtg cat gct gac gtg gcg tct ctc tcc ata aca      48
Met Arg Met Glu Met Val His Ala Asp Val Ala Ser Leu Ser Ile Thr
1               5                   10                  15 cct tgc ttc ccg tct tct ttg tct tcg tcc tca cat cat cac tat aac      96
Pro Cys Phe Pro Ser Ser Leu Ser Ser Ser His His His Tyr Asn
            20                  25                  30 caa caa caa cat tgt atc atg tcg gaa gat caa cac cat tcg atg gat     144
Gln Gln Gln His Cys Ile Met Ser Glu Asp Gln His His Ser Met Asp
        35                  40                  45 cag acc act tca tcg gac tac ttc tct tta aat atc gac aat gct caa     192
Gln Thr Thr Ser Ser Asp Tyr Phe Ser Leu Asn Ile Asp Asn Ala Gln
    50                  55                  60 cat ctc cgt agc tac tac aca agt cat aga gaa gaa gac atg aac cct     240
His Leu Arg Ser Tyr Tyr Thr Ser His Arg Glu Glu Asp Met Asn Pro
65                  70                  75                  80 aat cta agt gat tac agt aat tgc aac aag aaa gac aca aca gtc tat     288
Asn Leu Ser Asp Tyr Ser Asn Cys Asn Lys Lys Asp Thr Thr Val Tyr
                85                  90                  95 aga agc tgt gga cac tcg tca aaa gct tcg gtg tct aga gga cat tgg     336
Arg Ser Cys Gly His Ser Ser Lys Ala Ser Val Ser Arg Gly His Trp
            100                 105                 110 aga cca gct gaa gat act aag ctc aaa gaa cta gtc gcc gtc tac ggt     384
Arg Pro Ala Glu Asp Thr Lys Leu Lys Glu Leu Val Ala Val Tyr Gly
        115                 120                 125 cca caa aac tgg aac ctc ata gct gag aag ctc caa gga aga tcc ggg     432
Pro Gln Asn Trp Asn Leu Ile Ala Glu Lys Leu Gln Gly Arg Ser Gly
    130                 135                 140 aaa agc tgt agg ctt cga tgg ttt aac caa cta gac cca agg ata aat     480
Lys Ser Cys Arg Leu Arg Trp Phe Asn Gln Leu Asp Pro Arg Ile Asn
145                 150                 155                 160 aga aga gcc ttc act gag gaa gaa gaa gag agg cta atg caa gct cat     528
Arg Arg Ala Phe Thr Glu Glu Glu Glu Glu Arg Leu Met Gln Ala His
                165                 170                 175
```

```
agg ctt tat ggt aac aaa tgg gcg atg ata gcg agg ctt ttc cct ggt        576
Arg Leu Tyr Gly Asn Lys Trp Ala Met Ile Ala Arg Leu Phe Pro Gly
            180                 185                 190 agg act gat aat tct gtg aag aac cat tgg cat gtt ata atg gct cgc        624
Arg Thr Asp Asn Ser Val Lys Asn His Trp His Val Ile Met Ala Arg
    195                 200                 205 aag ttt agg gaa caa tct tct tct tac cgt agg agg aag acg atg gtt        672
Lys Phe Arg Glu Gln Ser Ser Ser Tyr Arg Arg Lys Thr Met Val
210                 215                 220 tct ctt aag cca ctc att aac cct aat cct cac att ttc aat gat ttt        720
Ser Leu Lys Pro Leu Ile Asn Pro Asn Pro His Ile Phe Asn Asp Phe
225                 230                 235                 240 gac cct acc cgg tta gct ttg acc cac ctt gct agt agt gac cat aag        768
Asp Pro Thr Arg Leu Ala Leu Thr His Leu Ala Ser Ser Asp His Lys
            245                 250                 255 cag ctt atg tta cca gtt cct tgc ttc cca ggt tat gat cat gaa aat        816
Gln Leu Met Leu Pro Val Pro Cys Phe Pro Gly Tyr Asp His Glu Asn
        260                 265                 270 gag agt cca tta atg gtg gat atg ttc gaa acc caa atg atg gtt ggc        864
Glu Ser Pro Leu Met Val Asp Met Phe Glu Thr Gln Met Met Val Gly
    275                 280                 285 gat tac att gca tgg aca caa gag gca act aca ttc gat ttc tta aac        912
Asp Tyr Ile Ala Trp Thr Gln Glu Ala Thr Thr Phe Asp Phe Leu Asn
290                 295                 300 caa acc ggg aag agt gag ata ttt gaa aga atc aat gag gag aag aaa        960
Gln Thr Gly Lys Ser Glu Ile Phe Glu Arg Ile Asn Glu Glu Lys Lys
305                 310                 315                 320 cca cca ttt ttc gat ttt ctt ggg ttg ggg acg gtg tga                    999
Pro Pro Phe Phe Asp Phe Leu Gly Leu Gly Thr Val  *
            325                 330

<210> SEQ ID NO 142
<211> LENGTH: 332
<212> TYPE: PRT
<213> ORGANISM: Arabidopsis thaliana
<220> FEATURE:
<221> NAME/KEY: DOMAIN
<222> LOCATION: (107)...(219)
<223> OTHER INFORMATION: Conserved domain

<400> SEQUENCE: 142

Met Arg Met Glu Met Val His Ala Asp Val Ala Ser Leu Ser Ile Thr
1               5                   10                  15

Pro Cys Phe Pro Ser Ser Leu Ser Ser Ser His His Tyr Asn
            20                  25                  30

Gln Gln Gln His Cys Ile Met Ser Glu Asp Gln His His Ser Met Asp
        35                  40                  45

Gln Thr Thr Ser Ser Asp Tyr Phe Ser Leu Asn Ile Asp Asn Ala Gln
    50                  55                  60

His Leu Arg Ser Tyr Tyr Thr Ser His Arg Glu Glu Asp Met Asn Pro
65                  70                  75                  80

Asn Leu Ser Asp Tyr Ser Asn Cys Asn Lys Lys Asp Thr Thr Val Tyr
                85                  90                  95

Arg Ser Cys Gly His Ser Ser Lys Ala Ser Val Ser Arg Gly His Trp
            100                 105                 110

Arg Pro Ala Glu Asp Thr Lys Leu Lys Glu Leu Val Ala Val Tyr Gly
        115                 120                 125

Pro Gln Asn Trp Asn Leu Ile Ala Glu Lys Leu Gln Gly Arg Ser Gly
    130                 135                 140
```

```
Lys Ser Cys Arg Leu Arg Trp Phe Asn Gln Leu Asp Pro Arg Ile Asn
145                 150                 155                 160

Arg Arg Ala Phe Thr Glu Glu Glu Arg Leu Met Gln Ala His
                165                 170                 175

Arg Leu Tyr Gly Asn Lys Trp Ala Met Ile Ala Arg Leu Phe Pro Gly
            180                 185                 190

Arg Thr Asp Asn Ser Val Lys Asn His Trp His Val Ile Met Ala Arg
                195                 200                 205

Lys Phe Arg Glu Gln Ser Ser Tyr Arg Arg Lys Thr Met Val
    210                 215                 220

Ser Leu Lys Pro Leu Ile Asn Pro Asn Pro His Ile Phe Asn Asp Phe
225                 230                 235                 240

Asp Pro Thr Arg Leu Ala Leu Thr His Leu Ala Ser Ser Asp His Lys
                245                 250                 255

Gln Leu Met Leu Pro Val Pro Cys Phe Pro Gly Tyr Asp His Glu Asn
                260                 265                 270

Glu Ser Pro Leu Met Val Asp Met Phe Glu Thr Gln Met Met Val Gly
            275                 280                 285

Asp Tyr Ile Ala Trp Thr Gln Glu Ala Thr Thr Phe Asp Phe Leu Asn
            290                 295                 300

Gln Thr Gly Lys Ser Glu Ile Phe Glu Arg Ile Asn Glu Lys Lys
305                 310                 315                 320

Pro Pro Phe Phe Asp Phe Leu Gly Leu Gly Thr Val
                325                 330
```

<210> SEQ ID NO 143
<211> LENGTH: 653
<212> TYPE: DNA
<213> ORGANISM: Arabidopsis thaliana
<220> FEATURE:
<221> NAME/KEY: CDS
<222> LOCATION: (38)...(607)

<400> SEQUENCE: 143

```
caaatcagaa aatatagagt ttgaaggaaa ctaaaag atg gta cat tcg agg aag      55
                                         Met Val His Ser Arg Lys
                                           1               5 ttc cga ggt gtc cgc cag cga caa tgg ggt tct tgg gtc tct gag att      103
Phe Arg Gly Val Arg Gln Arg Gln Trp Gly Ser Trp Val Ser Glu Ile
            10                  15                  20 cgc cat cct cta ttg aag aga aga gtg tgg ctt gga act ttc gaa acg      151
Arg His Pro Leu Leu Lys Arg Arg Val Trp Leu Gly Thr Phe Glu Thr
        25                  30                  35 gca gaa gcg gct gca aga gca tac gac caa gcg gct ctt cta atg aac      199
Ala Glu Ala Ala Ala Arg Ala Tyr Asp Gln Ala Ala Leu Leu Met Asn
    40                  45                  50 ggc caa aac gct aag acc aat ttc cct gtc gta aaa tca gag gaa ggc      247
Gly Gln Asn Ala Lys Thr Asn Phe Pro Val Val Lys Ser Glu Glu Gly
55                  60                  65                  70 tcc gat cac gtt aaa gat gtt aac tct ccg ttg atg tca cca aag tca      295
Ser Asp His Val Lys Asp Val Asn Ser Pro Leu Met Ser Pro Lys Ser
                75                  80                  85 tta tct gag ctt ttg aac gct aag cta agg aag agc tgc aaa gac cta      343
Leu Ser Glu Leu Leu Asn Ala Lys Leu Arg Lys Ser Cys Lys Asp Leu
            90                  95                  100 acg cct tct ttg acg tgt ctc cgt ctt gat act gac agt tcc cac att      391
Thr Pro Ser Leu Thr Cys Leu Arg Leu Asp Thr Asp Ser Ser His Ile
        105                 110                 115
```

```
gga gtt tgg cag aaa cgg gcc ggg tcg aaa aca agt ccg act tgg gtc       439
Gly Val Trp Gln Lys Arg Ala Gly Ser Lys Thr Ser Pro Thr Trp Val
    120                 125                 130 atg cgc ctc gaa ctt ggg aac gta gtc aac gaa agt gcg gtt gac tta       487
Met Arg Leu Glu Leu Gly Asn Val Val Asn Glu Ser Ala Val Asp Leu
135                 140                 145                 150 ggg ttg act acg atg aac aaa caa aac gtt gag aaa gaa gaa gaa           535
Gly Leu Thr Thr Met Asn Lys Gln Asn Val Glu Lys Glu Glu Glu
                155                 160                 165 gaa gaa gct att att agt gat gag gat cag tta gct atg gag atg atc       583
Glu Glu Ala Ile Ile Ser Asp Glu Asp Gln Leu Ala Met Glu Met Ile
                170                 175                 180 gag gag ttg ctg aat tgg agt tga cttttgactt taacttgttg caagtccaca     637
Glu Glu Leu Leu Asn Trp Ser *
            185 aggggtaagg gttttc                                                     653
```

<210> SEQ ID NO 144
<211> LENGTH: 189
<212> TYPE: PRT
<213> ORGANISM: Arabidopsis thaliana
<220> FEATURE:
<221> NAME/KEY: DOMAIN
<222> LOCATION: (4)...(71)
<223> OTHER INFORMATION: Conserved domain

<400> SEQUENCE: 144

```
Met Val His Ser Arg Lys Phe Arg Gly Val Arg Gln Arg Gln Trp Gly
1               5                   10                  15

Ser Trp Val Ser Glu Ile Arg His Pro Leu Leu Lys Arg Arg Val Trp
            20                  25                  30

Leu Gly Thr Phe Glu Thr Ala Glu Ala Ala Arg Ala Tyr Asp Gln
        35                  40                  45

Ala Ala Leu Leu Met Asn Gly Gln Asn Ala Lys Thr Asn Phe Pro Val
    50                  55                  60

Val Lys Ser Glu Glu Gly Ser Asp His Val Lys Asp Val Asn Ser Pro
65                  70                  75                  80

Leu Met Ser Pro Lys Ser Leu Ser Glu Leu Leu Asn Ala Lys Leu Arg
                85                  90                  95

Lys Ser Cys Lys Asp Leu Thr Pro Ser Leu Thr Cys Leu Arg Leu Asp
            100                 105                 110

Thr Asp Ser Ser His Ile Gly Val Trp Gln Lys Arg Ala Gly Ser Lys
        115                 120                 125

Thr Ser Pro Thr Trp Val Met Arg Leu Glu Leu Gly Asn Val Val Asn
    130                 135                 140

Glu Ser Ala Val Asp Leu Gly Leu Thr Thr Met Asn Lys Gln Asn Val
145                 150                 155                 160

Glu Lys Glu Glu Glu Glu Glu Ala Ile Ile Ser Asp Glu Asp Gln
                165                 170                 175

Leu Ala Met Glu Met Ile Glu Glu Leu Leu Asn Trp Ser
            180                 185
```

<210> SEQ ID NO 145
<211> LENGTH: 844
<212> TYPE: DNA
<213> ORGANISM: Arabidopsis thaliana
<220> FEATURE:
<221> NAME/KEY: CDS
<222> LOCATION: (89)...(658)

<400> SEQUENCE: 145

```
tctctctccc actctcactt tctctcctat tcttagttcg tgtcagaaac acacagagaa        60
attaagaacc ctaatttaaa acagaaga atg gta cat tcg aag aag ttc cga          112
                                 Met Val His Ser Lys Lys Phe Arg
                                  1               5 ggt gtc cgc cag cgt cag tgg ggt tct tgg gtt tct gag att cgt cat         160
Gly Val Arg Gln Arg Gln Trp Gly Ser Trp Val Ser Glu Ile Arg His
 10              15                  20 cct ctc ttg aag aga aga gtg tgg cta gga aca ttc gac acg gcg gaa         208
Pro Leu Leu Lys Arg Arg Val Trp Leu Gly Thr Phe Asp Thr Ala Glu
 25              30                  35                  40 aca gcg gct aga gcc tac gac caa gcc gcg gtt cta atg aac ggc cag         256
Thr Ala Ala Arg Ala Tyr Asp Gln Ala Ala Val Leu Met Asn Gly Gln
                 45                  50                  55 agc gcg aag act aac ttc ccc gtc atc aaa tcg aac ggt tca aat tcc         304
Ser Ala Lys Thr Asn Phe Pro Val Ile Lys Ser Asn Gly Ser Asn Ser
             60                  65                  70 ttg gag att aac tct gcg tta agg tct ccc aaa tca tta tcg gaa cta         352
Leu Glu Ile Asn Ser Ala Leu Arg Ser Pro Lys Ser Leu Ser Glu Leu
     75                  80                  85 ttg aac gct aag cta agg aag aac tgt aaa gac cag aca ccg tat ctg         400
Leu Asn Ala Lys Leu Arg Lys Asn Cys Lys Asp Gln Thr Pro Tyr Leu
 90                  95                 100 acg tgt ctc cgc ctc gac aac gac agc tca cac atc ggc gtc tgg cag         448
Thr Cys Leu Arg Leu Asp Asn Asp Ser Ser His Ile Gly Val Trp Gln
105                 110                 115                 120 aaa cgc gcc ggg tca aaa acg agt cca aac tgg gtc aag ctt gtt gaa         496
Lys Arg Ala Gly Ser Lys Thr Ser Pro Asn Trp Val Lys Leu Val Glu
                125                 130                 135 cta ggt gac aaa gtt aac gca cgt ccc ggt ggt gat att gag act aat         544
Leu Gly Asp Lys Val Asn Ala Arg Pro Gly Gly Asp Ile Glu Thr Asn
            140                 145                 150 aag atg aag gta cga aac gaa gac gtt cag gaa gat gat caa atg gcg         592
Lys Met Lys Val Arg Asn Glu Asp Val Gln Glu Asp Asp Gln Met Ala
        155                 160                 165 atg cag atg atc gag gag ttg ctt aac tgg acc tgt cct gga tct gga         640
Met Gln Met Ile Glu Glu Leu Leu Asn Trp Thr Cys Pro Gly Ser Gly
    170                 175                 180 tcc att gca cag gtc taa aggagaatca ttgaattata tgatcaagat                688
Ser Ile Ala Gln Val *
185 aataatatag ttgagggtta ataataatcg agggtaagta atttacgtgt agctaataat        748 taatataatt ttcgaacata tatatgaata tatgatagct ctagaaatga gtacgtatat        808 atacgtaaac attttttcctc aaatatagta tatgtg                                 844

<210> SEQ ID NO 146
<211> LENGTH: 189
<212> TYPE: PRT
<213> ORGANISM: Arabidopsis thaliana
<220> FEATURE:
<221> NAME/KEY: DOMAIN
<222> LOCATION: (4)...(71)
<223> OTHER INFORMATION: Conserved domain

<400> SEQUENCE: 146

Met Val His Ser Lys Lys Phe Arg Gly Val Arg Gln Arg Gln Trp Gly
 1               5                  10                  15

Ser Trp Val Ser Glu Ile Arg His Pro Leu Leu Lys Arg Arg Val Trp
                 20                  25                  30
```

-continued

```
Leu Gly Thr Phe Asp Thr Ala Glu Thr Ala Ala Arg Ala Tyr Asp Gln
         35                  40                  45

Ala Ala Val Leu Met Asn Gly Gln Ser Ala Lys Thr Asn Phe Pro Val
 50                  55                  60

Ile Lys Ser Asn Gly Ser Asn Ser Leu Glu Ile Asn Ser Ala Leu Arg
65                  70                  75                  80

Ser Pro Lys Ser Leu Ser Glu Leu Leu Asn Ala Lys Leu Arg Lys Asn
                 85                  90                  95

Cys Lys Asp Gln Thr Pro Tyr Leu Thr Cys Leu Arg Leu Asp Asn Asp
            100                 105                 110

Ser Ser His Ile Gly Val Trp Gln Lys Arg Ala Gly Ser Lys Thr Ser
        115                 120                 125

Pro Asn Trp Val Lys Leu Val Glu Leu Gly Asp Lys Val Asn Ala Arg
    130                 135                 140

Pro Gly Gly Asp Ile Glu Thr Asn Lys Met Lys Val Arg Asn Glu Asp
145                 150                 155                 160

Val Gln Glu Asp Asp Gln Met Ala Met Gln Met Ile Glu Glu Leu Leu
                165                 170                 175

Asn Trp Thr Cys Pro Gly Ser Gly Ser Ile Ala Gln Val
            180                 185
```

<210> SEQ ID NO 147
<211> LENGTH: 833
<212> TYPE: DNA
<213> ORGANISM: Arabidopsis thaliana
<220> FEATURE:
<221> NAME/KEY: CDS
<222> LOCATION: (46)...(591)
<220> FEATURE:
<221> NAME/KEY: misc_feature
<222> LOCATION: 810
<223> OTHER INFORMATION: n = A,T,C or G

<400> SEQUENCE: 147

```
caccaaactc acctgaaacc ctatttccat ttaccattca cacta atg gca cga cca        57
                                                  Met Ala Arg Pro
                                                   1 caa caa cgc ttt cga ggc gtt aga cag agg cat tgg ggc tct tgg gtc        105
Gln Gln Arg Phe Arg Gly Val Arg Gln Arg His Trp Gly Ser Trp Val
  5                  10                  15                  20 tcc gaa att cgt cac cct ctc ttg aaa aca aga atc tgg cta ggg acg        153
Ser Glu Ile Arg His Pro Leu Leu Lys Thr Arg Ile Trp Leu Gly Thr
                 25                  30                  35 ttt gag aca gcg gag gat gca gca agg gcc tac gac gag gcg gct agg        201
Phe Glu Thr Ala Glu Asp Ala Ala Arg Ala Tyr Asp Glu Ala Ala Arg
            40                  45                  50 cta atg tgt ggc ccg aga gct cgt act aat ttc cca tac aac cct aat        249
Leu Met Cys Gly Pro Arg Ala Arg Thr Asn Phe Pro Tyr Asn Pro Asn
        55                  60                  65 gcc att cct act tcc tct tcc aag ctt cta tca gca act ctt acc gct        297
Ala Ile Pro Thr Ser Ser Ser Lys Leu Leu Ser Ala Thr Leu Thr Ala
    70                  75                  80 aaa ctc cac aaa tgc tac atg gct tct ctt caa atg acc aag caa acg        345
Lys Leu His Lys Cys Tyr Met Ala Ser Leu Gln Met Thr Lys Gln Thr
85                  90                  95                 100 caa aca caa acg caa acg cag acc gca aga tca caa tcc gcg gac agt        393
Gln Thr Gln Thr Gln Thr Gln Thr Ala Arg Ser Gln Ser Ala Asp Ser
                105                 110                 115 gac ggt gtg acg gct aac gaa agt cat ttg aac aga gga gta acg gag        441
```

-continued

```
Asp Gly Val Thr Ala Asn Glu Ser His Leu Asn Arg Gly Val Thr Glu
        120                 125                 130 acg aca gag atc aag tgg gaa gat gga aat gcg aat atg caa cag aat      489
Thr Thr Glu Ile Lys Trp Glu Asp Gly Asn Ala Asn Met Gln Gln Asn
            135                 140                 145 ttt agg cca ttg gag gaa gat cat atc gag caa atg att gag gag ctg      537
Phe Arg Pro Leu Glu Glu Asp His Ile Glu Gln Met Ile Glu Glu Leu
    150                 155                 160 ctt cac tac ggt tcc att gag ctt tgc tct gtt tta cca act cag acg      585
Leu His Tyr Gly Ser Ile Glu Leu Cys Ser Val Leu Pro Thr Gln Thr
165                 170                 175                 180 ctg tga gaaatggcct tgtcgtttta gcgtattctt ttcatttttta ttttttgtttc     641
Leu * cacaaaaacg gcgtcgtaag tgatgagagt agtagtgaga gaaggctaat ttcaagacat    701
tttgatctga attggcctct tttgaaacac tgattctagt ttctataaga gcaatcgatc    761
atatgctatg ttatgtatag tattataaaa aaatgttatt ttctgattna aaaaaaaaa     821 aaaaaaaaaa aa                                                        833
```

<210> SEQ ID NO 148
<211> LENGTH: 181
<212> TYPE: PRT
<213> ORGANISM: Arabidopsis thaliana
<220> FEATURE:
<221> NAME/KEY: DOMAIN
<222> LOCATION: (5)...(72)
<223> OTHER INFORMATION: Conserved domain

<400> SEQUENCE: 148

```
Met Ala Arg Pro Gln Gln Arg Phe Arg Gly Val Arg Gln Arg His Trp
 1               5                  10                  15

Gly Ser Trp Val Ser Glu Ile Arg His Pro Leu Leu Lys Thr Arg Ile
            20                  25                  30

Trp Leu Gly Thr Phe Glu Thr Ala Glu Asp Ala Ala Arg Ala Tyr Asp
        35                  40                  45

Glu Ala Ala Arg Leu Met Cys Gly Pro Arg Ala Arg Thr Asn Phe Pro
    50                  55                  60

Tyr Asn Pro Asn Ala Ile Pro Thr Ser Ser Lys Leu Leu Ser Ala
65                  70                  75                  80

Thr Leu Thr Ala Lys Leu His Lys Cys Tyr Met Ala Ser Leu Gln Met
                85                  90                  95

Thr Lys Gln Thr Gln Thr Gln Thr Gln Thr Ala Arg Ser Gln
            100                 105                 110

Ser Ala Asp Ser Asp Gly Val Thr Ala Asn Glu Ser His Leu Asn Arg
        115                 120                 125

Gly Val Thr Glu Thr Thr Glu Ile Lys Trp Glu Asp Gly Asn Ala Asn
    130                 135                 140

Met Gln Gln Asn Phe Arg Pro Leu Glu Glu Asp His Ile Glu Gln Met
145                 150                 155                 160

Ile Glu Glu Leu Leu His Tyr Gly Ser Ile Glu Leu Cys Ser Val Leu
                165                 170                 175

Pro Thr Gln Thr Leu
            180
```